(12) United States Patent
McGuinness et al.

(10) Patent No.: US 7,776,862 B2
(45) Date of Patent: Aug. 17, 2010

(54) PYRIDYL AND PHENYL SUBSTITUTED PIPERAZINE-PIPERIDINES WITH CXCR3 ANTAGONIST ACTIVITY

(75) Inventors: Brian F. McGuinness, Plainsboro, NJ (US); Stuart B. Rosenblum, West Orange, NJ (US); Joseph A. Kozlowski, Princeton, NJ (US); Gopinadhan N. Anilkumar, Edison, NJ (US); Seong Heon Kim, Livingston, NJ (US); Neng-Yang Shih, Warren, NJ (US); Chung-Her Jenh, Annandale, NJ (US); Paul J. Zavodny, Mountainside, NJ (US); Douglas W. Hobbs, Yardley, PA (US); Guizhen Dong, Dayton, NJ (US); Yuefei Shao, Princeton, NJ (US); Lisa Guise Zawacki, Yardley, PA (US); Cangmeng Yang, Highland Park, NJ (US); Carolyn Dilanni Carroll, Yardley, PA (US)

(73) Assignee: Schering Corporation, Kenilworth, NJ (US)

( * ) Notice: Subject to any disclaimer, the term of this patent is extended or adjusted under 35 U.S.C. 154(b) by 596 days.

(21) Appl. No.: 11/353,697

(22) Filed: Feb. 14, 2006

(65) Prior Publication Data

US 2007/0021611 A1 Jan. 25, 2007

Related U.S. Application Data

(60) Provisional application No. 60/653,337, filed on Feb. 16, 2005.

(51) Int. Cl.
*A61K 31/497* (2006.01)
*C07D 401/00* (2006.01)

(52) U.S. Cl. ............... 514/253.01; 514/253.09; 514/253.1; 514/253.11; 514/253.13; 544/360

(58) Field of Classification Search ............ 514/253.11, 514/253.13, 253.01, 253.09, 253.1; 544/360
See application file for complete search history.

(56) References Cited

U.S. PATENT DOCUMENTS

| 6,124,319 | A | 9/2000 | MacCoss et al. |
| 7,417,045 | B2 | 8/2008 | Anilkumar et al. |
| 7,566,718 | B2 | 7/2009 | Wong et al. |
| 2002/0018776 | A1 | 2/2002 | Hancock |
| 2003/0055054 | A1 | 3/2003 | Medina et al. |
| 2006/0276448 | A1 | 12/2006 | Zeng et al. |
| 2006/0276457 | A1 | 12/2006 | Yu et al. |
| 2006/0276479 | A1 | 12/2006 | Kim et al. |
| 2007/0054919 | A1 | 3/2007 | Rosenblum et al. |
| 2007/0082913 | A1 | 4/2007 | Kim et al. |
| 2008/0039474 | A1 | 2/2008 | Rosenblum et al. |
| 2008/0058343 | A1 | 3/2008 | Rosenblum et al. |
| 2008/0292589 | A1 | 11/2008 | Anilkumar et al. |

FOREIGN PATENT DOCUMENTS

| WO | WO93/10091 | | 5/1993 |
| WO | WO 93/14077 | * | 7/1993 |
| WO | WO 93/14077 A | | 7/1993 |
| WO | WO99/20606 | | 4/1999 |
| WO | WO02/085861 | | 10/2002 |
| WO | WO03/070242 | | 8/2003 |
| WO | WO03/082335 | | 10/2003 |
| WO | WO03/098185 | | 11/2003 |
| WO | WO03/101970 | | 12/2003 |
| WO | WO 2004/113323 A | | 12/2004 |
| WO | WO2008/079279 | | 7/2008 |

OTHER PUBLICATIONS

West, Anthony R., Solid State Chemistry and Its Applications, Wiley, New York, 1988, 365.*
International Search Report for International Application No. PCT/US2006/005265 mailed Aug. 4, 2006 (4pgs.).

(Continued)

*Primary Examiner*—James O Wilson
*Assistant Examiner*—Erich A Leeser
(74) *Attorney, Agent, or Firm*—Palaiyur Kalyanaraman; Krishna G. Banerjee

(57) ABSTRACT

The present application discloses a compound, or enantiomers, stereoisomers, rotamers, tautomers, racemates or prodrug of said compound, or pharmaceutically acceptable salts, solvates or esters of said compound, or of said prodrug, said compound having the general structure shown in Formula 1:

Formula 1

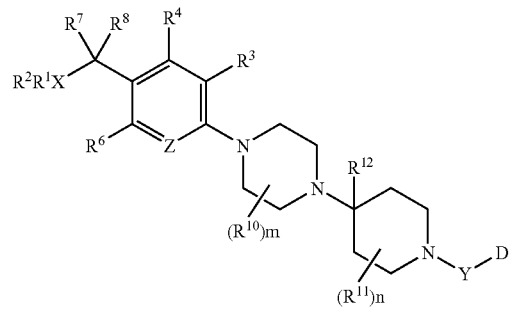

and the pharmaceutically acceptable salts, solvates and esters thereof. Also disclosed is a method of treating chemokine mediated diseases, such as, palliative therapy, curative therapy, prophylactic therapy of certain diseases and conditions such as inflammatory diseases (non-limiting example(s) include, psoriasis), autoimmune diseases (non-limiting example(s) include, rheumatoid arthritis, multiple sclerosis), graft rejection (non-limiting example(s) include, allograft rejection, xenograft rejection), infectious diseases (e.g, tuberculoid leprosy), fixed drug eruptions, cutaneous delayed-type hypersensitivity responses, ophthalmic inflammation, type I diabetes, viral meningitis and tumors using a compound of Formula 1.

47 Claims, No Drawings

OTHER PUBLICATIONS

Angiolilo, Anne L., et al.; "Human Interferon-inducible Protein 10 is a Potent Inhibitor of Angiogenesis In Vivo"; The Journal of Experimental Medicine; 182:155-162 (1995).

Baggiolini, Marco, et al.; "Interleukin-8 and Related Chemotactic Cytokines—CXC and CC Chemokines"; Advances in Immunol.; 55:97-179 (1994).

Baggiolini, Marco, et al.; "CC chemokines in allergic inflammation"; Immunology Today; 15(3):127-133 (1994).

Clark-Lewis, Ian, et al.; "Structure-Activity Relationships of Interleukin-8 Determined Using Chemically Synthesized Analogs"; The Journal of Biological Chemistry; 266(34):23128-23134 (1991).

Clark-Lewis, Ian, et al.; "Platelet factor 4 binds to interleukin 8 receptors and activates neutrophils when its N terminus is modified with Glu-Leu-Arg"; Proc. Natl. Acad. Sci. USA; 90:3574-3577 (1993).

Cole, Katherine E., et al.; "Interferon-inducible T Cell Alpha Chemoattractant (I-TAC): A Novel Non-ELR CXC Chemokine with Potent Activity on Activated T Cells through Selective High Affinity Binding to CXCR3"; J. Exp. Med.; 187(12):2009-2021 (1998).

Farber, Joshua M.; "A macrophage mRNA selectively induced by γ-interferon encodes a member of the platelet factor 4 family of cytokines"; Proc. Natl. Acad. Sci. USA; 87:5238-5242 (1990).

Farber, Joshua M.; "HuMIG: A New Human Member of the Chemokine Family of Cytokines"; Biochemical and Biophysical Research Communications; 192(1):223-230 (1993).

Galy, Anne H. M., et al.; "IL-1, IL-4, and IFN-γ Differentially Regulate Cytokine Production and Cell Surface Molecule Expression in Cultured Human Thymic Epithelial Cells"; The Journal of Immunology; 147(11):3823-3830 (1991).

Hebert, Caroline A., et al.; "Scanning Mutagenesis of Interleukin-8 Identifies a Cluster of Residues Required for Receptor Binding"; The Journal of Biological Chemistry; 266(28):18989-18994 (1991).

Liao, Fang, et al.; "Human Mig Chemokine: Biochemical and Functional Characterization"; J. Exp. Med.; 182:1301-1314 (1995).

Loetscher, Marcel, et al.; "Chemokine Receptor Specific for IP10 and Mig: Structure, Function, and Expression in Activated T-Lymphocytes"; J. Exp. Med.; 184:963-969 (1996).

Loetscher, Pius, et al.; "Monocyte chemotactic proteins MCP-1, MCP-2, and MCP-3 are major attractants for human CD4+ and CD8+ T lymphocytes"; FASEB J.; 8:1055-1060 (1994).

Luster, Andrew D., et al.; "IP-10,a—C-X-C- Chemokine, Elicits a Potent Thymus-dependent Antitumor Response In Vivo"; J. Exp. Med.; 178:1057-1065 (1993).

Luster, Andrew D., et al.; "The IP-10 Chemokine Binds to a Specific Cell Surface Heparan Sulfate Site Shared with Platelet Factor 4 and Inhibits Endothelial Cell Proliferation"; J. Exp. Med.; 182:219-231 (1995).

Luster, Andrew D., et al.; "γ-Interferon transcriptionally regulates an early-response gene containing homology to platelet proteins"; Nature; 315:672-676 (1985).

Qin, Shixin, et al.; "The Chemokine Receptors CXCR3 and CCR5 Mark Subsets of T Cells Associated with Certain Inflammatory Reactions"; J. Clin. Invest.; 101(4):746-754 (1998).

Schall, Thomas J., et al.; "Hemokines, leukocyte trafficking, and inflammation"; Current Opinion in Immunology; 6:865-873 (1994).

Seitz, Michael, et al.;. "Enhanced Production of Neutrophil-activating Peptide-1/Interleukin-8 in Rheumatoid Arthritis"; Journal Clin. Invest.; 87:463-469 (1991).

Springer, Timothy A.; "Traffic Signals on Endothelium for Lymphocyte Recirculation and Leukocyte Emigration"; Annu. Rev. Physiol.; 57:827-872 (1995).

Taub, Dennis D., et al.; "Recombinant Human Interferon-inducible Protein 10 is a Chemoattractant for Human Monocytes and T Lymphocytes and Promotes T Cell Adhesion to Endothelial Cells"; The Journal of Experimental Medicine; 177:1809-1814 (1993).

Taub, Dennis D., et al.; "α and β Chemokines Induce NK Cell Migration and Enhance NK-Mediated Cytolysis"; The Journal of Immunol.; 155:3877-3888 (1995).

Uguccioni, Mariagrazia, et al.; "Actions of the chemotactic cytokines MCP-1, MCP-2, MCP-3, Rantes, MIP-1α and MIP-β on human monocytes"; Eur. J. Immunol.; 25:64-68 (1995).

Wenshen Yu et al., U.S. Appl. No. 11/353,806; Notice of Allowance — mailed Aug. 24, 2009.

Preliminary Amendment for U.S. Appl. No. 12/519,970, submitted Jun. 18, 2009.

STN Search Results for Structural Formulas from WO 93/14077.

* cited by examiner

US 7,776,862 B2

PYRIDYL AND PHENYL SUBSTITUTED PIPERAZINE-PIPERIDINES WITH CXCR3 ANTAGONIST ACTIVITY

REFERENCE TO PRIORITY APPLICATIONS

This Application claims the benefit of U.S. Provisional Application Ser. No. 60/653,337 filed Feb. 16, 2005, which is incorporated herein in its entirety by reference.

FIELD OF THE INVENTION

The present invention relates to novel pyridyl and phenyl substituted piperazine-piperidines with CXCR3 antagonist activity, pharmaceutical compositions containing one or more such antagonists, one or more such antagonists in combination with other compounds with chemokine activity, one or more such antagonists in combination with known immunosuppressive agents, non-limiting example(s) include Methotrexate, interferon, cyclosporin, FK-506 and FTY720, methods of preparing such antagonists and methods of using such antagonists to modulate CXCR3 activity. This invention also discloses methods of using such CXCR3 antagonists for the treatment (non-limiting examples include palliative, curative and prophylactic therapies) of diseases and conditions where CXCR3 has been implicated. Diseases and conditions where CXCR3 has been implicated include but are not limited to inflammatory conditions (psoriasis and inflammatory bowel disease), autoimmune disease (multiple sclerosis, rheumatoid arthritis), fixed drug eruptions, cutaneous delayed-type hypersensitivity responses, type I diabetes, viral meningitis and tuberculoid leprosy. CXCR3 antagonist activity has also been indicated as a therapy for tumor growth suppression as well as graft rejection (allograft and zenograft rejections for example).

BACKGROUND OF THE INVENTION

Chemokines constitute a family of small cytokines that are produced in inflammation and regulate leukocyte recruitment (Baggiolini, M. et al., *Adv. Immunol.*, 55: 97-179 (1994); Springer, T. A., *Annu. Rev. Physio.*, 57: 827-872 (1995); and Schall, T. J. and K. B. Bacon, *Curr. Opin. Immunol*, 6: 865-873 (1994)). Chemokines are capable of selectively inducing chemotaxis of the formed elements of the blood (other than red blood cells), including leukocytes such as neutrophils, monocytes, macrophages, eosinophils, basophils, mast cells, and lymphocytes, such as T cells and B cells. In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

The chemokines are related in primary structure and share four conserved cysteines, which form disulfide bonds. Based upon this conserved cysteine motif, the family can be divided into distinct branches, including the C—X—C chemokines (α-chemokines) in which the first two conserved cysteines are separated by an intervening residue (e.g., IL-8, IP-10, Mig, I-TAC, PF4, ENA-78, GCP-2, GROα, GROβ, GROδ, NAP-2, NAP-4), and the C—C chemokines (β-chemokines), in which the first two conserved cysteines are adjacent residues (e.g., MIP-1α, MIP-1β, RANTES, MCP-1, MCP-2, MCP-3, I-309) (Baggiolini, M. and Dahinden, C. A., *Immunology Today*, 15: 127-133 (1994)). Most CXC-chemokines attract neutrophil leukocytes. For example, the CXC-chemokines interleukin 8 (IL-8), GRO alpha (GROα), and neutrophil-activating peptide 2 (NAP-2) are potent chemoattractants and activators of neutrophils. The CXC-chemokines designated Mig (monokine induced by gamma interferon) and IP-10 (interferon-gamma inducible 10 kDa protein) are particularly active in inducing chemotaxis of activated peripheral blood lymphocytes. CC-chemokines are generally less selective and can attract a variety of leukocyte cell types, including monocytes, eosinophils, basophils, T lymphocytes and natural killer cells. CC-chemokines such as human monocyte chemotactic proteins 1-3 (MCP-1, MCP-2 and MCP-3), RANTES (Regulated on Activation, Normal T Expressed and Secreted), and the macrophage inflammatory proteins 1α and 1β (MIP-1α and MIP-1β) have been characterized as chemoattractants and activators of monocytes or lymphocytes, but do not appear to be chemoattractants for neutrophils.

A chemokine receptor that binds the CXC-chemokines IP-10 and Mig has been cloned and characterized (Loetscher, M. et al., *J. Exp. Med.*, 184: 963-969 (1996)). CXCR3 is a G-protein coupled receptor with seven transmembrane-spanning domains and has been shown to be restrictively expressed in activated T cells, preferentially human Th1 cells. On binding of the appropriate ligand, chemokine receptors transduce an intracellular signal through the associated G-protein resulting in a rapid increase in intracellular calcium concentration.

The receptor mediates $Ca^{2+}$ (calcium ion) mobilization and chemotaxis in response to IP-10 and Mig. CXCR3 expressing cells show no significant response to the CXC-chemokines IL-8, GROα, NAP-2, GCP-2 (granulocyte chemotactic protein-2), ENA78 (epithelial-derived neutrophil-activating peptide 78), PF4 (platelet factor 4), or the CC-chemokines MCP-1, MCP-2, MCP-3, MCP-4, MIP-1α, MIP-1β, RANTES, I309, eotaxin or lymphotactin. Moreover, a third ligand for CXCR3, I-TAC (Interferon-inducible T cell Alpha Chemoattractant), has also been found to bind to the receptor with high affinity and mediate functional responses (Cole, K. E. et al., *J. Exp. Med.*, 187: 2009-2021 (1998)).

The restricted expression of human CXCR3 in activated T lymphocytes and the ligand selectivity of CXCR3 are noteworthy. The human receptor is highly expressed in IL-2 activated T lymphocytes, but was not detected in resting T lymphocytes, monocytes or granulocytes (Qin, S. et al., *J. Clin. Invest.*, 101: 746-754 (1998)). Additional studies of receptor distribution indicate that it is mostly $CD3^+$ cells that express CXCR3, including cells which are $CD95^+$, $CD45RO^+$, and $CD45RA^{low}$, a phenotype consistent with previous activation, although a proportion of $CD20^+$ (B) cells and $CD56^+$ (NK) cells also express this receptor. The selective expression in activated T lymphocytes is of interest, because other receptors for chemokines which have been reported to attract lymphocytes (e.g., MCP-1, MCP-2, MCP-3, MIP-1α, MIP-1β, RANTES) are also expressed by granulocytes, such as neutrophils, eosinophils, and basophils, as well as monocytes. These results suggest that the CXCR3 receptor is involved in the selective recruitment of effector T cells.

CXCR3 recognizes unusual CXC-chemokines, designated IP-10, Mig and I-TAC. Although these belong to the CXC-subfamily, in contrast to IL-8 and other CXC-chemokines which are potent chemoattractants for neutrophils, the primary targets of IP-10, Mig and I-TAC are lymphocytes, particularly effector cells such as activated or stimulated T lymphocytes and natural killer (NK) cells (Taub, D. D. et al., *J. Exp. Med.*, 177: 18090-1814 (1993); Taub, D. D. et al., *J. Immunol.*, 155: 3877-3888 (1995); Cole, K. E. et al., *J. Exp. Med.*, 187: 2009-2021 (1998)). (NK cells are large granular lymphocytes, which lack a specific T cell receptor for antigen recognition, but possess cytolytic activity against cells such as tumor cells and virally infected cells.) Consistently, IP-10, Mig and I-TAC lack the ELR motif, an essential binding epitope in those CXC-chemokines that efficiently induce neutrophil chemotaxis (Clark-Lewis, I. et al., *J. Biol. Chem.* 266: 23128-23134 (1991); Hebert, C. A. et al., *J. Biol. Chem.*, 266: 18989-18994 (1991); and Clark-Lewis, 1. et al., *Proc. Natl. Acad. Sci. USA*, 90: 3574-3577 (1993)). In addition, both recombinant human Mig and recombinant human IP-10 have been reported to induce calcium flux in tumor infiltrating lymphocytes (TIL) (Liao, F. et al., *J Exp. Med*, 182: 1301-1314 (1995)). While IP-10 has been reported to induce chemotaxis of monocytes in vitro (Taub, D. D. et al., *J. Exp. Med.*, 177: 1809-1814 (1993), the receptor responsible has not been identified), human Mig and I-TAC appear highly selective, and do not show such an effect (Liao, F. et al., *J. Exp. Med.*, 182: 1301-1314 (1995); Cole, K. E. et al., *J. Exp. Med.*, 187: 2009-2021 (1998)). IP-10 expression is induced in a variety of tissues in inflammatory conditions such as psoriasis, fixed drug eruptions, cutaneous delayed-type hypersensitivity responses and tuberculoid leprosy as well as tumors and in animal model studies, for example, experimental glomerulonephritis, and experimental allergic encephalomyelitis. IP-10 has a potent in vivo antitumor effect that is T cell dependent, is reported to be an inhibitor of angiogenesis in vivo and can induce chemotaxis and degranulation of NK cells in vitro, suggesting a role as a mediator of NK cell recruitment and degranulation (in tumor cell destruction, for example) (Luster, A. D. and P. Leder, *J. Exp. Med.*, 178: 1057-1065 (1993); Luster, A. D. et al., *J. Exp. Med.* 182: 219-231 (1995); Angiolillo, A. L. et al., *J. Exp. Med.*, 182: 155-162 (1995); Taub, D. D. et al., *J. Immunol.*, 155: 3877-3888 (1995)). The expression patterns of IP-10, Mig and I-TAC are also distinct from that of other CXC chemokines in that expression of each is induced by interferon-gamma (IFNδ), while the expression of IL-8 is down-regulated by IFNδ (Luster, A. D. et al., *Nature*, 315: 672-676 (1985); Farber, J. M., *Proc. Natl. Acad. Sci. USA*, 87: 5238-5242 (1990); Farber, J. M., *Biochem. Biophys. Res. Commun.*, 192 (1): 223-230 (1993), Liao, F. et al., *J. Exp. Med.*, 182: 1301-1314 (1995); Seitz, M. et al., *J. Clin. Invest.*, 87: 463-469 (1991); Galy, A. H. M. and H. Spits, *J. Immunol.*, 147: 3823-3830 (1991); Cole, K. E. et al., *J. Exp. Med.*, 187: 2009-2021 (1998)).

Chemokines are recognized as the long-sought mediators for the recruitment of lymphocytes. Several CC-chemokines were found to elicit lymphocyte chemotaxis (Loetscher, P. et al., *FASEB J.*, 8: 1055-1060 (1994)), however, they are also active on granulocytes and monocytes (Uguccioni, M. et al., *Eur. J. Immunol.*, 25: 64-68 (1995); Baggiolini, M. and C. A. Dahinden, *Immunol. Today*, 15: 127-133 (1994)). The situation is different for IP-10, Mig and I-TAC, which are selective in their action on lymphocytes, including activated T lymphocytes and NK cells, and which bind CXCR3, a receptor which does not recognize numerous other chemokines and which displays a selective pattern of expression.

In view of these observations, it is reasonable to conclude that the formation of the characteristic infiltrates in inflammatory lesions, such as, for example, delayed-type hypersensitivity lesions, sites of viral infection and certain tumors is a process mediated via CXCR3 and regulated by CXCR3 expression. Lymphocytes, particularly T lymphocytes, bearing a CXCR3 receptor as a result of activation can be recruited into inflammatory lesions, sites of infection and/or tumors by IP-10, Mig and/or I-TAC, which can be induced locally by interferon-gamma. Thus, CXCR3 plays a role in the selective recruitment of lymphocytes, particularly effector cells such as activated or stimulated T lymphocytes. Accordingly, activated and effector T cells have been implicated in a number of disease states such as graft-rejection, inflammation, rheumatoid arthritis, multiple sclerosis, inflammatory bowel disease and psoriasis. Thus, CXCR3 represents a promising target for the development of novel compounds having valuable pharmacological properties.

Reference is made to PCT Publication No. WO 93/10091 (Applicant: Glaxo Group Limited, Published May 27, 1993) which discloses piperidine acetic acid derivatives as inhibitors of fibrinogen-dependent blood platelet aggregation having the formula:

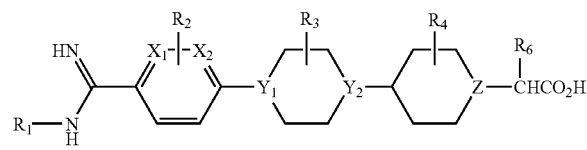

An illustrative compound of that series is:

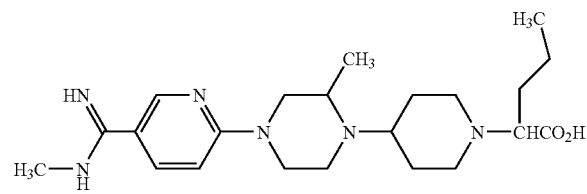

Reference is also made to PCT Publication No. WO 9/20606 (Applicant: J. Uriach & CIA. S. A., Published Apr. 29, 1999) which discloses piperazines as platelet aggregation inhibitors having the formula:

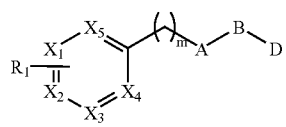

Reference is also made to US Patent Application No. US 2002/0018776 A1 (Applicant: Hancock, et al. Published Feb. 14, 2002) which discloses methods of treating graft rejection.

Reference is also made to PCT Publication No. WO 03/098185 A2 (Applicant: Renovar, Inc., Published Nov. 27, 2003) which discloses methods of diagnosing and predicting organ transplant rejection by detection of chemokines, for example, CXCR3 and CCL chemokines in urine.

Reference is also made to PCT Publication No. WO 03/082335 A1 (Applicant: Sumitomo Pharmaceuticals Co. Ltd., Published Oct. 9, 2003) which discloses methods of screening a CXCR3 ligand and methods of diagnosing type 2 diabetes by detecting the expression dose of a CXCR3 ligand in a biological sample.

Reference is also made to PCT Publication No. WO 02/085861 (Applicant: Millennium Pharmaceuticals, Inc. Published Oct. 31, 2002) which discloses imidazolidine compounds and their use as CXCR3 antagonists having the formula:

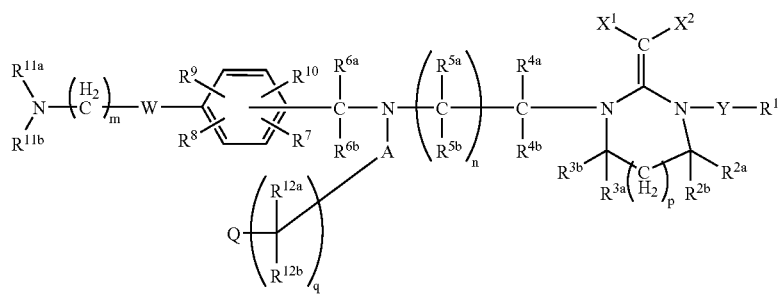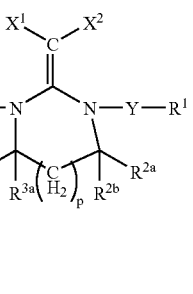

An illustrative compound of that series is:

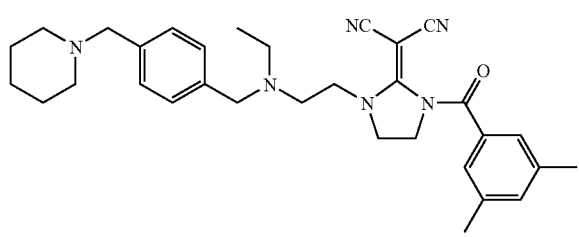

Reference is also made to PCT Publication No. WO 03/101970 (Applicant: SmithKline Beecham Corporation, Published Dec. 11, 2003) which discloses imidazolium compounds and their use as CXCR3 antagonists having the formula:

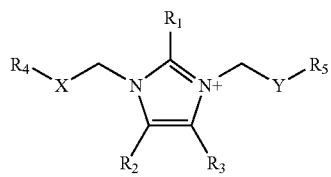

An illustrative example of that series is:

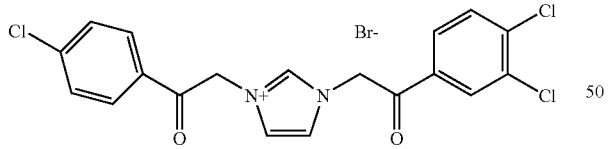

Reference is also made to US Patent Application No. US 2003/0055054 A1 (Applicant: Medina et al, Published Mar. 20, 2003) which discloses compounds having the formula:

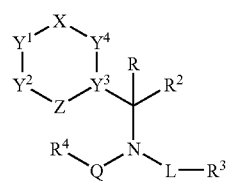

An illustrative compound of that series is:

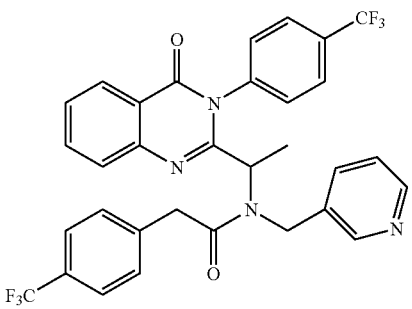

Reference is also made to U.S. Pat. No. 6,124,319 (Applicant: MacCoss et al., issued Sep. 6, 2000) which discloses compounds useful as chemokine receptor modulators having the formula:

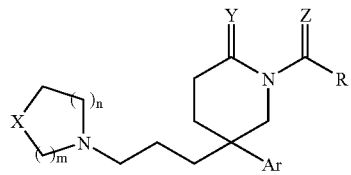

Reference is also made to PCT Publication WO 03/070242 A1 (Applicant: CELLTECH R & D limited, Published Aug. 28, 2003) which discloses compounds useful as "chemokine receptor inhibitors for the treatment of inflammatory diseases" having the formula:

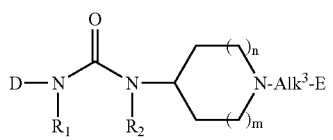

There is a need for compounds that are capable of modulating CXCR3 activity. For example, there is a need for new treatments and therapies for diseases and conditions associated with CXCR3 such as inflammatory conditions (psoriasis and inflammatory bowel disease), autoimmune disease (multiple sclerosis, rheumatoid arthritis) and graft rejection (allograft and zenograft rejections for example).

There is a need for methods of treatment or prevention or amelioration of one or more symptoms of diseases and conditions associated with CXCR3. There is a need for methods for modulating CXCR3 activity using the compounds provided herein.

SUMMARY OF THE INVENTION

In its many embodiments, the invention provides novel compounds of the Formula 1:

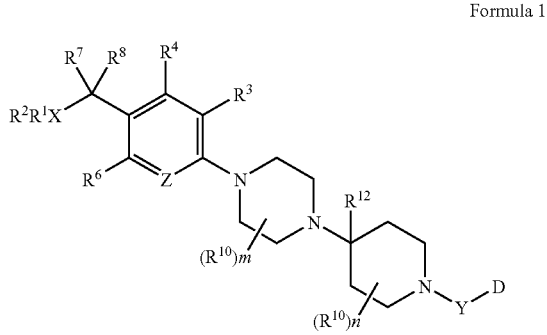

Formula 1 or pharmaceutically acceptable salts, solvates or esters thereof wherein:

Z is N, C($R^{29}$), NO or NOH;

X is N, O, alkyl, cycloalkyl, heteroaryl, heterocyclyl or heterocyclenyl;

$R^1$ and $R^2$ are independently absent or present, and if present each is independently selected from the group consisting of H, alkyl, alkoxy, alkenyl, carbonyl, cycloalkyl, cycloalkenyl, alkylaryl, arylalkyl, aryl, amino, alkylamino, amidinyl, carboxamido, cyano, hydroxyl, urea, —N=CH, =NCN, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, —C(=S)N(H)alkyl, —N(H)—S(O)$_2$-alkyl, —N(H)C(=O)N(H)-alkyl, —S(O)$_2$alkyl, —S(O)$_2$N(H)alkyl, —S(O)$_2$N(alkyl)$_2$, —S(O)$_2$aryl, —C(=S)N(H)cycloalkyl, —C(=O)N(H)NH$_2$, —C(=O)alkyl, -heteroaryl, heterocyclyl, and heterocyclenyl; or alternatively when X is N, the N taken together with the $R^1$ and $R^2$ forms a heterocycyl, heteroaryl or —N=C(NH$_2$)$_2$;

$R^3$, $R^4$, $R^6$ and $R^{29}$ moieties can be the same or different, each being independently selected from the group consisting of H, alkyl, alkylaryl, aralkyl, —CN, CF$_3$, haloalkyl, cycloalkyl, halogen, hydroxyalkyl, —N=CH—(R$^{31}$), —C(=O)N(R$^{30}$)$_2$, —N(R$^{30}$)$_2$, —OR$^{30}$, —SO$_2$(R$^{31}$), —N(R$^{30}$)C(=O)N(R$^{30}$)$_2$ and —N(R$^{30}$)C(=O)R$^{31}$;

$R^7$ and $R^8$ are the same or different, each being independently selected from the group consisting of H, alkyl, alkylaryl, heteroaryl, hydroxyl, —CN, alkoxy, alkylamino, —N(H)S(O)$_2$alkyl, —N(H)C(=O)N(H)alkyl, —(CH$_2$)$_q$OH, —(CH$_2$)$_q$Oalkyl, —(CH$_2$)$_q$N(H)-alkyl, —(CH$_2$)$_q$N(H)—S(O)$_2$alkyl, and —(CH$_2$)$_q$N(H)—CO—N(H)alkyl; or alternatively $R^7$ and $R^8$ taken together is =O, =S, =NH, =N(alkyl), =N(Oalkyl), =N(OH) or cycloalkyl;

the $R^{10}$ moieties can be the same or different, each being independently selected from the group consisting of H, alkyl, cycloalkyl, aryl, heteroaryl, heterocyclenyl, heterocyclyl, alkylaryl, arylalkyl, —CO$_2$H, hydroxyalkyl, —C(=O)N(R$^{30}$)$_2$, —(CH$_2$)$_q$OH, —(CH$_2$)$_q$OR$^{31}$—(CH$_2$)$_q$NHR$^{31}$, —(CH$_2$)$_q$N(R$^{31}$)$_2$, —OR$^{30}$, halogen, =O, and —C(=O)R$^{31}$;

the $R^{11}$ moieties can be the same or different, each being independently selected from the group consisting of H, alkyl, cycloalkyl, aryl, heteroaryl, heterocyclyl, heterocyclenyl, alkylaryl, arylalkyl, hydroxyalkyl, carboxamide, CO$_2$H, —(CH$_2$)$_q$OH, —(CH$_2$)$_q$OR$^{31}$, —(CH$_2$)$_q$NHR$^{31}$, —(CH$_2$)$_q$N(R$^{31}$)$_2$, —OR$^{30}$, halogen, =O, and —C(=O)R$^{31}$;

the $R^{12}$ moieties can be the same or different, each being independently selected from the group consisting of H, alkyl, —CN, —C(=O)N(R$^{30}$)$_2$, —(CH$_2$)$_q$OH, —(CH$_2$)$_q$OR$^{31}$, —(CH$_2$)$_q$NHR$^{31}$, —(CH$_2$)$_q$N(R$^{31}$)$_2$, and —S(O$_2$)R$^{31}$;

D is a five to nine membered cycloalkyl, cycloalkenyl, aryl, heteroaryl, heterocyclenyl or heterocyclyl ring having 0-4 heteroatoms independently selected from O, S or N, wherein ring D is unsubstituted or optionally substituted with 1-5 independently selected $R^{20}$ moieties;

the $R^{20}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$-alkynylC(R$^{31}$)$_2$OR$^{31}$, —C(=O)R$^{30}$, —C(=O)N(R$^{30}$)$_2$, —C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$; or alternatively two $R^{20}$ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 $R^{21}$ moieties;

the $R^{21}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, carboxamido, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$;

Y is selected from the group consisting of —(CR$^{13}$R$^{13}$)$_r$—, —CHR$^{13}$C(=O)—, —(CHR$^{13}$)$_r$O—, —(CHR$^{13}$)$_r$N(R$^{30}$)—, —C(=O)—, —C(=NR$^{30}$)—, —C(=N—OR$^{30}$)—, —CH(C(=O)NHR$^{30}$)—, CH-heteroaryl-, —C(R$^{13}$R$^{13}$)$_r$C(R$^{13}$)=C(R$^{13}$)—, —(CHR$^{13}$)$_r$C(=O)— and —(CHR$^{13}$)$_r$N(H)C(=O)—; or alternatively Y is cycloalkyl, heterocyclenyl, or heterocyclyl wherein the cycloalkyl, heterocyclenyl, or heterocyclyl is fused with ring D;

the $R^{13}$ moieties can be the same or different, each being independently selected from the group consisting of H, alkyl, alkylaryl, cycloalkyl, alkoxy, aryl, heteroaryl, heterocyclenyl, heterocyclyl, spiroalkyl, —CN, —CO$_2$H, —C(=O)R$^{30}$, —C(=O)N(R$^{30}$)$_2$, —(CHR$^{30}$)$_q$OH, —(CHR$^{30}$)$_q$OR$^{31}$, —(CHR$^{30}$)$_q$NH$_2$, —(CH R$^{30}$)$_q$NHR$^{31}$, —(CH$_2$)$_q$C(=O) NHR$^{31}$, —(CH$_2$)$_q$SO$_2$R$^{31}$, —(CH$_2$)$_q$NSO$_2$R$^{31}$, —(CH$_2$)$_q$ SO$_2$NHR$^{31}$, —NH$_2$, —N(R$^{30}$)$_2$, —N(R$^{30}$)C(=O)N(R$^{30}$)$_2$, —N(R$^{30}$)SO$_2$(R$^{31}$), —OH, OR$^{30}$, —SO$_2$N(R$^{30}$)$_2$, and —SO$_2$ (R$^{31}$);

the $R^{30}$ moieties can be the same or different, each being independently selected from the group consisting of H, alkyl, alkylaryl, aryl, aralkyl, cycloalkyl, CN, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N (alkyl)$_2$, —(CH$_2$)$_q$C(=O)NHalkylaryl, —(CH$_2$)$_q$C(=O) NHaryl, —(CH$_2$)$_q$C(=O)NHaralkyl, —(CH$_2$)$_q$C(=O) NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$ SO$_2$cycloalkyl, —(CH$_2$)$_q$NSO$_2$alkyl, —(CH$_2$)$_q$ NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$ SO$_2$NHalkylaryl, —(CH$_2$)$_q$SO$_2$NHaryl, —(CH$_2$)$_q$ SO$_2$NHaralkyl, —(CH$_2$)$_q$SO$_2$NHcycloalkyl, heterocyclenyl, heterocyclyl, and heteroaryl;

the $R^{31}$ moieties can be the same or different, each being independently selected from the group consisting of alkyl, alkylaryl, aryl, aralkyl, cycloalkyl, —(CH$_2$)$_q$OH, —(CH$_2$)$_q$ Oalkyl, —(CH$_2$)$_q$Oalkylaryl, —(CH$_2$)$_q$Oaryl, —(CH$_2$)$_q$ Oaralkyl, —(CH$_2$)$_q$Ocycloalkyl, —(CH$_2$)$_q$NH$_2$, —(CH$_2$)$_q$ NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N (alkyl)$_2$, —(CH$_2$)$_q$C(=O)NHalkylaryl, —(CH$_2$)$_q$C(=O) NHaryl, —(CH$_2$)$_q$C(=O)NHaralkyl, —(CH$_2$)$_q$C(=O) NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$ SO$_2$cycloalkyl, —(CH$_2$)$_q$NSO$_2$alkyl, —(CH$_2$)$_q$ NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$ SO$_2$NHalkylaryl, —(CH$_2$)$_q$SO$_2$NHaryl, —(CH$_2$)$_q$ SO$_2$NHaralkyl, —(CH$_2$)$_q$SO$_2$NHcycloalkyl, heterocyclenyl, heterocyclyl, and heteroaryl;

m is 0 to 4;

n is 0 to 4;

each q can be the same or different, each being independently selected from 1 to 5; and r is 1 to 4;

with the proviso that there are no two adjacent double bonds in any ring, and that when a nitrogen is substituted by two alkyl groups, said two alkyl groups may be optionally joined to each other to form a ring.

A further feature of the invention is a pharmaceutical composition containing as active ingredient at least one compound of Formula 1 together with at least one pharmaceutically acceptable carrier or excipient.

The invention provides methods of preparing compounds of Formula 1, as well as methods for treating diseases, for example, treatment (e.g., palliative therapy, curative therapy, prophylactic therapy) of certain diseases and conditions e.g., inflammatory diseases (e.g., psoriasis, inflammatory bowel disease), autoimmune diseases (e.g., rheumatoid arthritis, multiple sclerosis), graft rejection (e.g., allograft rejection, xenograft rejection), ophthalmic inflammation or dry eye, infectious diseases and tumors. The invention provides a method of treating a CXCR3 chemokine mediated disease in a patient in need of such treatment comprising administering to the patient a therapeutically effective amount of at least one compound of Formula 1, or a pharmaceutically acceptable salt, solvate or ester thereof.

The invention provides methods of treating diseases, for example, treatment (e.g., palliative therapy, curative therapy, prophylactic therapy) of certain diseases and conditions such as inflammatory diseases (e.g., psoriasis, inflammatory bowel disease), autoimmune diseases (e.g., rheumatoid arthritis, multiple sclerosis), graft rejection (e.g., allograft rejection, xenograft rejection), infectious diseases as well as cancers and tumors, fixed drug eruptions, cutaneous delayed-type hypersensitivity responses, ophthalmic inflammation or dry eye, type I diabetes, viral meningitis and tuberculoid leprosy comprising administering: (a) a therapeutically effective amount of at least one compound according to Formula 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives (such as cyclosporins and methotrexate); steroids (including corticosteroids such as glucorticoids); PDE IV inhibitors, anti-TNF-α compounds, TNF-α-convertase (TACE) inhibitors, MMP inhibitors, cytokine inhibitors, glucocorticoids, other chemokine inhibitors such as CCR2 and CCR5, CB2-selective inhibitors, p38 inhibitors, biological response modifiers; anti-inflammatory agents and therapeutics.

The invention also provides a method of modulating (inhibiting or promoting) an inflammatory response in an individual in need of such therapy. The method comprises administering a therapeutically effective amount of a compound (e.g., small organic molecule) which inhibits or promotes mammalian CXCR3 function in an individual in need thereof.

Also disclosed is a method of inhibiting or blocking T-cell mediated chemotaxis in a patient in need of such treatment comprising administering to the patient a therapeutically effective amount of a compound of Formula 1 or a pharmaceutically acceptable salt, solvate or ester thereof.

Also disclosed is a method of treating inflammatory bowel disease (such Crohn's disease, ulcerative colitis) in a patient in need of such treatment comprising administering to the patient a therapeutically effective amount of at least one compound of Formula 1, or a pharmaceutically acceptable salt, solvate or ester thereof.

Also disclosed is a method of treating inflammatory bowel disease in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: sulfasalazine, 5-aminosalicylic acid, sulfapyridine, anti-TNF compounds, anti-IL-12 compounds, corticosteroids, glucocorticoids, T-cell receptor directed therapies (such as anti-CD3 antibodies), immunosuppresives, methotrexate, azathioprine, and 6-mercaptopurines.

Also disclosed is a method of treating graft rejection in a patient in need of such treatment comprising administering to the patient a therapeutically effective amount of at least one compound of Formula 1, or a pharmaceutically acceptable salt, solvate or ester thereof.

Also disclosed is a method of treating graft rejection in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: cyclosporine A, FK-506, FTY720, beta-interferon, rapamycin, mycophenolate, prednisolone, azathioprine, cyclophosphamide and an antilymphocyte globulin.

Also disclosed is a method of treating multiple sclerosis in a patient in need of such treatment the method comprising administering to the patient a therapeutically effective amount of: (a) a therapeutically effective amount of at least one compound of Formula 1, or a pharmaceutically acceptable salt, solvate or ester thereof concurrently or sequentially with (b) at least one compound selected from the group consisting of: beta-interferon, glatiramer acetate, corticosteroids, glucocorticoids, methotrexate, azothioprine, mitoxantrone, VLA-4 inhibitors, FTY720, anti-IL-12 inhibitors, and CB2-selective inhibitors.

Also disclosed is a method of treating multiple sclerosis in a patient in need of such treatment the method comprising administering to the patient a therapeutically effective amount of: (a) a therapeutically effective amount of at least one compound of Formula 1, or a pharmaceutically acceptable salt, solvate or ester thereof concurrently or sequentially with (b) at least one compound selected from the group consisting of: methotrexate, cyclosporin, leflunomide, sulfasalazine, corticosteroids, β-methasone, β-interferon, glatiramer acetate, prednisone, etonercept, and infliximab.

Also disclosed is a method of treating rheumatoid arthritis in a patient in need of such treatment the method comprising administering to the patient a therapeutically effective amount of: (a) at least one compound of Formula 1, or a pharmaceutically acceptable salt, solvate or ester thereof concurrently or sequentially with (b) at least one compound selected from the group consisting of: non-steroidal anti-inflammatory agents, COX-2 inhibitors, COX-1 inhibitors, immunosuppressives, cyclosporine, methotrexate, steroids, PDE IV inhibitors, anti-TNF-α compounds, MMP inhibitors, corticosteroids, glucocorticoids, chemokine inhibitors, CB2-selective inhibitors, caspase (ICE) inhibitors and other classes of compounds indicated for the treatment of rheumatoid arthritis.

Also disclosed is a method of treating psoriasis in a patient in need of such treatment the method comprising administering to the patient a therapeutically effective amount of: a) at least one compound of Formula 1, or a pharmaceutically acceptable salt, solvate or ester thereof concurrently or sequentially with (b) at least one compound selected from the group consisting of: immunosuppressives, cyclosporins, methotrexate, steroids, corticosteroids, anti-TNF-α compounds, anti-IL compounds, anti-IL-23 compounds, vitamin A and D compounds and fumarates.

Also disclosed is a method of treating ophthalmic inflammation (including, for e.g., uveitis, posterior segment intraocular inflammation, Sjogren's syndrome) or dry eye in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, FK506, steroids, corticosteroids, and anti-TNF-α compounds.

Also disclosed is a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses, ophthalmic inflammation (including e.g., uveitis, posterior segment intraocular inflammation, and Sjogren's syndrome), tuberculoid leprosy and cancer in a patient in need of such treatment, such method comprising administering to the patient an effective amount of at least one compound according to Formula 1, or a pharmaceutically acceptable salt, solvate or ester thereof.

The invention also provides a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses and tuberculoid leprosy, ophthalmic inflammation, type I diabetes, viral meningitis and cancer in a patient in need of such treatment, such method comprising administering to the patient an effective amount of (a) at least one compound according to Formula 1, or a pharmaceutically acceptable salt, solvate or ester thereof concurrently or sequentially with (b) at least one medicament selected from the group consisting of: disease modifying antirheumatic drugs; nonsteroidal antiinflammatory drugs; COX-2 selective inhibitors; COX-1 inhibitors; immunosuppressives; steroids; PDE IV inhibitors, anti-TNF-α compounds, MMP inhibitors, corticosteroids, glucocorticoids, chemokine inhibitors, CB2-selective inhibitors, biological response modifiers; anti-inflammatory agents and therapeutics.

DETAILED DESCRIPTION OF THE INVENTION

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl,""haloalkyl," "alkoxy," etc.

As used above, and throughout the specification, the following terms, unless otherwise indicated, shall be understood to have the following meanings:

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The alkenyl group may be substituted by one or more substituents which may be the same or different, each substituent being independently selected from the group consisting of alkyl, alkenyl, alkynyl, alkoxyl, aryl, aryloxy, cycloalkyl, cycloalkenyl, cyano, heteroaryl, heterocyclyl, heterocyclenyl, amino, aminosulfonyl, halo, carboxyl, carboxyalkyl (non-limiting example(s) include ester), alkoxycarbonyl, hydroxyalkyl, carbonyl (non-limiting example(s) include ketone), —C(=O)heterocyclyl, formyl (non-limiting example(s) include aldehyde), carboxamido (i.e. amido, —C(=O)NH$_2$), —C(=O)N(alkyl)$_2$, —C(=O)NH(alkyl), —C(=O)N(cycloalkyl)$_2$, —C(=O)NH(cycloalkyl), —NHC(=O)alkyl, urea (e.g. —NH(C=O)NH$_2$, —NH(C=O)NH(alkyl), —NH(C=O)NH(alkyl)$_2$, —NH(C=O)NH(heteroaryl), —NH(C=O)NH(heterocyclyl)), guanidinyl, —NHC(=NCN)NH$_2$, —NHC(=NCN)N(alkyl)$_2$, carbamoyl (i.e. —CO$_2$NH$_2$), NHC(=O)Oalkyl, —CO$_2$N(alkyl)$_2$, —NHC(=O))NH—S(O)$_2$alkyl, —NHC(=O)N(alkyl)$_2$-S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$, alkylthiocarboxy, —S(O)$_2$alkyl, —S(O)$_2$aryl, —OS(O)$_2$alkyl, —OS(O)$_2$aryl, sulfonyl urea (non-limiting example(s) include NHC(=S)NHalkyl). Non-limiting examples of suitable alkenyl groups include ethenyl, propenyl, n-butenyl, 3-methylbut-2-enyl, n-pentenyl, octenyl and decenyl.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be substituted by one or more substituents which may be the same or different, each substituent being independently selected from the group consisting of alkyl, alkenyl, alkynyl, alkoxyl, aryl, aryloxy, cycloalkyl, cycloalkenyl, cyano, heteroaryl, heterocyclyl, heterocyclenyl,
amino, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, halo, hydroxy, carboxyl, carboxyalkyl (non-limiting example(s) include ester), alkoxycarbonyl, hydroxyalkyl, carbonyl (non-limiting example(s) include ketone), —C(=O)heterocyclyl, formyl, carboxamido (i.e. amido, —C(=O)NH$_2$, —C(=O)N(alkyl)$_2$, —C(=O)NH(alkyl), —C(=O)N(cycloalkyl)$_2$, —C(=O)NH(cycloalkyl)), —NHC(=O)alkyl, amidinyl, hydrazidyl, hydroxamate, —NHC(=O)H, —NHC(=O)alkyl, urea (non-limiting example(s) include —NH(C=O)NH$_2$, —NH(C=O)NH(alkyl), —NH(C=O)N(alkyl)$_2$, —NH(C=O)NH(heteroaryl), —NH(C=O)NH(heterocyclyl)), guanidinyl, —NHC(=NCN)NH$_2$, —NHC(=NCN)N(alkyl)$_2$, carbamoyl (i.e., —CO$_2$NH$_2$), —NHC(=O)Oalkyl, —CO$_2$N(alkyl)$_2$, —NHC(=O)NH—S(O)$_2$alkyl, —NHC(=O)N(alkyl)-S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$, thio, alkylthio, alkylthiocarboxy, —S(O)alkyl, —S(O)$_2$alkyl, —S(O)$_2$aryl, —OS(O)$_2$alkyl, —OS(O)$_2$aryl, sulfonyl urea (non-limiting example(s) include —NHC(=S)NHalkyl) and OSi(alkyl)$_3$. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkylheteroaryl" means an alkyl-heteroaryl-group wherein the alkyl is as previously described and the bond to the parent moiety is through the heteroaryl group.

"Alkylamino" means an —NH2 or —NH3+ group in which one or more of the hydrogen atoms on the nitrogen is replaced by an alkyl group as defined above. The bond to the parent is through the nitrogen.

"Alkylaryl" means an alkyl-aryl-group in which the alkyl and aryl are as described herein. Preferred alkylaryls comprise a lower alkyl group. Non-limiting examples of suitable alkylaryl groups include o-tolyl, p-tolyl and xylyl. The bond to the parent moiety is through the aryl.

"Alkylthio" means an alkyl-S— group in which the alkyl group is as described herein. Non-limiting examples of suitable alkylthio groups include methylthio, ethylthio, i-propylthio and heptylthio. The bond to the parent moiety is through the sulfur.

"Alkylthiocarboxy" means an alkyl-S—C(=O)O— group. Preferred groups are those in which the alkyl group is lower alkyl. The bond to the parent moiety is through the carboxy.

"Alkylsulfonyl" means an alkyl-S(O)$_2$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of alkyl, alkoxyl, aryl, aryloxy, cycloalkyl, cycloalkenyl, cyano, heteroaryl, heterocyclyl, heterocyclenyl, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, alkoxycarbonyl, hydroxyalkyl, carbonyl (non-limiting example(s) include ketone), —C(=O)heterocyclyl, carboxamido (i.e. amido, —C(=O)NH$_2$), —C(=O)N(alkyl)$_2$, —C(=O)NH(alkyl), —C(=O)N(cycloalkyl)$_2$, —C(=O)NH(cycloalkyl)), alkylC(=O)NH—, —NHC(=O)alkyl), urea (e.g. —NH(C=O)NH$_2$), —NH(C=O)NH(alkyl), —NH(C=O)NH(alkyl)$_2$, —NH(C=O)NH(heteroaryl), —NH(C=O)NH(heterocyclyl), —S(O)$_2$alkyl, and —S(O)$_2$aryl.

"Alkoxy" means an alkyl-O— group in which the alkyl group is as previously described. Non-limiting examples of suitable alkoxy groups include methoxy, ethoxy, n-propoxy, isopropoxy, n-butoxy, heptoxy and methylhydroxy. The bond to the parent moiety is through the ether oxygen.

"Alkoxycarbonyl" means an alkyl-O—C(=O)— group. Non-limiting examples of suitable alkoxycarbonyl groups include methoxycarbonyl and ethoxycarbonyl. The bond to the parent moiety is through the carbonyl.

"Aminoalkyl" means an amine-alkyl-group in which alkyl is as previously defined. Preferred aminoalkyls contain lower alkyl. Non-limiting examples of suitable aminoalkyl groups include aminomethyl and 2-Dimethlylamino-2-ethyl. The bond to the parent moiety is through the alkyl.

"Amidinyl" means —C(=NR)NHR group. The R groups are defined as H, alkyl, alkylaryl, heteroaryl, hydroxyl, alkoxy, amino, ester, CN, —NHSO$_2$alkyl, —NHSO$_2$Aryl, —NHC(=O)NHalkyl, and —NHalkyl. The bond to the parent moiety is through the carbon.

"Aralkyl" or "arylalkyl" means an aryl-alkyl-group in which the aryl and alkyl are as previously described. Preferred aralkyls comprise a lower alkyl group attached to the aryl group. Non-limiting examples of suitable aralkyl groups include phenymethylene, 2-phenethyl and naphthalenylmethyl. The bond to the parent moiety is through the alkyl.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkylthio" means an aralkyl-S— group in which the aralkyl group is as previously described. Non-limiting example of a suitable aralkylthio group is benzylthio. The bond to the parent moiety is through the sulfur.

"Aralkoxy" means an aralkyl-O— group in which the aralkyl group is as described above. The bond to the parent moiety is through the oxygen group.

"Aralkoxycarbonyl" means an aralkyl-O—C(=O)— group. Non-limiting example of a suitable aralkoxycarbonyl group is benzyloxycarbonyl. The bond to the parent moiety is through the carbonyl.

"Aroyl" means an aryl-C(=O)— group in which the aryl group is as previously described. The bond to the parent moiety is through the carbonyl. Non-limiting examples of suitable groups include benzoyl and 1- and 2-naphthoyl.

"Aryl" (sometimes abbreviated "Ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aryloxycarbonyl" means an aryl-O—C(=O)— group. Non-limiting examples of suitable aryloxycarbonyl groups include phenoxycarbonyl and naphthoxycarbonyl. The bond to the parent moiety is through the carbonyl.

"Arylsulfonyl" means an aryl-S(O)$_2$— group. The bond to the parent moiety is through the sulfonyl.

"Arylsulfinyl" means an aryl-S(O)— group. The bond to the parent moiety is through the sulfinyl.

"Arylthio" means an aryl-S— group in which the aryl group is as previously described. Non-limiting examples of suitable arylthio groups include phenylthio and naphthylthio. The bond to the parent moiety is through the sulfur.

"Carboxyalkyl" means an alkyl-C(=O)O— group. The bond to the parent moiety is through the carboxy.

"Carboxamido" means —C(=O)NRR wherein R is H, alkyl, amino, aryl, cycloalkyl, heterocyclenyl, heteroaryl and carboxamido. The bond to the parent moiety is through the carboxy.

Carbamates and urea substituents refer to groups with oxygens and nitrogens respectively adjacent an amide; representative carbamate and urea substituents include the following:

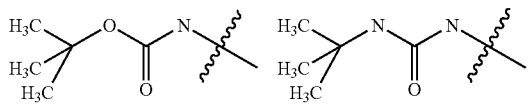

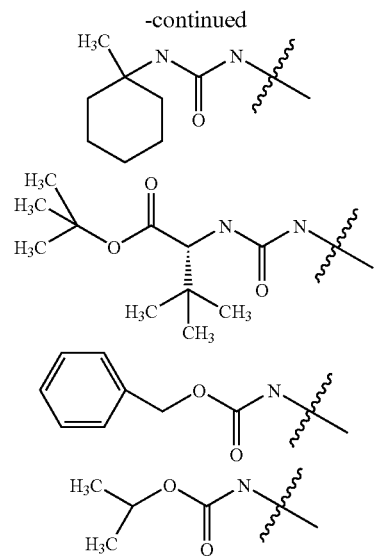

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples can include bicyclic cycloalkyls such as bicycloheptane. Non-limiting examples of suitable multicyclic cycloalkyls include 1-decalin, norbornyl, adamantyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl. The term "cycloalkenyl" additionally means moieties such as cyclobutenedione, cyclopentenone, cyclopentenedione and the like.

"Halogen" (or halo) means fluorine, chlorine, bromine, or iodine. Preferred are fluorine, chlorine and bromine.

"Haloalkyl" means an alkyl as defined above wherein one or more hydrogen atoms on the alkyl is replaced by a halo group defined above.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom.

The nitrogen or sulfur atom of the heteroaryl can be optionally oxidized to the corresponding N-oxide, S-oxide or S,S-dioxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, oxazolidinyl, imidazolidinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, dihydro-2-pyrrolinyl, dihydro-3-pyrrolinyl, dihydro-2-imidazolinyl, dihydro-2-pyrazolinyl, dihydro-4,5-trizolyl and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include thiophenyl, dihydrothiophenyl, dihydrothiopyranyl, and the like.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-(3-yl)methyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl. The bond to the parent moiety is through the alkyl.

"Hydroxamate" means an alkyl-C(=O)NH—O— group. The bond to the parent moiety is through the oxygen group.

"Spiroalkyl" means an alkylene group wherein two carbon atoms of an alkyl group are attached to one carbon atom of a parent molecular group thereby forming a carbocyclic or heterocyclic ring of three to eleven atoms. Representative structures include examples such as:

The spiroalkyl groups of this invention:

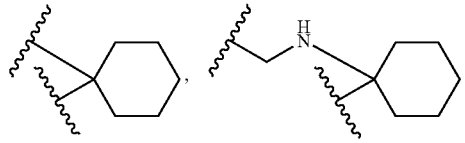

can be optionally substituted by one or more ring system substituents, wherein "ring system substituent" is as defined herein.

"Ring system substituent" means a substituent attached to an aromatic or non-aromatic ring system which, for example, replaces an available hydrogen on the ring system. Ring system substituents may be the same or different, each being independently selected from the group consisting of H, alkyl, alkenyl, alkynyl, alkoxyl, aryl, aroyl, aryloxy, cycloalkyl, cycloalkenyl, heteroaryl, heterocyclyl, heterocyclenyl, alkylaryl, alkylheteroaryl, aralkyl, aralkenyl, aralkoxy, aralkoxycarbonyl, amino, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, halo, hydroxy, carboxyl, carboxyalkyl (non-limiting example(s) include ester), cyano, alkoxycarbonyl, hydroxyalkyl, carbonyl (non-limiting example(s) include ketone), —C(=O)heterocyclyl, formyl (non-limiting example(s) include aldehyde), carboxamido (i.e. amido, —C(=O)NH$_2$), —C(=O)N(alkyl)$_2$, —C(=O)NH(alkyl), —C(=O)N(cycloalkyl)$_2$, —C(=O)NH(cycloalkyl), alkylC(=O)NH—, -amidino, hydrazido, hydroxamate, —NHC(=O)H, —NHC(=O)alkyl, urea (e.g. —NH(C=O)NH$_2$), —NH(C=O)NH(alkyl), —NH(C=O)NH(alkyl)$_2$, —NH(C=O)NH(heteroaryl), —NH(C=O)NH(heterocyclyl), guanidinyl, —NHC(=NCN)NH$_2$, —NHC(=NCN)N(alkyl)$_2$, carbamoyl (i.e. —CO$_2$NH$_2$), NHC(=O)Oalkyl, —CO$_2$N(alkyl)$_2$, —NHC(=O))NH—S(O)$_2$alkyl, —NHC(=O)N(alkyl)$_2$-S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$,thio, alkylthiocarboxy, —S(O)$_2$alkyl —S(O)$_2$aryl, —OS(O)$_2$alkyl, —OS(O)$_2$aryl, sulfonyl urea (non-limiting example(s) include —NHC(=S)NHalkyl) and OSi(alkyl)$_3$.

"Ring system substituent" also means a cyclic ring of 3 to 7 ring atoms of which may contain 1 or 2 heteroatoms, attached to an aryl, heteroaryl, heterocyclyl or heterocyclenyl ring by simultaneously substituting two ring hydrogen atoms on said aryl, heteroaryl, heterocyclyl or heterocyclenyl ring. Non-limiting examples include:

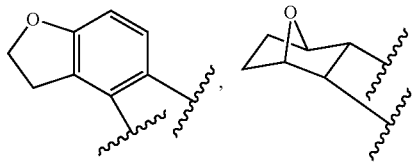

and the like.

The term "optionally substituted" means optional substitution with the specified groups, radicals or moieties, in available position or positions.

With reference to the number of moieties (non-limiting example(s) include, substituents, groups or rings) in a compound, unless otherwise defined, the phrases "one or more" and "at least one" mean that, there can be as many moieties as chemically permitted, and the determination of the maximum number of such moieties is well within the knowledge of those skilled in the art. Preferably, there are one to three substituents, or more preferably, one to two substituents, with at least one in the para position.

As used herein, the term "composition" is intended to encompass a product comprising the specified ingredients in the specified amounts, as well as any product which results, directly or indirectly, from combination of the specified ingredients in the specified amounts.

The straight line ⎯⎯ as a bond generally indicates a mixture of, or either of, the possible isomers, non-limiting example(s) include, containing (R)— and (S)— stereochemistry. For example,

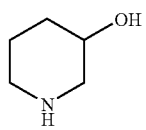

means containing both

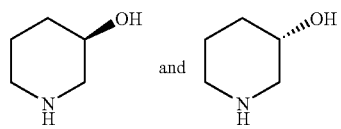

Lines drawn into the ring systems, such as, for example:

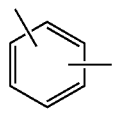

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

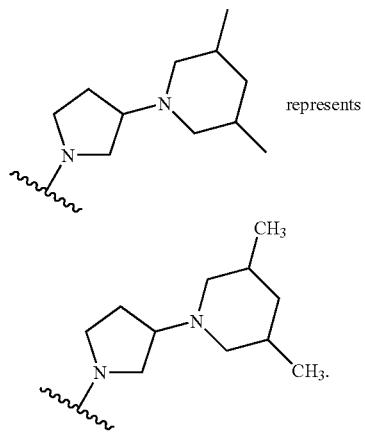

It should also be noted that any heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula 1 or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

Metabolic conjugates, for example, glucoronides and sulfates which can under reversible conversion to compounds of Formula 1 are contemplated in this application.

"Effective amount" or "therapeutically effective amount" is meant to describe an amount of compound or a composition of the present invention effective to antagonize CXCR3 and thus produce the desired therapeutic effect in a suitable patient.

"Mammal" means humans and other mammalian animals.

"Patient" includes both human and animals.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula 1 form salts which are also within the scope of this invention. Reference to a compound of Formula 1 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (non-limiting example(s) include, non-toxic, physiologically acceptable) salts are preferred, although other salts are also useful. Salts of the compounds of the Formula 1 may be formed, for example, by reacting a compound of Formula 1 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66 (1) 1-19; P. Gould, *International J. of Pharmaceutics* (1986) 33 201-217; Anderson et al, *The Practice of Medicinal Chemistry* (1996), Academic Press, New York; in The Orange Book (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (non-limiting example(s) include methyl, ethyl, propyl, and butyl chlorides, bromides and iodides), dialkyl sulfates (non-limiting example(s) include dimethyl, diethyl, dibutyl, and diamyl sulfates), long chain halides (non-limiting example(s) include decyl, lauryl, myristyl and stearyl chlorides, bromides and iodides), aralkyl halides (non-limiting example(s) include benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula 1, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

It should also be noted that throughout the specification and Claims appended hereto any formula, compound, moiety or chemical illustration with unsatisfied valences is assumed to have the hydrogen atom to satisfy the valences unless the context indicates a bond.

In one embodiment, the present invention discloses compounds of Formula 1, having CXCR3 antagonist activity, or a pharmaceutically acceptable derivative thereof, where the various definitions are given above.

In another embodiment of the present invention, $R^1$ and $R^2$ are independently absent or present, and if present each is independently selected from the group consisting of H, alkyl, aryl, amino, alkoxy, halogen, hydroxy, cycloalkyl, cycloalkenyl, arylalkyl, amidinyl, carboxamido, heteroaryl, heterocyclyl, heterocyclenyl, urea, —S(O)$_2$alkyl, —S(O)$_2$N(H)alkyl, —S(O)$_2$N(alkyl)$_2$, and —C(=S)N(H)cycloalkyl.

In another embodiment of the present invention, $R^1$ and $R^2$ are independently absent or present, and if present each is independently selected from the group consisting of H, alkylaryl, aryl, heteroaryl, —(CH$_2$)$_q$CF$_3$, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, —(CH$_2$)$_q$-amidinyl, cyclopropyl, cyclopropylhydroxyl, cyclobutyl, cyclobutylhydroxy, cyclopentyl, and cyclopentylhydroxy; and q is an integer from 1 to 5.

In another embodiment of the present invention, $R^1$ and $R^2$ are independently absent or present, and if present each is independently selected from the group consisting of H, —CH$_3$, fluorophenylmethylene, trifluoromethylphenylmethylene, indanyl, cyanophenylmethylene, difluorophenylmethylene, bromophenylmethylene, chlorophenylmethylene, —CH$_2$CH$_2$O phenyl, cyclopentyl, bromochlorophenylmethylene, fluorochlorophenylmethylene, dichlorophenylmethylene, phenylmethylene, —(CH$_2$)$_3$phenyl, —CH$_2$CF$_3$, methoxylphenylmethylene, —CH(CH$_3$)$_2$, —C$_2$H$_5$, —CH$_2$-cyclopropyl, —(CH$_2$)$_2$CH$_3$, cyclohexylmethylene, cyclohexyl, —CH$_2$CH$_2$SO$_2$CH$_3$, —CH$_2$—CH$_2$—NH$_2$, —CH$_2$CH$_2$OCH$_3$, cyclopropyl, isoxazolyl, —CH$_2$CH$_2$OH, —CH$_2$CH$_2$Ophenyl, —CH$_2$CH$_2$CH$_3$, —NH$_2$, —(CH$_2$)$_2$NH$_2$, pyrazolyl, 5-methyl-isoxazolyl, —CH$_2$CH(OCH$_2$CH$_3$)$_2$, —OCH$_3$, —NHC(=O)NH$_2$, chloropyridyl, pyridylmethylene, —C(=O)NHcyclopropyl, —C(=O)N(H)C$_2$H$_5$, —C(=O)N(H)CH$_2$CF$_3$, —C(=O)N(H)C(CH$_3$)$_3$, —C(=S)N(H)cyclopropyl, —C(=O)NH$_2$, —C(=O)N(H)CH$_3$, —S(O)$_2$CH$_3$, —S(O)$_2$N(CH$_3$)$_2$, —S(O)$_2$CH$_2$CH$_3$, —C(=O)CH$_3$, —S(O)$_2$(CH$_2$)$_2$CH$_3$, —C(=O)N(H)cyclohexyl, —C(=NH)NH$_2$, —C(=O)N(H)NH$_2$, —C(=O)N(H)CH(CH$_3$)$_2$, thiazolyl, —C(=O)N(CH$_3$)$_2$, —S(O)$_2$CH$_2$CF$_3$, cyclopropyl, —S(O)$_2$CF$_3$, —CH$_2$CH(OCH$_2$CH$_3$)$_2$,

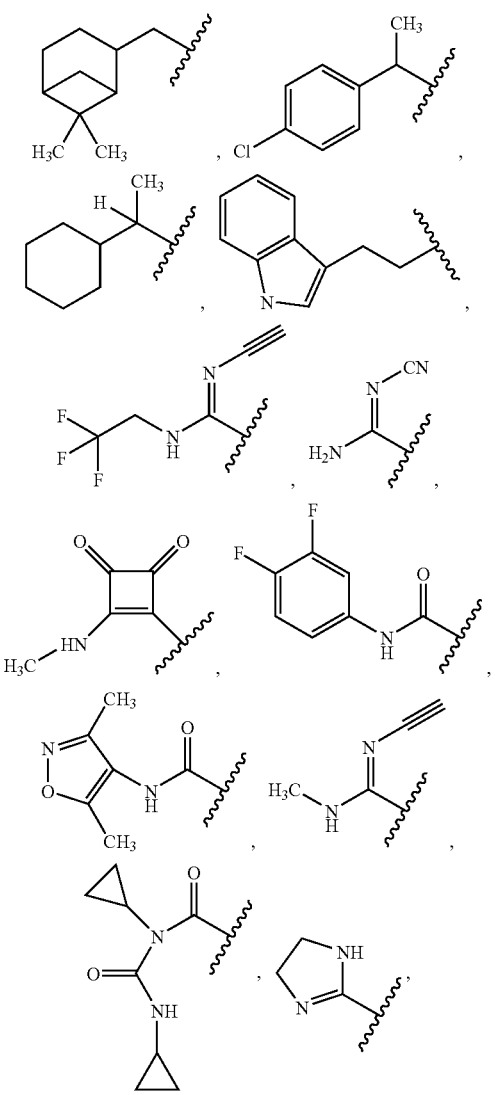

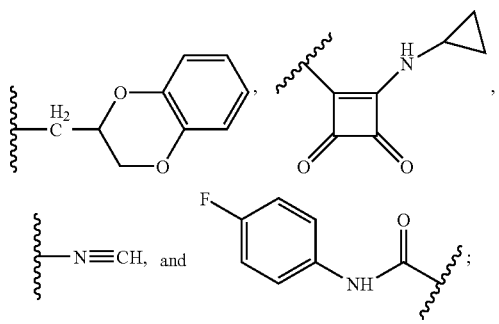

or when X is N, the N taken together with the R$^1$ and R$^2$ to which X is shown attached, forms a —N-cyclopropyl, —N-cyclobutyl, —N-cyclohexyl or

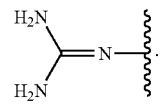

In another embodiment of the present invention, R$^1$ and R$^2$ are independently absent or present, and if present each is independently selected from the group consisting of H, —CH$_3$, —C$_2$H$_5$, difluorophenylmethylene, cyclopropyl, dichlorophenylmethylene, —CH(CH$_3$)$_2$, cyclohexylmethylene, cyclohexyl, isoxazolyl, isoxazoyl, oxadiazoyl, aminooxadiazoyl, substituted isoxazoyl, substituted oxadiazoyl, substituted aminooxadiazoyl, difluorophenyl, —CH$_2$CH$_2$OH, —CH$_2$CH$_2$N(CH$_3$))$_2$, —C(=O)N(H)cyclopropyl, —C(=O)N(H)C$_2$H$_5$, —C(=O)N(H)CH$_2$CF$_3$, —C(=O)N(H)CH(CH$_3$)$_2$, —C(=O)N(H)C(CH$_3$)$_3$, —C(=S)N(H)cyclopropyl, —C(=O)NH$_2$, —C(=O)N(H)CH$_3$, —S(O)$_2$CH$_3$, —S(O)$_2$N(CH$_3$)$_2$, —S(O)$_2$CH$_2$CH$_3$, —C(=O)CH$_3$, —S(O)$_2$(CH$_2$)$_2$CH$_3$, —C(=O)N(H)cyclohexyl, —C(=NH)NH$_2$, —C(=O)N(H)NH$_2$, thiazolyl,

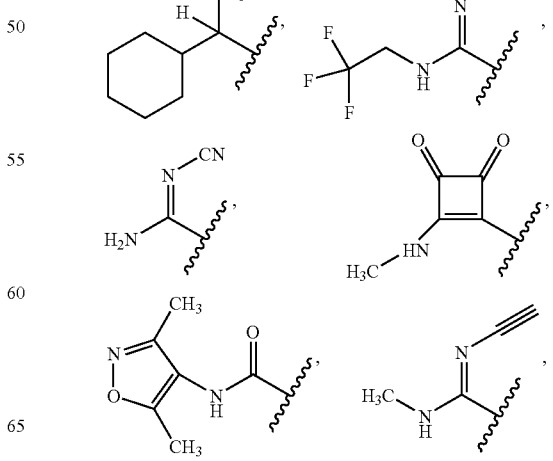

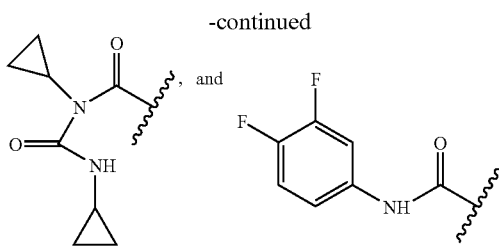

In another embodiment of the present invention, $R^1$ and $R^2$ are independently absent or present, and if present each is independently selected from the group consisting of H, —$CH_3$, —$C_2H_5$, difluorophenylmethylene, cyclopropyl, dichlorophenylmethylene, —$CH(CH_3)_2$, cyclohexylmethylene, cyclohexyl, isoxazolyl, difluorophenyl, —$CH_2CH_2OH$, —$CH_2$—$CH_2$—$N(CH_3))_2$, —C(=O)N(H)cyclopropyl, —C(=O)N(H)$C_2H_5$, —C(=O)N(H)$CH_2CF_3$, —C(=O)N(H)CH($CH_3$)$_2$, —C(=O)N(H)C($CH_3$)$_3$, —C(=S)N(H)cyclopropyl, —C(=O)$NH_2$, —C(=O)N(H)$CH_3$, —S(O)$_2$$CH_3$, —S(O)$_2$N($CH_3$)$_2$, —S(O)$_2$$CH_2CH_3$, —C(=O)$CH_3$, —S(O)$_2$($CH_2$)$_2$$CH_3$, —C(=O)N(H)cyclohexyl, —C(=NH)$NH_2$, —C(=O)N(H)$NH_2$, thiazolyl,

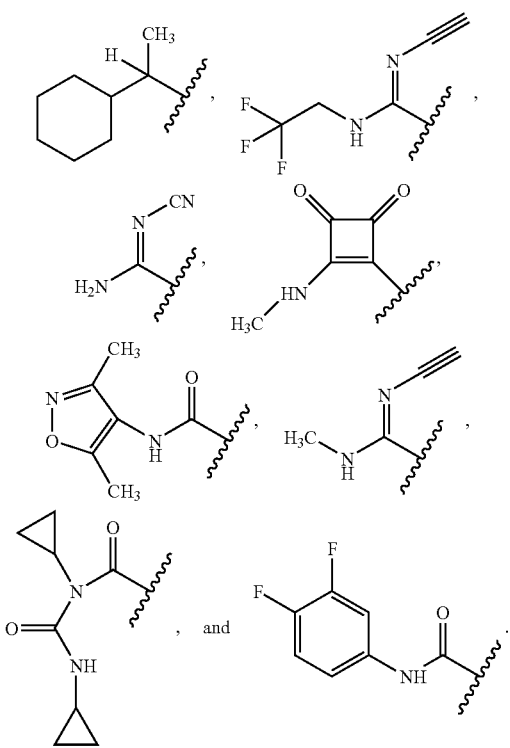

In another embodiment of the invention, X is selected from the group consisting of N, O, —$CH_3$, —$CH_2$—, —CH, —$CH_2CH_3$, —$CH_2CN$, —$NH_2$, cyclopropyl,

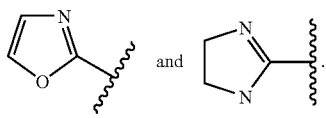

In another embodiment of the invention, X is N or O.
In another embodiment of the invention, X is N.
In another embodiment of the invention, Z is N or C($R^{29}$).
In another embodiment of the invention, Z is N.
In another embodiment of the invention, Z is C(H), C(alkyl), C(halogen), C($CF_3$) or C(N($R^{30}$)$_2$).
In another embodiment of the invention, Z is C(alkyl), C(F) or C($NH_2$).
In another embodiment of the invention, $R^3$ is selected from the group consisting of H, alkyl, haloalkyl, hydroxyalkyl, halogen, —N($R^{30}$)$_2$, —$OR^{30}$ and —$CF_3$.
In another embodiment of the invention, $R^3$ is selected from the group consisting of H, —$CH_3$, —$CH_2CH_3$, cyclopropyl, —F, —Cl, $OCH_3$, $OCF_3$ and $CF_3$.
In another embodiment of the invention, $R^4$ is selected from the group consisting of H, alkyl, hydroxyalkyl, halogen, $OR^{30}$, or $CF_3$.
In another embodiment of the invention, $R^7$ and $R^8$ are the same or different, each being independently selected from the group consisting of H, alkyl, alkylaryl, heteroaryl, hydroxyl, —CN, alkoxy, alkylamino, —N(H)S(O)$_2$alkyl and —N(H)C(=O)N(H)alkyl; or alternatively $R^7$ and $R^8$ taken together is =O, =S, =NH, =N(alkyl), =N(Oalkyl), =N(OH) or cycloalkyl.
In another embodiment of the invention, $R^6$ is selected from the group consisting of H, alkyl, halogen, hydroxyalkyl, —CN, —N($R^{30}$)$_2$, —$OR^{30}$, —N=CH-alkyl, and —$NR^{30}$C(=O)alkyl.
In another embodiment of the invention, $R^6$ is selected from the group consisting of H, —$NH_2$, —$CH_3$, —CN and —F.
In another embodiment of the invention, $R^7$ and $R^8$ are the same or different, each being independently selected from the group consisting of H, —($CH_2$)$_q$OH, —($CH_2$)$_q$Oalkyl, —($CH_2$)$_q$N(H)-alkyl, —($CH_2$)$_q$N(H)—S(O)$_2$alkyl, and —($CH_2$)$_q$N(H)—CO—N(H)alkyl; or alternatively $R^7$ and $R^8$ taken together is =O, =N(OAlkyl), or =S.
In another embodiment of the invention, $R^7$ and $R^8$ are the same or different, each being independently selected from the group consisting of H, —$CH_3$, and —OH; or alternatively $R^7$ and $R^8$ taken together is

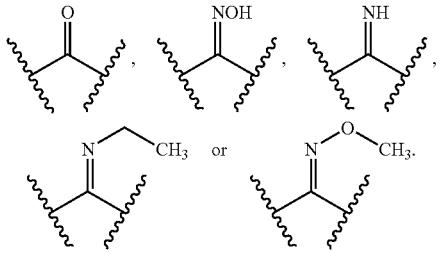

In another embodiment of the invention, $R^7$ and $R^8$ are each H; or
alternatively $R^7$ and $R^8$ taken together is

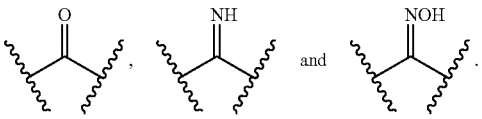

In another embodiment of the invention, $R^{10}$ is selected from the group consisting of H, alkyl, aralkyl, hydroxyalkyl, and carbonyl.

In another embodiment of the invention, $R^{10}$ is selected from the group consisting of: —$CH_3$, —$CH_2CH_3$ and —$CH_2CH_2CH_3$, and m is 0-2.

In another embodiment of the invention, $R^{11}$ is selected from the group consisting of H, alkyl, hydroxyalkyl and carbonyl.

In another embodiment of the invention, $R^{11}$ is H or —$CH_3$.

In another embodiment of the invention, $R^{12}$ is selected from the group consisting of H, CN, —C(=O)N($R^{30}$)$_2$ and alkyl.

In another embodiment of the invention, $R^{12}$ is selected from the group consisting of H, —$CH_3$, CN and —$CH_2CH_3$.

In another embodiment of the invention, the ring atoms of ring D are independently C or N and substituted by independently selected 0-4 $R^{20}$ moieties.

In another embodiment of the invention, ring D is a 5 to 6 membered aryl, heteroaryl, heterocyclenyl, or heterocyclyl ring and substituted by independently selected 0-4 $R^{20}$ moieties.

In another embodiment of the invention, the $R^{20}$ moieties can be the same or different, each being independently selected from the group consisting of H, alkyl, alkylaryl, alkynyl, alkoxy, alkylamino, alkylheteroaryl, alkylsulfinyl, alkoxycarbonyl, aminoalkyl, amidinyl, aralkyl, aralkoxy, aryl, aryloxy, cyano, cycloalkyl, cycloalkenyl, halogen, haloalkyl, heteroalkyl, heteroaryl, heterocyclyl, hydroxyalkyl, trifluromethyl, trifluoromethoxy, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —N(R$^{30}$)SO$_2$(R$^{31}$), —N(R$^{30}$)SO$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$.

In another embodiment of the invention, the $R^{20}$ moieties can be the same or different, each being independently selected from the group consisting of H, alkyl, amino, halogen, CN, CH$_3$, CF$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)OR$^{30}$, —N(R$^{30}$)$_2$—N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —OR$^{30}$, —OC(=O)N(R$^{30}$)$_2$, and —OSO$_2$(R$^{31}$).

In another embodiment of the invention, two $R^{20}$ moieties are linked together to form a five or six membered aryl, cycloalkyl, heterocyclenyl, heterocyclyl or heteroaryl ring wherein said five or six membered aryl, cycloalkyl, heterocyclenyl, heterocyclyl, and heteroaryl ring is fused to ring D and the fused ring is optionally substituted with 0 to 4 $R^{21}$ moieties.

In another embodiment of the invention, the $R^{20}$ moieties can be the same or different, each being independently selected from the group consisting of H, —CN, —CH$_3$, —CF$_3$, —CH$_2$OH, —CO$_2$H, —CO$_2$CH$_3$, —NH$_2$, —NHCH$_3$, —OCF$_3$, —OH, F, Cl, Br, —C(=NOH)NH$_2$, —OCH$_2$CH$_2$S(O$_2$)CH$_3$, —C(=O)NH$_2$,

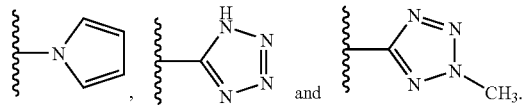

In another embodiment of the invention, Y is selected from the group consisting of: —(CHR$^{13}$)$_r$—, —(CR$^{13}$R$^{13}$)$_r$—, —C(=O)— and —CHR$^{13}$C(=O)—.

In another embodiment of the invention, Y is selected from the group consisting of: —CH$_2$—, —CH(CH$_3$)—, —CH(CH$_2$OH)—, —C(=O)— and —CH(CO$_2$alkyl)-.

In another embodiment of the invention, m is 0-3.
In another embodiment of the invention, n is 0-2.
In another embodiment of the invention, q is 1, 2 or 3.
In another embodiment of the invention, r is 1 or 2.
In another embodiment of the invention, Z is N, C(H), C(alkyl), C(F) or C(NH$_2$);

X is N;

$R^1$ and $R^2$ are independently absent or present, and if present each is independently selected from the group consisting of H, alkylaryl, aryl, heteroaryl, —(CH$_2$)$_q$CF$_3$, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$—N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, —(CH$_2$)$_q$-amidinyl, cyclopropyl, cyclopropylhydroxyl, cyclobutyl, cyclobutylhydroxy, cyclopentyl, and cyclopentylhydroxy;

$R^3$ is selected from the group consisting of H, alkyl, haloalkyl, hydroxyalkyl, halogen, —N(R$^{30}$)$_2$, —OR$^{30}$ and —CF$_3$;

$R^4$ is selected from the group consisting of H, alkyl, haloalkyl, hydroxyalkyl, halogen, —N(R$^{30}$)$_2$, —OR$^{30}$ and —CF$_3$;

$R^6$ is selected from the group consisting of H, alkyl, halogen, hydroxyalkyl, —CN, —N(R$^{30}$)$_2$, —OR$^{30}$, —N=CH-alkyl, and —NR$^{30}$C(=O)alkyl;

$R^7$ and $R^8$ are independently selected from the group consisting of =O, =S, =NH, =NOH, and =N(OAlkyl);

$R^{10}$ is selected from the group consisting of H, alkyl, aralkyl, hydroxyalkyl, and carbonyl;

$R^{11}$ is selected from the group consisting of H, alkyl, hydroxyalkyl, and carbonyl;

$R^{12}$ is selected from the group consisting of H, CN, —C(=O)N(R$^{30}$)$_2$ and alkyl;

ring D is a 5 to 6 membered aryl, heteroaryl, heterocyclenyl, or heterocyclyl ring and substituted by 0-4 $R^{20}$ moieties;

the $R^{20}$ moieties can be the same or different, each being independently selected from the group consisting of H, alkyl, amino, halogen, CN, CH$_3$, CF$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —OR$^{30}$, —OC(=O)N(R$^{30}$)$_2$,

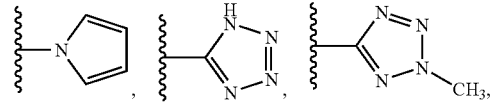

and —OSO$_2$(R$^{31}$);

Y is selected from the group consisting of: —CH$_2$—, —CH(CH$_3$)—, —CH(CH$_2$OH)—, —C(=O)— and —CH(CO$_2$alkyl)-;
m is 0-2;
n is 0-2;
q is 1 or 2; and
r is 1 or 2.

Formula 2
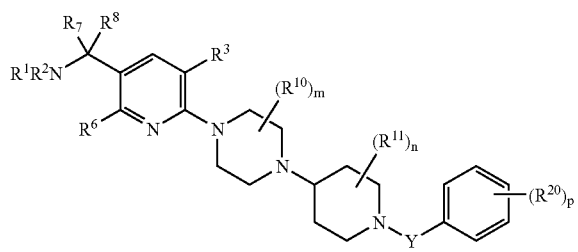

Formula 3
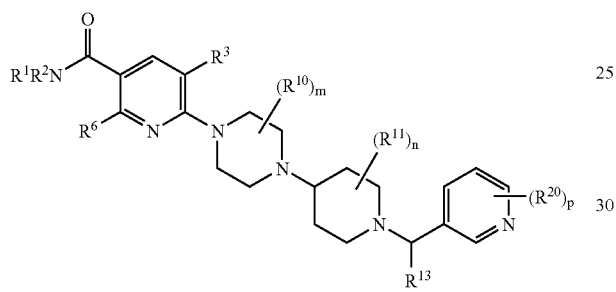

Formula 4
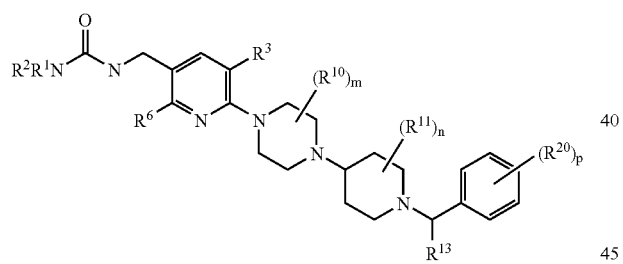

Formula 5
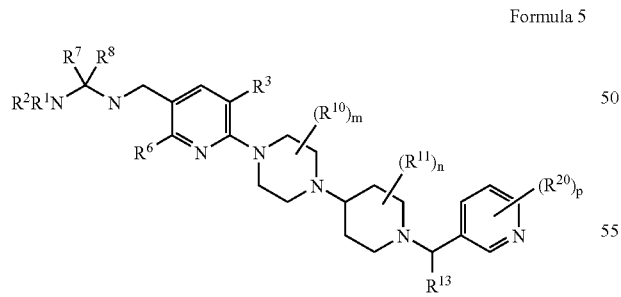

or pharmaceutically acceptable salts, solvates or esters thereof, wherein: wherein R$^1$ and R$^2$ are independently absent or present, and if present each is independently selected from the group consisting of H, —CH$_3$, fluorophenylmethylene, trifluoromethylphenylmethylene, indanyl, cyanophenylmethylene, difluorophenylmethylene, bromophenylmethylene, chlorophenylmethylene, —CH$_2$CH$_2$O phenyl, cyclopentyl, bromochlorophenylmethylene, fluorochlorophenylmethylene, dichlorophenylmethylene, phenylmethylene, —(CH$_2$)$_3$phenyl, —CH$_2$CF$_3$, methoxylphenylmethylene, —CH(CH$_3$)$_2$, —C$_2$H$_5$, —CH$_2$-cyclopropyl, —(CH$_2$)$_2$CH$_3$, cyclohexylmethylene, cyclohexyl, —CH$_2$CH$_2$SO$_2$CH$_3$, —CH$_2$—CH$_2$—NH$_2$, —CH$_2$CH$_2$OCH$_3$, cyclopropyl, isoxazolyl, —CH$_2$CH$_2$OH, —CH$_2$CH$_2$O phenyl, —CH$_2$CH$_2$CH$_3$, —NH$_2$, —(CH$_2$)$_2$NH$_2$, pyrazolyl, 5-methyl-isoxazolyl, —CH$_2$CH(OCH$_2$CH$_3$)$_2$, —OCH$_3$, —NHC(=O)NH$_2$, chloropyridyl, pyridylmethylene, —C(=O)NHcyclopropyl, —C(=O)N(H)C$_2$H$_5$, —C(=O)N(H)CH$_2$CF$_3$, —C(=O)N(H)C(CH$_3$)$_3$, —C(=S)N(H)cyclopropyl, —C(=O)NH$_2$, —C(=O)N(H)CH$_3$, —S(O)$_2$CH$_3$, —S(O)$_2$N(CH$_3$)$_2$, —S(O)$_2$CH$_2$CH$_3$, —C(=O)CH$_3$, —S(O)$_2$(CH$_2$)$_2$CH$_3$, —C(=O)N(H)cyclohexyl, —C(=NH)NH$_2$, —C(=O)N(H)NH$_2$, —C(=O)N(H)CH(CH$_3$)$_2$, thiazolyl, —C(=O)N(CH$_3$)$_2$, —S(O)$_2$CH$_2$CF$_3$, cyclopropyl, —S(O)$_2$CF$_3$, —CH$_2$CH(OCH$_2$CH$_3$)$_2$,

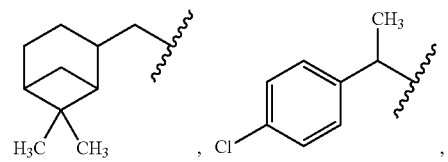

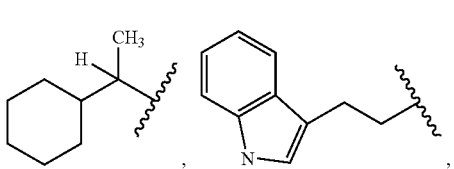

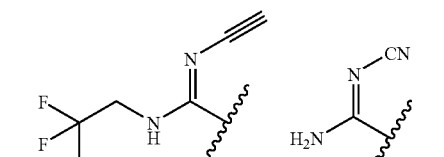

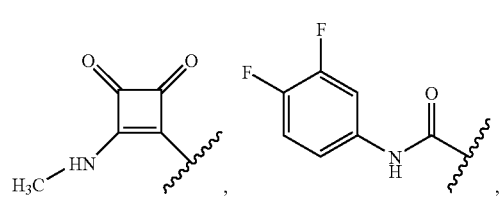

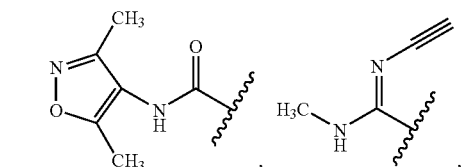

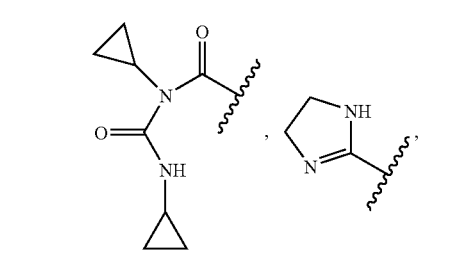

-continued

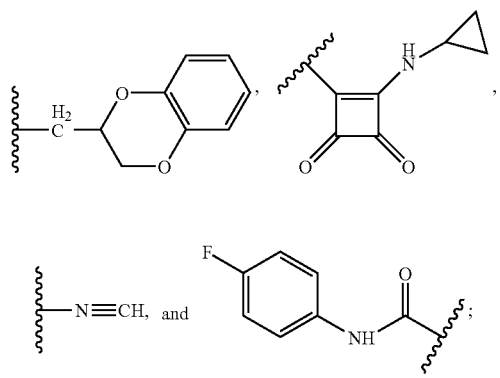

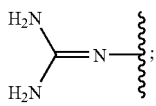

or when X is N, the N taken together with the R¹ and R² to which X is shown attached, forms a —N-cyclobutyl, —N-cyclohexyl or $R^3$ is selected from the group consisting of H, —CH₃, —CH₂CH₃, cyclopropyl, —F, —Cl, OCH₃, OCF₃ and CF₃;

$R^{10}$ is selected from the group consisting of H, alkyl, aralkyl, hydroxyalkyl, and carbonyl;

$R^{11}$ is selected from the group consisting of H, alkyl, hydroxyalkyl and carbonyl;

$R^{13}$ is selected from the group consisting of H, alkyl, alkylaryl, cycloalkyl, alkoxy, —C(=O)R³⁰, —C(=O)N(R³⁰)₂, —(CHR³⁰)$_q$OH, —(CHR³⁰)$_q$OR³¹, —(CHR³⁰)$_q$NH₂, —(CHR³⁰)$_q$NHR³¹, —(CH₂)$_q$C(=O)NHR³¹—N(R³⁰)₂, —N(R³⁰)SO₂(R³¹), —OR³⁰, —SO₂N(R³⁰)₂, and —SO₂(R³¹);

the R²⁰ moieties can be the same or different, each being independently selected from the group consisting of H, alkyl, amino, halogen, CN, CH₃, CF₃, OCF₃, —(CH₂)$_q$OR³¹, —(CH₂)$_q$NHR³¹, —(CH₂)$_q$C(=O)NHR³¹, —(CH₂)$_q$SO₂R³¹, —(CH₂)$_q$NSO₂R³¹, —(CH₂)$_q$SO₂NHR³¹, -alkynylC(R³¹)₂OR³¹, —C(=O)R³⁰, —C(=O)OR³⁰, —N(R³⁰)₂, —N(R³⁰)C(=O)R³¹, —NHC(=O)N(R³⁰)₂, —N(R³⁰)C(=O)OR³¹, —N(R³⁰)C(=NCN)N(R³⁰)₂, —N(R³⁰)C(=O)N(R³⁰)₂, —OR³⁰, —OC(=O)N(R³⁰)₂, and —OSO₂(R³¹); and m, n, $R^6$, $R^7$, $R^8$, $R^{20}$, $R^{30}$ and $R^{31}$ are as defined in Formula 1.

In still another embodiment of the present invention, a compound is selected from the following structures in Table 1 below (or a pharmaceutically acceptable salt, solvate or ester thereof) which are shown along with their IC₅₀ ratings. The IC₅₀ values are rated, "A" for IC₅₀ values less than about 25 nanomolar (nM), "B" for IC₅₀ values in the range of from about 25 to about 100 nM and "C" for IC₅₀ values greater than about 100 nM. For example, Compound Number 212 has a IC₅₀ of 0.2 nM.

TABLE 1

| Compound No. | Compound Structure | IC₅₀ |
|---|---|---|
| 1 | 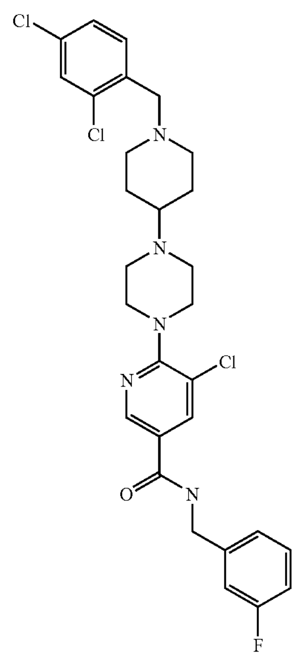 | C |

TABLE 1-continued

| Compound No. | Compound Structure | IC$_{50}$ |
|---|---|---|
| 2 | 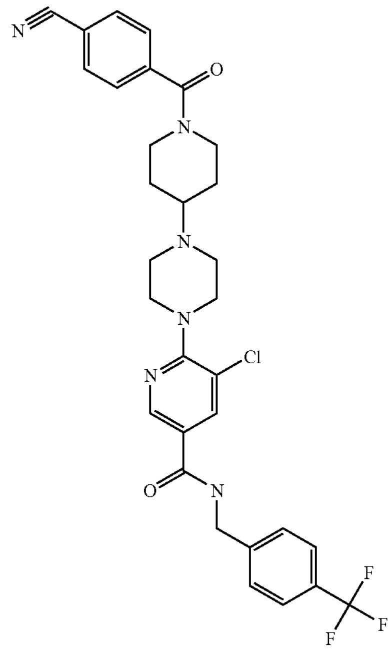 | C |
| 3 | 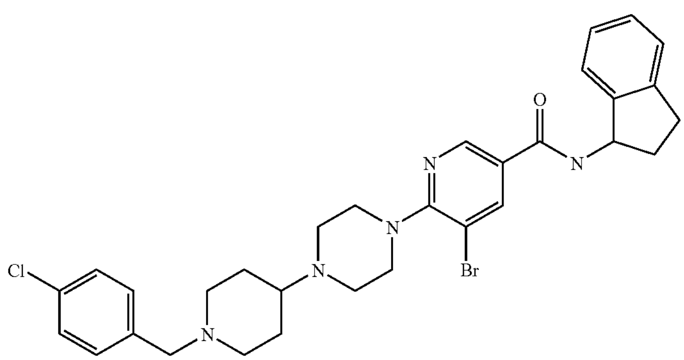 | C |
| 4 | 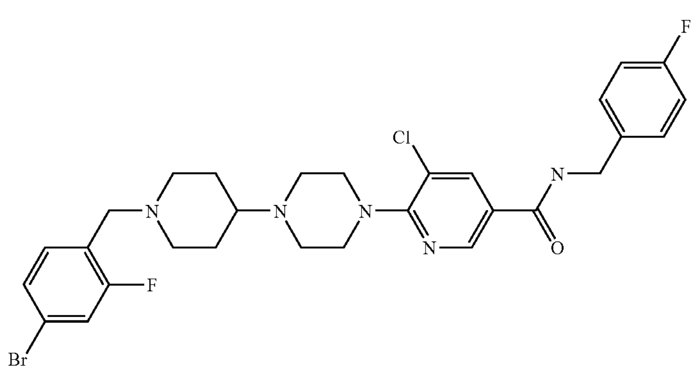 | C |

TABLE 1-continued

| Compound No. | Compound Structure | IC$_{50}$ |
|---|---|---|
| 5 | 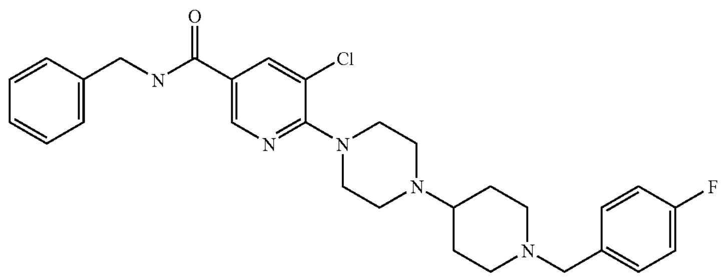 | C |
| 6 | 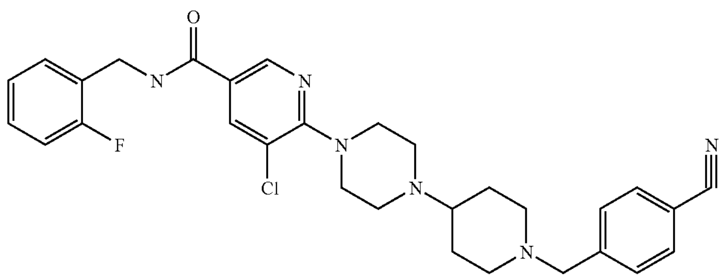 | C |
| 7 | 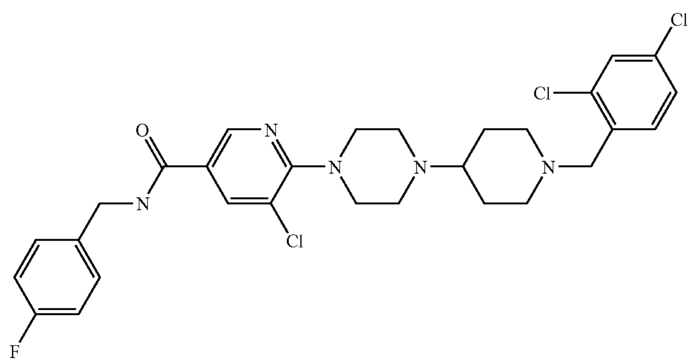 | C |
| 8 | 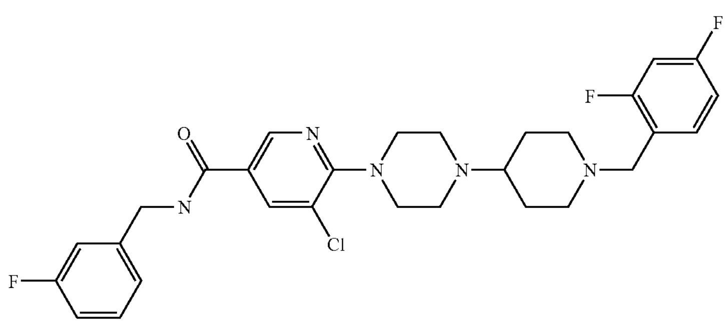 | C |
| 9 | 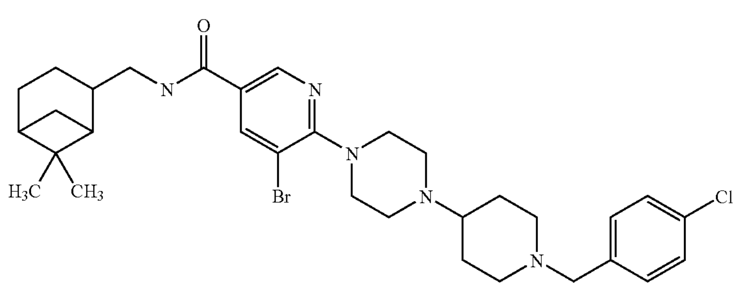 | C |

TABLE 1-continued
| Compound No. | Compound Structure | IC$_{50}$ |
|---|---|---|
| 10 | 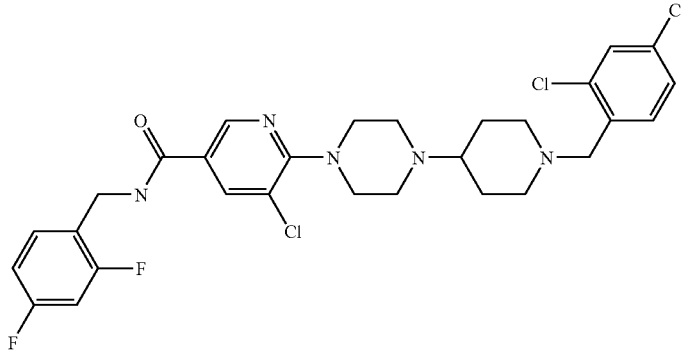 | C |
| 11 | 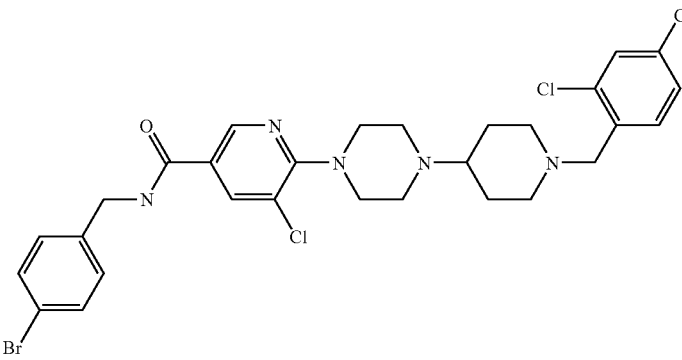 | C |
| 12 | 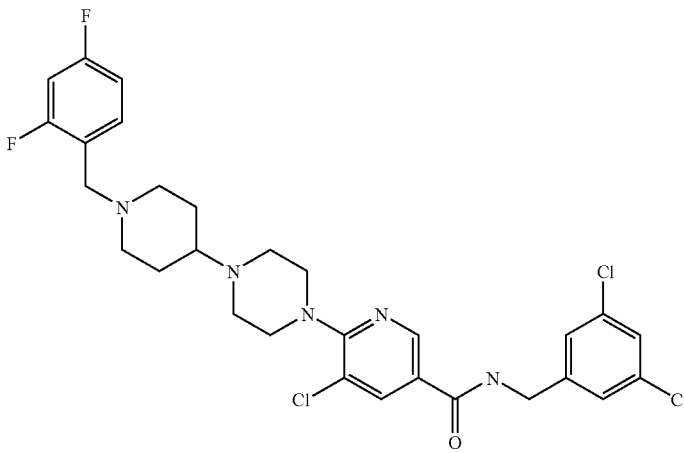 | C |

TABLE 1-continued

| Compound No. | Compound Structure | IC$_{50}$ |
|---|---|---|
| 13 | 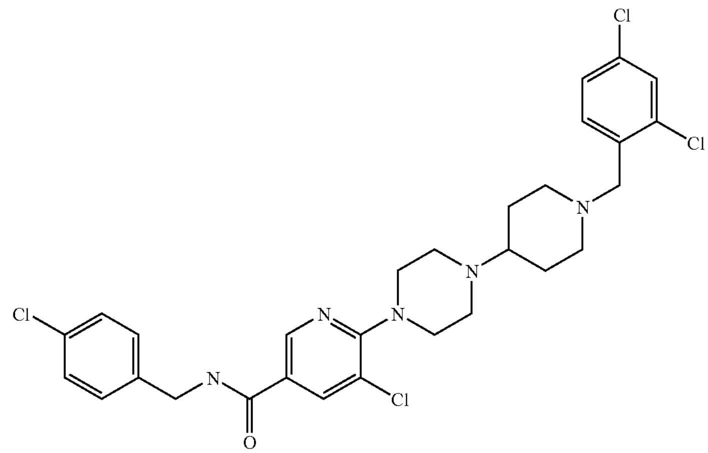 | C |
| 14 | 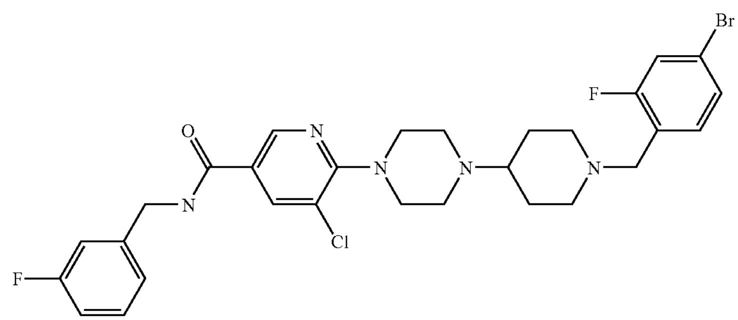 | C |
| 15 | 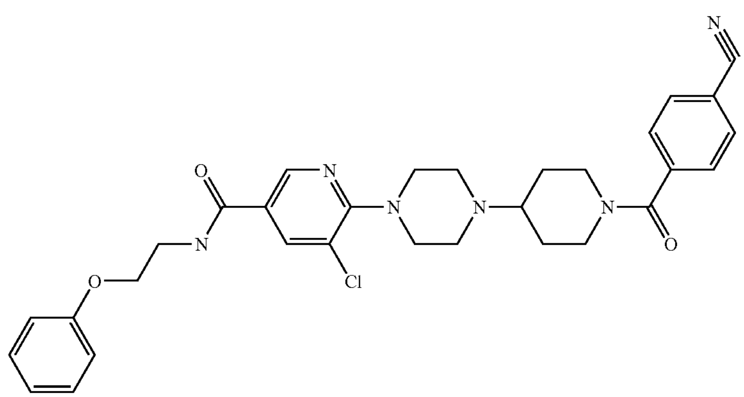 | C |
| 16 | 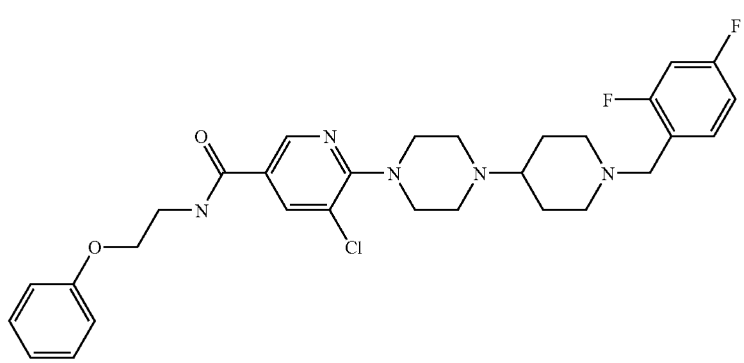 | C |

TABLE 1-continued

| Compound No. | Compound Structure | IC$_{50}$ |
|---|---|---|
| 17 | 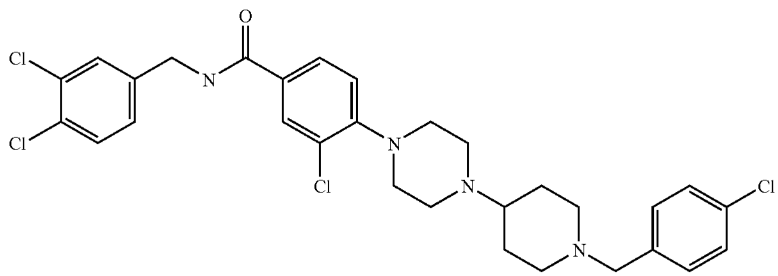 | C |
| 18 | 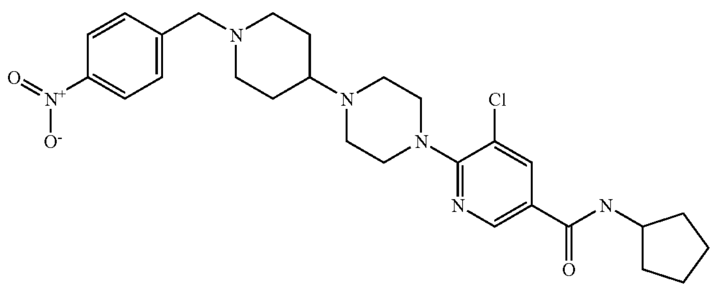 | C |
| 19 | 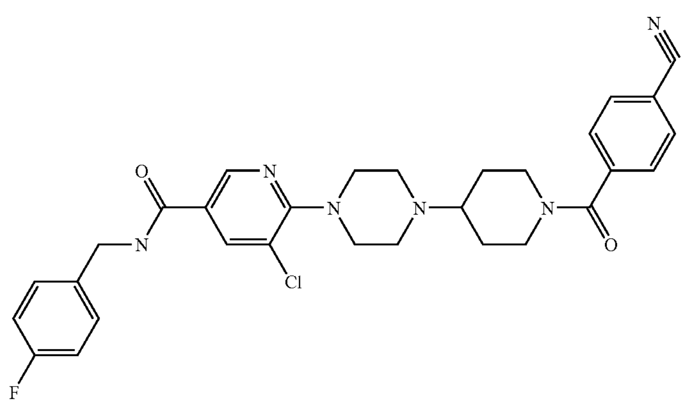 | C |
| 20 | 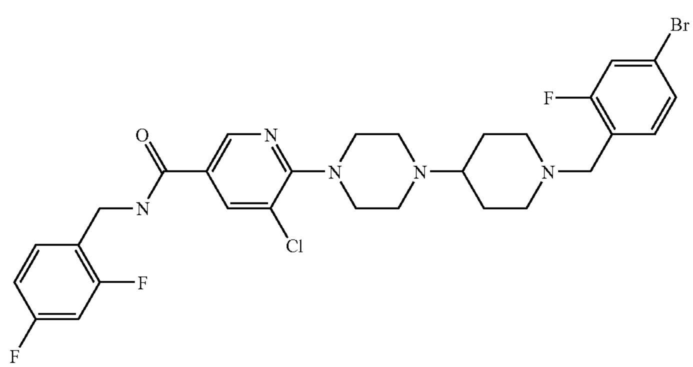 | C |

TABLE 1-continued
| Compound No. | Compound Structure | IC$_{50}$ |
|---|---|---|
| 21 | 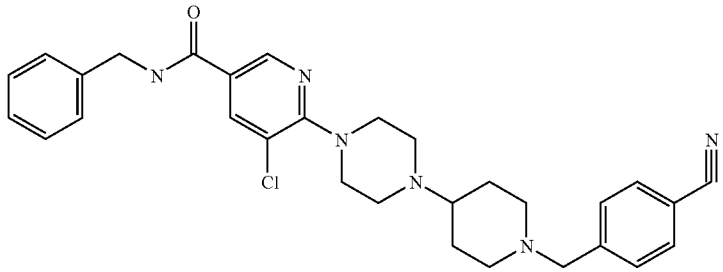 | C |
| 22 | 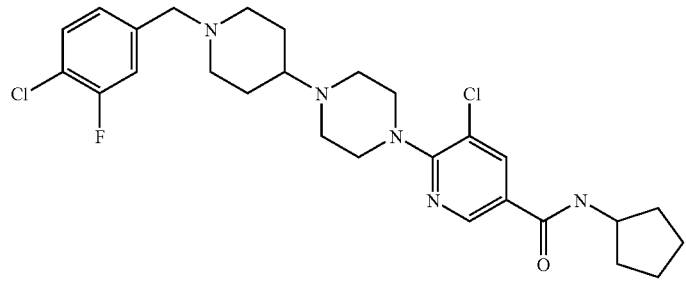 | C |
| 23 | 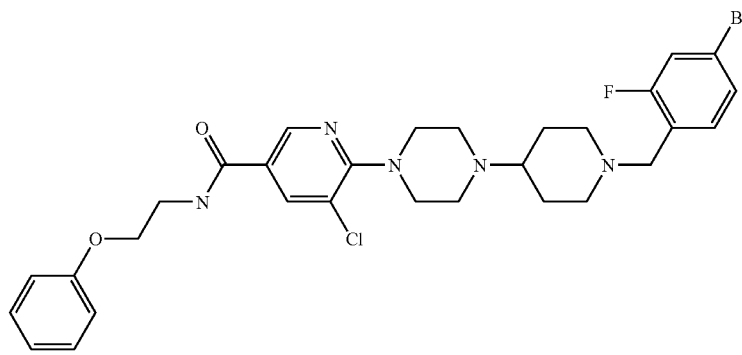 | C |
| 24 | 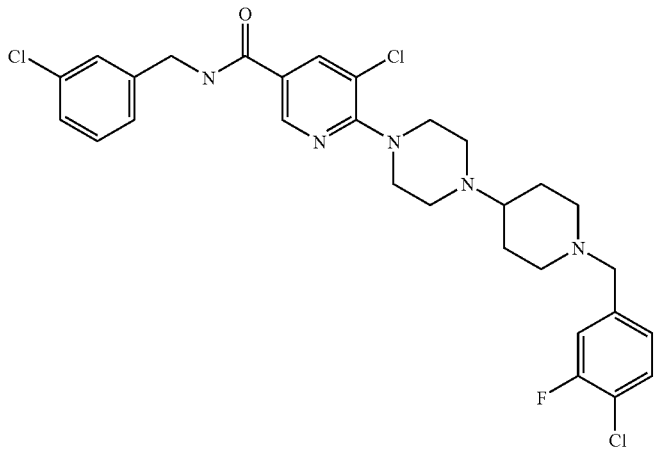 | C |

TABLE 1-continued
| Compound No. | Compound Structure | IC$_{50}$ |
|---|---|---|
| 25 | 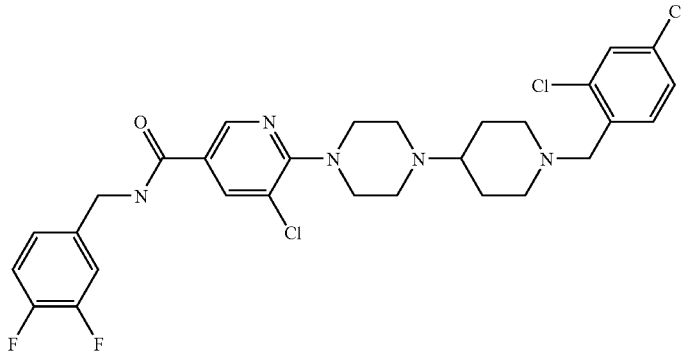 | C |
| 26 | 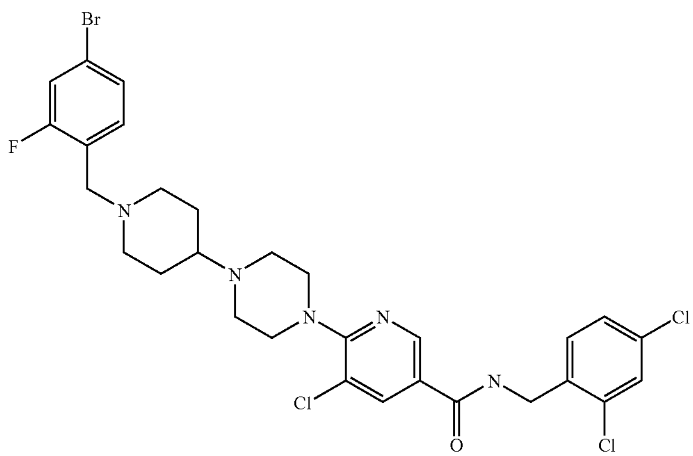 | C |
| 27 | 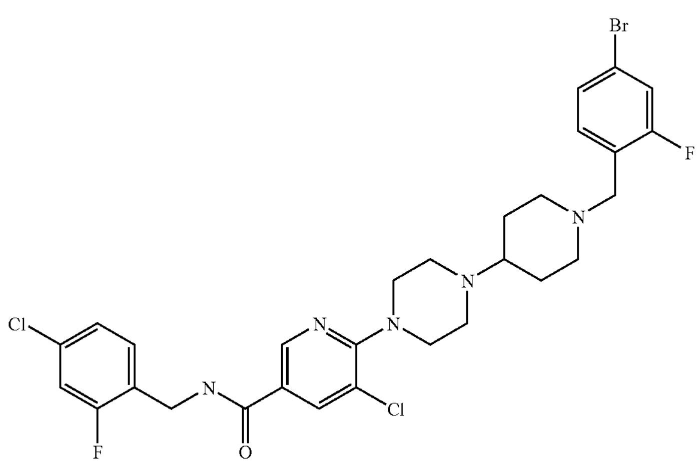 | C |

TABLE 1-continued

| Compound No. | Compound Structure | IC$_{50}$ |
|---|---|---|
| 28 | 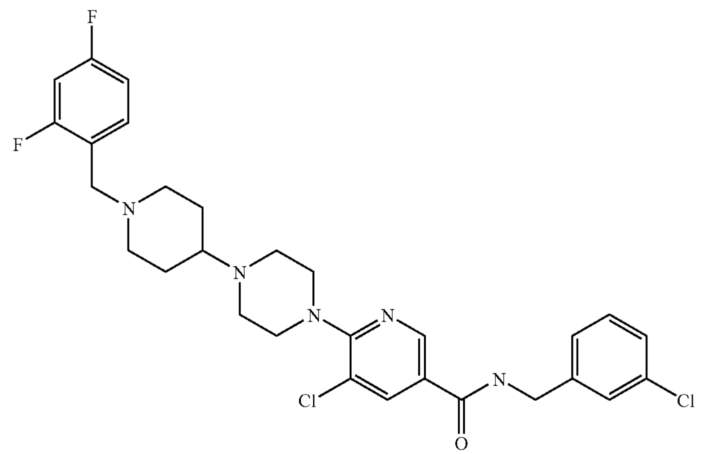 | C |
| 29 | 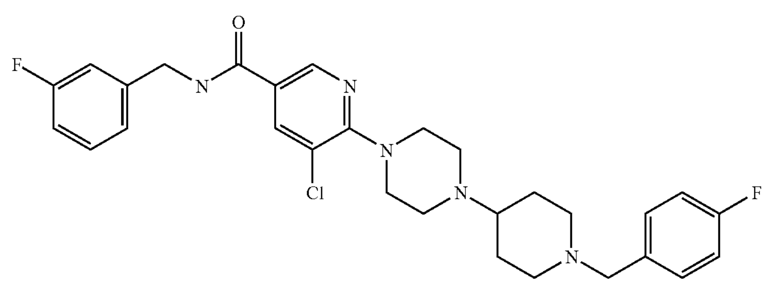 | C |
| 30 | 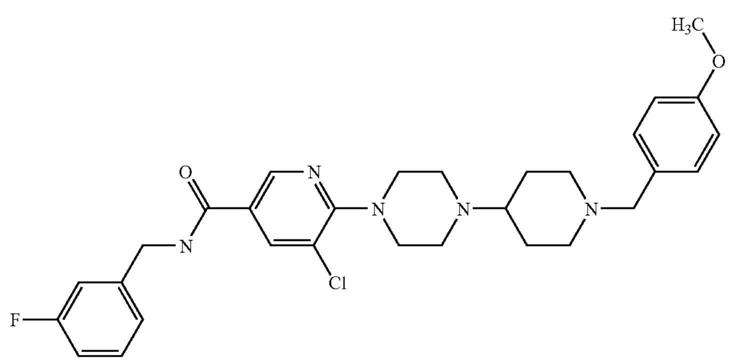 | C |
| 31 | 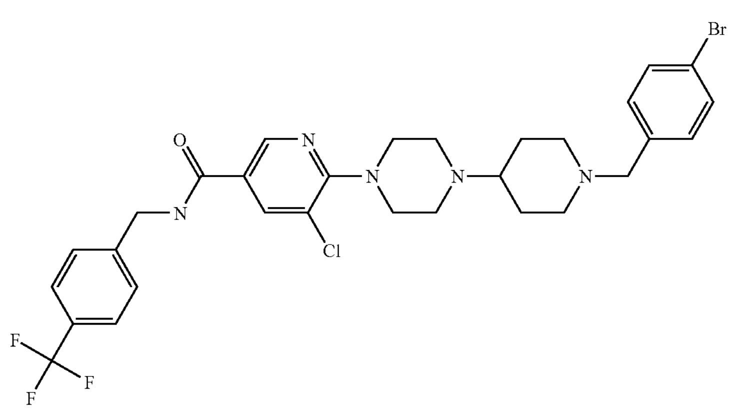 | C |

TABLE 1-continued

| Compound No. | Compound Structure | IC$_{50}$ |
|---|---|---|
| 32 | 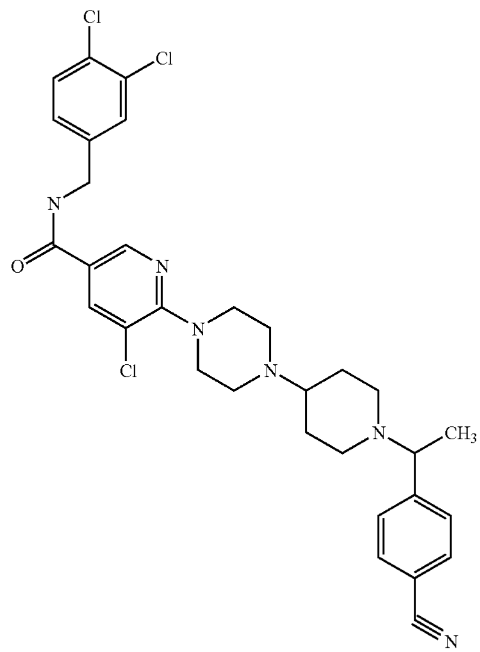 | C |
| 33 | 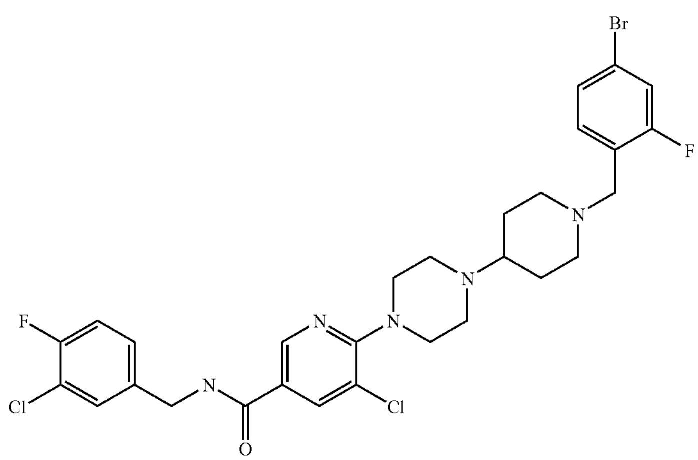 | C |
| 34 | 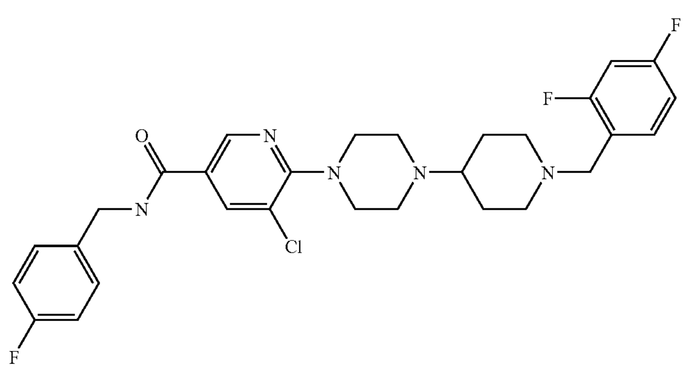 | C |

TABLE 1-continued

| Compound No. | Compound Structure | IC$_{50}$ |
|---|---|---|
| 35 | (structure) | C |
| 36 | (structure) | C |
| 37 | (structure) | C |
| 38 | (structure) | C |

TABLE 1-continued

| Compound No. | Compound Structure | IC$_{50}$ |
|---|---|---|
| 39 | 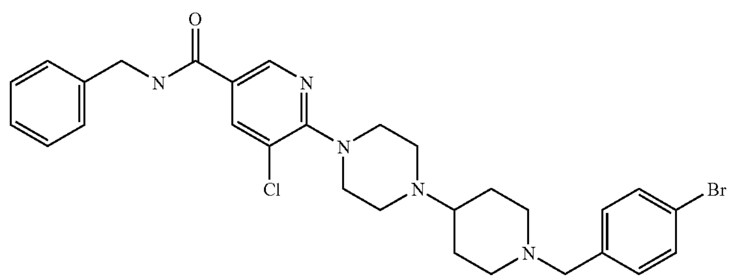 | C |
| 40 | 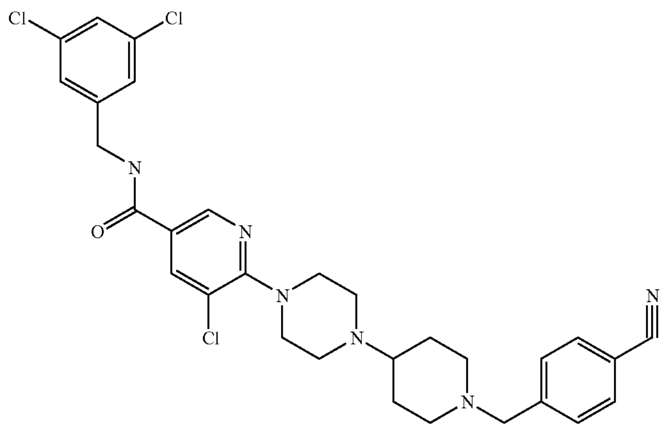 | C |
| 41 | 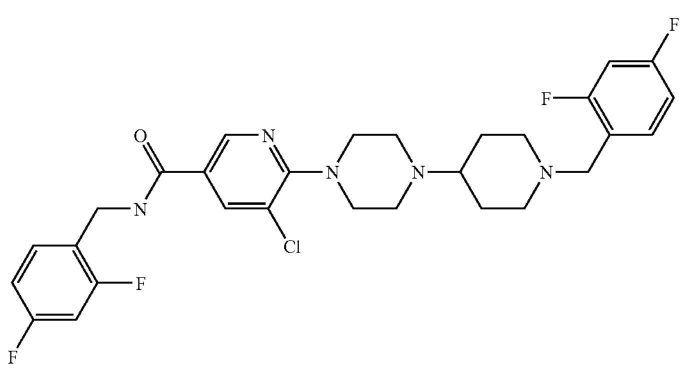 | C |
| 42 | 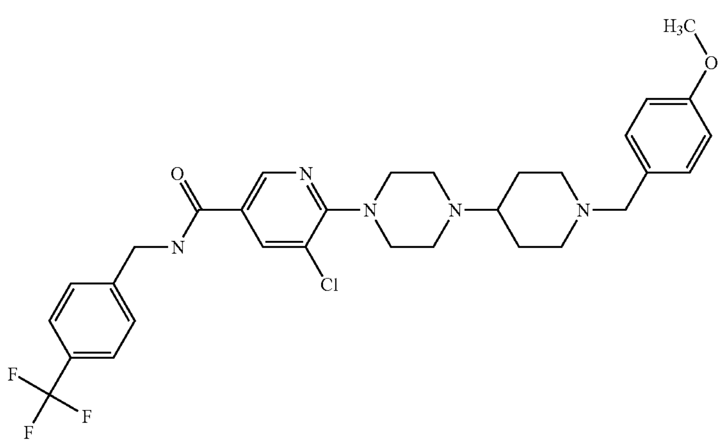 | C |

TABLE 1-continued

| Compound No. | Compound Structure | IC$_{50}$ |
|---|---|---|
| 43 | 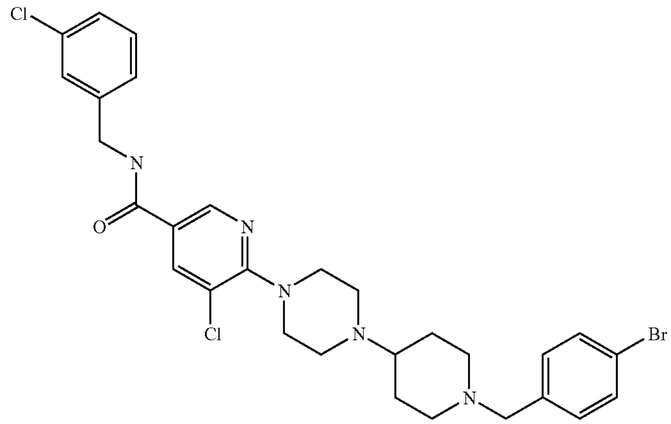 | C |
| 44 | 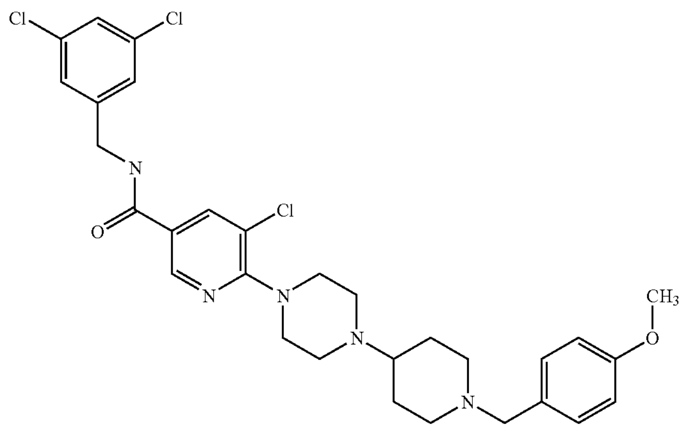 | C |
| 45 | 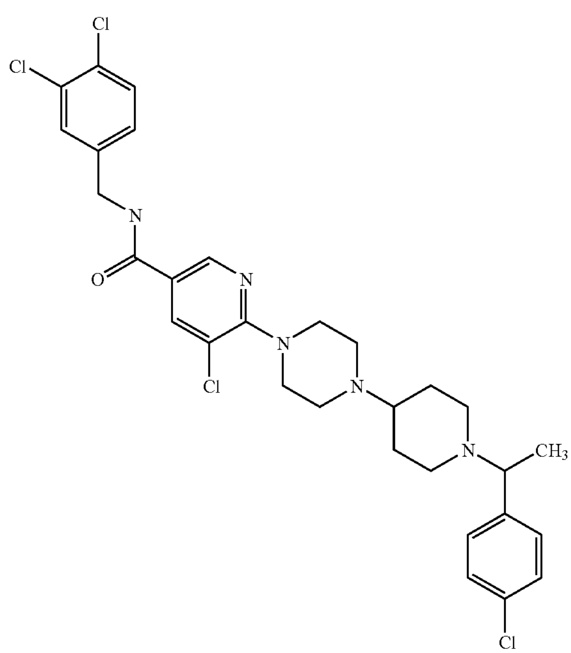 | C |

TABLE 1-continued

| Compound No. | Compound Structure | IC$_{50}$ |
|---|---|---|
| 46 | 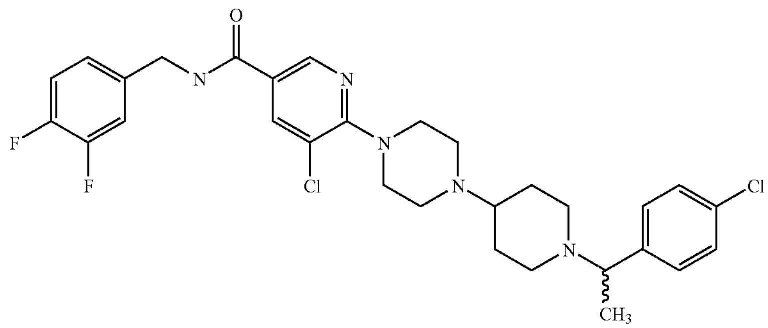 | C |
| 47 | 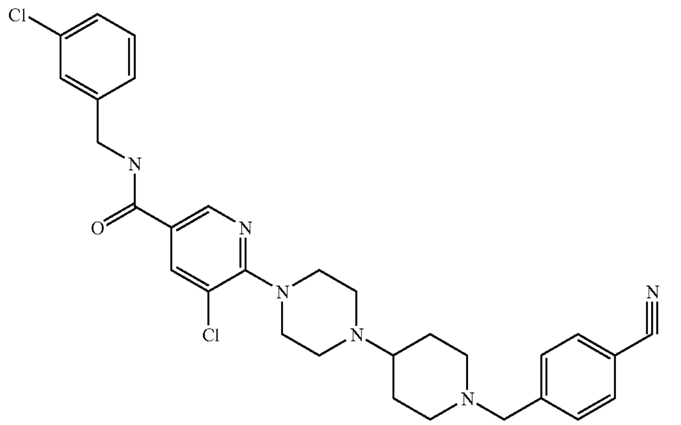 | C |
| 48 | 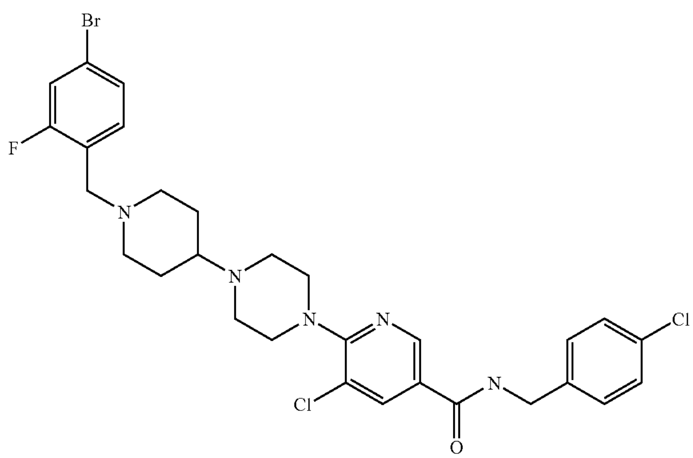 | C |
| 49 | 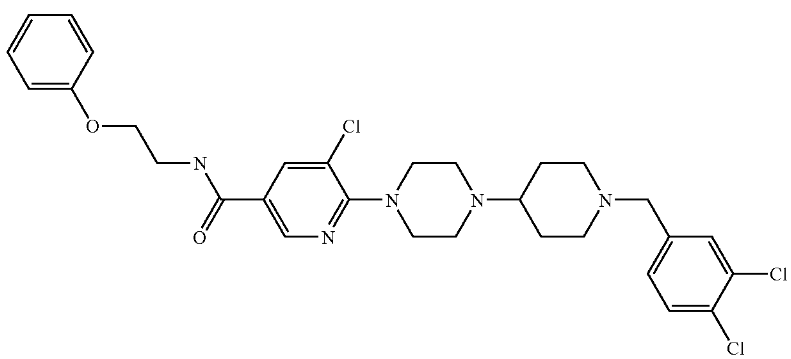 | C |

TABLE 1-continued
| Compound No. | Compound Structure | IC$_{50}$ |
|---|---|---|
| 50 | 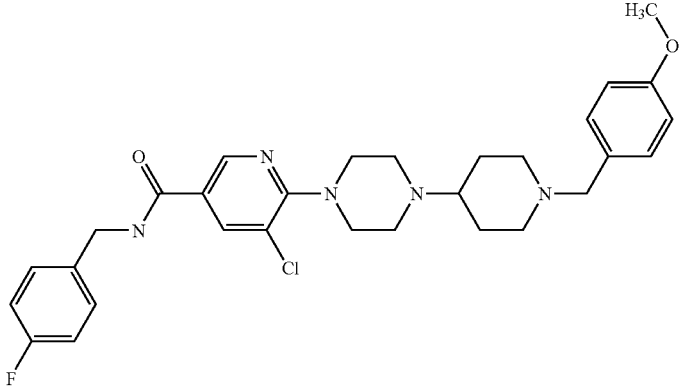 | C |
| 51 | 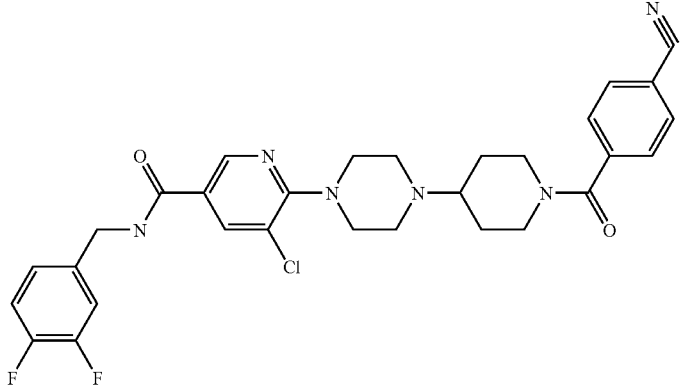 | C |
| 52 | 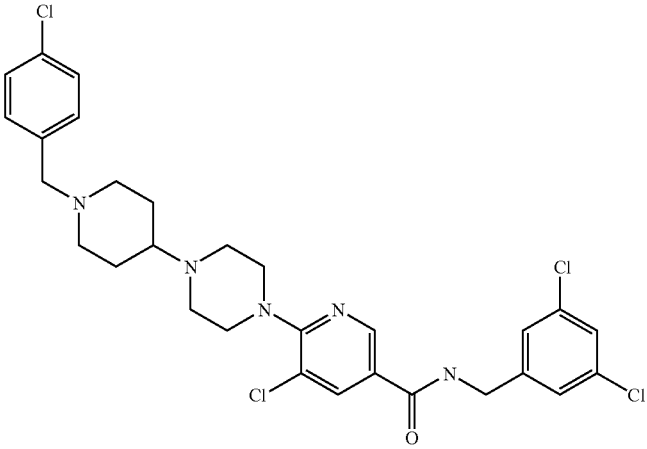 | C |

TABLE 1-continued

| Compound No. | Compound Structure | IC$_{50}$ |
| --- | --- | --- |
| 53 | 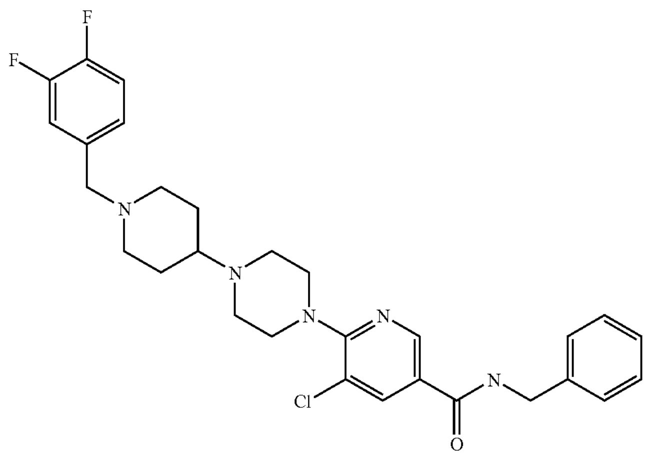 | C |
| 54 | 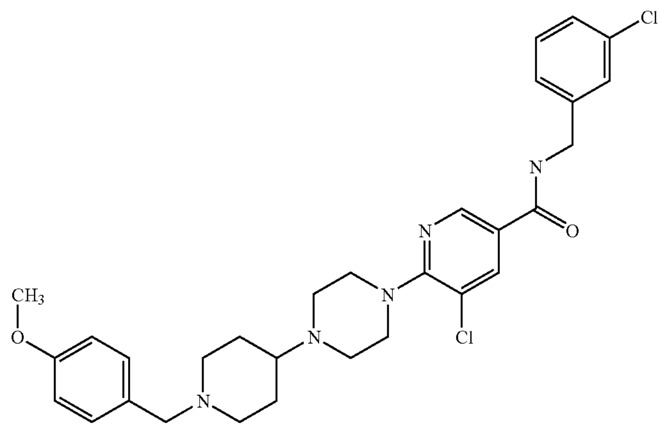 | C |
| 55 | 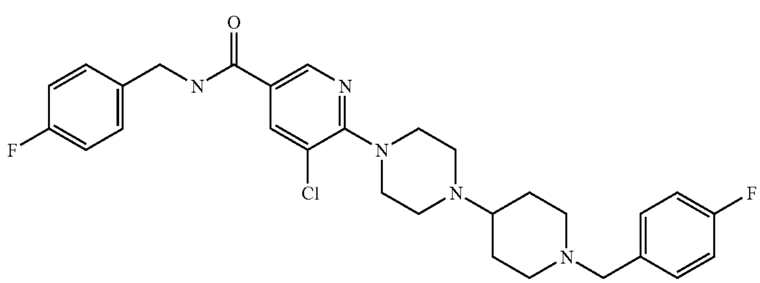 | C |
| 56 | 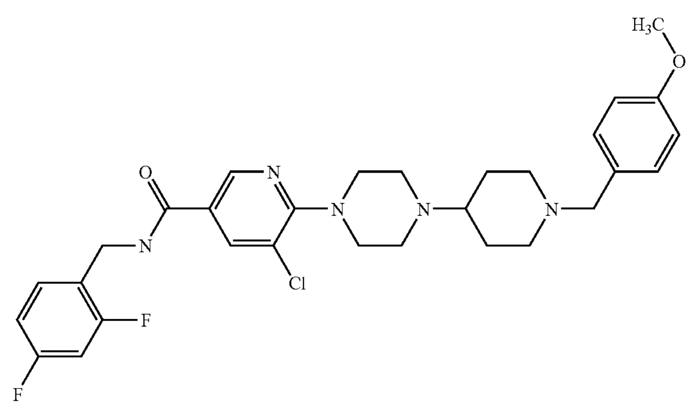 | C |

TABLE 1-continued
| Compound No. | Compound Structure | IC$_{50}$ |
|---|---|---|
| 57 | 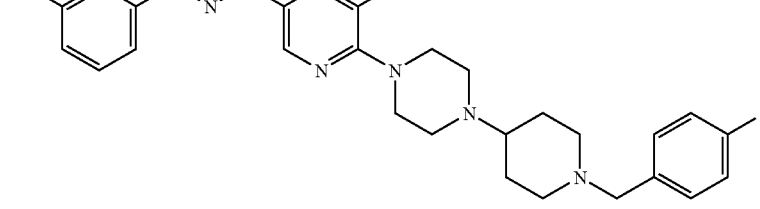 | C |
| 58 | 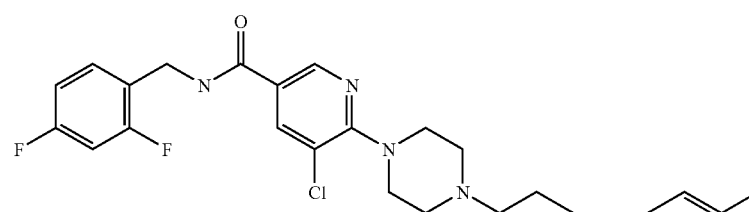 | C |
| 59 | 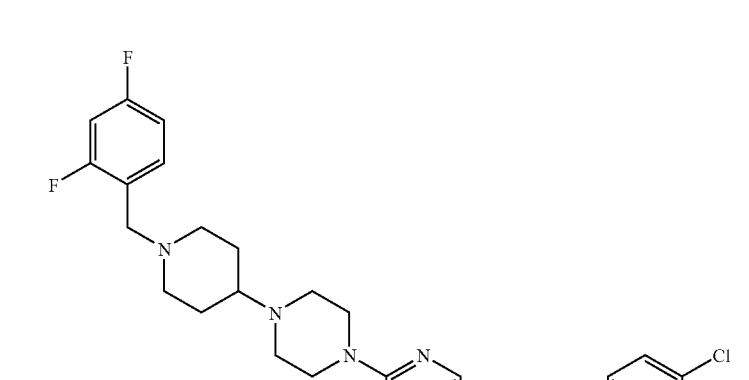 | C |
| 60 | 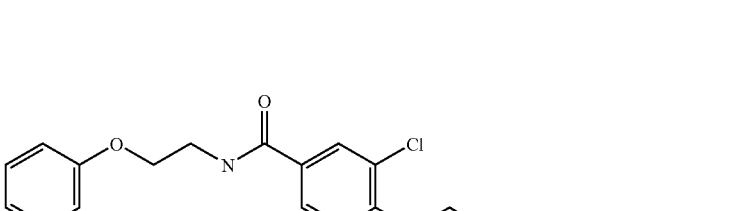 | C |

TABLE 1-continued

| Compound No. | Compound Structure | IC$_{50}$ |
|---|---|---|
| 61 | 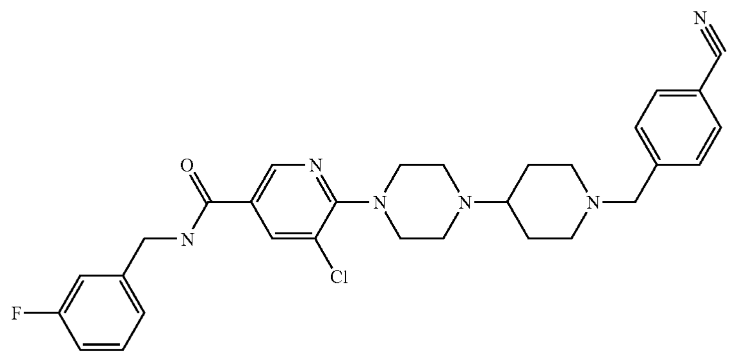 | C |
| 62 | 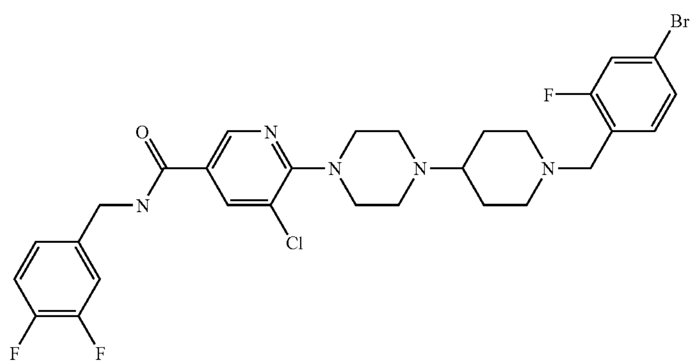 | C |
| 63 | 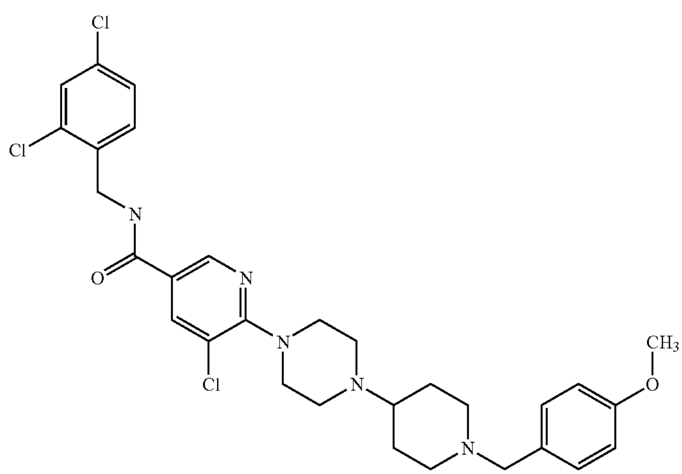 | C |
| 64 | 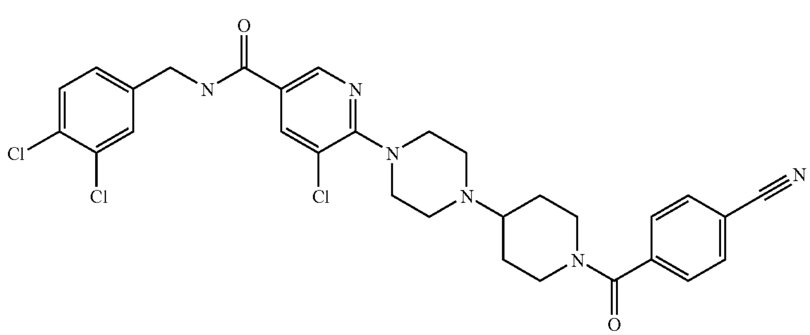 | C |

TABLE 1-continued

| Compound No. | Compound Structure | IC$_{50}$ |
|---|---|---|
| 65 | 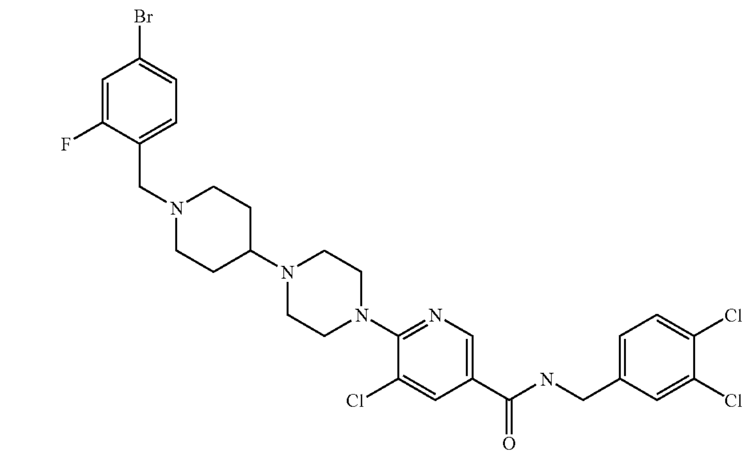 | C |
| 66 | 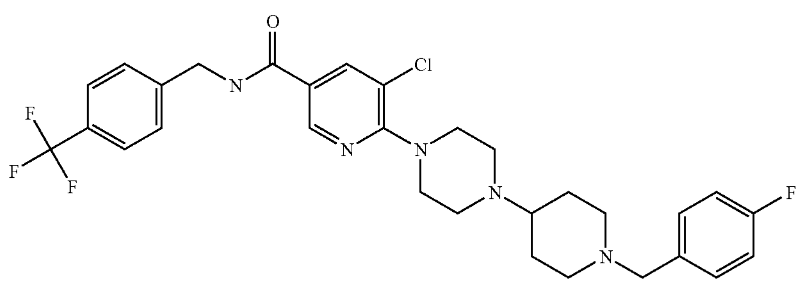 | C |
| 67 | 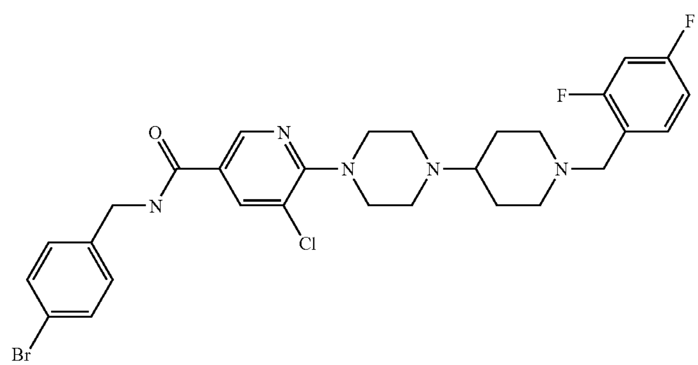 | C |
| 68 | 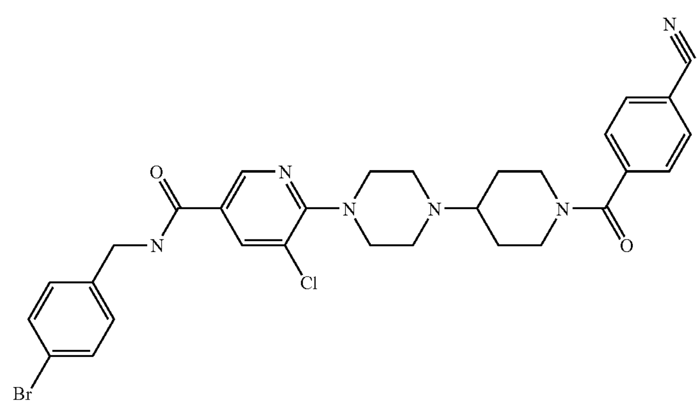 | C |

TABLE 1-continued
| Compound No. | Compound Structure | IC$_{50}$ |
|---|---|---|
| 69 | 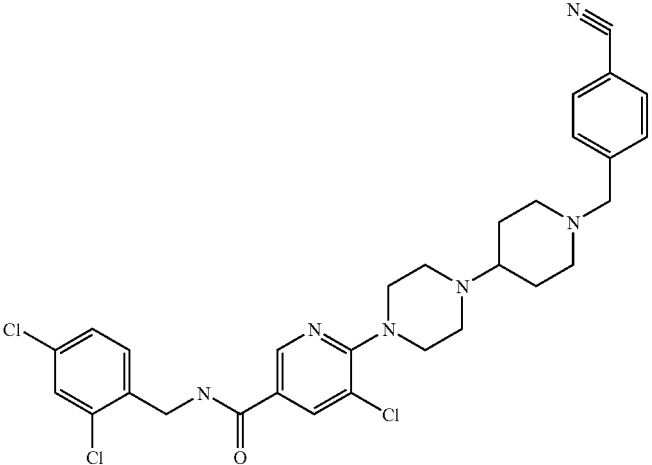 | C |
| 70 | 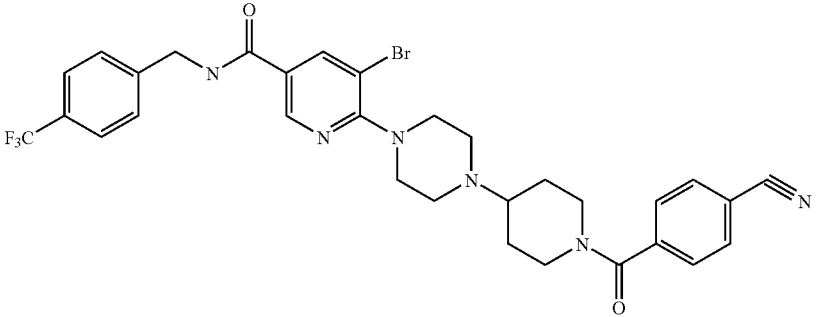 | C |
| 71 | 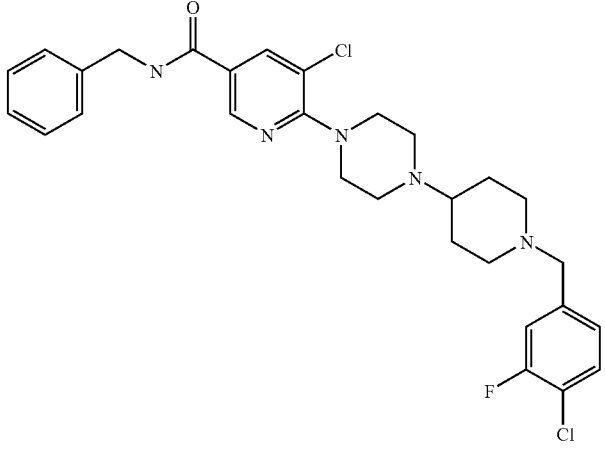 | C |
| 72 | 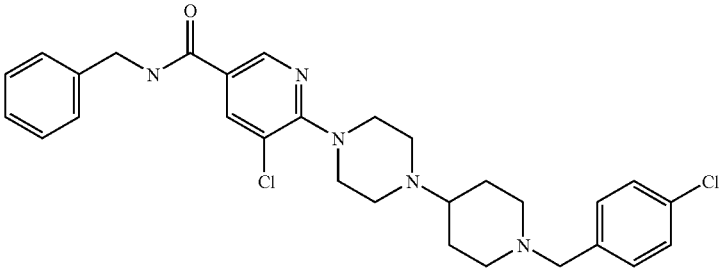 | C |

TABLE 1-continued

| Compound No. | Compound Structure | IC$_{50}$ |
|---|---|---|
| 73 | 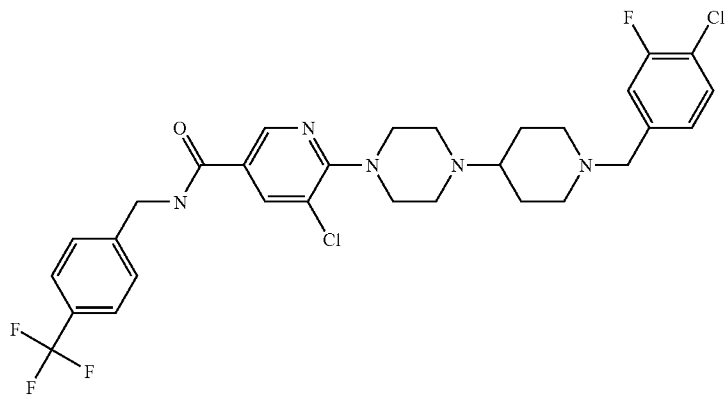 | C |
| 74 | 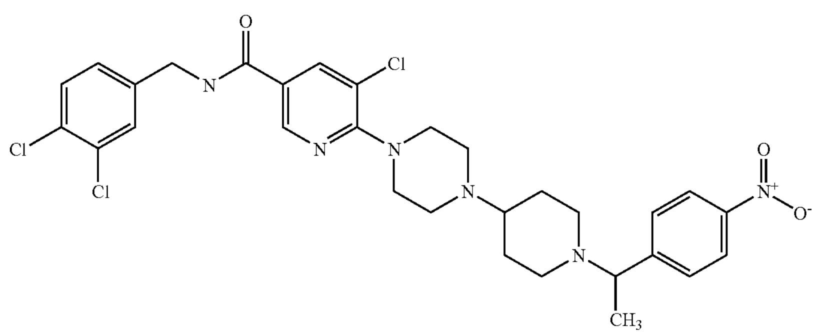 | C |
| 75 | 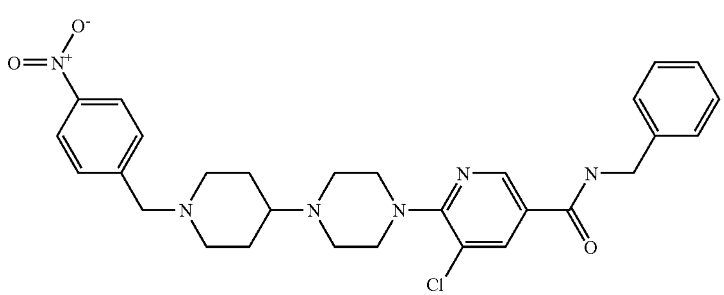 | C |
| 76 | 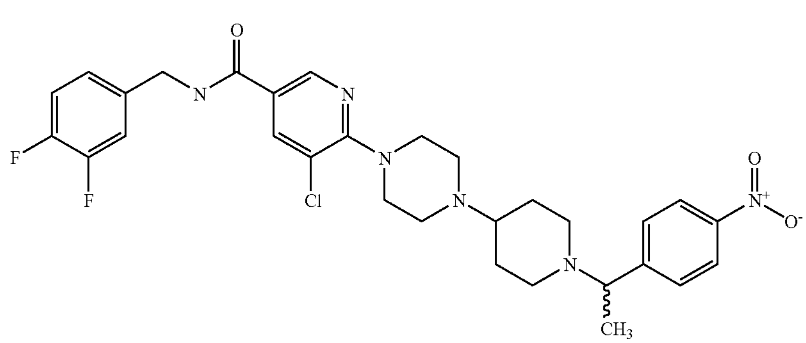 | C |

TABLE 1-continued

| Compound No. | Compound Structure | IC$_{50}$ |
|---|---|---|
| 77 | 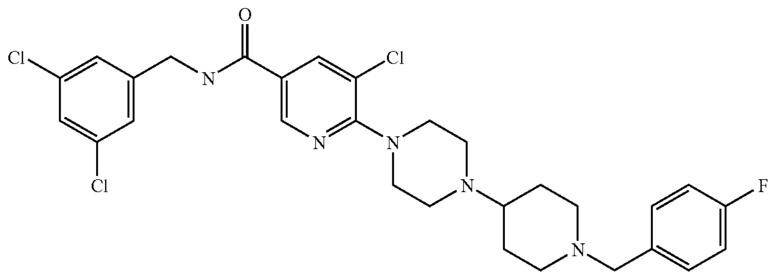 | C |
| 78 | 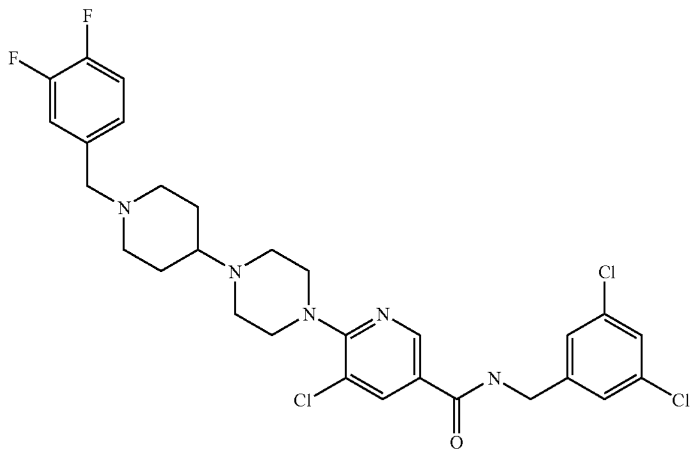 | C |
| 79 | 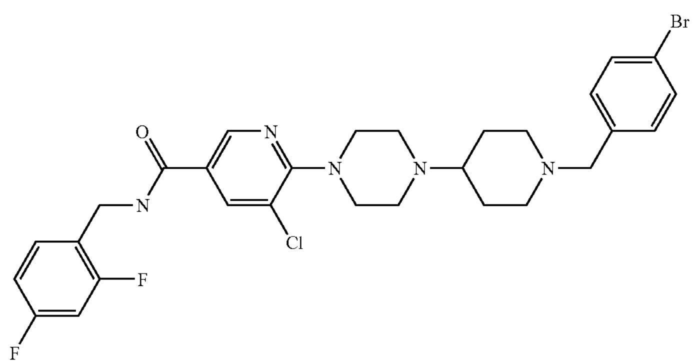 | C |
| 80 | 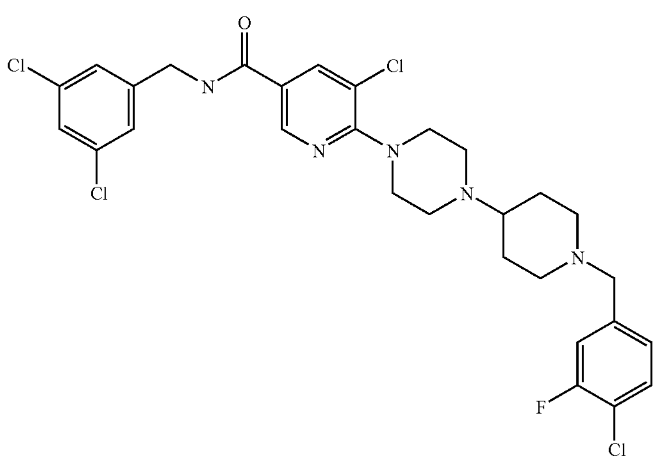 | C |

TABLE 1-continued

| Compound No. | Compound Structure | IC$_{50}$ |
|---|---|---|
| 81 | 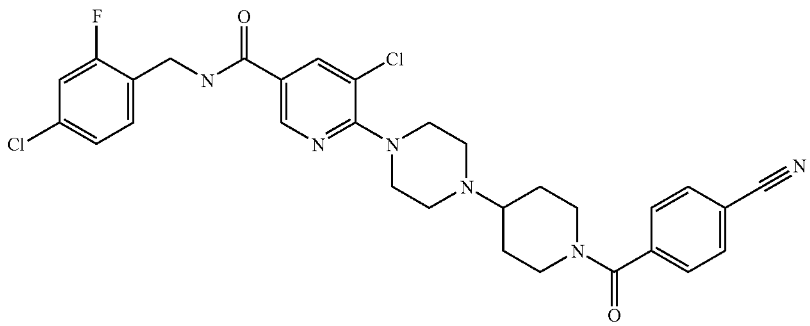 | C |
| 82 | 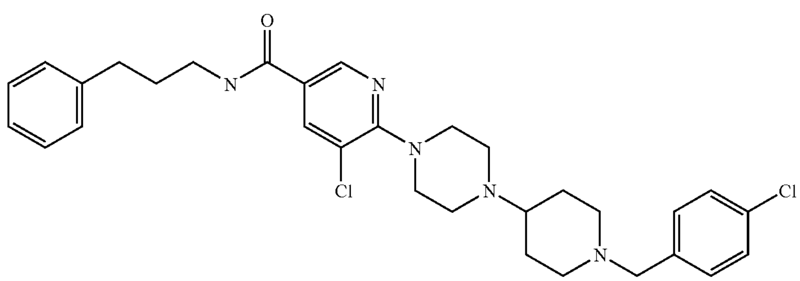 | C |
| 83 | 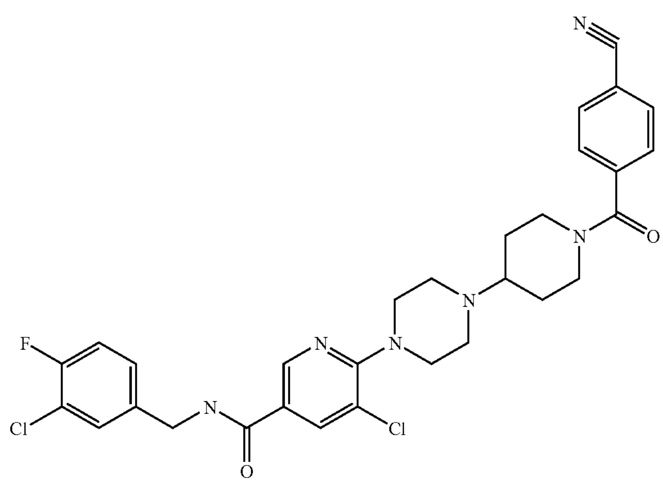 | C |
| 84 | 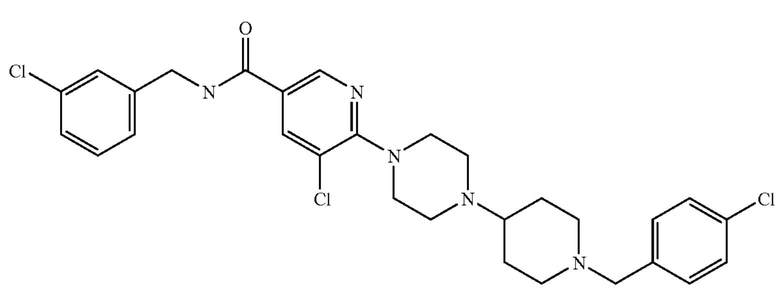 | C |

TABLE 1-continued
| Compound No. | Compound Structure | IC$_{50}$ |
|---|---|---|
| 85 | 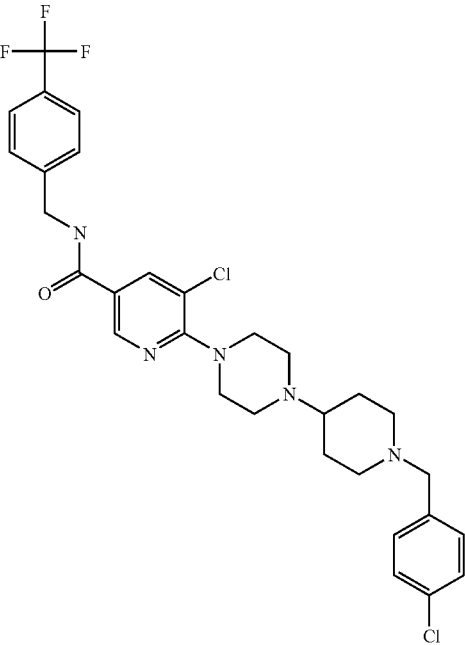 | C |
| 86 | 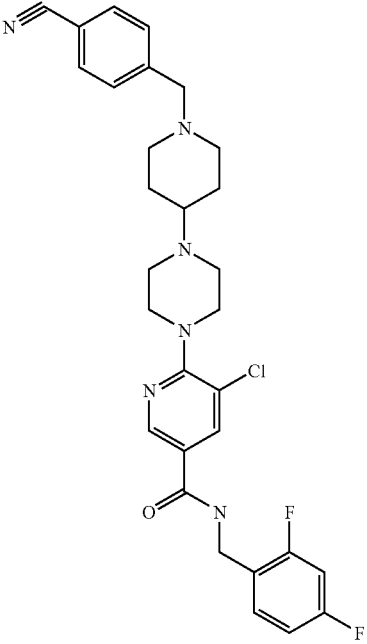 | C |

TABLE 1-continued

| Compound No. | Compound Structure | IC$_{50}$ |
|---|---|---|
| 87 | 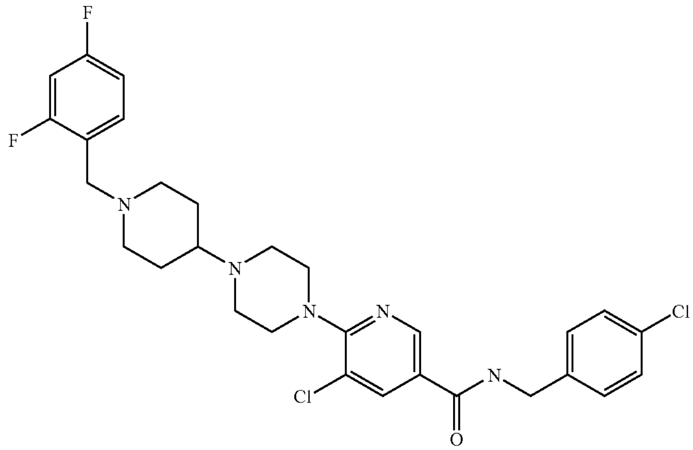 | C |
| 88 | 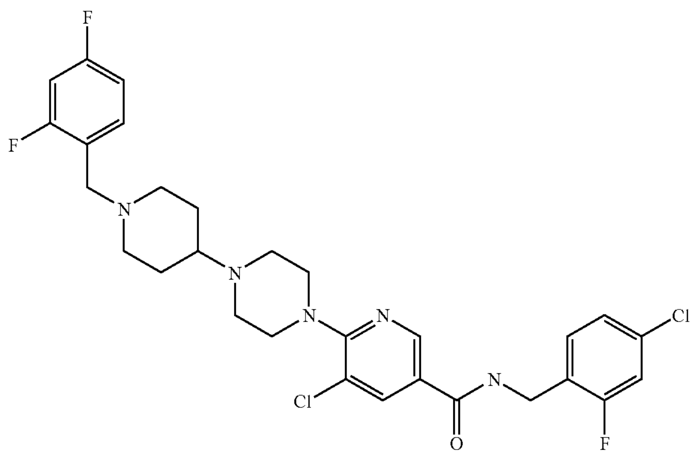 | C |
| 89 | 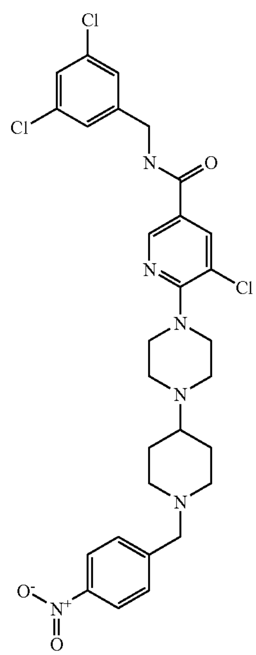 | C |

TABLE 1-continued
| Compound No. | Compound Structure | IC$_{50}$ |
|---|---|---|
| 90 | 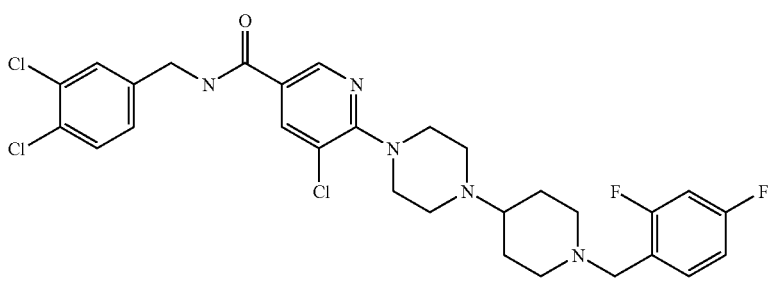 | C |
| 91 | 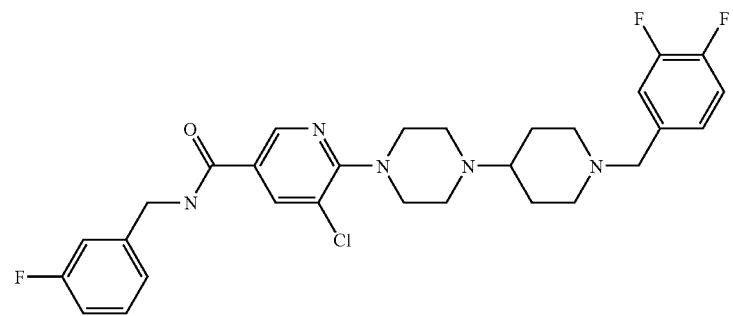 | C |
| 92 | 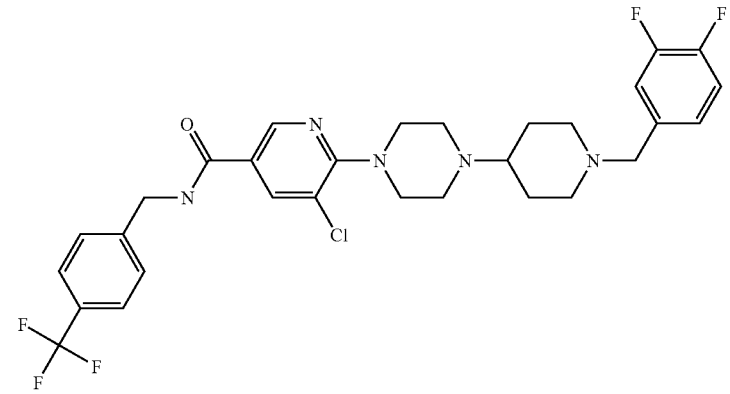 | C |
| 93 | 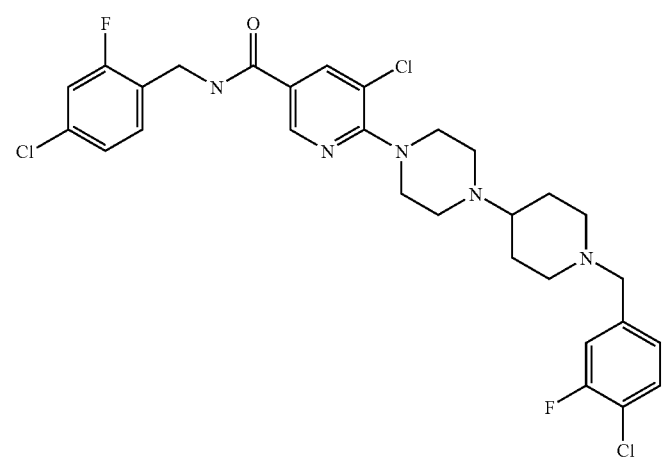 | C |

TABLE 1-continued

| Compound No. | Compound Structure | IC$_{50}$ |
|---|---|---|
| 94 | 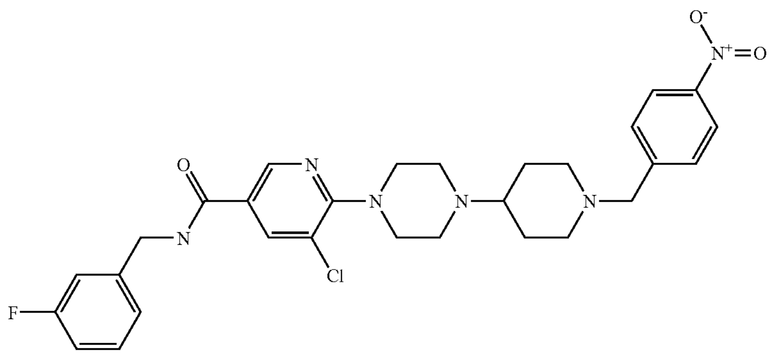 | B |
| 95 | 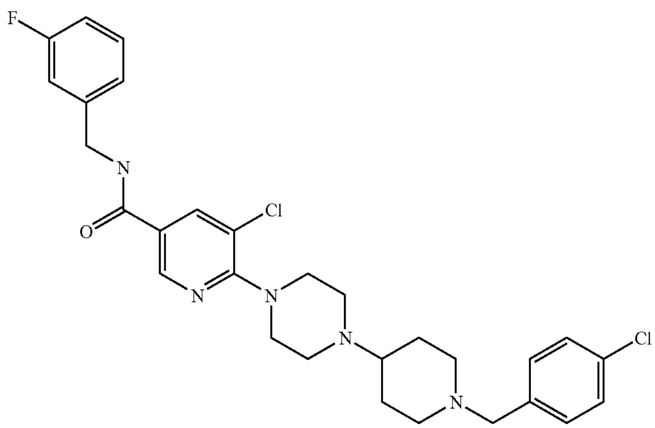 | B |
| 96 | 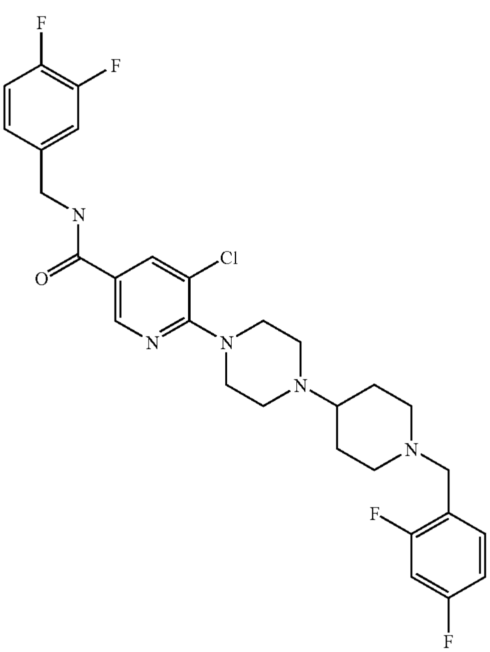 | B |

TABLE 1-continued
| Compound No. | Compound Structure | IC$_{50}$ |
|---|---|---|
| 97 | 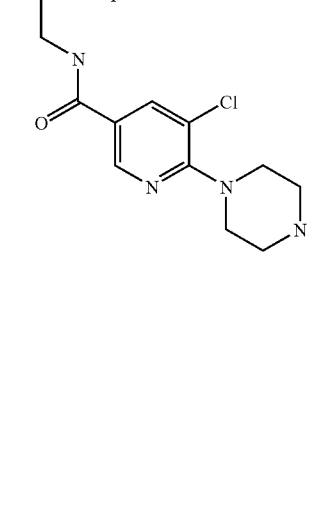 | B |
| 98 | 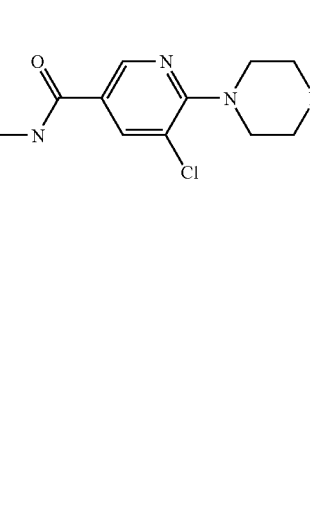 | B |
| 99 | 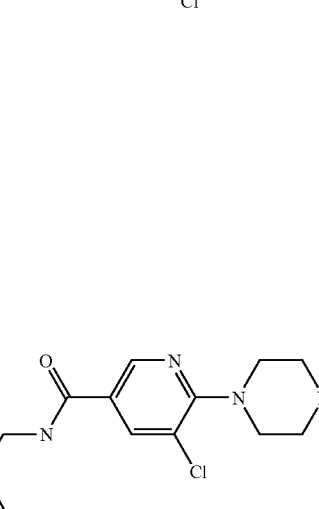 | B |

TABLE 1-continued

| Compound No. | Compound Structure | IC$_{50}$ |
|---|---|---|
| 100 | 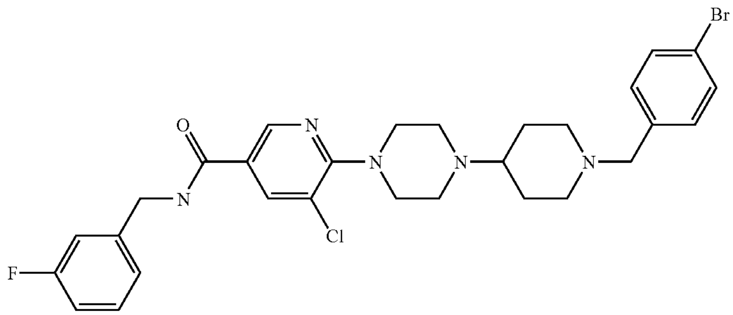 | B |
| 101 | 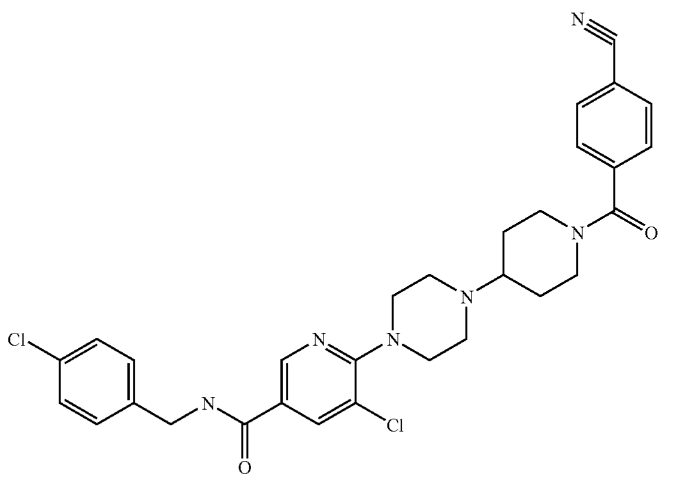 | B |
| 102 | 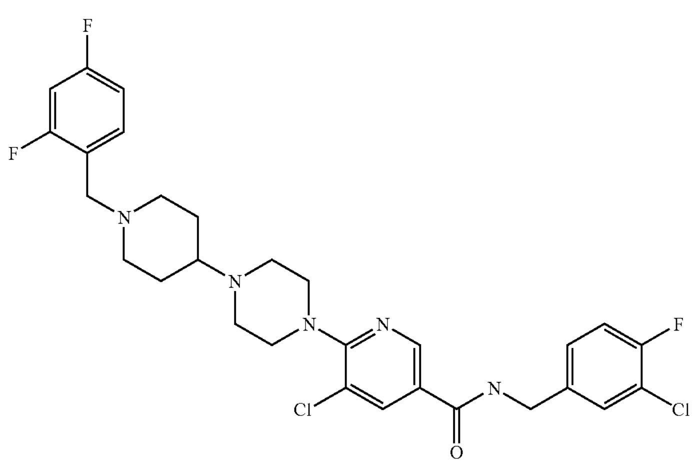 | B |

TABLE 1-continued

| Compound No. | Compound Structure | IC$_{50}$ |
|---|---|---|
| 103 | 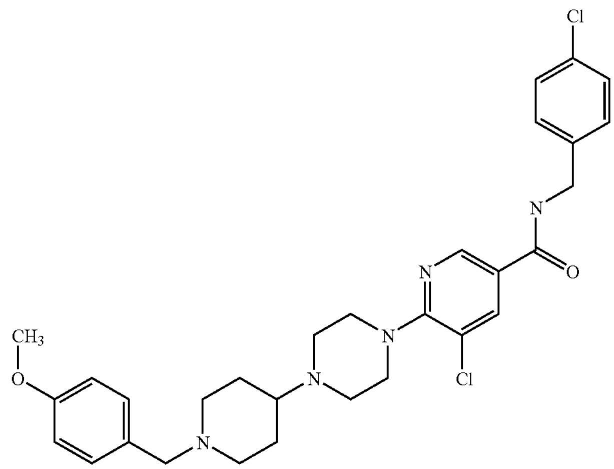 | B |
| 104 | 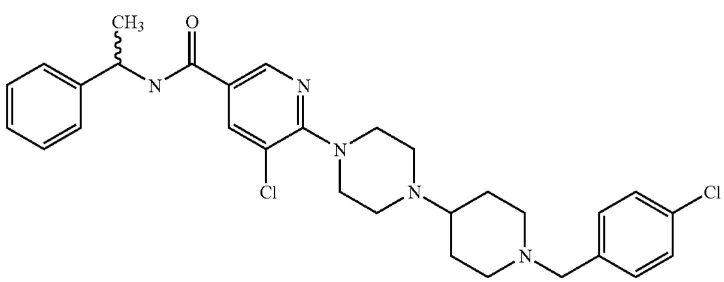 | B |
| 105 | 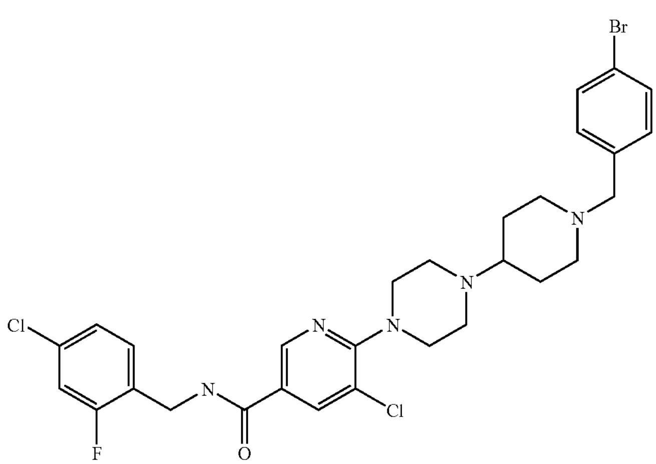 | B |

TABLE 1-continued

| Compound No. | Compound Structure | IC$_{50}$ |
|---|---|---|
| 106 | 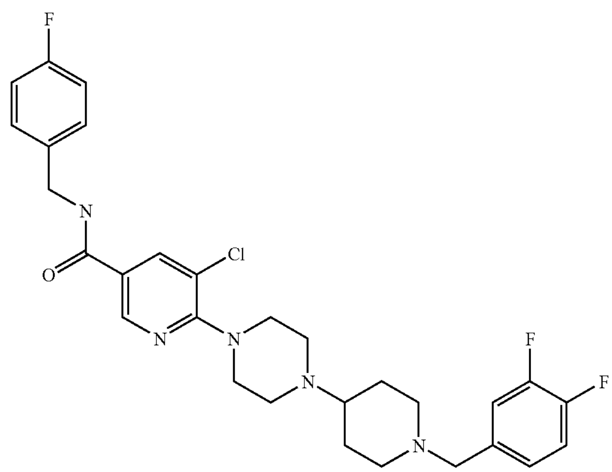 | B |
| 107 | 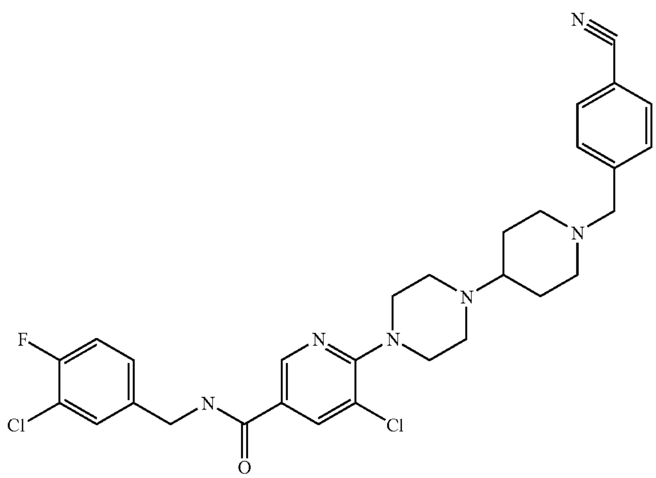 | B |
| 108 | 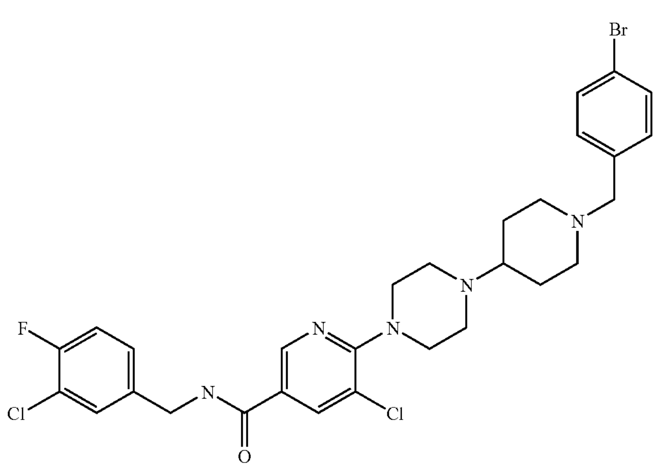 | B |

TABLE 1-continued

| Compound No. | Compound Structure | IC$_{50}$ |
|---|---|---|
| 109 | 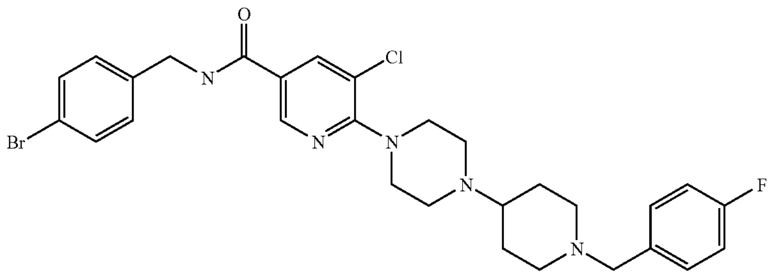 | B |
| 110 | 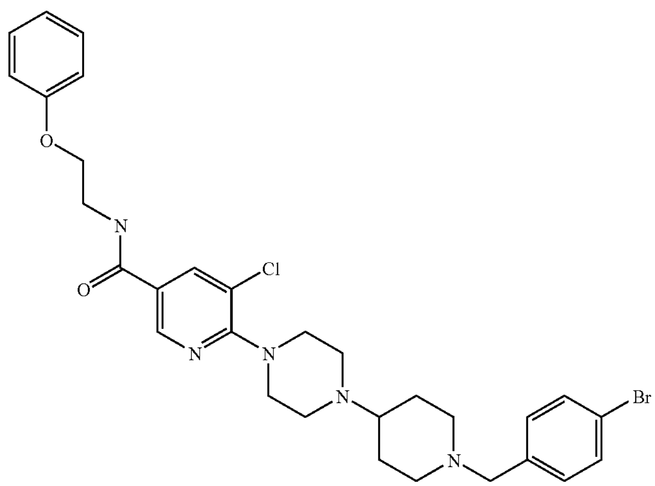 | B |
| 111 | 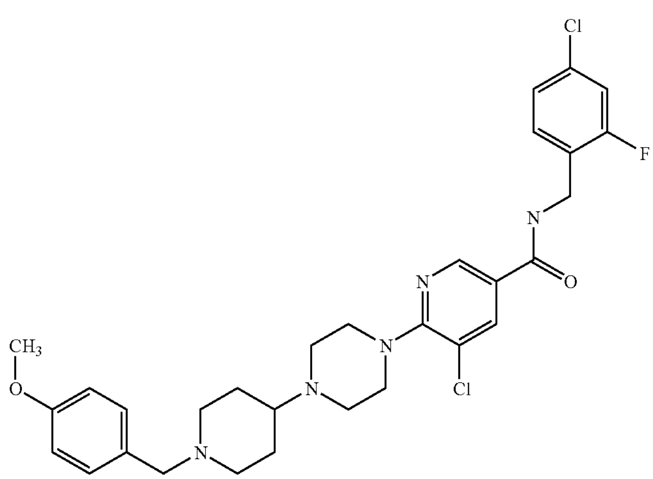 | B |

TABLE 1-continued

| Compound No. | Compound Structure | IC$_{50}$ |
|---|---|---|
| 112 | 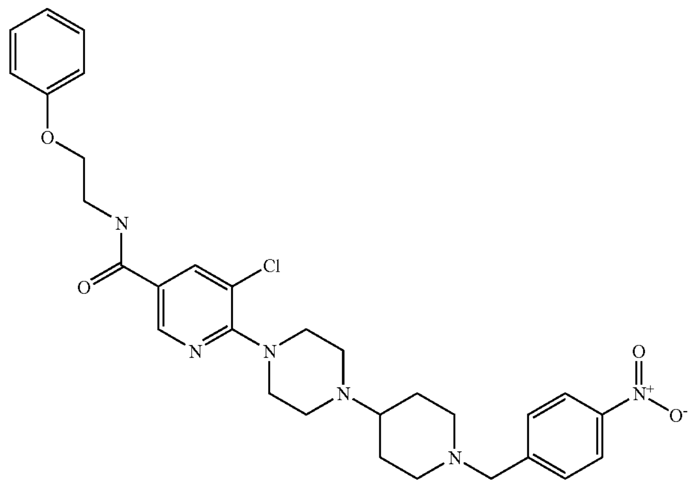 | B |
| 113 | 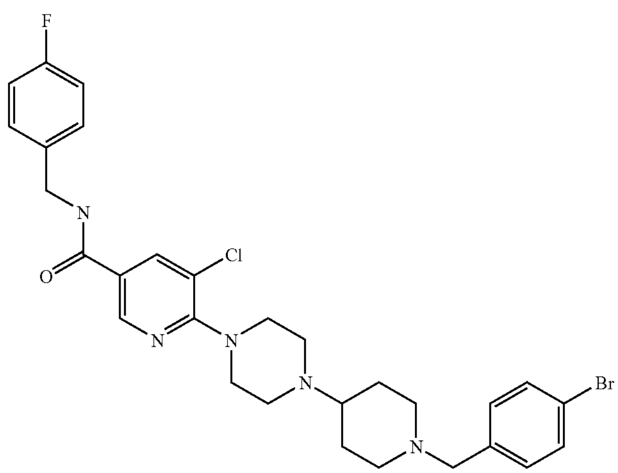 | B |
| 114 | 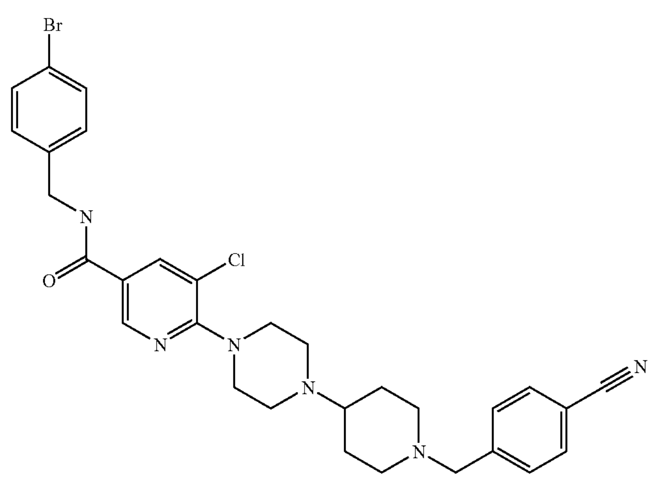 | B |

TABLE 1-continued
| Compound No. | Compound Structure | IC$_{50}$ |
|---|---|---|
| 115 | 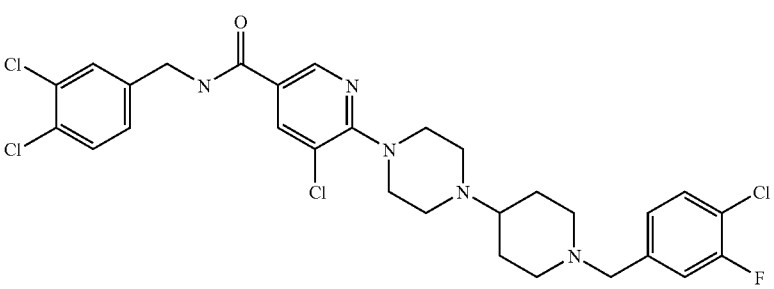 | B |
| 116 | 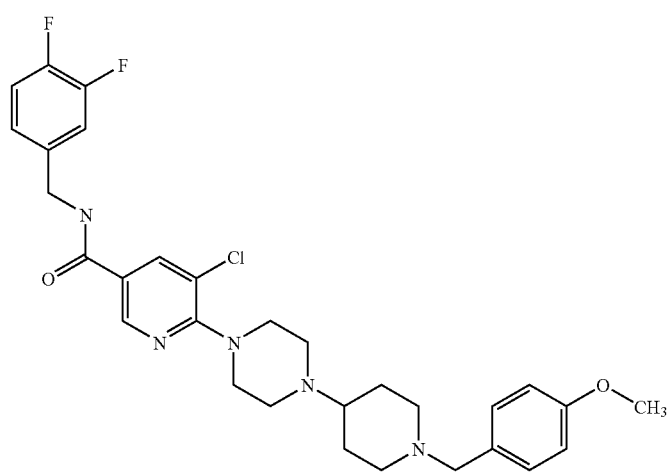 | B |
| 117 | 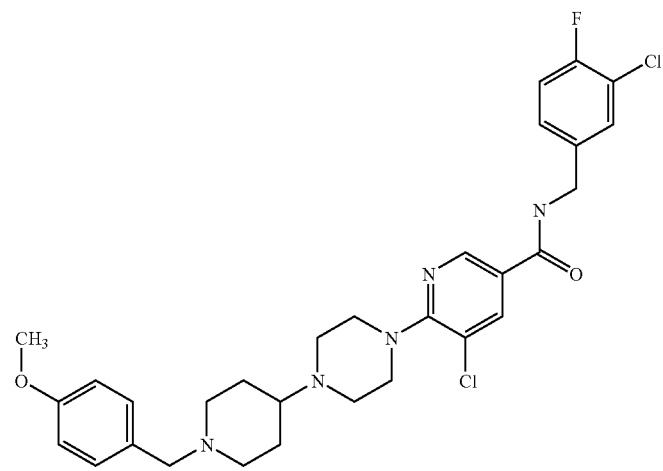 | B |

TABLE 1-continued

| Compound No. | Compound Structure | IC$_{50}$ |
|---|---|---|
| 118 | 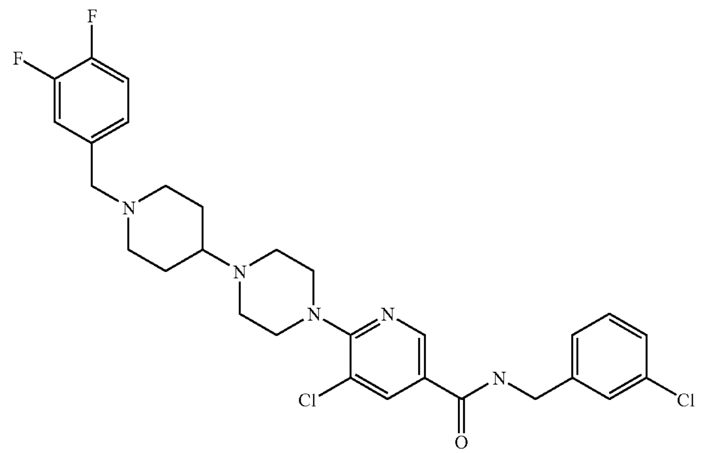 | B |
| 119 | 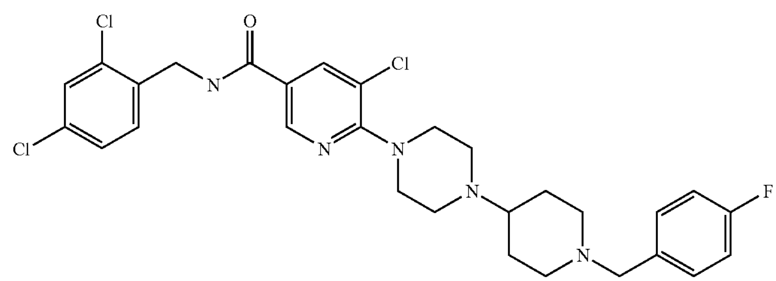 | B |
| 120 | 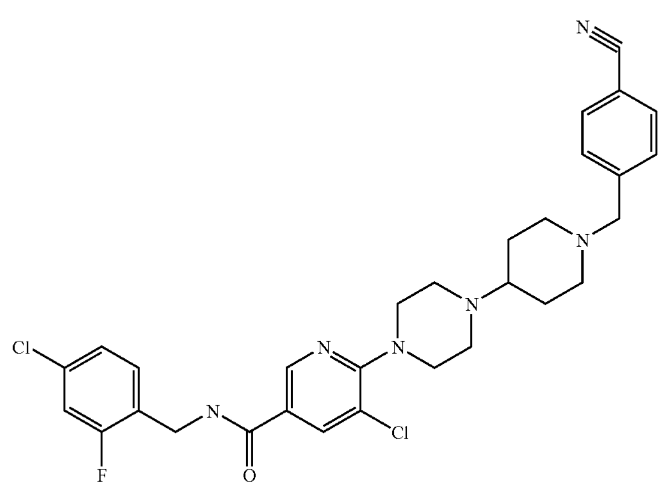 | B |

TABLE 1-continued
| Compound No. | Compound Structure | IC$_{50}$ |
|---|---|---|
| 121 | 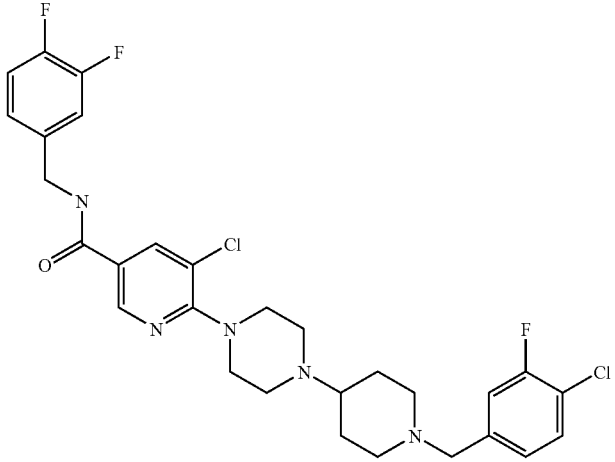 | B |
| 122 | 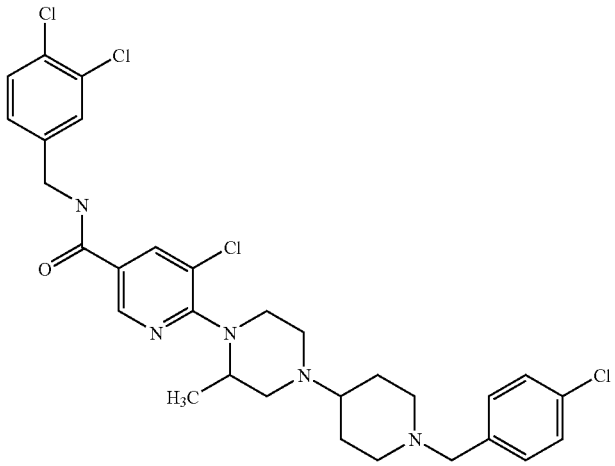 | B |
| 123 | 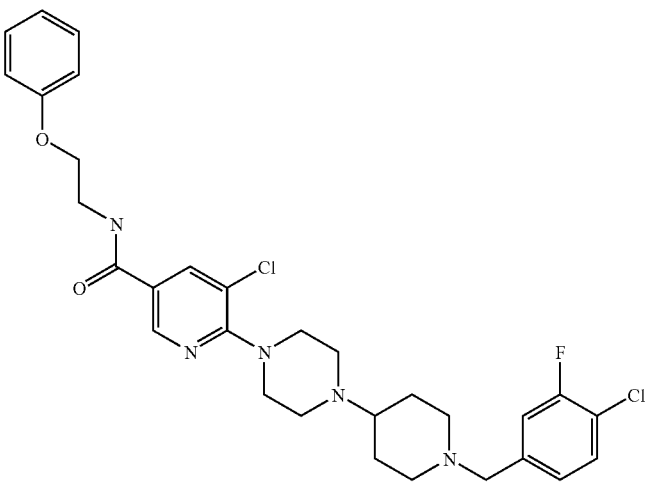 | B |

TABLE 1-continued

| Compound No. | Compound Structure | IC$_{50}$ |
|---|---|---|
| 124 | 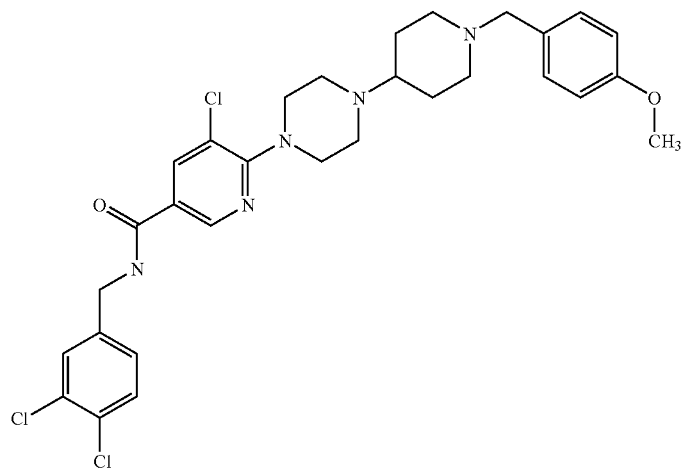 | B |
| 125 | 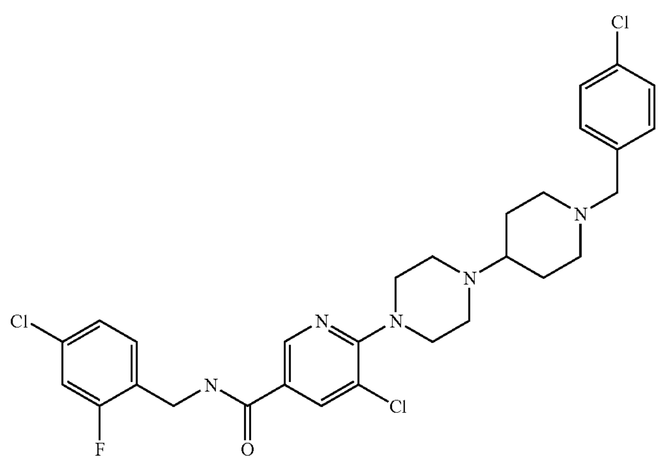 | B |
| 126 | 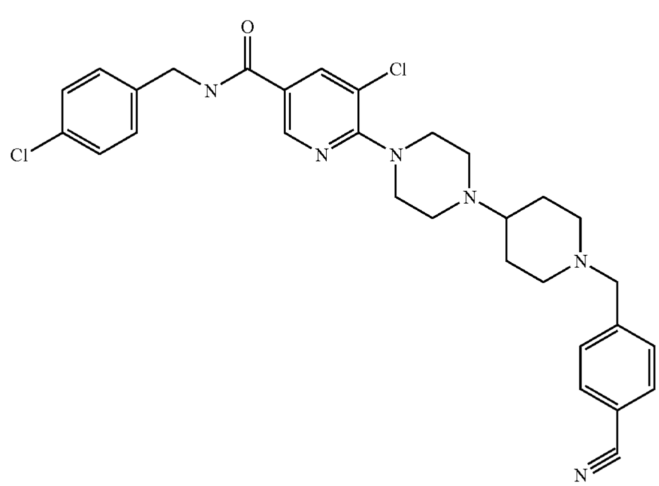 | B |

TABLE 1-continued
| Compound No. | Compound Structure | IC$_{50}$ |
|---|---|---|
| 127 | 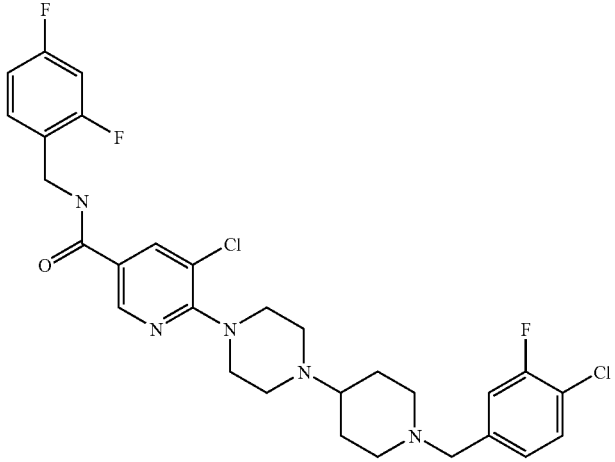 | B |
| 128 | 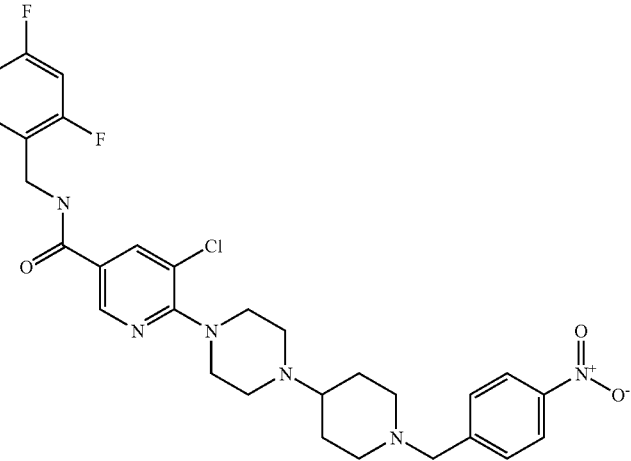 | B |
| 129 | 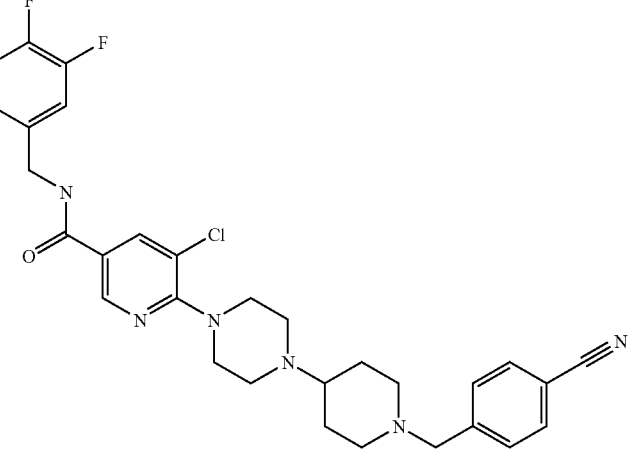 | B |

TABLE 1-continued
| Compound No. | Compound Structure | IC$_{50}$ |
|---|---|---|
| 130 | 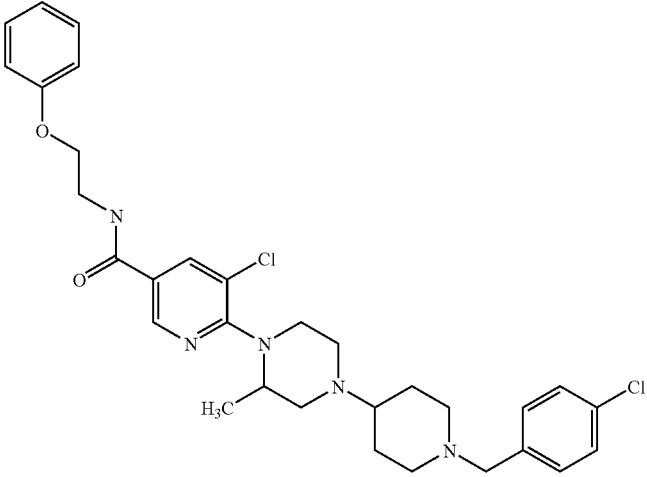 | B |
| 131 | 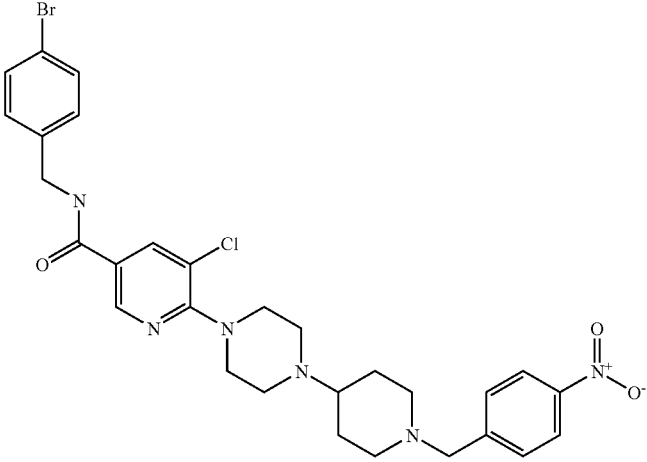 | B |
| 132 | 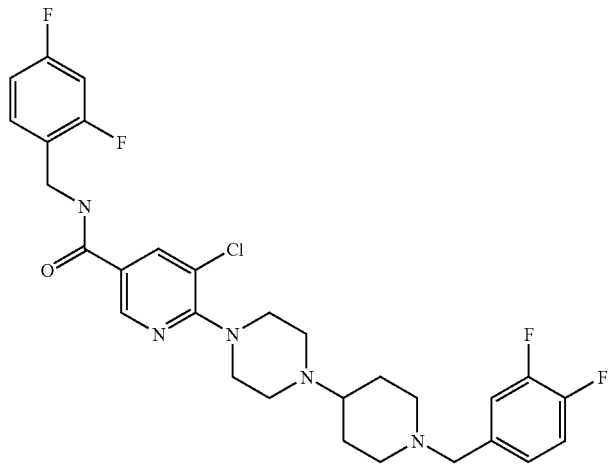 | B |

TABLE 1-continued

| Compound No. | Compound Structure | IC$_{50}$ |
|---|---|---|
| 133 | 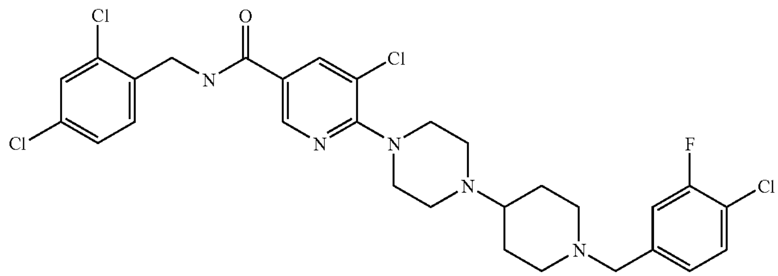 | B |
| 134 | 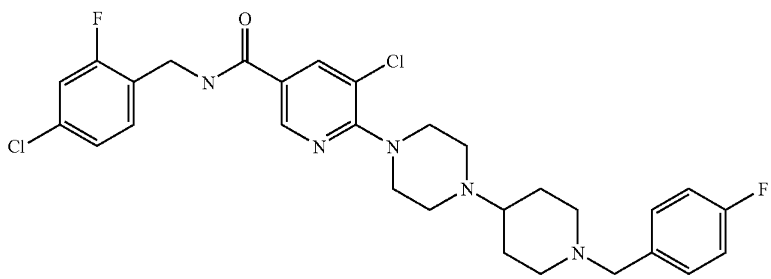 | B |
| 135 | 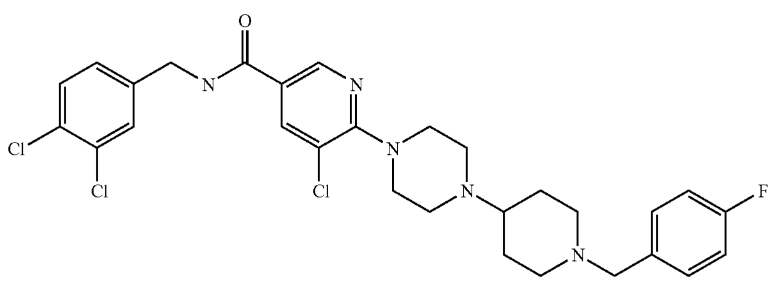 | B |
| 136 | 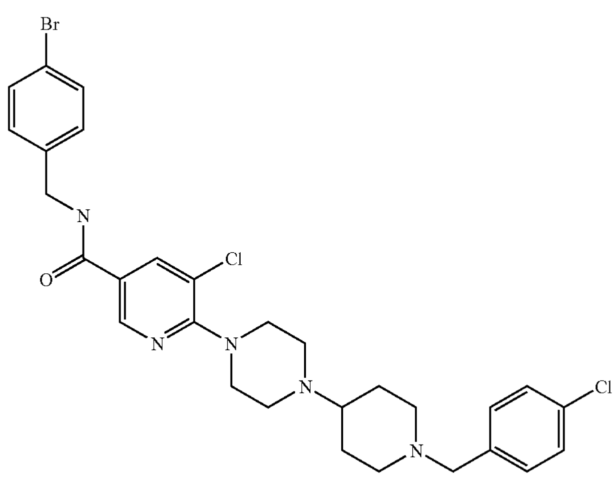 | B |

TABLE 1-continued

| Compound No. | Compound Structure | IC$_{50}$ |
|---|---|---|
| 137 | 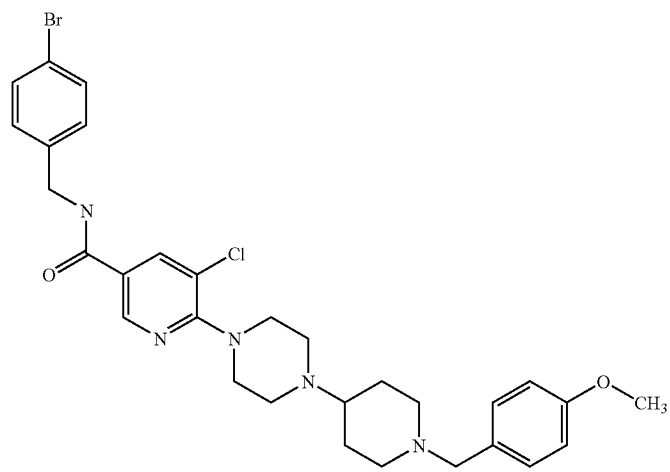 | B |
| 138 | 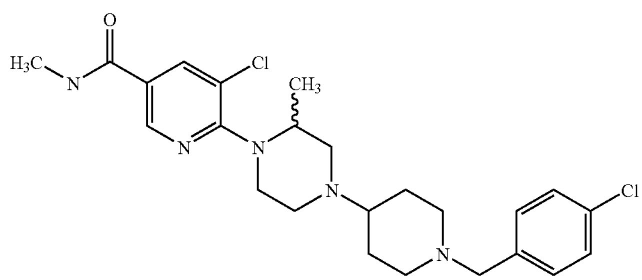 | B |
| 139 | 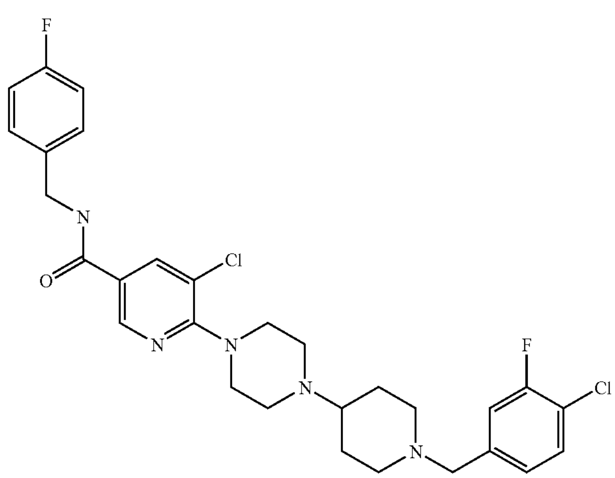 | B |
| 140 | 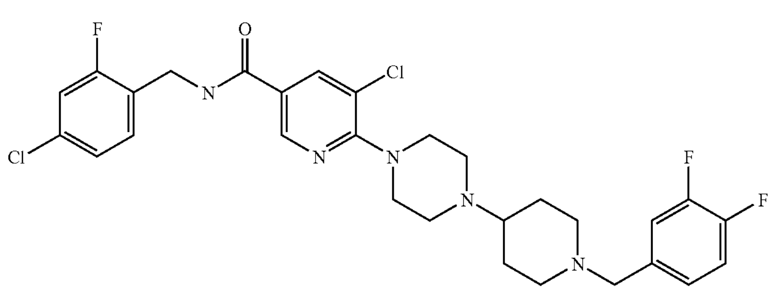 | B |

TABLE 1-continued

| Compound No. | Compound Structure | IC$_{50}$ |
|---|---|---|
| 141 | 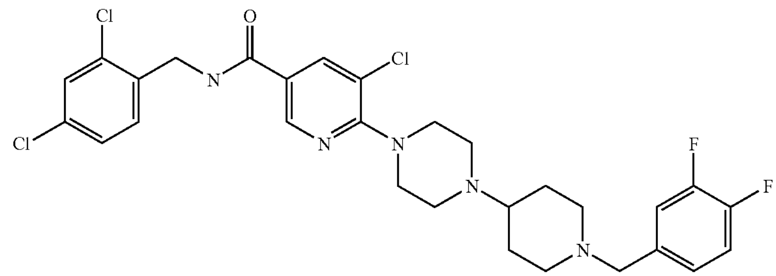 | B |
| 142 | 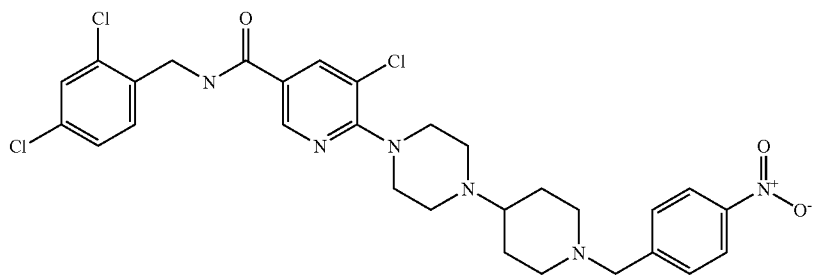 | B |
| 143 | 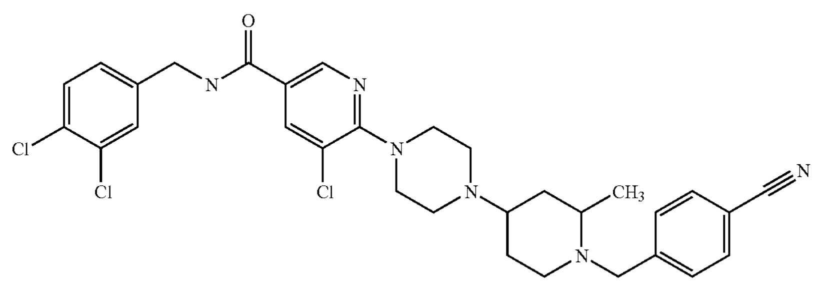 | B |
| 144 | 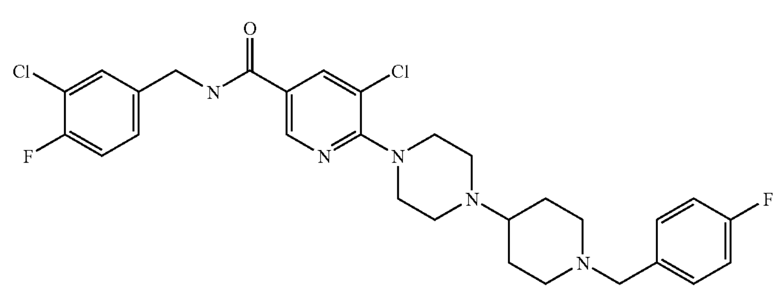 | B |

TABLE 1-continued

| Compound No. | Compound Structure | IC$_{50}$ |
|---|---|---|
| 145 | 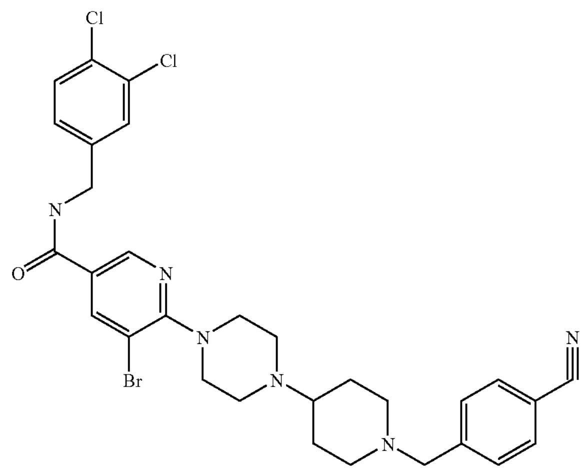 | B |
| 146 | 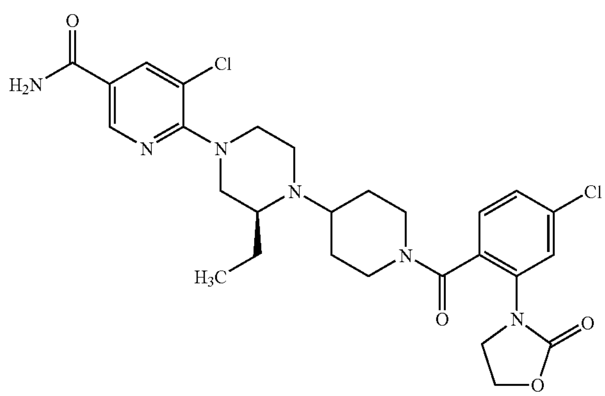 | B |
| 147 | 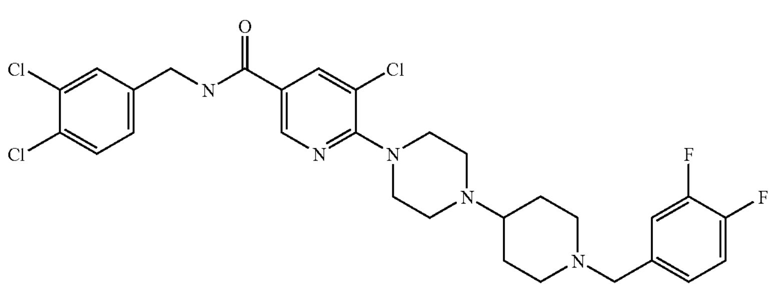 | B |
| 148 | 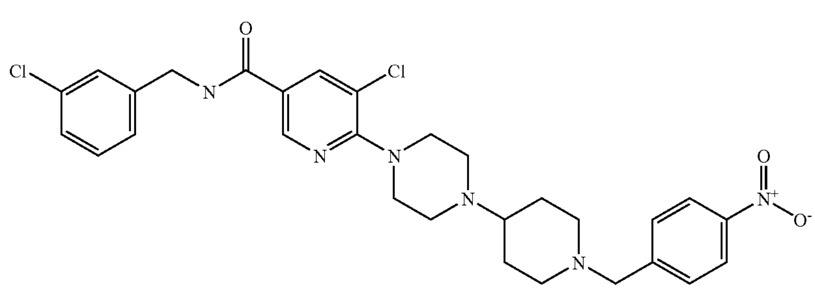 | B |

TABLE 1-continued

| Compound No. | Compound Structure | IC$_{50}$ |
|---|---|---|
| 149 | 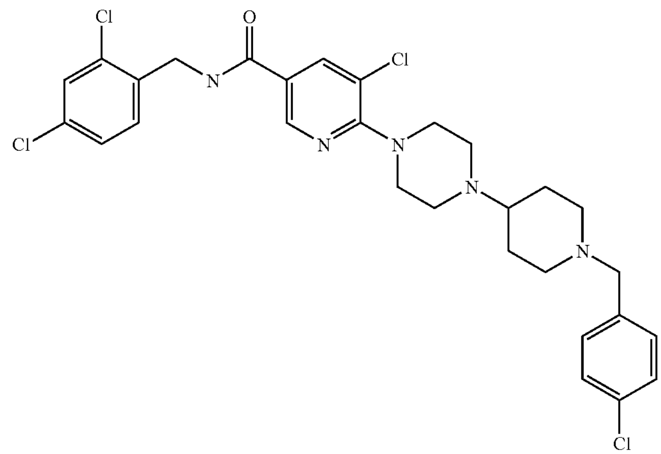 | B |
| 150 | 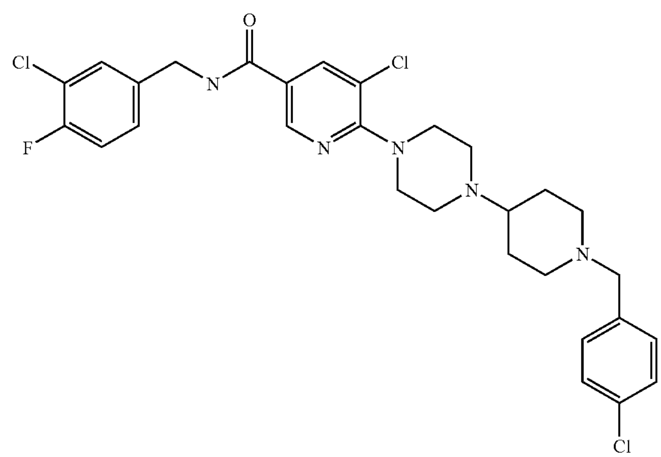 | B |
| 151 | 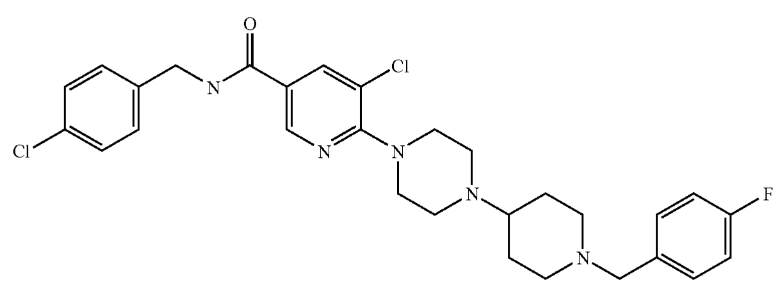 | B |
| 152 | 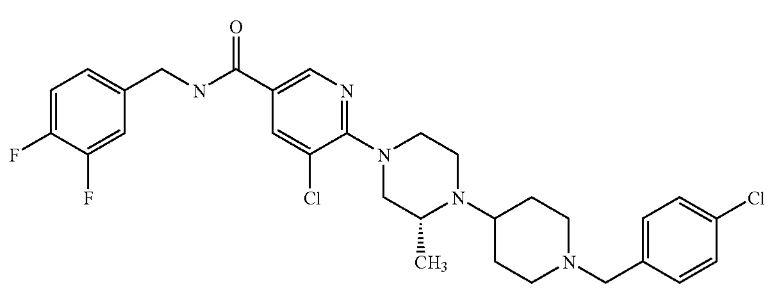 | B |

TABLE 1-continued

| Compound No. | Compound Structure | IC$_{50}$ |
|---|---|---|
| 153 | 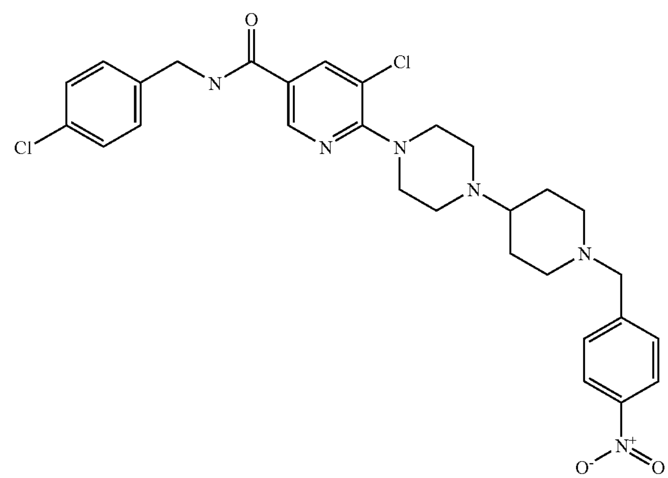 | B |
| 154 | 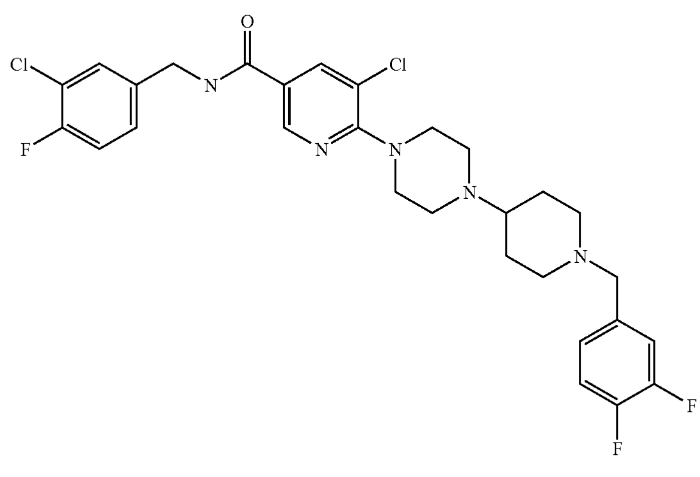 | B |
| 155 | 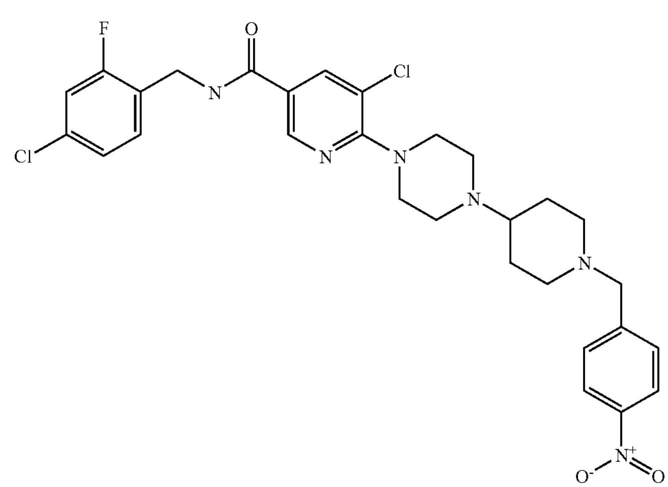 | B |

TABLE 1-continued

| Compound No. | Compound Structure | IC$_{50}$ |
|---|---|---|
| 156 | 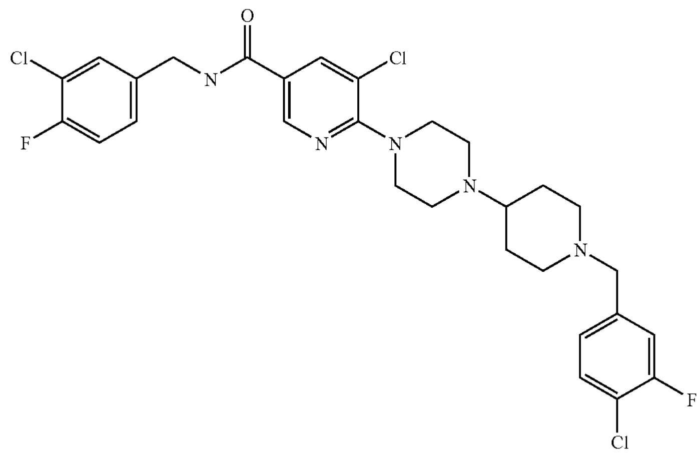 | B |
| 157 | 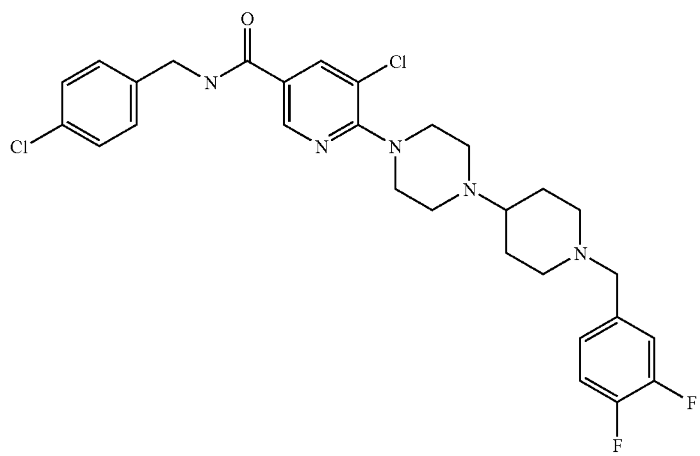 | B |
| 158 | 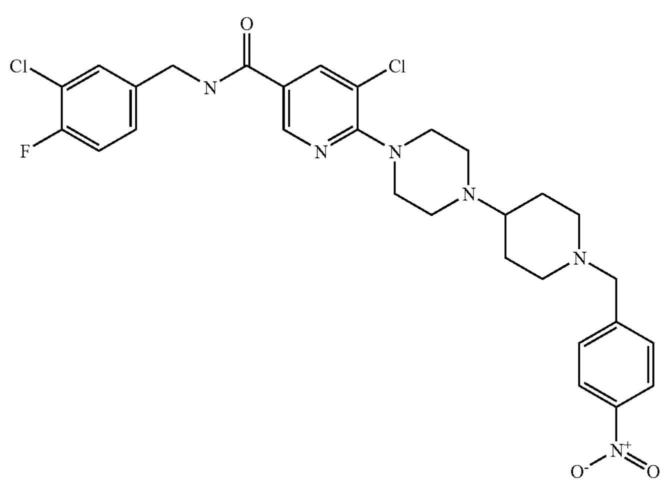 | B |

TABLE 1-continued

| Compound No. | Compound Structure | IC$_{50}$ |
|---|---|---|
| 159 | 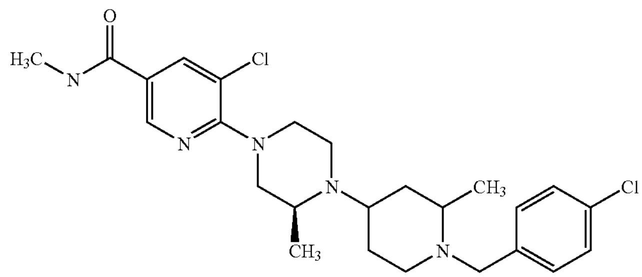 | B |
| 160 | 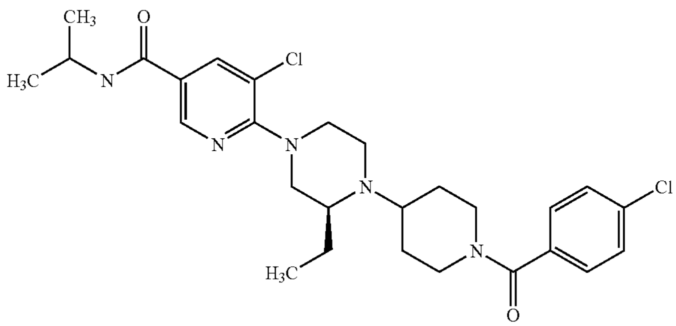 | B |
| 161 | 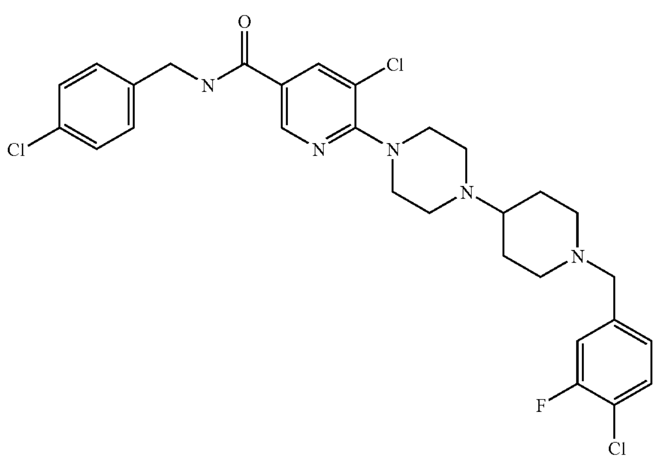 | B |
| 162 | 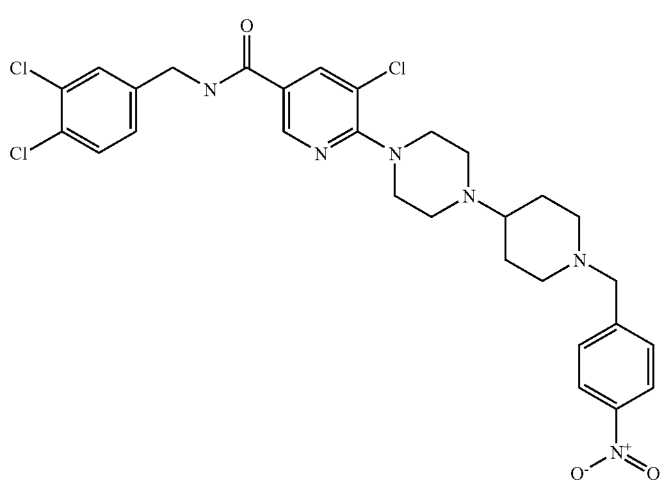 | A |

TABLE 1-continued

| Compound No. | Compound Structure | IC$_{50}$ |
|---|---|---|
| 163 | 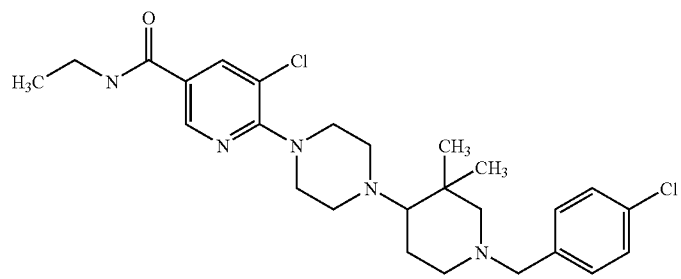 | A |
| 164 | 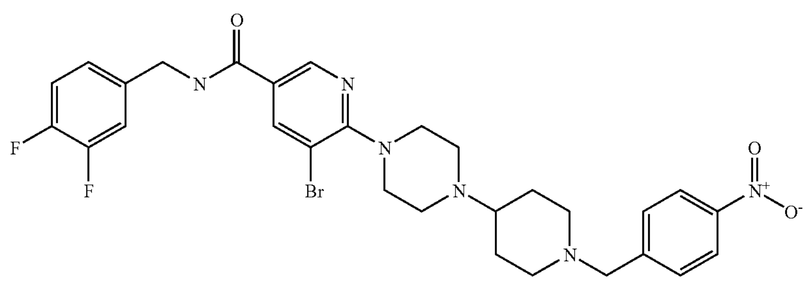 | A |
| 165 | 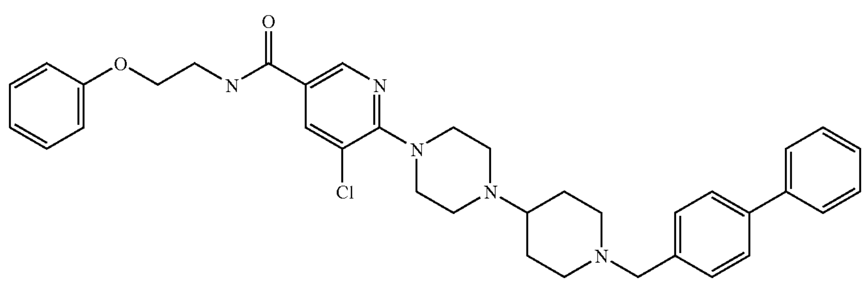 | C |
| 166 | 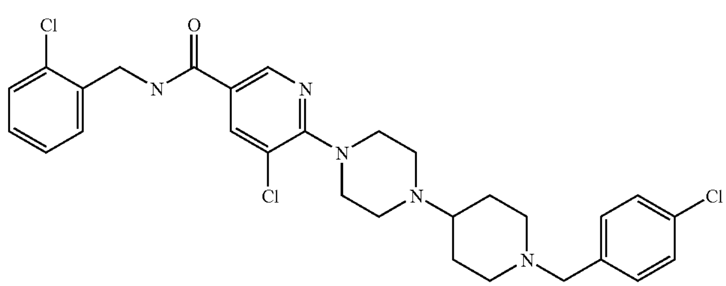 | C |
| 167 | 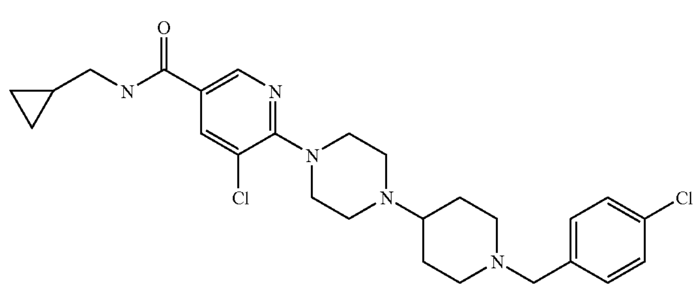 | C |

TABLE 1-continued

| Compound No. | Compound Structure | IC$_{50}$ |
|---|---|---|
| 168 | 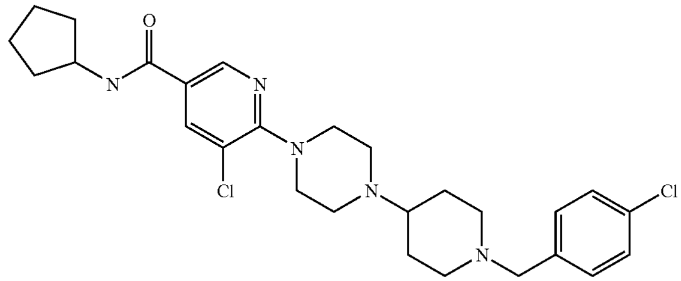 | C |
| 169 | 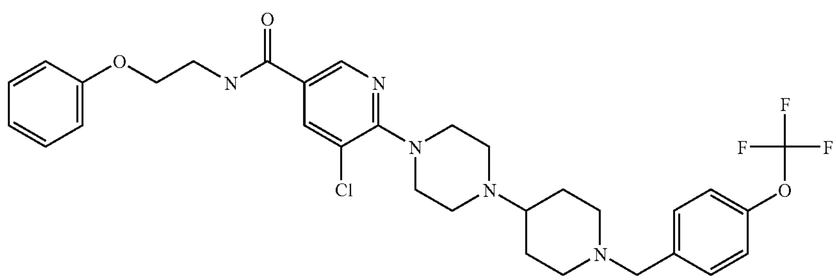 | C |
| 170 | 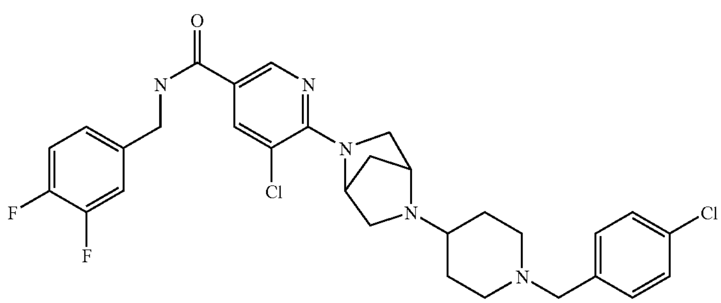 | C |
| 171 | 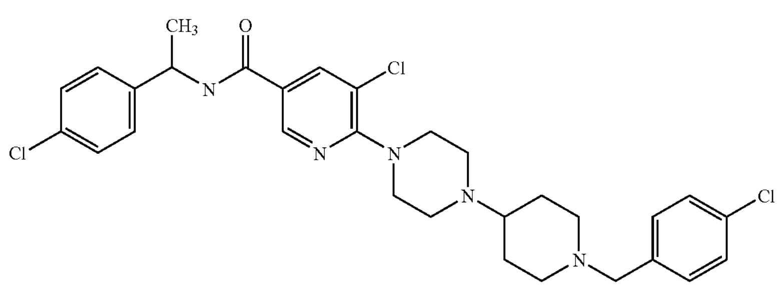 | B |
| 172 | 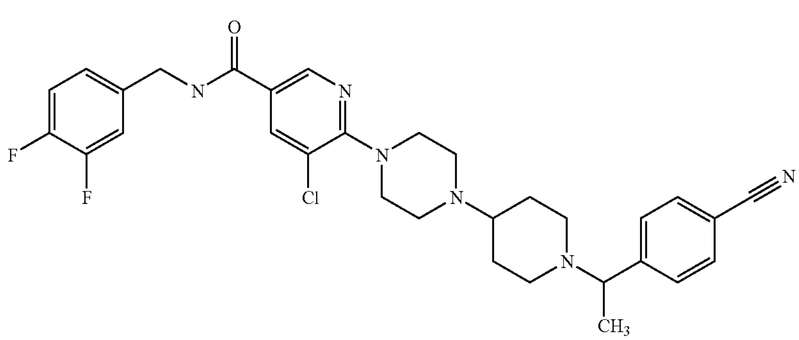 | C |

TABLE 1-continued
| Compound No. | Compound Structure | IC$_{50}$ |
|---|---|---|
| 173 | 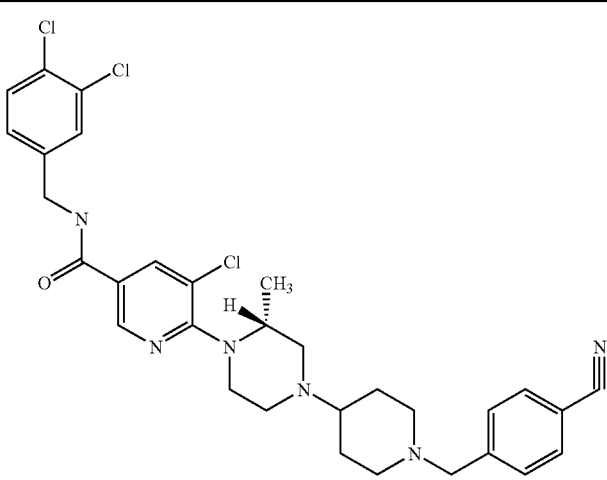 | C |
| 174 | 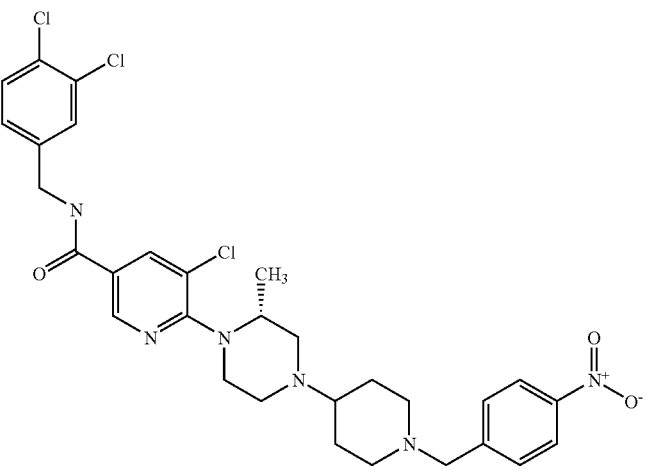 | B |
| 175 | 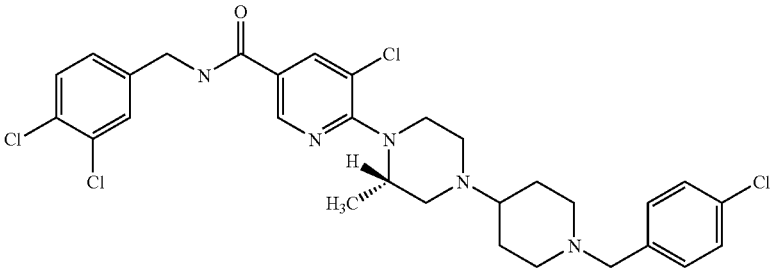 | B |
| 176 | 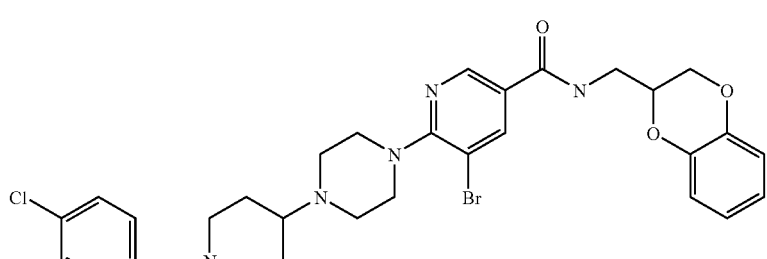 | C |

TABLE 1-continued
| Compound No. | Compound Structure | IC$_{50}$ |
|---|---|---|
| 177 | 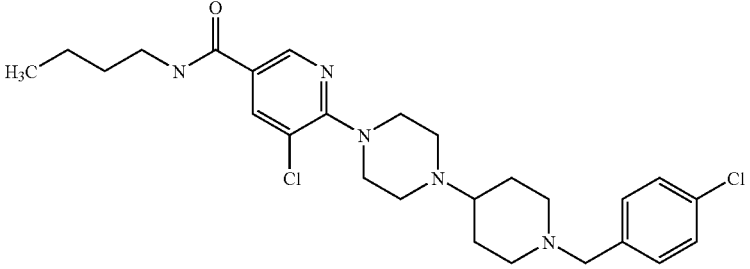 | C |
| 178 | 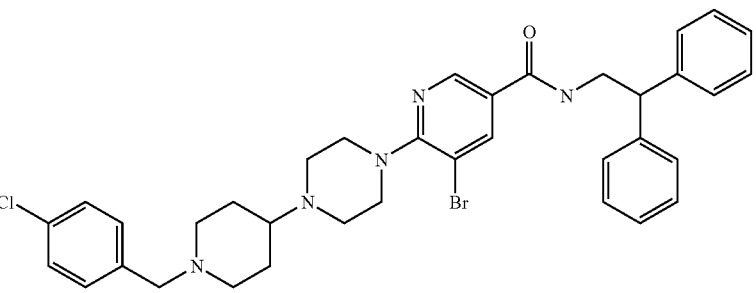 | C |
| 179 | 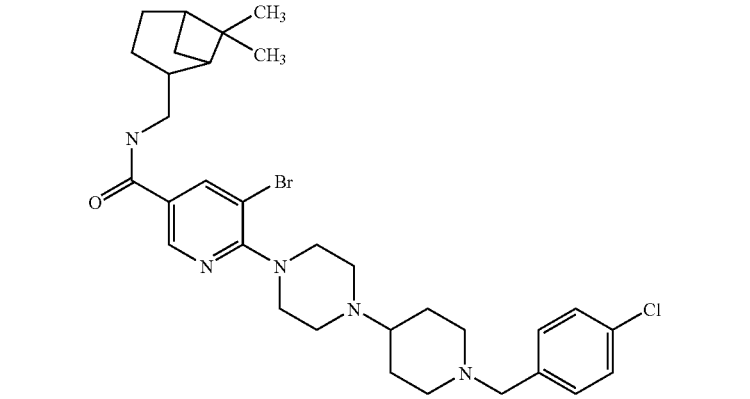 | C |
| 180 | 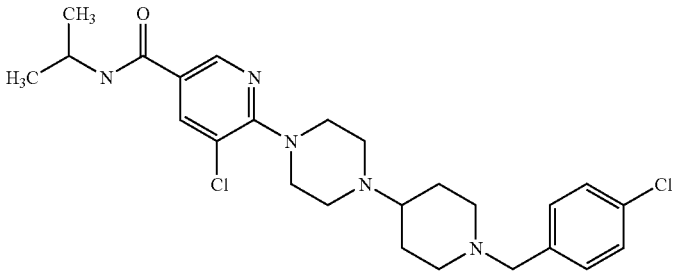 | C |
| 181 | 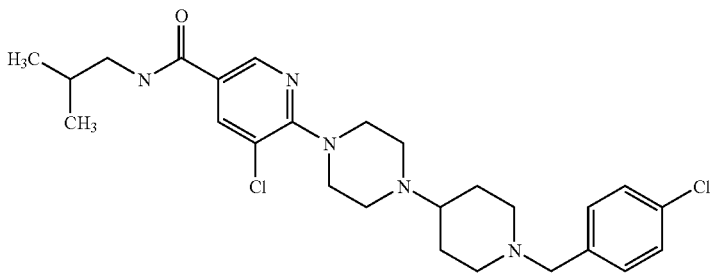 | C |

TABLE 1-continued

| Compound No. | Compound Structure | IC$_{50}$ |
|---|---|---|
| 182 | 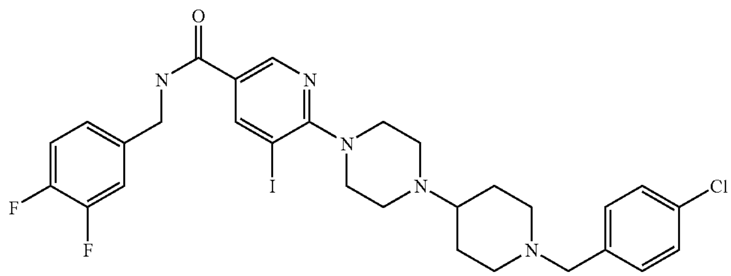 | A |
| 183 | 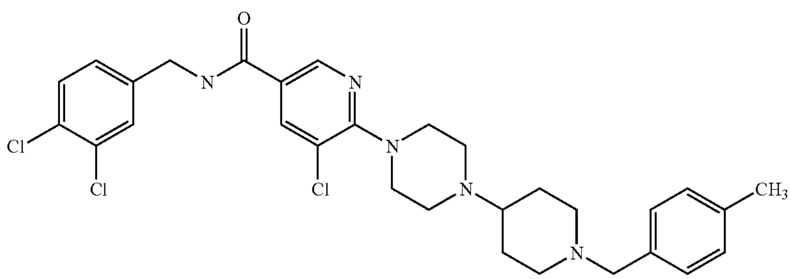 | C |
| 184 | 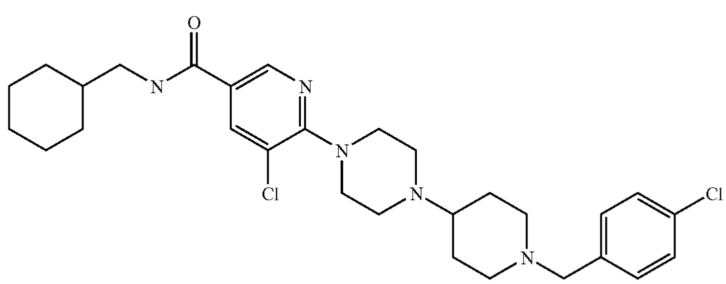 | B |
| 185 | 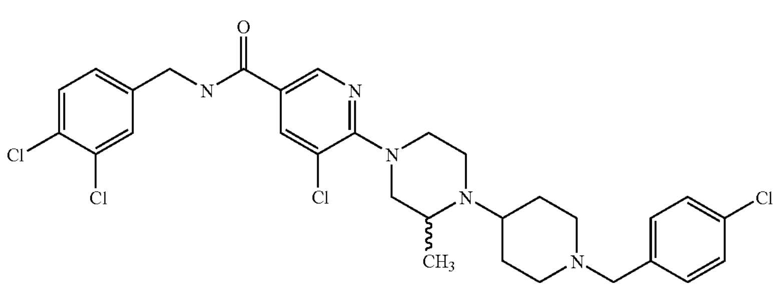 | A |

TABLE 1-continued
| Compound No. | Compound Structure | IC$_{50}$ |
|---|---|---|
| 186 | 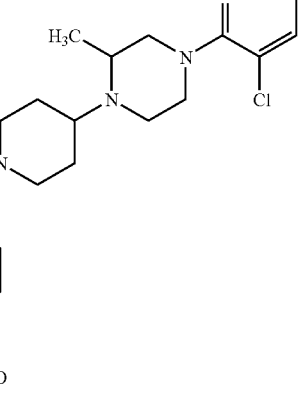 | A |
| 187 | 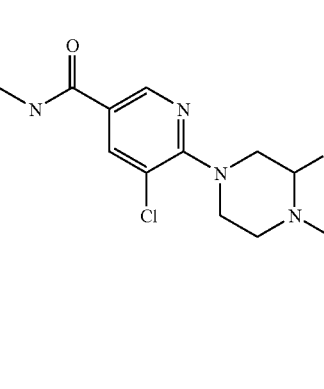 | A |
| 188 | 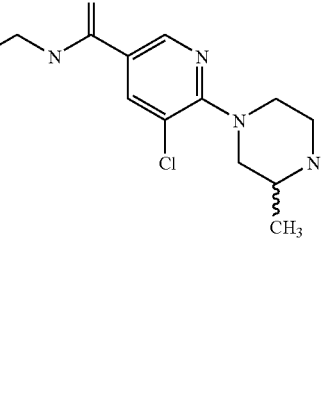 | B |
| 189 | 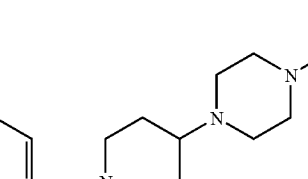 | C |

TABLE 1-continued

| Compound No. | Compound Structure | IC$_{50}$ |
|---|---|---|
| 190 | 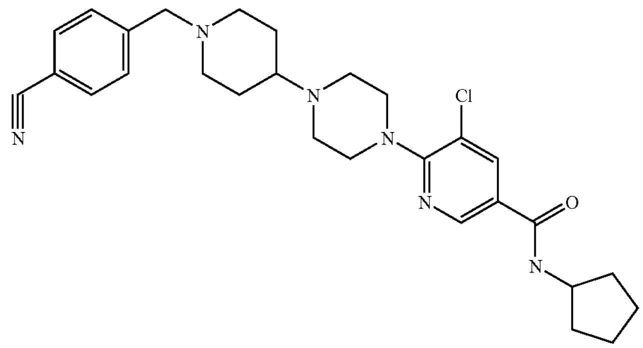 | C |
| 191 | 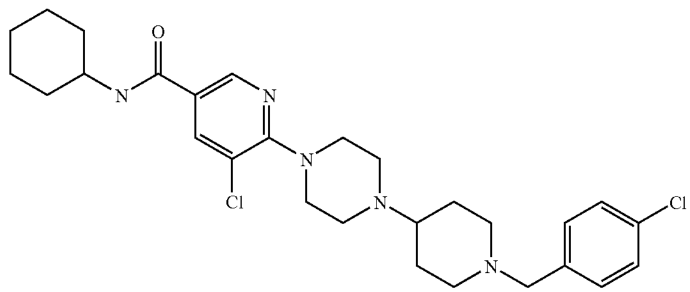 | C |
| 192 | 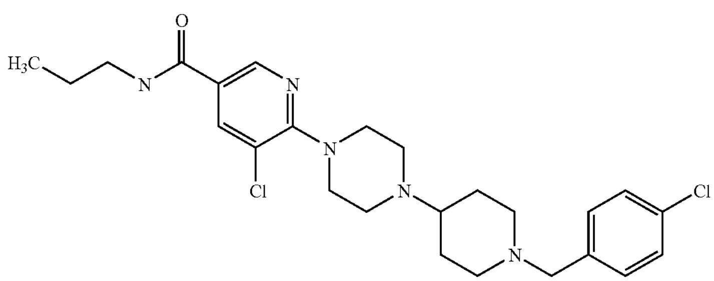 | C |
| 193 | 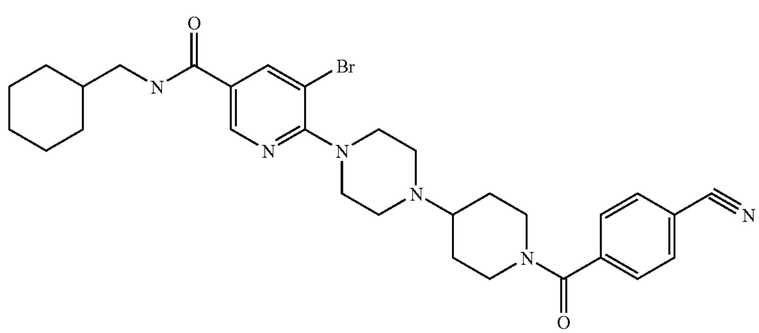 | B |
| 194 | 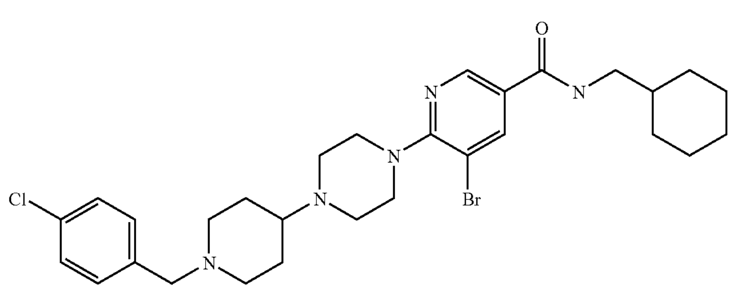 | B |

TABLE 1-continued
| Compound No. | Compound Structure | IC$_{50}$ |
|---|---|---|
| 195 | 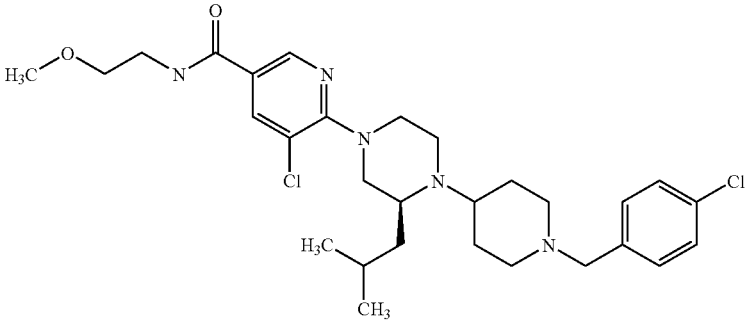 | C |
| 196 | 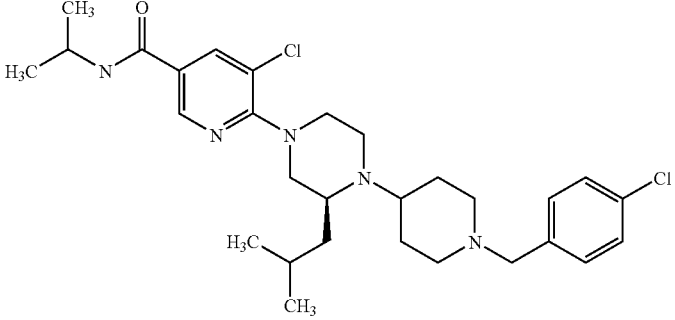 | C |
| 197 | 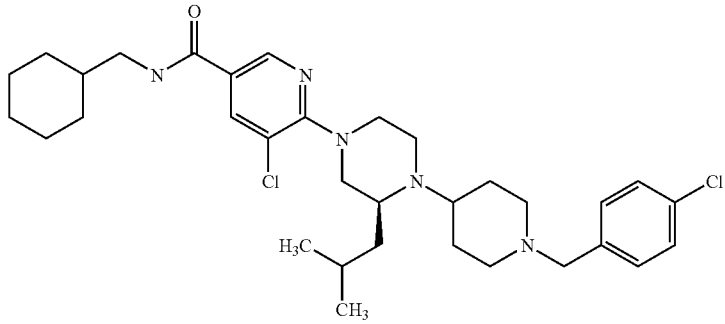 | B |
| 198 | 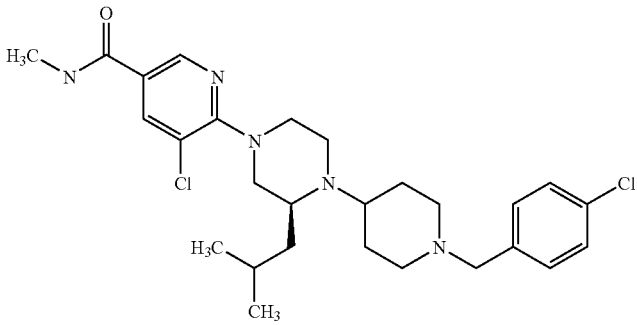 | C |

TABLE 1-continued
| Compound No. | Compound Structure | IC$_{50}$ |
|---|---|---|
| 199 | 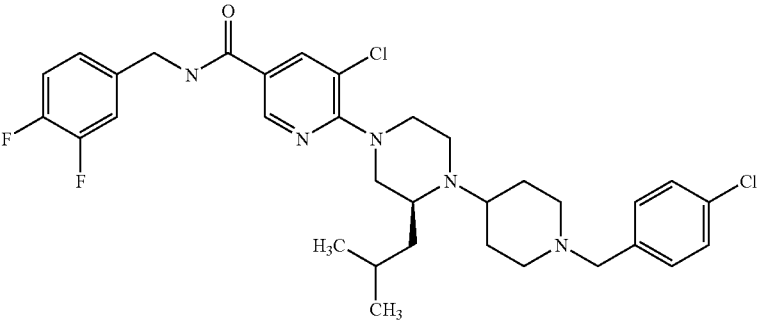 | C |
| 200 | 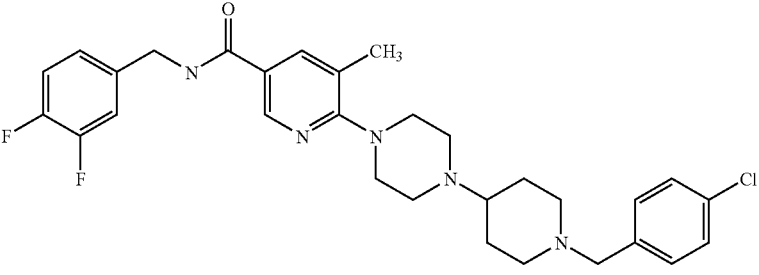 | C |
| 201 | 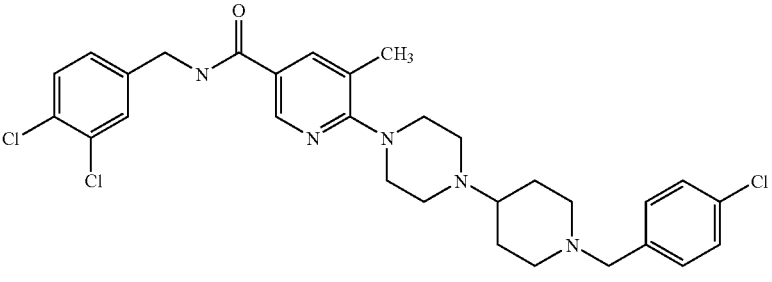 | C |
| 202 | 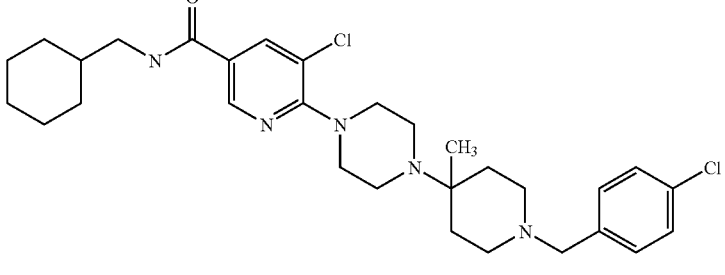 | B |
| 203 | 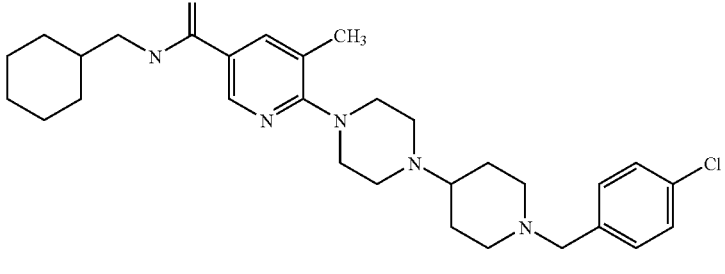 | C |

TABLE 1-continued

| Compound No. | Compound Structure | IC$_{50}$ |
|---|---|---|
| 204 | 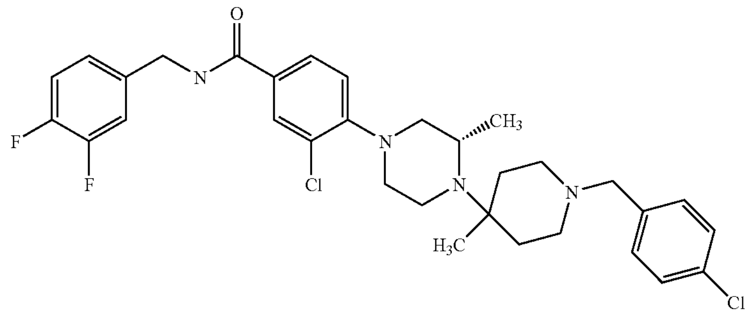 | B |
| 205 | 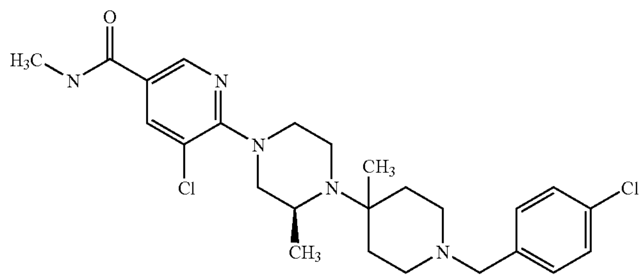 | C |
| 206 | 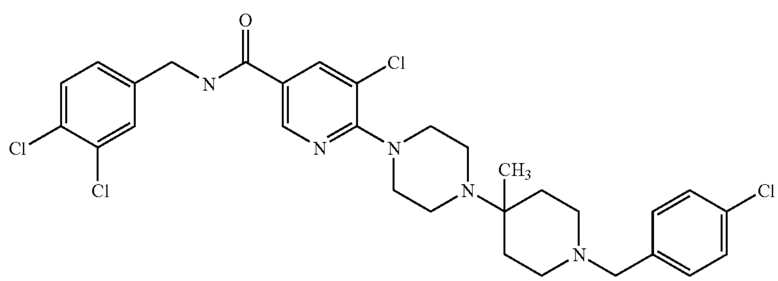 | B |
| 207 | 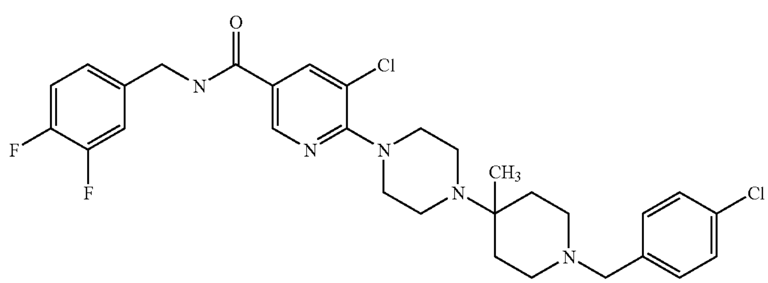 | C |
| 208 | 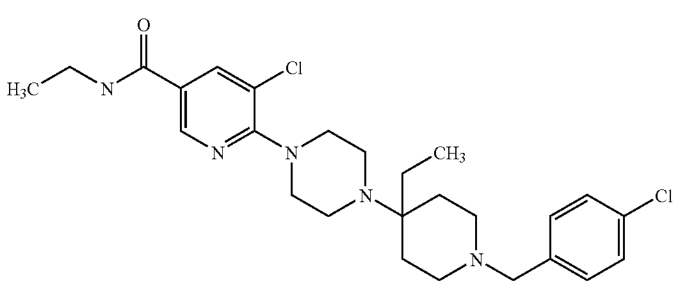 | C |

TABLE 1-continued
| Compound No. | Compound Structure | IC$_{50}$ |
|---|---|---|
| 209 | 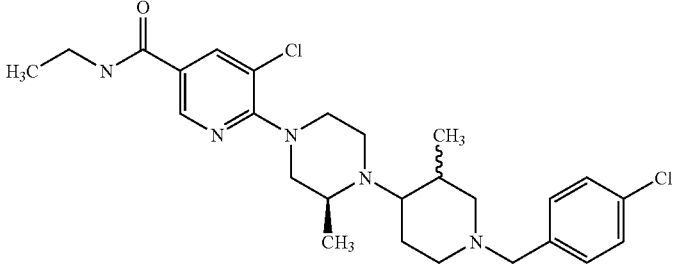 | A |
| 210 | 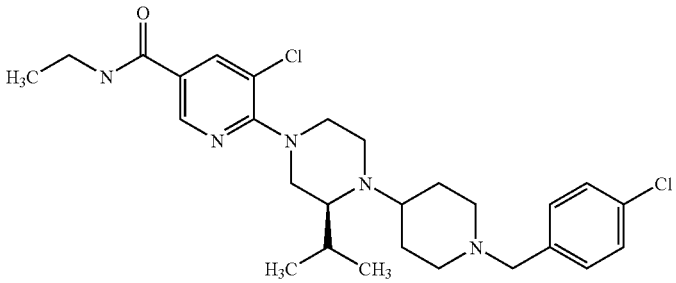 | A |
| 211 | 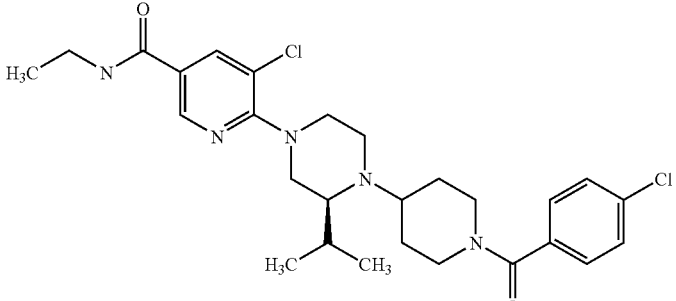 | C |
| 212 | 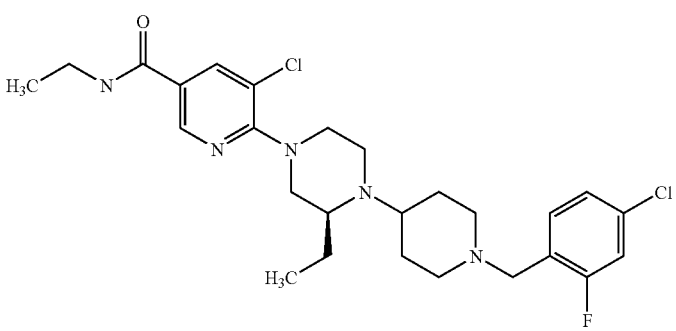 | A |
| 213 | 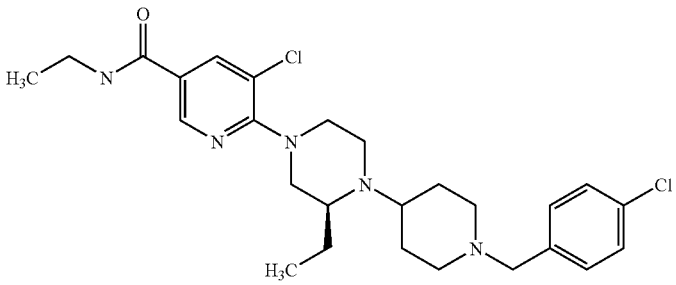 | A |

TABLE 1-continued

| Compound No. | Compound Structure | IC$_{50}$ |
|---|---|---|
| 214 | 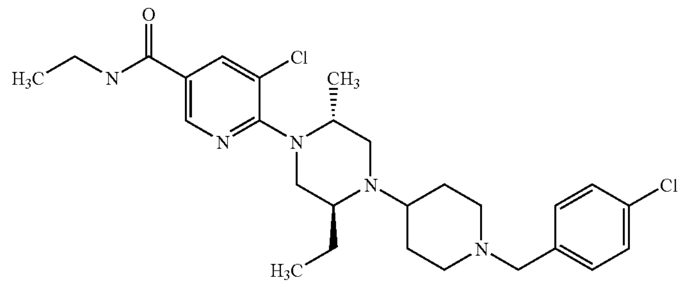 | A |
| 215 | 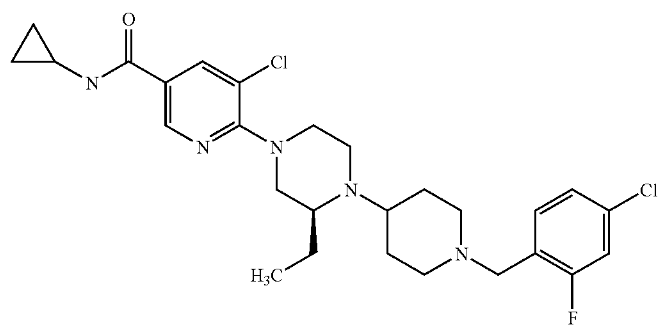 | A |
| 216 | 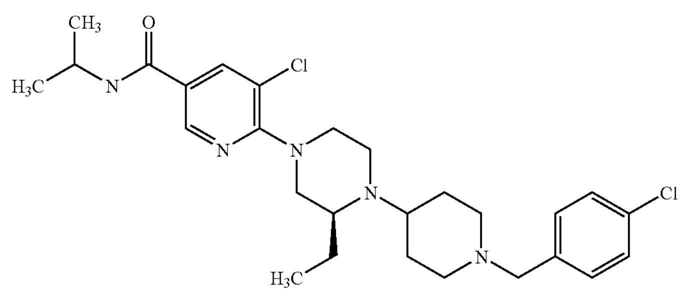 | A |
| 217 | 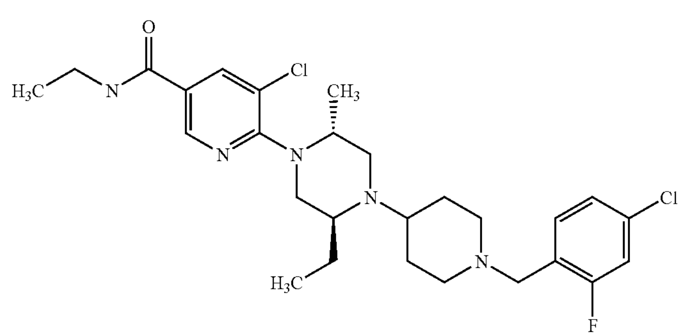 | A |
| 218 | 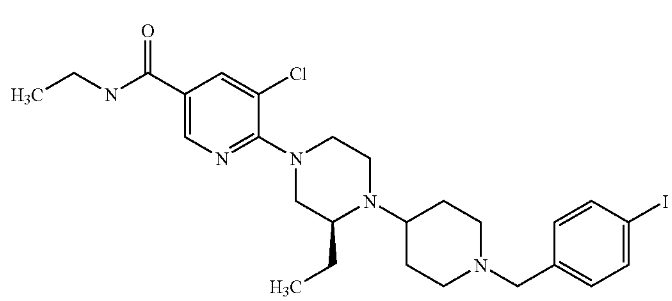 | A |

TABLE 1-continued

| Compound No. | Compound Structure | IC$_{50}$ |
|---|---|---|
| 219 | 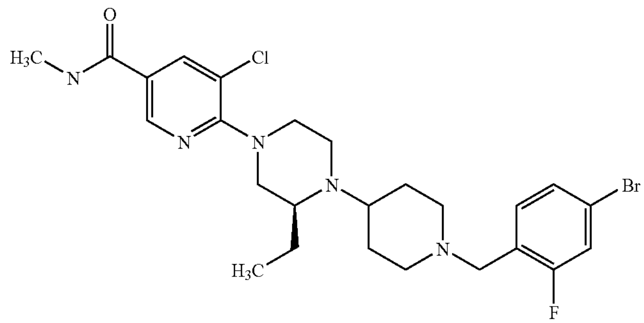 | A |
| 220 | 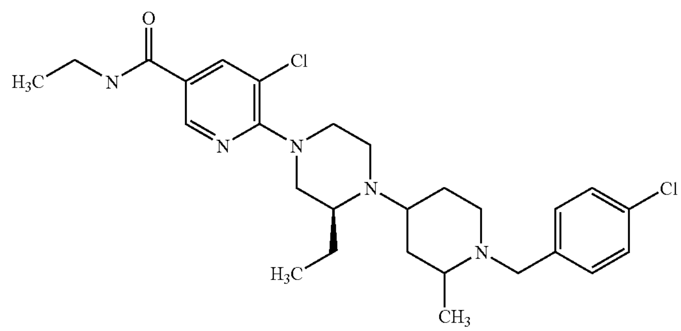 | A |
| 221 | 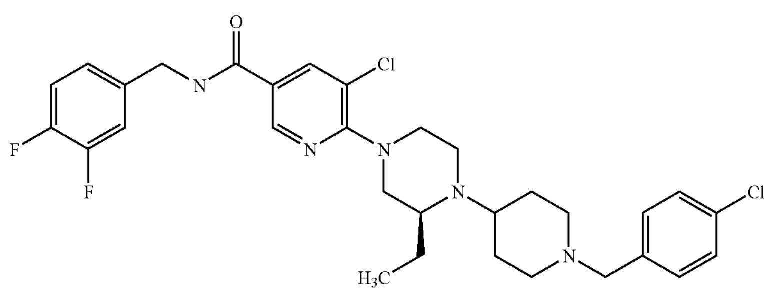 | A |
| 222 | 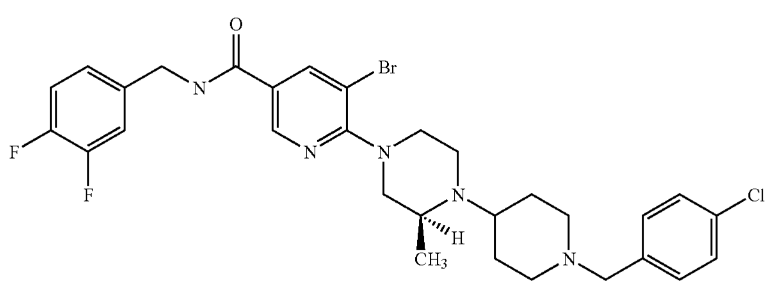 | A |
| 223 | 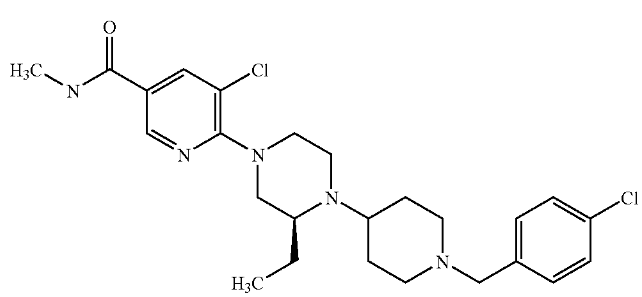 | A |

TABLE 1-continued

| Compound No. | Compound Structure | IC$_{50}$ |
|---|---|---|
| 224 | 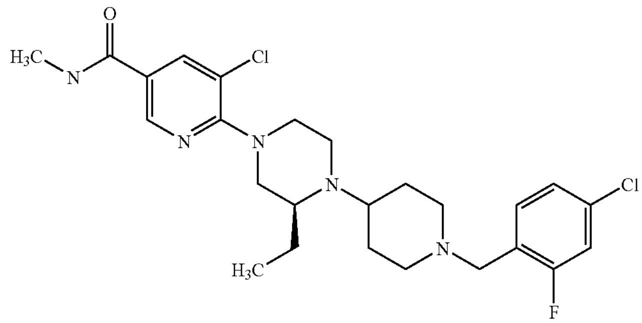 | A |
| 225 | 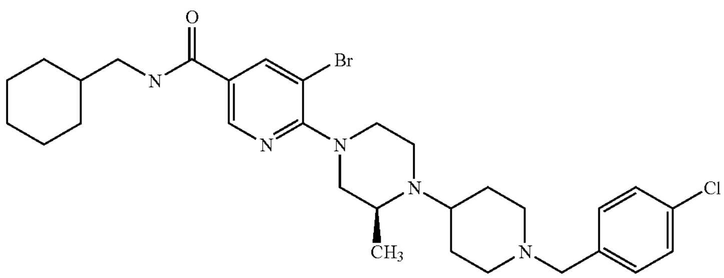 | A |
| 226 | 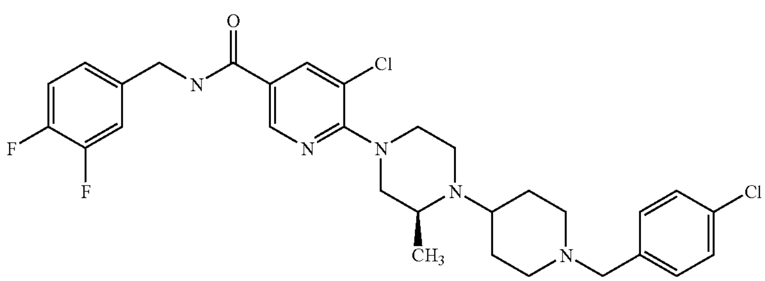 | A |
| 227 | 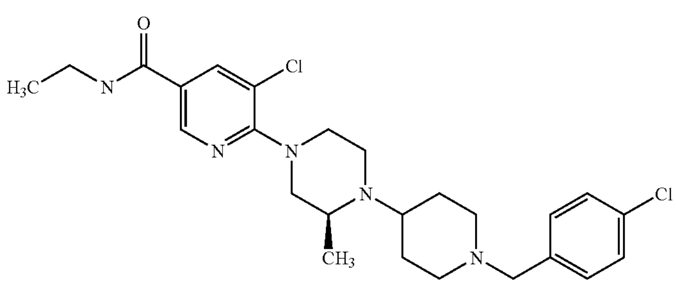 | A |
| 228 | 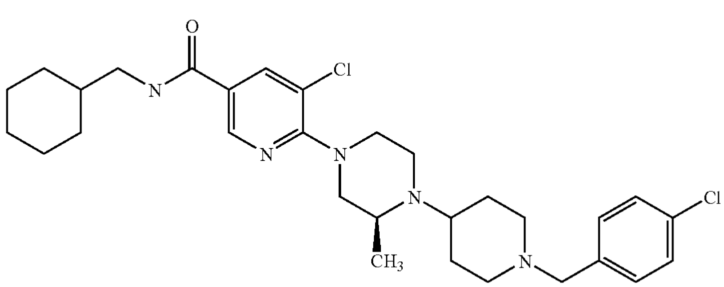 | A |

TABLE 1-continued

| Compound No. | Compound Structure | IC$_{50}$ |
|---|---|---|
| 229 | 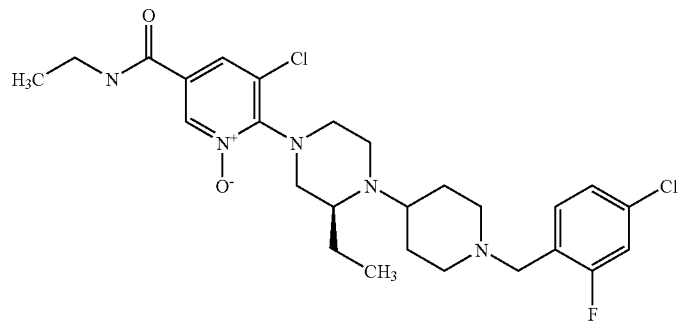 | A |
| 230 | 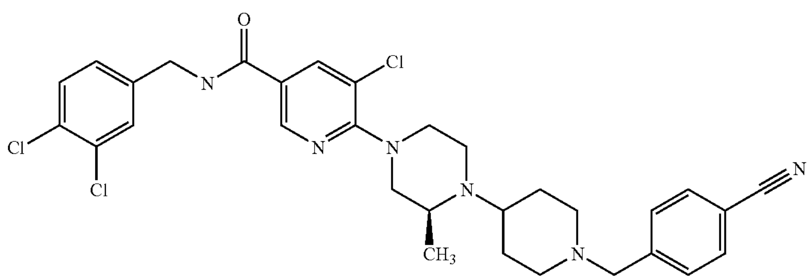 | A |
| 231 | 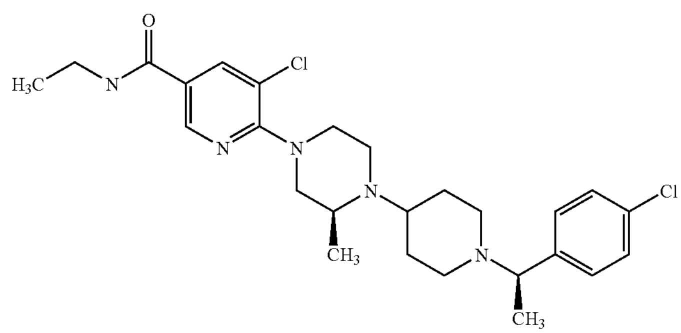 | A |
| 232 | 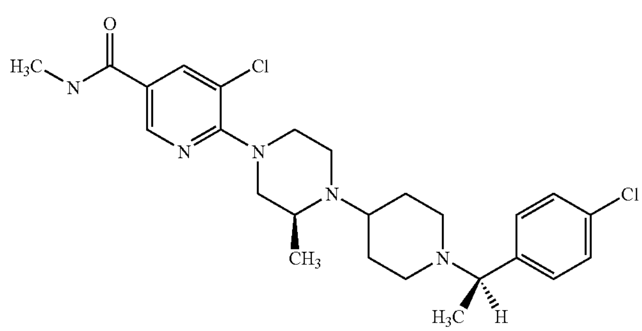 | A |
| 233 | 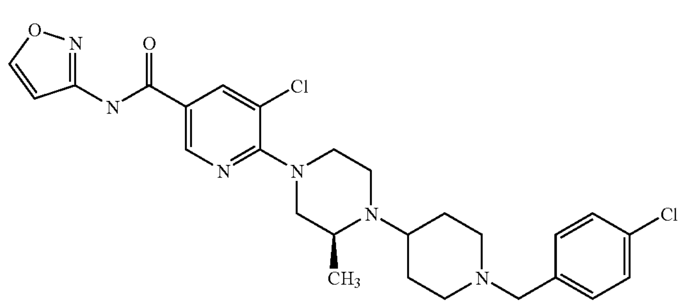 | A |

TABLE 1-continued

| Compound No. | Compound Structure | IC$_{50}$ |
|---|---|---|
| 234 | 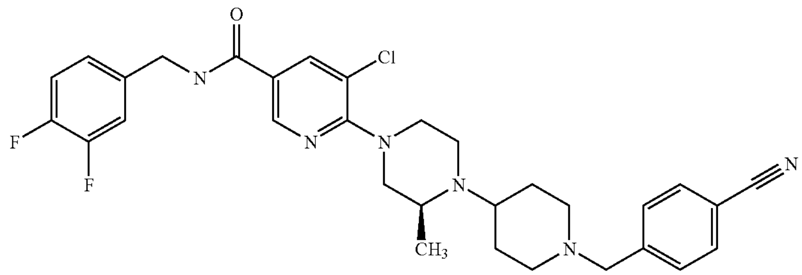 | A |
| 235 | 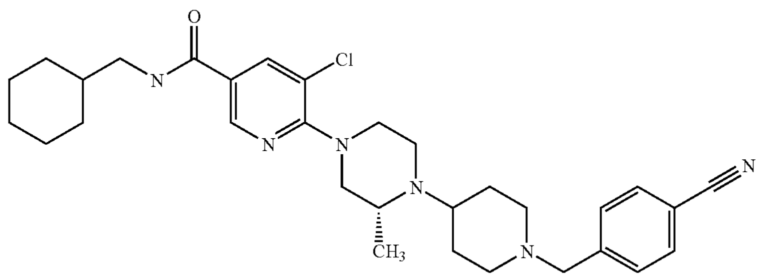 | A |
| 236 | 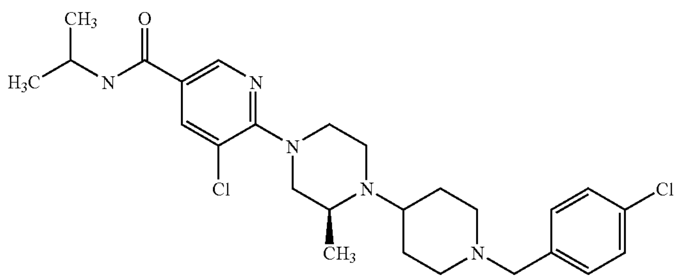 | A |
| 237 | 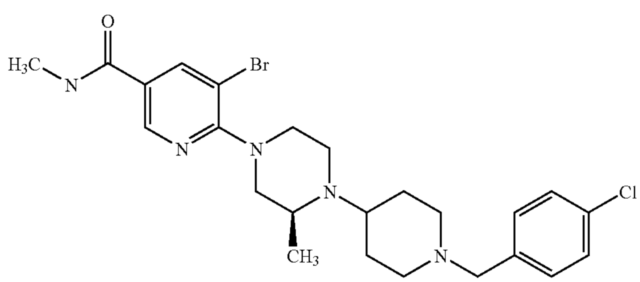 | A |
| 238 | 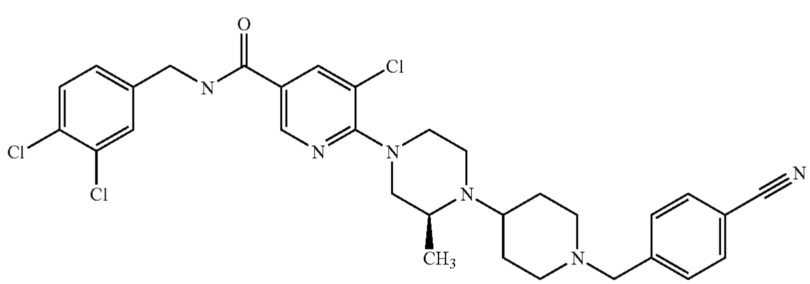 | A |

TABLE 1-continued

| Compound No. | Compound Structure | IC$_{50}$ |
|---|---|---|
| 239 | 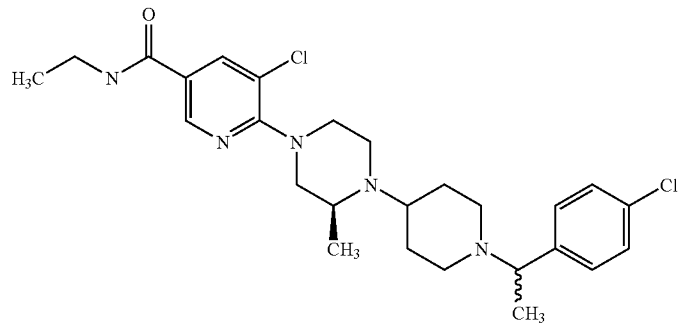 | A |
| 240 | 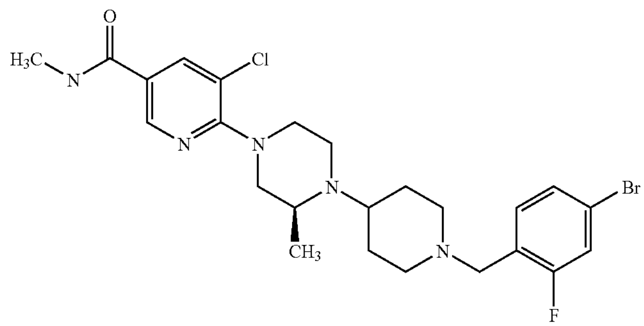 | A |
| 241 | 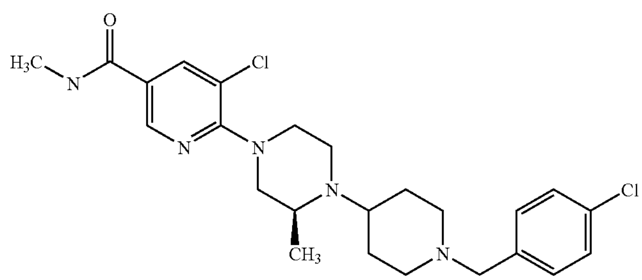 | A |
| 242 | 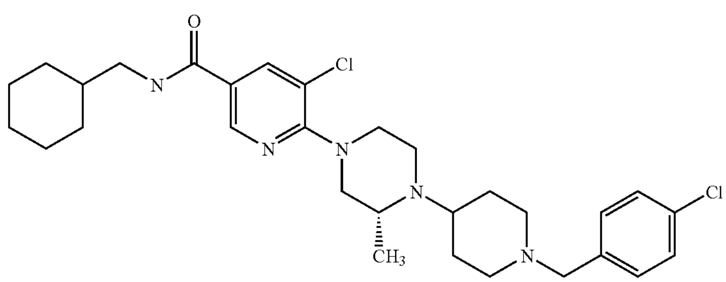 | A |
| 243 | 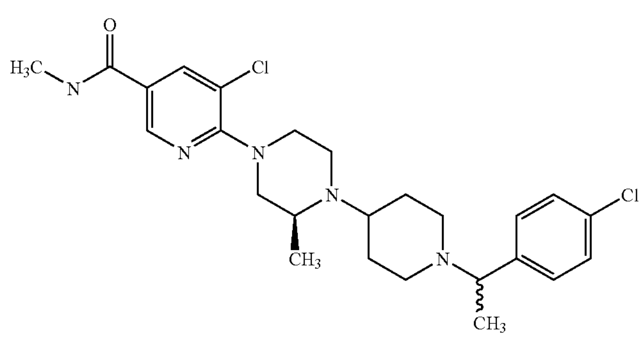 | A |

TABLE 1-continued

| Compound No. | Compound Structure | IC$_{50}$ |
|---|---|---|
| 244 | 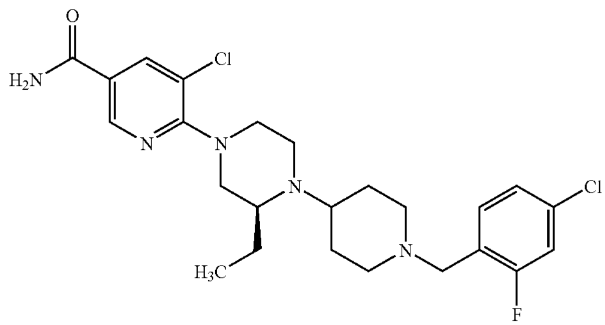 | A |
| 245 | 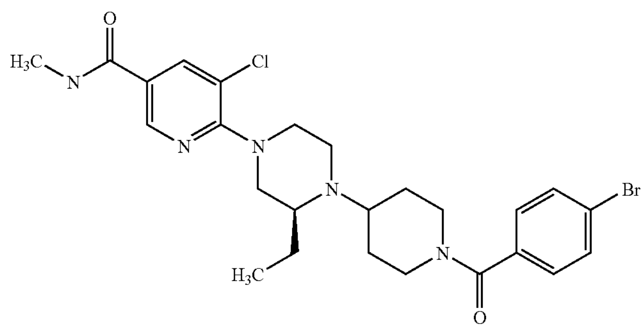 | A |
| 246 | 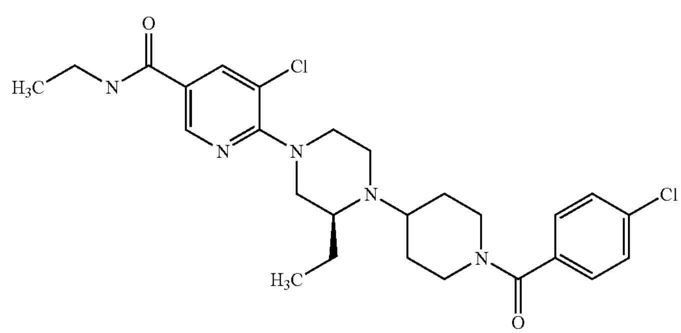 | A |
| 247 | 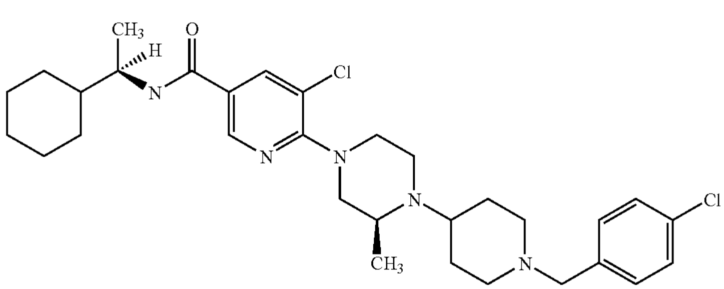 | A |

TABLE 1-continued
| Compound No. | Compound Structure | IC$_{50}$ |
|---|---|---|
| 248 | 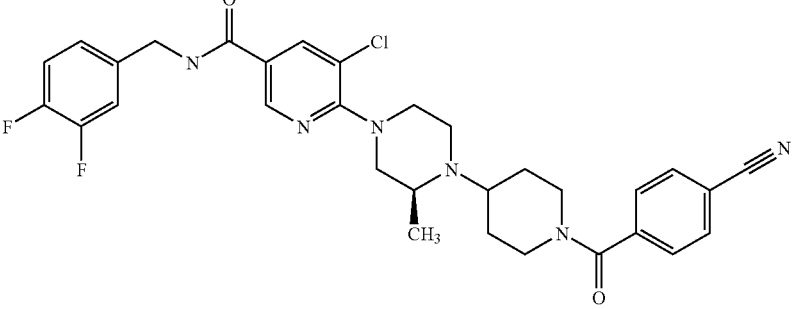 | A |
| 249 | 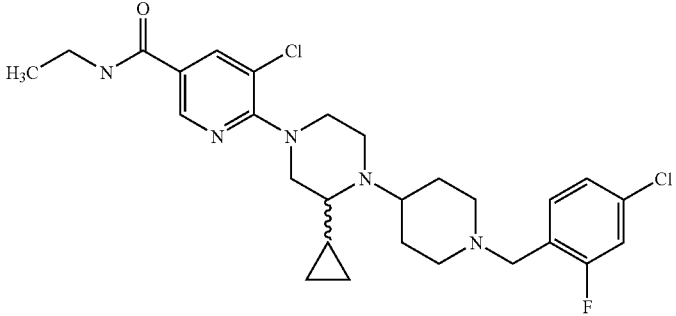 | A |
| 250 | 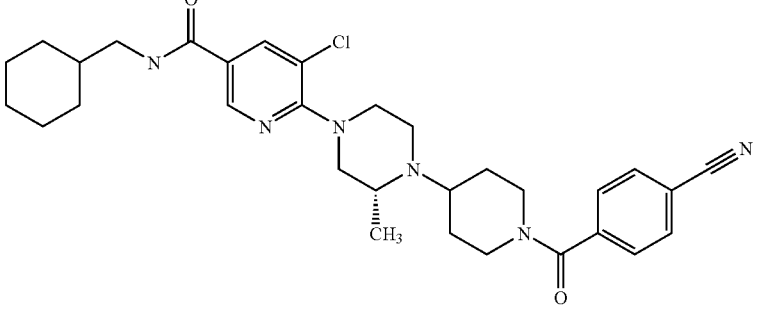 | A |
| 251 | 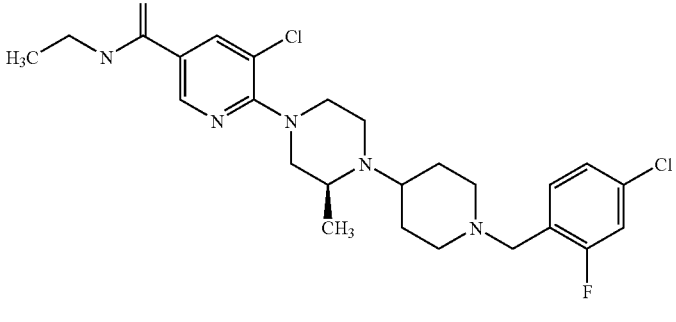 | A |

TABLE 1-continued

| Compound No. | Compound Structure | IC$_{50}$ |
|---|---|---|
| 252 | 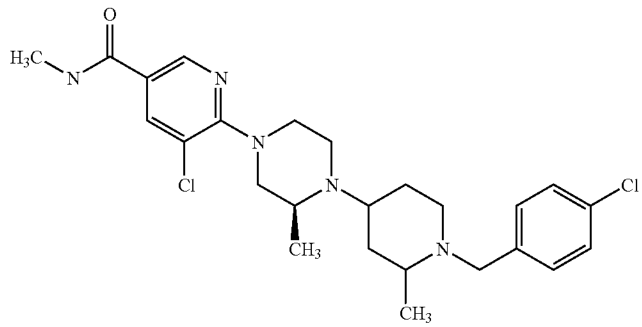 | A |
| 253 | 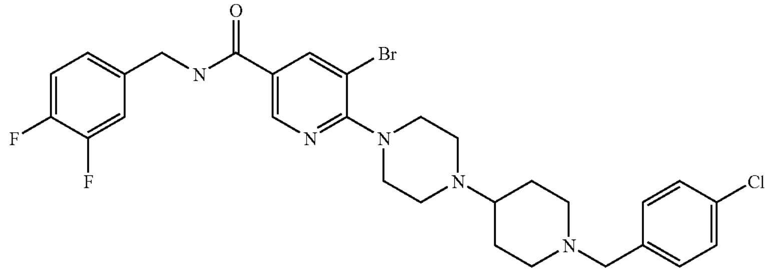 | A |
| 254 | 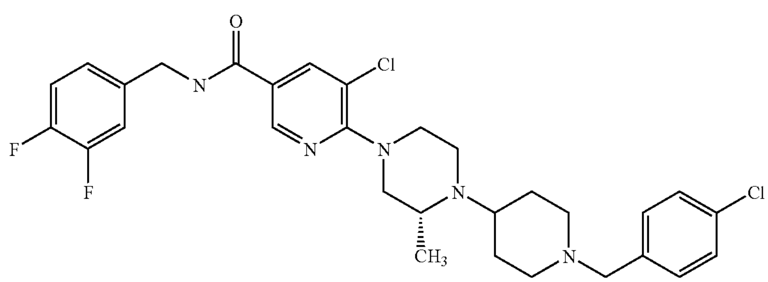 | A |
| 255 | 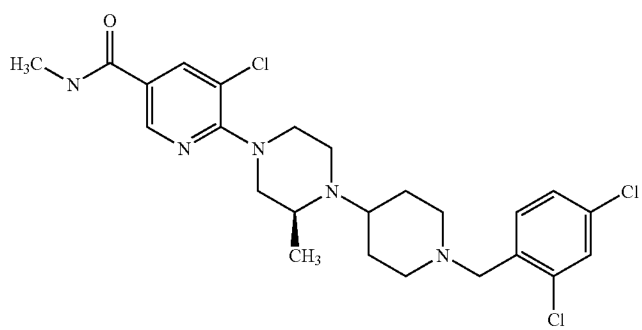 | A |
| 256 | 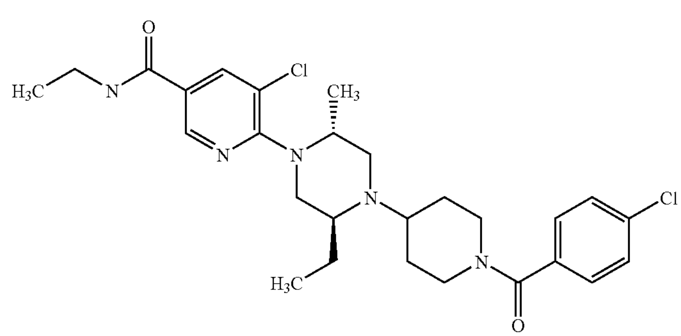 | A |

TABLE 1-continued
| Compound No. | Compound Structure | IC$_{50}$ |
|---|---|---|
| 257 | 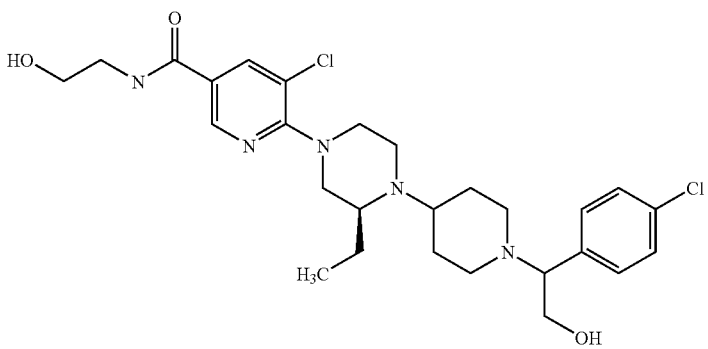 | A |
| 258 | 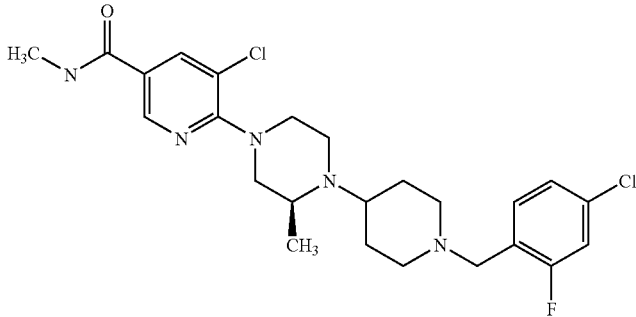 | A |
| 259 | 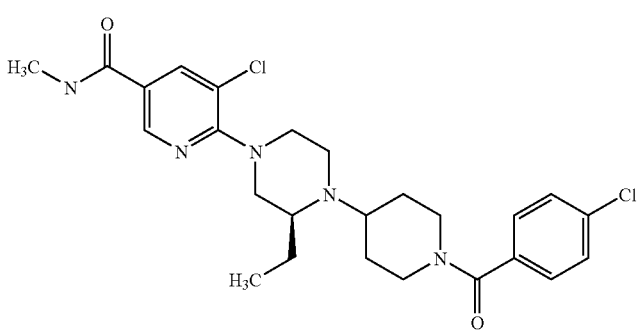 | A |
| 260 | 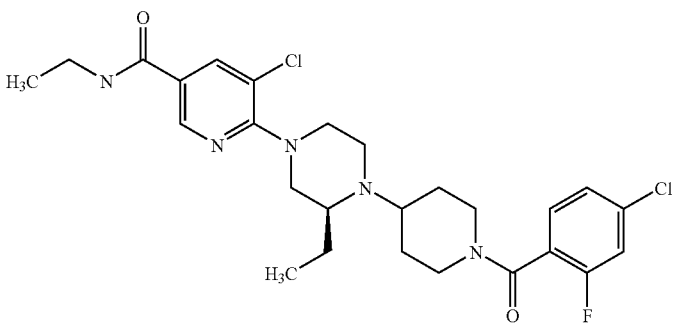 | A |

TABLE 1-continued

| Compound No. | Compound Structure | IC$_{50}$ |
|---|---|---|
| 261 | 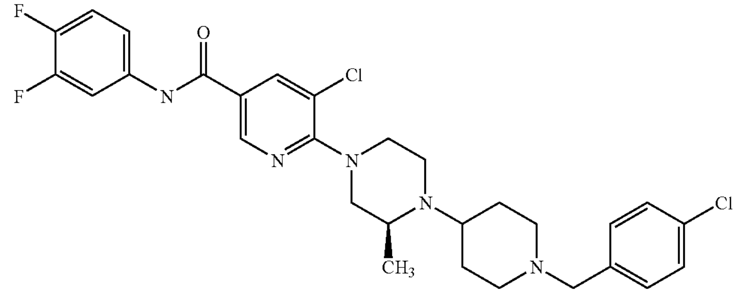 | A |
| 262 | 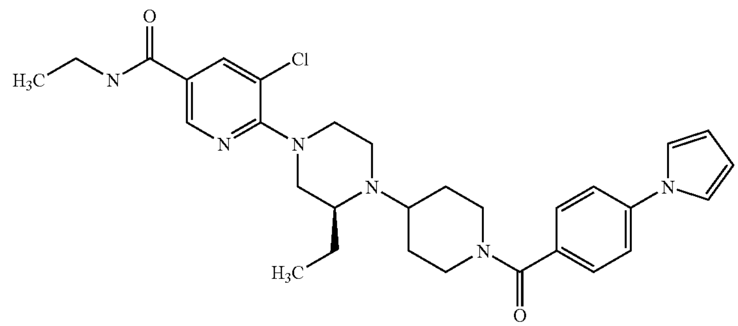 | A |
| 263 | 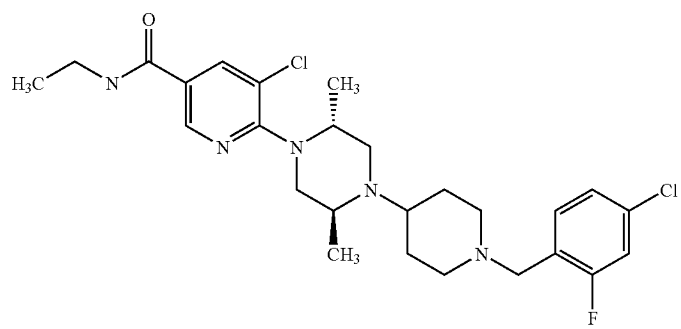 | A |
| 264 | 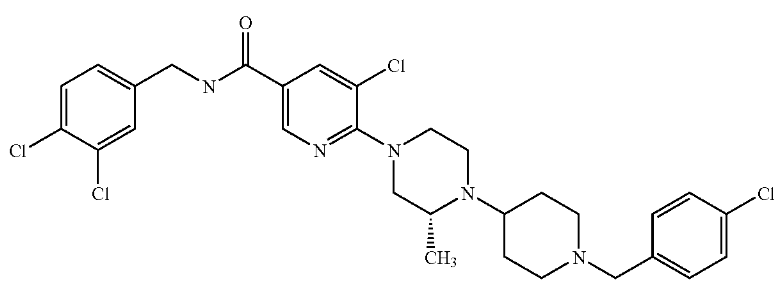 | A |
| 265 | 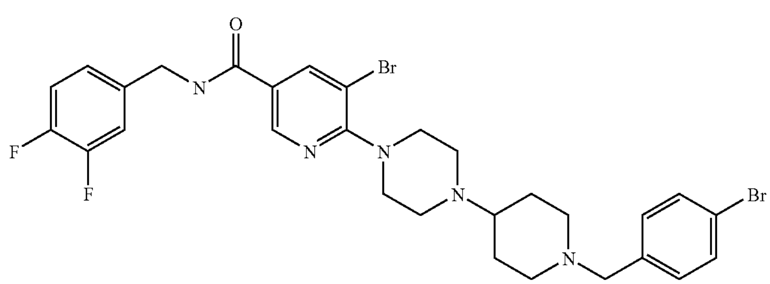 | A |

TABLE 1-continued

| Compound No. | Compound Structure | IC$_{50}$ |
|---|---|---|
| 266 | 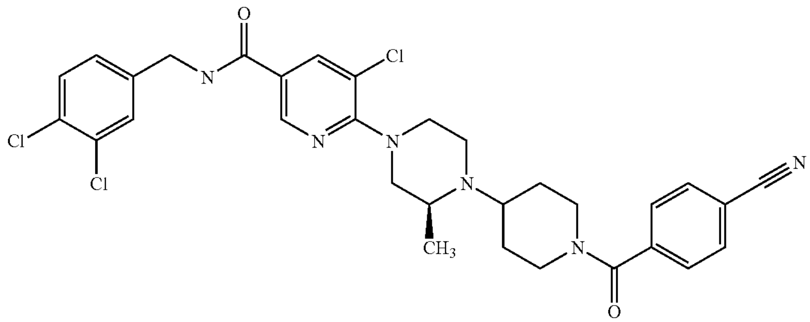 | A |
| 267 | 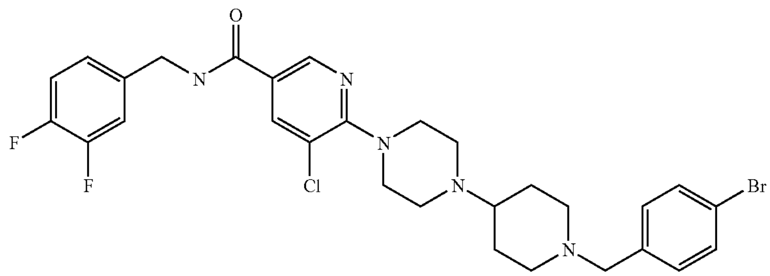 | B |
| 268 | 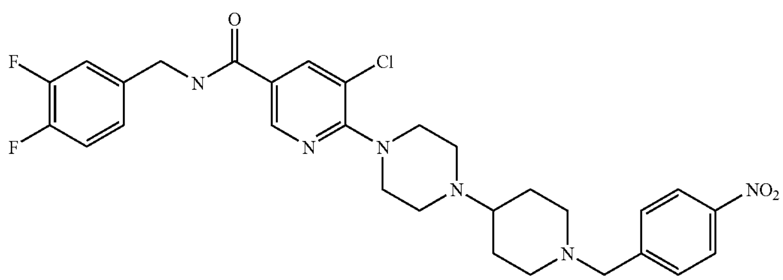 | B |
| 269 | 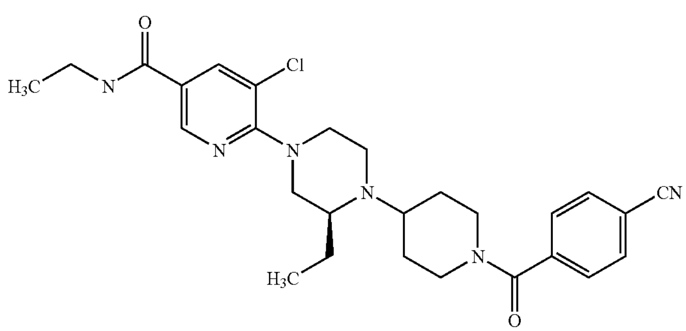 | B |
| 270 | 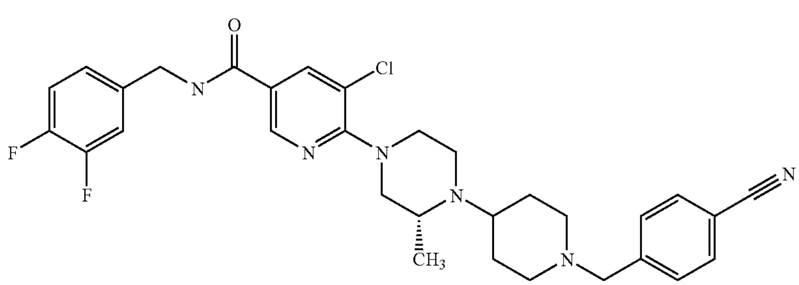 | B |

TABLE 1-continued

| Compound No. | Compound Structure | IC$_{50}$ |
|---|---|---|
| 271 | 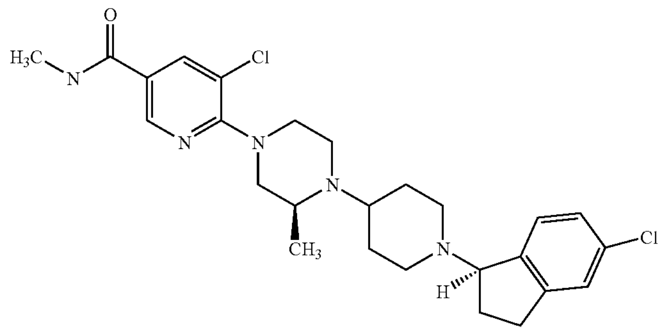 | B |
| 272 | 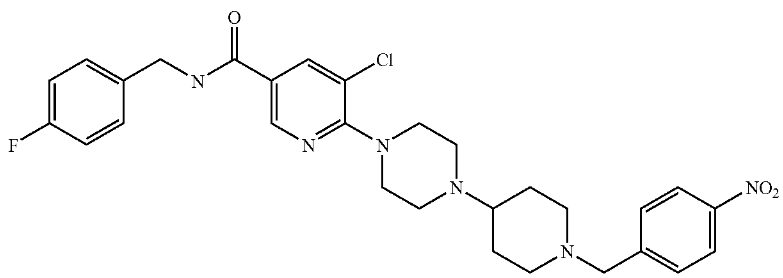 | B |
| 273 | 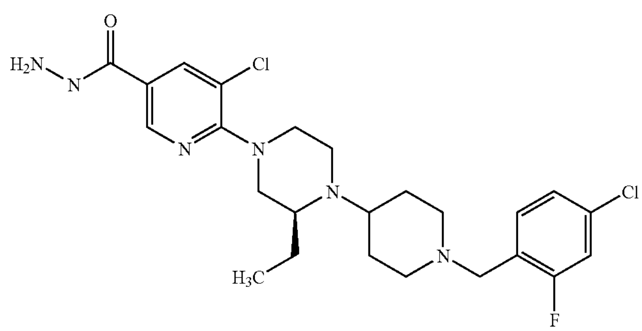 | B |
| 274 | 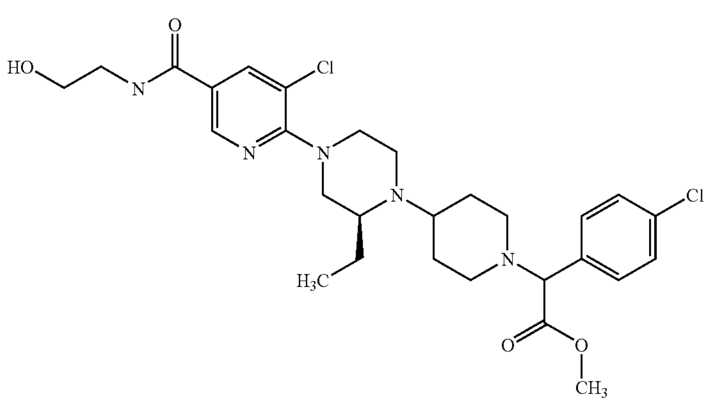 | B |

TABLE 1-continued

| Compound No. | Compound Structure | IC$_{50}$ |
|---|---|---|
| 275 | 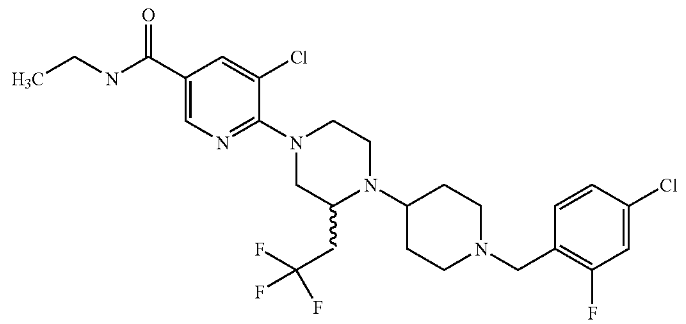 | B |
| 276 | 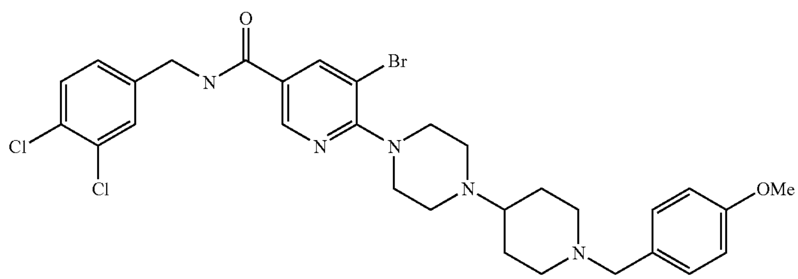 | B |
| 277 | 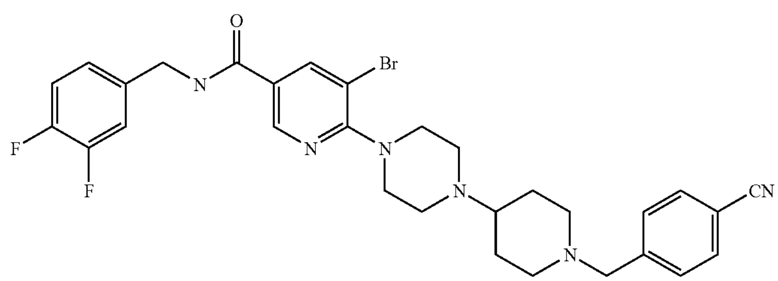 | B |
| 278 | 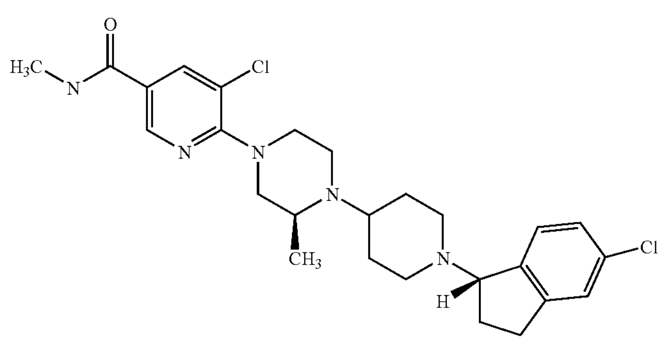 | B |
| 279 | 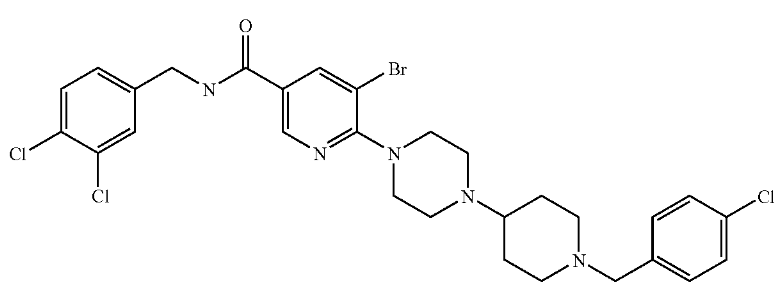 | B |

TABLE 1-continued

| Compound No. | Compound Structure | IC$_{50}$ |
|---|---|---|
| 280 | 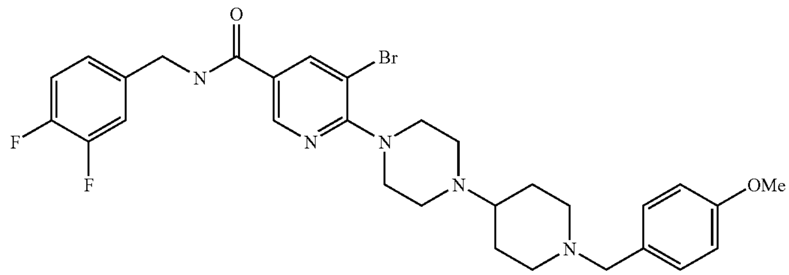 | B |
| 281 | 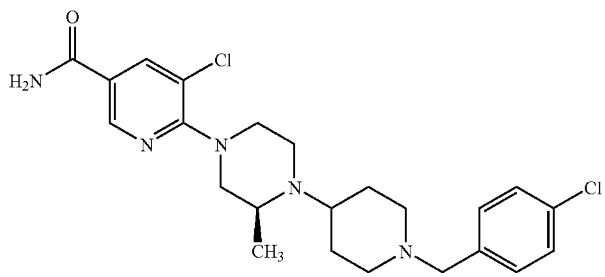 | B |
| 282 | 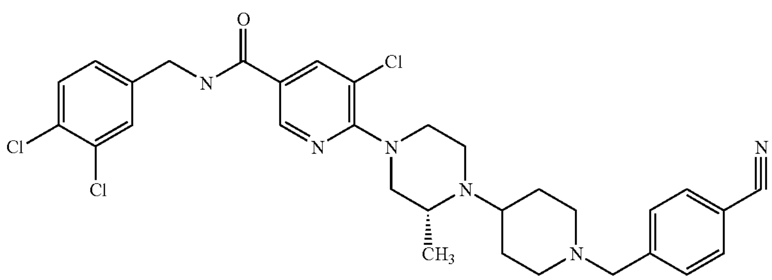 | B |
| 283 | 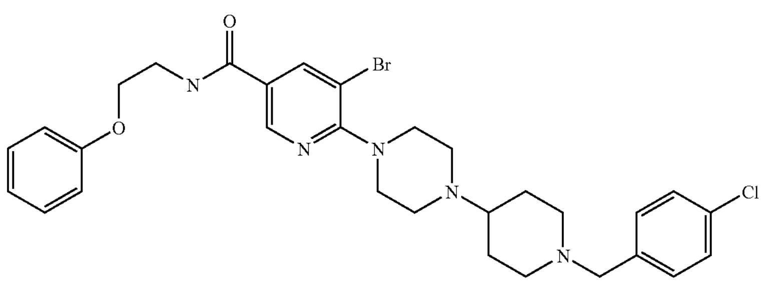 | B |
| 284 | 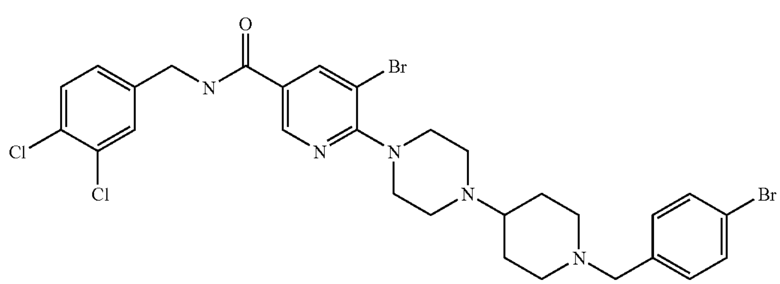 | B |

TABLE 1-continued

| Compound No. | Compound Structure | IC$_{50}$ |
|---|---|---|
| 285 | 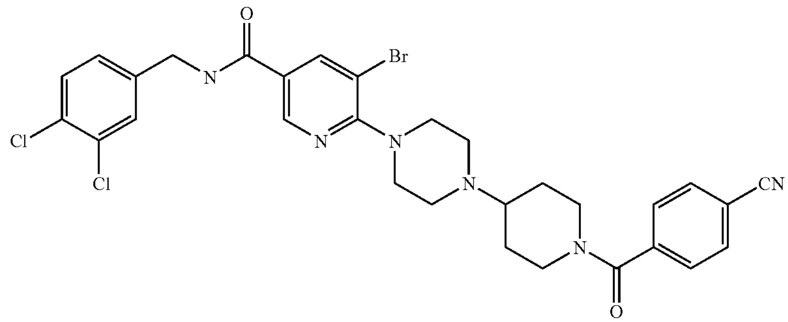 | B |
| 286 | 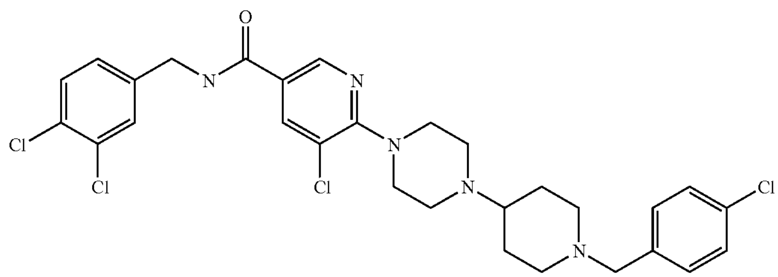 | B |
| 287 | 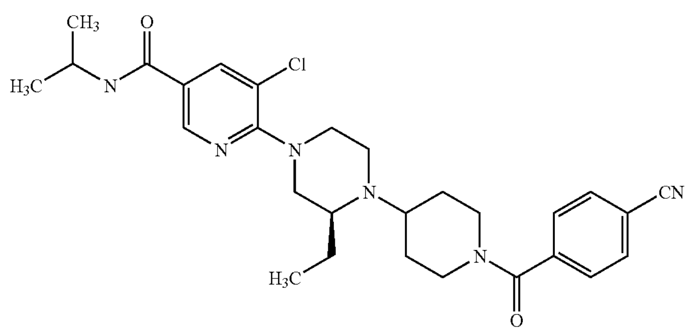 | B |
| 288 | 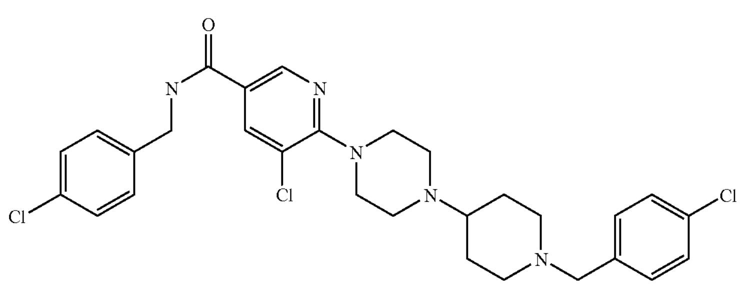 | B |
| 289 | 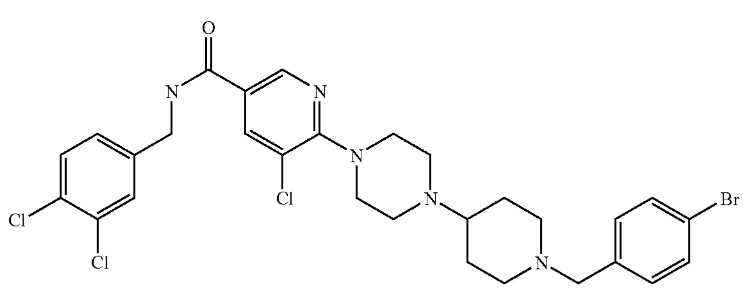 | B |

TABLE 1-continued

| Compound No. | Compound Structure | IC$_{50}$ |
|---|---|---|
| 290 | 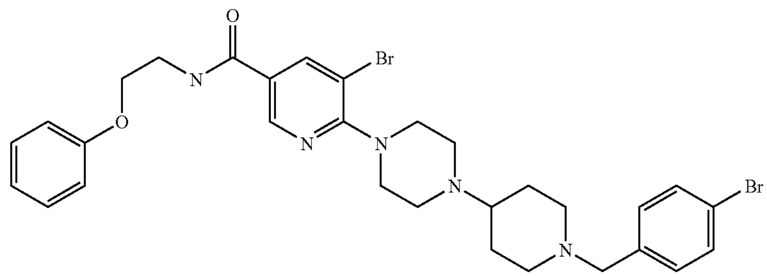 | B |
| 291 | 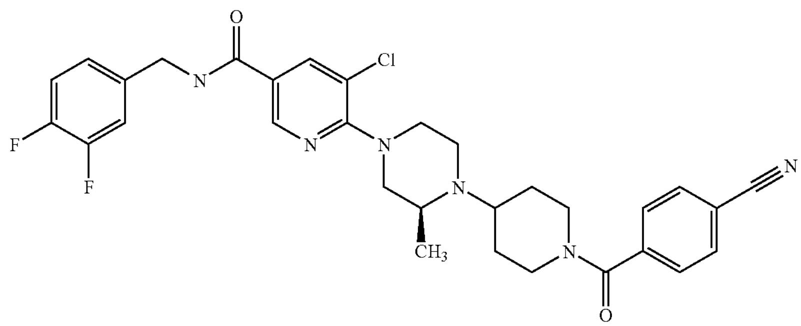 | B |
| 292 | 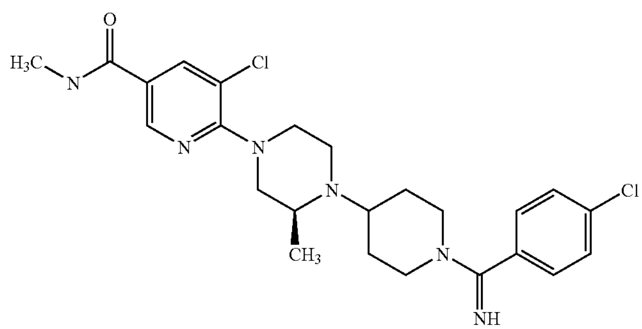 | B |
| 293 | 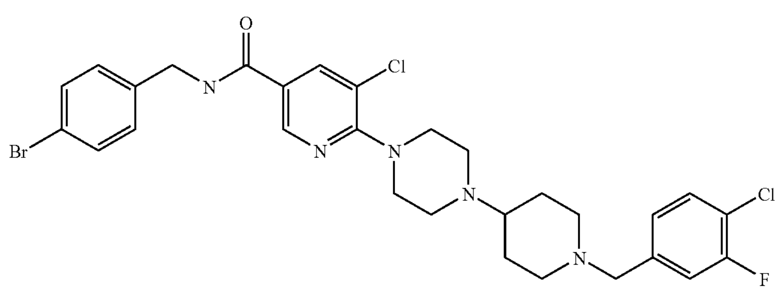 | B |
| 294 | 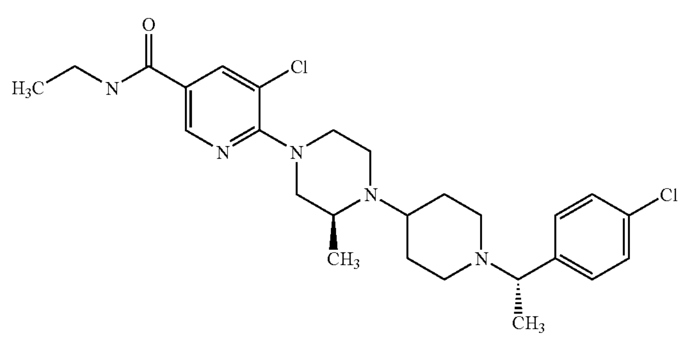 | B |

TABLE 1-continued

| Compound No. | Compound Structure | IC$_{50}$ |
|---|---|---|
| 295 | 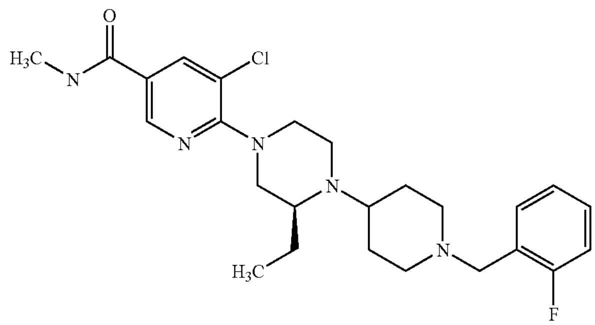 | B |
| 296 | 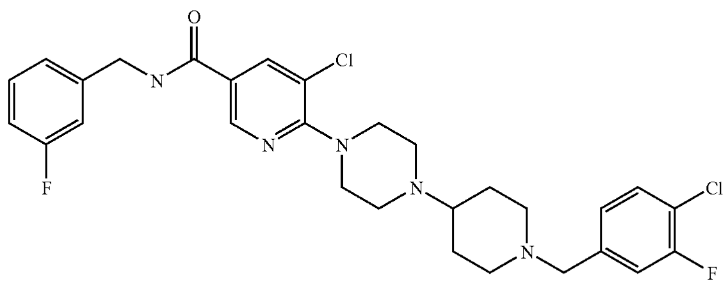 | B |
| 297 | 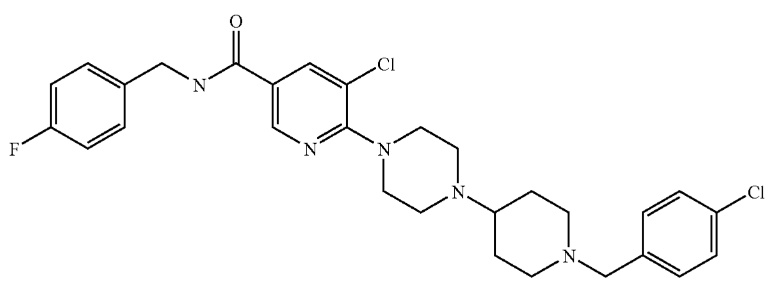 | B |
| 298 | 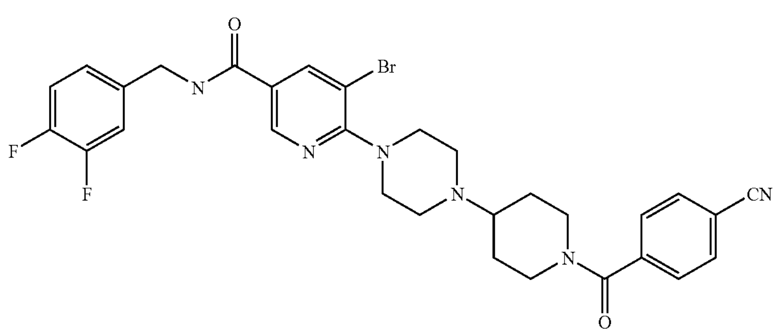 | B |
| 299 | 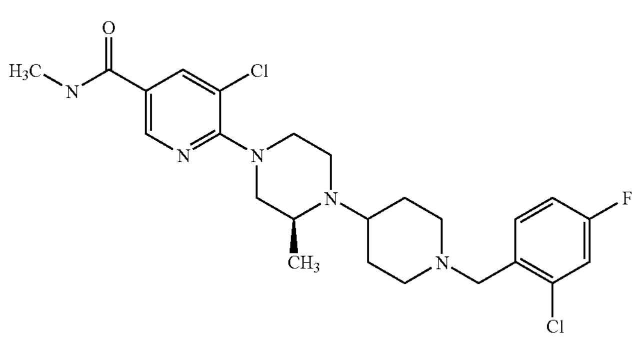 | B |

TABLE 1-continued

| Compound No. | Compound Structure | IC$_{50}$ |
| --- | --- | --- |
| 300 | 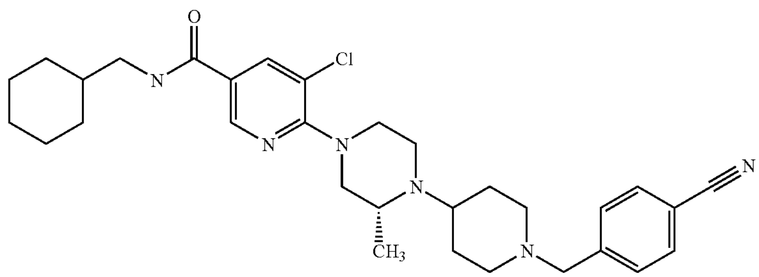 | B |
| 301 | 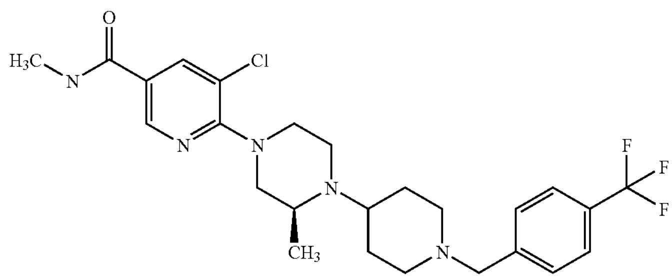 | B |
| 302 | 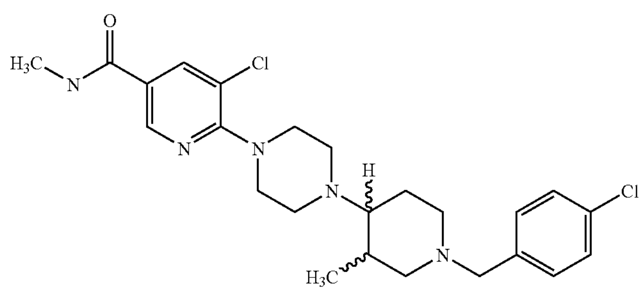 | B |
| 303 | 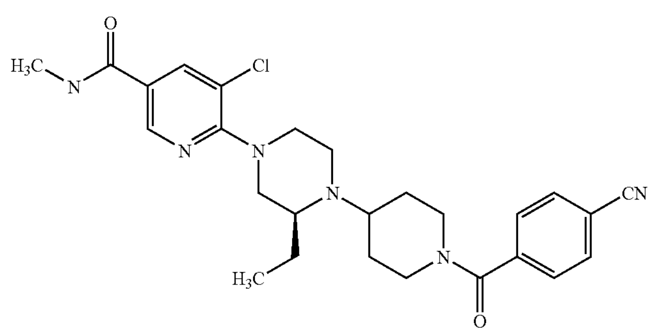 | B |
| 304 | 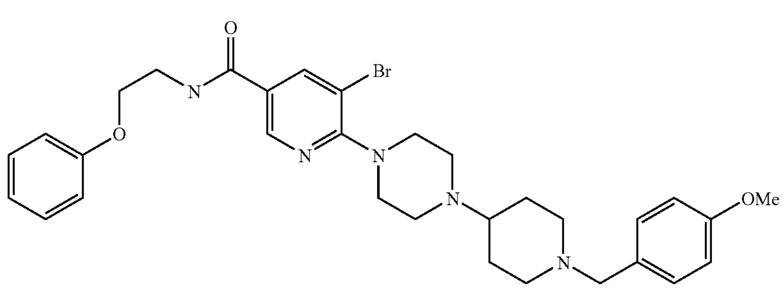 | B |

TABLE 1-continued

| Compound No. | Compound Structure | IC$_{50}$ |
|---|---|---|
| 305 | 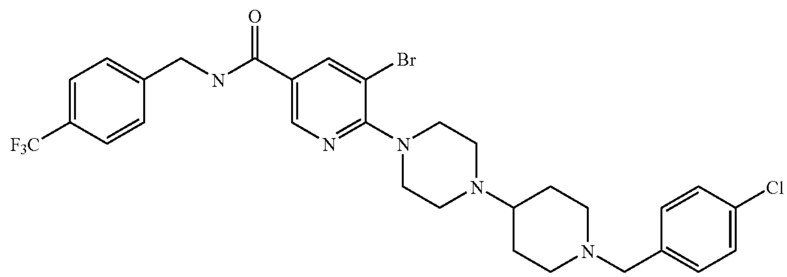 | B |
| 306 | 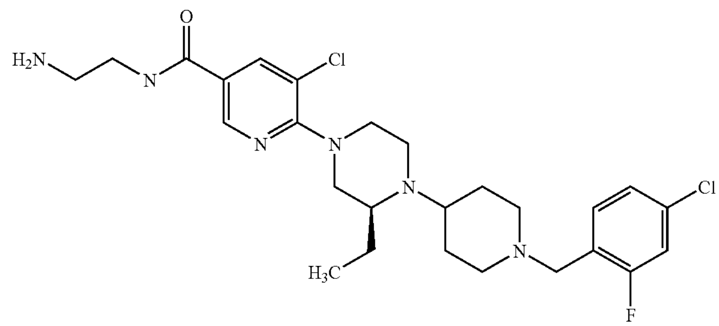 | B |
| 307 | 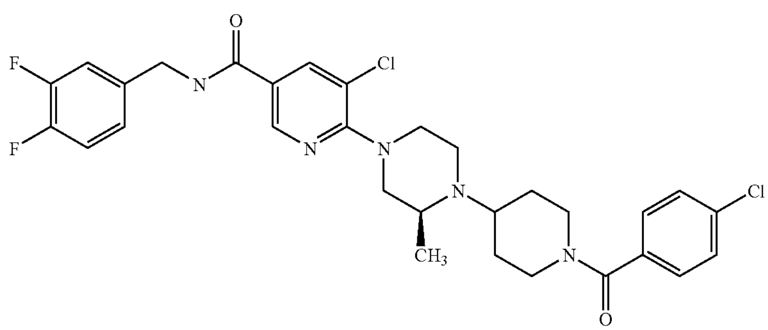 | B |
| 308 | 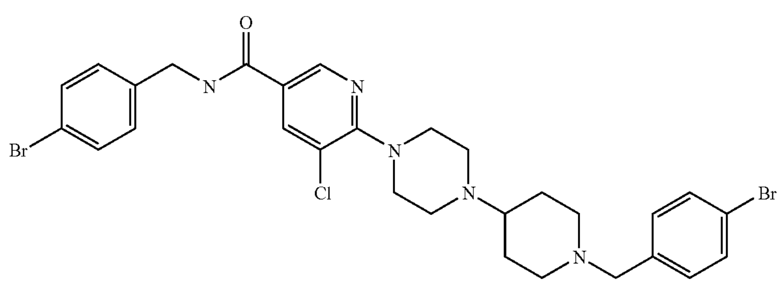 | B |
| 309 | 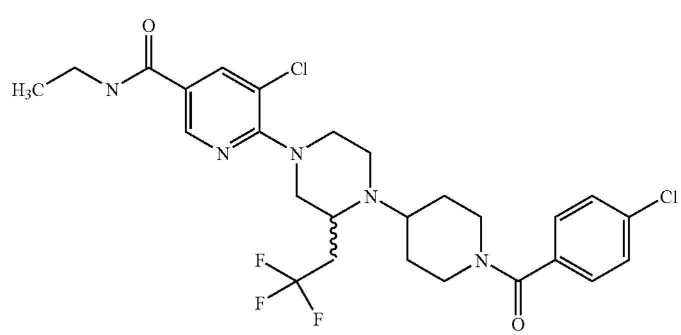 | B |

TABLE 1-continued

| Compound No. | Compound Structure | IC$_{50}$ |
|---|---|---|
| 310 | 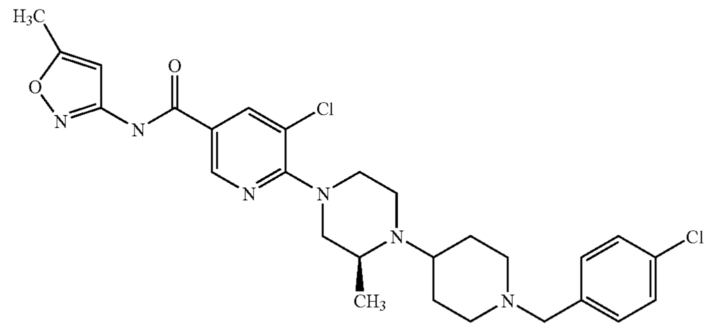 | B |
| 311 | 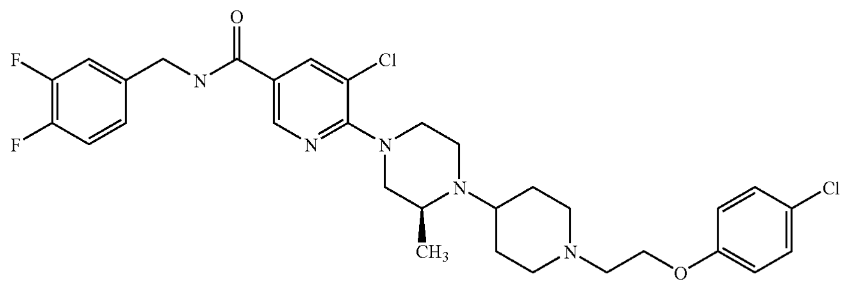 | B |
| 312 | 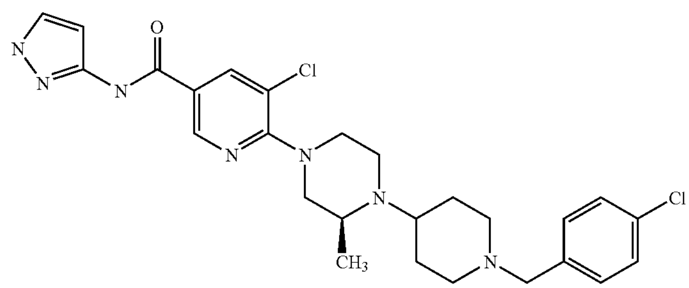 | B |
| 313 | 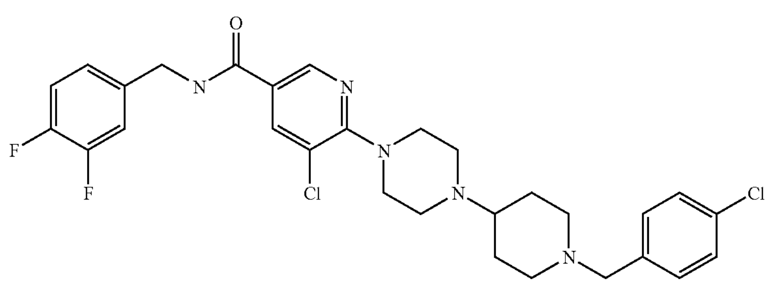 | B |
| 314 | 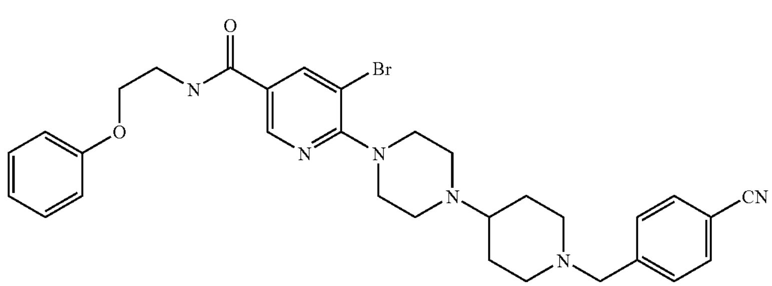 | B |

TABLE 1-continued
| Compound No. | Compound Structure | IC$_{50}$ |
|---|---|---|
| 315 | 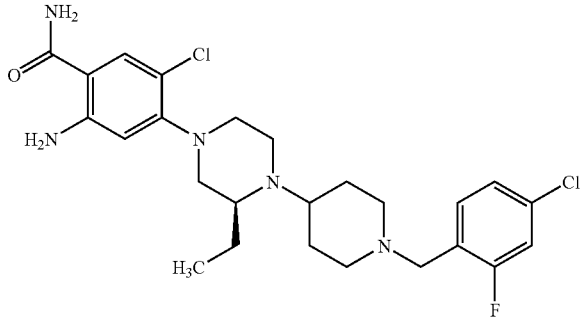 | B |
| 316 | 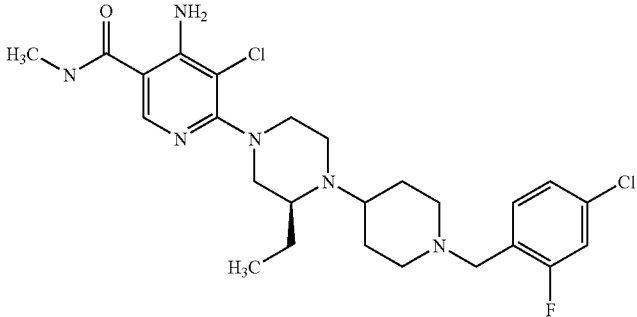 | B |
| 317 | 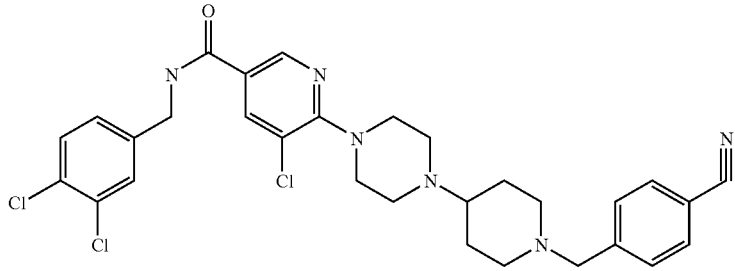 | B |
| 318 | 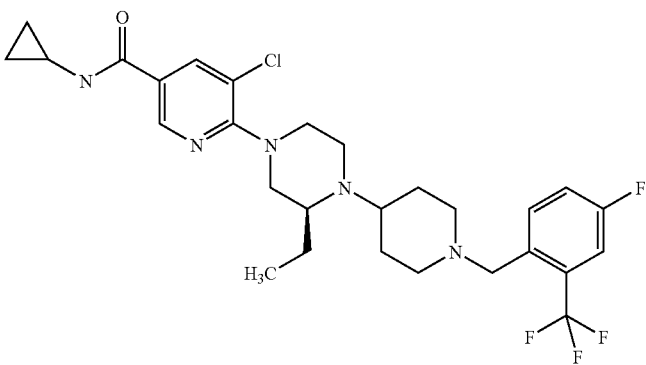 | B |

TABLE 1-continued

| Compound No. | Compound Structure | IC$_{50}$ |
|---|---|---|
| 319 | 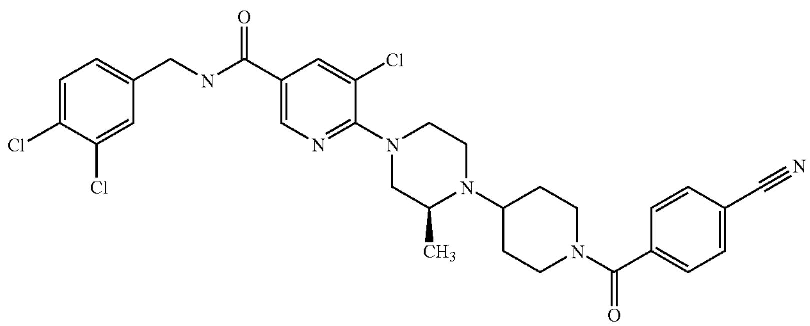 | B |
| 320 | 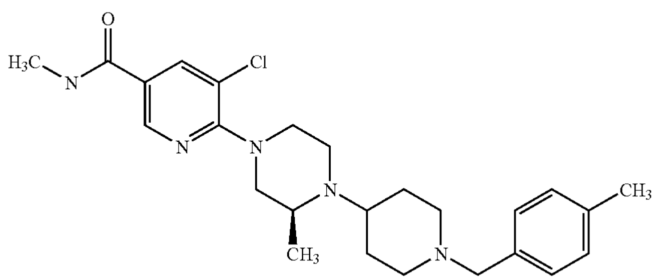 | B |
| 321 | 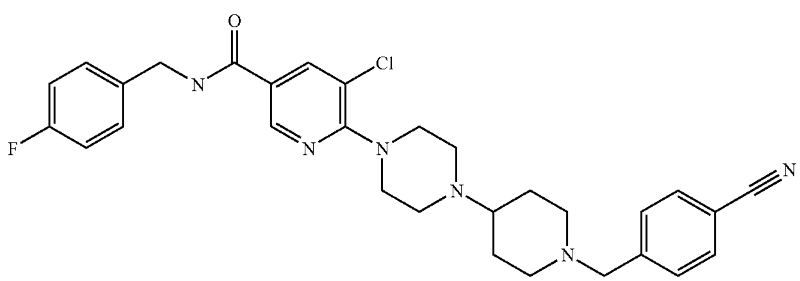 | B |
| 322 | 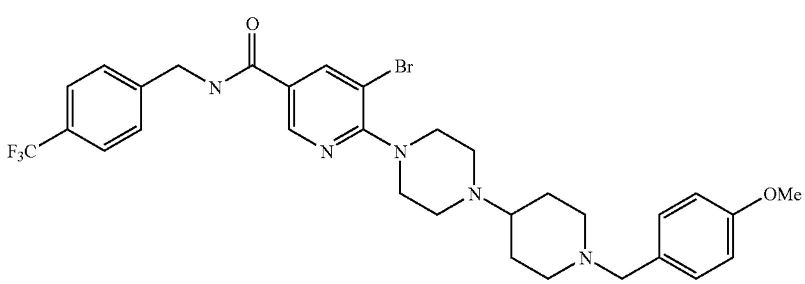 | B |
| 323 | 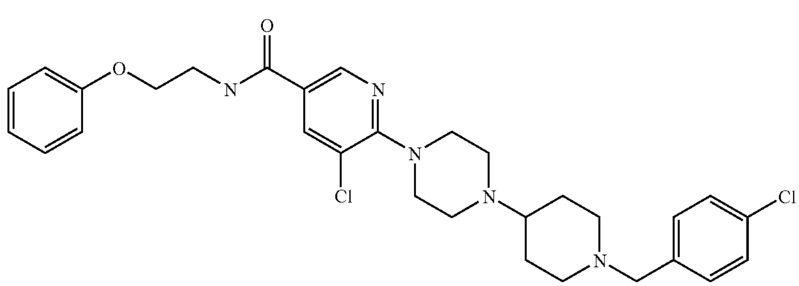 | B |

TABLE 1-continued
| Compound No. | Compound Structure | IC$_{50}$ |
|---|---|---|
| 324 | 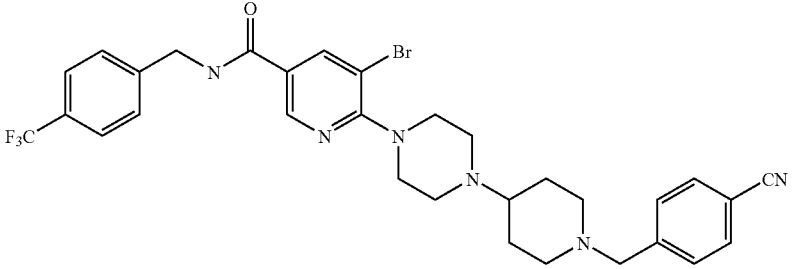 | B |
| 325 | 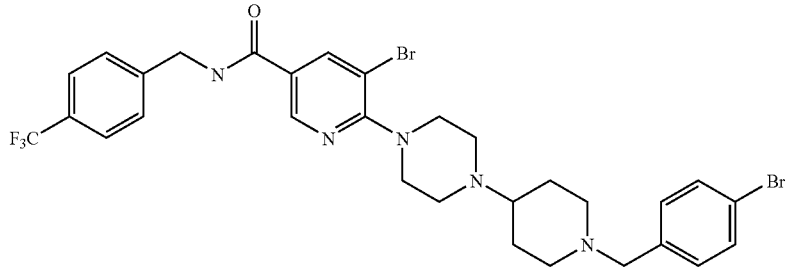 | C |
| 326 | 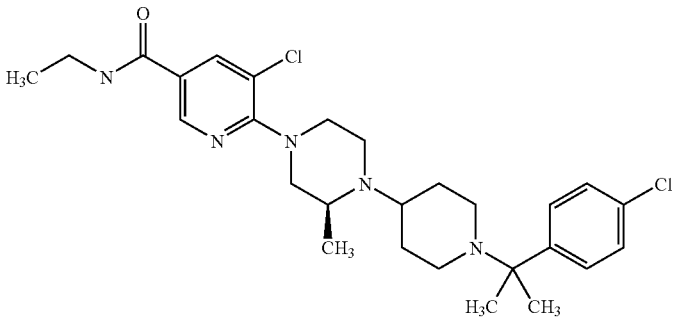 | C |
| 327 | 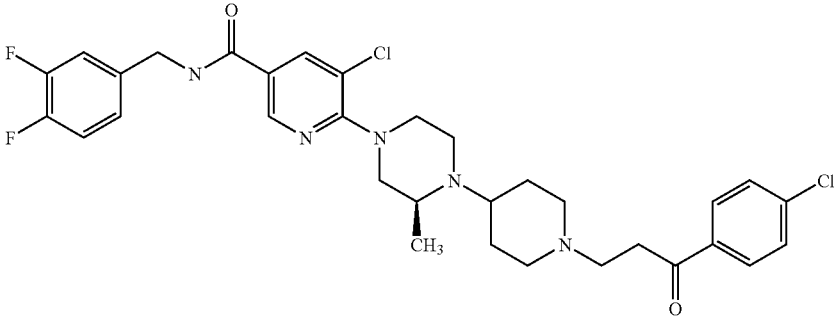 | C |
| 328 | 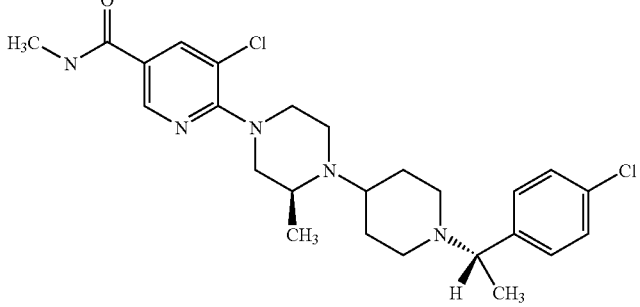 | C |

TABLE 1-continued
| Compound No. | Compound Structure | IC$_{50}$ |
|---|---|---|
| 329 | 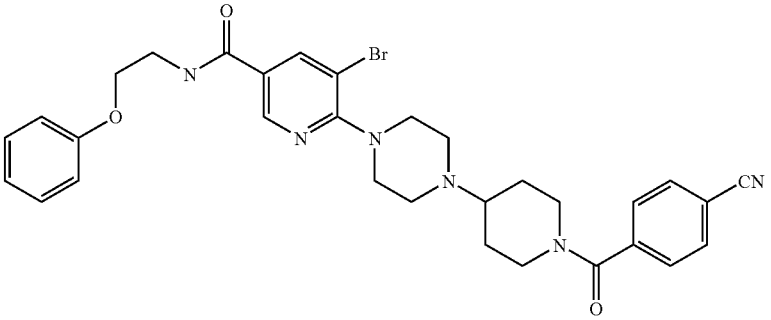 | C |
| 330 | 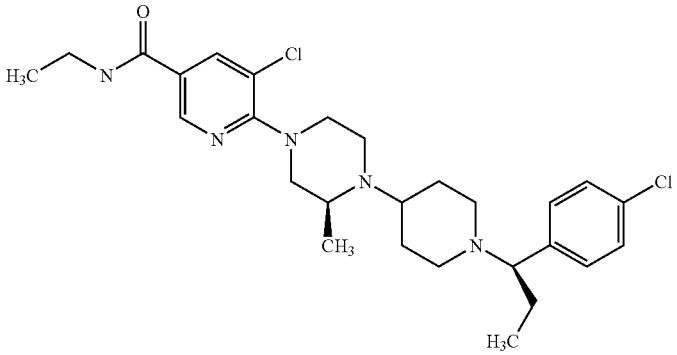 | C |
| 331 | 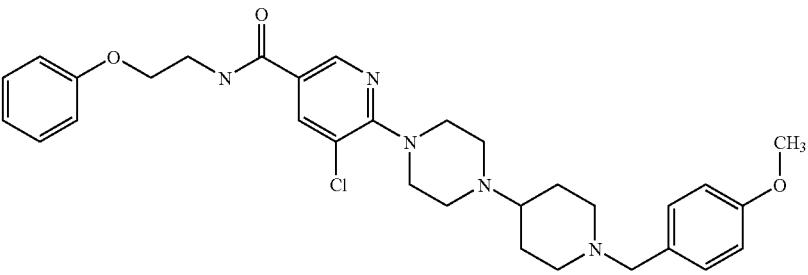 | C |
| 332 | 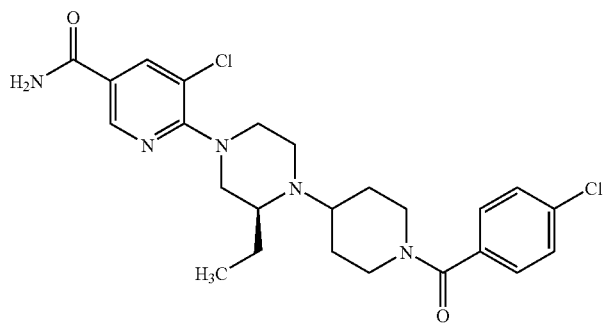 | C |

TABLE 1-continued

| Compound No. | Compound Structure | IC$_{50}$ |
|---|---|---|
| 333 | 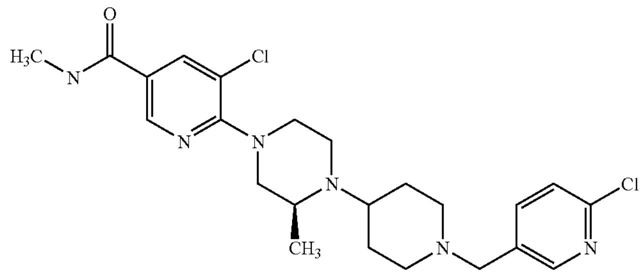 | C |
| 334 | 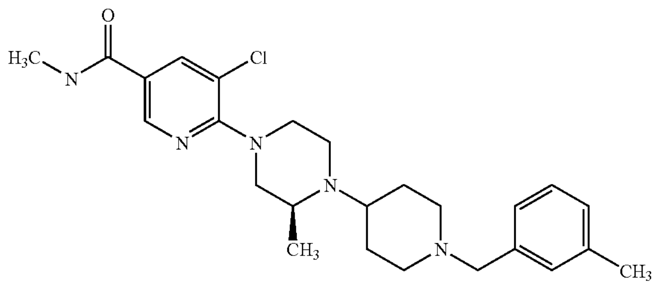 | C |
| 335 | 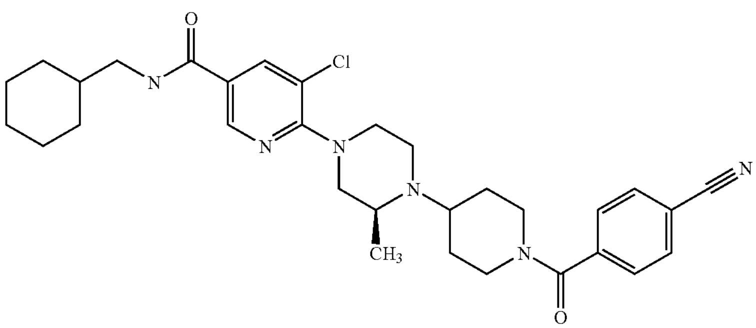 | C |
| 336 | 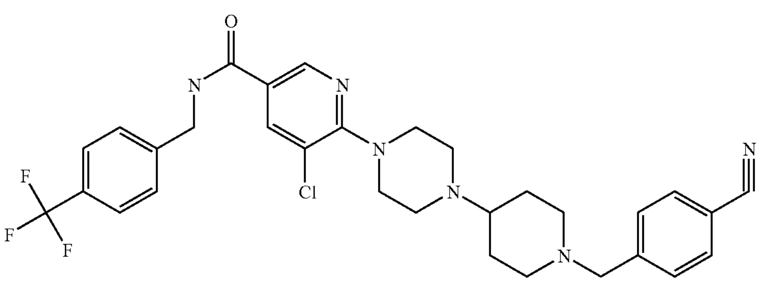 | C |
| 337 | 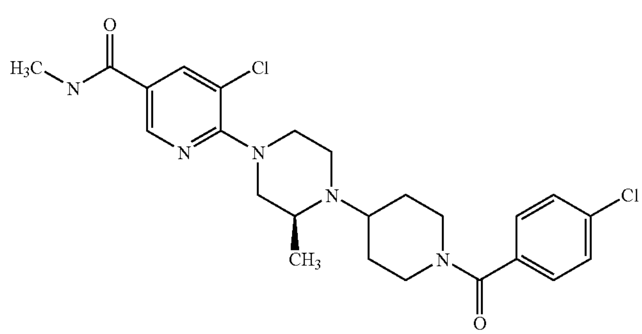 | C |

TABLE 1-continued

| Compound No. | Compound Structure | IC$_{50}$ |
|---|---|---|
| 338 | 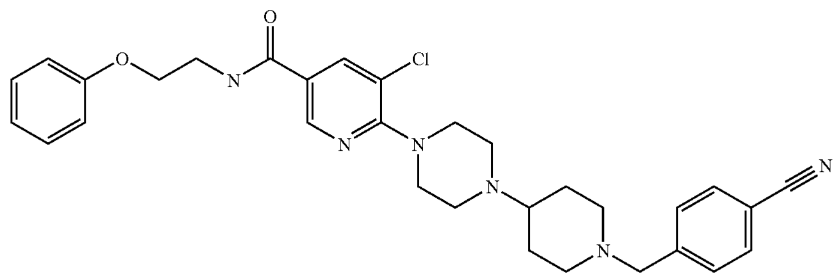 | C |
| 339 | 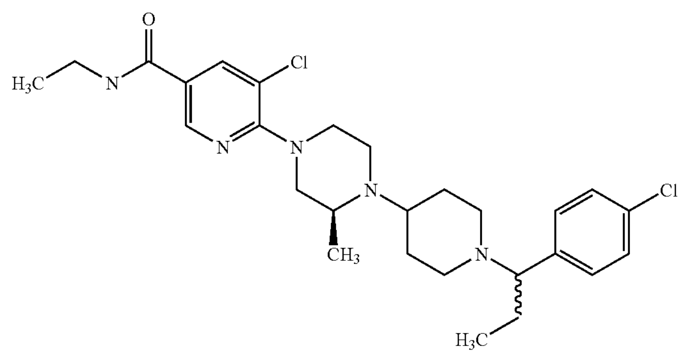 | C |
| 340 | 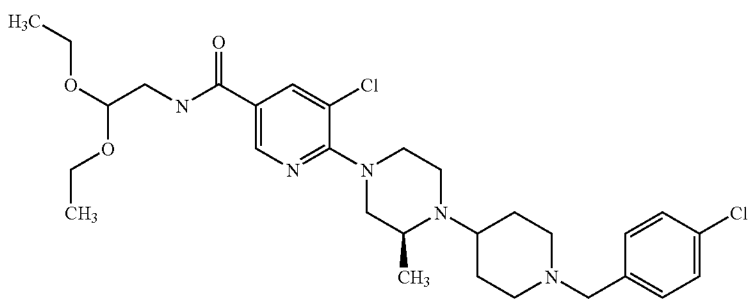 | C |
| 341 | 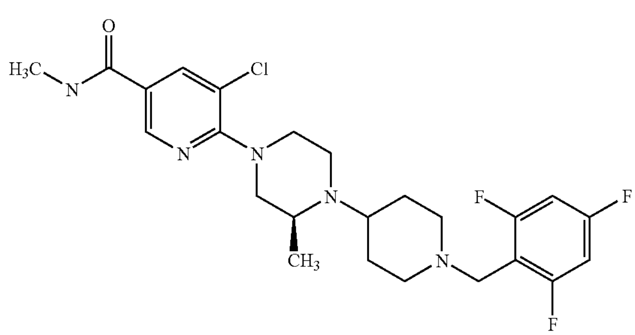 | C |

TABLE 1-continued

| Compound No. | Compound Structure | IC$_{50}$ |
|---|---|---|
| 342 | 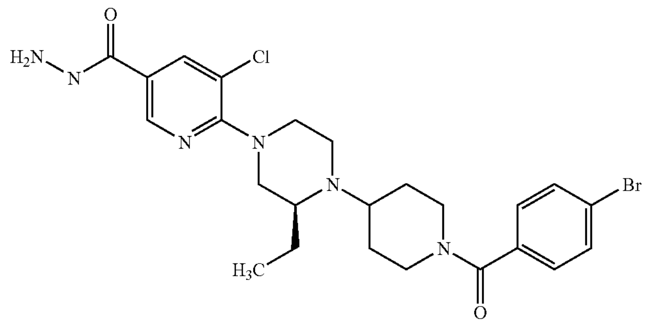 | C |
| 343 | 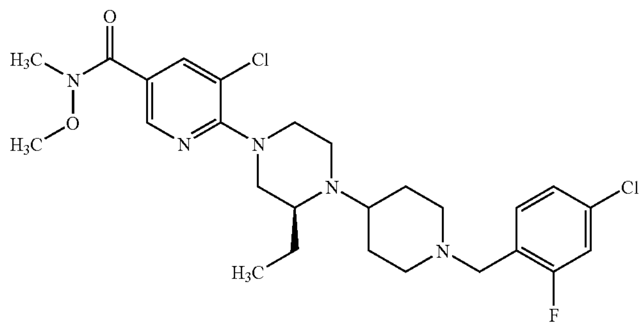 | C |
| 344 | 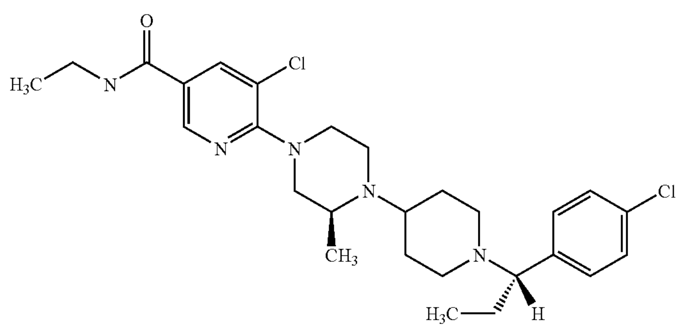 | C |
| 345 | 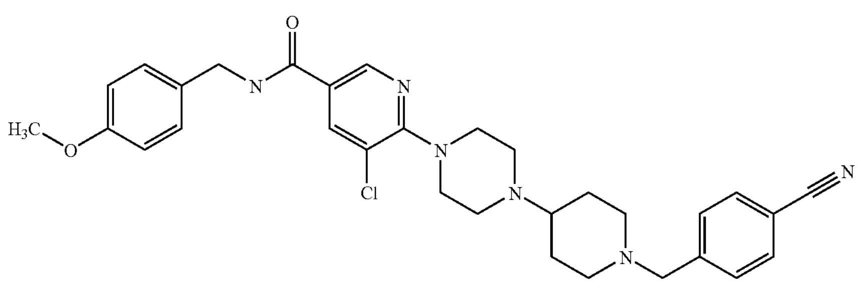 | C |
| 346 | 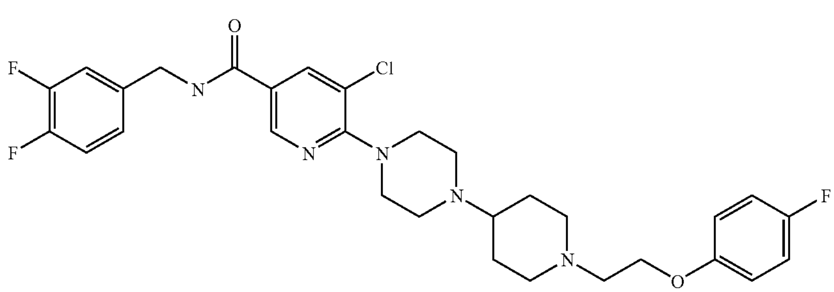 | C |

TABLE 1-continued
| Compound No. | Compound Structure | IC$_{50}$ |
|---|---|---|
| 347 | 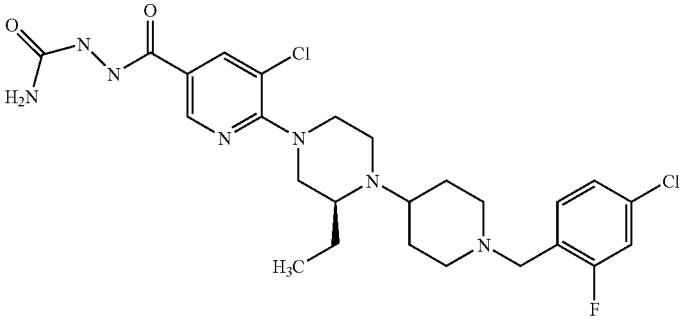 | C |
| 348 | 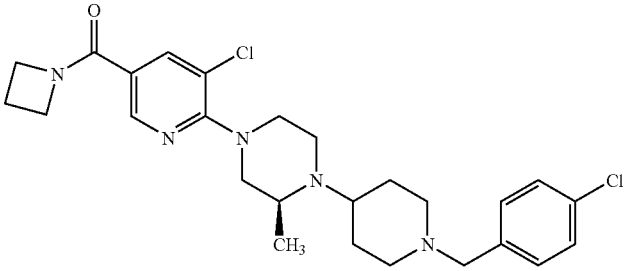 | C |
| 349 | 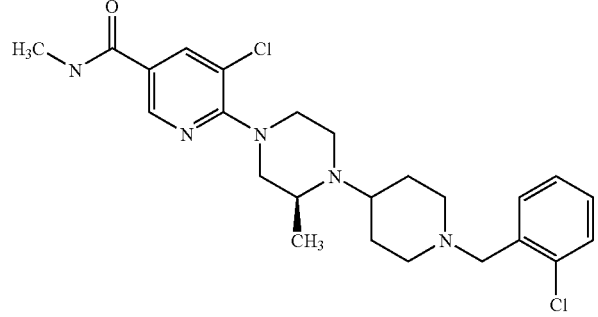 | C |
| 350 | 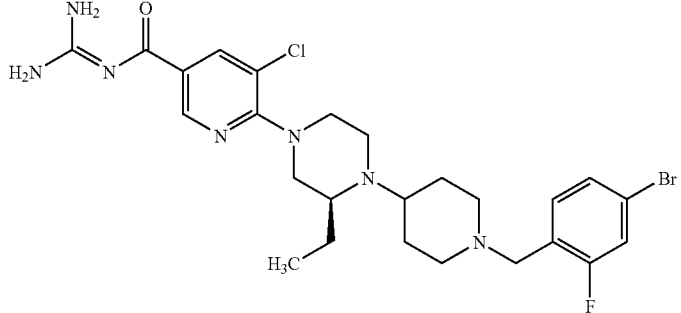 | C |

TABLE 1-continued
| Compound No. | Compound Structure | IC$_{50}$ |
|---|---|---|
| 351 | 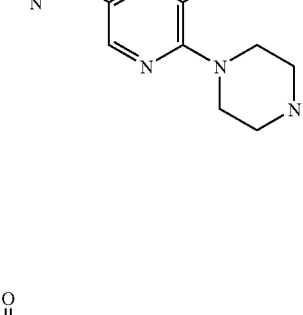 | C |
| 352 | 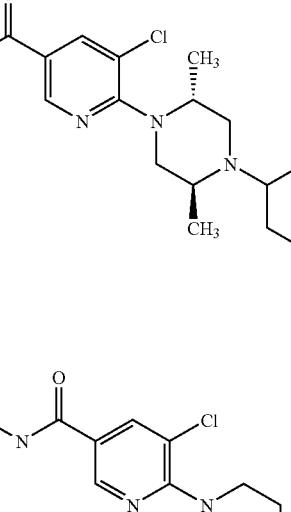 | C |
| 353 | 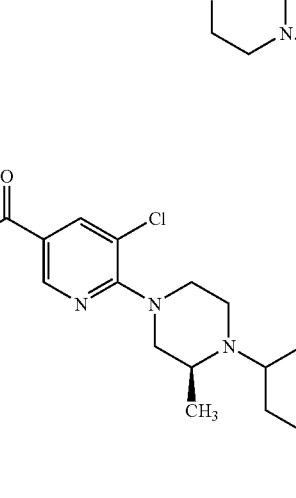 | C |
| 354 | 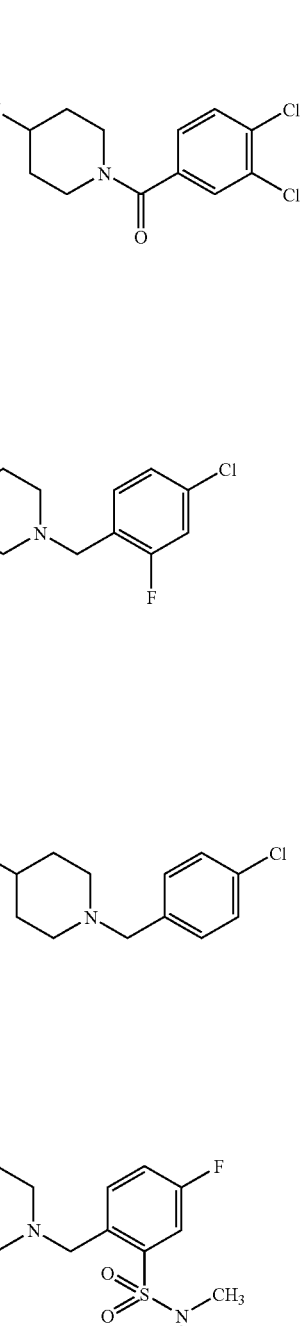 | C |

TABLE 1-continued
| Compound No. | Compound Structure | IC$_{50}$ |
|---|---|---|
| 355 | 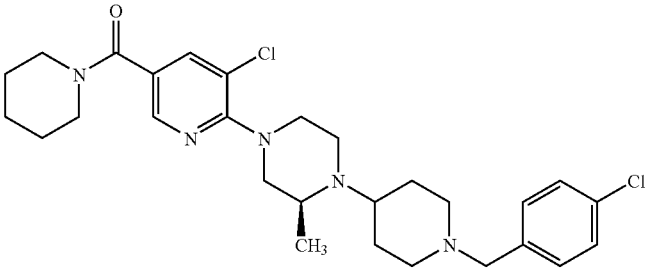 | C |
| 356 | 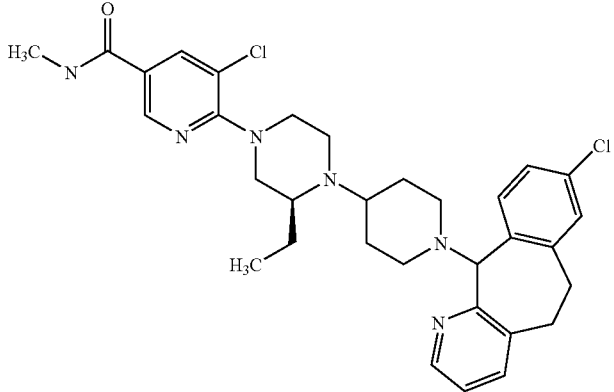 | C |
| 357 | 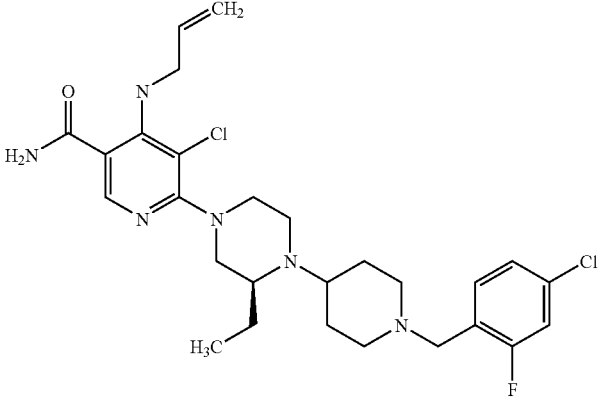 | C |
| 358 | 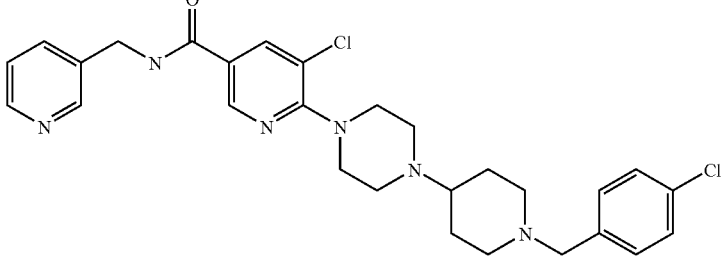 | C |

TABLE 1-continued

| Compound No. | Compound Structure | IC$_{50}$ |
|---|---|---|
| 359 | 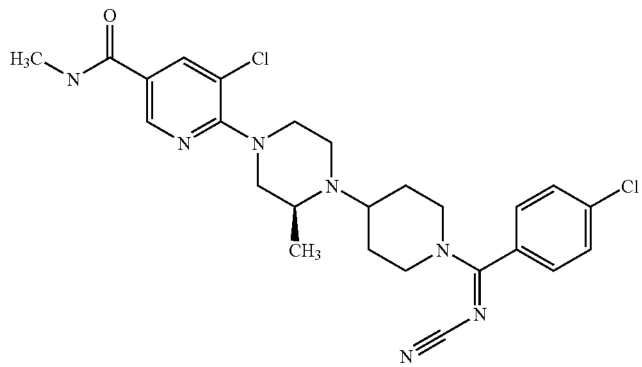 | C |
| 360 | 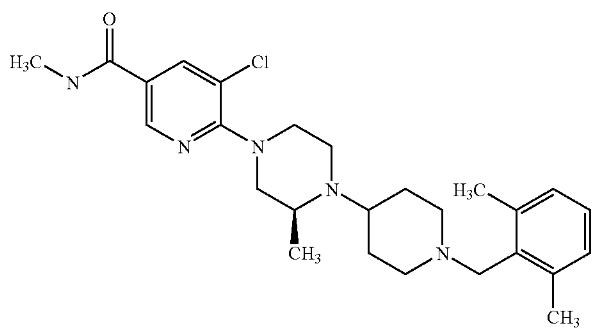 | C |
| 361 | 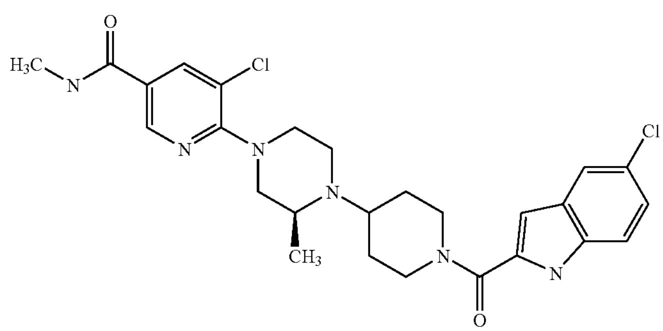 | C |
| 362 | 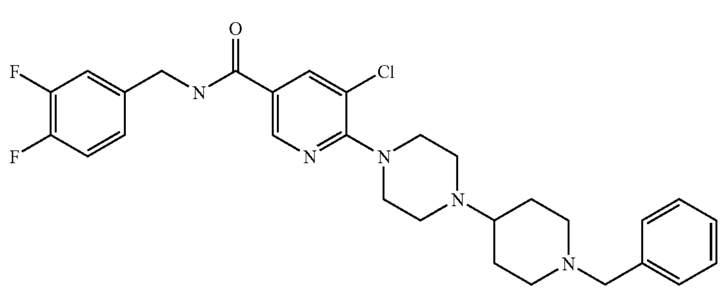 | C |

TABLE 1-continued

| Compound No. | Compound Structure | IC$_{50}$ |
|---|---|---|
| 363 | 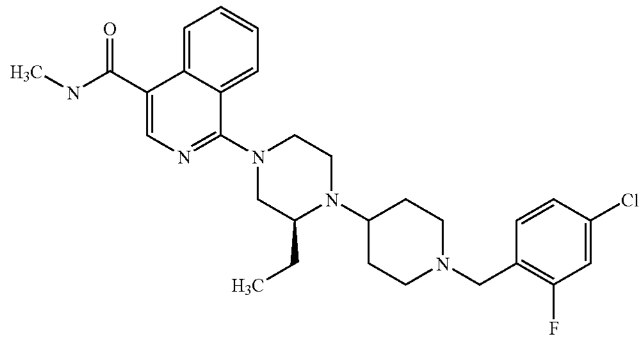 | C |
| 364 | 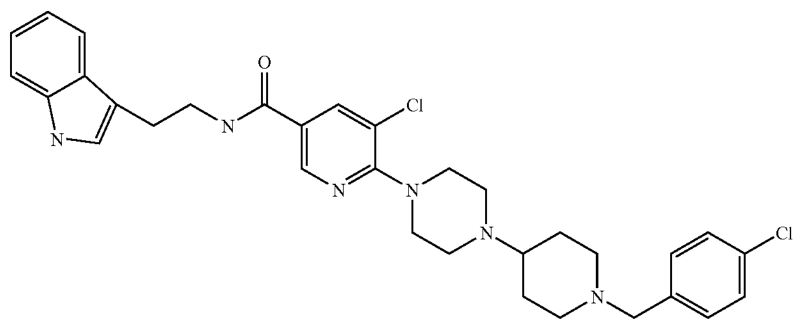 | C |
| 365 | 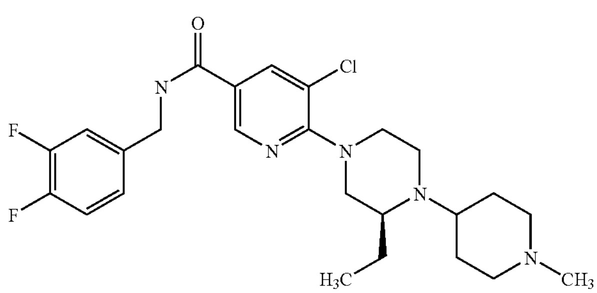 | C |
| 366 | 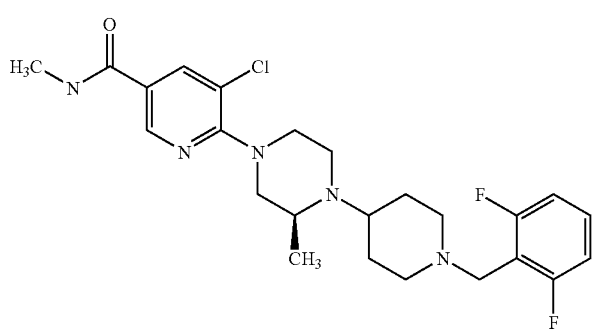 | C |

TABLE 1-continued
| Compound No. | Compound Structure | IC$_{50}$ |
|---|---|---|
| 367 | 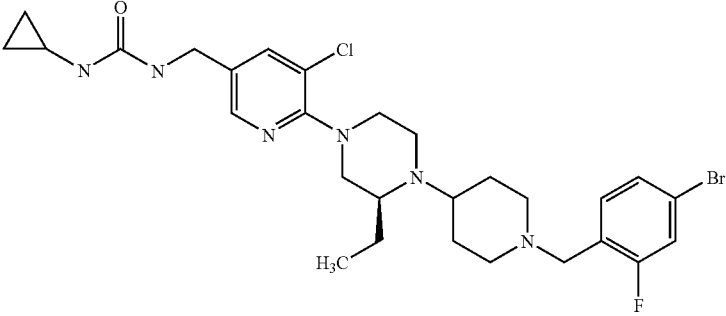 | A |
| 368 | 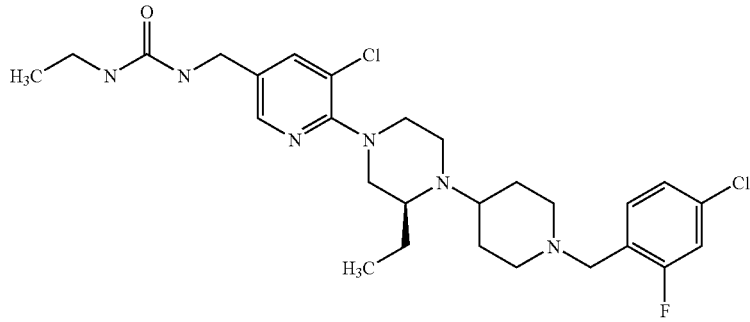 | A |
| 369 | 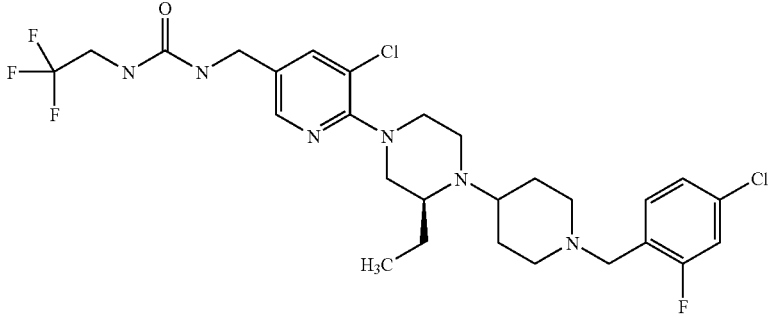 | A |
| 370 | 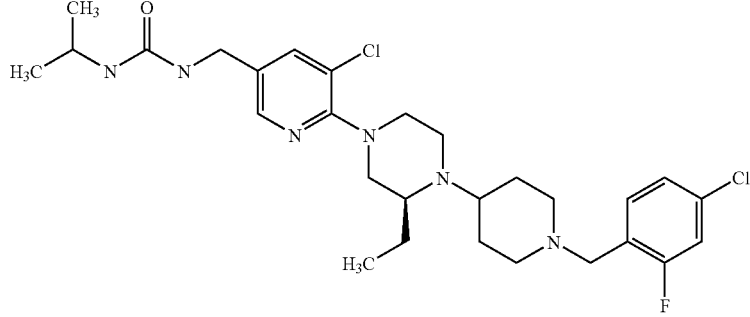 | A |

TABLE 1-continued
| Compound No. | Compound Structure | IC$_{50}$ |
|---|---|---|
| 371 | 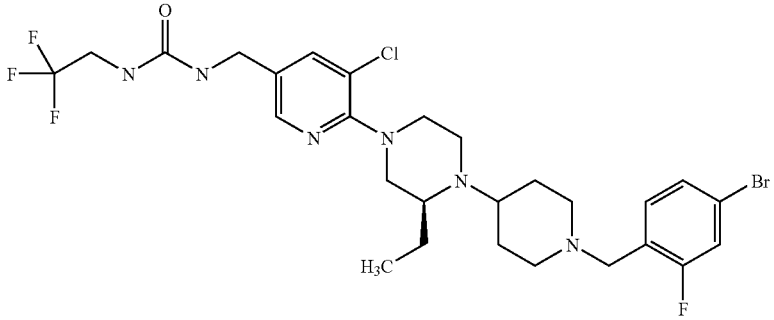 | A |
| 372 | 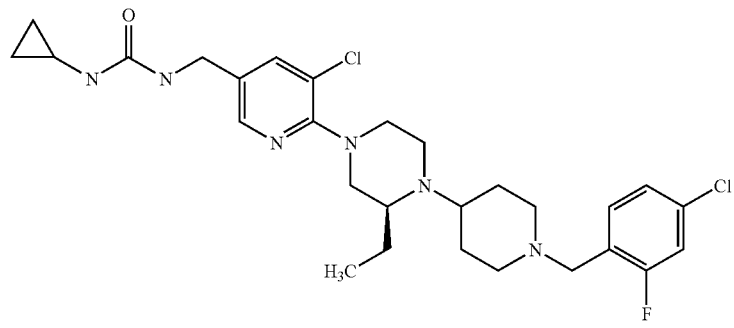 | A |
| 373 | 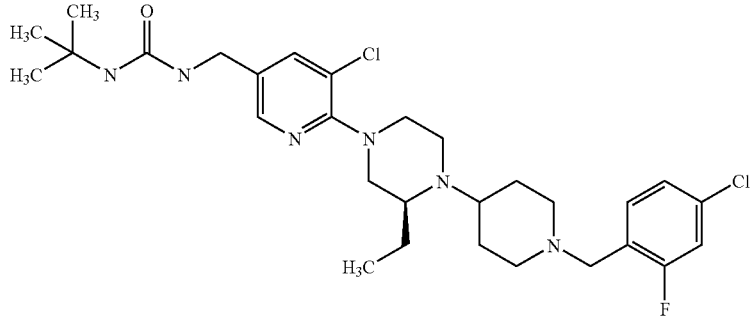 | A |
| 374 | 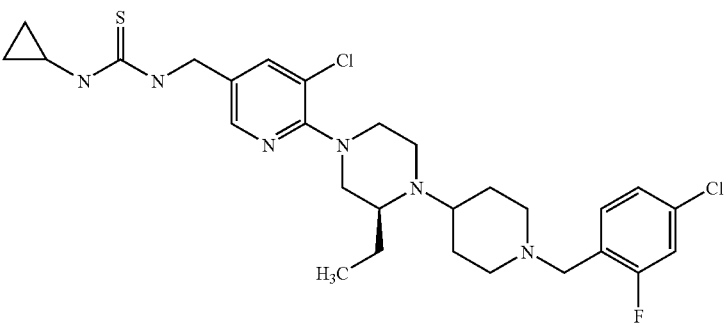 | A |
| 375 | 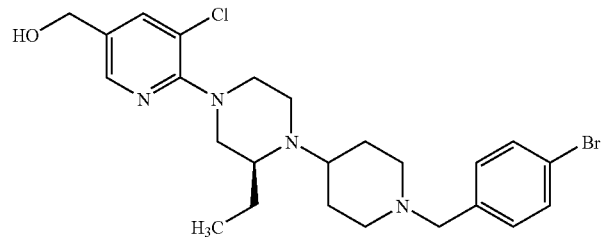 | A |

TABLE 1-continued
| Compound No. | Compound Structure | IC$_{50}$ |
|---|---|---|
| 376 | 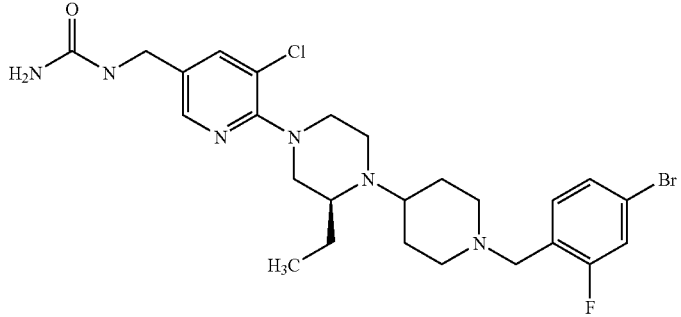 | A |
| 377 | 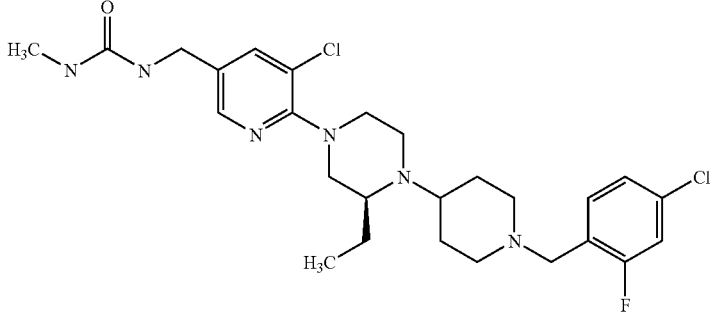 | A |
| 378 | 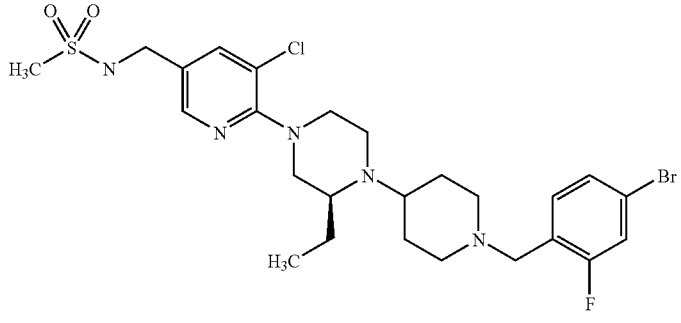 | A |
| 379 | 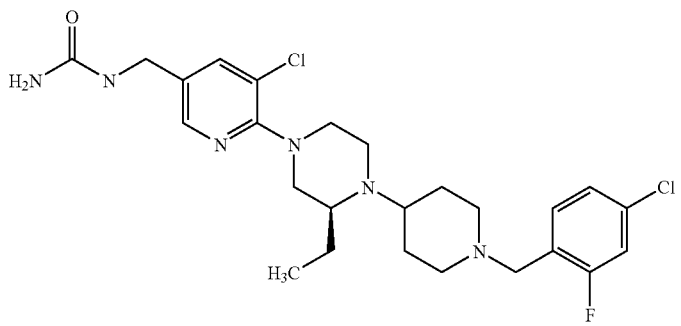 | A |

TABLE 1-continued

| Compound No. | Compound Structure | IC$_{50}$ |
|---|---|---|
| 380 | 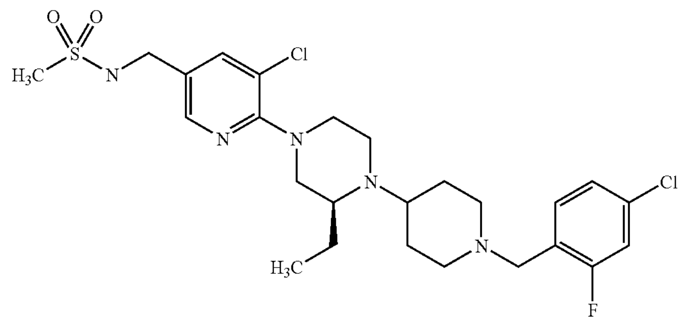 | A |
| 381 | 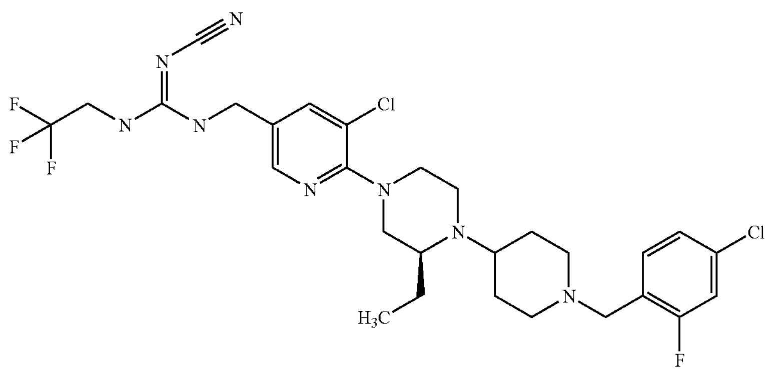 | A |
| 382 | 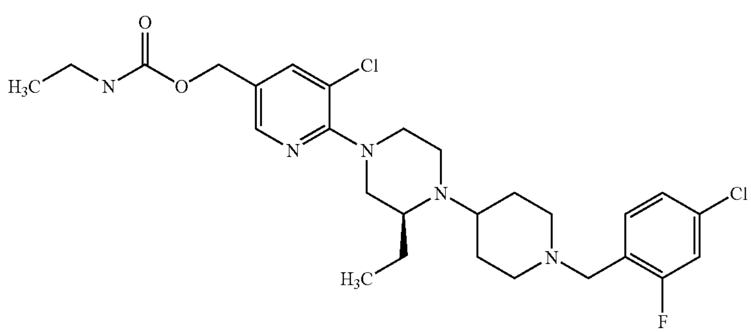 | A |
| 383 | 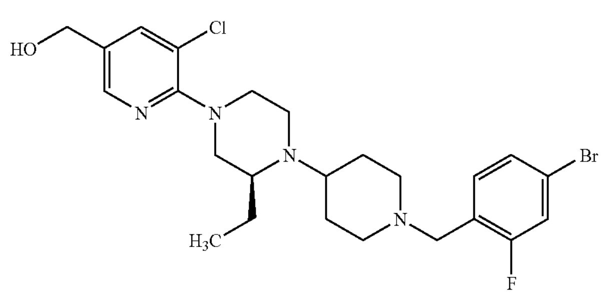 | A |

TABLE 1-continued
| Compound No. | Compound Structure | IC$_{50}$ |
|---|---|---|
| 384 | 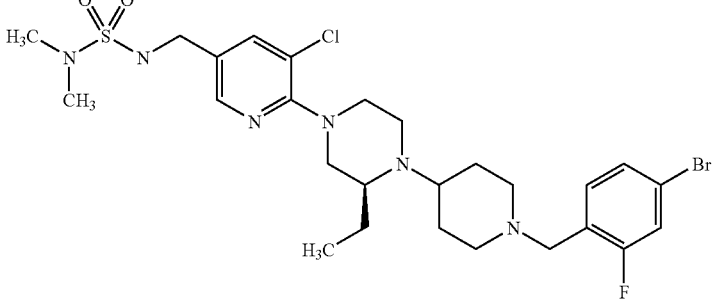 | A |
| 385 | 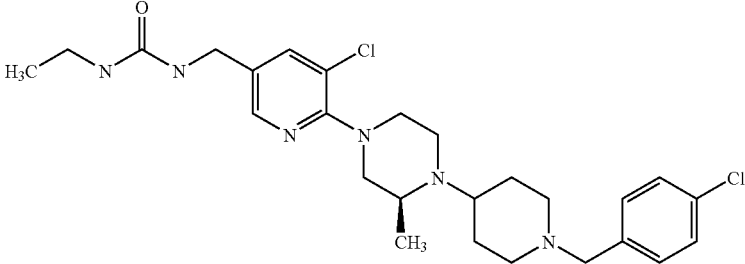 | A |
| 386 | 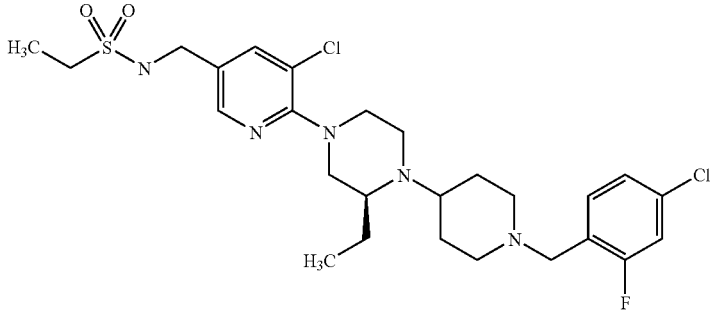 | A |
| 387 | 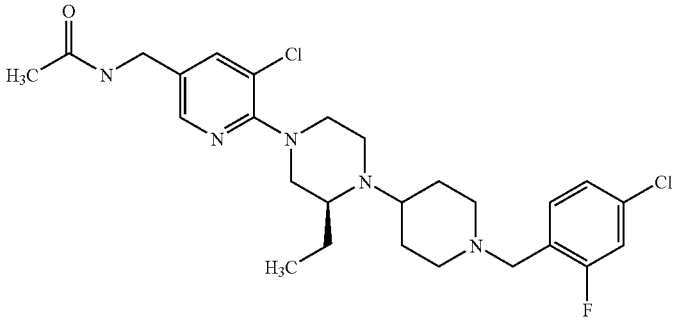 | A |
| 388 | 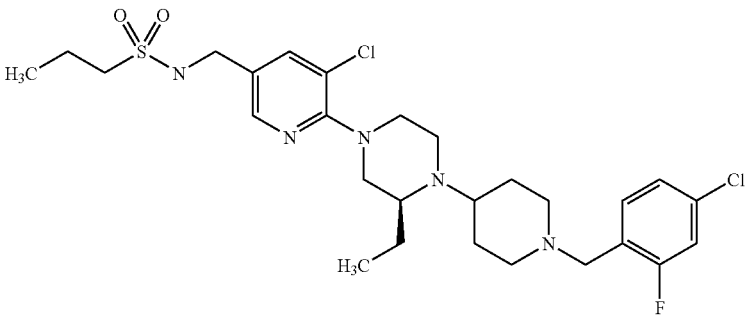 | A |

TABLE 1-continued

| Compound No. | Compound Structure | IC$_{50}$ |
|---|---|---|
| 389 | 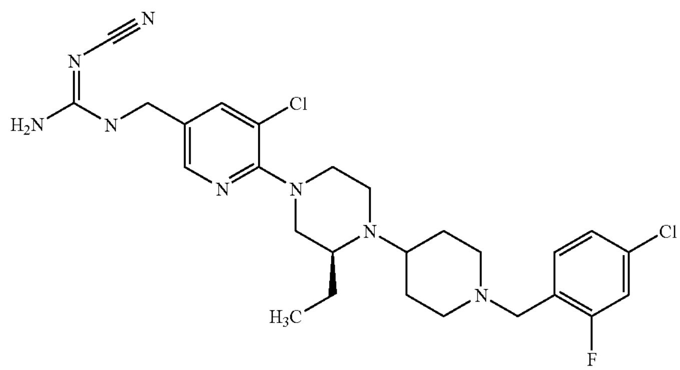 | A |
| 390 | 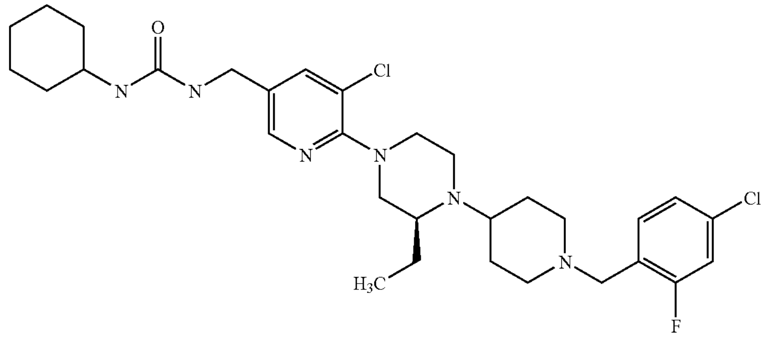 | A |
| 391 | 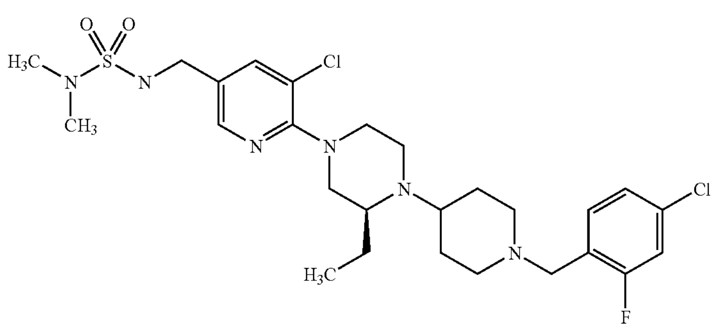 | A |
| 392 | 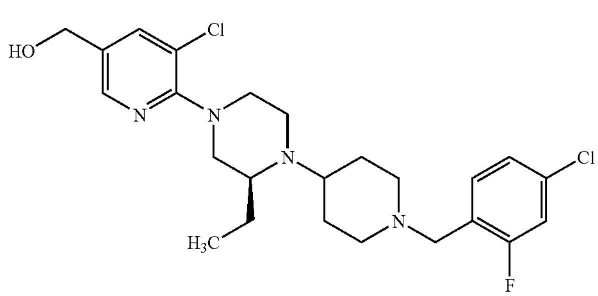 | A |

TABLE 1-continued

| Compound No. | Compound Structure | IC$_{50}$ |
|---|---|---|
| 393 | 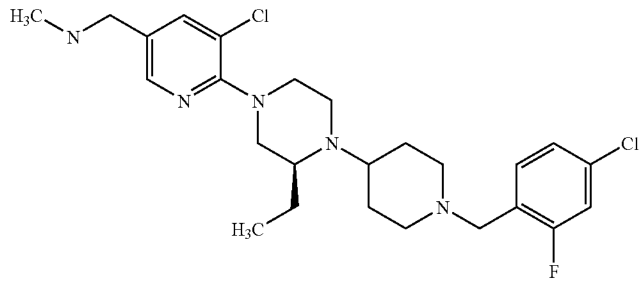 | A |
| 394 | 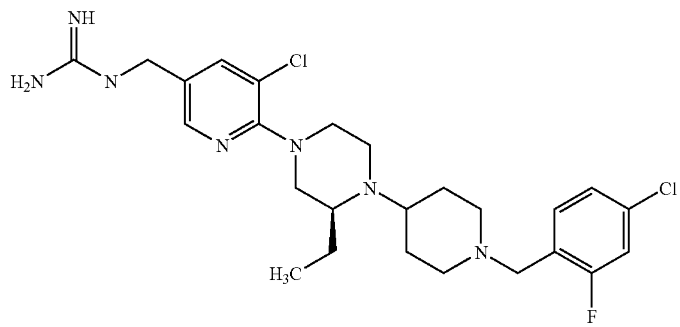 | A |
| 395 | 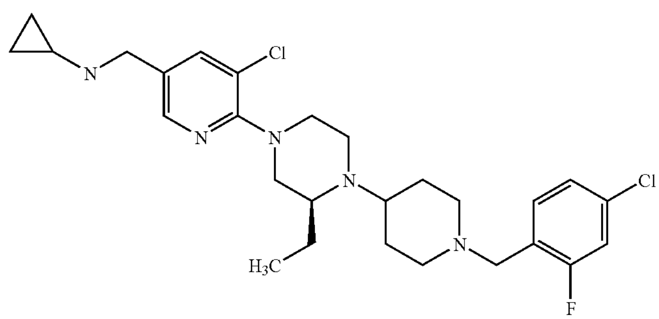 | A |
| 396 | 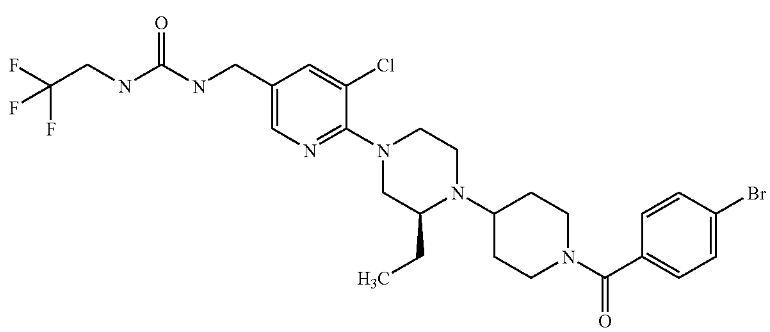 | A |
| 397 | 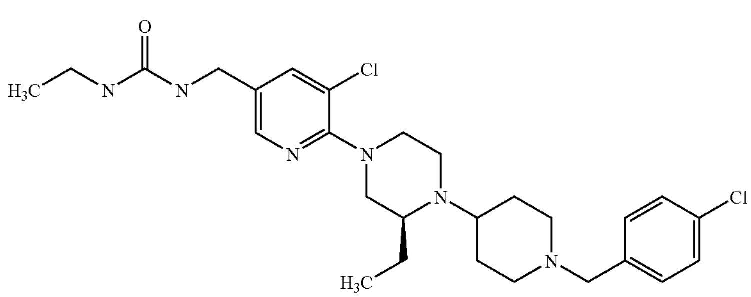 | A |

TABLE 1-continued
| Compound No. | Compound Structure | IC$_{50}$ |
|---|---|---|
| 399 | 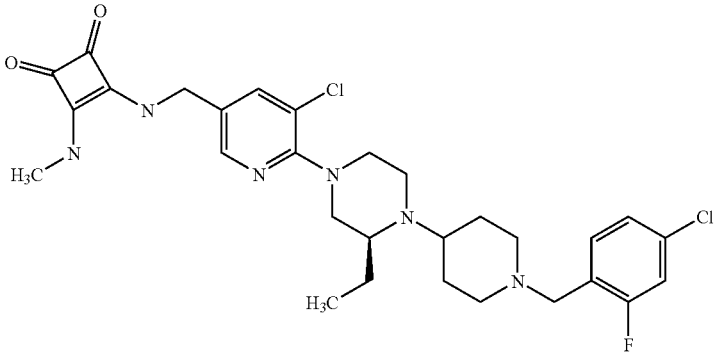 | A |
| 399 | 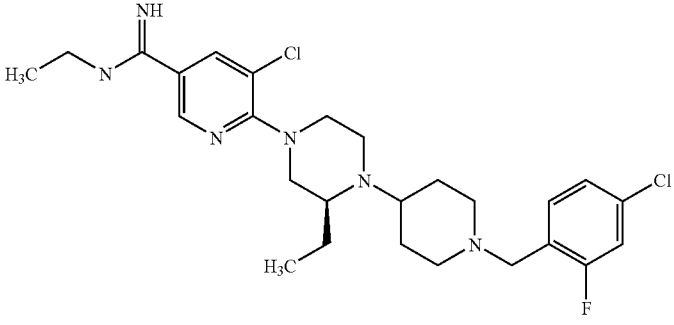 | A |
| 400 | 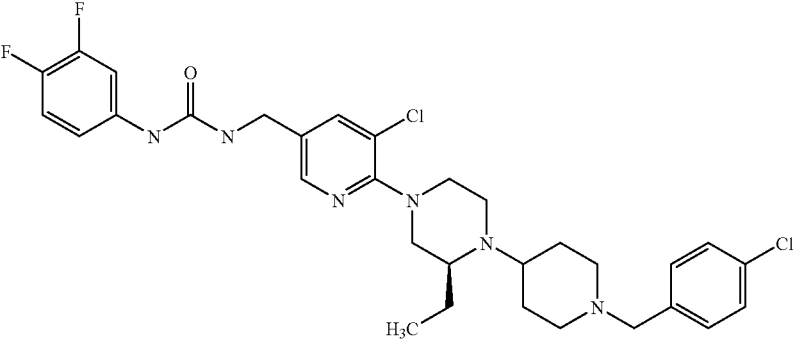 | A |
| 401 | 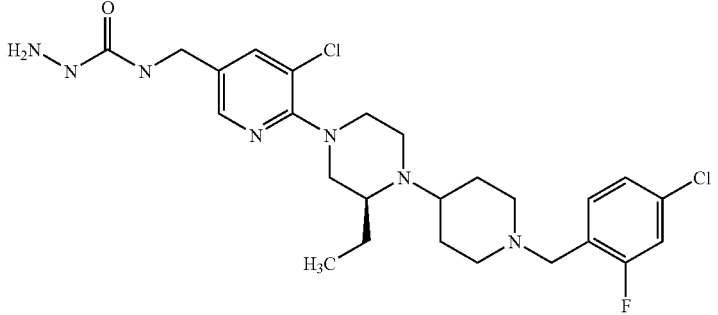 | A |

TABLE 1-continued
| Compound No. | Compound Structure | IC$_{50}$ |
|---|---|---|
| 402 | 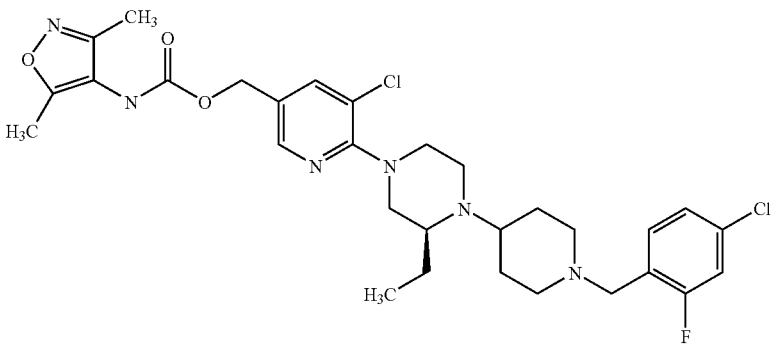 | A |
| 403 | 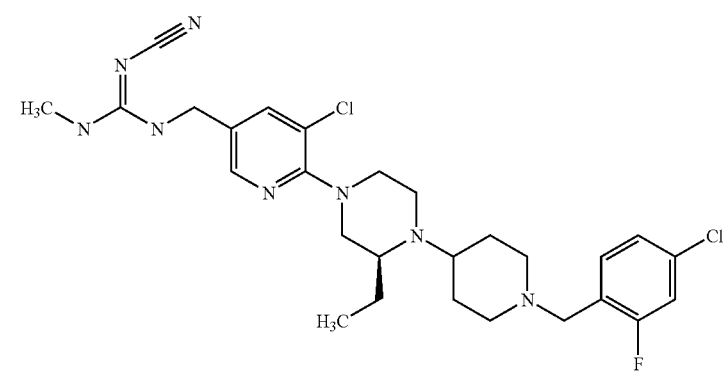 | A |
| 404 | 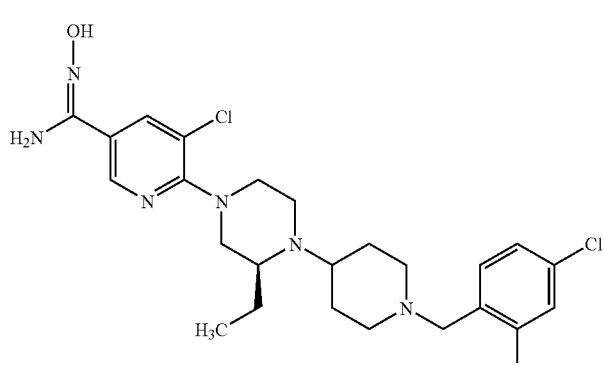 | A |
| 405 | 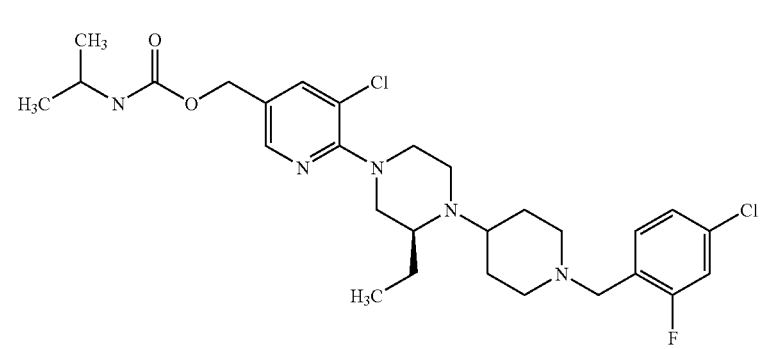 | A |

TABLE 1-continued
| Compound No. | Compound Structure | IC$_{50}$ |
|---|---|---|
| 406 | 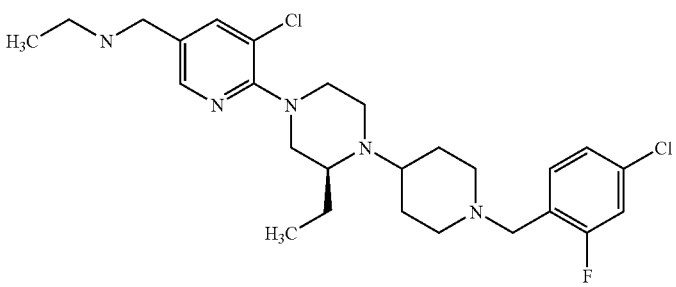 | A |
| 407 | 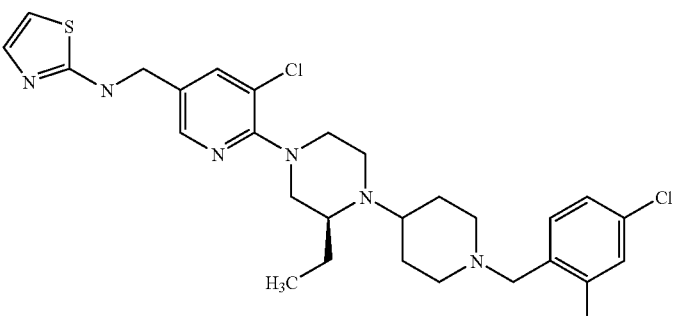 | A |
| 408 | 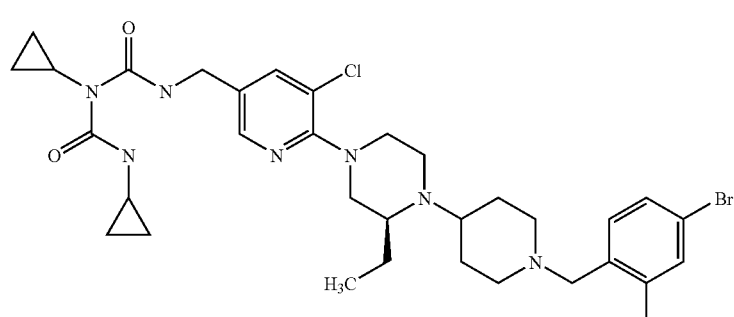 | A |
| 409 | 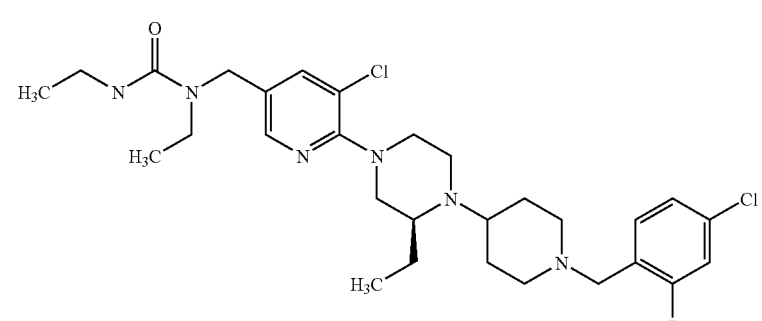 | B |

TABLE 1-continued

| Compound No. | Compound Structure | IC$_{50}$ |
|---|---|---|
| 410 | 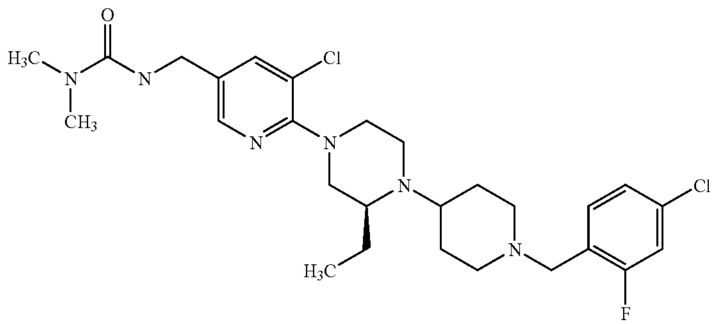 | B |
| 411 | 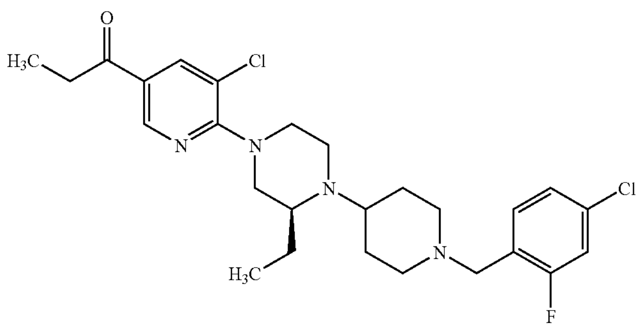 | B |
| 412 | 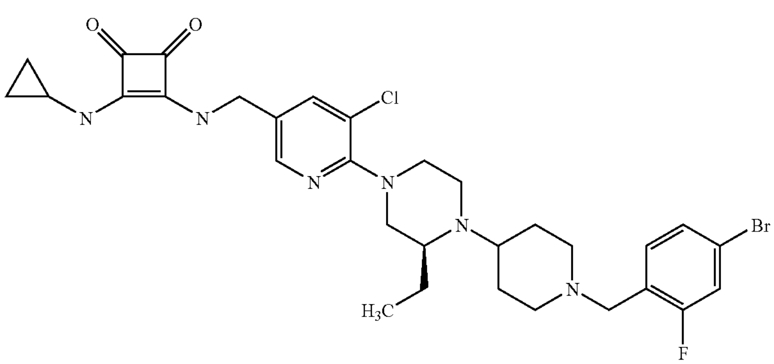 | B |
| 413 | 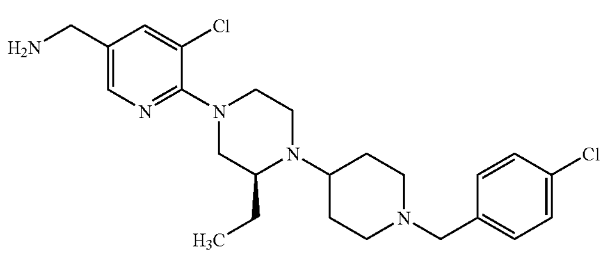 | B |

TABLE 1-continued
| Compound No. | Compound Structure | IC$_{50}$ |
|---|---|---|
| 414 | 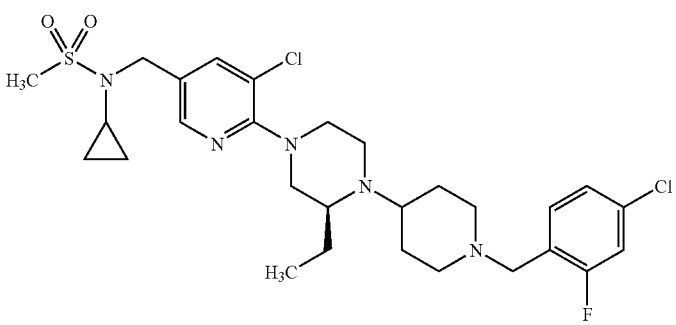 | B |
| 415 | 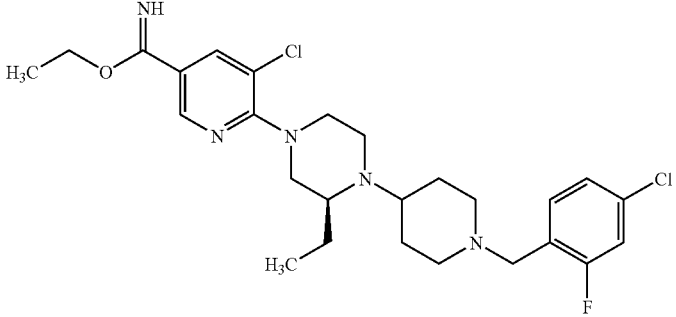 | B |
| 416 | 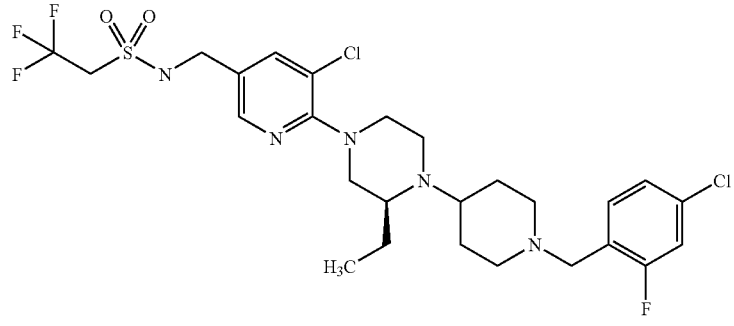 | B |
| 417 | 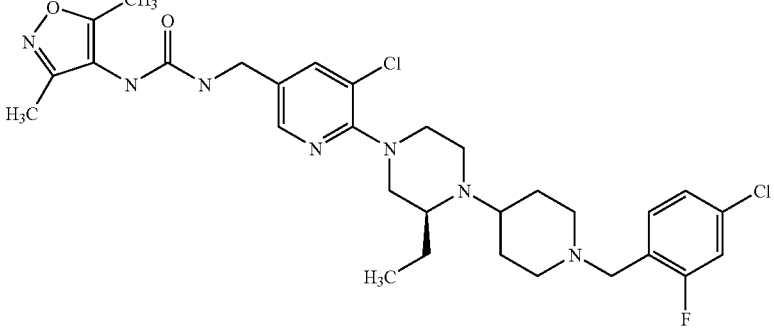 | B |

TABLE 1-continued
| Compound No. | Compound Structure | IC$_{50}$ |
|---|---|---|
| 418 | 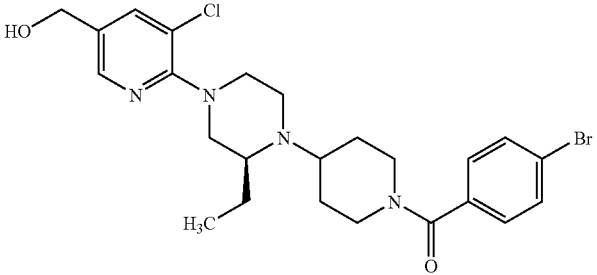 | B |
| 419 | 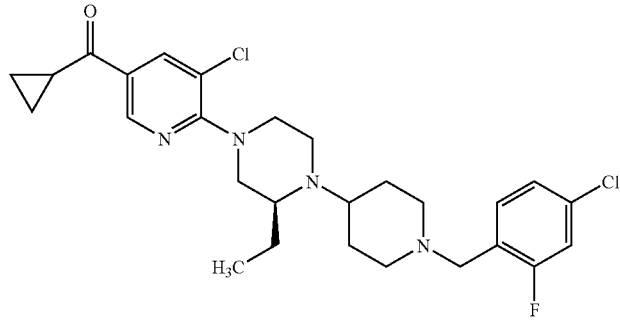 | B |
| 420 | 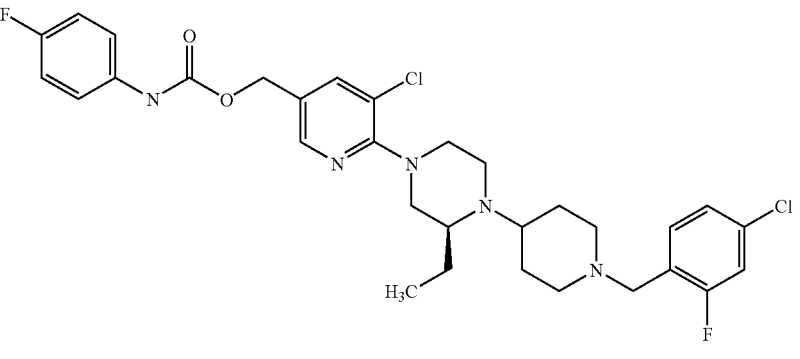 | B |
| 421 | 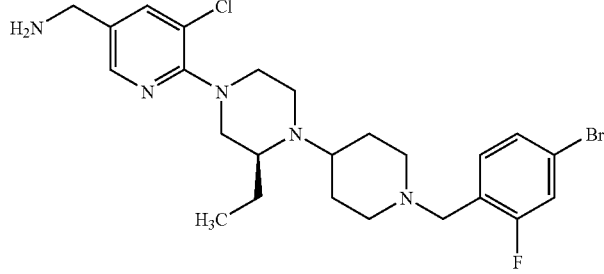 | B |

TABLE 1-continued
| Compound No. | Compound Structure | IC$_{50}$ |
|---|---|---|
| 422 | 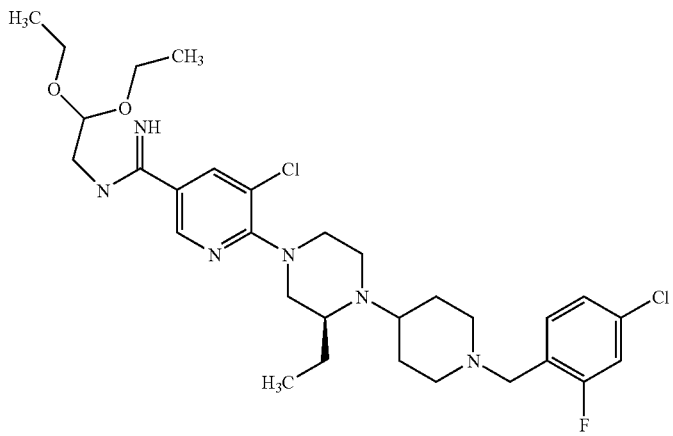 | B |
| 423 | 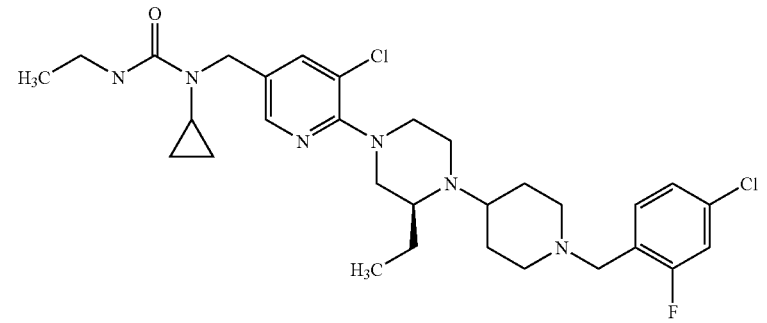 | B |
| 424 | 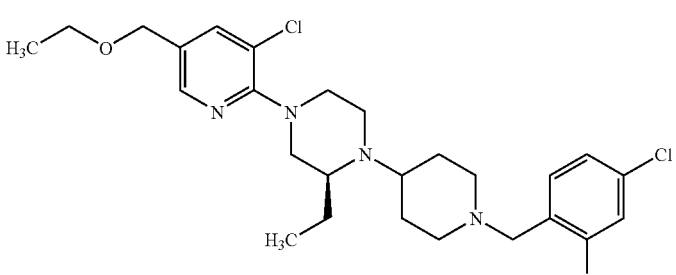 | B |
| 425 | 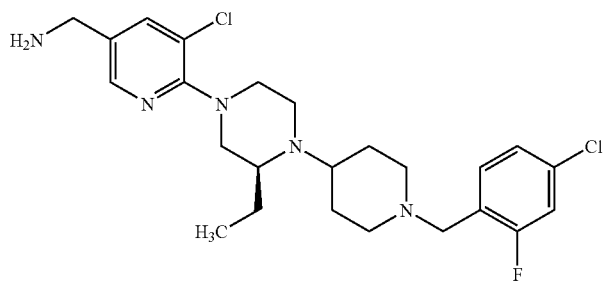 | B |

TABLE 1-continued

| Compound No. | Compound Structure | IC$_{50}$ |
|---|---|---|
| 426 | 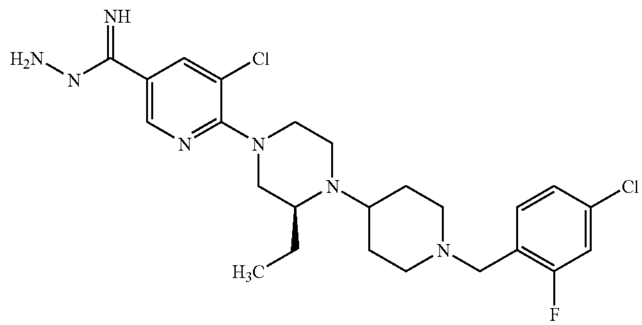 | B |
| 427 | 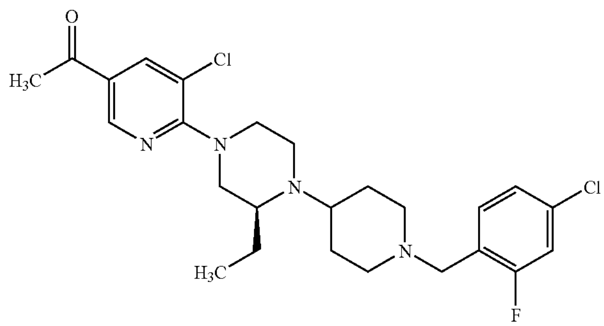 | B |
| 428 | 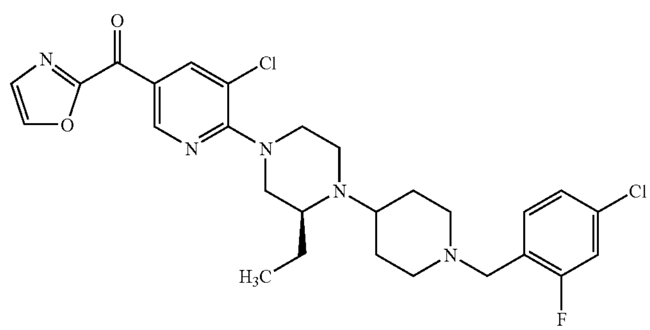 | B |
| 429 | 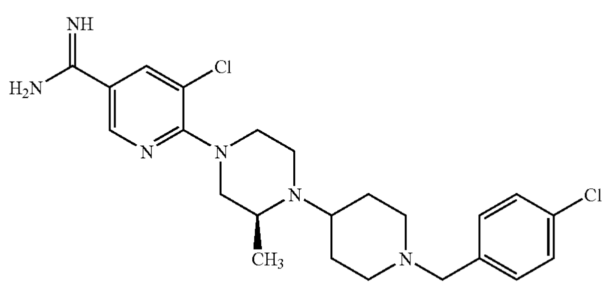 | B |
| 430 | 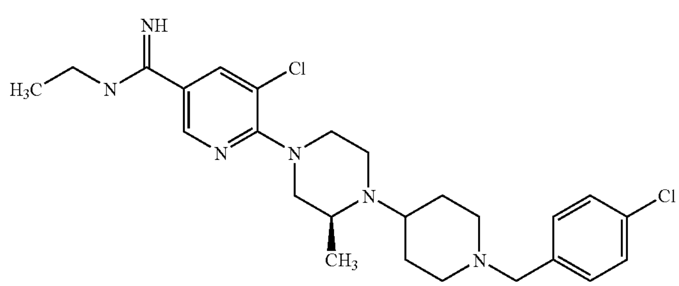 | B |

TABLE 1-continued
| Compound No. | Compound Structure | IC$_{50}$ |
|---|---|---|
| 431 | 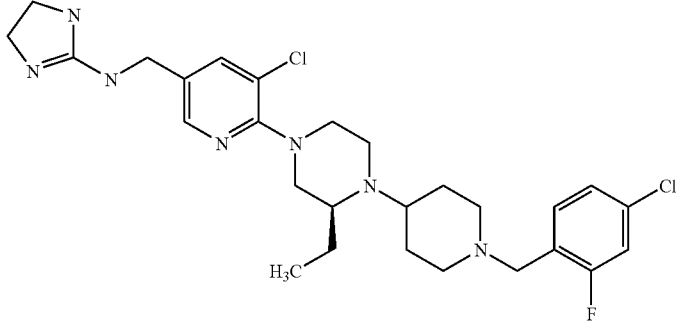 | B |
| 432 | 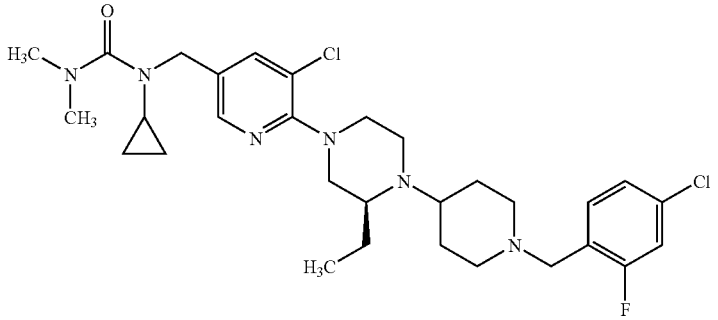 | B |
| 433 | 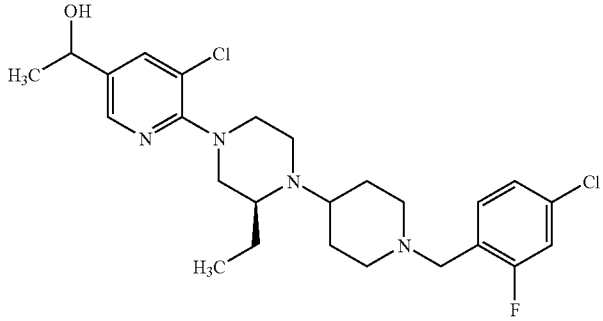 | C |
| 434 | 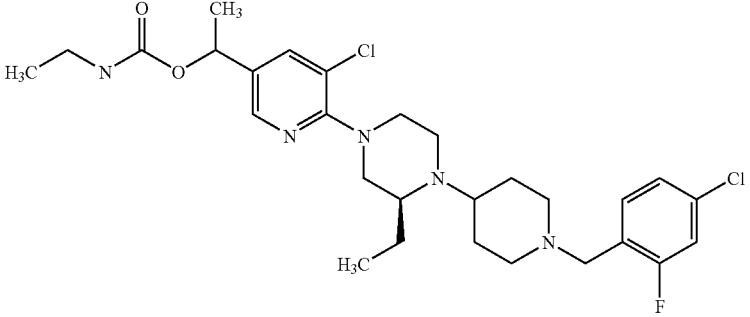 | C |

TABLE 1-continued
| Compound No. | Compound Structure | IC$_{50}$ |
|---|---|---|
| 435 | 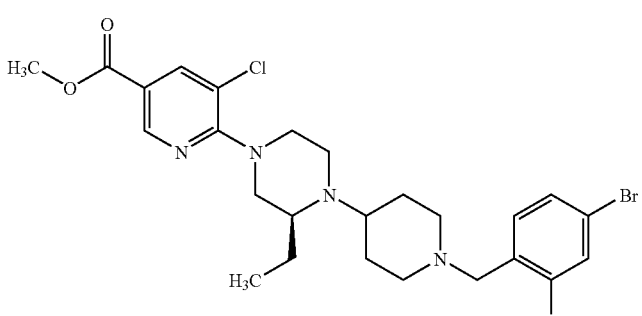 | C |
| 436 | 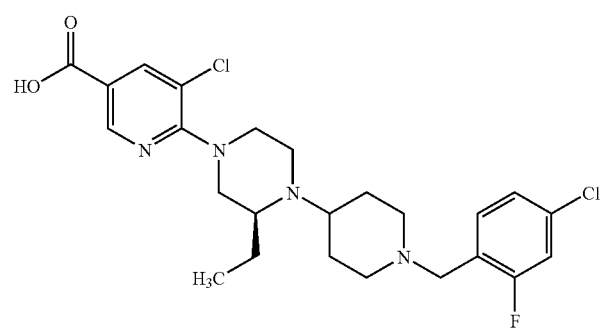 | C |
| 437 | 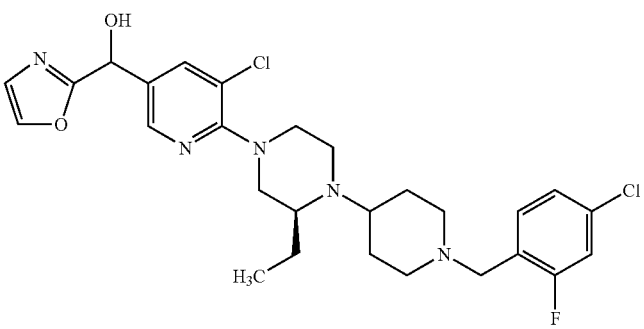 | C |
| 438 | 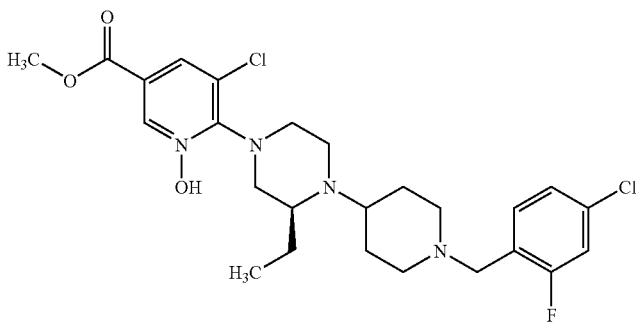 | C |

TABLE 1-continued
| Compound No. | Compound Structure | IC$_{50}$ |
|---|---|---|
| 439 | 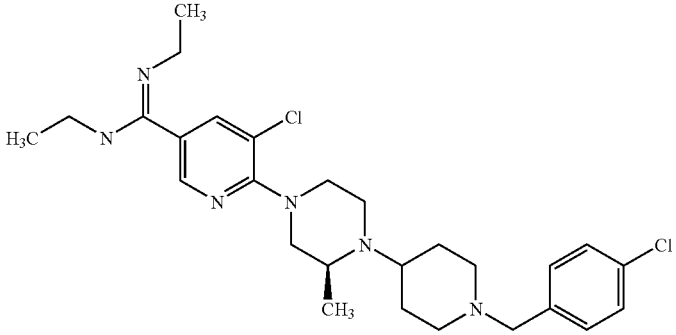 | C |
| 440 | 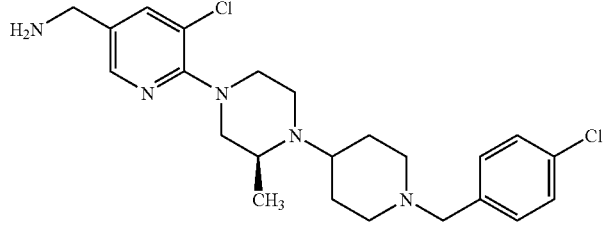 | C |
| 441 | 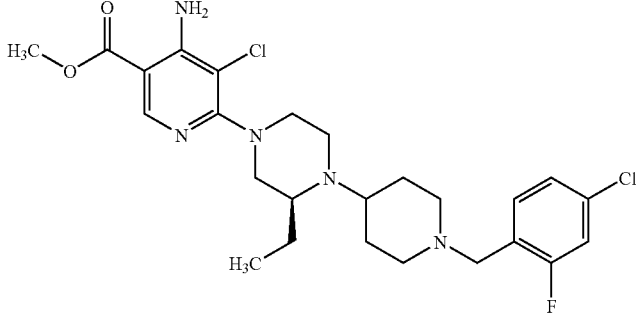 | C |
| 442 | 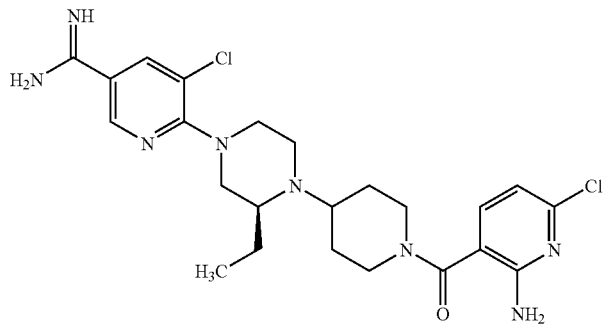 | C |
| 443 | 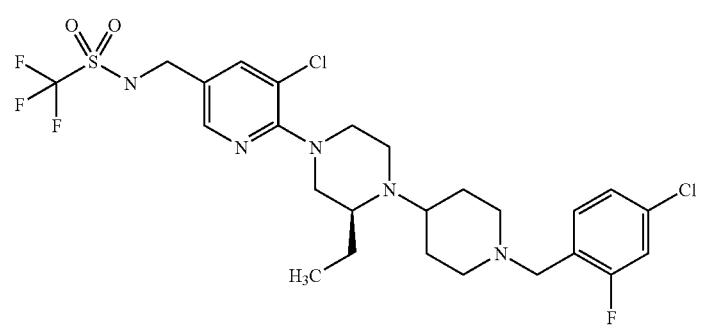 | C |

TABLE 1-continued

| Compound No. | Compound Structure | IC$_{50}$ |
|---|---|---|
| 444 | 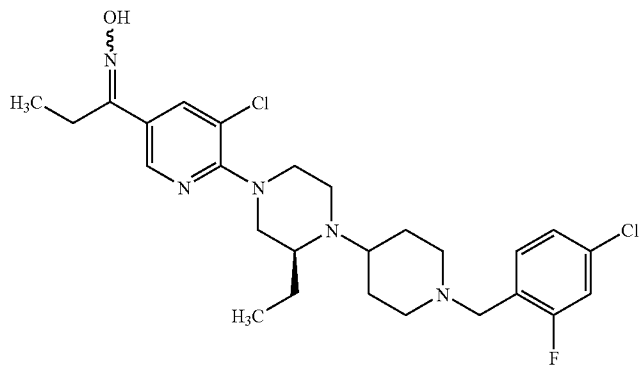 | C |
| 445 | 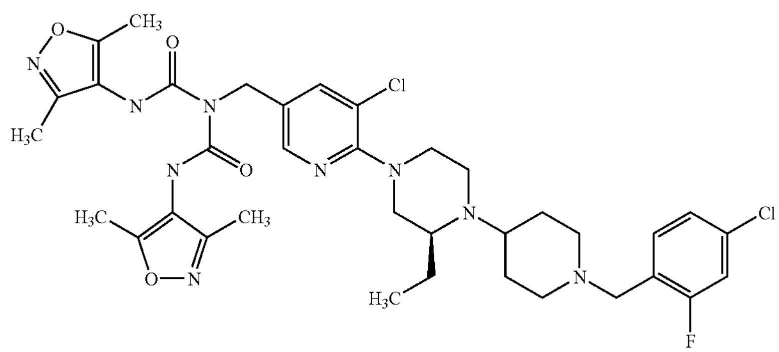 | C |
| 446 | 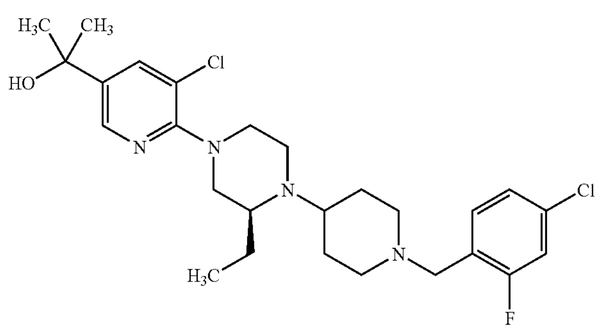 | C |
| 447 | 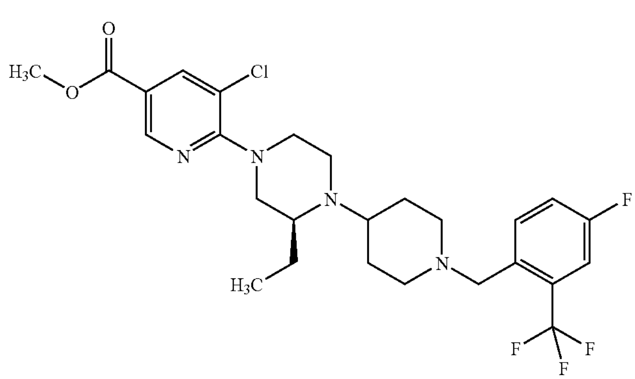 | C |

TABLE 1-continued
| Compound No. | Compound Structure | IC$_{50}$ |
|---|---|---|
| 448 | 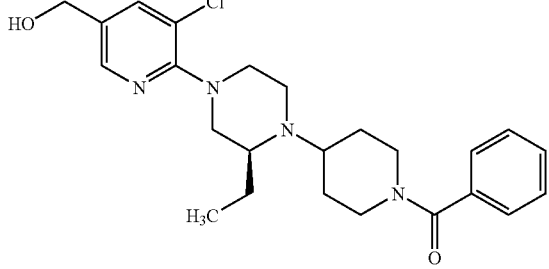 | C |
| 449 | 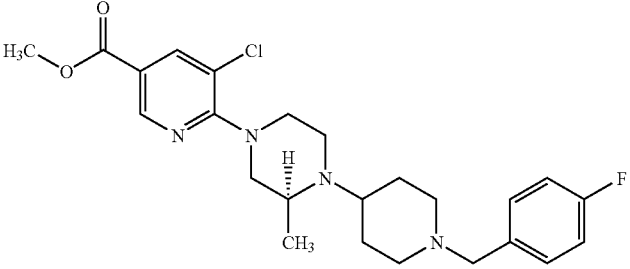 | C |
| 450 | 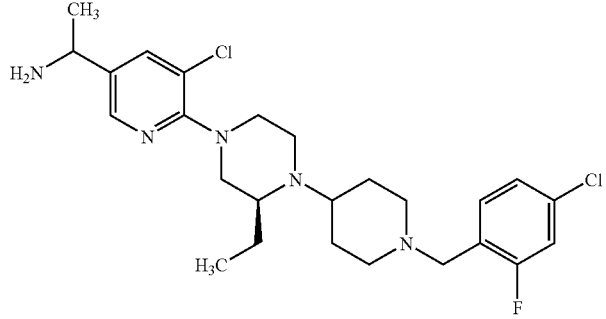 | C |
| 451 | 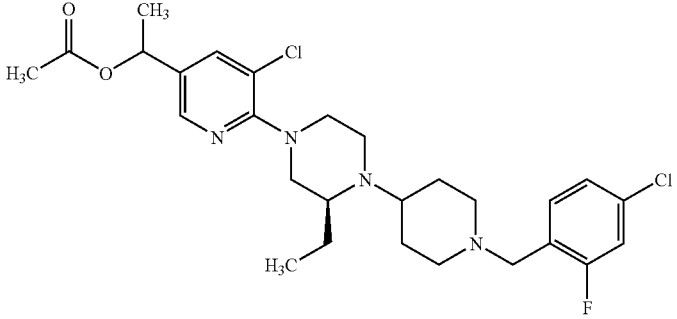 | C |
| 452 | 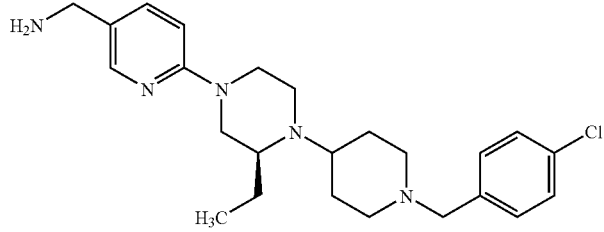 | C |

TABLE 1-continued
| Compound No. | Compound Structure | IC$_{50}$ |
|---|---|---|
| 453 | 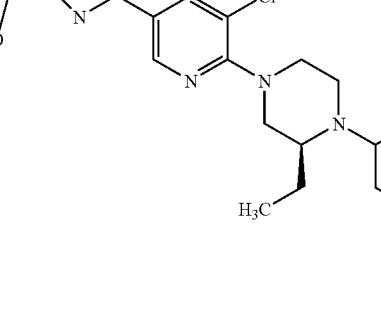 | C |
| 454 | 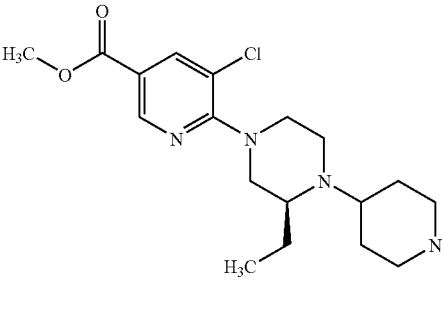 | C |
| 455 | 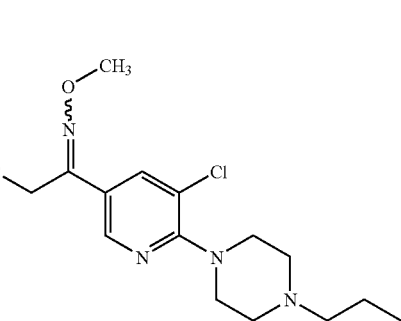 | C |
| 456 | 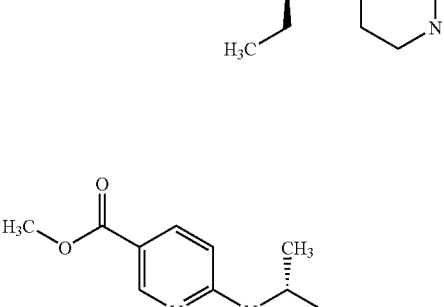 | C |

TABLE 1-continued

| Compound No. | Compound Structure | IC$_{50}$ |
|---|---|---|
| 457 | 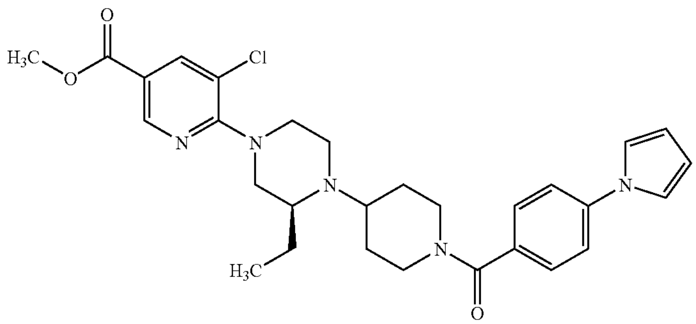 | C |
| 458 | 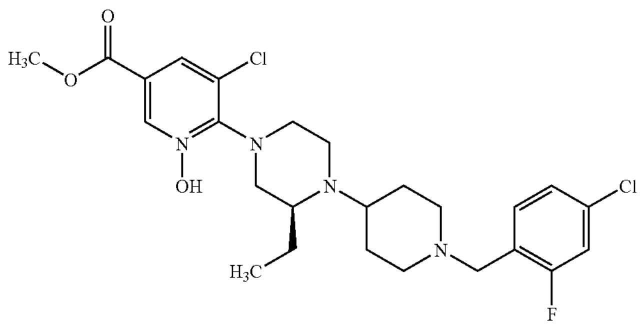 | B |
| 459 | 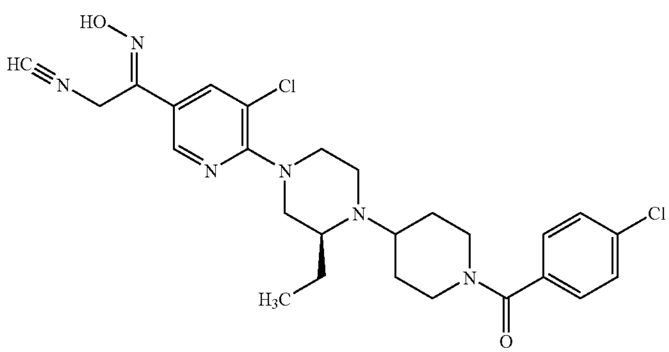 | C |
| 460 | 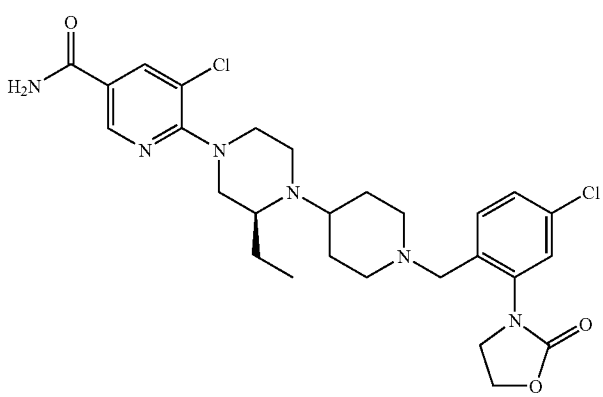 | B |

TABLE 1-continued

| Compound No. | Compound Structure | IC$_{50}$ |
|---|---|---|
| 461 | *[structure of N-cyclopropyl pyridine carboxamide with methyl, piperazine, ethyl, piperidine, 4-chlorobenzoyl]* | A | or pharmaceutically acceptable salts, solvates or esters thereof.

For example, the compound according to Formula 1 can be selected from the group consisting of compounds of the formulae:

*[structure]* (0.2 nM)

*[structure]* (0.3 nM)

*[structure]* (0.4 nM)

*[structure]* (0.4 nM)

-continued

*[structure]* (0.3 nM)

*[structure]* (0.4 nM)

*[structure]* (0.4 nM)

*[structure]* (0.3 nM)

-continued

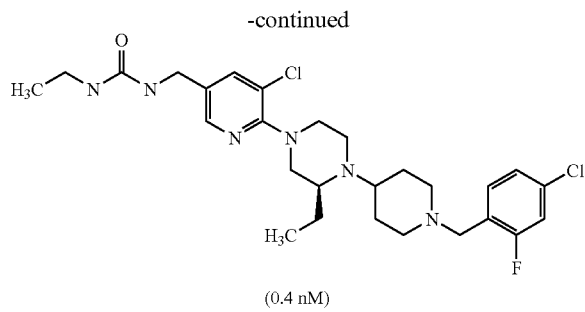

(0.4 nM)

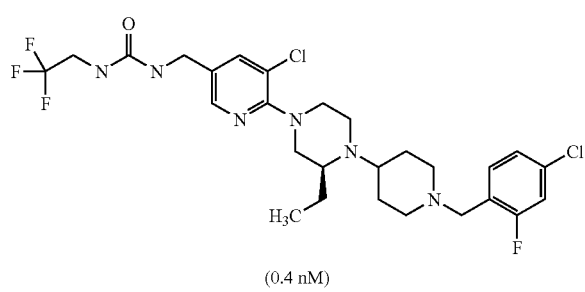

(0.4 nM)

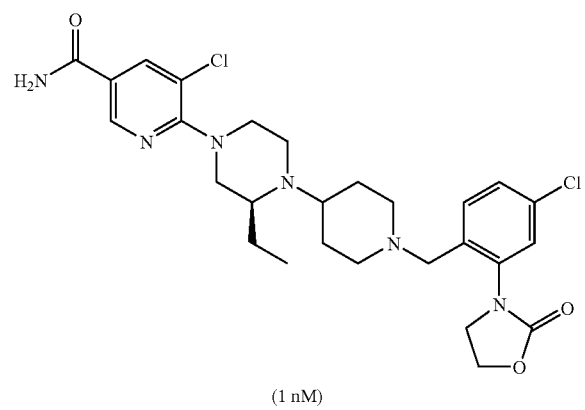

(1 nM)

or pharmaceutically acceptable salts, solvates or esters thereof. The human $IC_{50}$ values (in nM) for the above compounds have been set forth above underneath the compounds structures.

In yet another aspect, ths invention discloses a compound of Formula 6 and Formula 7:

Formula 6

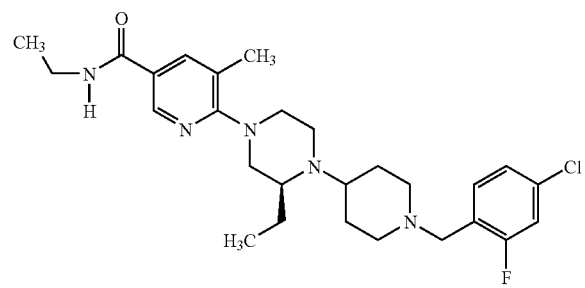

Formula 7

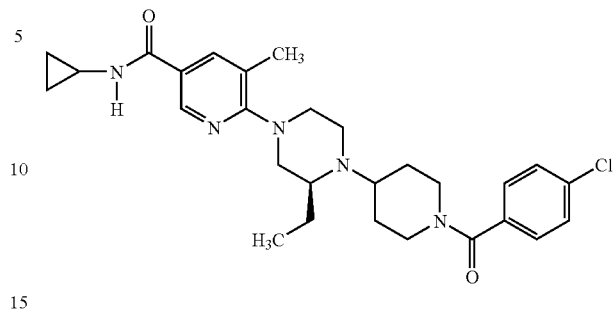

or pharmaceutically acceptable salts, solvates or esters thereof.

In yet another aspect, the compound according to Formula 1 is in purified form.

In another embodiment, this invention provides a pharmaceutical composition comprising at least one compound of Formula 1, or a pharmaceutically acceptable salt, solvate or ester thereof in combination with at least one pharmaceutically acceptable carrier.

In still another embodiment, the invention provides a pharmaceutical composition of Formula 1, further comprising at least one additional agent, drug, medicament, antibody and/or inhibitor for treating a CXCR3 chemokine receptor mediated disease.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a compound of Formula III and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In yet another embodiment, the present invention discloses methods for preparing pharmaceutical compositions comprising the inventive heterocyclic substituted piperazine compounds of Formula 1 as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution—refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

It will be apparent to those skilled in the art that many modifications, variations and alterations to the present disclosure, both to materials and methods, may be practiced. Such modifications, variations and alterations are intended to be within the spirit and scope of the present invention.

As stated earlier, the invention includes tautomers, enantiomers and other stereoisomers of the compounds also. Thus, as one skilled in the art knows, certain imidazole compounds may exist in tautomeric forms. Such variations are contemplated to be within the scope of the invention. Certain compounds of the present invention may exist in multiple crystalline forms or amorphous forms. All physical forms of the current invention are contemplated.

Compounds of this invention which contain unnatural proportions of atomic isotopes (i.e. "radiolabeled compounds") whether their use is therapeutic, diagnostic or as a research reagent are contemplated under this invention.

Another embodiment of the invention discloses the use of the pharmaceutical compositions disclosed above for treatment of diseases of a CXCR3 chemokine receptor mediated disease in a patient in need of such treatment comprising administering to the patient a therapeutically effective amount of at least one compound according to Formula 1, or a pharmaceutically acceptable salt, solvate or ester thereof.

In another embodiment, the method is directed to administering to the patient (a) an effective amount of at least one compound according to Formula 1, or a pharmaceutically acceptable salt, solvate or ester thereof concurrently or sequentially with (b) at least one additional agent, drug, medicament, antibody and/or inhibitor for treating a CXCR3 chemokine receptor mediated disease, in combination with a pharmaceutically acceptable carrier.

In another embodiment, at least one compound of Formula 1 binds to a CXCR3 receptor.

The method can further comprise administering: (a) a therapeutically effective amount of at least one compound according to Formula 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives (such as cyclosporins and methotrexate); steroids (including corticosteroids such as glucorticoids); PDE IV inhibitors, anti-TNF-α compounds, TNF-α-convertase (TACE) inhibitors, MMP inhibitors, cytokine inhibitors, glucocorticoids, other chemokine inhibitors such as CCR2 and CCR5, CB2-selective inhibitors, p38 inhibitors, biological response modifiers; anti-inflammatory agents and therapeutics. The disease can be an inflammatory disease (e.g., psoriasis, inflammatory bowel disease)

Another embodiment of this invention is directed to a method of inhibiting or blocking T-cell mediated chemotaxis in a patient in need of such treatment the method comprising administering to the patient a therapeutically effective amount of at least one compound according to Formula 1 or a pharmaceutically acceptable salt, solvate or ester thereof.

Another embodiment of this invention is directed to a method of treating inflammatory bowel disease (such Crohn's disease, ulcerative colitis) in a patient in need of such treatment comprising administering to the patient a therapeutically effective amount of at least one compound according to Formula 1, or a pharmaceutically acceptable salt, solvate or ester thereof.

Another embodiment of this invention is directed to a method of treating inflammatory bowel disease in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: sulfasalazine, 5-aminosalicylic acid, sulfapyridine, anti-TNF compounds, anti-IL-12 compounds, corticosteroids, glucocorticoids, T-cell receptor directed therapies (such as anti-CD3 antibodies), immunosuppresives, methotrexate, azathioprine, and 6-mercaptopurines.

Another embodiment of this invention is directed to a method of treating or preventing graft rejection in a patient in need of such treatment comprising administering to the patient a therapeutically effective amount of at least one compound according to Formula 1, or a pharmaceutically acceptable salt, solvate or ester thereof.

Another embodiment of this invention is directed to a method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: cyclosporine A, FK-506, FTY720, beta-interferon, rapamycin, mycophenolate, prednisolone, azathioprine, cyclophosphamide and an antilymphocyte globulin.

Another embodiment of this invention is directed to a method of treating multiple sclerosis in a patient in need of such treatment the method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: beta-interferon, glatiramer acetate, corticosteroids, glucocorticoids, methotrexate, azathioprine, mitoxantrone, VLA4 inhibitors, FTY720, anti-IL-12 inhibitors, and CB2-selective inhibitors.

Another embodiment of this invention is directed to a method of treating multiple sclerosis in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: methotrexate, cyclosporin, leflunomide, sulfasalazine, corticosteroids, β-methasone, β-interferon, glatiramer acetate, prednisone, etonercept, and infliximab.

Another embodiment of this invention is directed to a method of treating rheumatoid arthritis in a patient in need of such treatment the method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: non-steroidal anti-inflammatory agents, COX-2 inhibitors, COX-1 inhibitors, immunosuppressives, cyclosporine, methotrexate, steroids, PDE IV inhibitors, anti-TNF-α compounds, MMP inhibitors, corticosteroids, glucocorticoids, chemokine inhibitors, CB2-selective inhibitors, caspase (ICE) inhibitors and other classes of compounds indicated for the treatment of rheumatoid arthritis.

Another embodiment of this invention is directed to a method of treating psoriasis in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, steroids, corticosteroids, anti-TNF-α compounds, anti-IL compounds, anti-IL-23 compounds, vitamin A and D compounds and fumarates.

Another embodiment of this invention is directed to a method of treating ophthalmic inflammation (including, for e.g., uveitis, posterior segment intraocular inflammation, Sjogren's syndrome) or dry eye in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, FK506, steroids, corticosteroids, and anti-TNF-α compounds.

Another embodiment of this invention is directed to a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses, ophthalmic inflammation (including e.g., uveitis, posterior segment intraocular inflammation, and Sjogren's syndrome), tuberculoid leprosy and cancer in a patient in need of such treatment, such method comprising administering to the patient an effective amount of at least one compound according to Formula 1, or a pharmaceutically acceptable salt, solvate or ester thereof.

Another embodiment of this invention is directed to a method of treating a disease selected from the group consisting of inflammatory disease, rheumatoid arthritis, multiple sclerosis, inflammatory bowel disease, graft rejection, psoriasis, fixed drug eruptions, cutaneous delayed-type hypersensitivity responses and tuberculoid leprosy, ophthalmic inflammation, type I diabetes, viral meningitis and cancer in a patient in need of such treatment, such method comprising administering to the patient an effective amount of (a) at least one compound according to Formula 1, or a pharmaceutically acceptable salt, solvate or ester thereof concurrently or sequentially with (b) at least one medicament selected from the group consisting of: disease modifying antirheumatic drugs; nonsteroidal antiinflammatory drugs; COX-2 selective inhibitors; COX-1 inhibitors; immunosuppressives; steroids; PDE IV inhibitors, anti-TNF-α compounds, MMP inhibitors, corticosteroids, glucocorticoids, chemokine inhibitors, CB2-selective inhibitors, biological response modifiers; anti-inflammatory agents and therapeutics.

Another embodiment of the invention discloses a method of making the inventive compounds disclosed above.

For the procedures described below and unless otherwise stated, the following abbreviations have the stated meanings in the Preparative Examples below:
DBU=1,8-diazabicyclo[5.4.0]undec-7-ene
DBN=1,5-diazabicyclo[4.3.0]non-5-ene
EDCI=1-(3-dimethylaminopropyl)-3-ethylcarbodiimide
HOBT=1-hydroxybenzotriazole
HATU=O-(7-Azabenzotriazol-1-yl)-N,N,N',N'-tetramethyluronium hexafluorophosphate
DCC=dicyclohexylcarbodiimide
Dibal-H=diisobutylaluminum hydride
DIEA=Diisopropylethylamide
DMF=Dimethylformamide
LAH=lithium aluminum hydride
$NaBH(OAc)_3$=sodium triacetoxyborohydride
$NaBH_4$=sodium borohydride
$NaBH_3CN$=sodium cyanoborohydride
LDA=lithium diisopropylamide
p-TsOH=p-toluenesulfonic acid
m-CPBA=m-Chloroperbenzoic acid
TMAD=N,N,N',N'-tetramethylazodicarboxamide
CSA=camphorsulfonic acid
NaHMDS=sodium hexamethyl disilylazide
HRMS=High Resolution Mass Spectrometry
HPLC=High Performance Liquid Chromatography
LRMS=Low Resolution Mass Spectrometry
nM=nanomolar
Ki=Dissociation Constant for substrate/receptor complex
pA2=−log $EC_{50}$, as defined by J. Hey, *Eur. J. Pharmacol.*, (1995), Vol. 294, 329-335.
Ci/mmol=Curie/mmol (a measure of specific activity)
Tr=Triphenylmethyl
Tris=Tris (hydroxymethyl)aminomethane

GENERAL SYNTHESIS

Compounds of the present invention can be prepared by a number of ways evident to one skilled in the art. Preferred methods include, but are not limited to, the general synthetic procedures described herein. Compounds can be made on solid support or by traditional methods in solution. One skilled in the art will recognize that one route will be optimal depending on the choice of appendage substituents. Additionally, one skilled in the art will recognize that in some cases the order of steps has to be controlled to avoid functional group incompatibilities. One skilled in the art will recognize that a more convergent route (i.e. non-linear or preassembly of certain portions of the molecule) is a more efficient method of assembly of the target compounds. Two such methods for the preparation of compounds of general Formula 1 where variables [$R^1$, $R^2$, $R^3$, $R^4$, $R^6$, $R^7$, $R^8$, $R^{10}$, $R^{11}$, $R^{12}$, $R^{20}$, Y, X, Z, L, m, n, q, r etc.] are as defined above, are shown in Scheme 1, Scheme 2 and Scheme 3. $Pr^1$, $Pr^2$ and $Pr^3$ are protecting groups exemplified below.

The prepared compounds may be analyzed for their composition and purity as well as characterized by standard analytical techniques such as, for example, elemental analysis, NMR, mass spectroscopy, and IR spectroscopy.

Scheme 1. Method A
Late Introduction of R¹R²N—
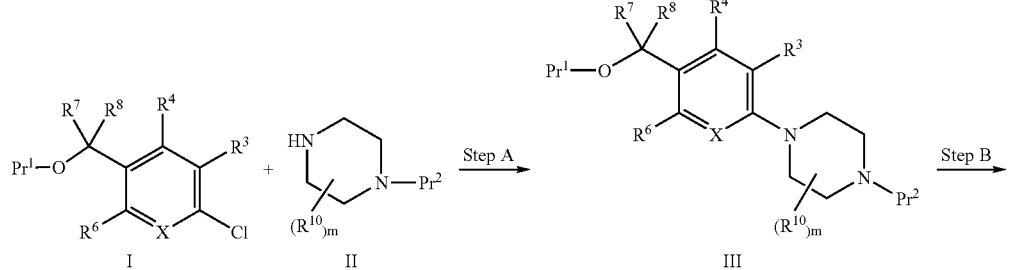
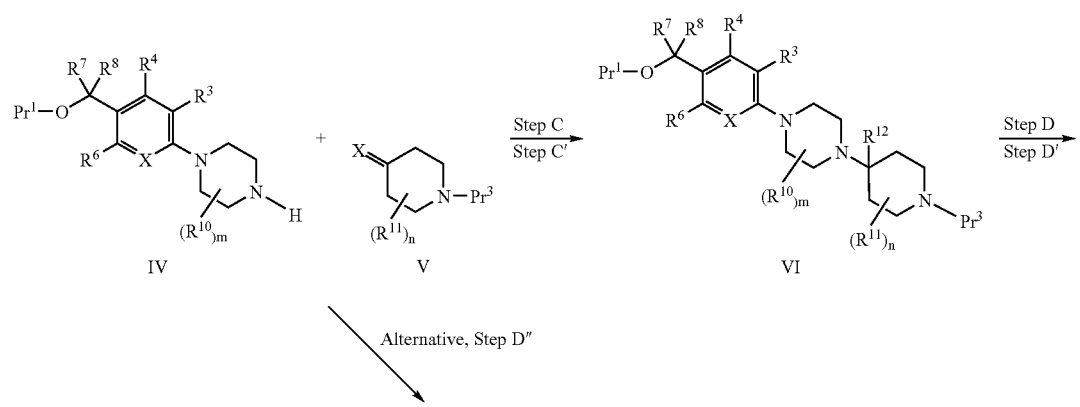
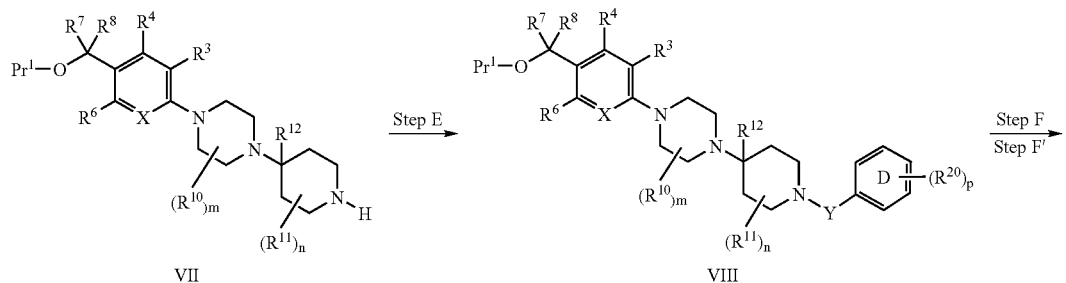
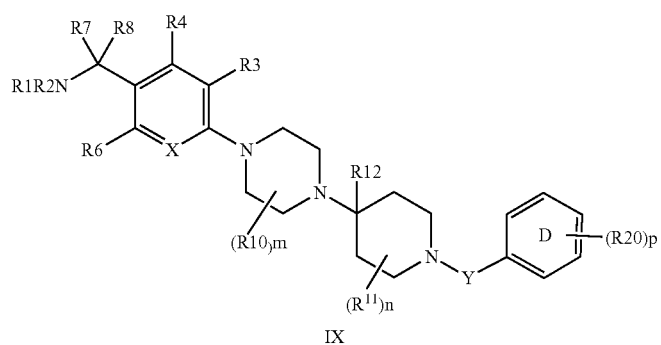

Scheme 2. Method B.
Early Introduction of R¹R²N—
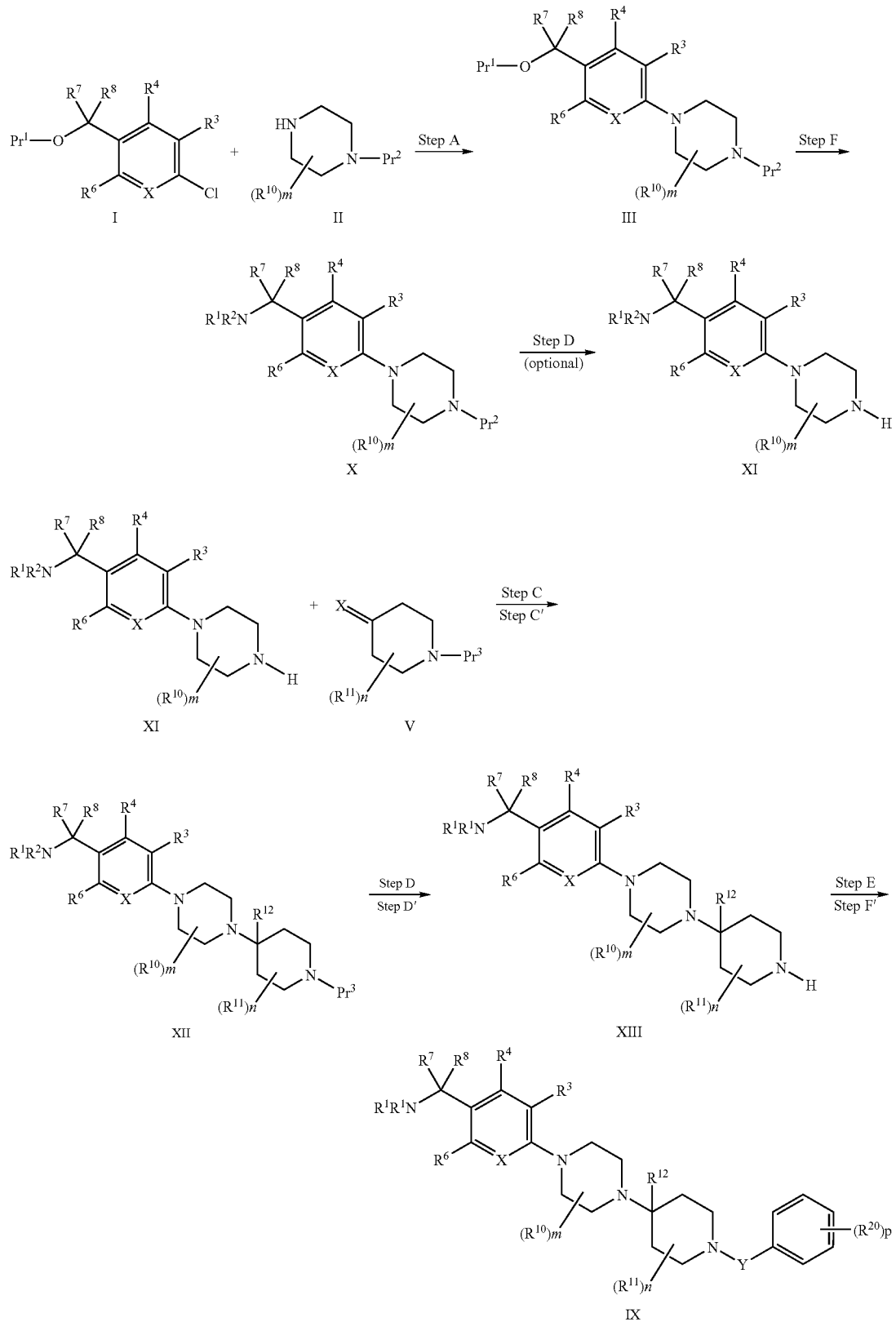

-continued
Alternatively,
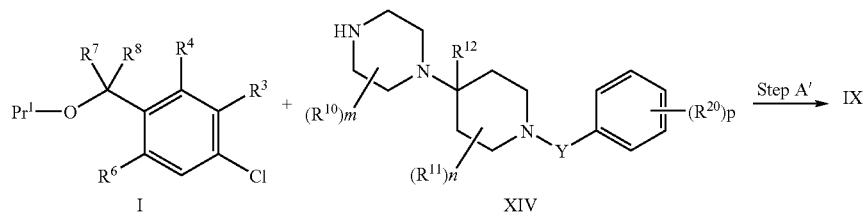
Alternatively,
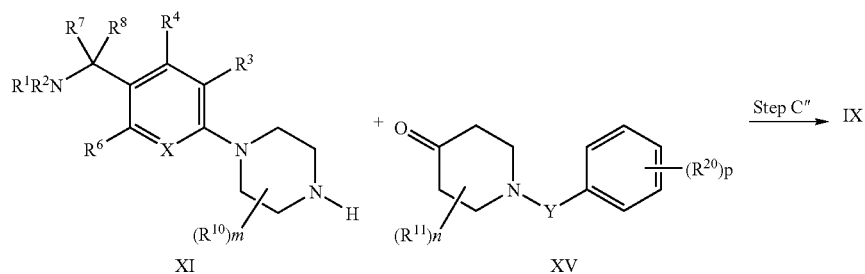
Scheme 3. Method C
Early Introduction of $R^1R^2N-$
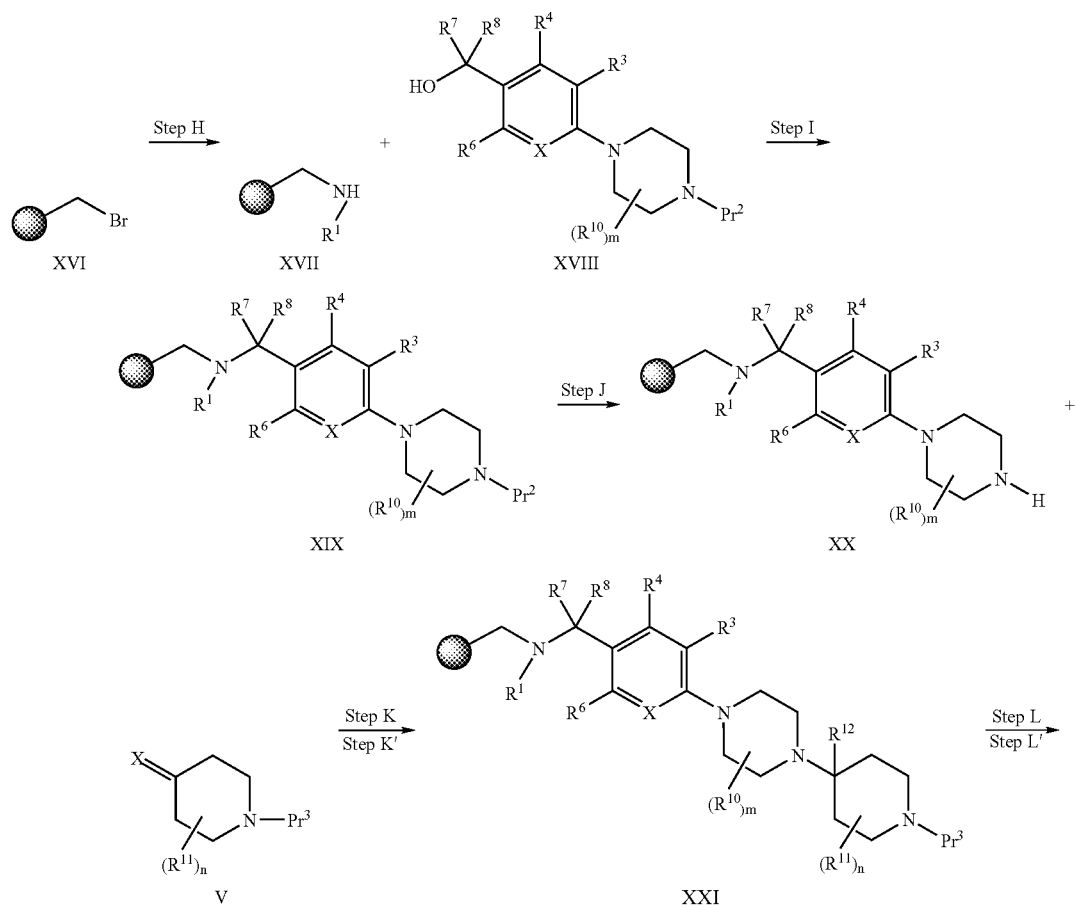

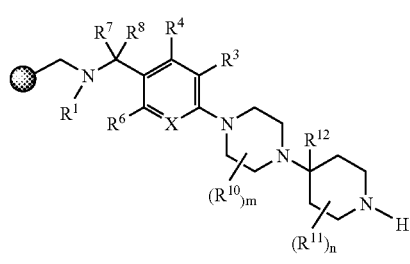 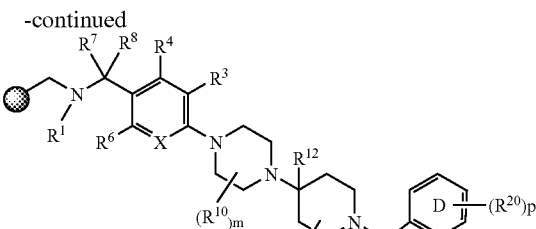

XXII → Step M → XXIII → Step N / Step N'

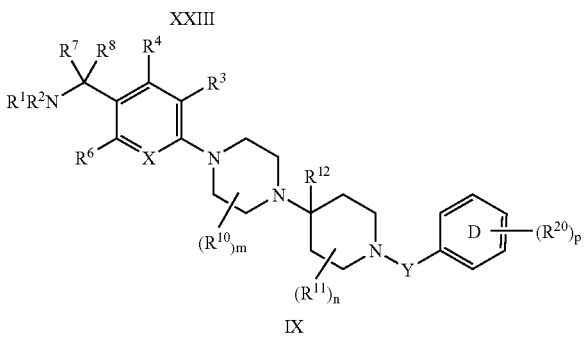

IX

The starting material and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

The preparation of arylpiperazine compounds related to intermediate III has been reported in WO-03037862 (Nippon Shinyaku).

One skilled in the art will recognize that the synthesis of compounds of Formula 1 may require the need for the protection of certain functional groups (i.e. derivatization for the purpose of chemical compatibility with a particular reaction condition). Suitable protecting groups for a carboxylic acid ($Pr^1$, when $R^7$ taken together with $R^8$ is =O) includes methyl, ethyl, isopropyl, or benzyl ester and the like. Suitable protecting groups for an amine ($Pr^2$ and $Pr^3$) include methyl, benzyl, ethoxyethyl, t-butoxycarbonyl, phthaloyl and the like. All protecting groups can be appended to and removed by literature methods known to those skilled in the art.

One skilled in the art will recognize that the synthesis of compounds of Formula 1 may require the construction of an amide bond. Methods include but are not limited to the use of a reactive carboxy derivative (e.g. acid halide, or ester at elevated temperatures) or the use of an acid with a coupling reagent (e.g. EDCI, DCC, HATU) with an amine at 0° C. to 100° C. Suitable solvents for the reaction are halogenated hydrocarbons, ethereal solvents, dimethylformamide and the like. The reaction may be conducted under pressure or in a sealed vessel.

One skilled in the art will recognize that the synthesis of compounds of Formula 1 may require the construction of an amine bond. One such method is, but not limited to, the reaction of a primary or secondary amine with a reactive carbonyl (e.g. aldehyde or ketone) under reductive amination conditions. Suitable reducing reagents of the intermediate imine are sodium borohydride, sodium triacetoxyborohydride and the like at 0° C. to 100° C. Suitable solvents for the reaction are halogenated hydrocarbons, ethereal solvents, dimethylformamide and the like. Another such method is, but not limited to, the reaction of a primary or secondary amine with a reactive alkylating agent such as an alkyl halide, benzyl halide, mesylate, tosylate or the like. Suitable solvents for the reaction are halogenated hydrocarbons, ethereal solvents, dimethylformamide and the like. The reaction may be conducted under pressure or in a sealed vessel at 0°. to 100° C.

One skilled in the art will recognize that the synthesis of compounds of Formula 1 may require the reduction of a reducible functional group. Suitable reducing reagents include sodium borohydride, lithium aluminum hydride, diborane and the like at −20° C. to 100° C. Suitable solvents for the reaction are halogenated hydrocarbons, ethereal solvents, dimethylformamide and the like.

One skilled in the art will recognize that the synthesis of compounds of Formula 1 may require the oxidation of a functional group. Suitable oxidizing reagents include oxygen, hydrogen peroxide, m-chloroperoxybenzoic acid and the like at −20° C. to 100° C. Suitable solvents for the reaction are halogenated hydrocarbons, ethereal solvents, water and the like.

The starting materials and the intermediates of a reaction may be isolated and purified if desired using conventional techniques, including but not limited to filtration, distillation, crystallization, chromatography and the like. Such materials can be characterized using conventional means, including physical constants and spectral data.

General Description of Methods A & B

Step A and A'. Amination:

A suitably protected 2-halo pyridine or phenyl compound of structure I is reacted with a piperazine of structure II or structure XIV to form a compound of general structure III or IX. Preferably the reaction is carried out in a solvent such as dioxane in the presence of a base such as potassium carbonate or cesium carbonate. Optionally, a catalyst such as palladium acetate may be added and or the reaction heated to a temperature of between 30° C. and 150° C.

In certain cases where regioselectivity is not required or where regioselectivity is determined by the differential reactivity of the piperazine nitrogens, no protection of the piperazine is required.

Step B.

If the product of Step A is a protected piperazine of structure III, deprotection is required. When $Pr^2$ is benzyl or substituted benzyl deprotection can be effected by reaction under a pressure of hydrogen gas in the presence of a catalyst such as palladium. When $Pr^2$ is ethoxyethyl deprotection can be effected by reaction with trimethylsilyl iodide. When $Pr^2$ is t-butoxycarbonyl deprotection can be effected with a strong acid such as trifluoroacetic acid.

Step C and Step D".

A piperazine of structure IV or structure XI is reacted with an activated piperidine of structure V. When X=O in general structure V, the reaction is performed in the presence of a reducing agent to form a compound of structure VI or structure XII where $R^{12}$ is hydrogen. Alternatively, a piperazine of structure IV is reacted with an elaborated piperidine to form structure VIII. Conditions for the reductive amination reaction are described herein.

Step C'

A piperazine of structure IV or structure XI is reacted with a ketone of structure V in the presence of a reducing agent to form a compound of structure VI or structure XII where $R^{12}$ is a cyanide residue. Typical conditions are the reaction of an equi-molar quantity of a piperazine of structures IV or XI and a ketone of structure V in the presence of titanium isopropoxide in a halogenated solvent such as methylene chloride for 1-48 hours. Subsequent addition of a cyanide source such as dimethylaluminum cyanide affords a compound of structure VI or structure XII where $R^{12}$ is a cyanide residue.

Step C"

A piperazine of structure XI is reacted with a ketone of structure XV in the presence of a reducing agent to form a compound of structure IX where $R^{12}$ is hydrogen. General conditions for the reductive amination reaction are described above.

Step D

Optionally, a compound of structure VI or structure XII, when $R^3$=Cl or Br is reacted with a organometallic alkylating agent such a alkyl boronic acid, or an alkyl halide in the presence of a metal to promote heterocoupling, or a nucleophile to yield a different structure of general structure VI or XII where the halogen at the $R^3$ position has been replaced by the appropriate group described for $R^3$.

Step D'

A protected piperidine of structure VI or structure XII is deprotected to provide the secondary amine of structure VII or structure XIII. When $Pr^2$ is benzyl or substituted benzyl deprotection can be effected by reaction under a pressure of hydrogen gas in the presence of a catalyst such as palladium. When $Pr^2$ is ethoxyethyl deprotection can be effected by reaction with trimethylsilyl iodide. When $Pr^2$ is t-butoxycarbonyl deprotection can be effected with a strong acid such as trifluoroacetic acid.

Step E

A secondary piperidine of structure VII or structure XIII is either alkylated or acylated to provide compounds of structure VII or structure IX. General methods for such alkyations and acylations are described above and are well known to those skilled in the art.

Step F

A suitable protected ester of structure VIII (Method A) or structure III (Method B) where $R^7$ and $R^8$ taken together is =O and $Pr^1$ is alkyl, is reacted with a primary or secondary amine to provide title compounds of structure IX or intermediate X. Typical conditions include the reaction of the ester and the amine in a polar solvent such as methanol in a sealed tube at 25° C. to 100° C.

Step F'

Optionally, functional group manipulation of a compound of structure IX may be done to provide additional related compounds of structure IX.

Compounds of Formula 1 can be prepared by the general methods outlined in schemes 1 and 2. Analogous reactions as those described in schemes 1 and 2 can be accomplished on the solid phase as outlined in Scheme 3. The syntheses of the specifically exemplified compounds are described in detail below. The following PREPARATIVE EXAMPLES are being provided to further illustrate the present invention. They are for illustrative purposes only and the scope of the invention is not to be considered limited in any way thereby.

PREPARATIVE EXAMPLES

The following preparative examples are intended to illustrate, but not to limit, the scope of the invention.

Preparative Example 1

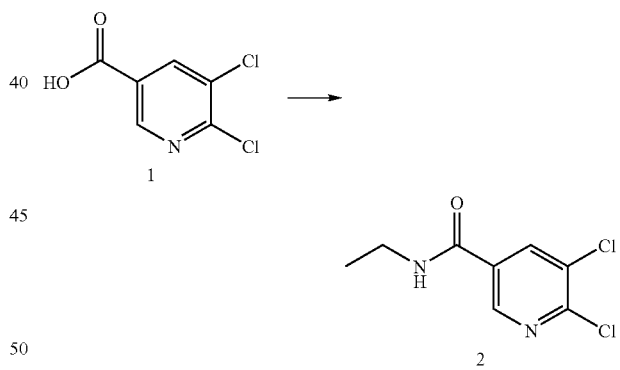

A round bottomed flask was charged with 5,6-dichlorornicotic acid (30 g, 156 mmol), ethylamine HCl salt (14 g, 170 mmol), dimethylformamide (300 ml), dichloromethane (100 ml), triethylamine (26.1 ml, 187 mmol), and 1-[3-(dimethylamino)propyl]-3-ethylcarbodiimide hydrochloride (32.9 g, 170 mmol). The reaction mixture was stirred at room temperature overnight. The solvent was removed in vacuo, the residue was dissolved in ethyl acetate (500 mL) and was washed with 1N HCl (2x), saturated aqueous sodium bicarbonate (1x), brine (1x), and dried over magnesium sulfate. The solution was filtered and concentrated in vacuo to provide the desired 5,6-Dichloro-N-ethyl-nicotinamide 2 (29 g, 85%). MS: M+H=219.

Preparative Example 2

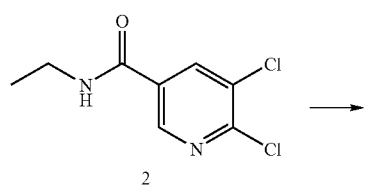

2

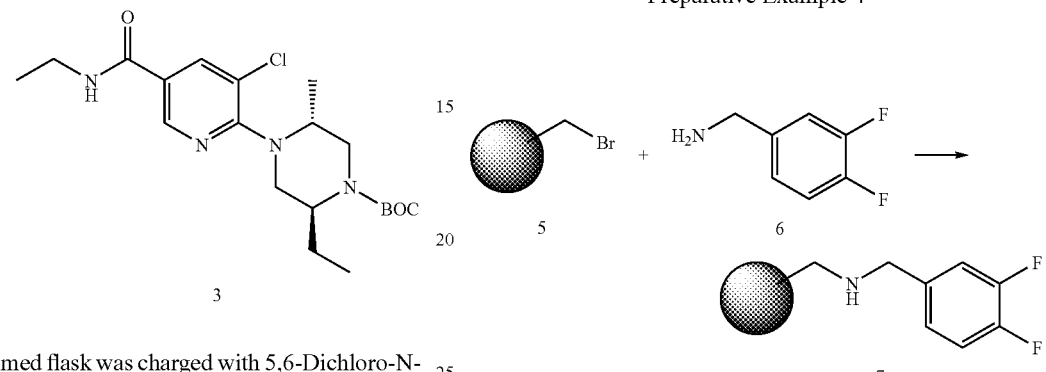

3

A round bottomed flask was charged with 5,6-Dichloro-N-ethyl-nicotinamide (0.200 g, 1.3 mmol), Boc-2-(S)-Ethyl-5-(R)-methyl-piperazine (0.200 mg, 0.88 mmol), potassium carbonate (1.2 g, 8.8 mmol), and dimethylformamide (5 ml). The mixture was stirred at 90° C. overnight. After filtration, solvent was removed in vacuo and the residue was purified by flash chromatography to produce the desired product 3 (0.172 g, 48%). MS: M+H=411.

Preparative Example 3

Preparation of Compound No. 214 of Table 1

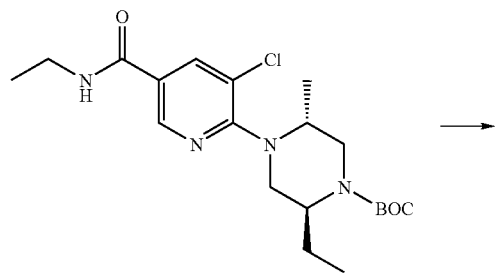

3

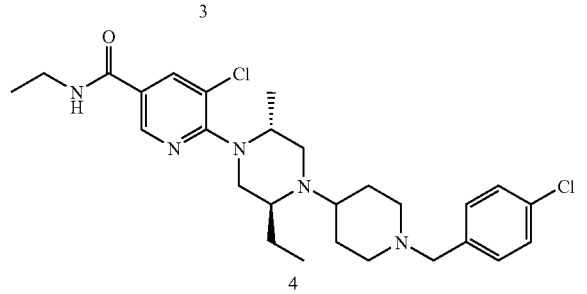

4

A round bottomed flask was charged with intermediate 3 (0.050 g, 0.161 mmol), methylene chloride (3 mL), and trifluoroacetic acid (1 mL). The mixture was stirred for 1 hour and the volatiles were removed in vacuo. To the crude material was added triethylamine (0.1 ml) and methylene chloride (1 mL) to neutralize the TFA salt. Volatiles were removed in vacuo. To the residue was added 1-(4-Chloro-benzyl)-piperidin-4-one (0.036 g, 0.32 mmol) and 3% acetic acid/dichloroethane. After addition of NaBH(OAc)$_3$ (0.102 g, 0.48 mmol), the mixture was stirred at room temperature overnight. After usual workup the crude product was purified by preparative HPLC to yield the desired compound 4 (0.030 g, 36%). MS: M+H=518.

Preparative Example 4

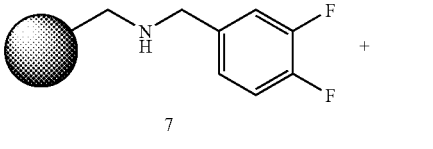

A peptide shaker vessel containing photocleavable resin 5 (Argogel, 0.750 g, 0.8 mmol/g) was charged with 3,4-difluorobenzylamine (1.71 mL, 14 mmol) and tetrahydrofuran (7 mL). The vessel was shaken at room temperature overnight. The solvent was drained and the resin was washed with dimethylformamide (3×10 mL) and methylene chloride (3×10 mL). A chloranil bead test for presence of secondary amines was positive. (The symbol in the formulas indicates the photocleavable resin, as is obvious to one skilled in the art.)

Preparative Example 5

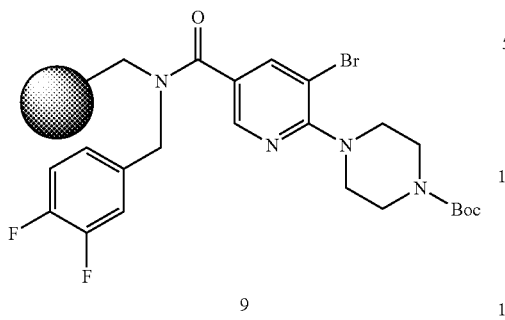

9

A shaker vessel with the amine intermediate 7 was treated with a solution of HATU (0.685 g, 1.8 mmol), DIEA (0.63 mL, 1.8 mmol) and bromopyridyl carboxylic acid 8 (0.695 g, 1.8 mmol) in dimethylformamide (7 mL). The vessel was shaken at 45° C. overnight. The solvent was drained and the resin was washed with dimethylformamide (3×10 mL) and methylene chloride (3×10 mL). A chloranil bead test for presence of secondary amines was negative.

Preparative Example 6

A shaker vessel containing bromo intermediate 9 was treated with a 30% trifluoroacetic acid/methylene chloride solution (V/V). The vessel was shaken at room temperature for 1 hour. The solvent was drained and the resin was washed with methylene chloride (3×10 mL), 5% triethylamine/methylene chloride (3×10 mL) and methylene chloride (3×10 mL). A chloranil bead test for presence of secondary amines was positive.

Preparative Example 7

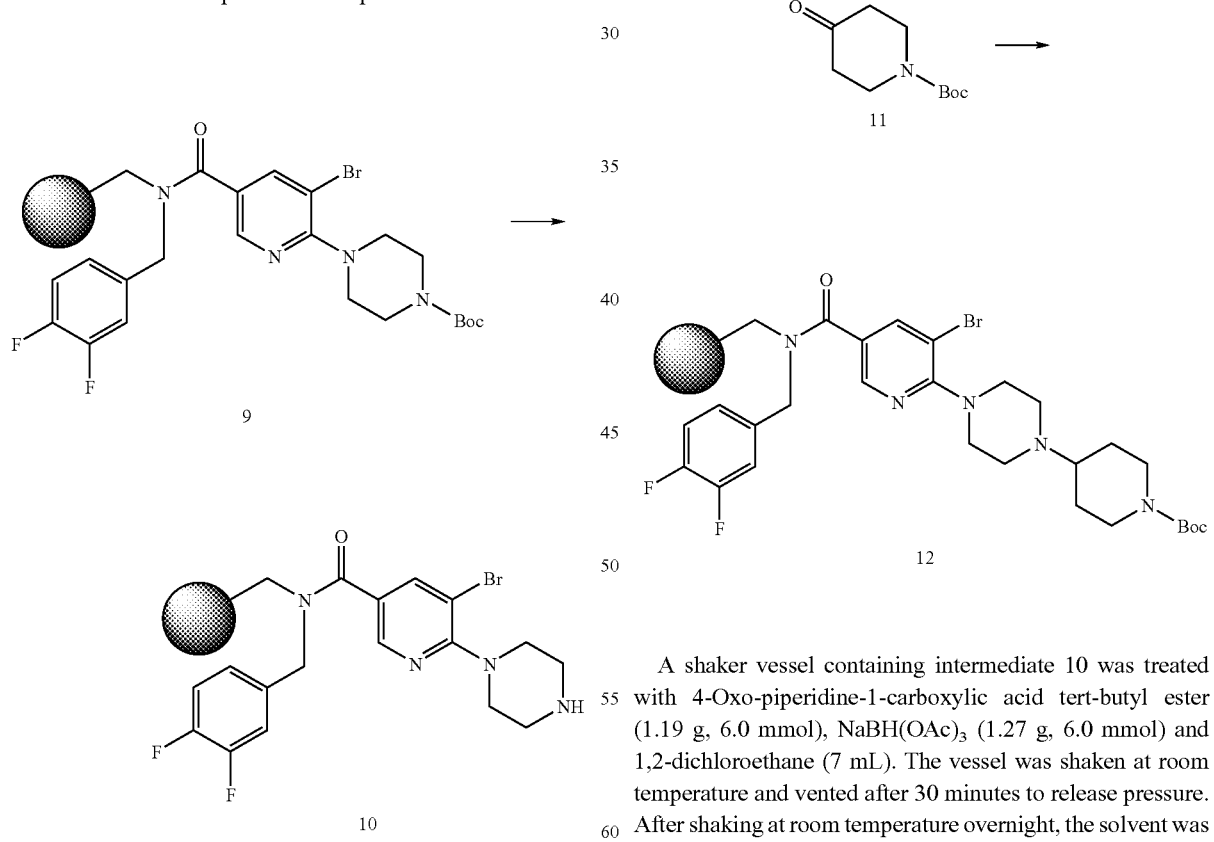

A shaker vessel containing intermediate 10 was treated with 4-Oxo-piperidine-1-carboxylic acid tert-butyl ester (1.19 g, 6.0 mmol), NaBH(OAc)$_3$ (1.27 g, 6.0 mmol) and 1,2-dichloroethane (7 mL). The vessel was shaken at room temperature and vented after 30 minutes to release pressure. After shaking at room temperature overnight, the solvent was drained and the resin was washed with 1:1 methanol/methylene chloride (3×10 mL), 1:1 methylene chloride/dimethylformamide (3×10 mL), dimethylformamide (2×10 mL), 1:1 methylene chloride/dimethylformamide (1×10 mL), methylene chloride (3×10 mL). A chloranil bead test for presence of secondary amines was negative.

Preparative Example 8

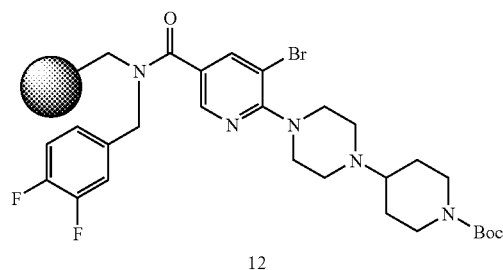

12

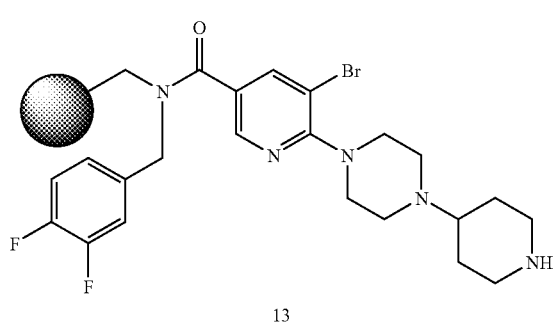

13

A shaker vessel containing bromo intermediate 12 was treated with a 30% trifluoroacetic acid/methylene chloride solution (v/v). The vessel was shaken at room temperature for 1 hour. The solvent was drained and the resin was washed with methylene chloride (3×10 mL), 5% triethylamine/methylene chloride (3×10 mL) and methylene chloride (3×10 mL). A chloranil bead test for presence of secondary amines was positive.

Preparative Example 9

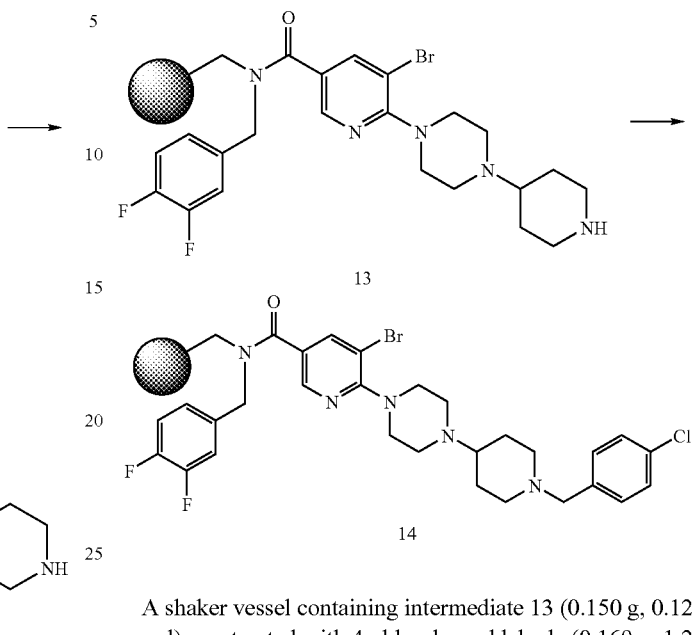

13

14

A shaker vessel containing intermediate 13 (0.150 g, 0.12 mmol) was treated with 4-chlorobenzaldehyde (0.169 g, 1.2 mmol), NaBH(OAc)$_3$ (0.254 g, 1.2 mmol) and 1,2-dichloroethane (2 mL). The vessel was shaken at room temperature and vented after 30 minutes to release pressure. After shaking at room temperature overnight, the solvent was drained and the resin was washed with methanol (3×2 mL), dimethylformamide (3×2 mL), methylene chloride (3×2 mL). A chloranil bead test for presence of secondary amines was negative.

Preparative Example 10

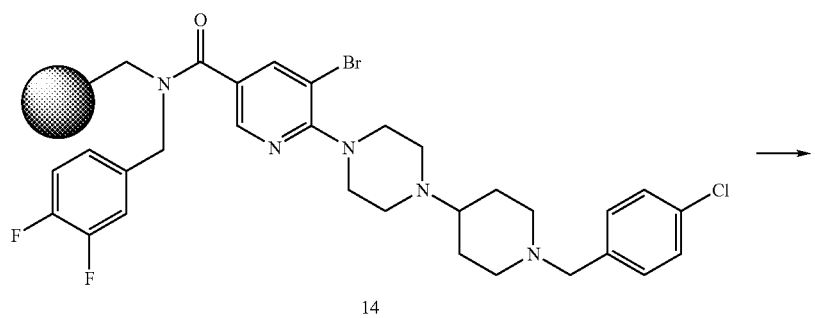

14

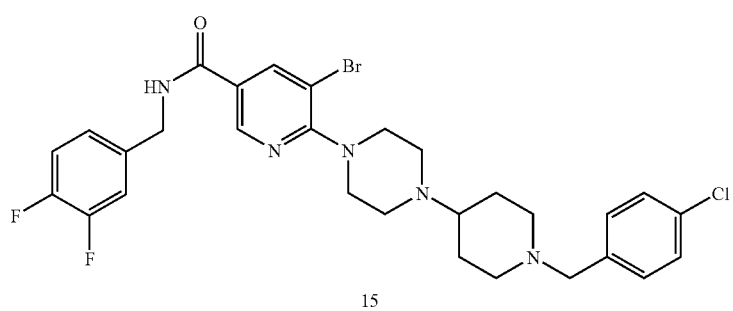

15

283

The resin 14 was then transferred to a vial and treated with 3% trifluoroacetic acid/methanol (v/v) and photolyzed at 365 nm for 2.0 hours at 50° C., with vigorous stirring. The resin was then filtered, and washed with MeOH and CH₂Cl₂. The filtrate was concentrated in vacuo. The crude product was purified by reverse phase preparative HPLC to provide product 15 (0.0274 g, 60%). MS: M+H=618.1.

Preparative Example 11

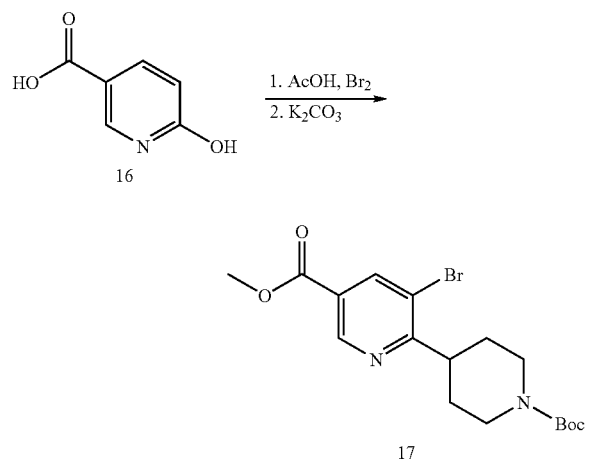

To a stirred suspension of 6-hydroxynicotinic acid (6.95 g, 50 mmol) in acetic acid (12.5 mL) was added bromine (3.8 mL, 75 mmol). The solution was heated to 50° C., stirred overnight and concentrated to dryness under reduced pressure. To the crude residue was added phosphorus oxychloride (12.5 mL, 134 mmol) and phosphorus pentachloride (21.0 g, 100 mmol). The resulting mixture was heated at reflux overnight. Excess phosphorus oxychloride was removed in vacuo while maintaining the bath temperature below 50° C. The crude brown residue was dissolved in methylene chloride (62 mL) and methanol (25 ml) and heated at reflux for 2 hours. The solvents were removed in vacuo. The residue was extracted with ether and saturated aqueous sodium bicarbonate. The organics were dried over magnesium sulfate, filtered and concentrated. Further purification by silica chromatography (5% to 25% ethyl acetate/hexanes) afforded the desired product in 60% yield (7.5 g). 1H NMR (300 MHz, CDCl3): 9.0 (s, 1H), 8.6 (s, 1H), 4.1 (s, 3H).

A round bottomed flask was charged with preceding product (3.0 g, 12.0 mmol), potassium carbonate (9.95 g, 72.0 mmol), piperazine-1-carboxylic acid tert-butyl ester (2.46 g, 13.2 mmol) and dimethylformamide (75 mL). The mixture was heated at 65° C. overnight and the solvent removed in vacuo. The residue was dissolved in ethyl acetate and washed with 0.5 N HCl, 0.5 N NaOH, and brine. The organics were dried over magnesium sulfate, filtered and concentrated in vacuo. There was obtained 4.79 g of product 17 which was not purified further. 1H NMR (300 MHz, CDCl3): 8.8 (s, 1H), 8.35 (s, 1H), 3.9 (s, 3H), 3.5 (m, 8H), 1.5 (s, 9H).

284

Preparative Example 12

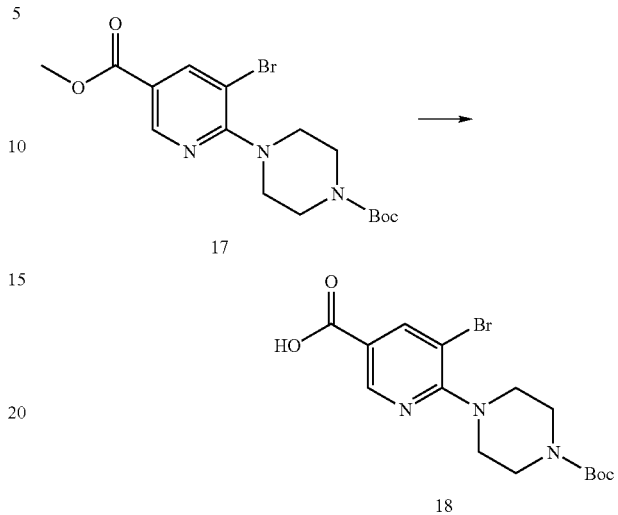

A round bottomed flask was charged with intermediate 17 (3.35 g, 8.68 mmol), lithium hydroxide (1.09 g, 26.0 mmol), and 1:1 methanol/water (v/v, 50 mL). The mixture was stirred at room temperature overnight. The solvent was removed in vacuo. The residue was dissolved in water and acidified to pH 6 with concentrated hydrochloric acid. The solution was then extracted with ethyl acetate (2×50 mL). The organic layer were dried over magnesium sulfate, filtered and concentrated in vacuo. There was obtained 3.2 g of product 18 which was used as is.

Preparative Example 13

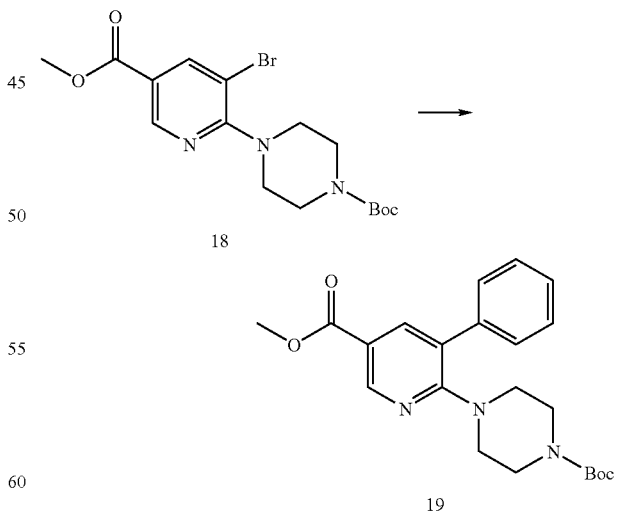

A round bottomed flask was charged with intermediate 18 (0.471 g, 1.18 mmol), phenylboronic acid (0.158 g, 1.3 mmol), and isopropyl alcohol (4 mL) were stirred for 30 minutes. To the solution was added palladium acetate (0.0024 g, 0.0106 mmol), triphenylphosphine (0.0031 g, 0.0118 mmol), sodium carbonate (0.149 g, 1.42 mmol) and water (0.8 mL), and it was then heated at reflux for 1 hour. After cooling to room temperature, the solution was stirred for an additional 1.5 hours. The reaction was diluted with water and extracted with ethyl acetate. The organics were dried over magnesium sulfate, filtered and concentrated in vacuo. The product was purified by silica chromatography (5% to 25% ethyl acetate/hexanes) to give intermediate 19 (0.48 g, 95%). 1H NMR (300 MHz, CDCl3): 8.9 (s, 1H), 8.1 (s, 1H), 7.55 (m, 5H), 4.0 (s, 3H), 3.4 (m, 8H), 1.6 (s, 9H).

Preparative Example 14

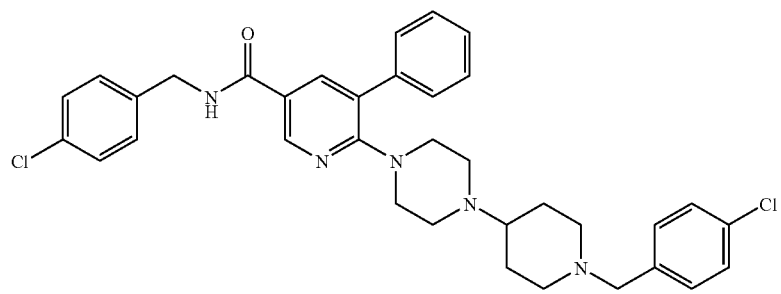

The compound of Example 14 was prepared by the same method shown for Examples 4 through 10. MS (M+H)= 648.2.

Preparative Example 15

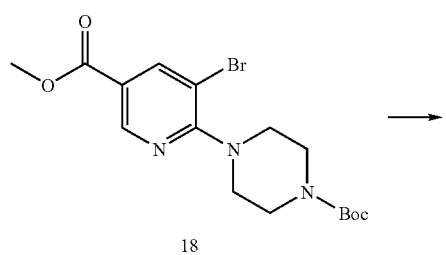

18

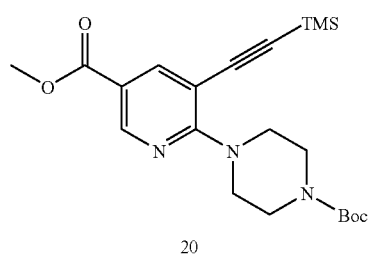

20

A sealed tube was charged with intermediate 18 (4.14 g, 10.0 mmol), dichlorobis(triphenylphosphine)-palladium(II) (0.20 g, 0.28 mmol), copper (I) iodide (0.10 g, 0.53 mmol), and triethylamine (3 mL, 21.5 mmol). The mixture was stirred. Trimethylsilyl acetylene (1.2 g, 12.0 mmol) was added. After stirring, the tube was carefully placed under vacuum and sealed. The tube was heated at 80° C. in an oil bath overnight. After cooling to room temperature, the solution was diluted with water (30 mL) and extracted with ethyl ether (2×100 mL). The organics were dried over sodium sulfate, filtered and concentrated in vacuo. The product was purified by silica chromatography (7:1 hexanes/ethyl acetate) to give intermediate 20 (1.08 g, 26%).

Preparative Example 16

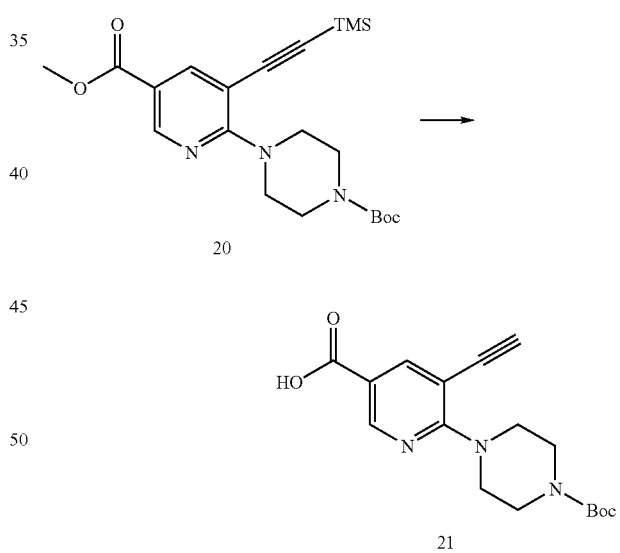

A round bottomed flask was charged with intermediate 20 (1.08 g, 2.6 mmol), and 1N potassium hydroxide in methanol (10 mL). The mixture was stirred overnight at room temperature. The solvent was removed in vacuo. The residue was dissolved in water (10 mL) and extracted with ethyl ether (1×10 mL). The aqueous phase was acidified with 1N hydrochloric acid and extracted with ethyl acetate (3×20 mL). The organics were dried over sodium sulfate, filtered and concentrated in vacuo to give intermediate 21 (1.0 g, quantitative yield).

Preparative Example 17

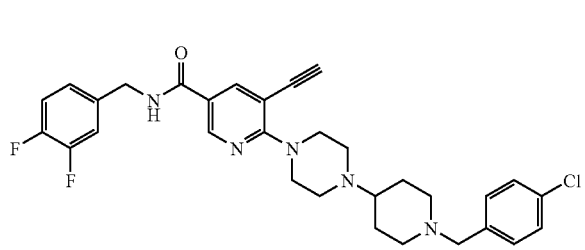

The compound of Preparative Example 17 was prepared by the same method shown for Examples 4 through 10 MS (M+H)=564.2.

Preparative Example 18

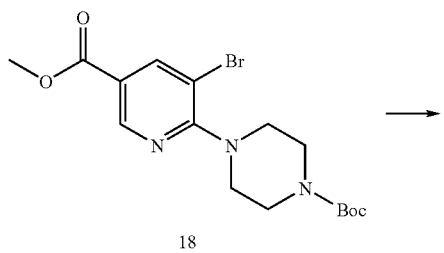

Ester 18 (1.8 g; 4.5 mmol) was heated to 90° C. in 10 ml DMF with trimethylboroxine (0.63 ml; 4.5 mmol), K2CO3 (1.87 g; 13.5 mmol), and tetrakis(triphenylphosphine)palladium(0) (0.52 mg; 0.45 mmol). DMF was removed in vacuo and the reaction was directly purified via silica chromatography to give 22 (1.24 g; 82% yield).

Preparative Example 19

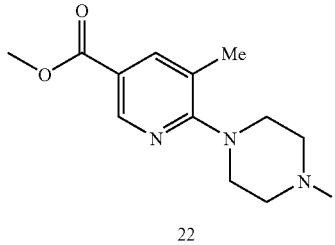

A round bottomed flask was charged with 2,6-dichloro-5-fluoronicitinoyl chloride (20.0 g, 88.0 mmol) and ethanol (140 mL). The mixture was cooled in an ice/water bath and treated with triethylamine (18.0 mL, 129 mmol) added dropwise. The mixture was then stirred for 2.25 hours at room temperature. The solvent was removed in vacuo. The resulting product (8.0 g, 33.6 mmol) was then treated with piperazine-1-carboxylic acid tert-butyl ester (8.2 g, 43.7 mmol), triethylamine (7 mL, 50.4 mmol), and acetonitrile (40 mL). The resulting mixture was stirred at 80° C. overnight. The solvent was removed in vacuo. The residue was washed with 1N hydrochloric acid (75 mL) and extracted with toluene (75 mL). The organics were dried over sodium sulfate, filtered and concentrated in vacuo. The product was purified by silica chromatography (gradient 10% to 15% ethyl acetate/hexanes) to provide product 24 (10.48 g, 81%). 1H NMR (300 MHz, CDCl3): 7.8 (d, 1H), 4.35 (q, 2H), 3.7 (m, 4H), 3.55 (m, 4H), 1.5 (s, 9H), 1.4 (t, 3H).

Preparative Example 20

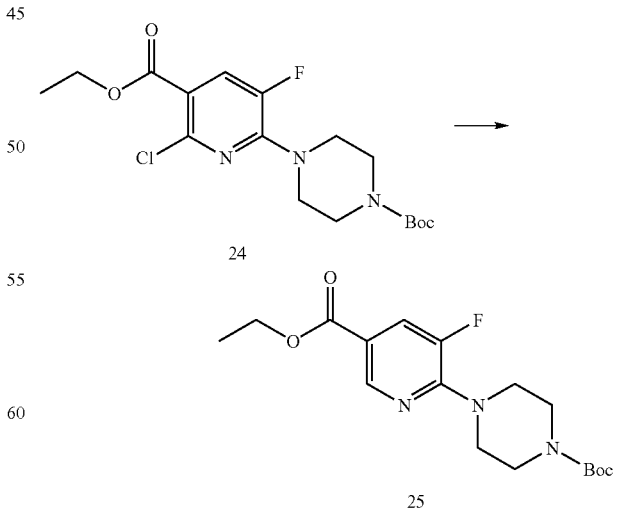

A round bottomed flask was charged with intermediate 24 (1.0 g, 2.58 mmol), ethanol (25 mL), and triethylamine (0.50 mL, 3.6 mmol). The mixture was then stirred at room temperature for 30 min. The reaction vessel was placed under vacuum and filled with argon (2×). To the vessel was then added 10% palladium on carbon (0.080 g). The flask was again evacuated and flushed with argon. The argon was evacuated and the contents placed under a balloon of hydrogen gas. The mixture was stirred at room temperature overnight and filtered through celite to remove the catalyst. The filtrate was concentrated in vacuo to dryness and washed with hexanes. The solid was removed by filtration and the filtrate evaporated to dryness. Obtained product 25 (0.840 g, 92%). 1H NMR (300 MHz, CDCl3): 8.75 (s, 1H), 7.85 (d, 1H), 4.45 (q, 2H), 3.8 (m, 4H), 3.65 (m, 4H), 1.6 (s, 9H), 1.5 (t, 3H). MS (M+H)=353.8.

Preparative Example 21

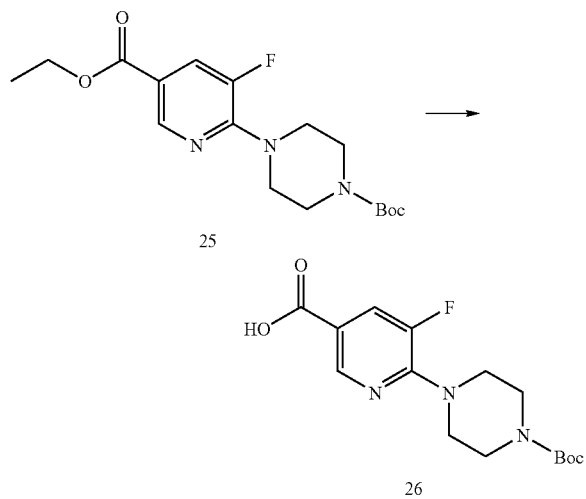

A round bottomed flask was charged with intermediate 25 (3.6 g, 10.2 mmol), ethanol (20 mL), potassium hydroxide (85%, 2.0 g, 30.6 mmol) and water (0.8 mL). The mixture was then stirred for at 80° C. for 1.5 hours. The solvent was removed in vacuo and the residue diluted with water (20 mL). The solution was extracted with ethyl ether (50 mL), acidified to pH=3 with 1N hydrochloric acid (38 mL). The solution was extracted with ethyl ether (3×50 mL). The organics were dried over sodium sulfate, filtered and concentrated in vacuo to give intermediate 26 (3.16 g, 95%).

Preparative Example 22

The compound shown in Preparative Example 22 was prepared by the same method shown for Examples 4 through 10. MS (M+H)=590.2.

Preparative Example 23

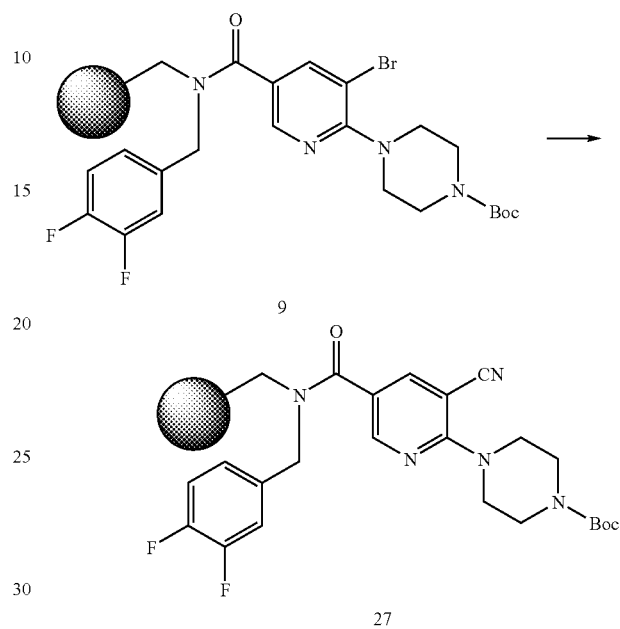

A shaker vessel containing bromo intermediate 9 (0.25 g, 0.2 mmol) was treated with zinc cyanide (0.070 g, 0.6 mmol) and tetrakis(triphenylphosphine)palladium(0) (0.023 g, 0.02 mmol) in 2 ml DMF. The vessel was shaken overnight at 85° C. After draining, the resin was washed with dimethylformamide (3×2 mL) and methylene chloride (3×2 mL).

Preparative Example 24

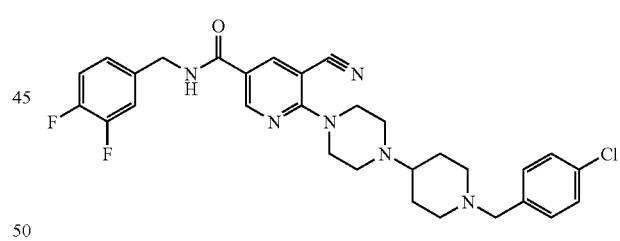

Preparation of Preparative Example 24 can be prepared following Examples 1 through 3. MS: M+H=565.2.

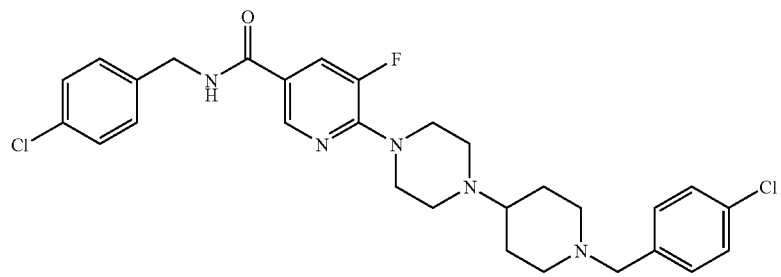

Preparative Example 25

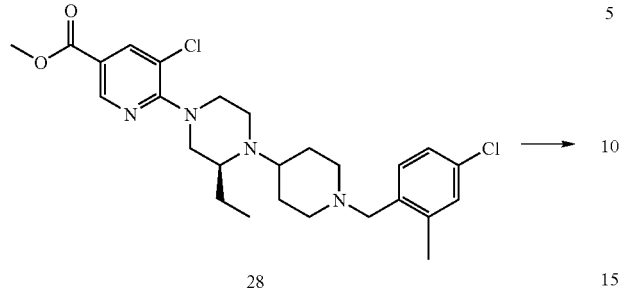

28

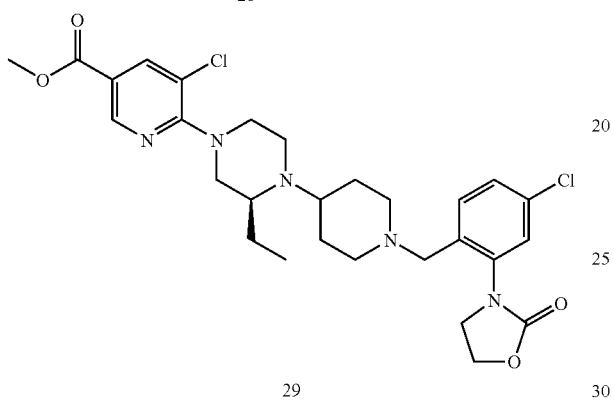

29

A Pyrex tube was charged with intermediate 28 (0.050 g, 0.08 mmol), copper iodide (0.001 g, 0.004 mmol), potassium phosphate (0.035 g, 0.16 mmol), N,N-dimethylethylenediamine (0.005 mL, 0.008 mmol) and toluene (1 ml). The tube was heated to 80° C. in a rotating oven overnight. After cooling to room temperature, the solution was diluted with ethyl acetate (5 mL) and filtered through a silica gel SPE plug. The plug was washed with ethyl acetate (5 mL), methylene chloride (5 mL), and 5% methanol/methylene chloride (v/v, 5 mL). The solvent was removed in vacuo. The crude product was purified by reverse phase preparative HPLC to provide compound 29 (contaminated with 20% of intermediate N1 where I=H). MS, M+H=491.1, 576.1.

Preparative Example 26

Preparation of Compound No. 460 of Table 1

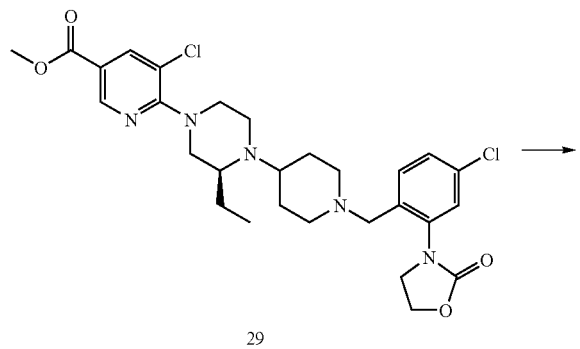

29

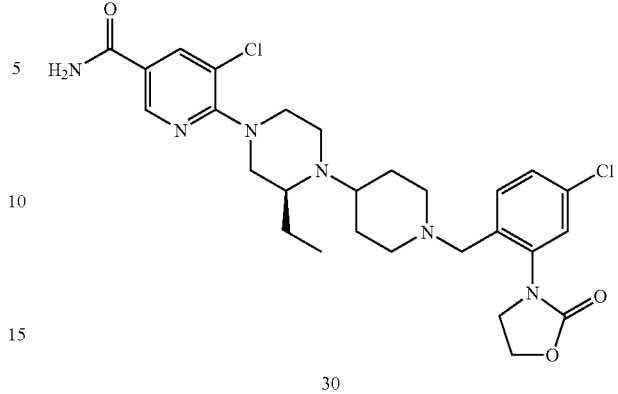

30

Product 30 was prepared by the same method shown for Examples 1 through 3 (contaminated with 20% of intermediate 28 where I=H). MS: M+H=476.2, 561.1.

Preparative Example 27

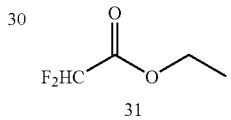

31

1. LAH, -78°C
2. Chlorobenzyl amine, 100° C.
3. Danishefsky diene
4. NaBH$_4$
5. (CO)$_2$Cl$_2$, DMSO

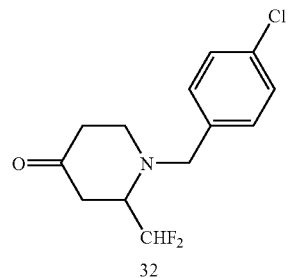

32

A round bottomed flask containing ethyl difluoroacetate (12.4 g, 100 mmol) dry ethyl ether (15 mL) was cooled to −78°. To the flask was added lithium aluminum hydride (1 M in THF, 25 mL) slowly over 10 minutes. The mixture was stirred at −78° C. for 2 hours. Ethanol (3 mL) was added and the reaction mixture was warmed to room temperature. The solvent was removed in vacuo and 20% H$_2$SO$_4$ (100 mL) was added. The mixture was extracted with ether three times. The organic phase was washed with brine, dried over magnesium sulfate, and filtered. After removing solvent, 5.5 g of crude product was obtained. It was purified by distillation to yield 4.5 g (36%) of product as a colorless liquid.

To the hemiacetal (2.5 g, 20 mmol) was added 4-Chlororbenzylamine (2.8 g, 20 mmol) and toluene (50 mL) at 0°. The mixture was heated at 100°. for 2 hours. Solvent was removed and 3.4 g (85%) of crude product were obtained. This crude compound went to next step without further purification.

The imine (2.6 g, 12.8 mmol) from the previous step was combined with 3-Trimethylsilyloxy-1-methoxy-1,3-butadiene (3.7 ml, 19.2 mmol), zinc chloride (3.5 g, 25 mmol) and tetrahydrofuran (15 mL). The mixture was stirred at room temperature overnight. The solution was poured into water (100 mL) and extracted with ethyl acetate. The organic phase was dried over magnesium sulfate and purified by flash chromatography to yield 1.3 g (38%) of the desired product as a brown oil. MS: M+H=272

To the above intermediate (0.30 g, 1.11 mmol) in ethanol (5 mL) was added sodium borohydride (0.17 g, 4 mmol). The reaction mixture was heated to reflux for 2 hours. After workup the resulting alcohol was purified by flash chromatography (50% ethyl acetate/hexanes) to yield 0.29 g of the reduced alcohol as a liquid. MS: M+H=276. A two-neck flask was charged with oxalyl chloride (0.160 g, 1.2 mmol) in methylene chloride (5 mL) and cooled to −60° C. Dimethylsulfoxide (0.21 mL, 3 mmol) was added in one portion and the mixture was stirred for 5 minutes. The above alcohol in methylene chloride (2 mL) was added dropwise over a period of 10 minutes. After stirring at −60° C. for 15 minutes, triethylamine (0.8 mL) was added and the mixture was warmed to room temperature. To the reaction mixture was added water (10 mL), and the mixture was extracted with methylene chloride three times. The organic phase was washed with brine, dried over sodium sulfate, filtered, and concentrated in vacuo to yield 0.280 g (93%) of the desired product 32 as a liquid. MS: M+H=274.

Preparative Example 28

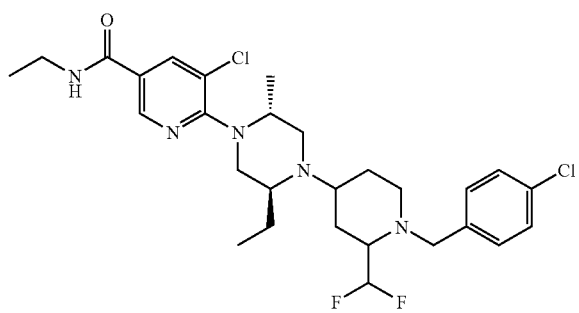

The compound shown in Preparative Example 28 was prepared by the same method shown for Examples 1 through 3. MS (M+H)=568.

Preparative Example 29

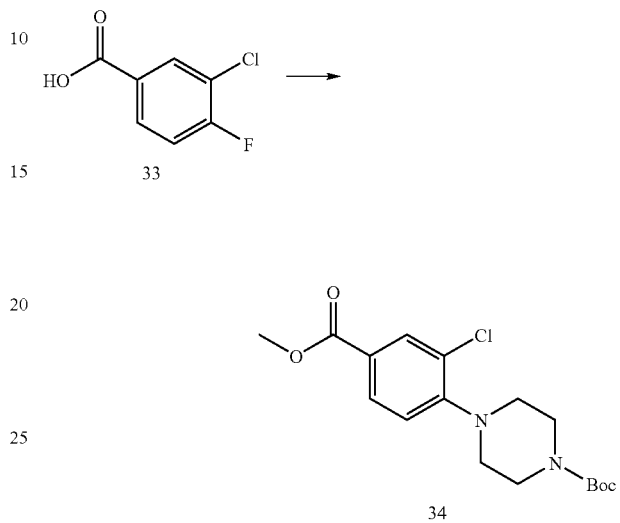

A round bottomed flask was charged with 3-chloro-4-fluorobenzoic acid (5.0 g, 28.6 mmol), sulfuric acid (0.84 g, 8.6 mmol), and methanol (60 mL). The solution was heated at reflux overnight. The methanol was removed in vacuo. The residue was extracted with ethyl acetate (5×), dried over sodium sulfate, filtered and concentrated in vacuo to yield 4.73 g (88%).

A round bottomed flask was charged with the ester intermediate (4.73 g, 25 mmol), potassium carbonate (3.45 g, 25 mmol), piperazine-1-carboxylic acid tert-butyl ester (5.59 g, 30 mmol) and acetonitrile (6 mL). The mixture was heated at 65° C. overnight and the solvent removed in vacuo. The residue was dissolved in ethyl acetate and washed with 0.5 N HCl, 0.5 N NaOH, and brine. The organics were dried over magnesium sulfate, filtered and concentrated in vacuo. There was obtained 4.79 g of intermediate 34 which was not purified further.

Preparative Example 30

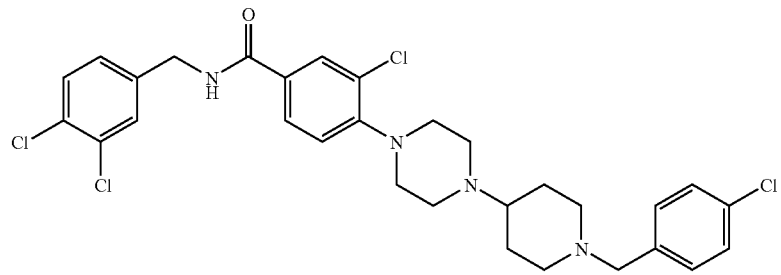

The compound shown in Preparative Example 30 was prepared by the same method shown for Preparative Examples 4 through 10. MS (M+H)=607.5.

Preparative Example 31

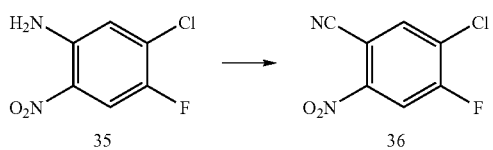

To a suspension of copper cyanide (1.4 g, 15.7 mmol) in acetonitrile (20 ml), was added tert-butyl nitrite (2.5 mL, 21 mmol). The mixture was heated to 70° C. and stirred for 15 min. 5-Chloro-4-fluoro-2-nitro-phenylamine (2.0 g, 10.5 mmol) was with additional acetonitrile (10 mL). The brown solution was heated at 70° C. for 5 hours. The solvent was removed in vacuo, water was added and the solution extracted with ethyl acetate. The organics were dried over magnesium sulfate, filtered and concentrated in vacuo. There was obtained 2.31 g of product 36 which was not purified further.

Preparative Example 32

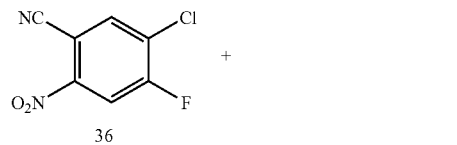

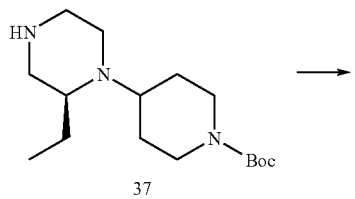

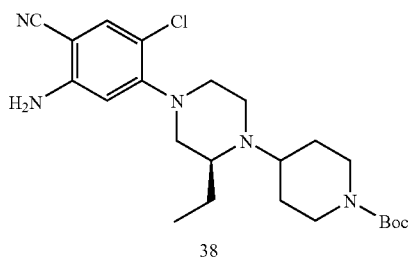

A round bottomed flask was charged with -Chloro-4-fluoro-2-nitro-benzonitrile (0.294 g, 1.47 mmol), potassium carbonate (1.49 g, 7.35 mmol), 4-(2-Ethyl-piperazin-1-yl)-piperidine-1-carboxylic acid tert-butyl ester (0.435 g, 1.47 mmol) and dimethylformamide (15 mL). The mixture was heated at 70° C. overnight and the solvent removed in vacuo. The residue was dissolved in water and extracted with ethyl acetate. The organics were dried over magnesium sulfate, filtered and concentrated in vacuo. There was obtained 0.910 g of product 38 which was not purified further. MS (M+H)=478.

Preparative Example 33

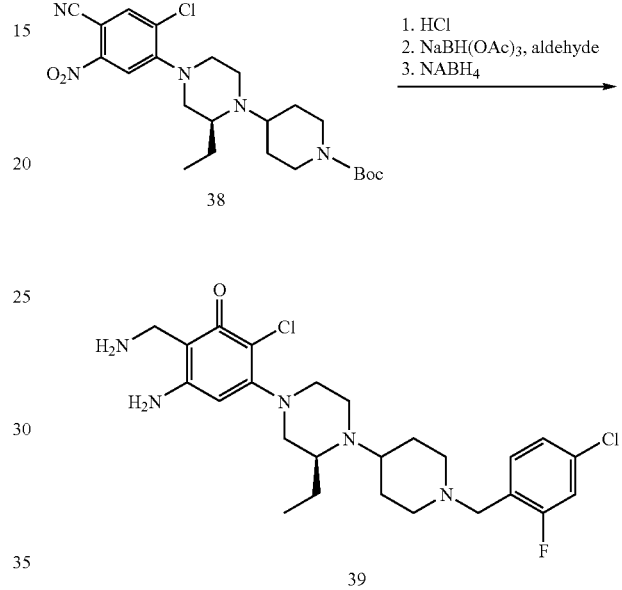

To intermediate 38 (0.306 g, 0.64 mmol), was added hydrogen chloride in dioxane (10 mL). The mixture was stirred at room temperature for 10 min. followed by the addition of diisopropylethylamine (0.23 mL, 1.28 mmol). To the resulting mixture was then added 4-Chloro-2-fluoro-benzaldehyde (0.202 g, 1.28 mmol), acetic acid (0.1 mL) and 1,2-dichloroethane (10 mL). After stirring for 15 min., NaBH(OAc)$_3$ (0.271 g, 1.28 mmol) was added. The solution was stirred at room temperature overnight. The reaction mixture was treated with aqueous saturated sodium bicarbonate and extracted with ethyl acetate. The organics were dried over magnesium sulfate, filtered and concentrated in vacuo. The product was purified by silica flash chromatography (50% ethyl acetate/hexanes, ethyl acetate, 5% methanol/ethyl acetate). There was obtained 0.331 g (98%) of product.

A round bottomed flask containing the above product (0.081 g, 0.156 mmol) in ethanol (2 mL) was stirred at room temperature overnight. To the flask was then added NaBH$_4$ (0.018 g, 0.468 mmol) in portions. The solvent was then removed in vacuo and the residue washed with aqueous ammonium chloride and aqueous sodium bicarbonate. The organics were dried over magnesium sulfate, filtered and concentrated in vacuo. The product was purified by reverse phase preparative HPLC to afford 0.042 g (53%) of product 39. MS (M+H)=508.1.

Preparative Example 34

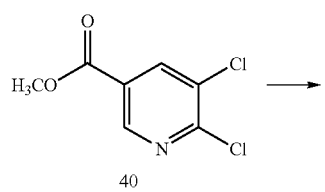
40

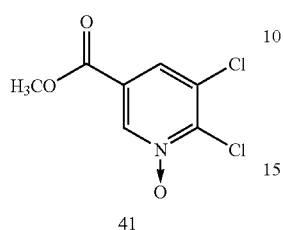
41

A round bottomed flask was charged with 5,6-Dichloronicotinic acid methyl ester (0.353 g, 1.72 mmol), urea hydrogen peroxide addition compound (0.340 g, 3.62 mmol), and trifluoroacetic anhydride (0.486 mL, 3.44 mmol). The mixture was stirred at room temperature for 2 hours. To the mixture was added an aqueous solution of sodium thiosulfate. After stirring for 15 min., the solution was poured into 0.5M HCl and extracted with methylene chloride. The organics were washed with saturated aqueous sodium bicarbonate, dried over sodium sulfate, filtered and concentrated in vacuo. There was obtained 0.306 g of product 41 which was not purified further. 1H NMR (300 MHz, CDCl3): 8.94 (s, 1H), 8.03 (s, 1H), 4.09 (s, 3H).

Preparative Example 35

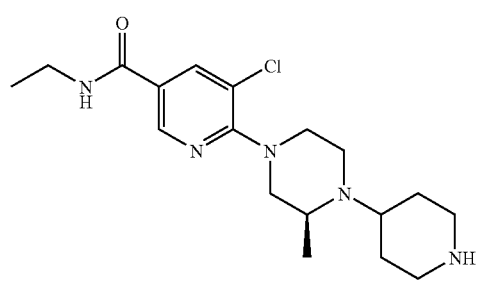
42

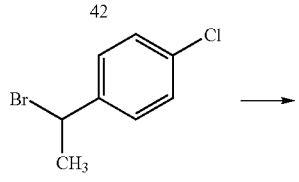
43

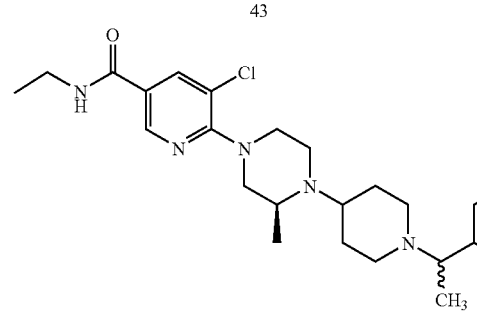
44

A round bottomed flask was charged with intermediate 42 (0.10 g, 0.27 mmol), 1-(1-Bromo-ethyl)-4-chloro-benzene (0.072 g, 0.33 mmol), triethylamine (0.136 mL, 1.35 mmol), and 1,2-dichloroethane (4 mL). The solution was heated to 80° C. for 2 days. The reaction mixture was diluted with methylene chloride and washed with water. The organic layer was evaporated, and the crude product was purified by reverse phase preparative HPLC to provide the separated isomers of product 44 (Isomer A, 0.030 g, Isomer B 0.022 g, mixture 0.042 g).

Preparative Example 36

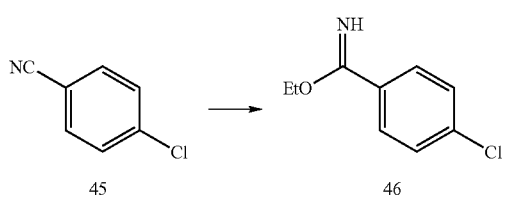
45     46

A round bottomed flask was charged with 4-Chloro-benzonitrile (0.138 g, 13 mmol) and anhydrous ethanol (100 mL). Hydrogen chloride gas was then bubbled into the solution via dispersion tube. The reaction very exothermic and it was cooled in a water bath (22° C.) after stirring for 15 min. The solution was allowed to stand at room temperature overnight. The solvent was removed to provide intermediate 46 (2.38 g, 95%). MS: M+H=184.

Preparative Example 37

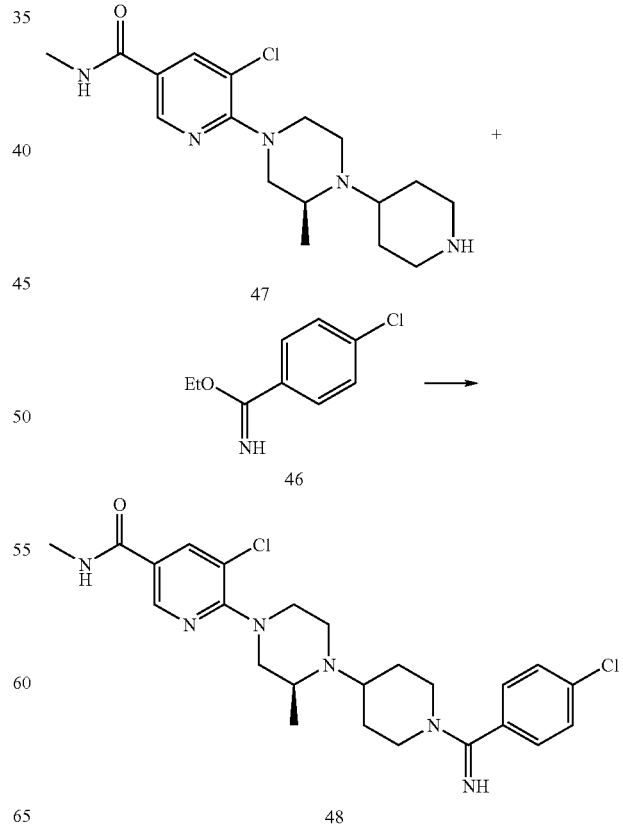
47

46

48

A round bottomed flask was charged with intermediate 47 (0.159 g, 0.452 mmol), 4-Chloro-benzimidic acid ethyl ester 46 (0.104 g, 0.568 mmol), methylene chloride (2 mL), and triethylamine (2×0.10 mL). The solution was heated to 40° C. for 2 days. The reaction mixture was concentrated to solid, resuspended in ethanol (2 mL) and heated at 60° C. overnight. The mixture was filtered and concentrated to an oil. To the oil was added dimethylformamide (2 mL) and 4-Chloro-benzimidic acid ethyl ester (0.104 g, 0.568 mmol). The solution was heated at 100° C. for 2 hours. The solution was concentrated in vacuo. The crude product was purified by silica flash chromatography to provide product 48 (0.040 g, 18%). MS: M+H=489.

Preparative Example 38

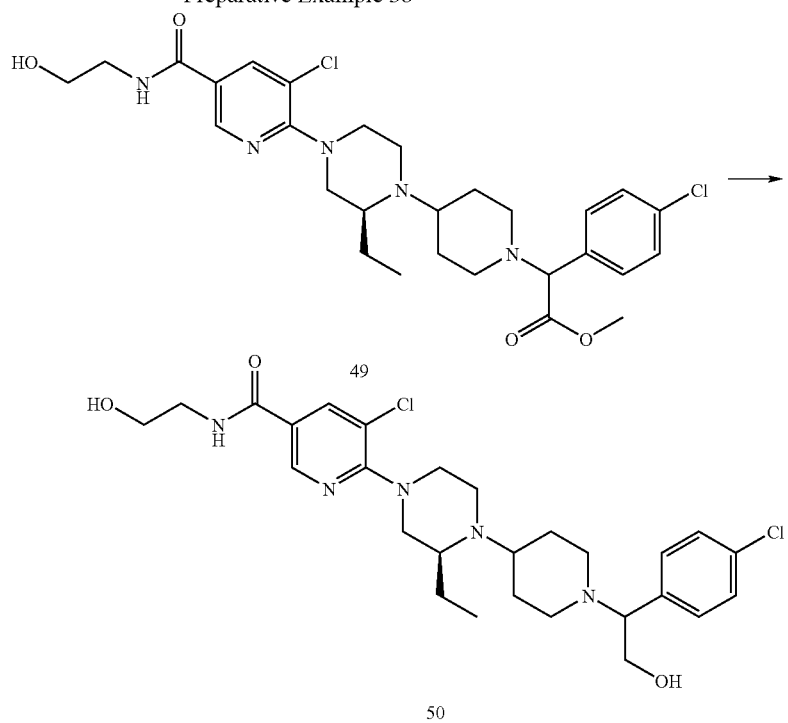

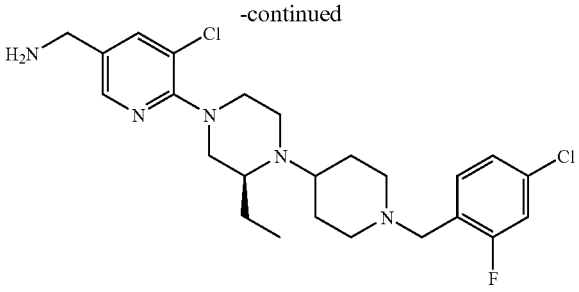

A round bottoed flask was charged with intermediate 49 (0.210 g, 0.353 mmol) and tetrahydrofuran (1.8 mL). To the solution was added lithium borohydride (1.8 mL, 2.0M in tetrahydrofuran). The solution was stirred at room temperature overnight. The reaction mixture was diluted with methylene chloride and treated with 1N sodium hydroxide. The resulting mixture was stirred at room temperature for 30 min. The organics were concentrated in vacuo to provide 0.190 g. The crude product (0.060 g) was purified by silica chromatography (10% methanol/methylene chloride) to provide 0.0128 g of product 50. MS: M+H=550.1.

Preparative Example 39

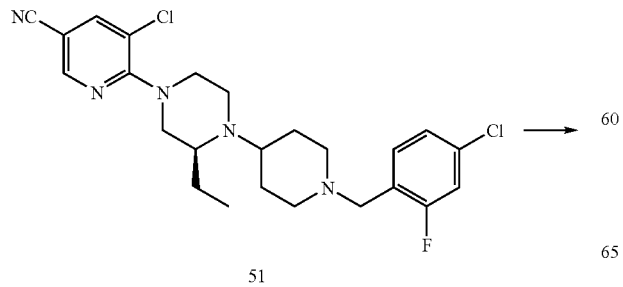

A round bottomed flask was charged with intermediate 51 (0.20 g, 0.42 mmol) and tetrahydrofuran (2 mL) and cooled in an ice bath. To the solution was added LAH (0.0238 g, 0.63 mmol) followed by stirring for 4 hours at room temperature. An additional portion of LAH (0.012 g, 0.3 mmol) followed by stirring for 3 hours. The reaction was quenched by the addition of ice chips and stirred for 2 hours. The reaction mixture was diluted with ethyl acetate and dried over sodium sulfate. The organics were concentrated in vacuo, and the crude product was purified by silica chromatography (96.5: 2.5:1 methylene chloride/methanol/ammonium hydroxide) to provide 0.033 g (17%) of product 52.

Preparative Example 40

Preparation of Compound No. 368 of Table 1

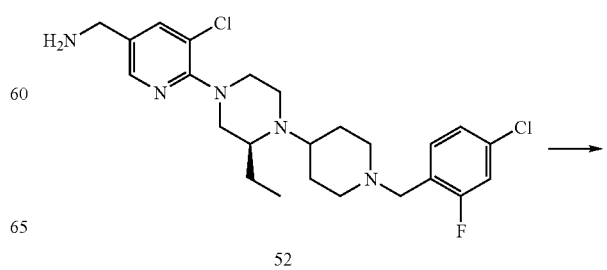

-continued

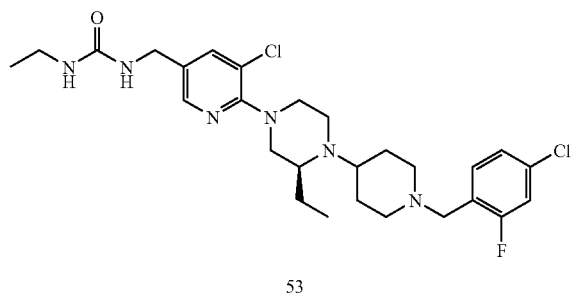

53

A round bottomed flask was charged with intermediate 52 (0.27 g, 0.056 mmol), 1,2-dichloroethane (2 mL), and ethyl isocyanate (0.020 g, 0.28 mmol). The solution was stirred at room temperature for 4 hours. The solvent was removed in vacuo. The crude product was purified by silica chromatography (5% methanol/methylene chloride then 93:5:2 methylene chloride/methanol/ammonium hydroxide) to provide 0.031 g (quantitative) of product 53.

Preparative Example 41

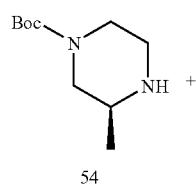

54

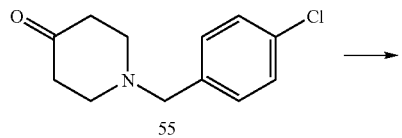

55

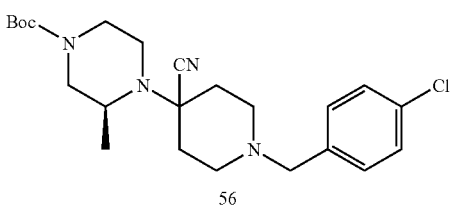

56

1-(4-Chloro-benzyl)-piperidin-4-one 55 (0.223 g; 1 mmol) and 3-S-Methyl-piperazine-1-carboxylic acid tert-butyl ester 54 (290 mg; 1.6 mmol) were stirred in methylene chloride (6 ml) at room temperature overnight in the presence of titanium isopropoxide (0.4 ml, 0.963 mmol). Al(Et)$_2$CN (3 ml of a 1M toluene solution, 3 mmol) was added via syringe and the reaction was stirred for an additional 20 hours. The methylene chloride was removed in vacuo, and the residue was extracted between ethyl acetate and 10% sodium bicarbonate. The organic layer was washed with water, brine, dried over sodium sulfate, and concentrated to give 0.170 g of a colorless oil (41% yield).

Preparative Example 42

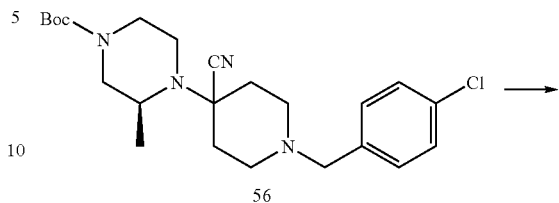

56

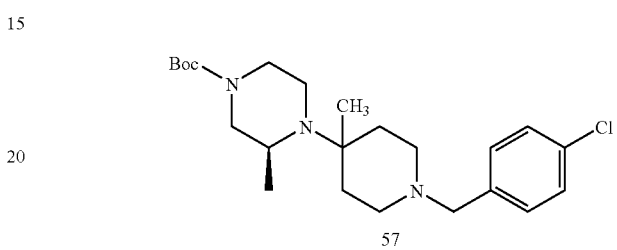

57

A round bottomed flask of intermediate 56 (0.216 g,; 0.5 mmol) and tetrahydrofuran (10 mL) was treated with methyl magnesium bromide (1.7 ml of a 3M ether solution; 5 mmol). After heating to 60° C. for 2.5 hours, the reaction was quenched with water (1 ml) and saturated NaHCO$_3$ (20 ml) and extracted with ethyl acetate. After washing with brine, the organic layer was dried over Na$_2$SO$_4$ and concentrated to give 57 (0.141 g; 67% yield).

Preparative Example 43

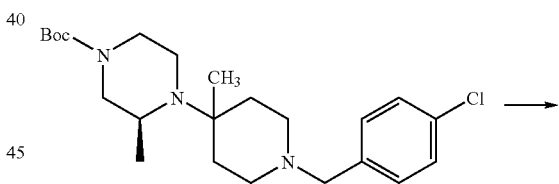

57

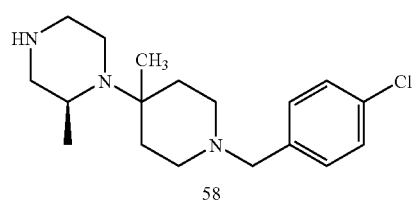

58

Intermediate 57 (0.127 g, 0.3 mmol) was stirred with HCl (1 ml of 6M solution) in ethyl acetate at room temperature for 2 hours. Saturated NaHCO$_3$ was added to pH=9 and the mixture was extracted with ethyl acetate. The organic layer was washed with brine, dried over Na$_2$SO$_4$ and concentrated in vacuo give 58 (0.090 g; 93% yield).

Preparative Example 44

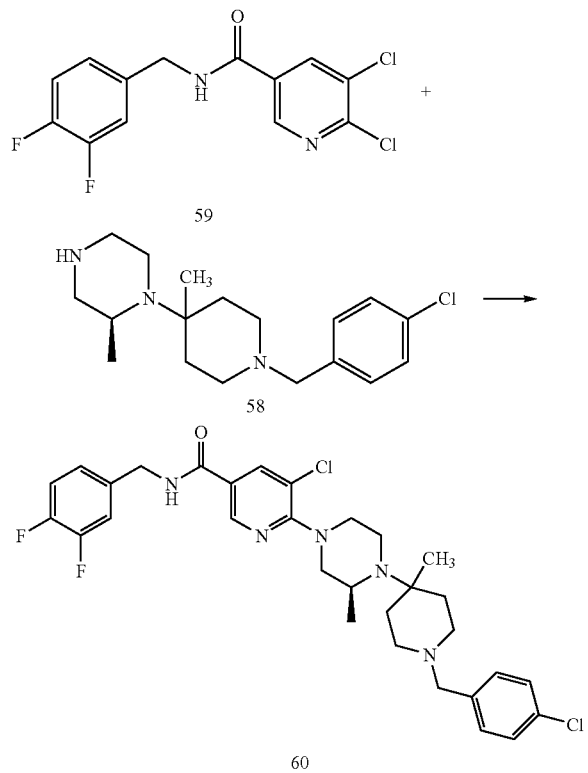

Amine 58 (0.032 g, 0.1 mmol) was stirred with intermediate 58 (0.032 g, 0.1 mmol), 2-(Di-t-butylphosphin)biphenylpalladium (0.003 g, 0.01 mmol), Pd(OAC)$_2$ (0.0023 g, 0.01 mmol), and cesium carbonate (0.070 g, 2 mmol) for 16 hours at 90° C. in dioxane. Dioxane was removed in vacuo and the residue was purified directly via preparative reverse-phase chromatography to yield product 60. MS: M+H=602.0.

Preparative Example 45

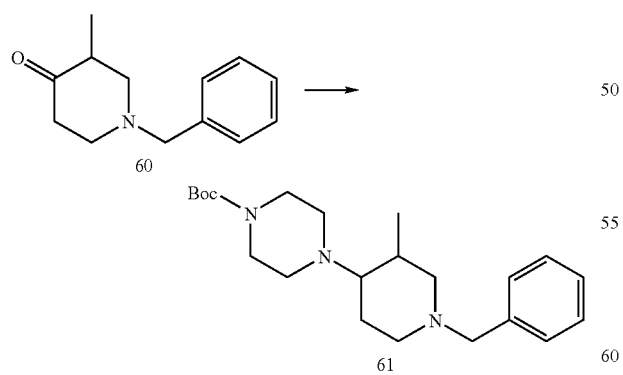

1-Benzyl-3-methyl-piperidin-4-one 60 (2.0 g, 10 mmol), Boc-piperazine (2 g, 10.75 mmol), Na(OAc)$_3$BH (4.2 g; 20 mmol), and acetic acid (1 ml) were stirred in dichloroethane (30 ml) overnight. Saturated NaHCO$_3$ was added, and the mixture was extracted with ethyl acetate, washed with brine, and dried over Na$_2$SO$_4$. After concentration in vacuo, the material was purified on silica gel chromatography to give intermediate 61 (1.2 g; 37% yield).

Preparative Example 46

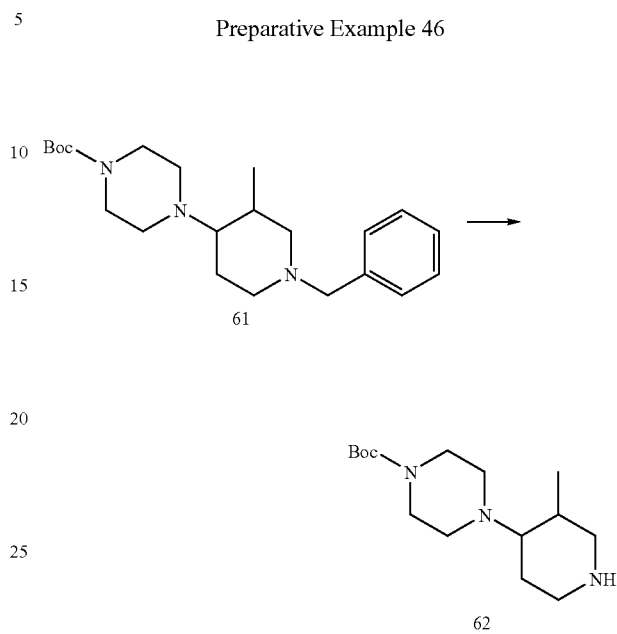

Intermediate 61 (1.2 g, 3.21 mmol) was stirred with 10% Pd/C (0.240 g) in methanol (50 ml) under a hydrogen atmosphere overnight. After catalyst was removed by filtration over celite, methanol was removed in vacuo to give intermediate 62 (0.839 g, 93%).

Preparative Example 47

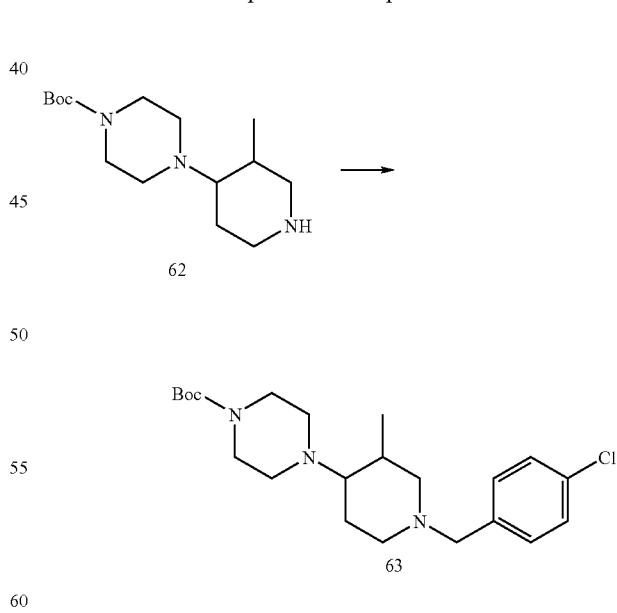

Intermediate 62 (0.426 g, 1.5 mmol) was stirred at 70° C. overnight with 4-chlorobenzyl chloride (0.290 g, 1.8 mmol) and triethylamine (0.5 ml, 3.6 mmol) in dichloroethane (30 ml). Solvent was removed and the reaction was purified by silica gel chromatography to give intermediate 63 (0.240 g; 59% yield).

Preparative Example 48

Preparation of Compound No. 229 of Table 1

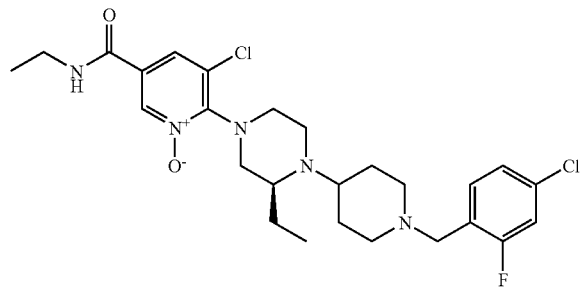

Table 1 Compound No. 229 was prepared by a method analogous to Examples 1 through 3. MS: m/e M+H=539.5.

Preparative Example 49

Preparation of Compound No. 214 of Table 1

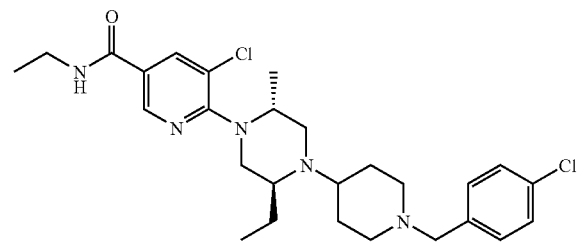

Table 1 Compound No. 214 was prepared by a method analogous to Preparative Examples 1 through 3. MS: m/e M+H=519.5.

Preparative Example 50

Preparation of Compound No. 215 of Table 1

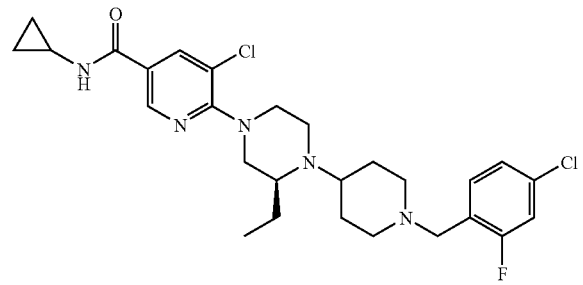

Table 1 Compound No. 215 was prepared by a method analogous to Preparative Examples 1 through 3. MS: m/e M+H=535.5.

Preparative Example 51

Preparation of Compound No. 216 of Table 1

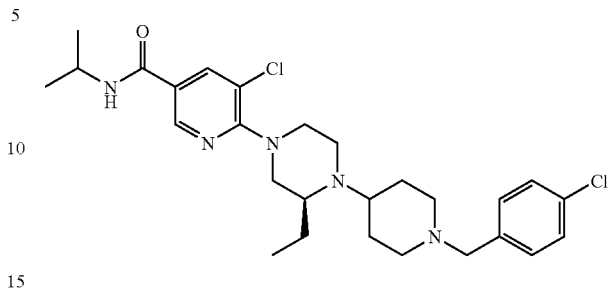

Table 1 Compound No. 216 was prepared by a method analogous to Preparative Examples 1 through 3. MS: m/e M+H=519.5.

Preparative Example 52

Preparation of Compound No. 217 of Table 1

Table 1 Compound No. 217 was prepared by a method analogous to Preparative Examples 1 through 3. MS: m/e M+H=537.5.

Preparative Example 53

Preparation of Compound No. 367 of Table 1

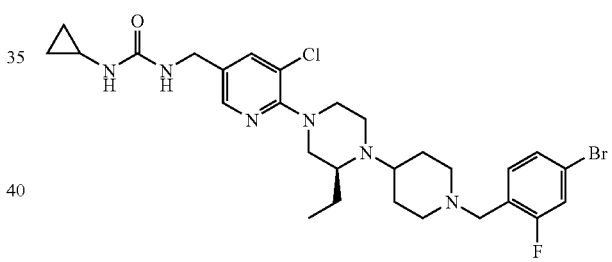

Table 1 Compound No. 367 was prepared by a method analogous to Preparative Examples 40 through 41. MS: m/e M+H=609.0.

Preparative Example 54

Preparation of Compound No. 369 of Table 1

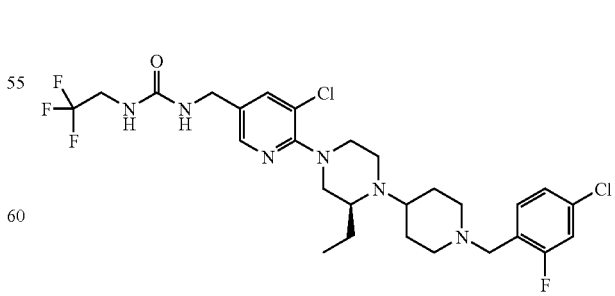

Table 1 Compound No. 369 was prepared by a method analogous to Preparative Examples 40 through 41. MS: m/e M+H=606.5.

Preparative Example 55

Preparation of Compound No. 212 of Table 1

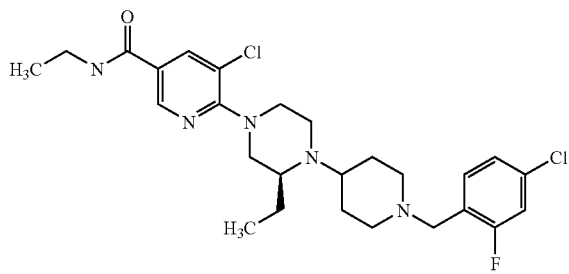

Table 1 Compound No. 212 was prepared by a method analogous to Examples 1 through 3. MS: m/e M+H=523.5.

Biological Examples

The inventive compounds can readily be evaluated to determine activity at the CXCR3 receptors by known methods, such as, for example, development of a human CXCR3 (N-delta 4) Binding Assay.

Cloning and expression of human CXCR3 (N-delta 4):

The DNA encoding human CXCR3 was cloned by PCR using human genomic DNA (Promega, Madison, Wis.) as a template. The PCR primers were designed based on the published sequence of human orphan receptor GPR9 (1) with incorporated restriction sites, a Kozak consensus sequence, CD8 leader and Flag tag. The PCR product was subcloned into the mammalian expression vector pME18Sneo, a derivative of the SR-alpha expression vector (designated as pME18Sneo-hCXCR3 (N-delta 4).

IL-3-dependent mouse pro-B cells Ba/F3 were transfected by electroporation in 0.4 ml Dulbecco's PBS containing $4 \times 10^6$ cells with 20 µg of pME18Sneo-hCXCR3 (N-delta 4) plasmid DNA. Cells were pulsed at 400 Volts, 100 OHMs, 960 µFd. The transfected cells were under selection with 1 mg/ml G418 (Life Technologies, Gaithersburg, Md.). G418-resistant Ba/F3 clones were screened for CXCR3 expression by specific binding of [$^{125}$I] IP-10 (NEN Life Science Products, Boston, Mass.).

Preparation of Ba/F3-hCXCR3 (N-delta 4) membranes:

Ba/F3 cells expressing human CXCR3 (N-delta 4) were pelleted and resuspended in the lysis buffer containing 10 mM HEPES, pH 7.5 and Complete® protease inhibitors (1 tablet per 100 ml) (Boehringer Mannheim, Indianapolis, Ind.) at a cell density of $20 \times 10^6$ cells per ml. After 5 minute incubation on ice, cells were transferred to 4639 cell disruption bomb (Parr Instrument, Moline, Ill.) and applied with 1,500 psi of nitrogen for 30 minutes on ice. Large cellular debris was removed by centrifugation at 1,000×g. Cell membrane in the supernatant was sedimented at 100,000×g. The membrane was resuspended in the lysis buffer supplemented with 10% sucrose and stored at −80° C. Total protein concentration of the membrane was determined by BCA method from Pierce (Rockford, Ill.).

Human CXCR3 (N-delta 4) scintillation proximity assay (SPA):

For each assay point, 2 µg of membrane was preincubated for 1 hr with 300 µg wheat germ agglutinin (WGA) coated SPA beads (Amersham, Arlington Heights, Ill.) in the binding buffer (50 mM HEPES, 1 mM $CaCl_2$, 5 mM $MgCl_2$, 125 mM NaCl, 0.002% $NaN_3$, 1.0% BSA) at room temperature. The beads were spun down, washed once, resuspended in the binding buffer and transferred to a 96-well Isoplate (Wallac, Gaithersburg, Md.). 25 pM of [$^{125}$I] IP-10 with tested compounds in a series of titration were added to start the reaction. After 3 hr reaction at room temperature, the amount of [$^{125}$I] IP-10 bound to the SPA beads was determined with a Wallac 1450 Microbeta counter.

The Ki ratings for the various compounds of the present invention are given in the afore-mentioned Table 1. From these ratings and value ranges, it would be apparent to the skilled artisan that the compounds of the invention have excellent utility as CXCR3 receptor antagonists.

While the present invention has been describe in conjunction with the specific embodiments set forth above, many alternatives, modifications and variations thereof will be apparent to those of ordinary skill in the art. All such alternatives, medications and variations are intended to fall within the spirit and scope of the present invention.

What is claimed is:

1. A compound having the general structure shown in Formula 1:

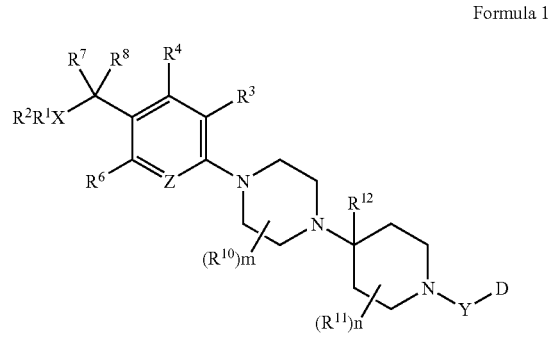

Formula 1 or pharmaceutically acceptable salts, solvates or esters thereof wherein:

Z is N, C($R^{29}$), or NO;

X is N, O, alkyl, cycloalkyl, heteroaryl, heterocyclyl or heterocyclenyl;

$R^1$ and $R^2$ are independently absent or present, and if present each is independently selected from the group consisting of H, alkyl, alkoxy, alkenyl, carbonyl, cycloalkyl, cycloalkenyl, alkylaryl, arylalkyl, aryl, amino, alkylamino, amidinyl, carboxamido, cyano, hydroxyl, urea, —N≡CH, =NCN, —$(CH_2)_q$OH, —$(CH_2)_q$O$R^{31}$, —$(CH_2)_q$C$F_3$, —$(CH_2)_q$N$H_2$, —$(CH_2)_q$NH$R^{31}$, —$(CH_2)_q$N$(R^{31})_2$, —$(CH_2)_q$C(=O)NH$R^{31}$, —$(CH_2)_q$S$O_2R^{31}$, —$(CH_2)_q$NHS$O_2R^{31}$, —$(CH_2)_q$S$O_2$NH$R^{31}$, —C(=S)N(H)alkyl, —N(H)—S(O)$_2$-alkyl, —N(H)C(=O)N(H)-alkyl, —S(O)$_2$alkyl, —S(O)$_2$N(H)alkyl, —S(O)$_2$N(alkyl)$_2$, —S(O)$_2$aryl, —C(=S)N(H)cycloalkyl, —C(=O)N(H)N$H_2$, —C(=O)alkyl, -heteroaryl, heterocyclyl, and heterocyclenyl, fluorophenylmethylene, trifluoromethylphenylmethylene, cyanophenylmethylene, difluorophenylmethylene, bromophenylmethylene, chlorophenylmethylene, bromochlorophenylmethtlene, fluorochlorophenylmethylene, dichlorophenylmethylene, methoxylphenylmethylene, —$CH_2$-cyclopropyl, cyclohexylmethylene, aminooxadiazoyl, 5-methylisoxazolyl, chloropyridyl, pyridylimethylene,

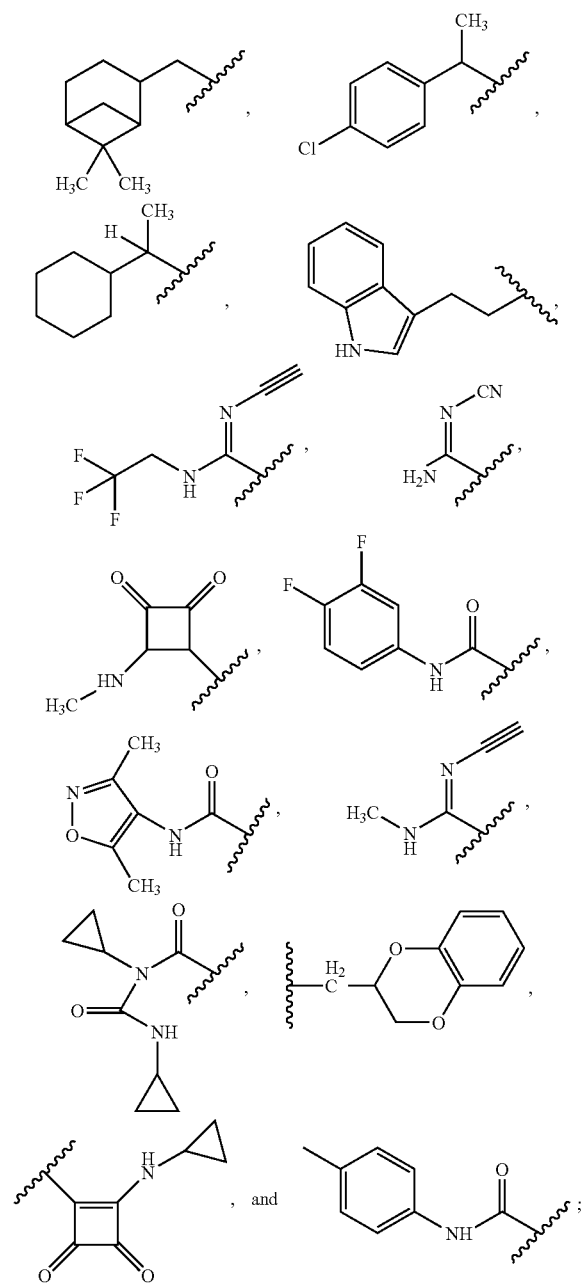

or alternatively when X is N, the N taken together with the $R^1$ and $R^2$ forms a heterocyclyl, heteroaryl or —N=C(NH$_2$)$_2$;

$R^3$, $R^4$, $R^6$ and $R^{29}$ moieties can be the same or different, each being independently selected from the group consisting of H, alkyl, alkylaryl, aralkyl, —CN, CF$_3$, haloalkyl, cycloalkyl, halogen, hydroxyalkyl, —N=CH—(R$^{31}$), —C(=O)N(R$^{30}$)$_2$, —N(R$^{30}$)$_2$, —OR$^{30}$, —SO$_2$(R$^{31}$), —N(R$^{30}$)C(=O)N(R$^{30}$)$_2$ and —N(R$^{30}$)C(=O)R$^{31}$;

$R^7$ and $R^8$ are the same or different, each being independently selected from the group consisting of H, alkyl, alkylaryl, heteroaryl, hydroxyl, —CN, alkoxy, alkylamino, —N(H)S(O)$_2$alkyl and —N(H)C(=O)N(H)alkyl; or alternatively $R^7$ and $R^8$ taken together with the carbon atom to which they are shown attached is —C=O—, —C=S—, —C=N(H)—, —C=N(alkyl)—, —C=N(Oalkyl)—, —C=N(OH)— or cycloalkyl;

the $R^{10}$ moieties can be the same or different, each being independently selected from the group consisting of H, alkyl, cycloalkyl, aryl, heteroaryl, heterocyclenyl, heterocyclyl, alkylaryl, arylalkyl, —CO$_2$H, hydroxyalkyl, —C(=O)N(R$^{30}$)$_2$, —(CH$_2$)$_q$OH, —(CH$_2$)$_q$OR$^{31}$, —(CH$_2$)$_q$NHR$^{31}$, —(CH$_2$)$_q$N(R$^{31}$)$_2$, —OR$^{30}$, halogen, =O, and —C(=O)R$^{31}$;

the $R^{11}$ moieties can be the same or different, each being independently selected from the group consisting of H, alkyl, cycloalkyl, aryl, heteroaryl, heterocyclyl, heterocyclenyl, alkylaryl, arylalkyl, hydroxyalkyl, carboxamide, CO$_2$H, —(CH$_2$)$_q$OH, —(CH$_2$)$_q$OR$^{31}$, —(CH$_2$)$_q$NHR$^{31}$, —(CH$_2$)$_q$N(R$^{31}$)$_2$, —OR$^{30}$, halogen, =O, and —C(=O)R$^{31}$;

the $R^{12}$ moieties can be the same or different, each being independently selected from the group consisting of H, alkyl, —CN, —C(=O)N(R$^{30}$)$_2$, —(CH$_2$)$_q$OH, —(CH$_2$)$_q$OR$^{31}$, —(CH$_2$)$_q$NHR$^{31}$, —(CH$_2$)$_q$N(R$^{31}$)$_2$, and —S(O$_2$)R$^{31}$;

D is a five to nine membered cycloalkyl, cycloalkenyl, aryl, heteroaryl, heterocyclenyl or heterocyclyl ring having 0-4 heteroatoms independently selected from O, S or N, wherein ring D is unsubstituted or optionally substituted with 1-5 independently selected $R^{20}$ moieties;

the $R^{20}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=NR$^{30}$)NHR$^{30}$, —C(=NOH)N(R$^{30}$)$_2$, —C(=NOR$^3$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$; or alternatively two $R^{20}$ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 $R^{21}$ moieties;

the $R^{21}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, carboxamido, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$ $NH_2$, $-(CH_2)_qNHR^{31}$, $-(CH_2)_qN(R^{31})_2$, $-(CH_2)_qC(=O)NHR^{31}$, $-(CH_2)_qSO_2R^{31}$, $-(CH_2)_qNSO_2R^{31}$, $-(CH_2)_qSO_2NHR^{31}$, -alkynylC($R^{31}$)$_2OR^{31}$, $-C(=O)R^{30}$, $-C(=O)N(R^{30})_2$, $-C(=NR^{30})NHR^{30}$, $-C(=NOH)N(R^{30})_2$, $-C(=NOR^{31})N(R^{30})_2$, $-C(=O)OR^{30}$, $-N(R^{30})_2$, $-N(R^{30})C(=O)R^{31}$, $-NHC(=O)N(R^{30})_2$, $-N(R^{30})C(=O)OR^{31}$, $-N(R^{30})C(=NCN)N(R^{30})_2$, $-N(R^{30})C(=O)N(R^{30})SO_2(R^{31})$, $-N(R^{30})C(=O)N(R^{30})_2$, $-N(R^{30})SO_2(R^{31})$, $-N(R^{30})S(O)_2N(R^{30})_2$, $-OR^{30}$, $-OC(=O)N(R^{30})_2$, $-SR^{30}$, $-SO_2N(R^{30})_2$, $-SO_2(R^{31})$, $-OSO_2(R^{31})$, and $-OSi(R^{30})_3$;

Y is selected from the group consisting of $-(CR^{13}R^{13})_r-$, $-CHR^{13}C(=O)-$, $-(CHR^{13})_rO-$, $-(CHR^{13})_rN(R^{30})-$, $-C(=O)-$, $-C(=NR^{30})-$, $-C(=NOR^{30})-$, $-CH(C(=O)NHR^{30})-$, CH-heteroaryl-, $-C(R^{13}R^{13})_rC(R^{13})=C(R^{13})-$, $-(CHR^{13})_rC(=O)-$ and $-(CHR^{13})_rN(H)C(=O)-$;

the $R^{13}$ moieties can be the same or different, each being independently selected from the group consisting of H, alkyl, alkylaryl, cycloalkyl, alkoxy, aryl, heteroaryl, heterocyclenyl, heterocyclyl, spiroalkyl, $-CN$, $-C(=O)R^{30}$, $-C(=O)N(R^{30})_2$, $-(CHR^{30})_qOH$, $-(CHR^{30})_qOR^{31}$, $-(CHR^{30})_qNH_2$, $-(CHR^{30})_qNHR^{31}$, $-(CH_2)_qC(=O)NHR^{31}$, $-(CH_2)_qSO_2R^{31}$, $-(CH_2)_qNSO_2R^{31}$, $-(CH_2)_qSO_2NHR^{31}$, $-NH_2$, $-N(R^{30})_2$, $-N(R^{30})C(=O)N(R^{30})_2$, $-N(R^{30})SO_2(R^{31})$, $-OH$, $OR^{30}$, $-SO_2N(R^{30})_2$, and $-SO_2(R^{31})$;

the $R^{30}$ moieties can be the same or different, each being independently selected from the group consisting of H, alkyl, alkylaryl, aryl, aralkyl, cycloalkyl, CN, $-(CH_2)_qOH$, $-(CH_2)_qOalkyl$, $-(CH_2)_qOalkylaryl$, $-(CH_2)_qOaryl$, $-(CH_2)_qOaralkyl$, $-(CH_2)_qOcycloalkyl$, $-(CH_2)_qNH_2$, $-(CH_2)_qNHalkyl$, $-(CH_2)_qN(alkyl)_2$, $-(CH_2)_qNHalkylaryl$, $-(CH_2)_qNHaryl$, $-(CH_2)_qNHaralkyl$, $-(CH_2)_qNHcycloalkyl$, $-(CH_2)_qC(=O)NHalkyl$, $-(CH_2)_qC(=O)N(alkyl)_2$, $-(CH_2)_qC(=O)NHalkylaryl$, $-(CH_2)_qC(=O)NHaryl$, $-(CH_2)_qC(=O)NHaralkyl$, $-(CH_2)_qC(=O)NHcycloalkyl$, $-(CH_2)_qSO_2alkyl$, $-(CH_2)_qSO_2alkylaryl$, $-(CH_2)_qSO_2aryl$, $-(CH_2)_qSO_2aralkyl$, $-(CH_2)_qSO_2cycloalkyl$, $-(CH_2)_qNSO_2alkyl$, $-(CH_2)_qNSO_2alkylaryl$, $-(CH_2)_qNSO_2aryl$, $-(CH_2)_qNSO_2aralkyl$, $-(CH_2)_qNSO_2cycloalkyl$, $-(CH_2)_qSO_2NHalkyl$, $-(CH_2)_qSO_2NHalkylaryl$, $-(CH_2)_qSO_2NHaryl$, $-(CH_2)_qSO_2NHaralkyl$, $-(CH_2)_qSO_2NHcycloalkyl$, heterocyclenyl, heterocyclyl, and heteroaryl;

the $R^{31}$ moieties can be the same or different, each being independently selected from the group consisting of alkyl, alkylaryl, aryl, aralkyl, cycloalkyl, $-(CH_2)_qOH$, $-(CH_2)_qOalkyl$, $-(CH_2)_qOalkylaryl$, $-(CH_2)_qOaryl$, $-(CH_2)_qOaralkyl$, $-(CH_2)_qOcycloalkyl$, $-(CH_2)_qNH_2$, $-(CH_2)_qNHalkyl$, $-(CH_2)_qN(alkyl)_2$, $-(CH_2)_qNHalkylaryl$, $-(CH_2)_qNHaryl$, $-(CH_2)_qNHaralkyl$, $-(CH_2)_qNHcycloalkyl$, $-(CH_2)_qC(=O)NHalkyl$, $-(CH_2)_qC(=O)N(alkyl)_2$, $-(CH_2)_qC(=O)NHalkylaryl$, $-(CH_2)_qC(=O)NHaryl$, $-(CH_2)_qC(=O)NHaralkyl$, $-(CH_2)_qC(=O)NHcycloalkyl$, $-(CH_2)_qSO_2alkyl$, $-(CH_2)_qSO_2alkylaryl$, $-(CH_2)_qSO_2aryl$, $-(CH_2)_qSO_2aralkyl$, $-(CH_2)_qSO_2cycloalkyl$, $-(CH_2)_qNSO_2alkyl$, $-(CH_2)_qNSO_2alkylaryl$, $-(CH_2)_qNSO_2aryl$, $-(CH_2)_qNSO_2aralkyl$, $-(CH_2)_qNSO_2cycloalkyl$, $-(CH_2)_qSO_2NHalkyl$, $-(CH_2)_qSO_2NHalkylaryl$, $-(CH_2)_qSO_2NHaryl$, $-(CH_2)_qSO_2NHaralkyl$, $-(CH_2)_qSO_2NHcycloalkyl$, heterocyclenyl, heterocyclyl, and heteroaryl;

m is 0 to 4;

n is 0 to 4;

each q can be the same or different, each being independently selected from 1 to 5; and r is 1 to 4;

with the proviso that there are no two adjacent double bonds in any ring, and that when a nitrogen is substituted by two alkyl groups, said two alkyl groups may be optionally joined to each other to form a ring.

2. The compound according to claim 1, wherein $R^1$ and $R^2$ are independently absent or present, and if present each is independently selected from the group consisting of H, alkyl, aryl, amino, alkoxy, hydroxy, cycloalkyl, cycloalkenyl, arylalkyl, amidinyl, carboxamido, heteroaryl, heterocyclyl, heterocyclenyl, urea, $-S(O)_2alkyl$, $-S(O)_2N(H)alkyl$, $-S(O)_2N(alkyl)_2$, and $-C(=S)N(H)cycloalkyl$.

3. The compound according to claim 1, wherein $R^1$ and $R^2$ are independently absent or present, and if present each is independently selected from the group consisting of H, alkylaryl, aryl, heteroaryl, $-(CH_2)_qCF_3$, $-(CH_2)_qOH$, $-(CH_2)_qOR^{31}$, $-(CH_2)_qNH_2$, $-(CH_2)_qNHR^{31}$, $-(CH_2)_qN(R^{31})_2$, $-(CH_2)_qC(=O)NHR^{31}$, $-(CH_2)_qSO_2R^{31}$, $-(CH_2)_qNHSO_2R^{31}$, $-(CH_2)_qSO_2NHR^{31}$, $-(CH_2)_q$-amidinyl, cyclopropyl, cyclopropylhydroxyl, cyclobutyl, cyclobutylhydroxy, cyclopentyl, and cyclopentylhydroxy; and q is an integer from 1 to 5.

4. The compound according to claim 1, wherein $R^1$ and $R^2$ are independently absent or present, and if present each is independently selected from the group consisting of H, $-CH_3$, fluorophenylmethylene, trifluoromethylphenylmethylene, indanyl, cyanophenylmethylene, difluorophenylmethylene, bromophenylmethylene, chlorophenylmethylene, $-CH_2CH_2O$ phenyl, cyclopentyl, bromochlorophenylmethylene, fluorochlorophenylmethylene, dichlorophenylmethylene, phenylmethylene, $-(CH_2)_3phenyl$, $-CH_2CF_3$, methoxyphenylmethylene, $-CH(CH_3)_2$, $-C_2H_5$, $-CH_2$-cyclopropyl, $-(CH_2)_2CH_3$, cyclohexylmethylene, cyclohexyl, $-CH_2CH_2SO_2CH_3$, $-CH_2-CH_2-NH_2$, $-CH_2CH_2OCH_3$, cyclopropyl, isoxazolyl, oxadiazoyl, aminooxadiazoyl, $-CH_2CH_2OH$, $-CH_2CH_2Ophenyl$, $-CH_2CH_2CH_3$, $-NH_2$, $-(CH_2)_2NH_2$, pyrazolyl, 5-methyl-isoxazolyl, $-CH_2CH(OCH_2CH_3)_2$, $-OCH_3$, $-NHC(=O)NH_2$, chloropyridyl, pyridylmethylene, $-C(=O)NH$-cyclopropyl, $-C(=O)N(H)C_2H_5$, $-C(=O)N(H)CH_2CF_3$, $-C(=O)N(H)C(CH_3)_3$, $-C(=S)N(H)cyclopropyl$, $-C(=O)NH_2$, $-C(=O)N(H)CH_3$, $-S(O)_2CH_3$, $-S(O)_2N(CH_3)_2$, $-S(O)_2CH_2CH_3$, $-C(=O)CH_3$, $-S(O)_2(CH_2)_2CH_3$, $-C(=O)N(H)cyclohexyl$, $-C(=NH)NH_2$, $-C(=O)N(H)NH_2$, $-C(=O)N(H)CH(CH_3)_2$, thiazolyl, $-C(=O)N(CH_3)_2$, $-S(O)_2CH_2CF_3$, $-S(O)_2CF_3$, $-CH_2CH(OCH_2CH_3)_2$,

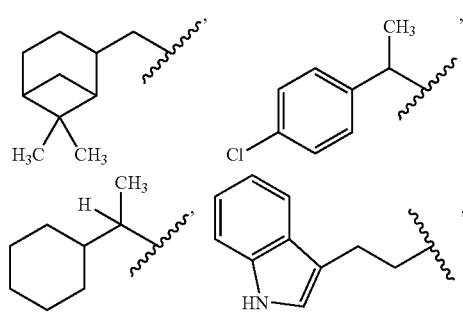

-continued

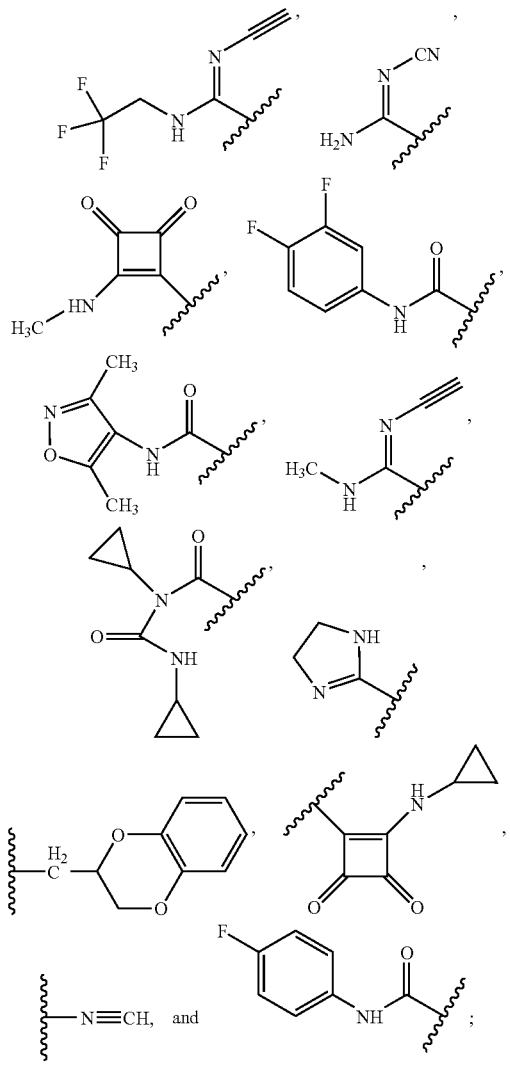

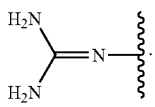

or when X is N, the N taken together with the R¹ and R² to which X is shown attached, forms an aziridine, an azetidine, a piperidine or 5. The compound according to claim 1, wherein R¹ and R² are independently absent or present, and if present each is independently selected from the group consisting of H, —CH₃, —C₂H₅, difluorophenylmethylene, cyclopropyl, dichlorophenylmethylene, —CH(CH₃)₂, cyclohexylmethylene, cyclohexyl, isoxazolyl, oxadiazoyl, aminooxadiazoyl, difluorophenyl, —CH₂CH₂OH, —CH₂CH₂N(CH₃))₂, —C(=O)N(H)cyclopropyl, —C(=O)N(H)C₂H₅, —C(=O)N(H)CH₂CF₃, —C(=O)N(H)CH(CH₃)₂, —C(=O)N(H)C(CH₃)₃, —C(=S)N(H)cyclopropyl, —C(=O)NH₂, —C(=O)N(H)CH₃, —S(O)₂CH₃, —S(O)₂N(CH₃)₂, —S(O)₂CH₂CH₃, —C(=O)CH₃, —S(O)₂(CH₂)₂ CH₃, —C(=O)N(H)cyclohexyl, —C(=NH)NH₂, —C(=O)N(H)NH₂, thiazolyl,

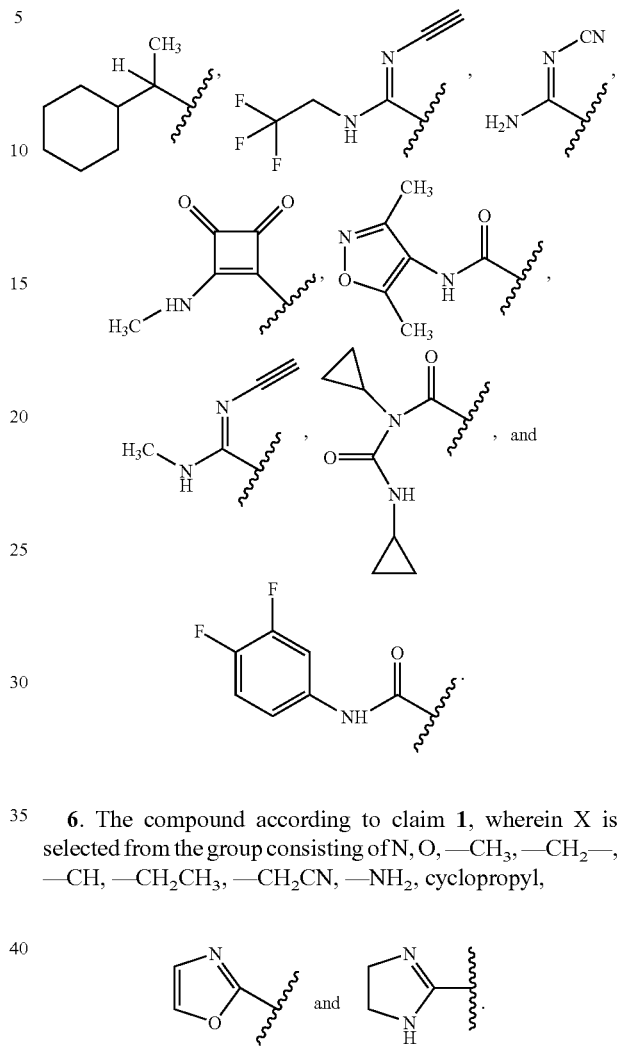

6. The compound according to claim 1, wherein X is selected from the group consisting of N, O, —CH₃, —CH₂—, —CH, —CH₂CH₃, —CH₂CN, —NH₂, cyclopropyl, 7. The compound according to claim 6, wherein X is N or O.

8. The compound according to claim 7, wherein X is N.

9. The compound according to claim 1, wherein Z is N or C(R²⁹).

10. The compound according to claim 9, wherein Z is N.

11. The compound according to claim 9, wherein Z is C(H), C(alkyl), C(halogen), C(CF₃) or C(N(R³⁰)₂).

12. The compound according to claim 11, wherein Z is C(alkyl), C(F) or C(NH₂).

13. The compound according to claim 1, wherein R³ is selected from the group consisting of H, alkyl, haloalkyl, hydroxyalkyl, halogen, —N(R³⁰)₂, —OR³⁰ and —CF₃.

14. The compound according to claim 1, wherein R³ is selected from the group consisting of H, —CH₃, —CH₂CH₃, cyclopropyl, —F, —Cl, OCH₃, OCF₃ and CF₃.

15. The compound according to claim 1, wherein R⁴ is selected from the group consisting of H, alkyl, hydroxyalkyl, halogen, OR³⁰, or CF₃.

16. The compound according to claim 1, wherein $R^6$ is selected from the group consisting of H, alkyl, halogen, hydroxyalkyl, —CN, —N($R^{30}$)$_2$, —O$R^{30}$, —N=CH-alkyl, and —N$R^{30}$C(=O)alkyl.

17. The compound according to claim 16, wherein $R^6$ is selected from the group consisting of H, —NH$_2$, —CH$_3$, —CN and —F.

18. The compound according to claim 1, wherein $R^7$ and $R^8$ are the same or different, each being independently selected from the group consisting of H, —(CH$_2$)$_q$OH, —(CH$_2$)$_q$Oalkyl, —(CH$_2$)$_q$N(H)-alkyl, —(CH$_2$)$_q$N(H)—S(O)$_2$alkyl, and —(CH$_2$)$_q$N(H)—CO—N(H)alkyl; or alternatively $R^7$ and $R^8$ taken together with the carbon atoms to which they are shown attached is —C=O—, —C=N(OAlkyl)—, or —C=S—.

19. The compound according to claim 1, wherein $R^7$ and $R^8$ are the same or different, each being independently selected from the group consisting of H, —CH$_3$, and —OH; or alternatively $R^7$ and $R^8$ taken together with the carbon atom to which $R^7$ and $R^8$ are attached, is

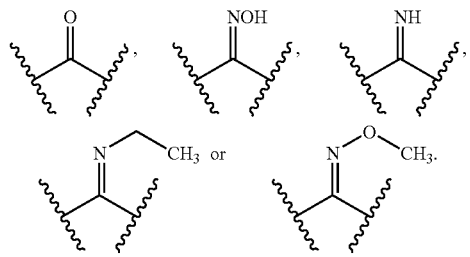

20. The compound according to claim 1, wherein $R^7$ and $R^8$ are each H; or alternatively $R^7$ and $R^8$ taken together with the carbon atom to which $R^7$ and $R^8$ are attached, is

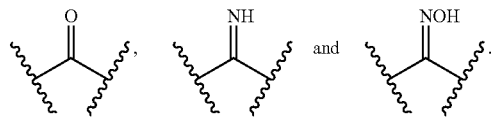

21. The compound according to claim 1, wherein $R^{10}$ is selected from the group consisting of H, alkyl, aralkyl, hydroxyalkyl, and carbonyl.

22. The compound according to claim 21, wherein $R^{10}$ is selected from the group consisting of —CH$_3$, —CH$_2$CH$_3$ and —CH$_2$CH$_2$CH$_3$, and m is 0-2.

23. The compound according to claim 1, wherein $R^{11}$ is selected from the group consisting of H, alkyl, hydroxyalkyl and carbonyl.

24. The compound according to claim 23, wherein $R^{11}$ is H or —CH$_3$.

25. The compound according to claim 1, wherein $R^{12}$ is selected from the group consisting of H, CN, —C(=O)N($R^{30}$)$_2$ and alkyl.

26. The compound according to claim 25, wherein $R^{12}$ is selected from the group consisting of H, —CH$_3$, CN and —CH$_2$CH$_3$.

27. The compound according to claim 1, wherein the ring atoms of ring D are independently C or N and substituted by independently selected 0-4 $R^{20}$ moieties.

28. The compound according to claim 1, wherein ring D is a 5 to 6 membered aryl, heteroaryl, heterocyclenyl, or heterocyclyl ring and substituted by independently selected 0-4 $R^{20}$ moieties.

29. The compound according to claim 1, wherein the $R^{20}$ moieties can be the same or different, each being independently selected from the group consisting of H, alkyl, alkylaryl, alkynyl, alkoxy, alkylamino, alkylheteroaryl, alkylsulfinyl, alkoxycarbonyl, aminoalkyl, amidinyl, aralkyl, aralkoxy, aryl, aryloxy, cyano, cycloalkyl, cycloalkenyl, halogen, haloalkyl, heteroalkyl, heteroaryl, heterocyclyl, hydroxyalkyl, trifluoromethyl, trifluoromethoxy, —(CH$_2$)$_q$O$R^{31}$, —(CH$_2$)$_q$NH$R^{31}$, —(CH$_2$)$_q$C(=O)NH$R^{31}$, —(CH$_2$)$_q$SO$_2$$R^{31}$, —(CH$_2$)$_q$NSO$_2$$R^{31}$, —(CH$_2$)$_q$SO$_2$NH$R^{31}$, -alkynylC($R^{31}$)$_2$O$R^{31}$, —C(=O)$R^{30}$, —C(=O)N($R^{30}$)$_2$, —C(=O)O$R^{30}$, —N($R^{30}$)$_2$, —N($R^{30}$)C(=O)$R^{31}$, —NHC(=O)N($R^{30}$)$_2$, —N($R^{30}$)C(=O)O$R^{31}$, —N($R^{30}$)C(=NCN)N($R^{30}$)$_2$, —N($R^{30}$)C(=O)N($R^{30}$)$_2$, —N($R^{30}$)SO$_2$($R^{31}$), —N($R^{30}$)SO$_2$N($R^{30}$)$_2$, —O$R^{30}$, —OC(=O)N($R^{30}$)$_2$, —S$R^{30}$, —SO$_2$N($R^{30}$)$_2$—SO$_2$($R^{31}$), —OSO$_2$($R^{31}$), and —OSi($R^{30}$)$_3$.

30. The compound according to claim 1, wherein the $R^{20}$ moieties can be the same or different, each being independently selected from the group consisting of H, alkyl, amino, halogen, CN, CH$_3$, CF$_3$, OCF$_3$, —(CH$_2$)$_q$O$R^{31}$, —(CH$_2$)$_q$NH$R^{31}$, —(CH$_2$)$_q$C(=O)NH$R^{31}$, —(CH$_2$)$_q$SO$_2$$R^{31}$, —(CH$_2$)$_q$NSO$_2$$R^{31}$, —(CH$_2$)$_q$SO$_2$NH$R^{31}$, -alkynylC($R^{31}$)$_2$O$R^{31}$, —C(=O)$R^{30}$-C(=O)O$R^{30}$, —N($R^{30}$)$_2$, —N($R^{30}$)C(=O)$R^{31}$, —NHC(=O)N($R^{30}$)$_2$, —N($R^{30}$)C(=O)O$R^{31}$, —N($R^{30}$)C(=NCN)N($R^{30}$)$_2$, —N($R^{30}$)C(=O)N($R^{30}$)$_2$, —O$R^{30}$, —OC(=O)N($R^{30}$)$_2$, and —OSO$_2$($R^{31}$).

31. The compound according to claim 1, wherein two $R^{20}$ moieties are linked together to form a five or six membered aryl, cycloalkyl, heterocyclenyl, heterocyclyl or heteroaryl ring wherein said five or six membered aryl, cycloalkyl, heterocyclenyl, heterocyclyl, and heteroaryl ring is fused to ring D and the fused ring is optionally substituted with 0 to 4 $R^{21}$ moieties.

32. The compound according to claim 1, wherein the $R^{20}$ moieties can be the same or different, each being independently selected from the group consisting of H, —CN, —CH$_3$, —CF$_3$, —CH$_2$OH, —CO$_2$H, —CO$_2$CH$_3$, —NH$_2$, —NHCH$_3$, —OCF$_3$, —OH, F, Cl, Br, —C(=NOH)NH$_2$, —OCH$_2$CH$_2$S(O$_2$)CH$_3$, —C(=O)NH$_2$,

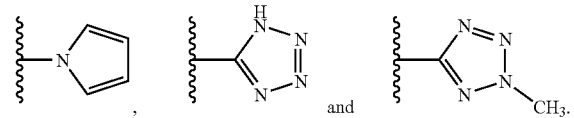

33. The compound according to claim 1, wherein Y is selected from the group consisting of: —(CH$R^{13}$)$_r$—, —(C$R^{13}$$R^{13}$)$_r$—, —C(=O)— and —CH$R^{13}$C(=O)—.

34. The compound according to claim 1, wherein Y is selected from the group consisting of: —CH$_2$—, —CH(CH$_3$)—, —CH(CH$_2$OH)—, and —C(=O)—.

35. The compound according to claim 1, wherein m is 0-3.

36. The compound according to claim 1, wherein n is 0-2.

37. The compound according to claim 1, wherein q is 1, 2 or 3.

38. The compound according to claim 1, wherein r is 1 or 2.

39. The compound according to claim 1, wherein Z is N, C(H), C(alkyl), C(F) or C(NH₂);

X is N;

R¹ and R² are independently absent or present, and if present each is independently selected from the group consisting of H, alkylaryl, aryl, heteroaryl, —(CH₂)_q CF₃, —(CH₂)_q OH, —(CH₂)_q OR³¹, —(CH₂)_q NH₂, —(CH₂)_q NHR³¹, —(CH₂)_q —N(R³¹)₂, —(CH₂)_q C (=O)NHR³¹, —(CH₂)_q SO₂R³¹, —(CH₂)_q NHSO₂R³¹, —(CH₂)_q SO₂NHR³¹, —(C H₂)_q-amidinyl, cyclopropyl, cyclopropylhydroxyl, cyclobutyl, cyclobutylhydroxy, cyclopentyl, and cyclopentylhydroxy;

R³ is selected from the group consisting of H, alkyl, haloalkyl, hydroxyalkyl, halogen, —N(R³⁰)₂, —OR³⁰ and —CF₃;

R⁴ is selected from the group consisting of H, alkyl, haloalkyl, hydroxyalkyl, halogen, —N(R³⁰)₂, —OR³⁰ and —CF₃;

R⁶ is selected from the group consisting of H, alkyl, halogen, hydroxyalkyl, —CN, —N(R³⁰)₂, —OR³⁰, —N=CH-alkyl, and —NR³⁰C(=O)alkyl;

R⁷ and R⁸ together with the carbon atom to which they are shown attached is selected from the group consisting of —C=O—, —C=S—, —C=N(H)—, —C=N (OH)—, and —C=N(Oalkyl)-;

R¹⁰ is selected from the group consisting of H, alkyl, aralkyl, hydroxyalkyl, and carbonyl;

R¹¹ is selected from the group consisting of H, alkyl, hydroxyalkyl, and carbonyl;

R¹² is selected from the group consisting of H, CN, —C(=O)N(R³⁰)₂ and alkyl;

ring D is a 5 to 6 membered aryl, heteroaryl, heterocyclenyl, or heterocyclyl ring and substituted by 0-4 R²⁰ moieties;

the R²⁰ moieties can be the same or different, each being independently selected from the group consisting of H, alkyl, amino, halogen, CN, CH₃, CF₃, OCF₃, —(CH₂)_q OR³¹, —(CH₂)_q NHR³¹, —(CH₂)_q C(=O)NHR³¹, —(CH₂)_q SO₂R³¹, —(CH₂)_q NSO₂R³¹, —(CH₂)_q SO₂NHR³¹, -alkynylC(R³¹)₂OR³¹, —C(=O)R³⁰, —C(=O)OR³⁰, —N(R³⁰)₂, —N(R³⁰)C(=O)R³¹, —NHC(=O)N(R³⁰)₂, —N(R³⁰)C(=O)OR³¹, —N(R³⁰)C(=NCN)N(R³⁰)₂, —N(R³⁰)C(=O)N (R³⁰)₂, —OR³⁰, —OC(=O)N(R³⁰)₂,

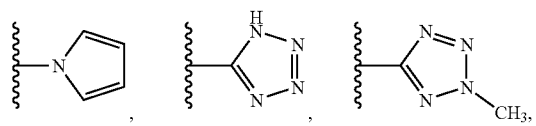

and —OSO₂(R³¹);

Y is selected from the group consisting of: —CH₂—, —CH(CH₃)—, —CH(CH₂OH)—, and —C(=O)—;

m is 0-2;

n is 0-2;

q is 1 or 2; and r is 1 or 2.

40. The compound according to claim 1, represented by structural Formula 2, Formula 3, Formula 4 or Formula 5:

Formula 2
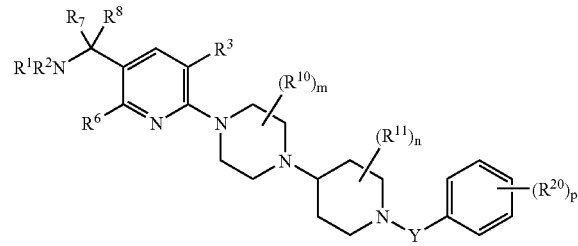

Formula 3
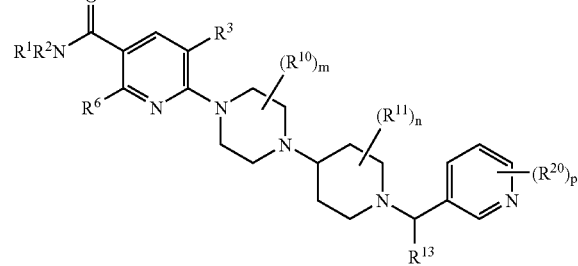

Formula 4
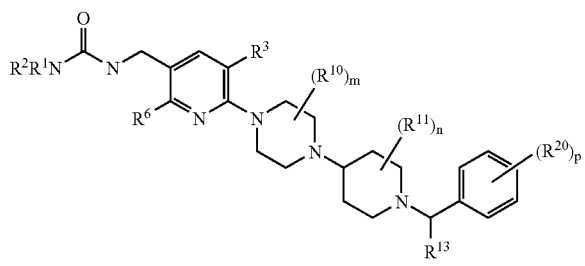

Formula 5
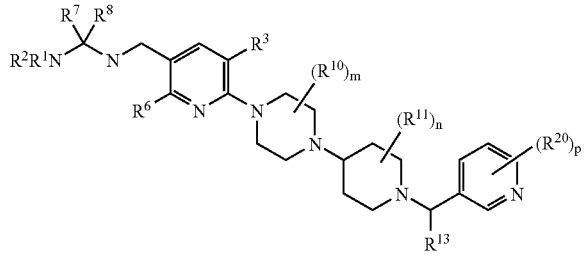

or pharmaceutically acceptable salts, solvates or esters thereof, wherein:

R¹ and R² are independently absent or present, and if present each is independently selected from the group consisting of H, —CH₃, fluorophenylmethylene, trifluoromethylphenylmethylene, indanyl, cyanophenylmethylene, difluorophenylmethylene, bromophenylmethylene, chlorophenylmethylene, —CH₂CH₂O phenyl, cyclopentyl, bromochlorophenylmethylene, fluorochlorophenylmethylene, dichlorophenylmethylene, phenylmethylene, —(CH$_2$)$_3$phenyl, —CH$_2$CF$_3$, methoxyphenylmethylene, —CH(CH$_3$)$_2$, —C$_2$H$_5$, —CH$_2$-cyclopropyl, —(CH$_2$)$_2$CH$_3$, cyclohexylmethylene, cyclohexyl, —CH$_2$CH$_2$SO$_2$CH$_3$, —CH$_2$—CH$_2$-NH$_2$, —CH$_2$CH$_2$OCH$_3$, cyclopropyl, isoxazolyl, —CH$_2$CH$_2$OH, —CH$_2$CH$_2$O phenyl, —CH$_2$CH$_2$CH$_3$, —NH$_2$, —(CH$_2$)$_2$NH$_2$, pyrazolyl, 5-methyl-isoxazolyl, —CH$_2$CH(OCH$_2$CH$_3$)$_2$, —OCH$_3$, —NHC(=O)NH$_2$, chloropyridyl, pyridylmethylene, —C(=O)NHcyclopropyl, —C(=O)N(H)C$_2$H$_5$, —C(=O)N(H)CH$_2$CF$_3$, —C(=O)N(H)C(CH$_3$)$_3$, —C(=S)N(H)cyclopropyl, —C(=O)NH$_2$, —C(=O)N(H)CH$_3$, —S(O)$_2$CH$_3$, —S(O)$_2$N(CH$_3$)$_2$, —S(O)$_2$CH$_2$CH$_3$, —C(=O)CH$_3$, —S(O)$_2$(CH$_2$)$_2$CH$_3$, —C(=O)N(H)cyclohexyl, —C(=NH)NH$_2$, —C(=O)N(H)NH$_2$, —C(=O)N(H)CH(CH$_3$)$_2$, thiazolyl, —C(=O)N(CH$_3$)$_2$, —S(O)$_2$CH$_2$CF$_3$, —S(O)$_2$CF$_3$, —CH$_2$CH(OCH$_2$CH$_3$)$_2$,

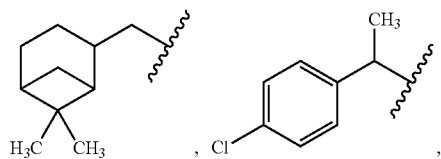

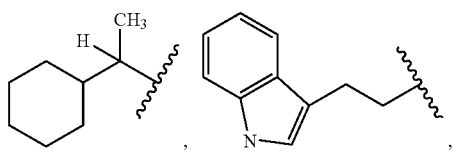

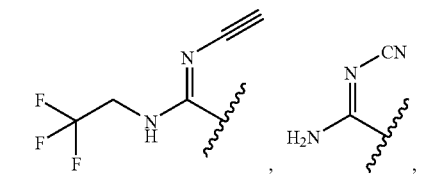

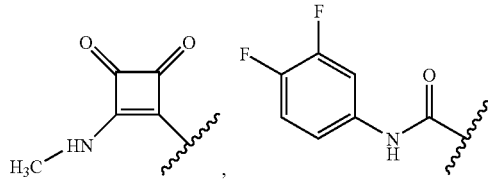

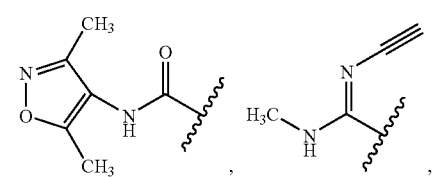

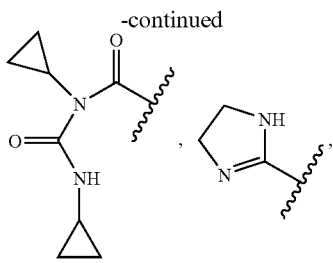

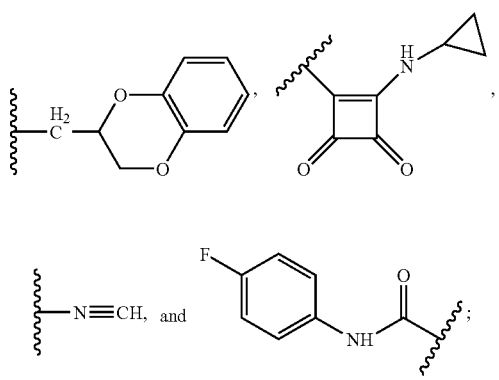

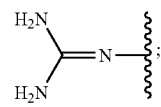

or when X is N, the N taken together with the R$^1$ and R$^2$ to which X is shown attached, forms an azetidine, a piperidine or R$^3$ is selected from the group consisting of H, —CH$_3$, —CH$_2$CH$_3$, cyclopropyl, —F, —Cl, OCH$_3$, OCF$_3$ and CF$_3$;

R$^{10}$ is selected from the group consisting of H, alkyl, aralkyl, hydroxyalkyl, and carbonyl;

R$^{11}$ is selected from the group consisting of H, alkyl, hydroxyalkyl and carbonyl;

R$^{13}$ is selected from the group consisting of H, alkyl, alkylaryl, cycloalkyl, alkoxy, —C(=O)R$^{30}$, —C(=O)N(R$^{30}$)$_2$, —(CHR$^{30}$)$_q$OH, —(CHR$^{30}$)$_q$OR$^{31}$, —(CHR$^{30}$)$_q$NH$_2$, —(CHR$^{30}$)$_q$NHR$^{31}$, —(CH$_2$)$_q$C(=O)NHR$^{31}$ —N(R$^{30}$)$_2$, —N(R$^{30}$)SO$_2$(R$^{31}$), —OR$^{30}$, —SO$_2$N(R$^{30}$)$_2$, and —SO$_2$(R$^{31}$);

the R$^{20}$ moieties can be the same or different, each being independently selected from the group consisting of H, alkyl, amino, halogen, CN, CH$_3$, CF$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —OR$^{30}$, —OC(=O)N(R$^{30}$)$_2$, and —OSO$_2$(R$^{31}$); and m, n, R$^6$, R$^7$, R$^8$, R$^{20}$, R$^{30}$ and R$^{31}$ are as defined in claim 1.

41. The compound according to claim 1, selected from the group consisting of:

| Compound No. | Compound Structure |
|---|---|
| 1 | *(structure)* |
| 2 | *(structure)* |
| 3 | *(structure)* |

-continued
| Compound No. | Compound Structure |
|---|---|
| 4 | 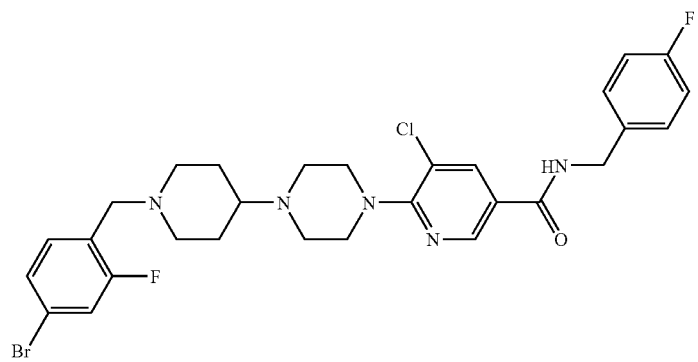 |
| 5 | 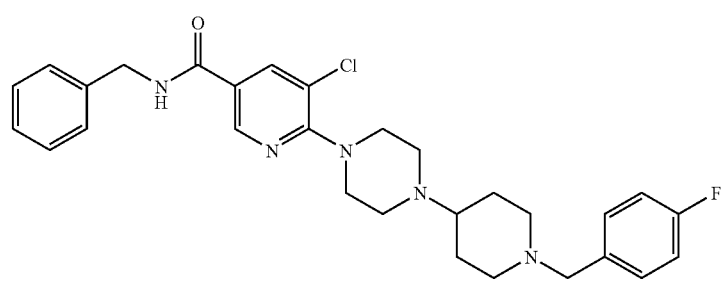 |
| 6 | 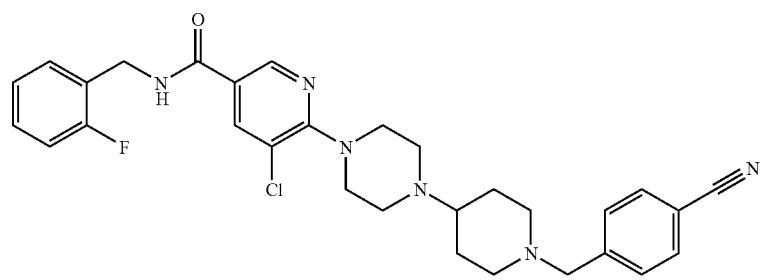 |
| 7 | 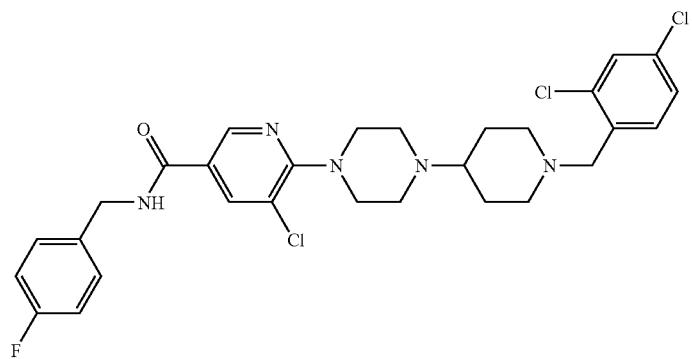 |

-continued

| Compound No. | Compound Structure |
|---|---|
| 8 | 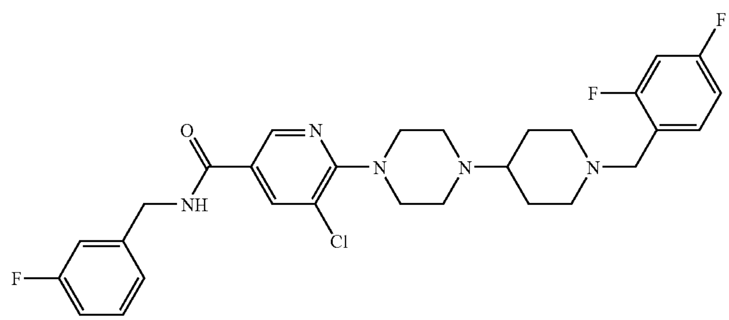 |
| 9 | 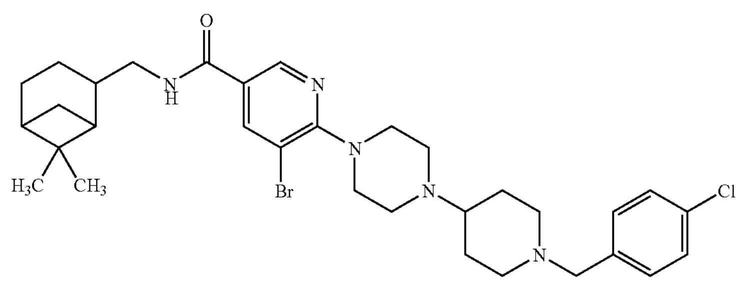 |
| 10 | 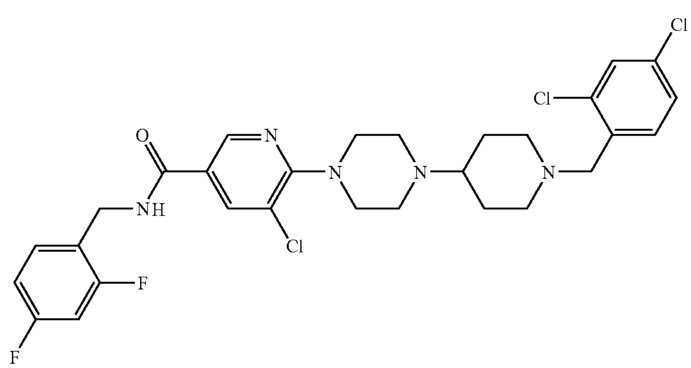 |
| 11 | 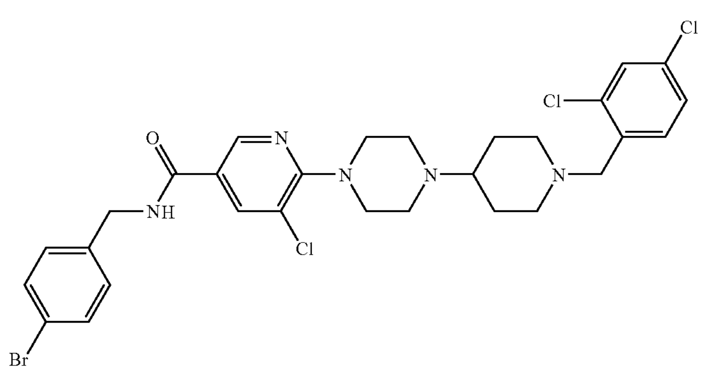 |

| Compound No. | Compound Structure |
|---|---|
| 12 | 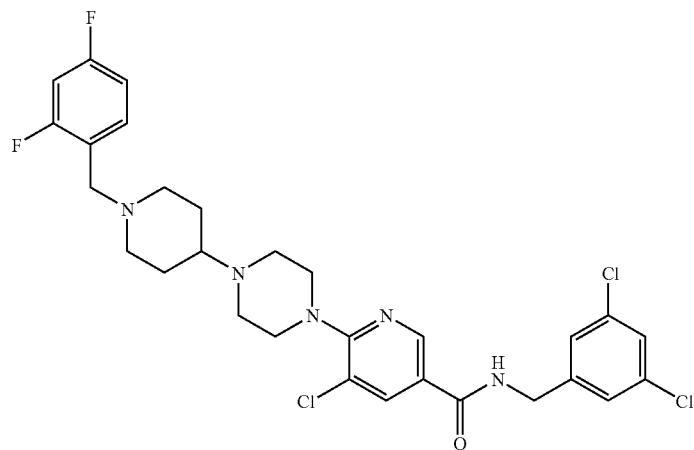 |
| 13 | 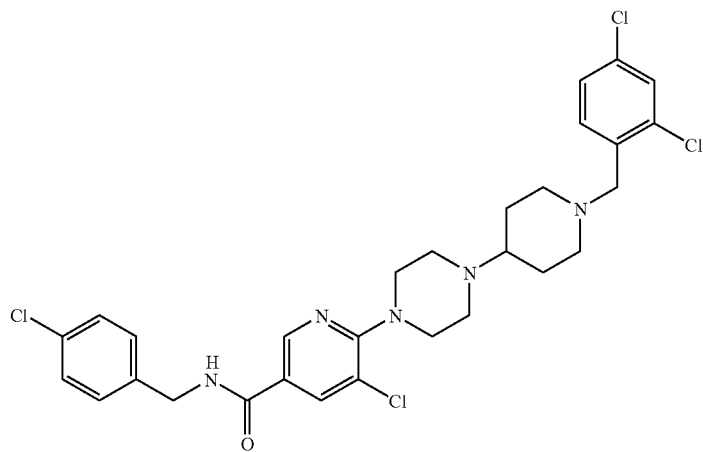 |
| 14 | 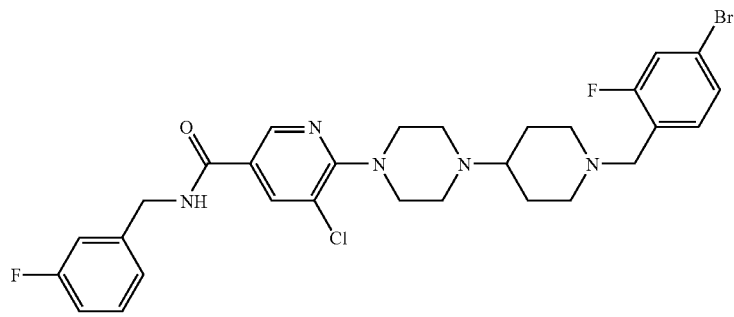 |

| Compound No. | Compound Structure |
|---|---|
| 15 | 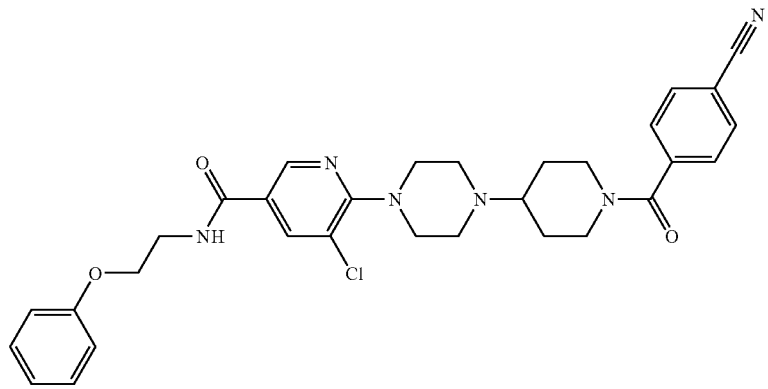 |
| 16 | 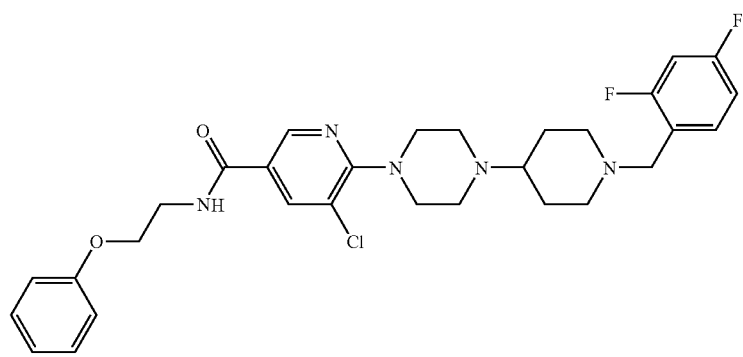 |
| 17 | 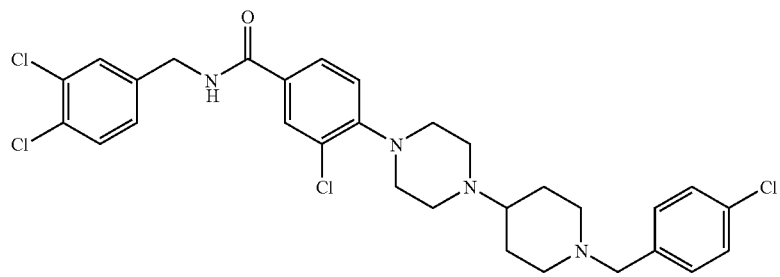 |
| 18 | 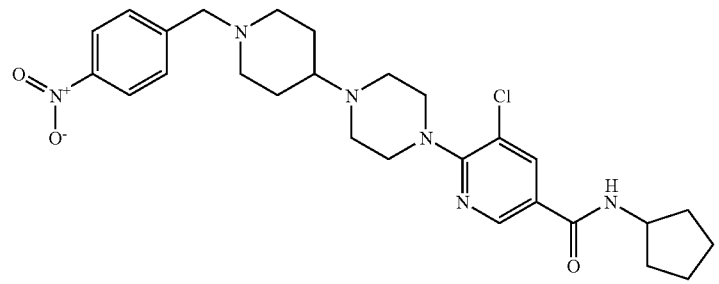 |

-continued
| Compound No. | Compound Structure |
|---|---|
| 19 | 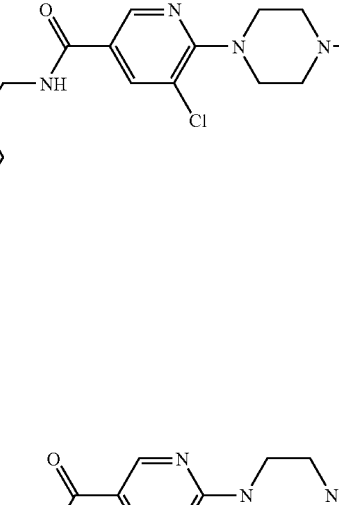 |
| 20 | 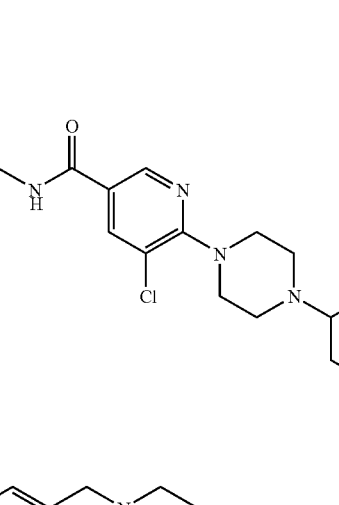 |
| 21 | 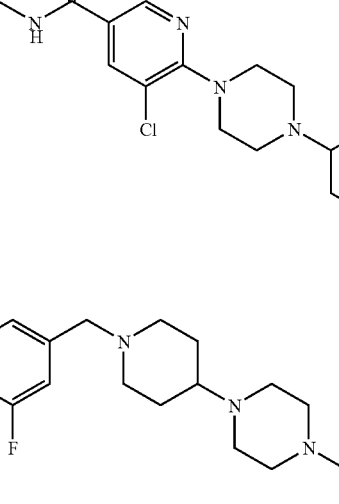 |
| 22 | 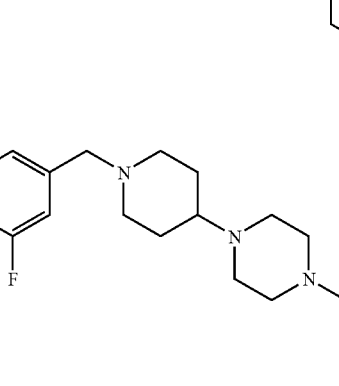 |

-continued
| Compound No. | Compound Structure |
|---|---|
| 23 | 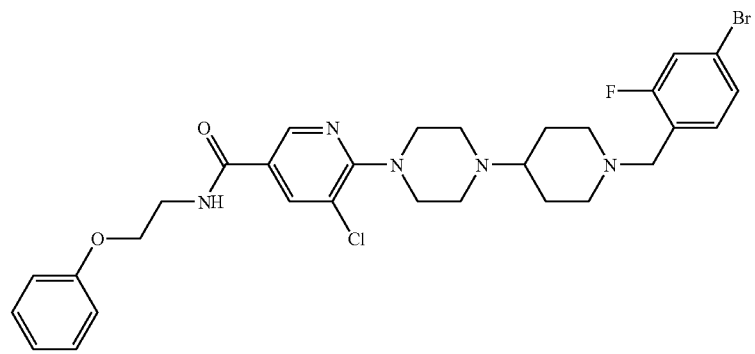 |
| 24 | 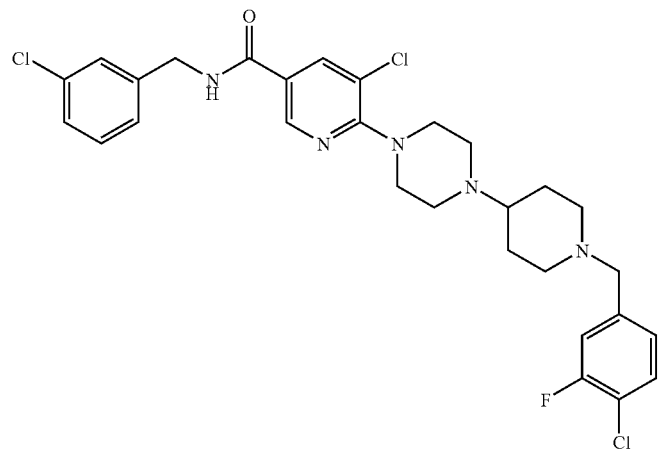 |
| 25 | 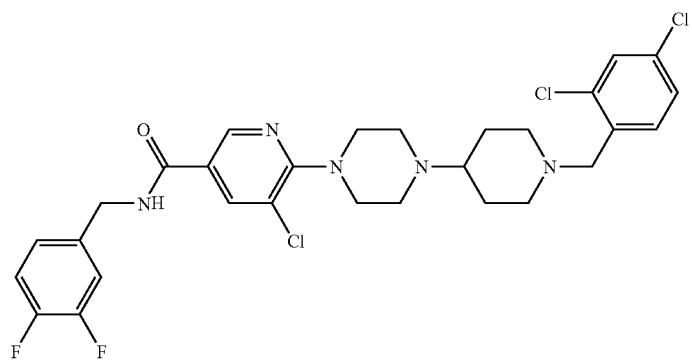 |
| 26 | 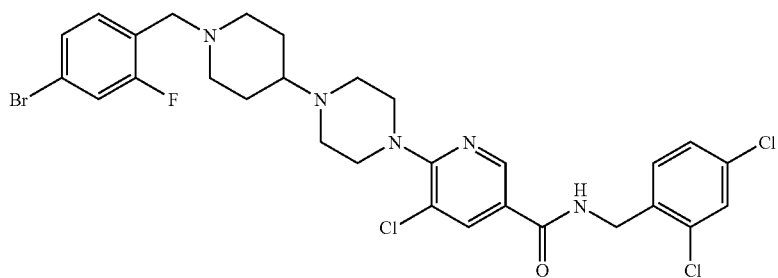 |

-continued
| Compound No. | Compound Structure |
|---|---|
| 27 | 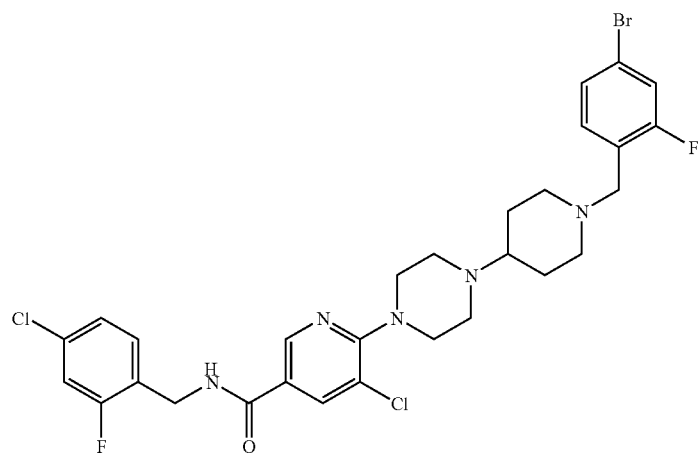 |
| 28 | 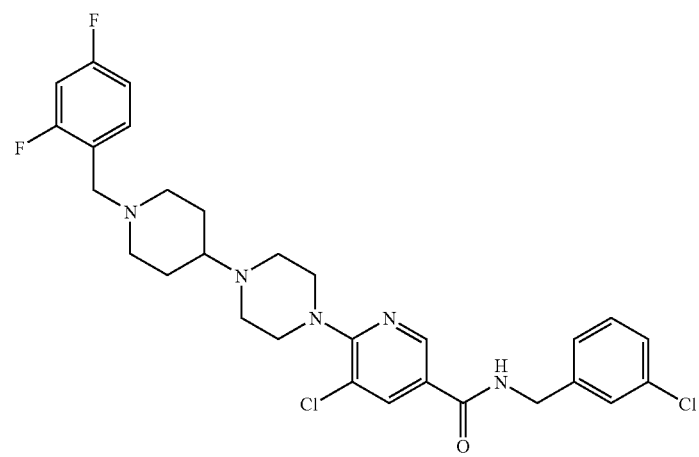 |
| 29 | 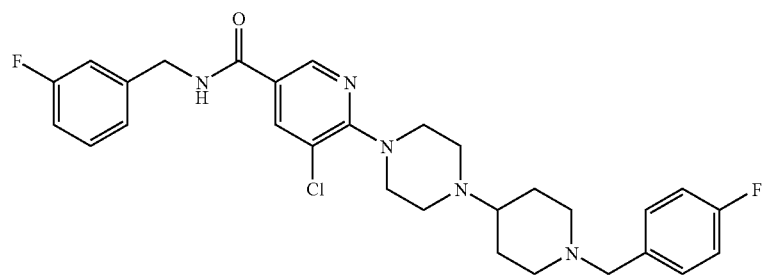 |
| 30 | 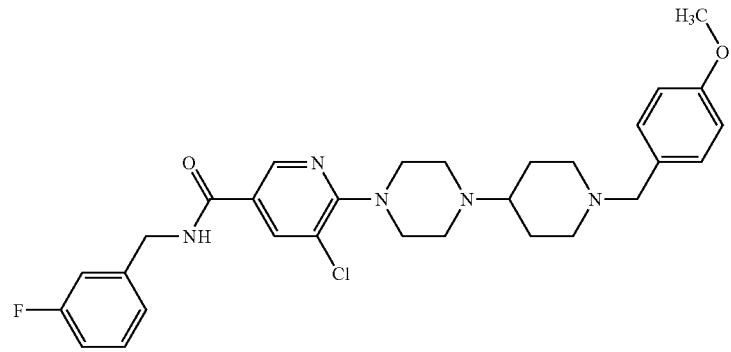 |

-continued

| Compound No. | Compound Structure |
|---|---|
| 31 | 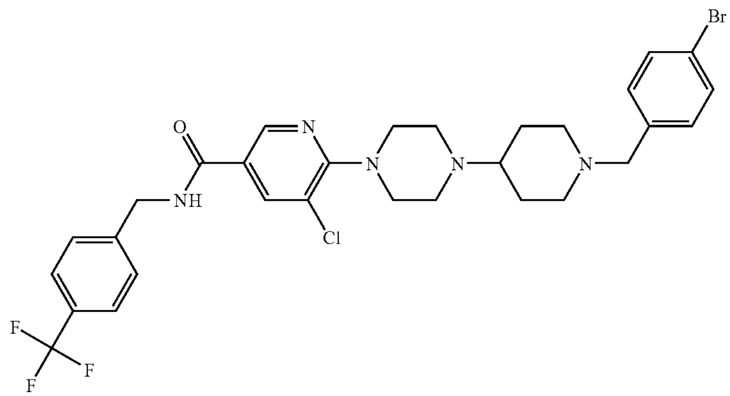 |
| 32 | 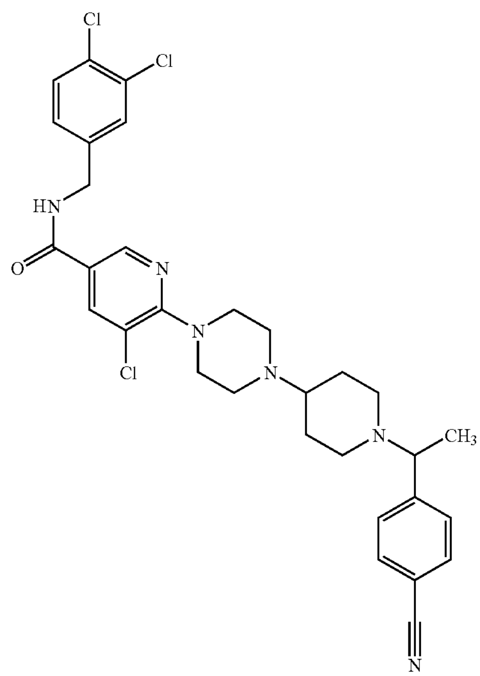 |
| 33 | 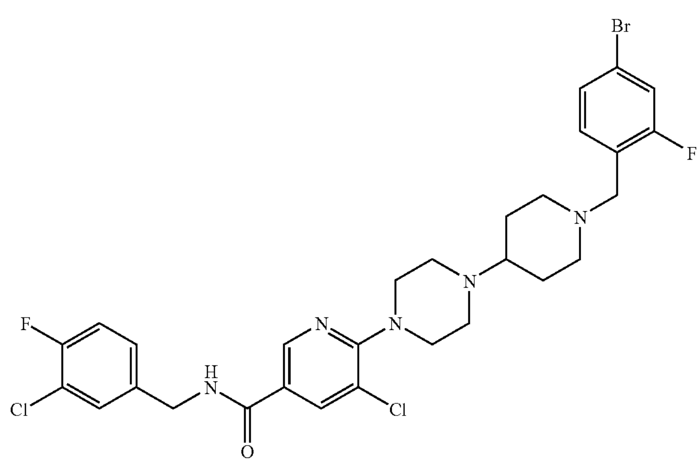 |

| Compound No. | Compound Structure |
|---|---|
| 34 | 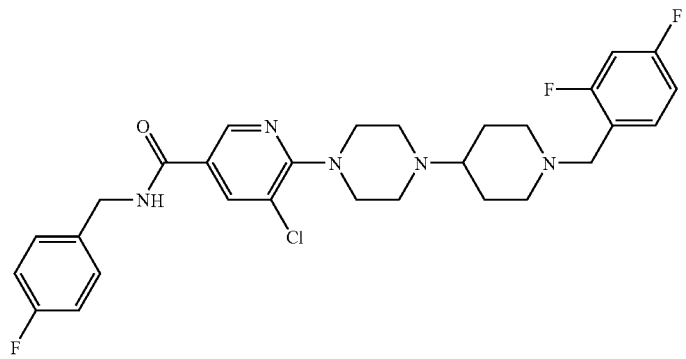 |
| 35 | 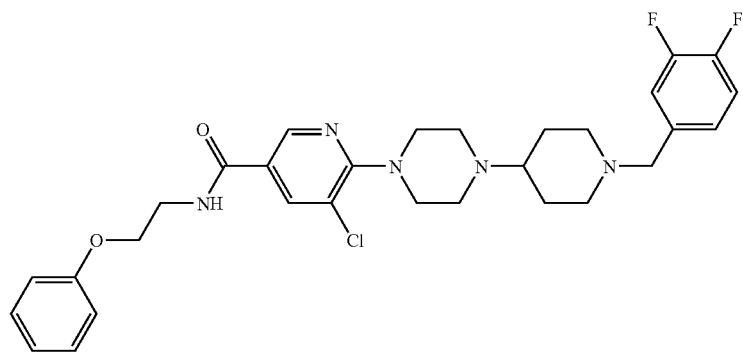 |
| 36 | 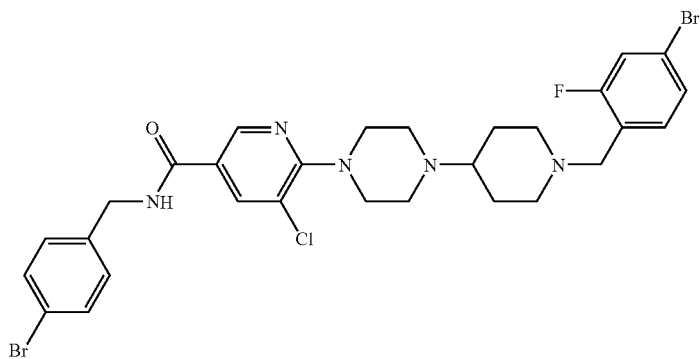 |
| 37 | 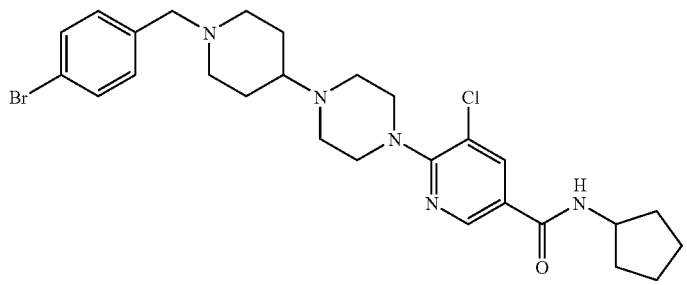 |

-continued
| Compound No. | Compound Structure |
|---|---|
| 38 | 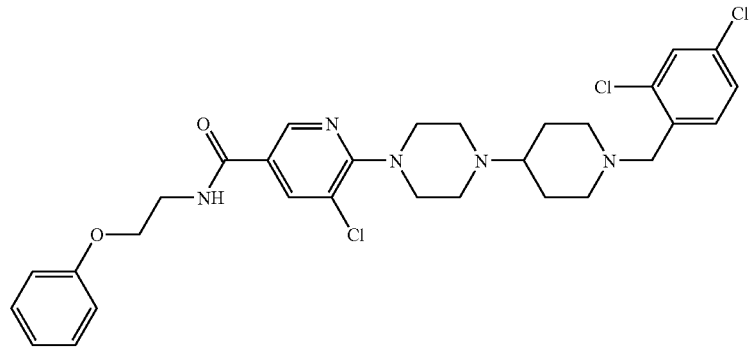 |
| 39 | 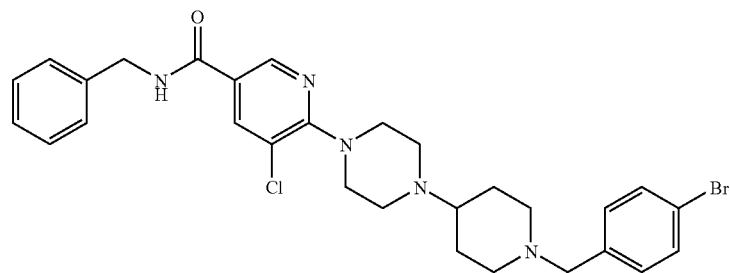 |
| 40 | 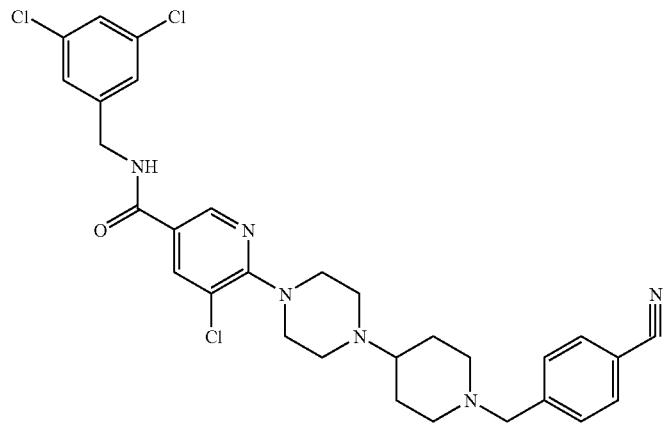 |
| 41 | 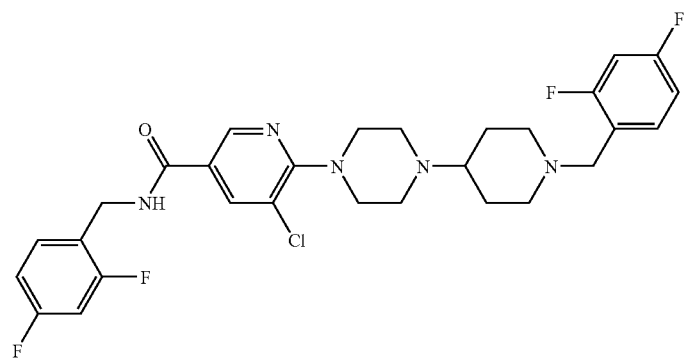 |

| Compound No. | Compound Structure |
|---|---|
| 42 | 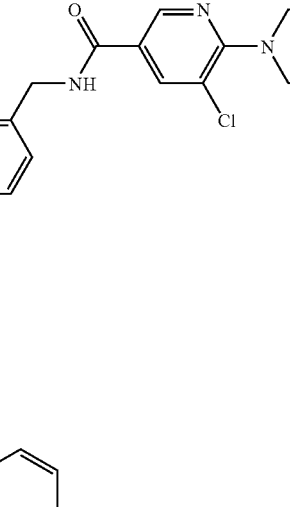 |
| 43 | 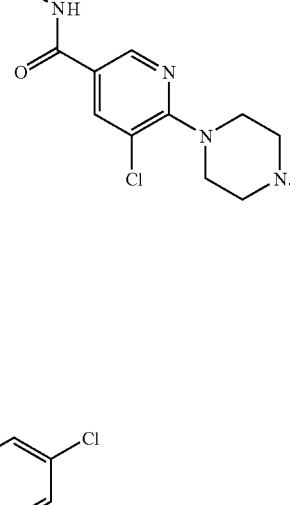 |
| 44 | 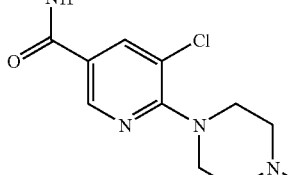 |

-continued
| Compound No. | Compound Structure |
|---|---|
| 45 | 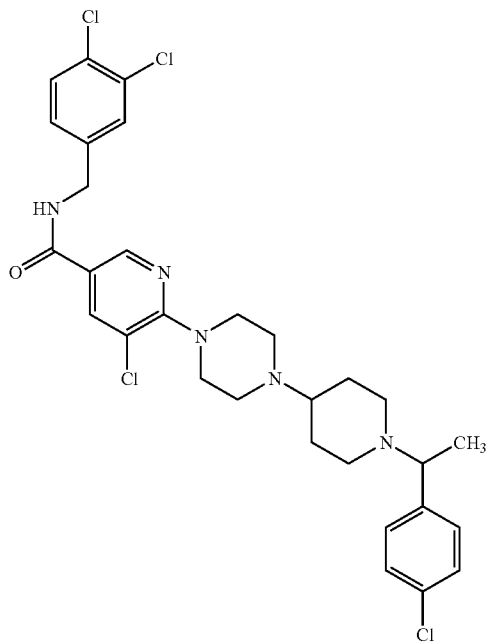 |
| 46 | 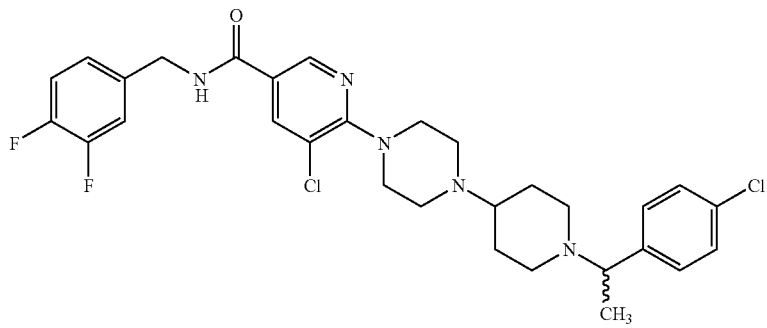 |
| 47 | 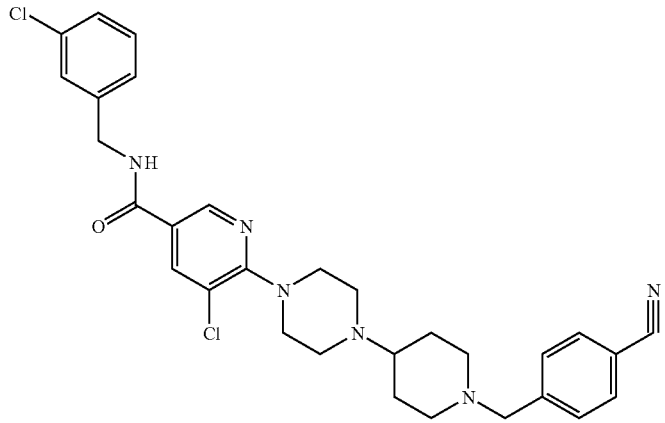 |

-continued
| Compound No. | Compound Structure |
|---|---|
| 48 | 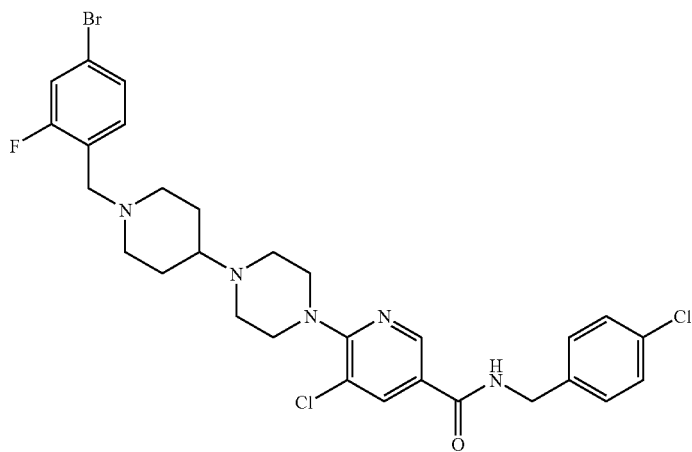 |
| 49 | 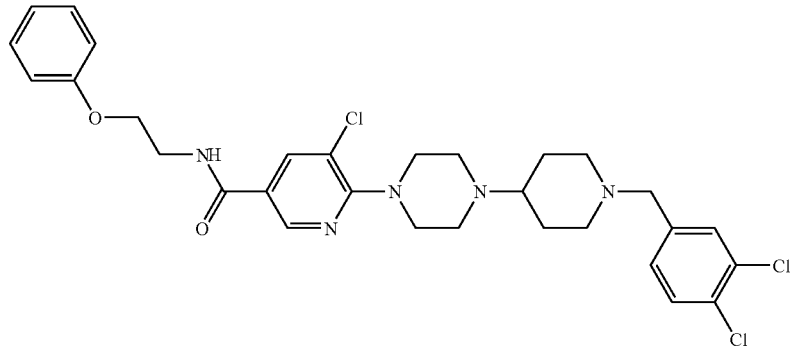 |
| 50 | 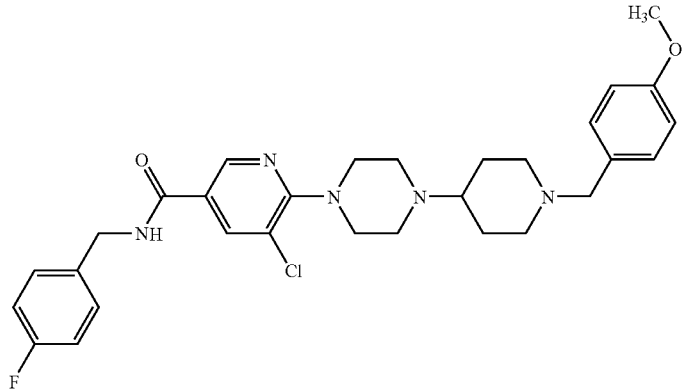 |

-continued
| Compound No. | Compound Structure |
|---|---|
| 51 | 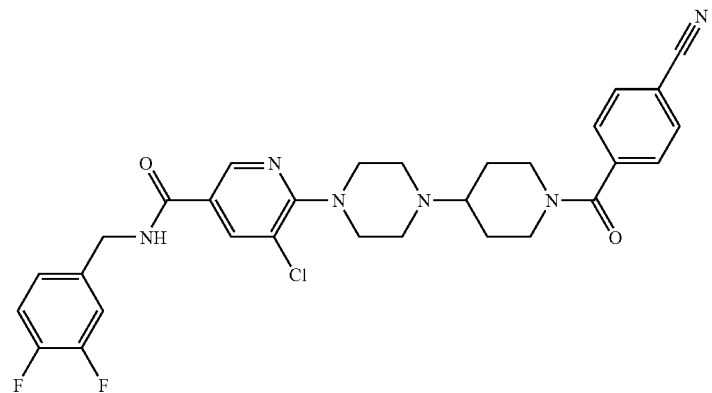 |
| 52 | 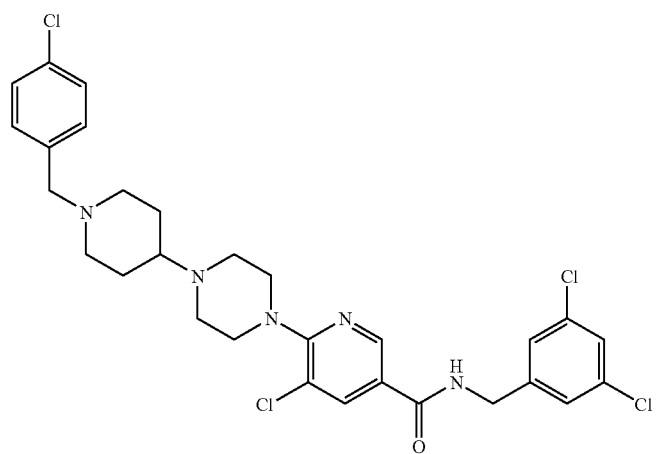 |
| 53 | 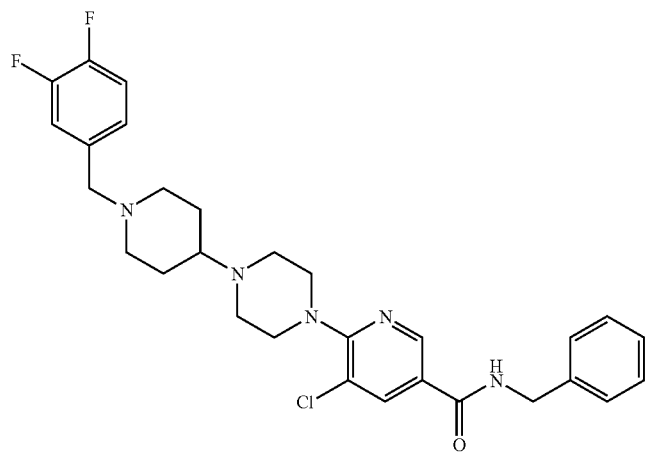 |

-continued
| Compound No. | Compound Structure |
|---|---|
| 54 | 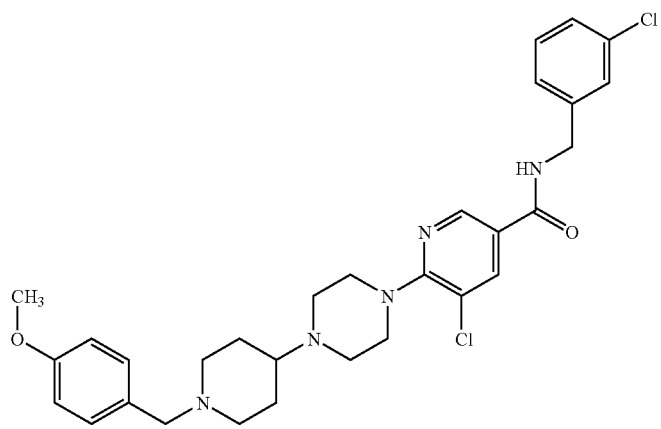 |
| 55 | 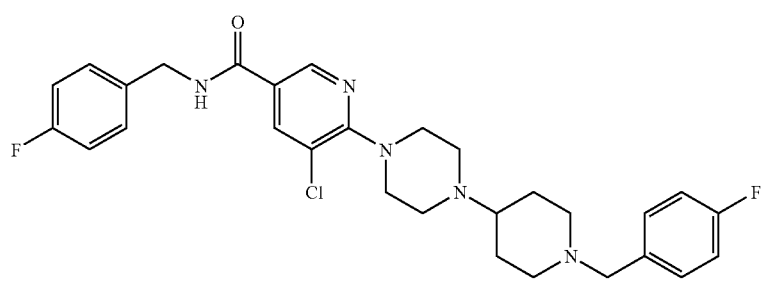 |
| 56 | 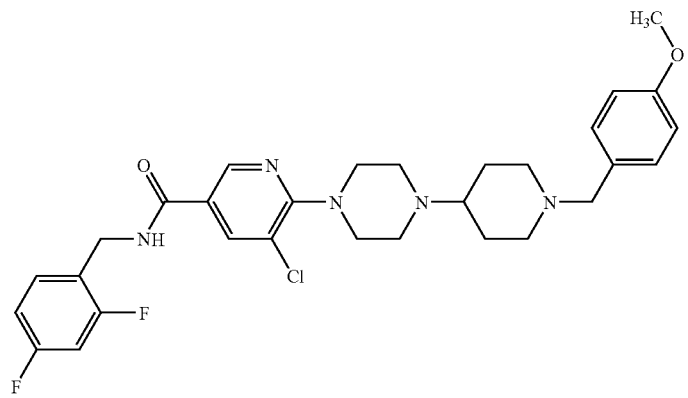 |
| 57 | 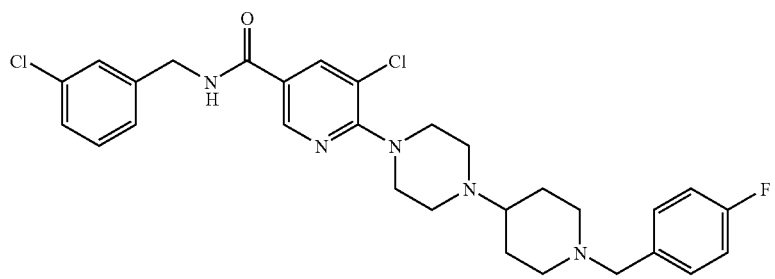 |

-continued

| Compound No. | Compound Structure |
|---|---|
| 58 | 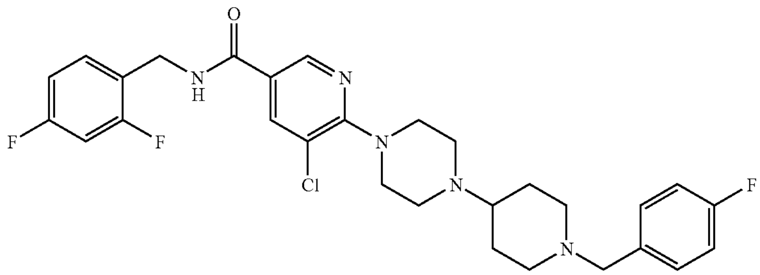 |
| 59 | 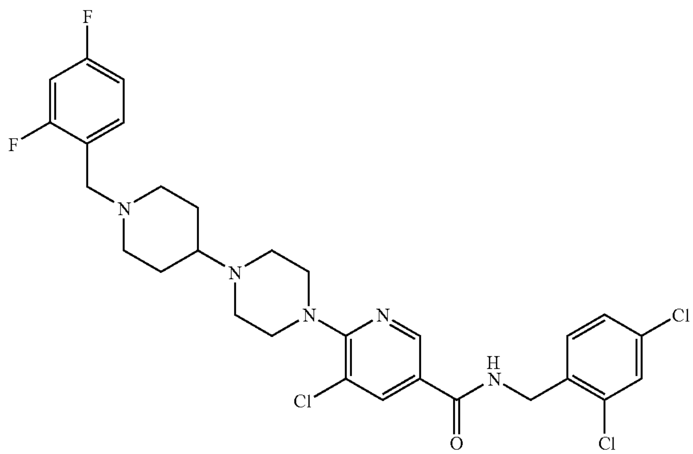 |
| 60 | 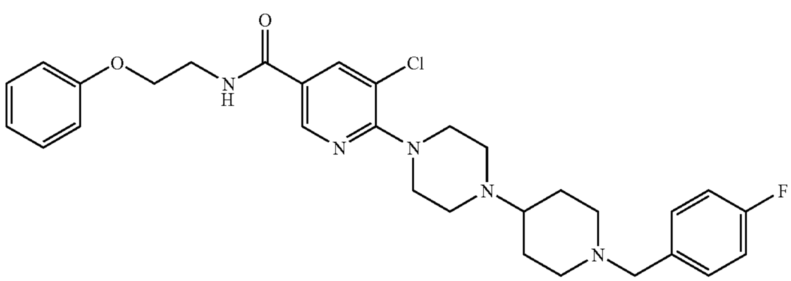 |
| 61 | 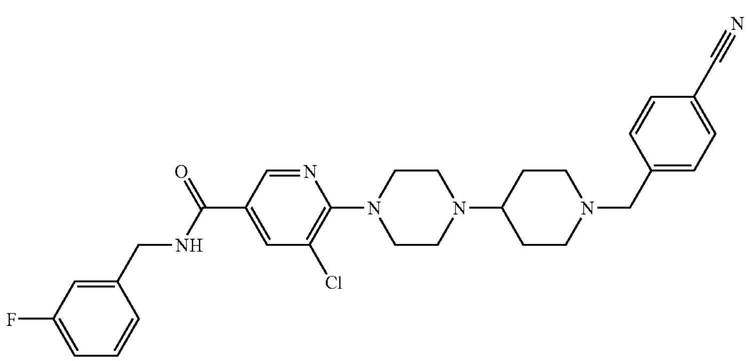 |

-continued

| Compound No. | Compound Structure |
|---|---|
| 62 | 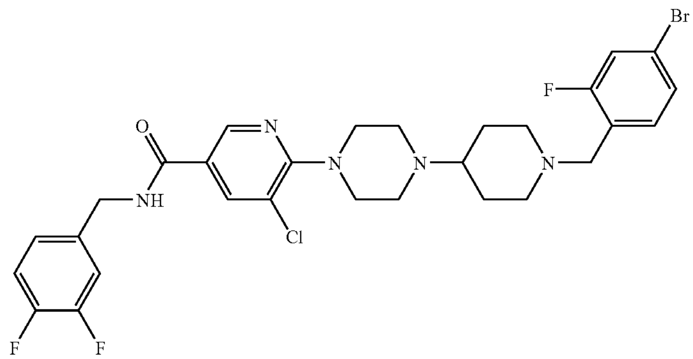 |
| 63 | 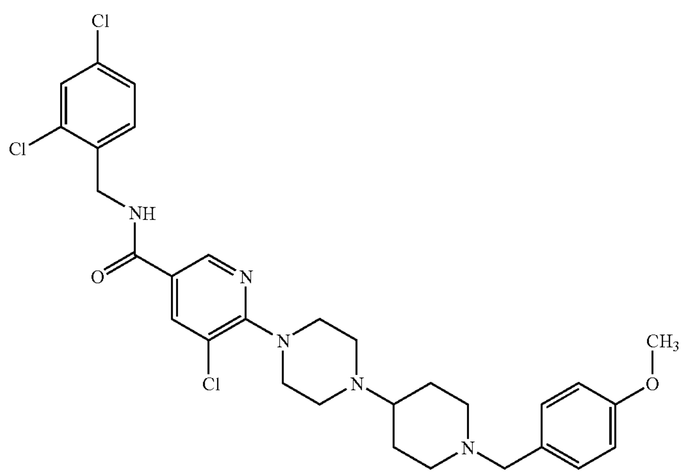 |
| 64 | 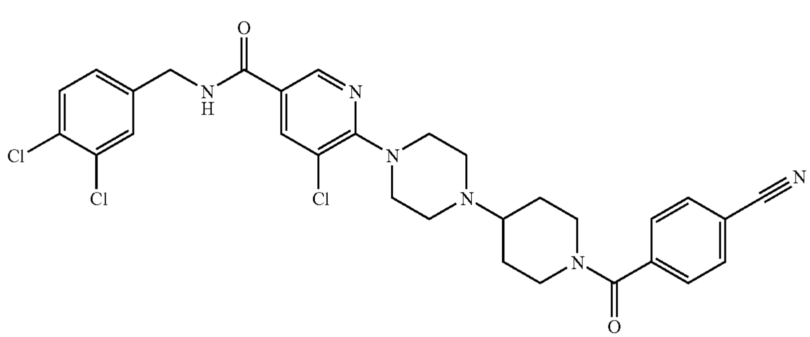 |

-continued
| Compound No. | Compound Structure |
|---|---|
| 65 | 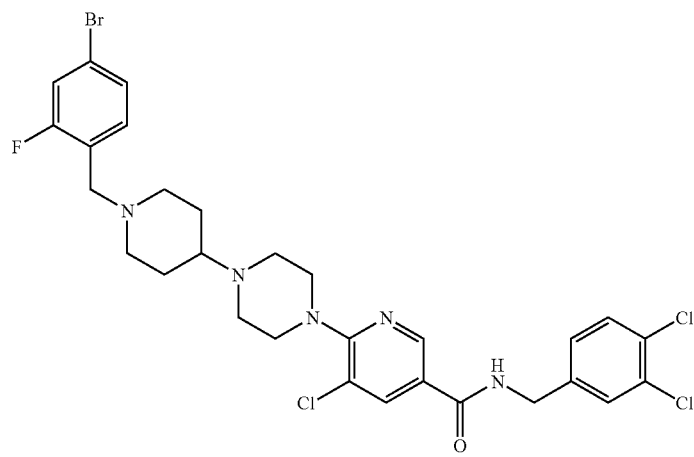 |
| 66 | 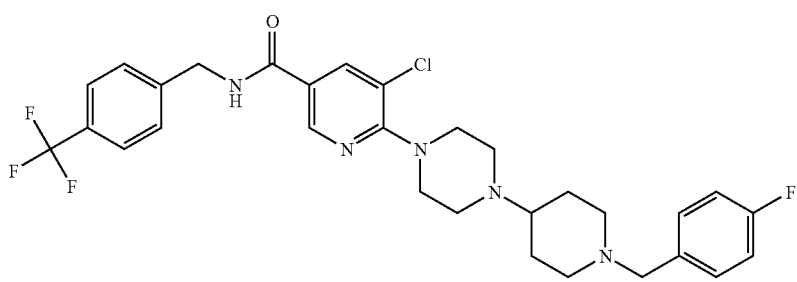 |
| 67 | 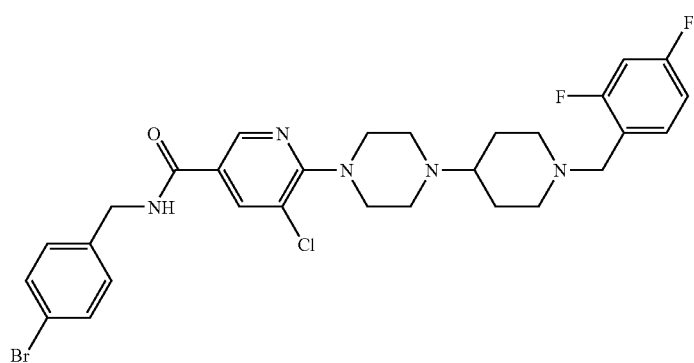 |
| 68 | 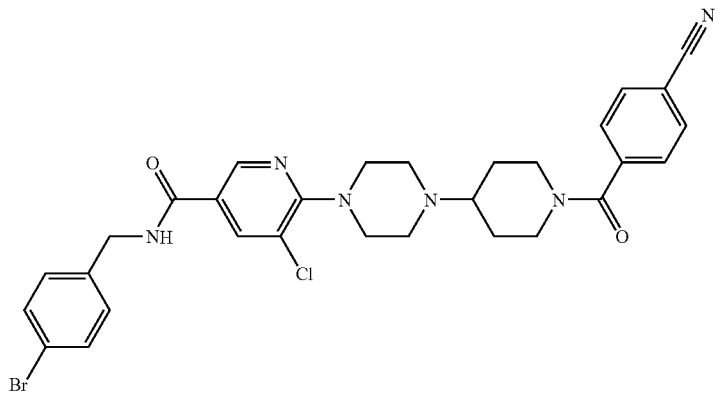 |

-continued
| Compound No. | Compound Structure |
|---|---|
| 69 | 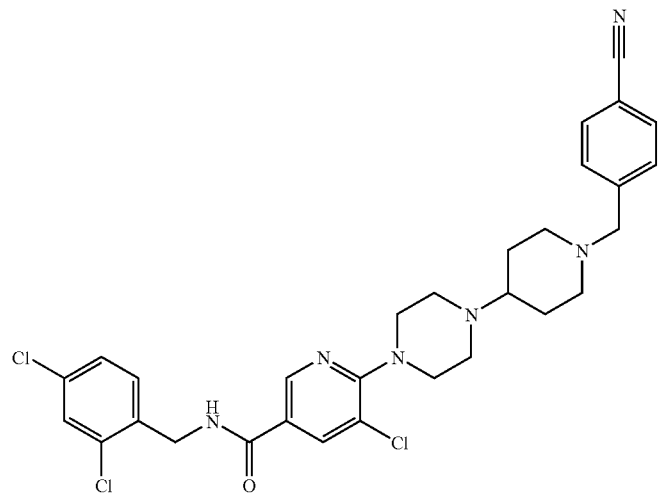 |
| 70 | 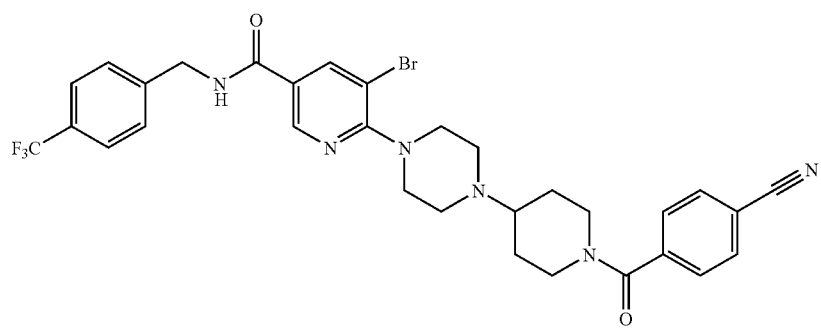 |
| 71 | 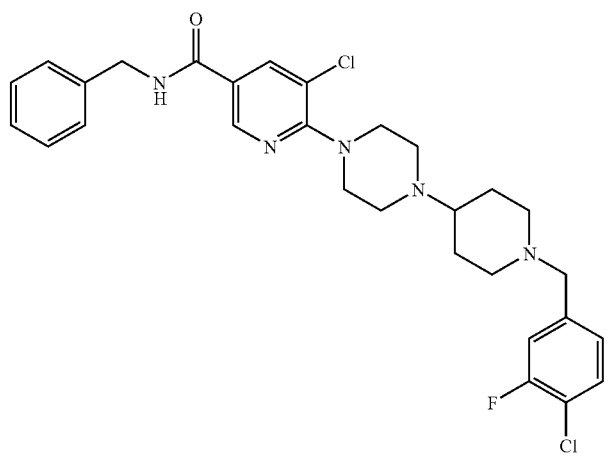 |
| 72 | 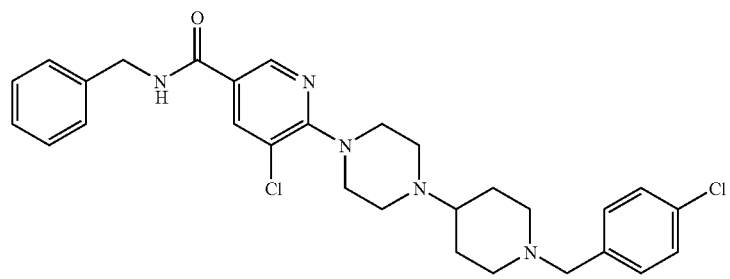 |

-continued

| Compound No. | Compound Structure |
|---|---|
| 73 | 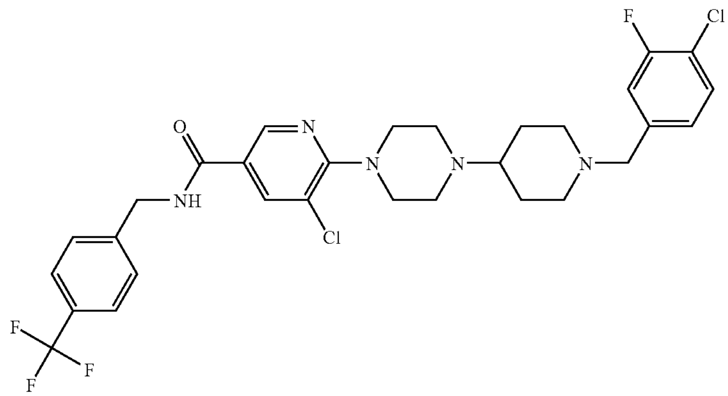 |
| 74 | 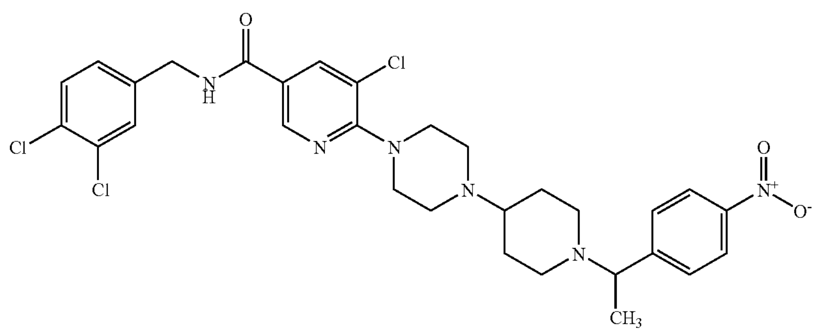 |
| 75 | 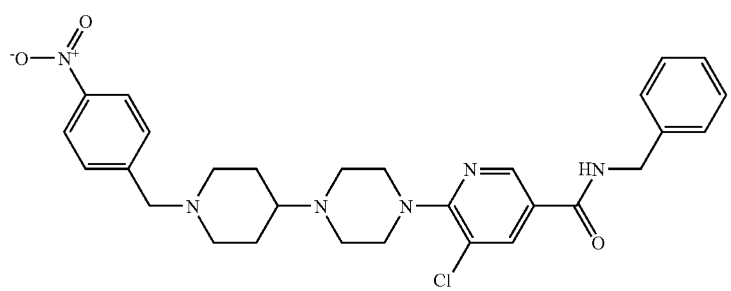 |
| 76 | 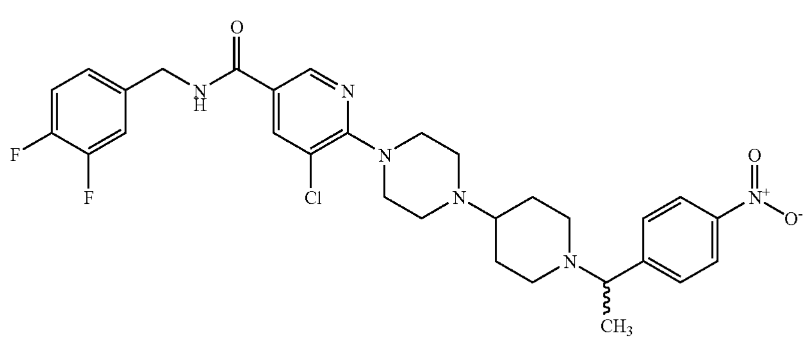 |

-continued
| Compound No. | Compound Structure |
|---|---|
| 77 | 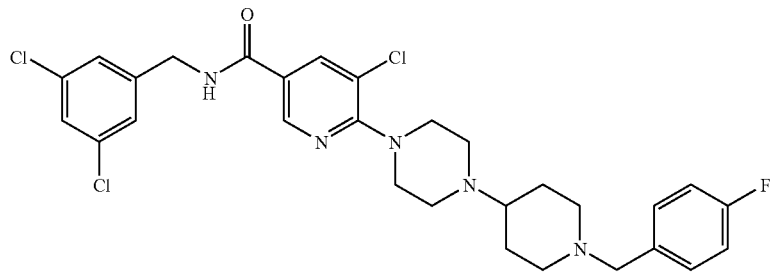 |
| 78 | 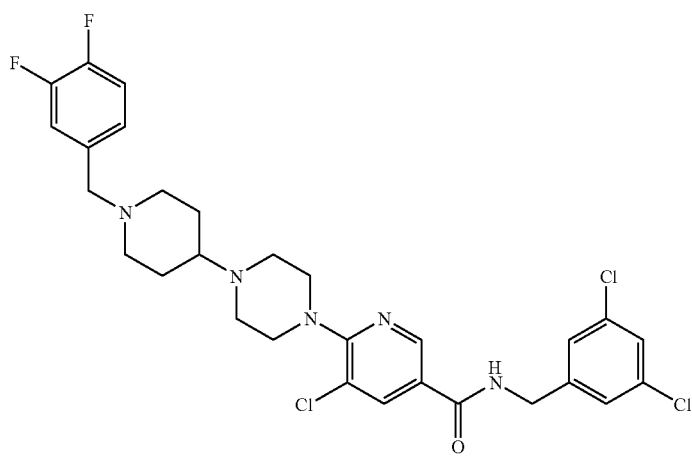 |
| 79 | 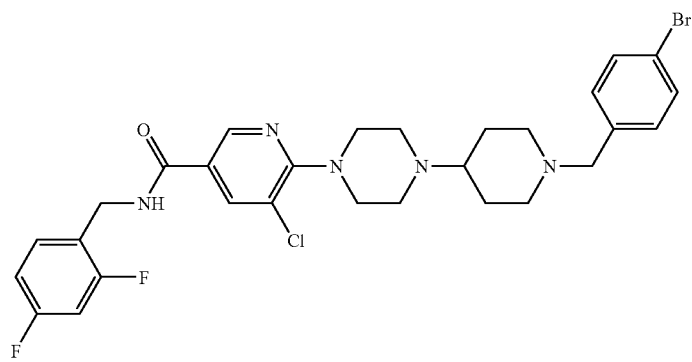 |
| 80 | 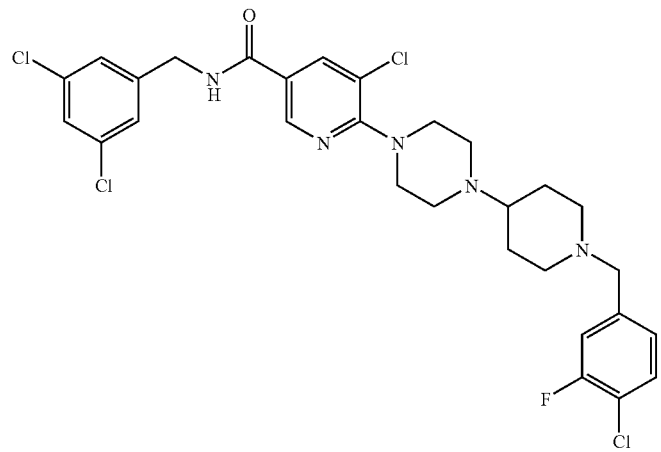 |

-continued
| Compound No. | Compound Structure |
|---|---|
| 81 | 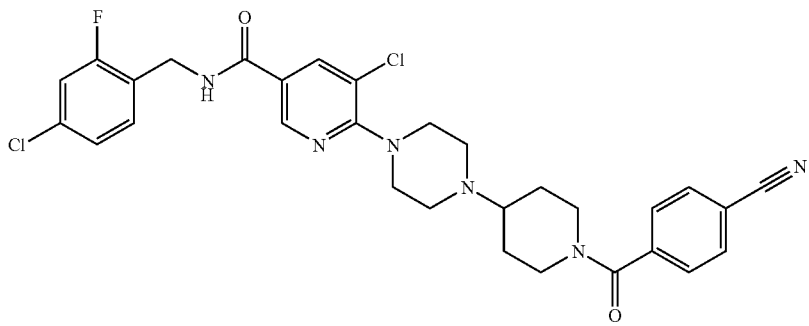 |
| 82 | 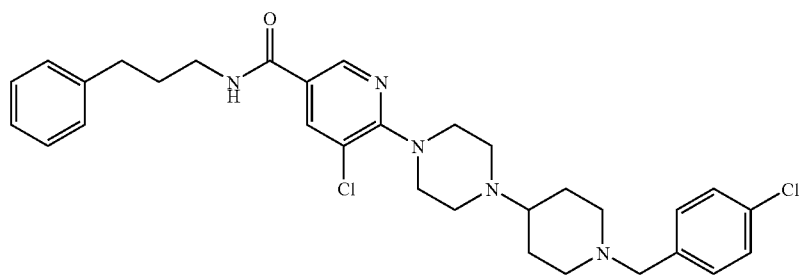 |
| 83 | 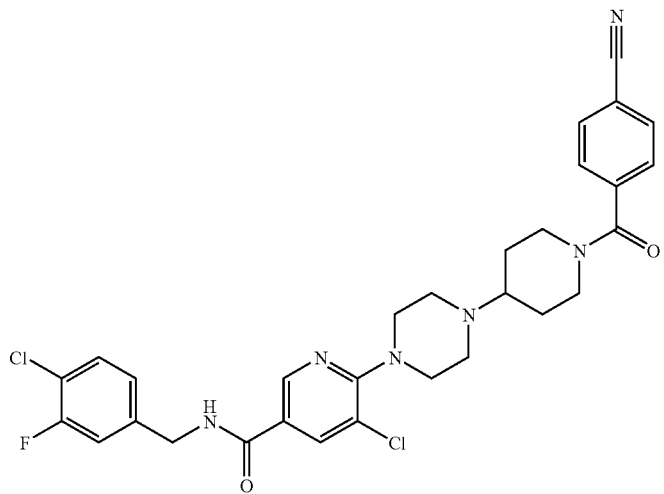 |
| 84 | 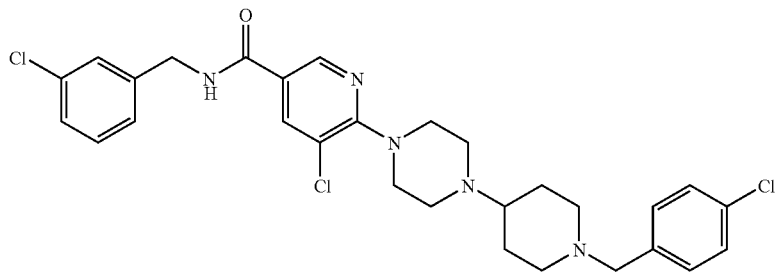 |

| Compound No. | Compound Structure |
|---|---|
| 85 | 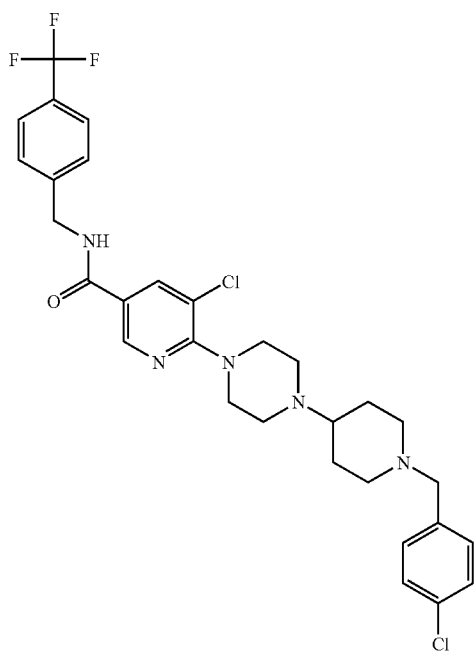 |
| 86 | 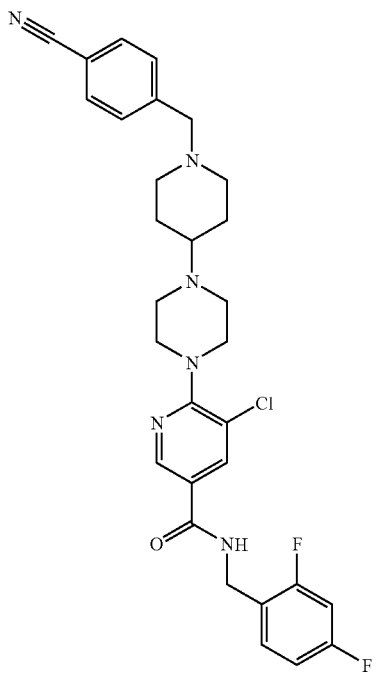 |

-continued

| Compound No. | Compound Structure |
|---|---|
| 87 | 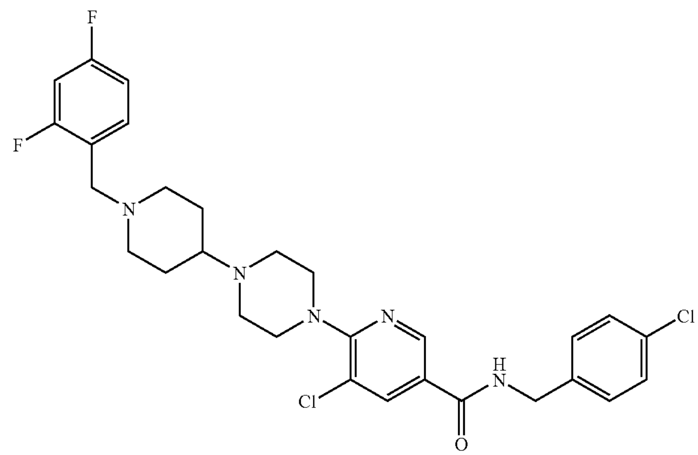 |
| 88 | 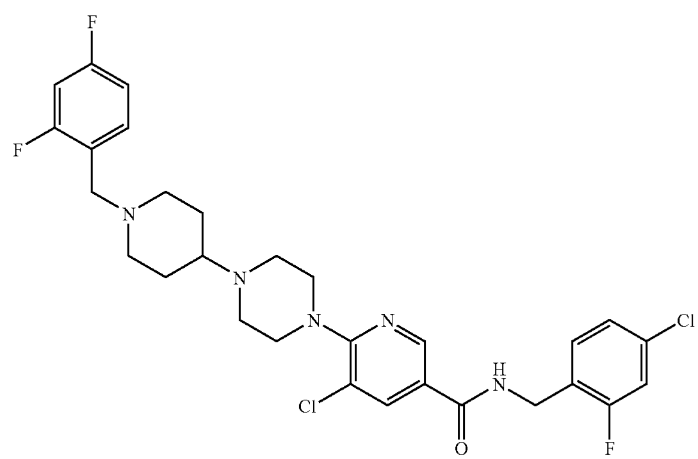 |
| 89 | 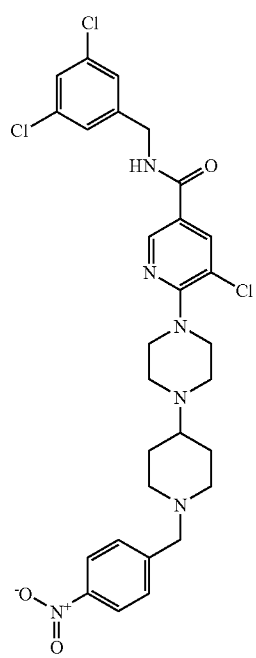 |

-continued
| Compound No. | Compound Structure |
|---|---|
| 90 | 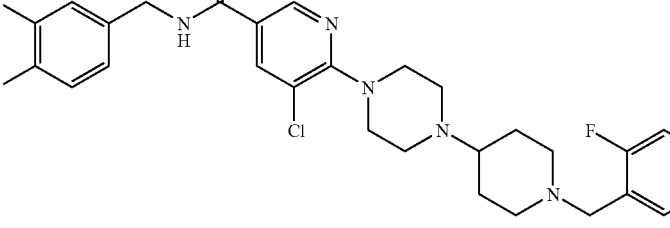 |
| 91 | 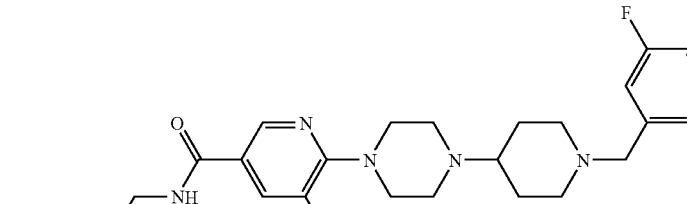 |
| 92 | 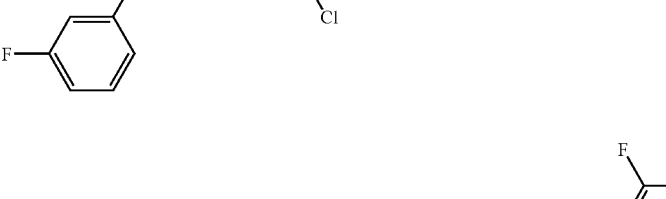 |
| 93 | 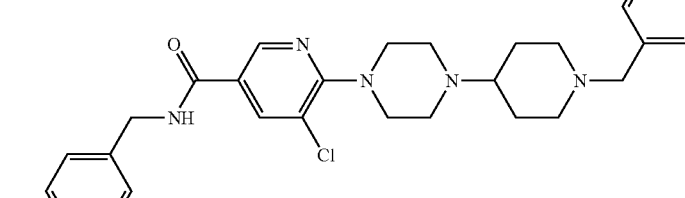 |

-continued
| Compound No. | Compound Structure |
|---|---|
| 94 | 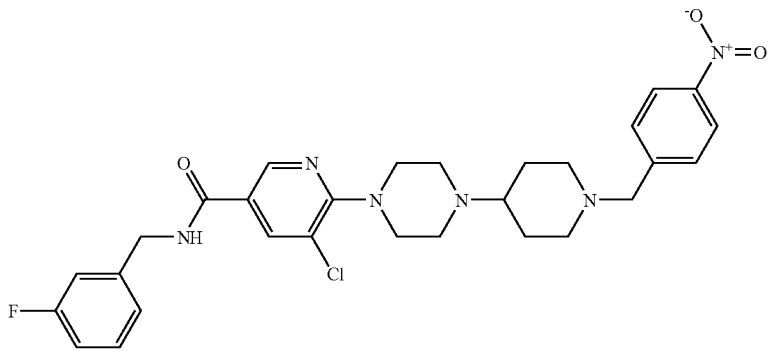 |
| 95 | 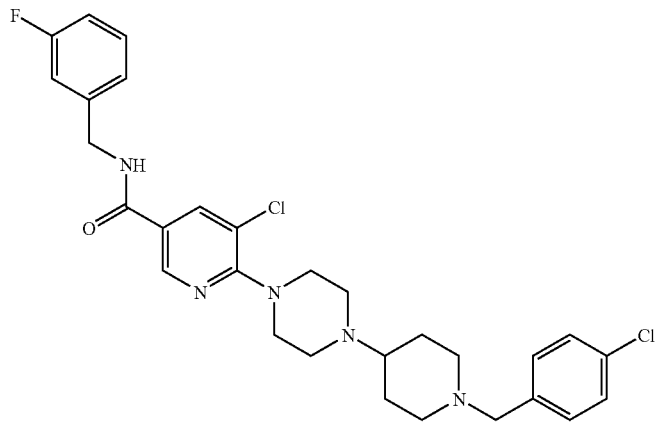 |
| 96 | 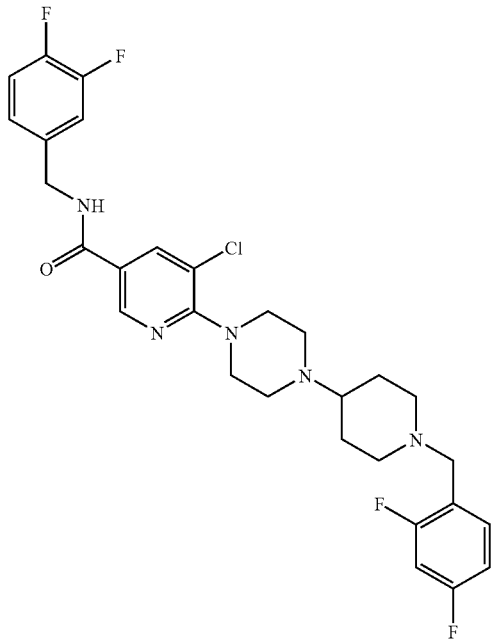 |

-continued
| Compound No. | Compound Structure |
|---|---|
| 97 | 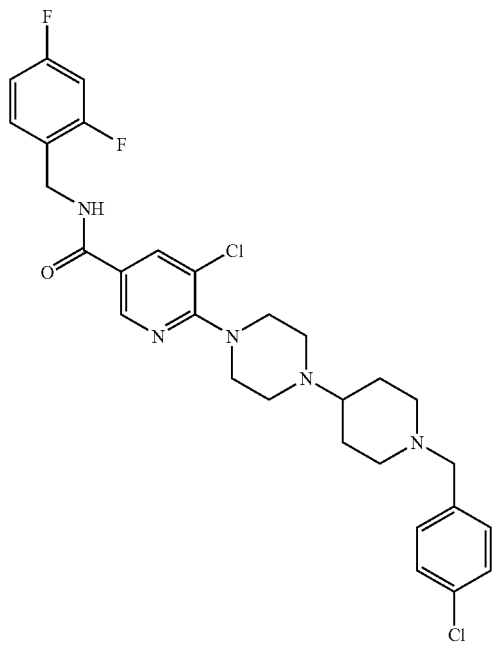 |
| 98 | 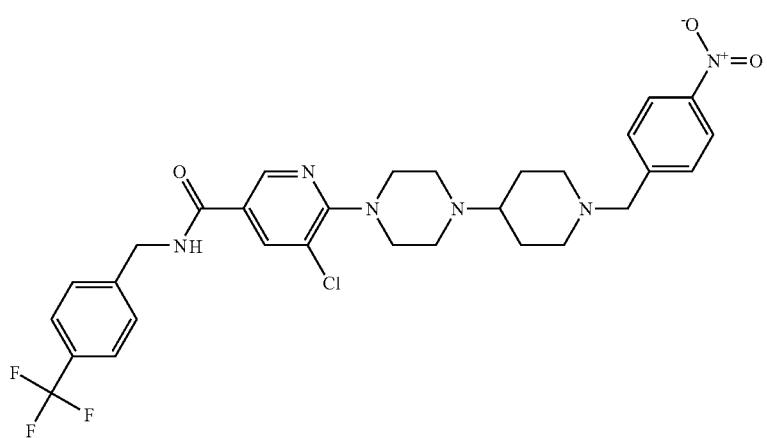 |
| 99 | 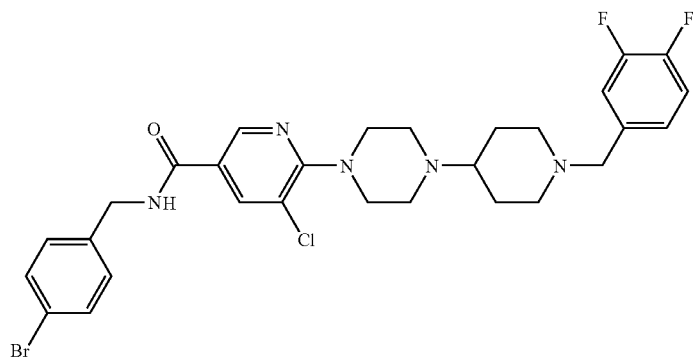 |

-continued
| Compound No. | Compound Structure |
|---|---|
| 100 | 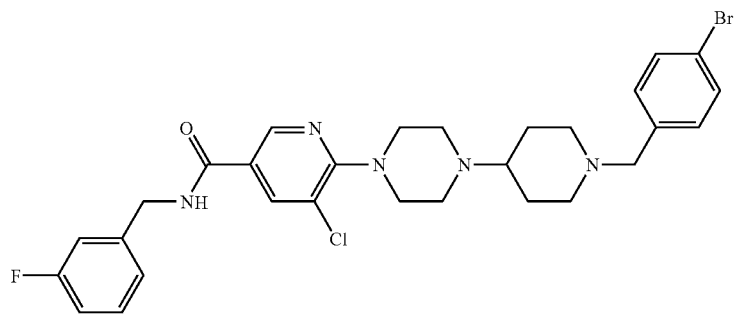 |
| 101 | 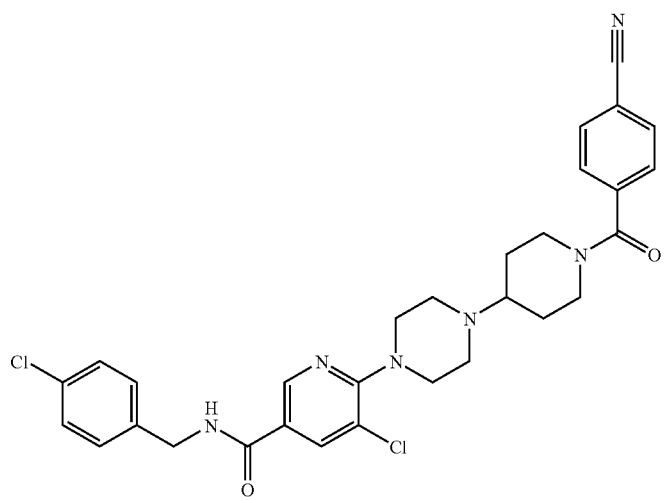 |
| 102 | 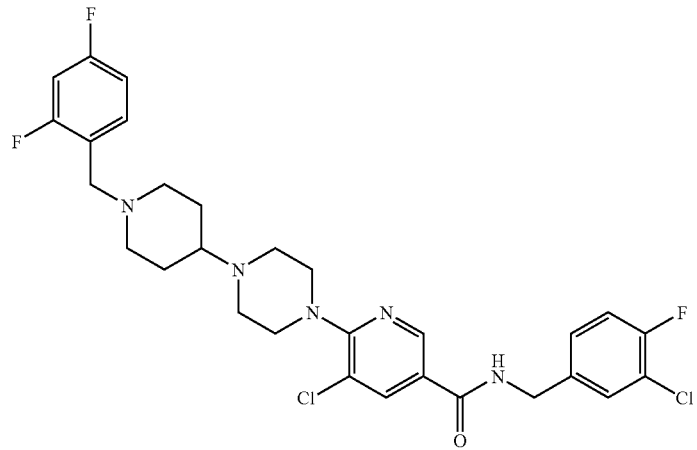 |

-continued
| Compound No. | Compound Structure |
|---|---|
| 103 | 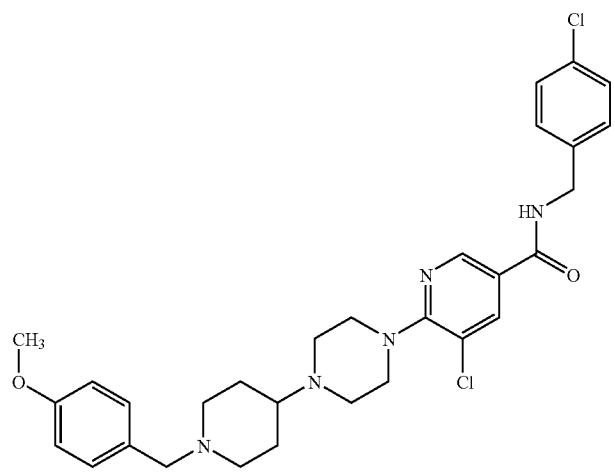 |
| 104 | 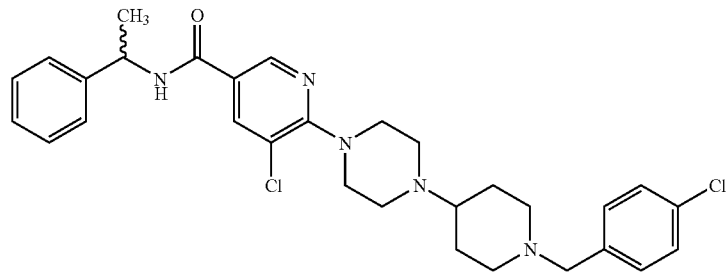 |
| 105 | 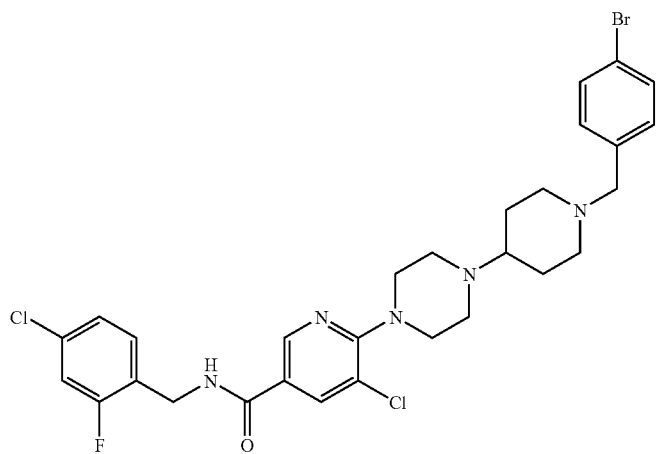 |

-continued
| Compound No. | Compound Structure |
| --- | --- |
| 106 | 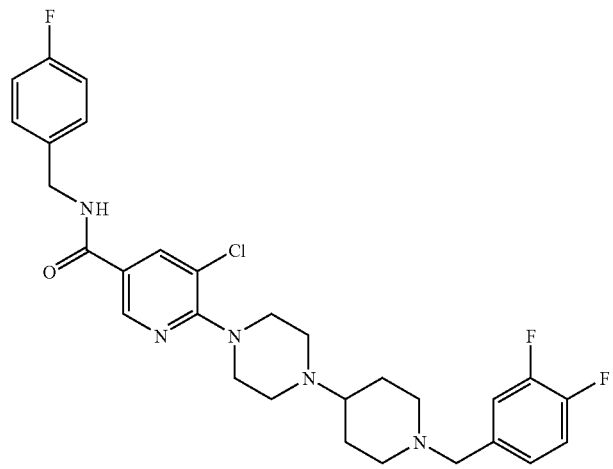 |
| 107 | 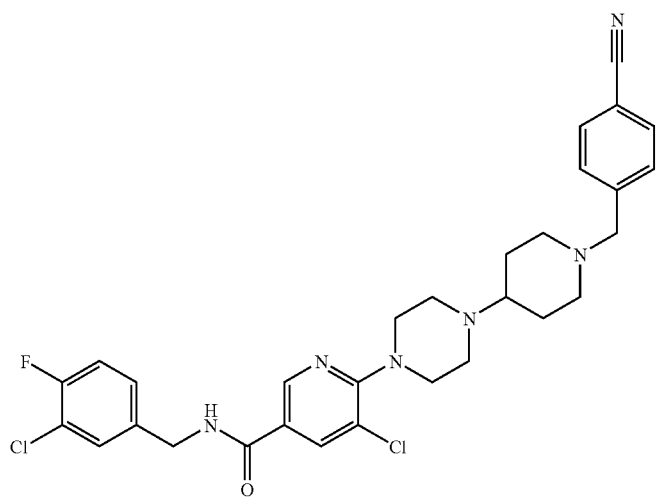 |
| 108 | 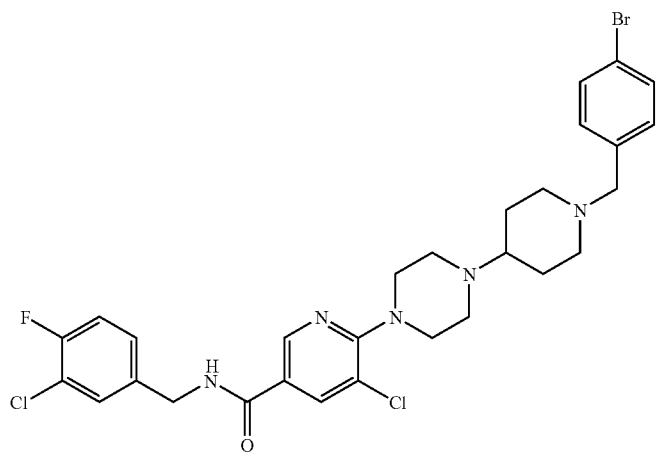 |

-continued
| Compound No. | Compound Structure |
|---|---|
| 109 | 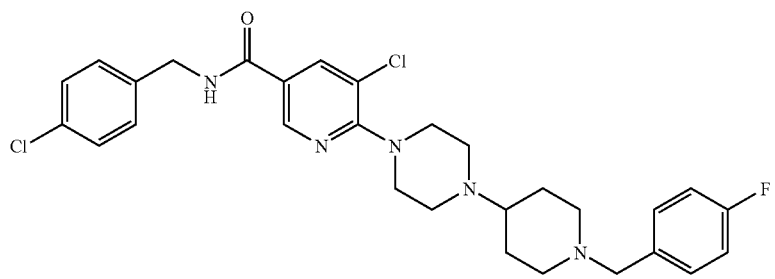 |
| 110 | 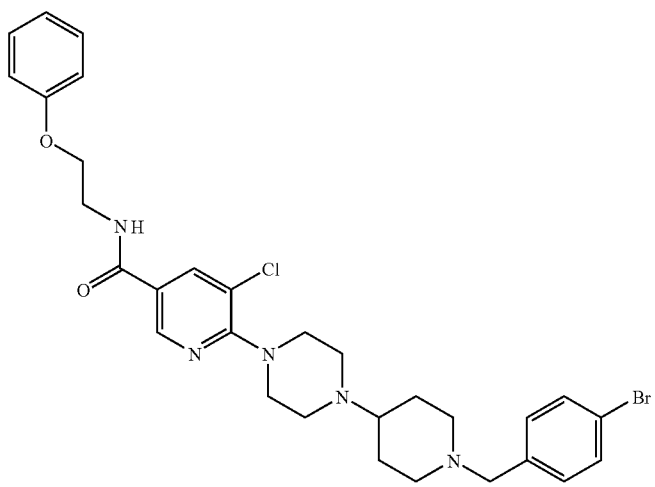 |
| 111 | 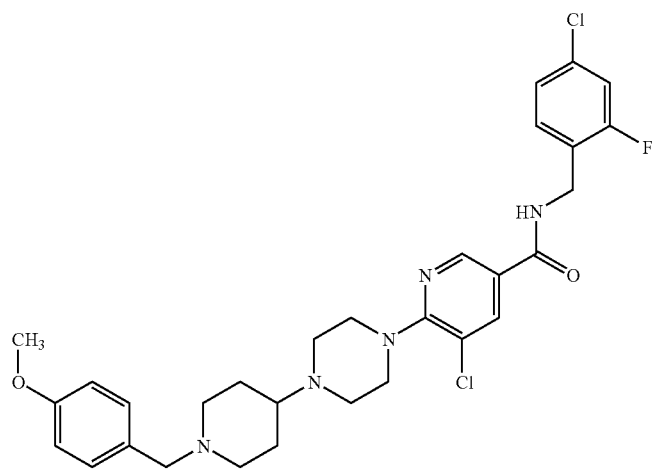 |

-continued

| Compound No. | Compound Structure |
|---|---|
| 112 | 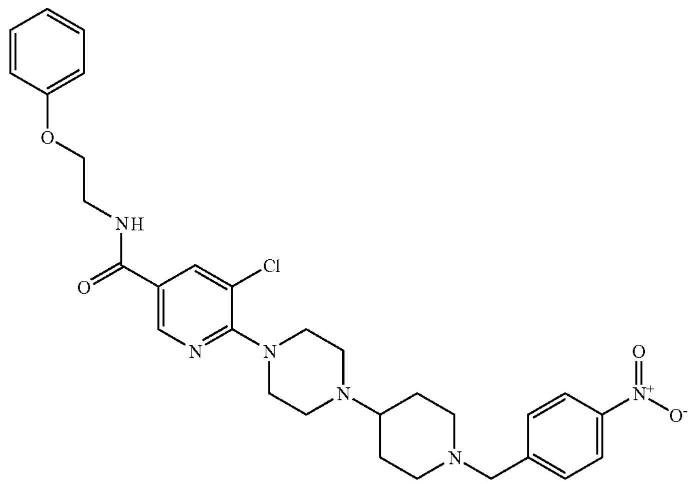 |
| 113 | 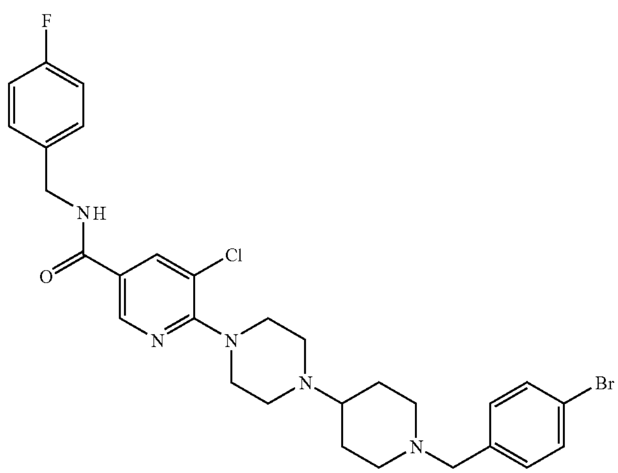 |
| 114 | 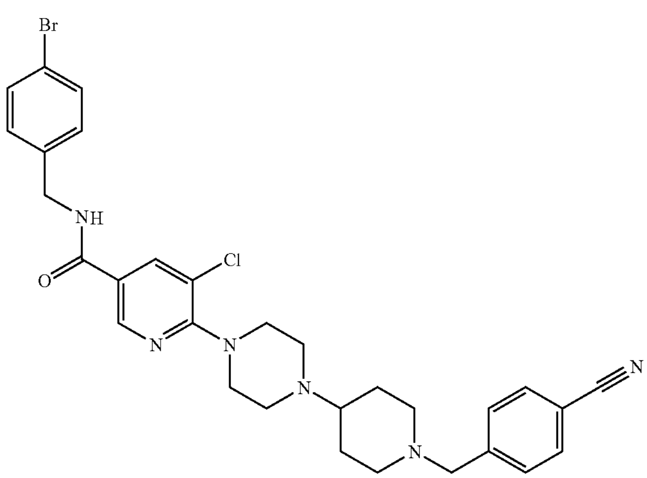 |

| Compound No. | Compound Structure |
|---|---|
| 115 | 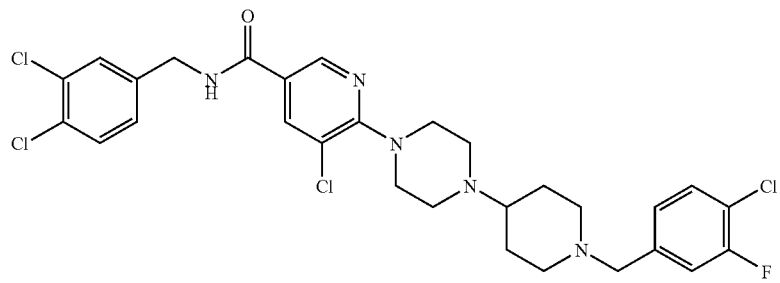 |
| 116 | 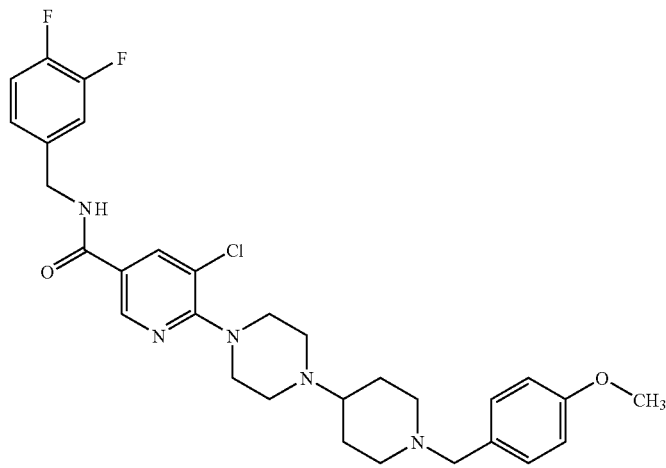 |
| 117 | 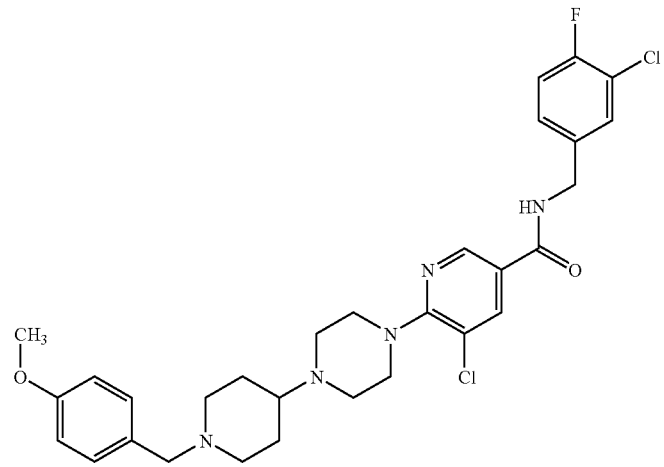 |

| Compound No. | Compound Structure |
|---|---|
| 118 | 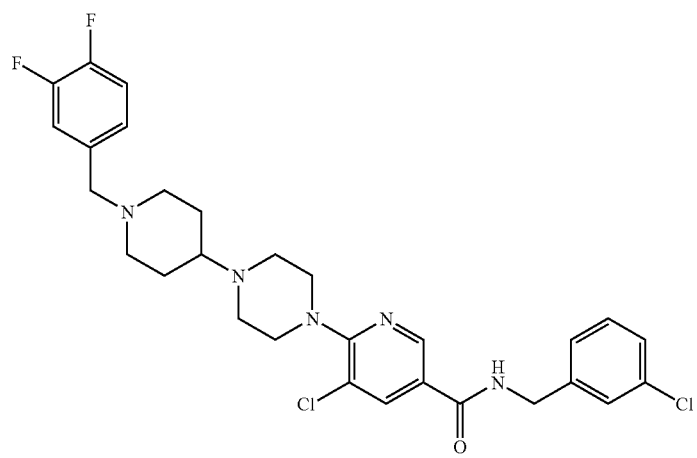 |
| 119 | 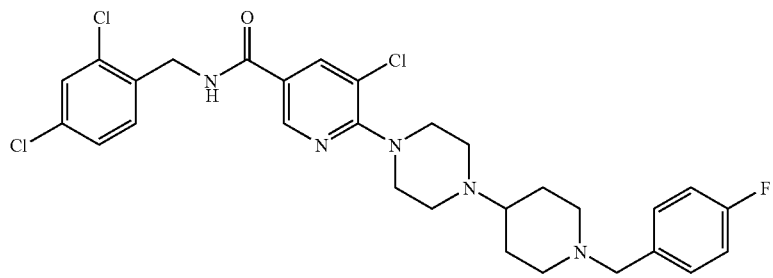 |
| 120 | 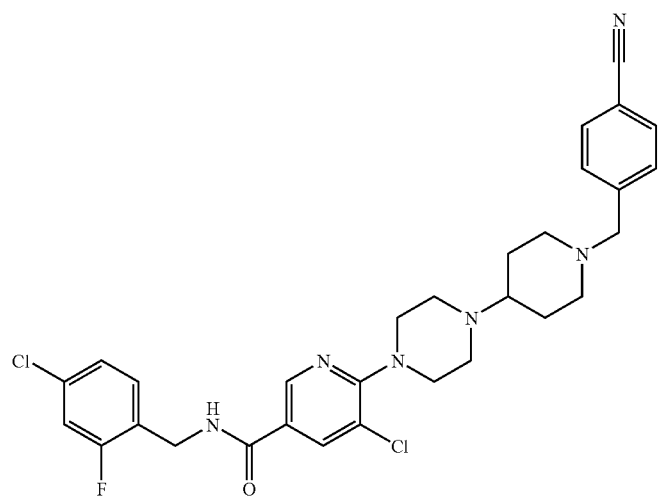 |

-continued
| Compound No. | Compound Structure |
|---|---|
| 121 | 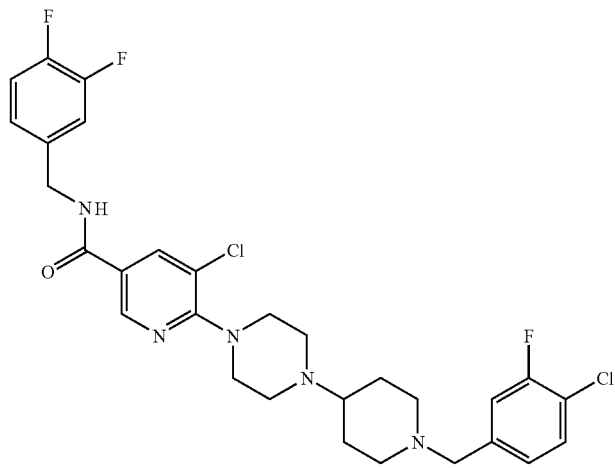 |
| 122 | 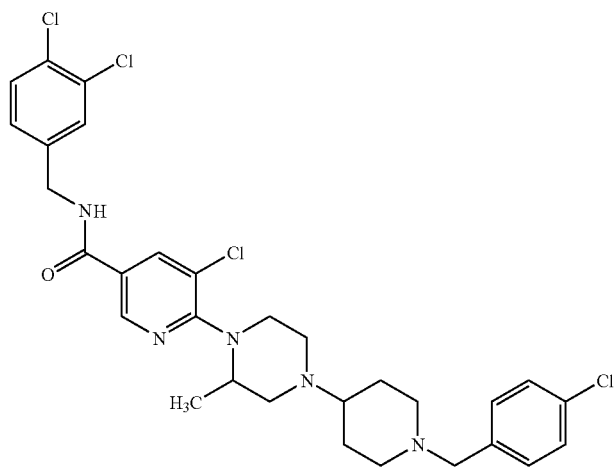 |
| 123 | 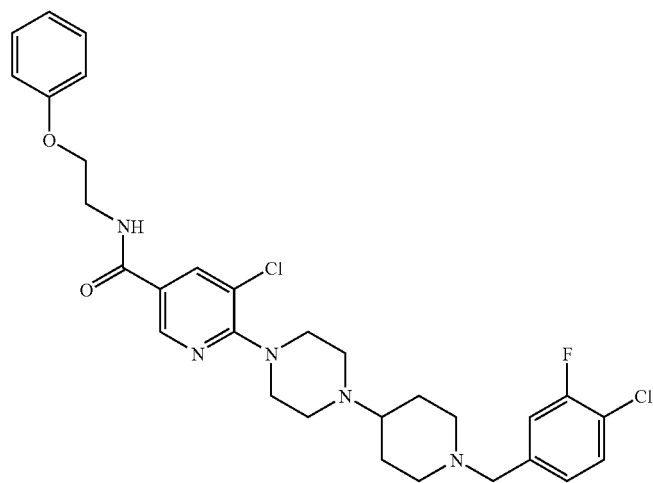 |

-continued
| Compound No. | Compound Structure |
|---|---|
| 124 | 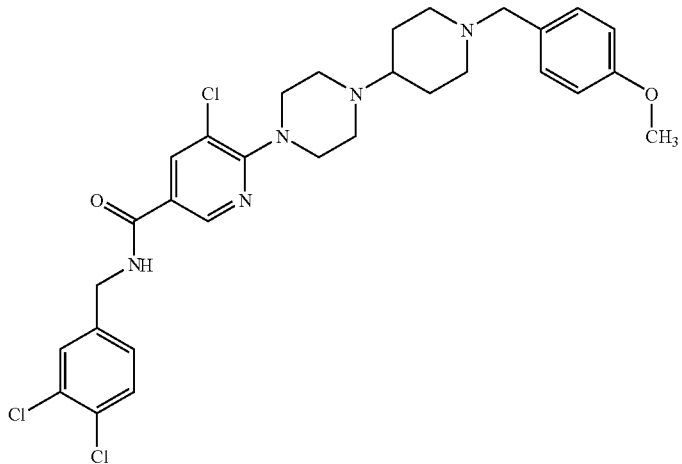 |
| 125 | 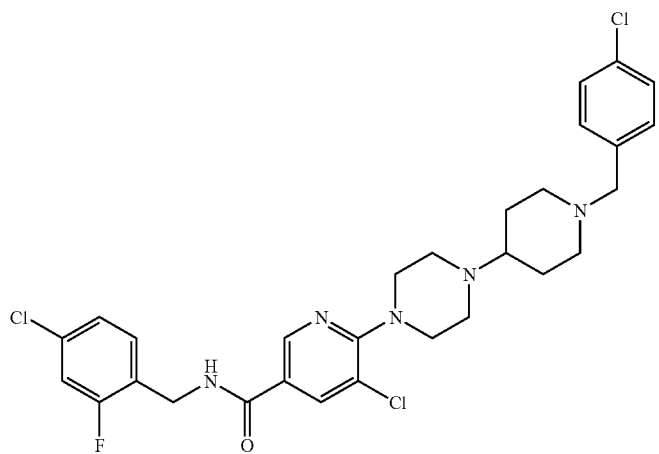 |
| 126 | 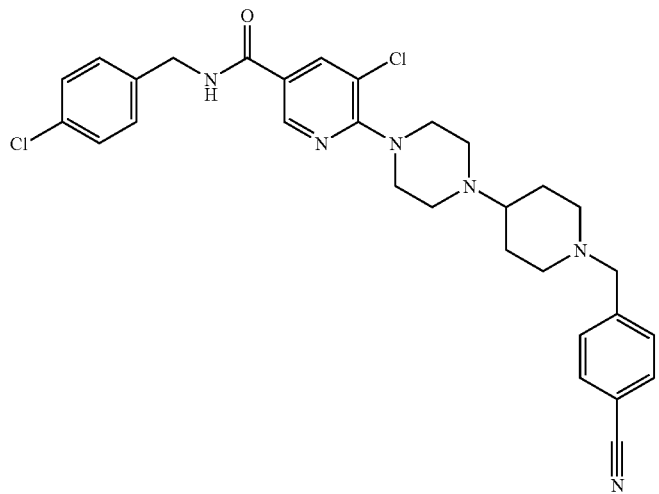 |

| Compound No. | Compound Structure |
|---|---|
| 127 | 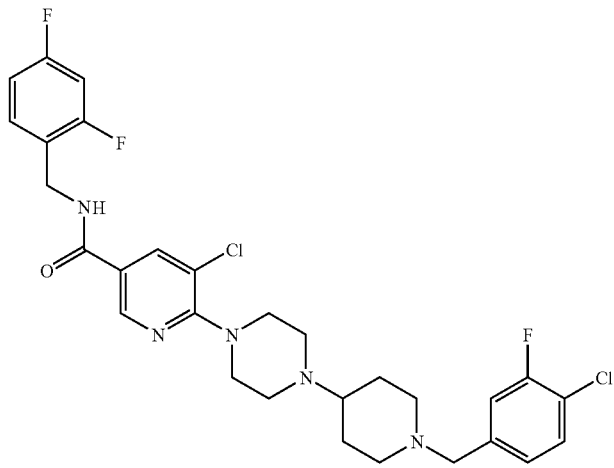 |
| 128 | 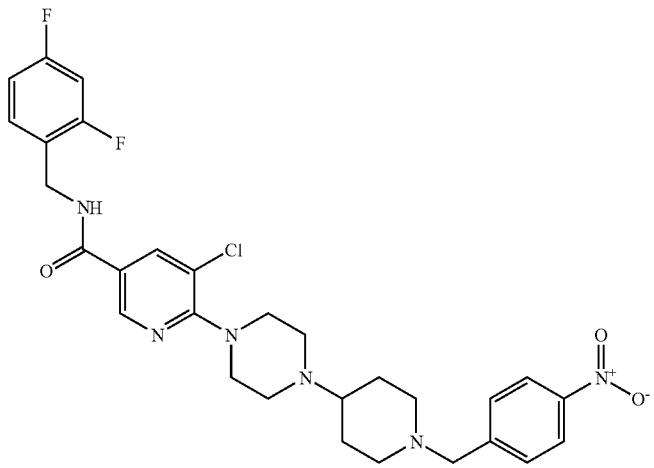 |
| 129 | 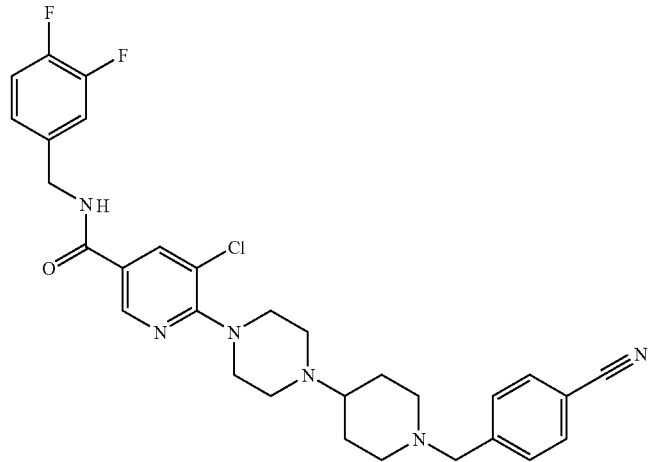 |

-continued
| Compound No. | Compound Structure |
|---|---|
| 130 | 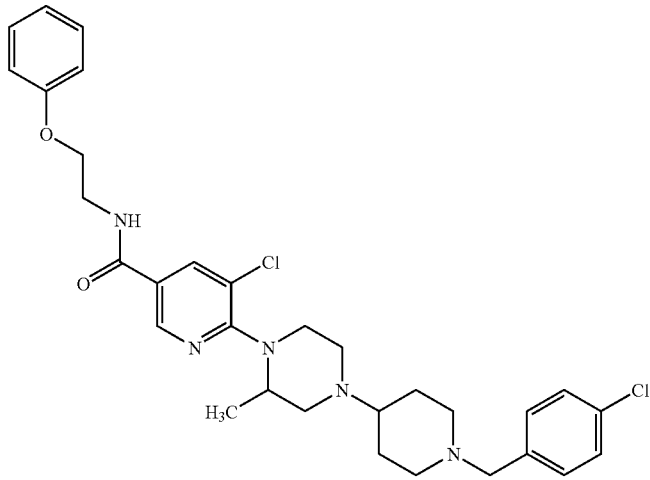 |
| 131 | 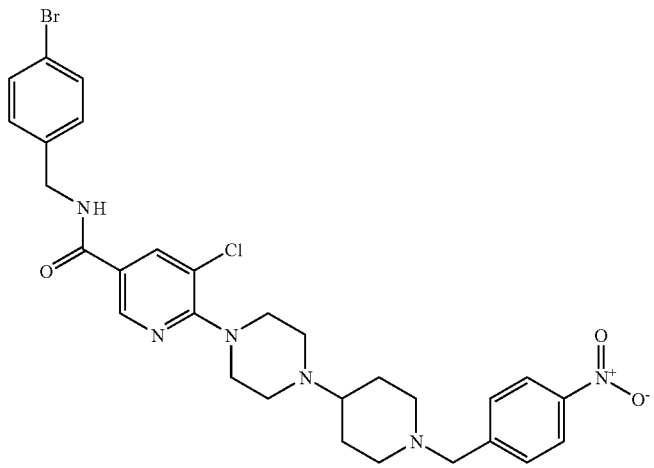 |
| 132 | 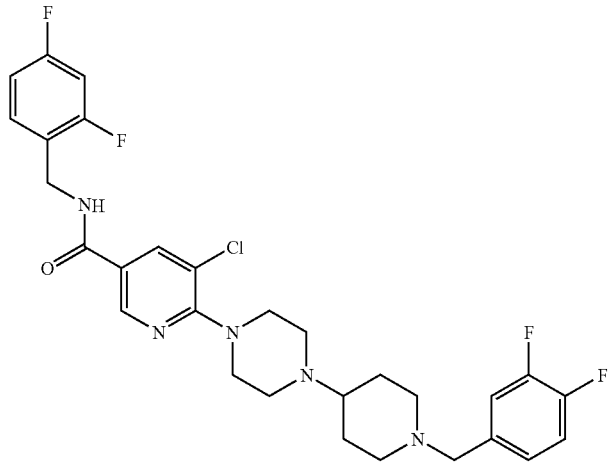 |

| Compound No. | Compound Structure |
|---|---|
| 133 | 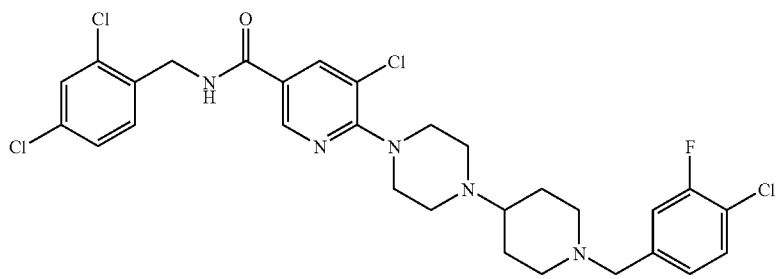 |
| 134 | 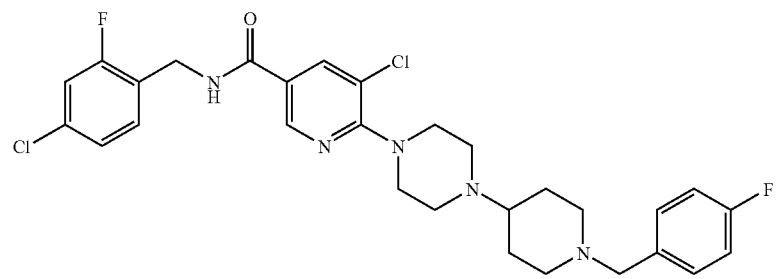 |
| 135 | 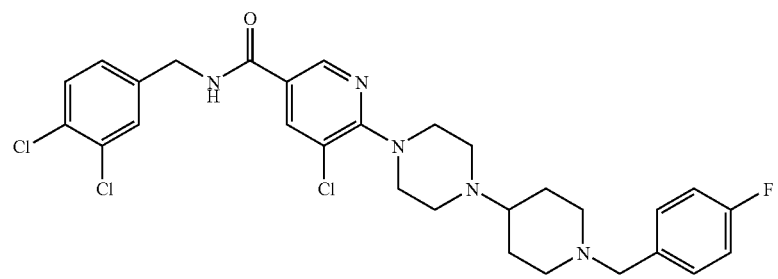 |
| 136 | 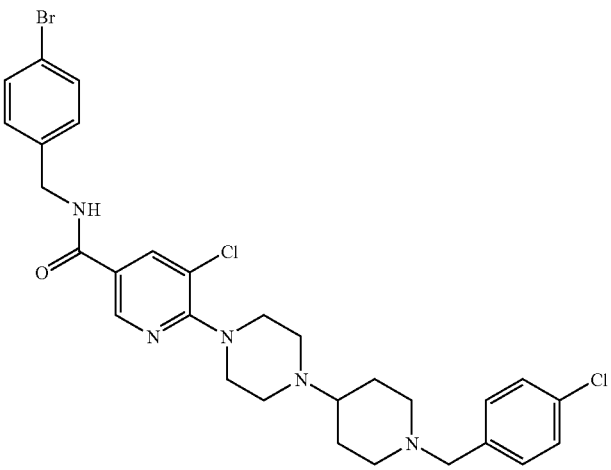 |

-continued
| Compound No. | Compound Structure |
|---|---|
| 137 | 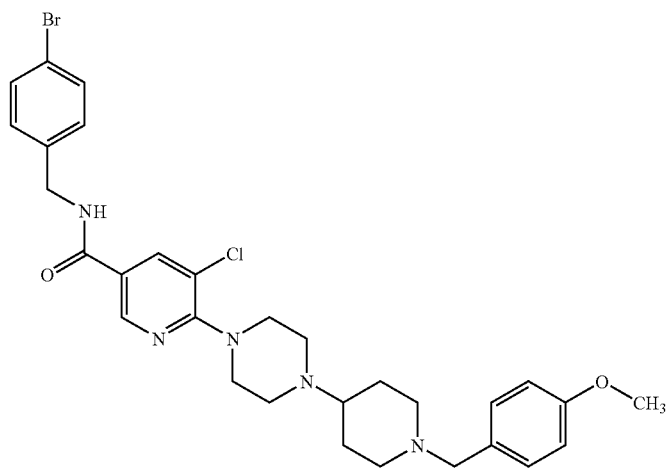 |
| 138 | 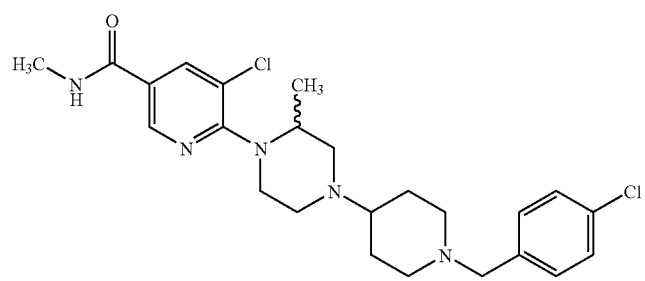 |
| 139 | 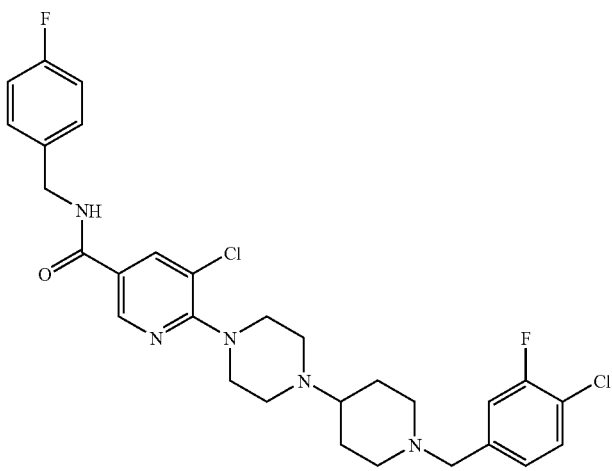 |
| 140 | 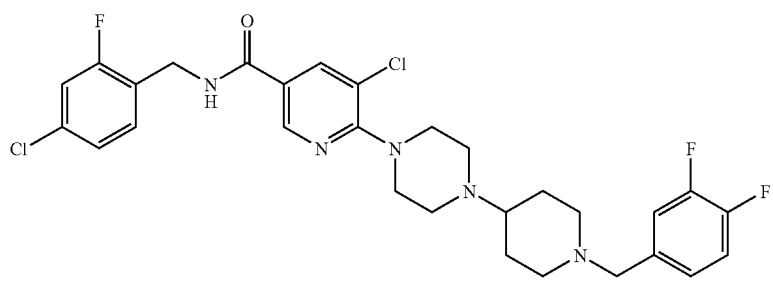 |

-continued
| Compound No. | Compound Structure |
|---|---|
| 141 | 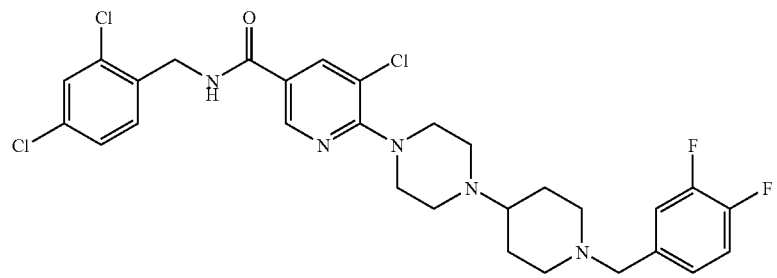 |
| 142 | 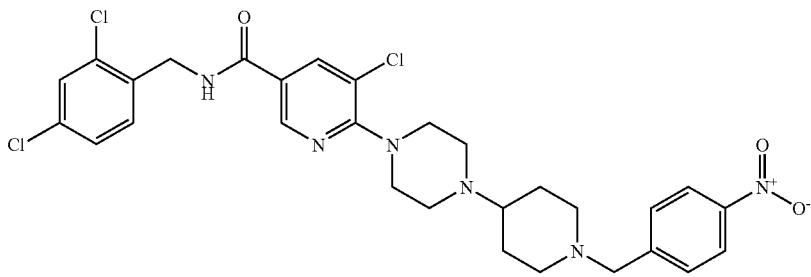 |
| 143 | 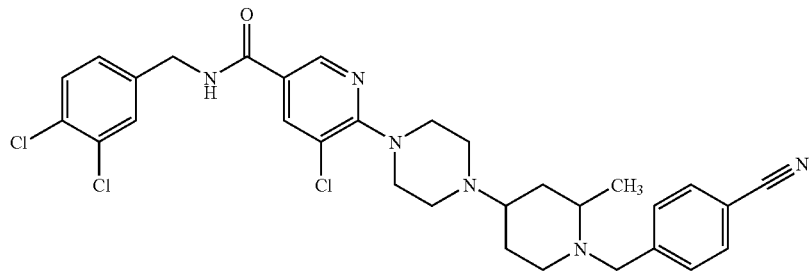 |
| 144 | 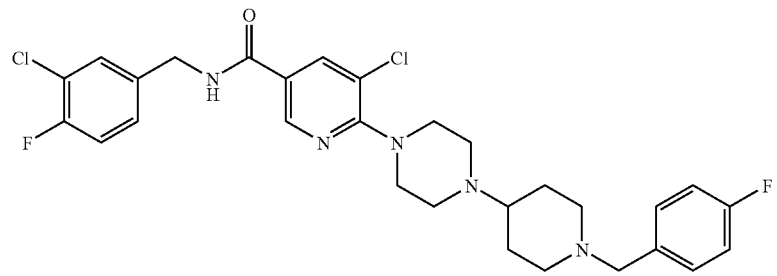 |

-continued

| Compound No. | Compound Structure |
|---|---|
| 145 | 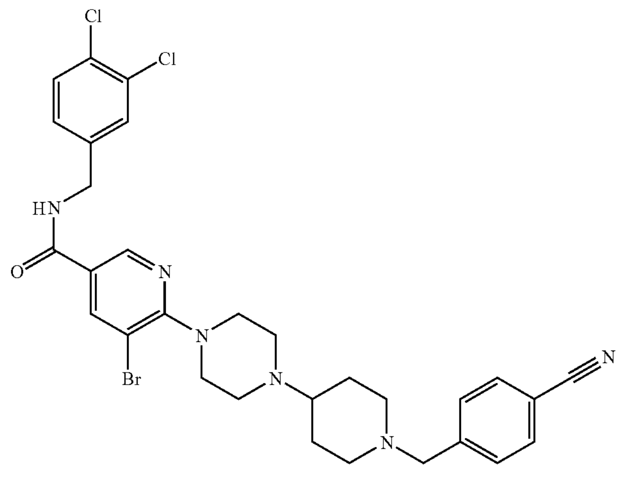 |
| 146 | 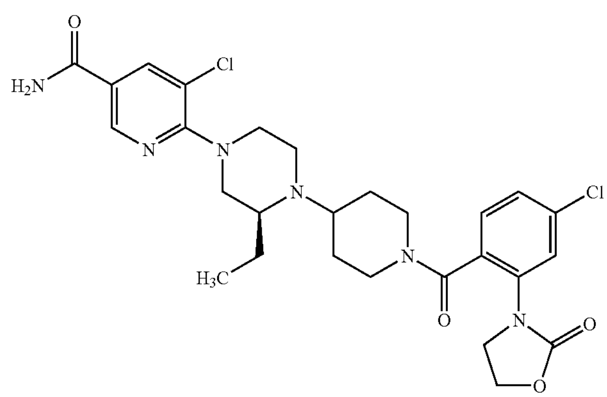 |
| 147 | 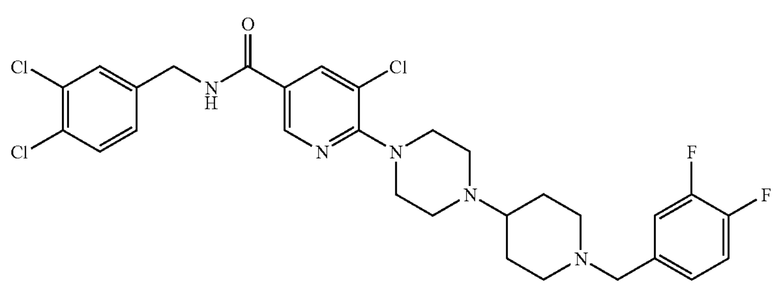 |
| 148 | 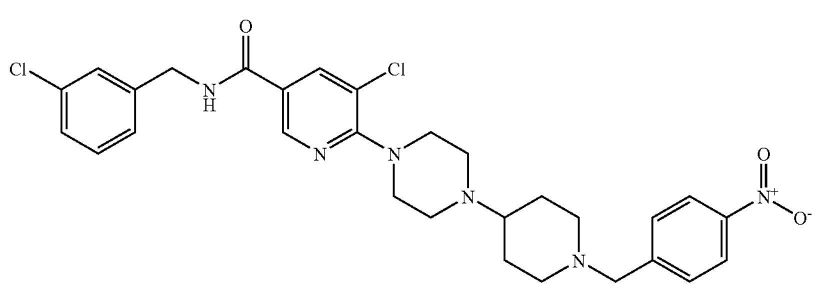 |

-continued
| Compound No. | Compound Structure |
|---|---|
| 149 | 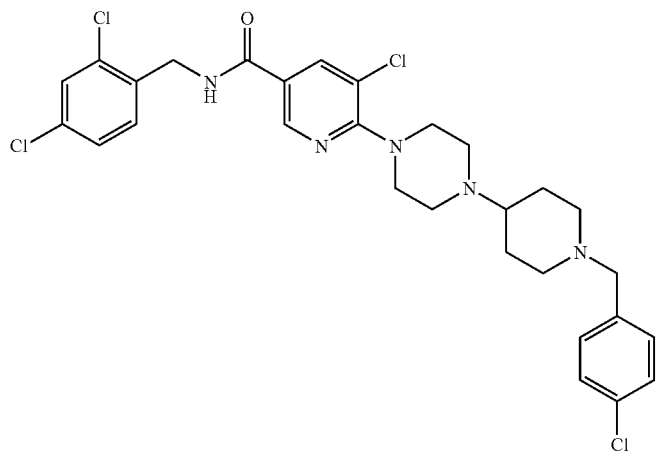 |
| 150 | 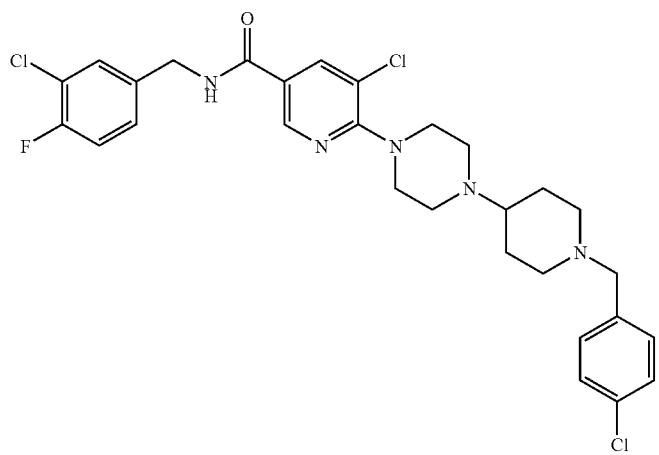 |
| 151 | 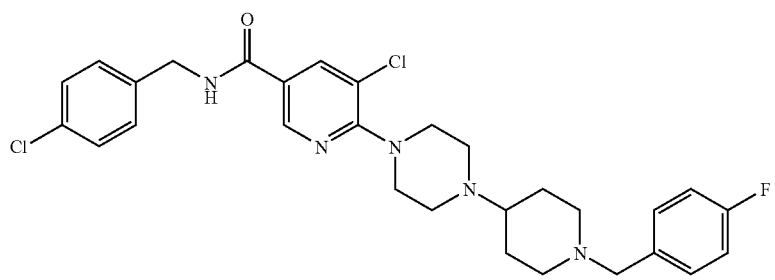 |
| 152 | 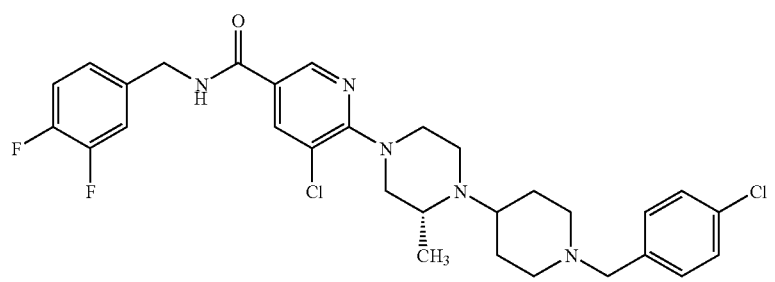 |

-continued
| Compound No. | Compound Structure |
|---|---|
| 153 | 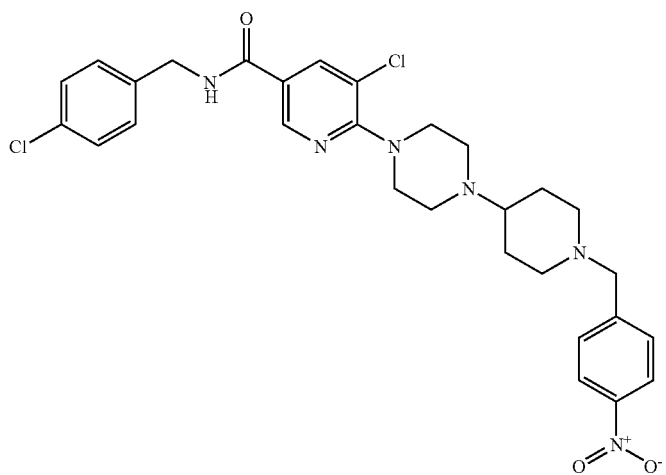 |
| 154 | 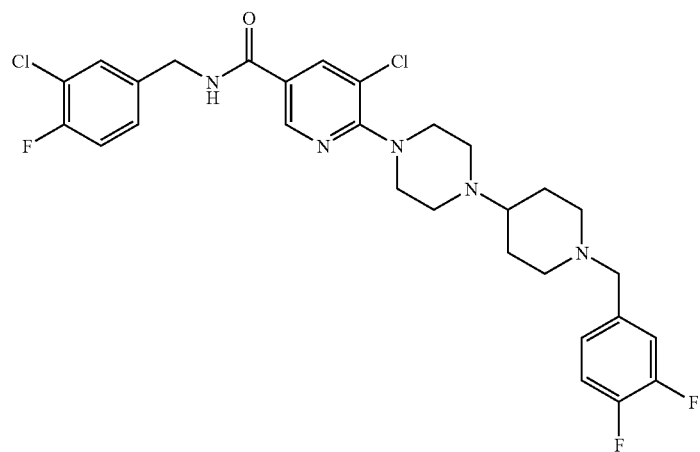 |
| 155 | 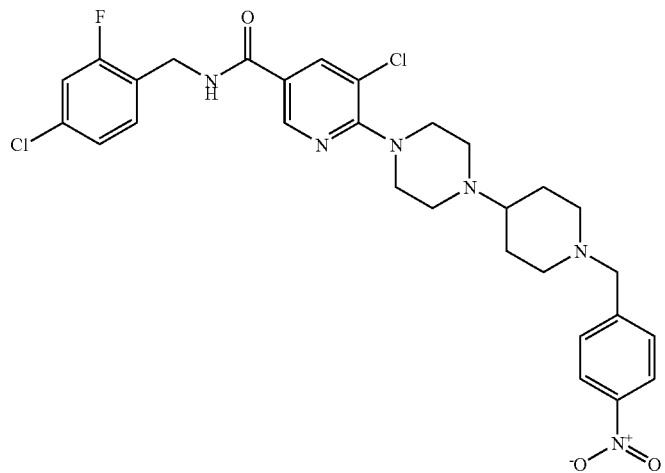 |

| Compound No. | Compound Structure |
|---|---|
| 156 | 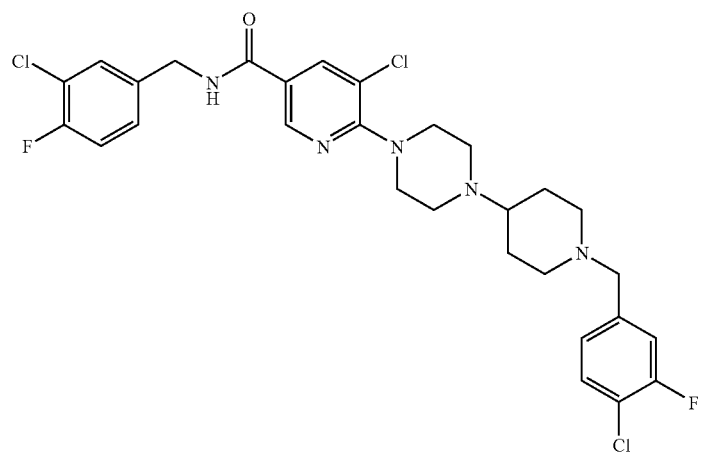 |
| 157 | 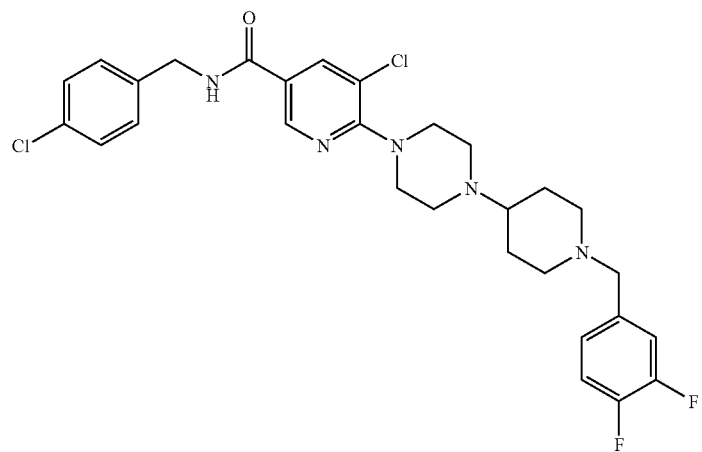 |
| 158 | 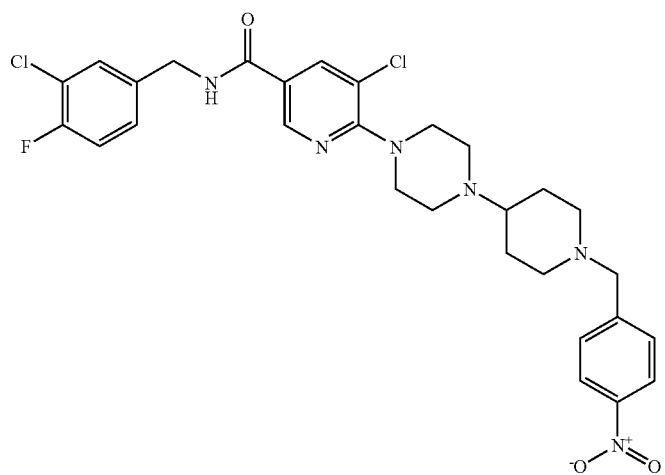 |

-continued
| Compound No. | Compound Structure |
|---|---|
| 159 | 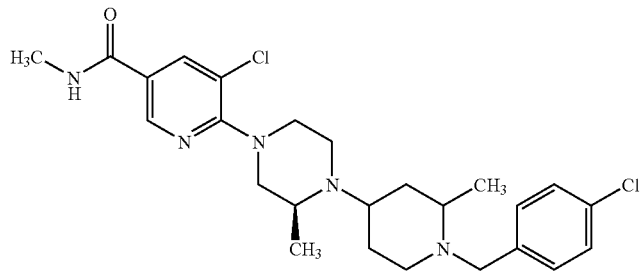 |
| 160 | 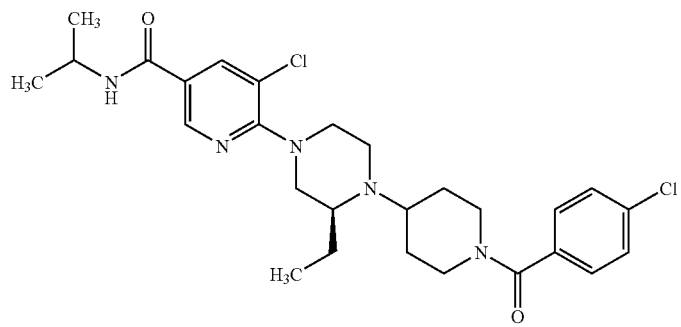 |
| 161 | 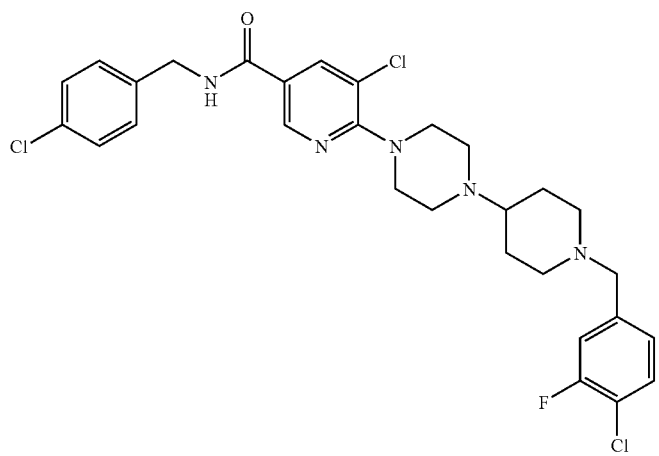 |
| 162 | 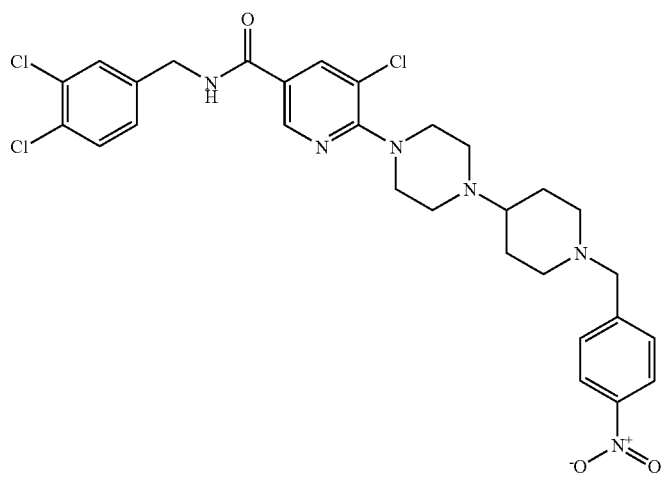 |

-continued
| Compound No. | Compound Structure |
|---|---|
| 163 | 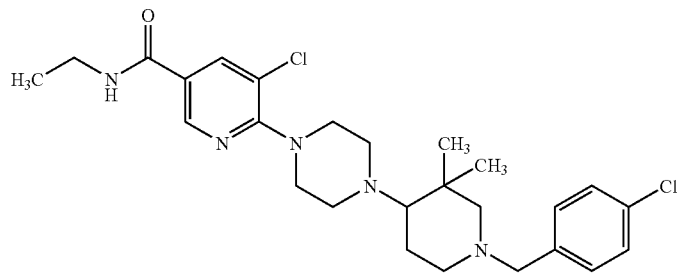 |
| 164 | 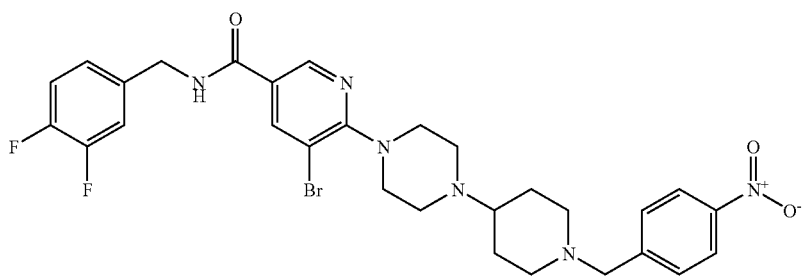 |
| 165 | 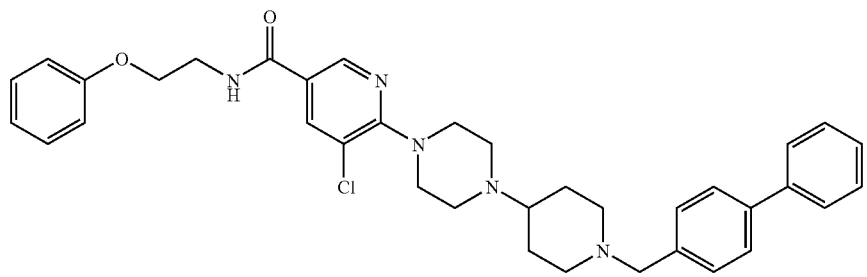 |
| 166 | 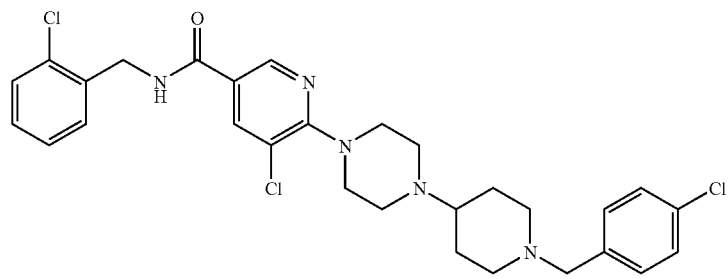 |
| 167 | 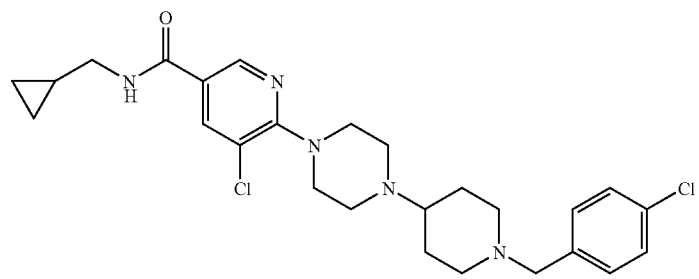 |

| Compound No. | Compound Structure |
|---|---|
| 168 | 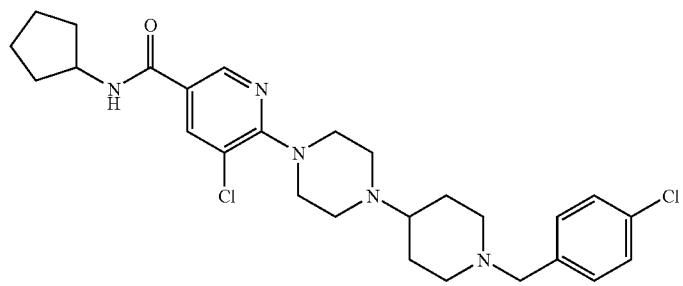 |
| 169 | 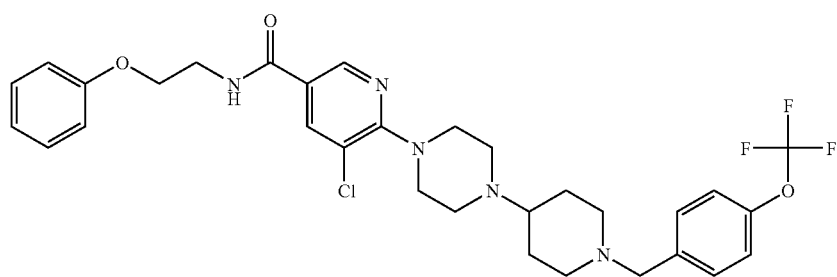 |
| 170 | 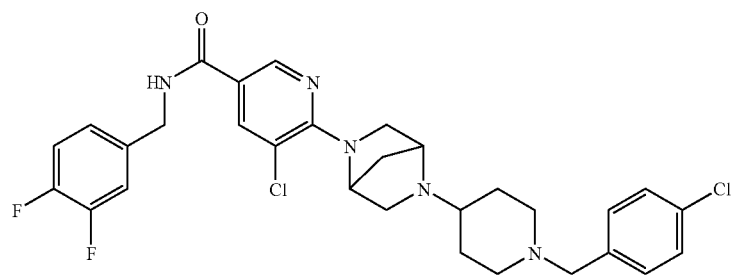 |
| 171 | 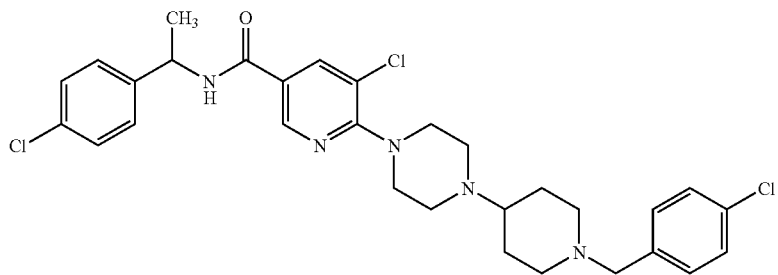 |
| 172 | 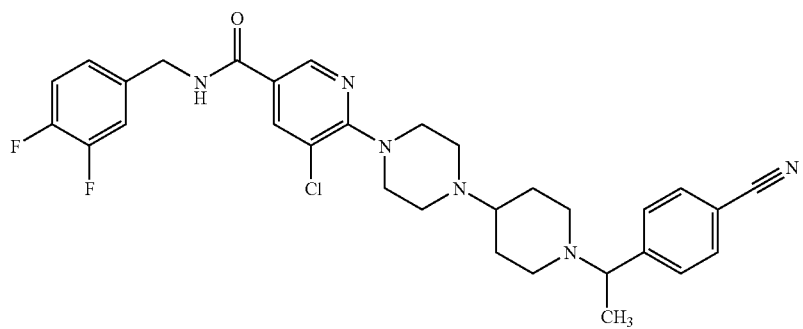 |

| Compound No. | Compound Structure |
|---|---|
| 173 | 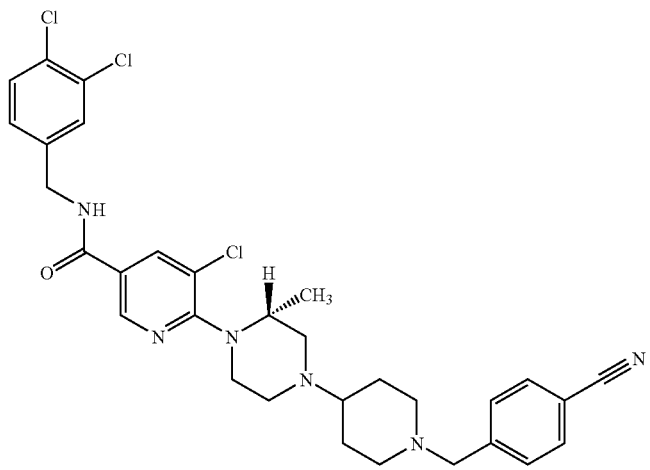 |
| 174 | 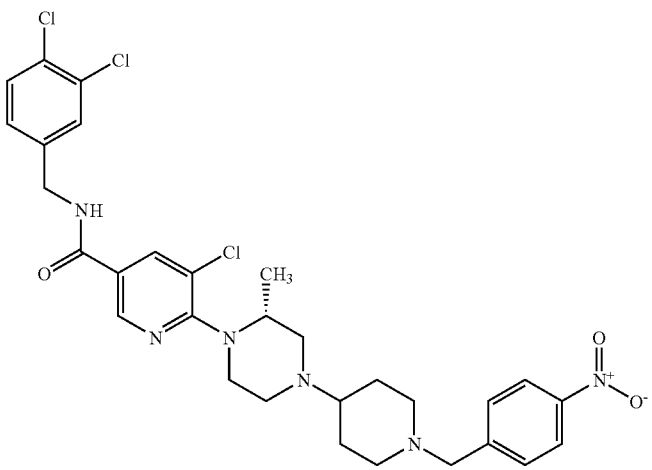 |
| 175 | 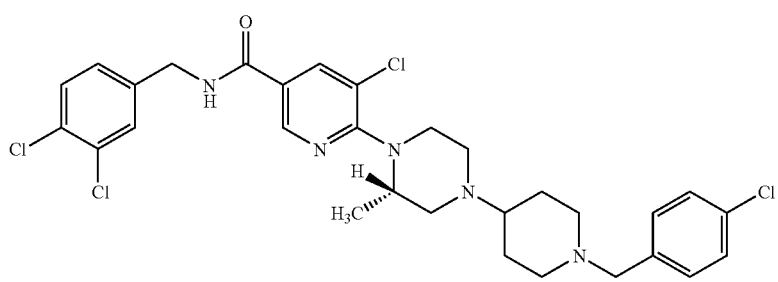 |
| 176 | 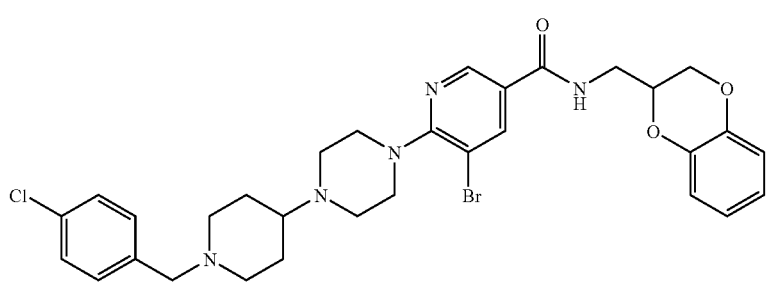 |

-continued
| Compound No. | Compound Structure |
|---|---|
| 177 | 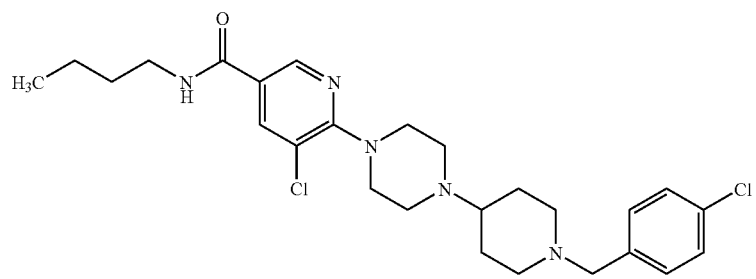 |
| 178 | 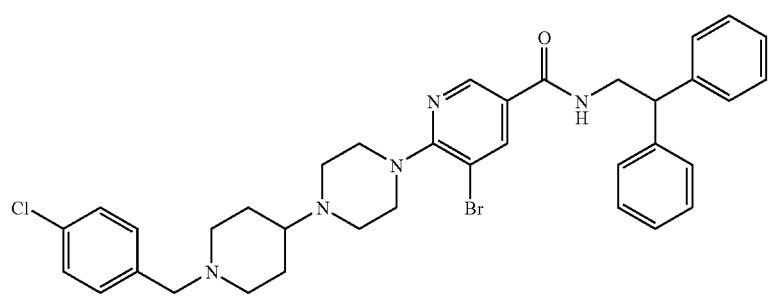 |
| 179 | 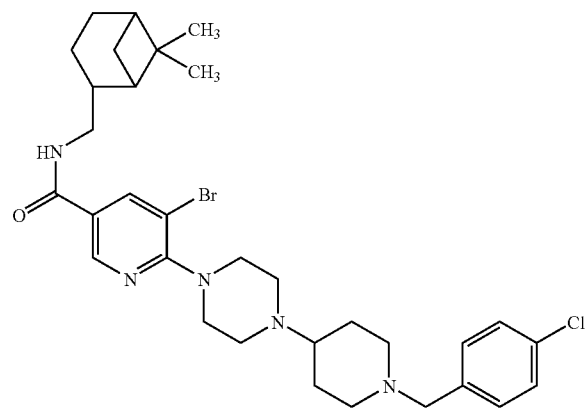 |
| 180 | 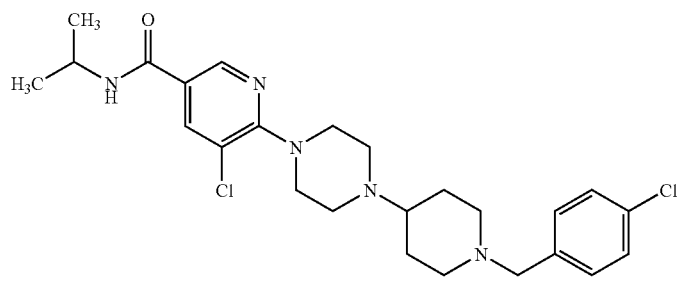 |
| 181 | 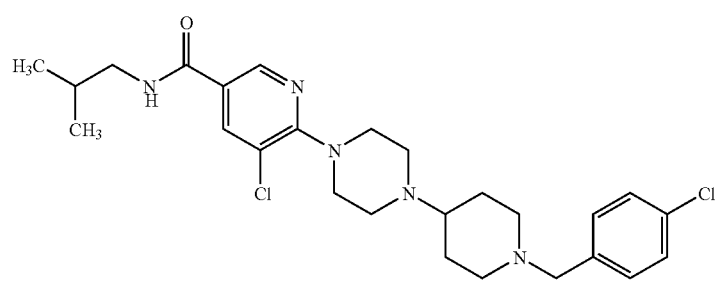 |

| Compound No. | Compound Structure |
|---|---|
| 182 | 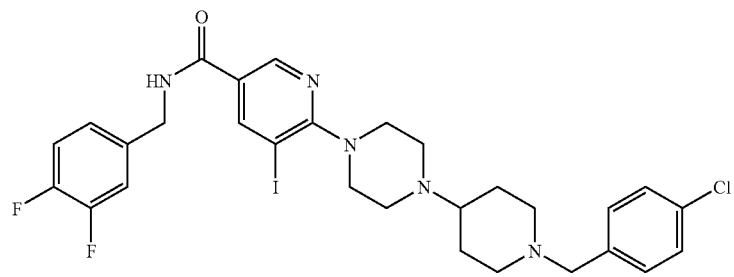 |
| 183 | 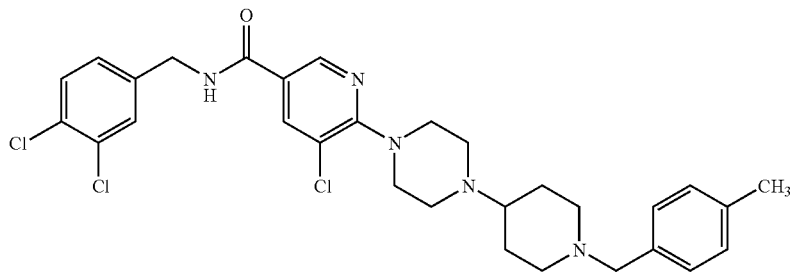 |
| 184 | 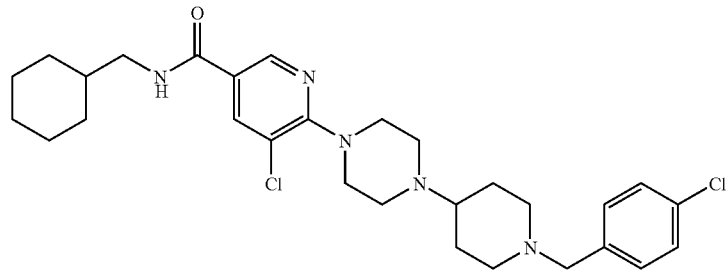 |
| 185 | 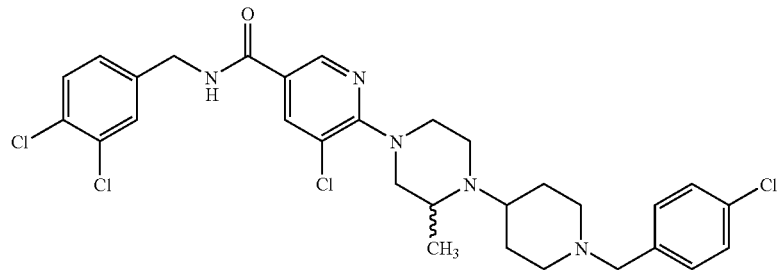 |

-continued
| Compound No. | Compound Structure |
|---|---|
| 186 | 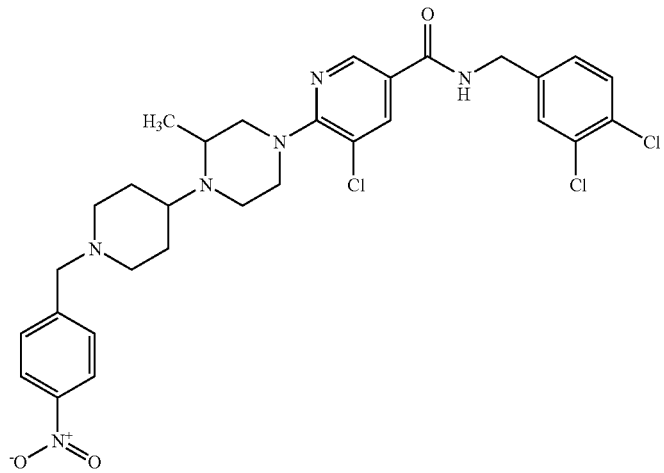 |
| 187 | 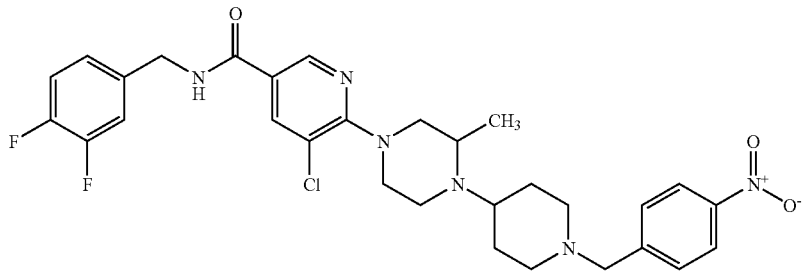 |
| 188 | 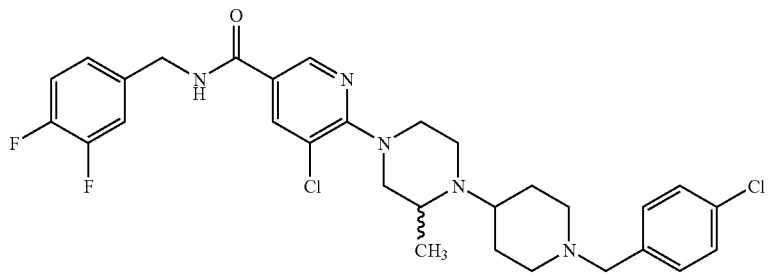 |
| 189 | 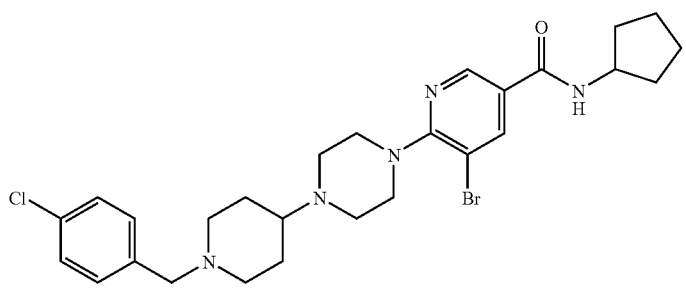 |

| Compound No. | Compound Structure |
|---|---|
| 190 | 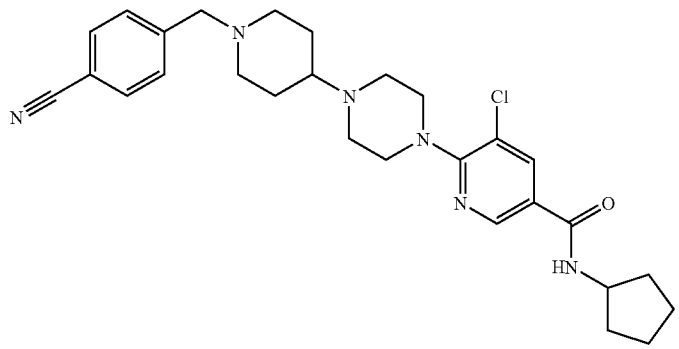 |
| 191 | 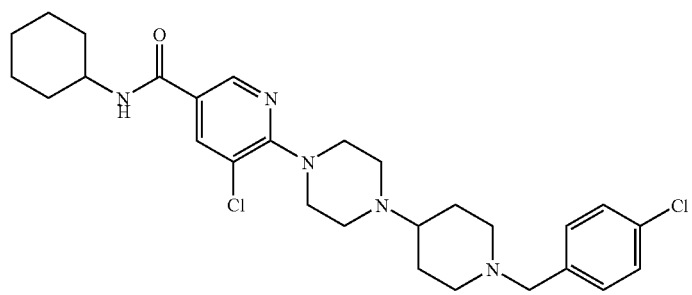 |
| 192 | 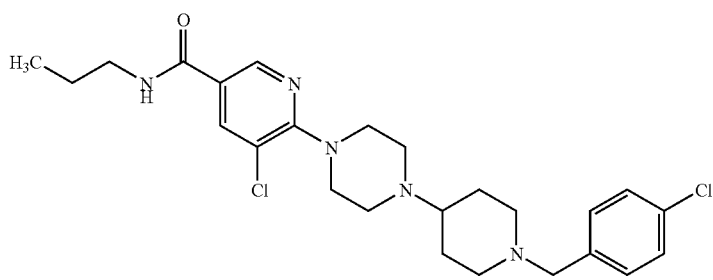 |
| 193 | 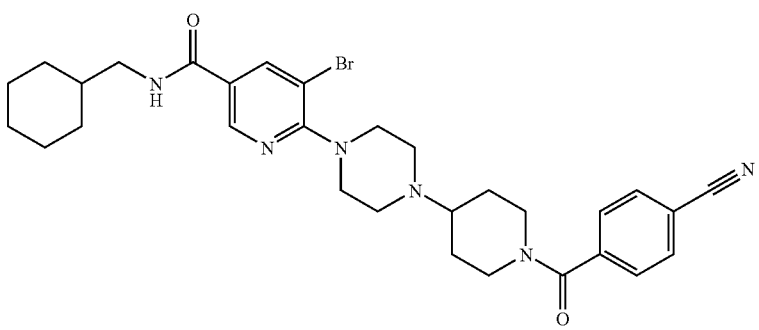 |
| 194 | 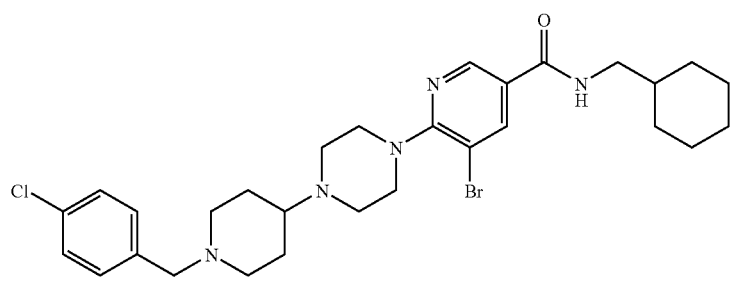 |

-continued
| Compound No. | Compound Structure |
|---|---|
| 195 | 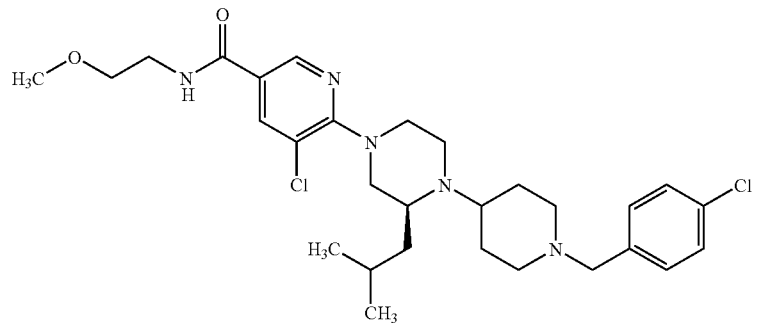 |
| 196 | 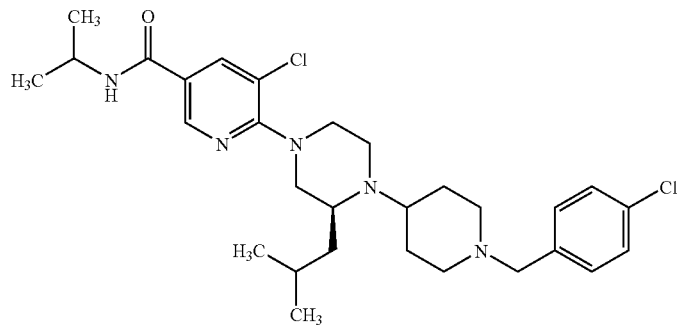 |
| 197 | 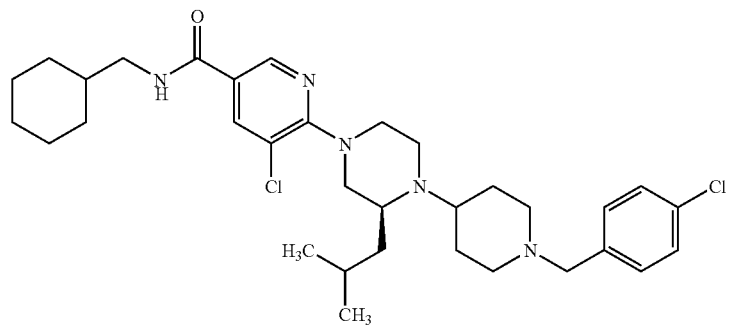 |
| 198 | 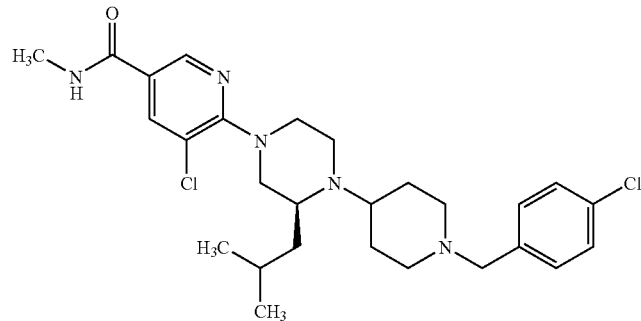 |

-continued

| Compound No. | Compound Structure |
|---|---|
| 199 | 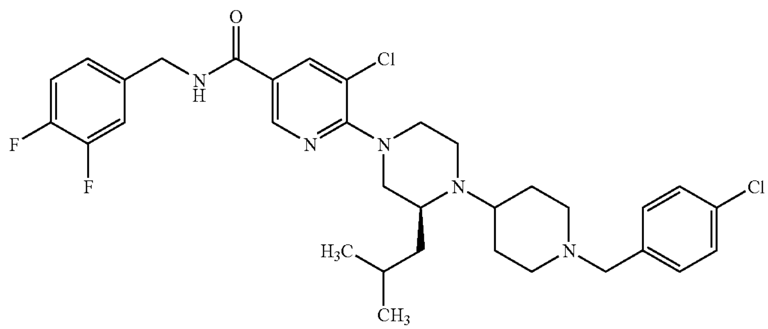 |
| 200 | 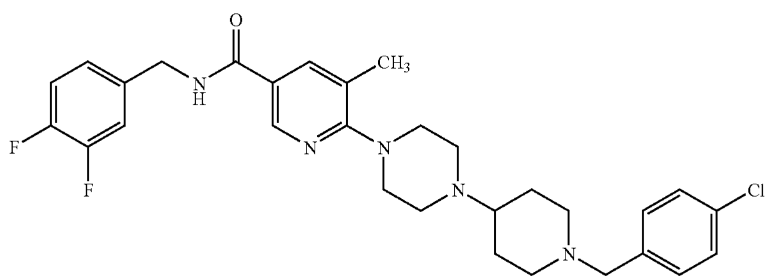 |
| 201 | 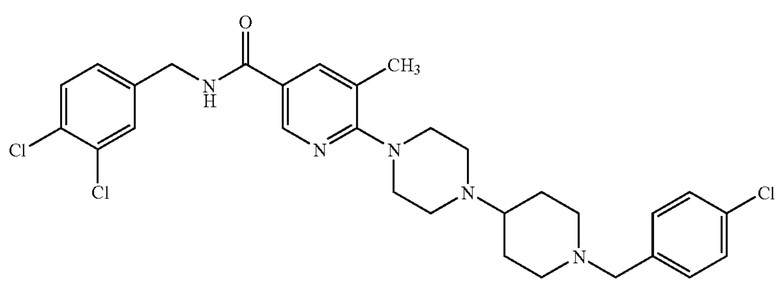 |
| 202 | 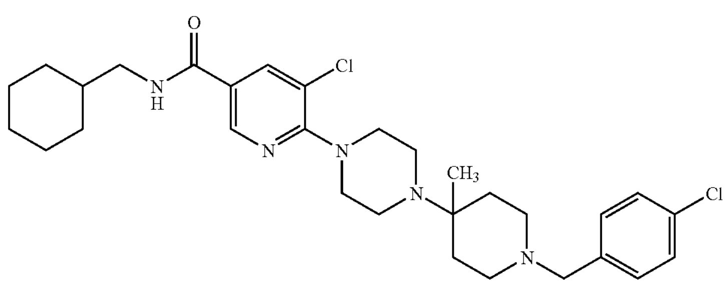 |
| 203 | 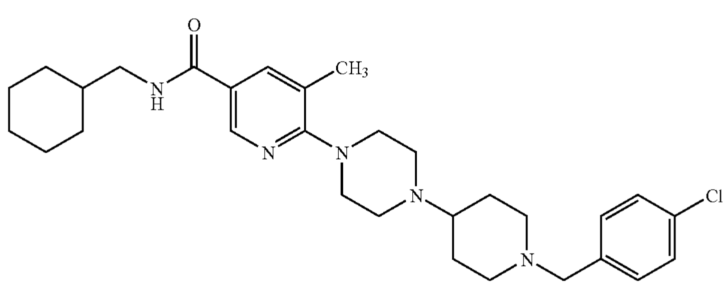 |

-continued

| Compound No. | Compound Structure |
|---|---|
| 204 | 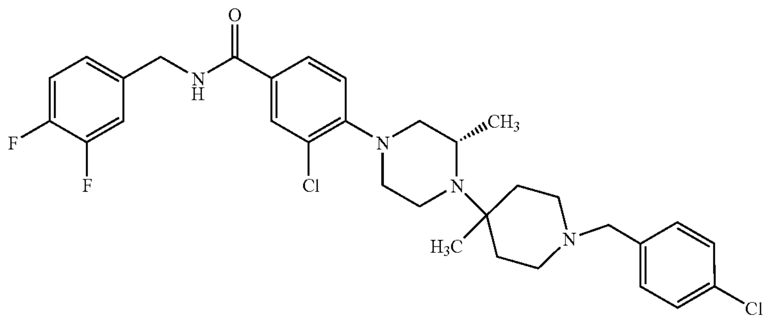 |
| 205 | 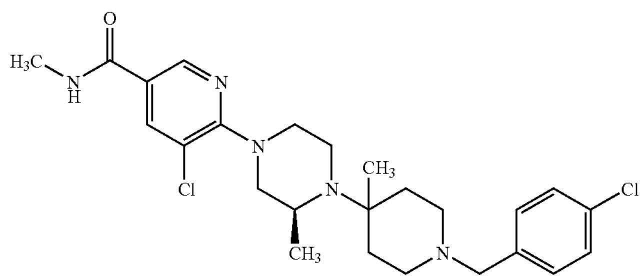 |
| 206 | 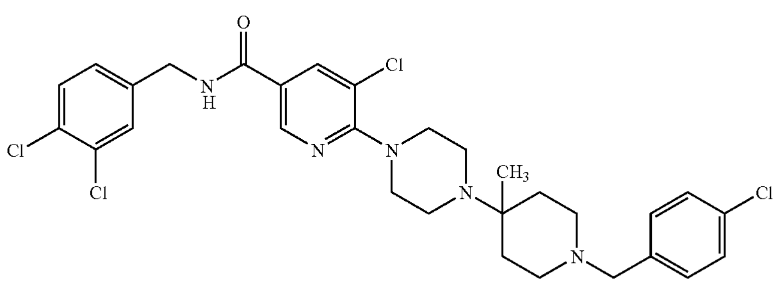 |
| 207 | 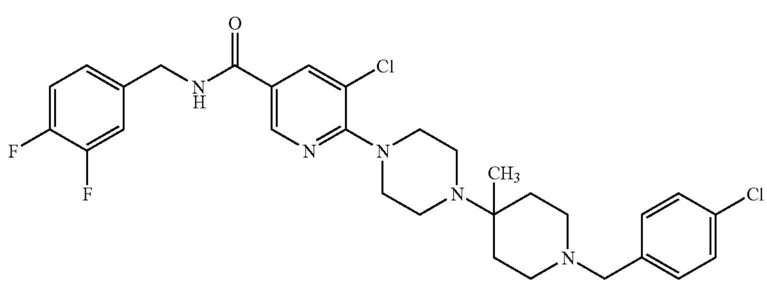 |
| 208 | 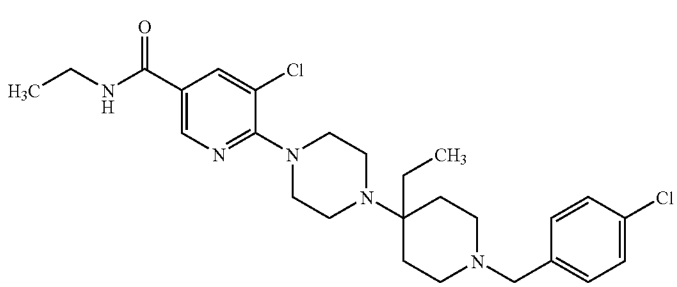 |

-continued
| Compound No. | Compound Structure |
|---|---|
| 209 | 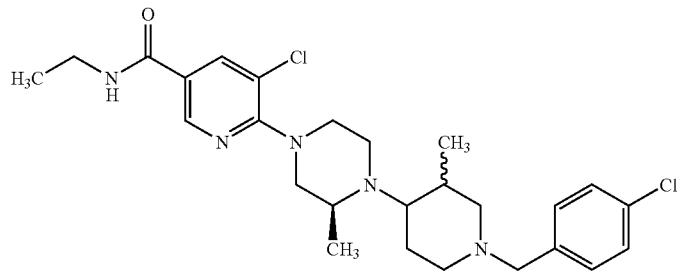 |
| 210 | 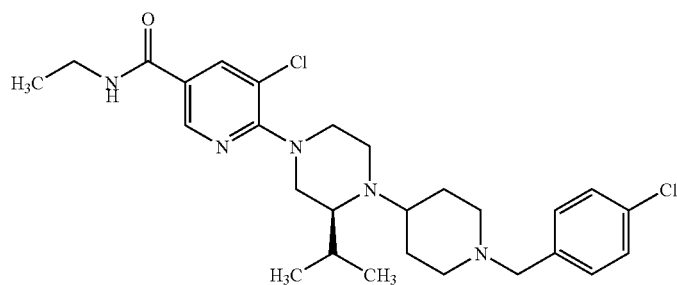 |
| 211 | 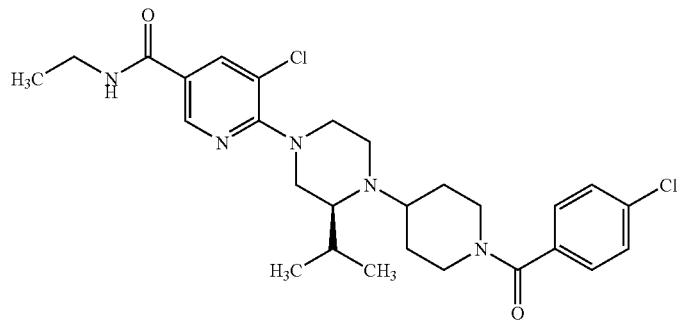 |
| 212 | 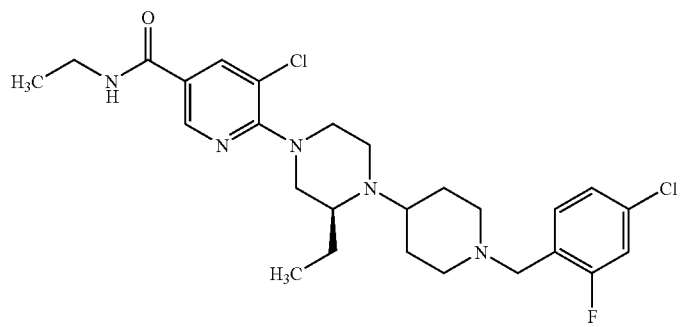 |
| 213 | 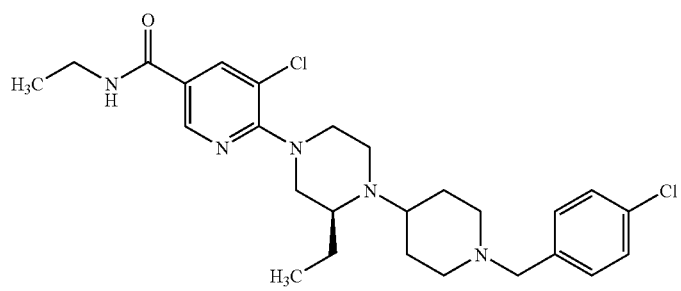 |

-continued
| Compound No. | Compound Structure |
|---|---|
| 214 | 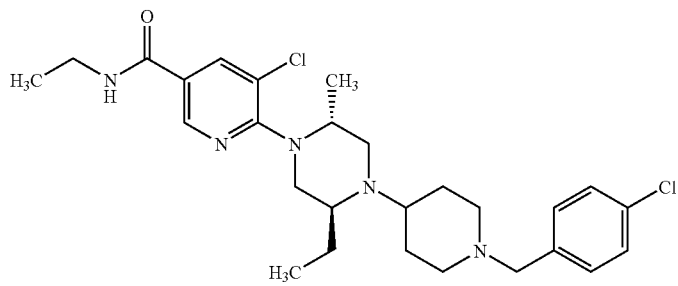 |
| 215 | 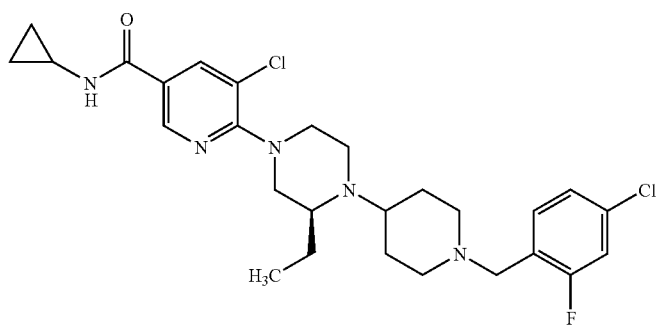 |
| 216 | 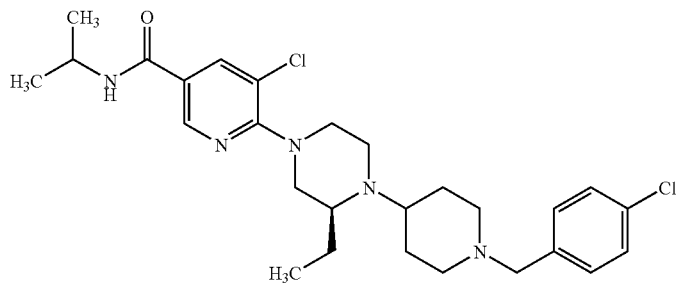 |
| 217 | 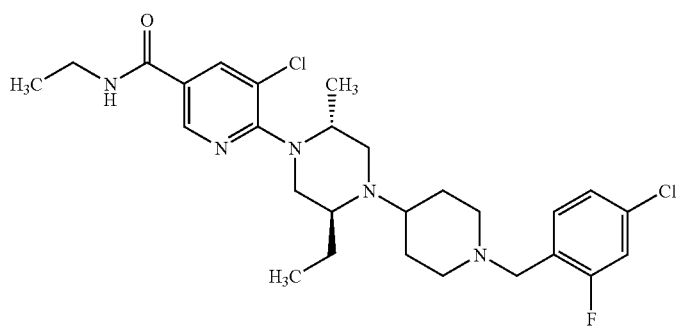 |
| 218 | 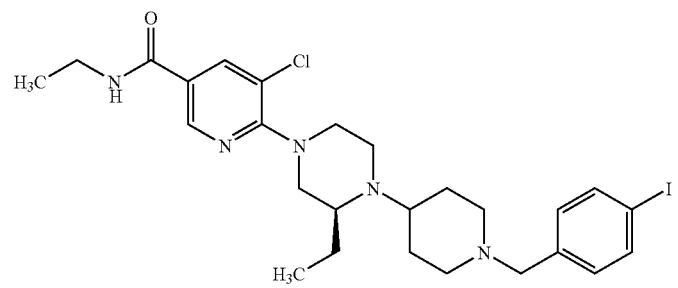 |

-continued
| Compound No. | Compound Structure |
|---|---|
| 219 | 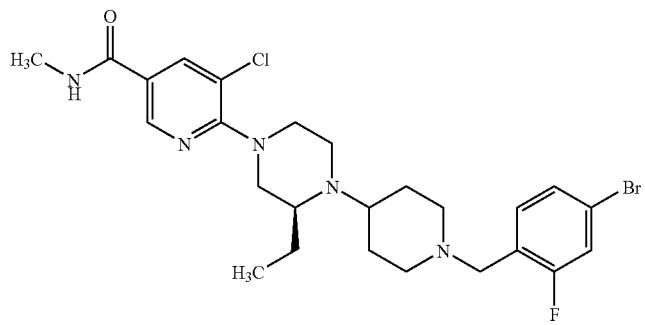 |
| 220 | 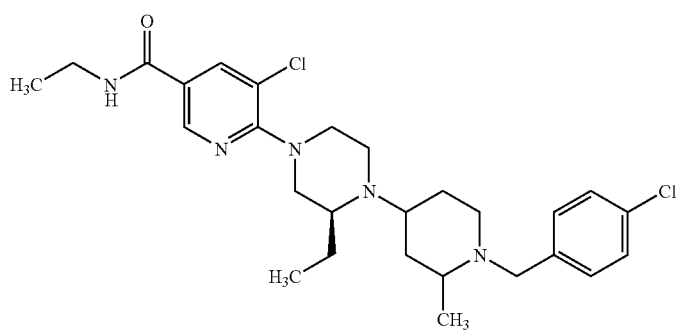 |
| 221 | 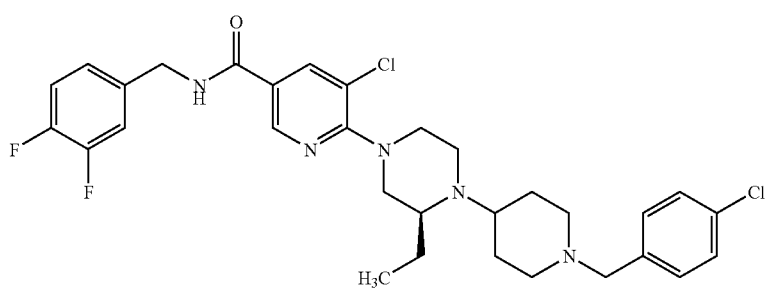 |
| 222 | 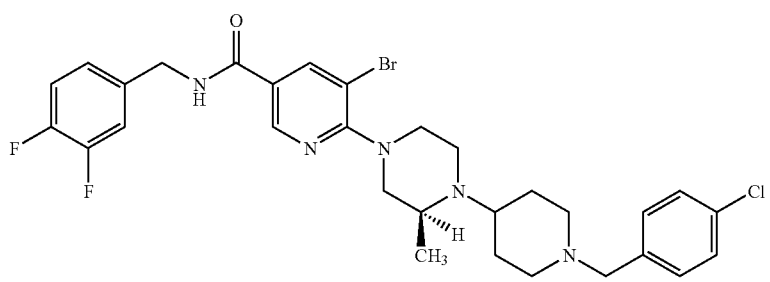 |
| 223 | 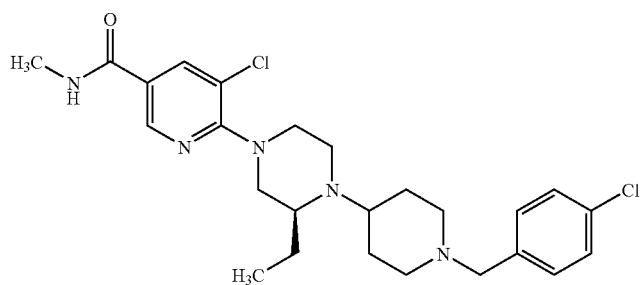 |

-continued
| Compound No. | Compound Structure |
|---|---|
| 224 | 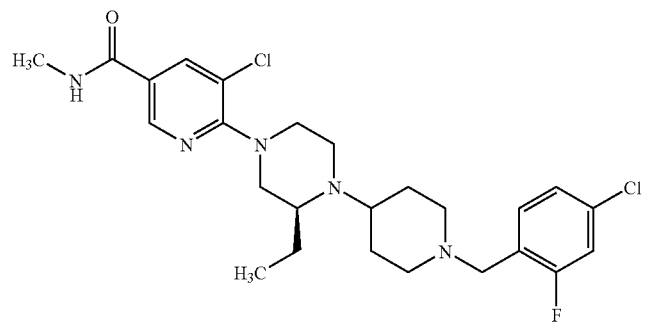 |
| 225 | 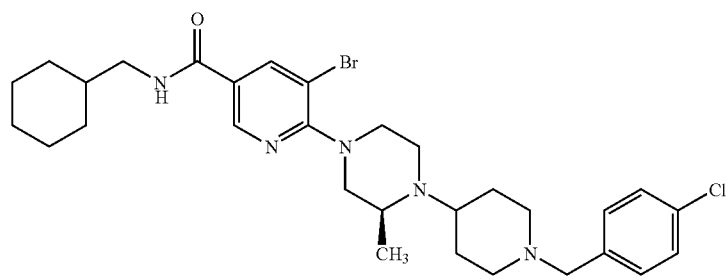 |
| 226 | 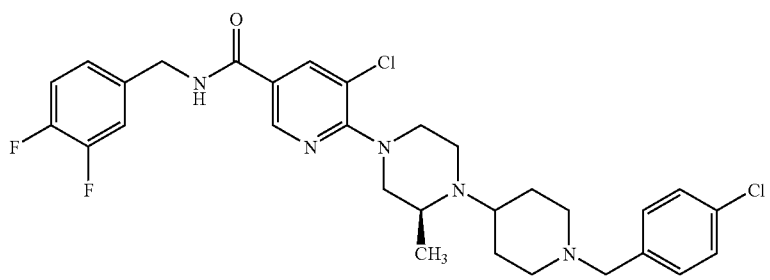 |
| 227 | 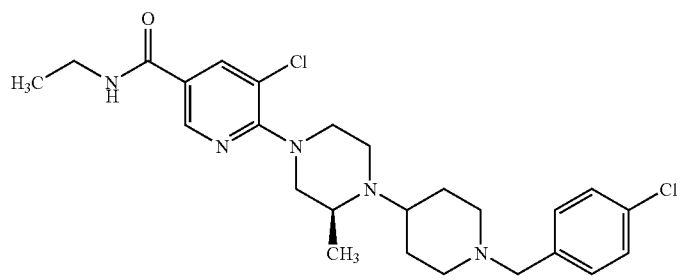 |
| 228 | 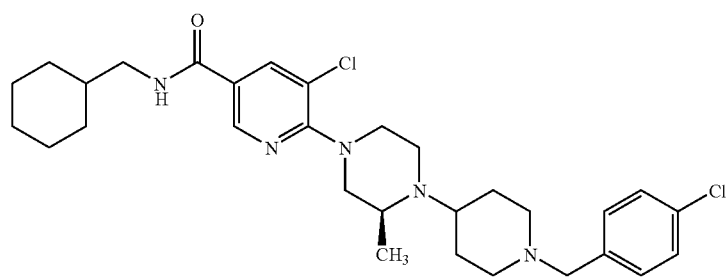 |

-continued
| Compound No. | Compound Structure |
|---|---|
| 229 | 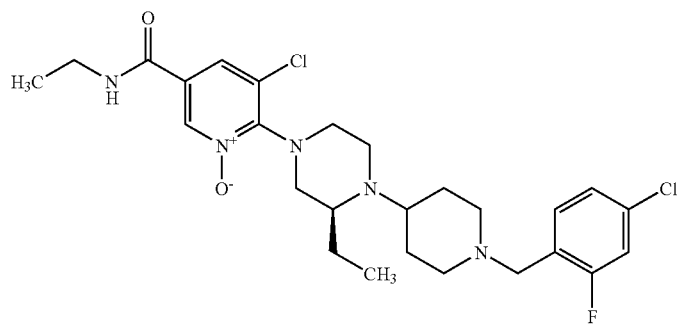 |
| 230 | 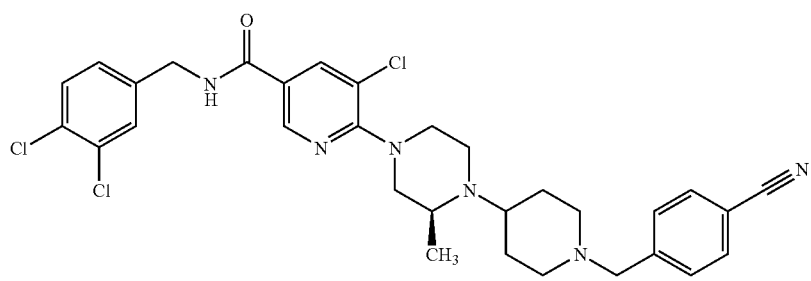 |
| 231 | 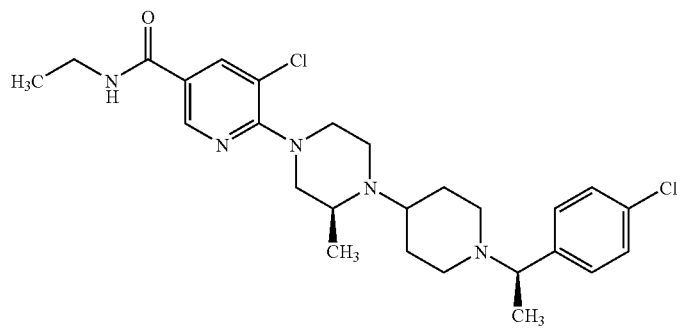 |
| 232 | 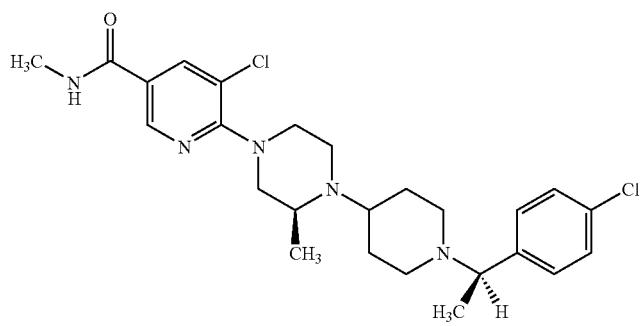 |
| 233 | 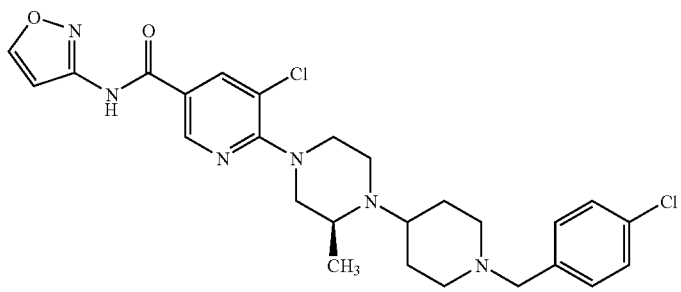 |

-continued
| Compound No. | Compound Structure |
|---|---|
| 234 | 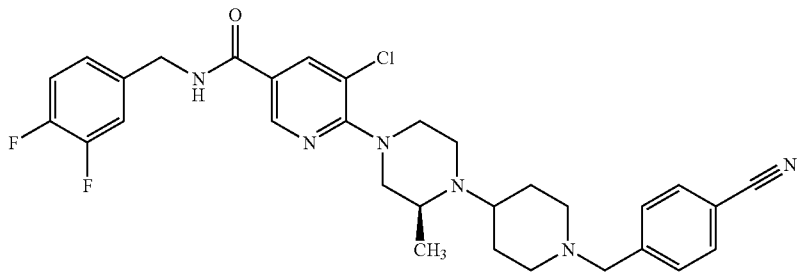 |
| 235 | 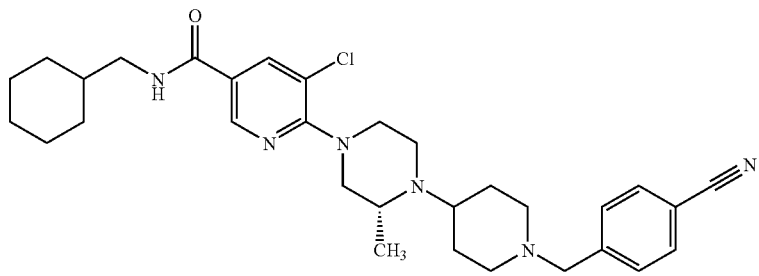 |
| 236 | 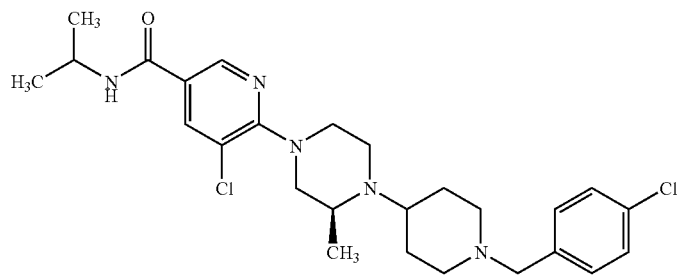 |
| 237 | 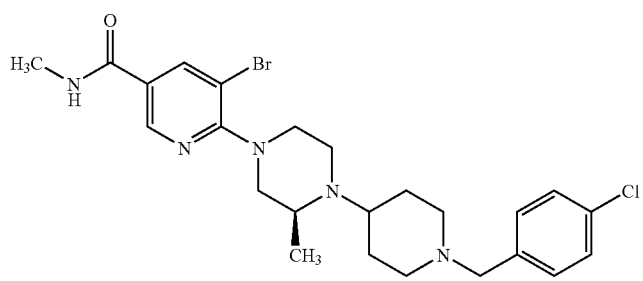 |
| 238 | 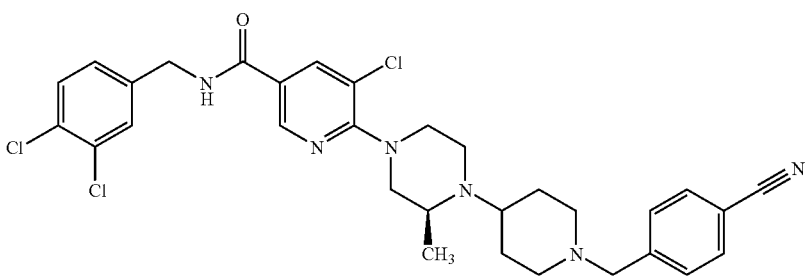 |

-continued
| Compound No. | Compound Structure |
|---|---|
| 239 | 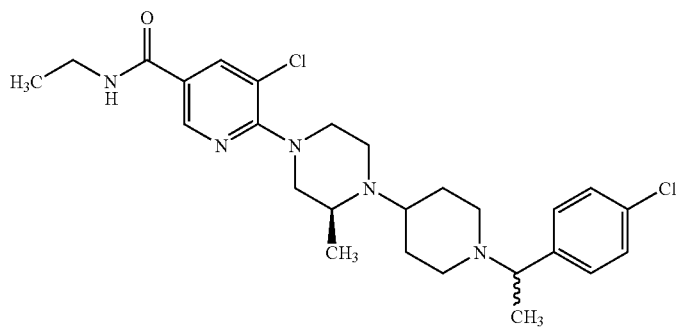 |
| 240 | 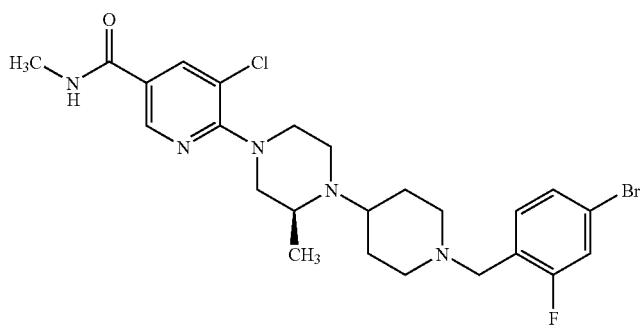 |
| 241 | 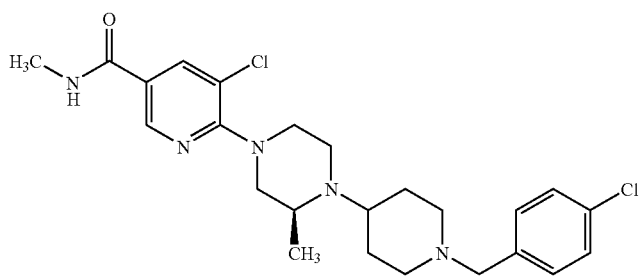 |
| 242 | 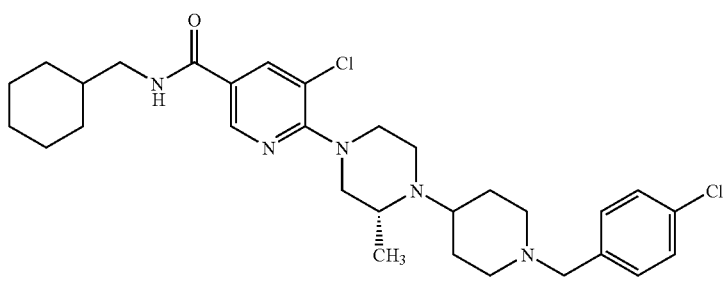 |
| 243 | 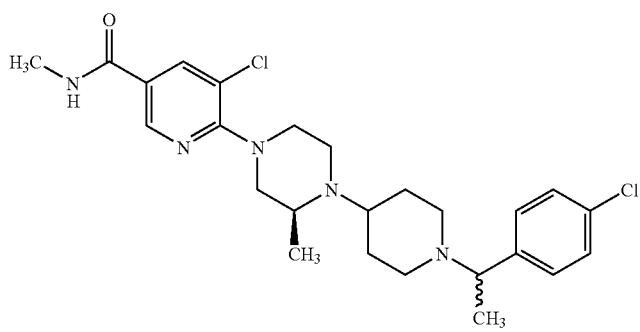 |

-continued
| Compound No. | Compound Structure |
|---|---|
| 244 | 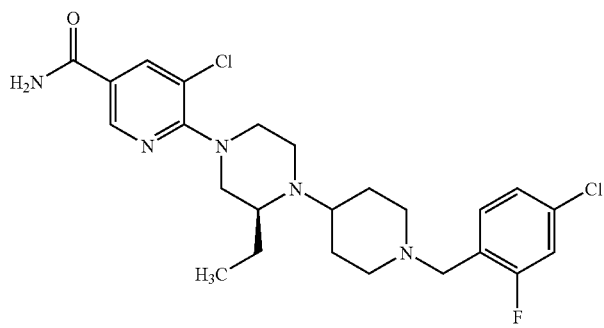 |
| 245 | 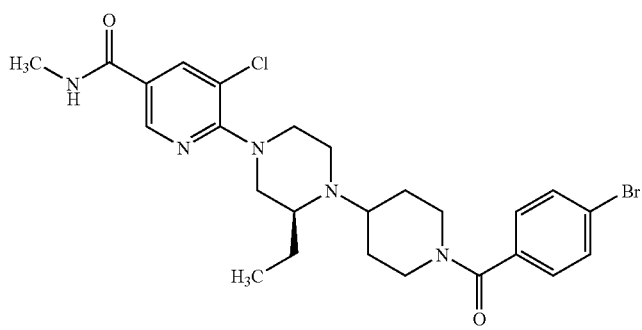 |
| 246 | 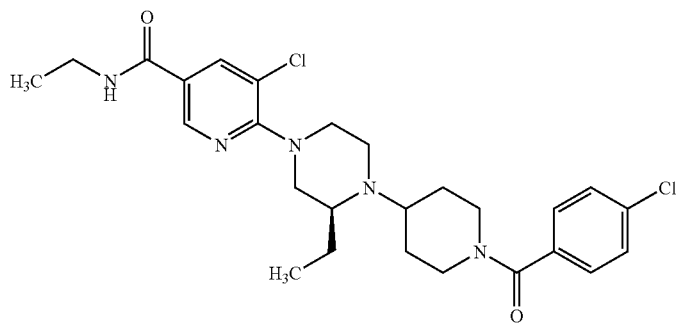 |
| 247 | 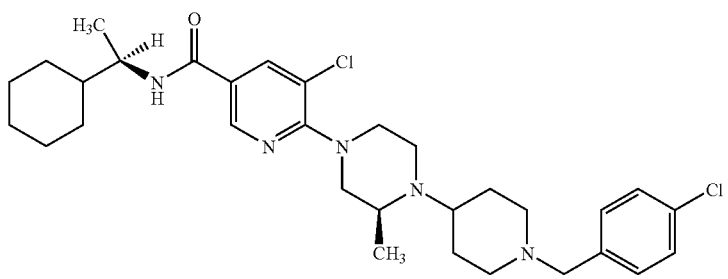 |

-continued
| Compound No. | Compound Structure |
|---|---|
| 248 | 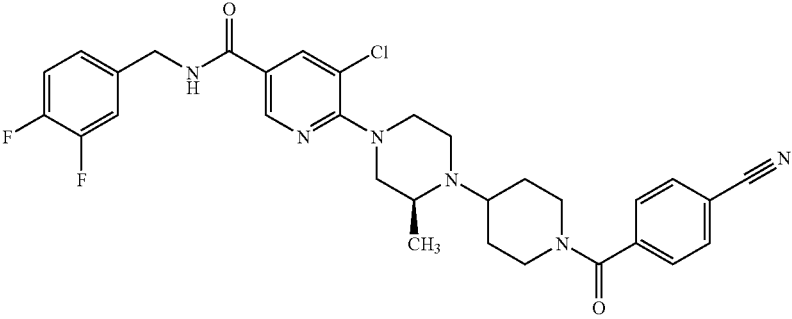 |
| 249 | 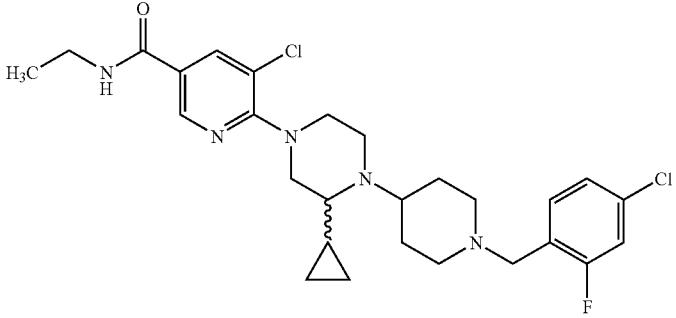 |
| 250 | 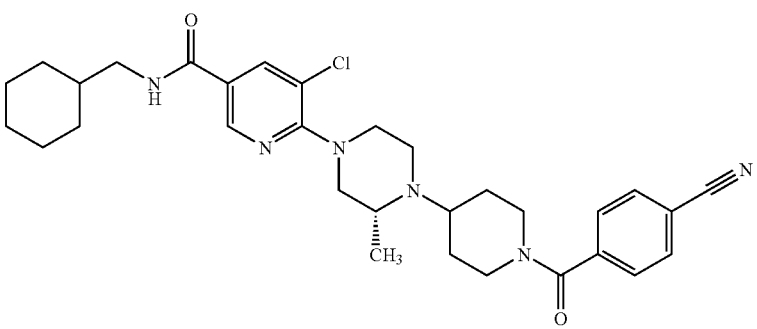 |
| 251 | 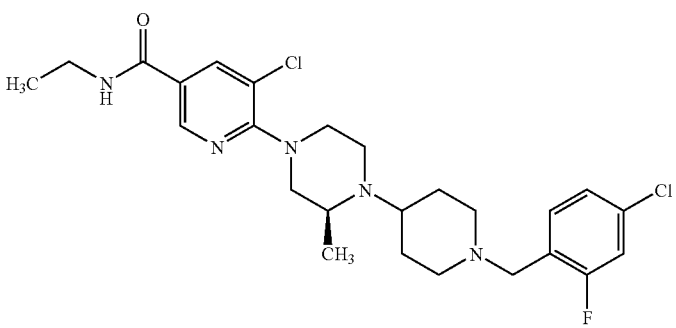 |

-continued

| Compound No. | Compound Structure |
|---|---|
| 252 | 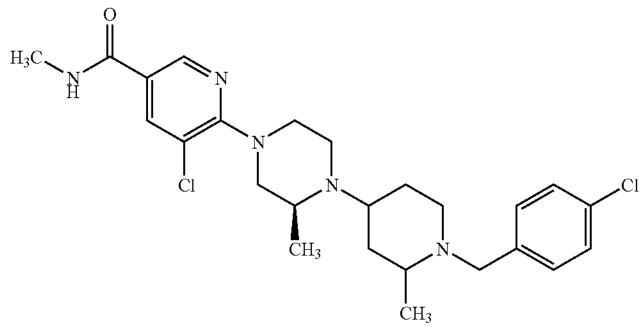 |
| 253 | 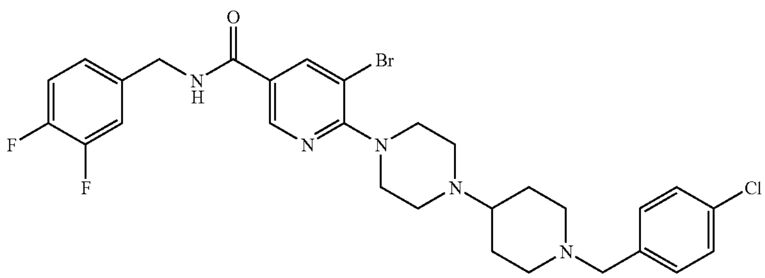 |
| 254 | 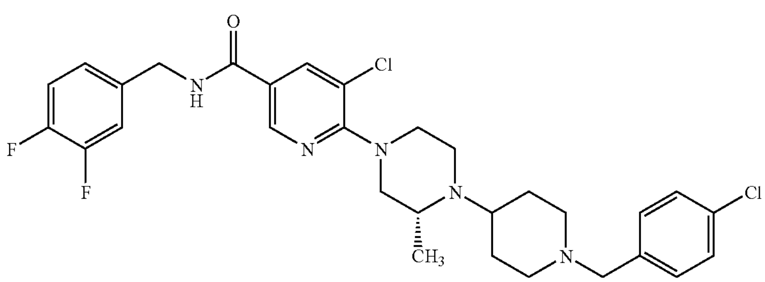 |
| 255 | 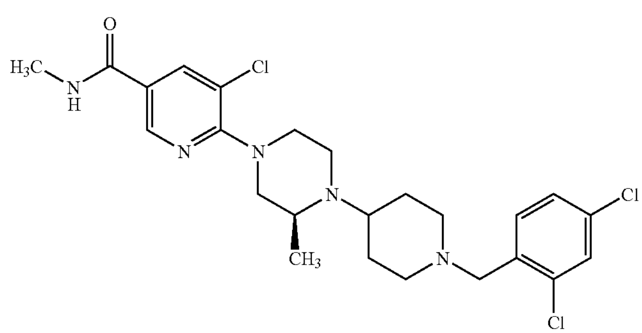 |
| 256 | 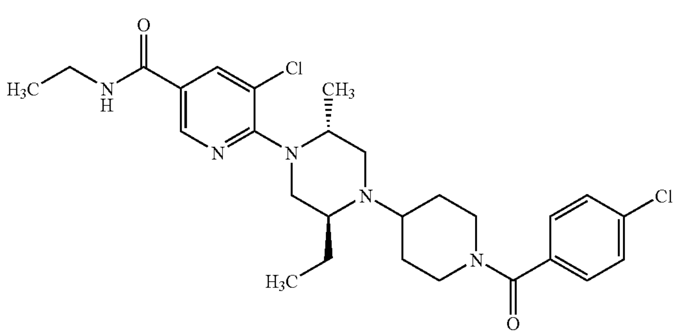 |

-continued
| Compound No. | Compound Structure |
|---|---|
| 257 | 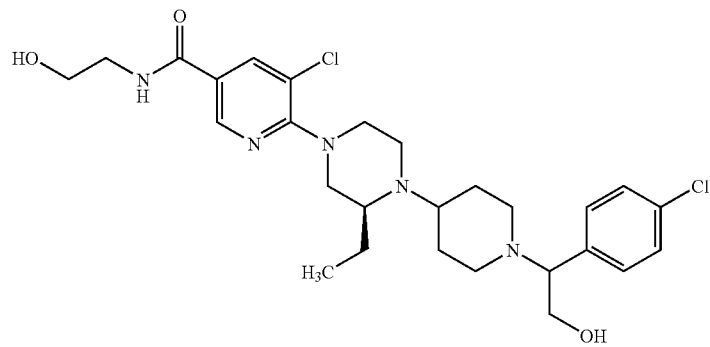 |
| 258 | 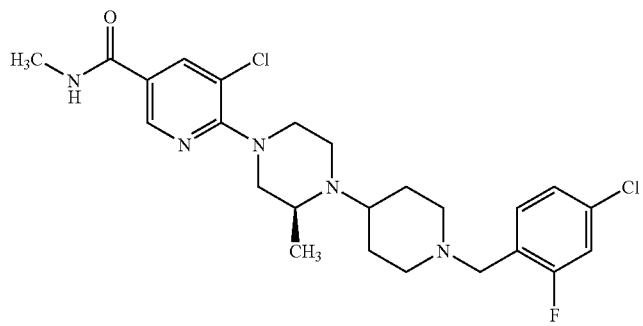 |
| 259 | 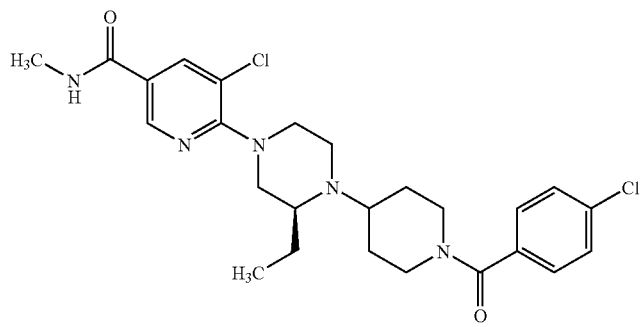 |
| 260 | 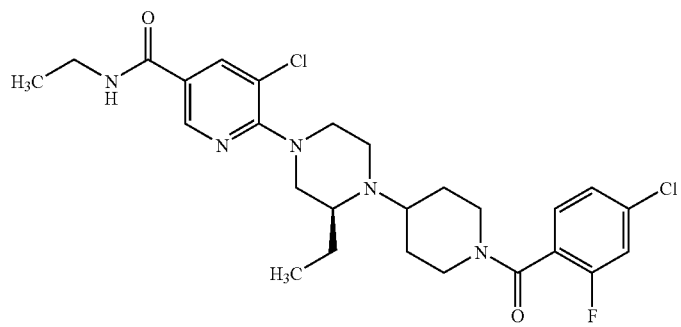 |

-continued
| Compound No. | Compound Structure |
|---|---|
| 261 | 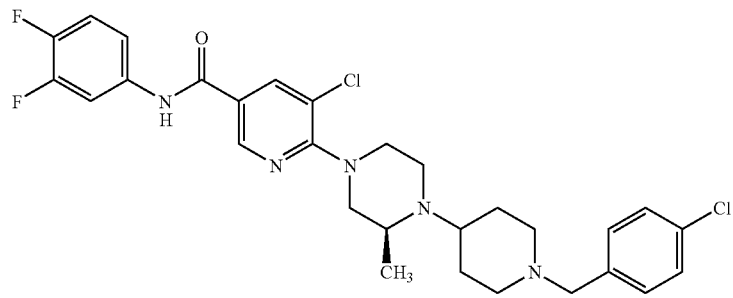 |
| 262 | 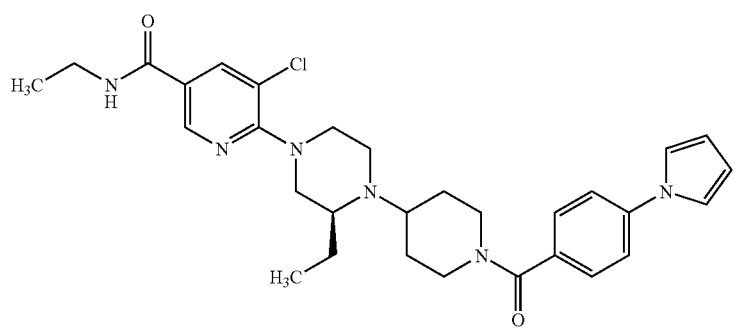 |
| 263 | 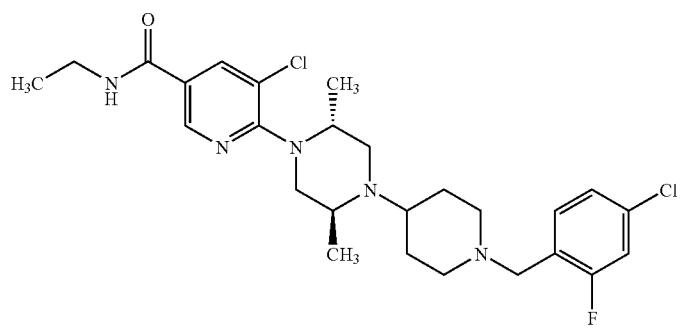 |
| 264 | 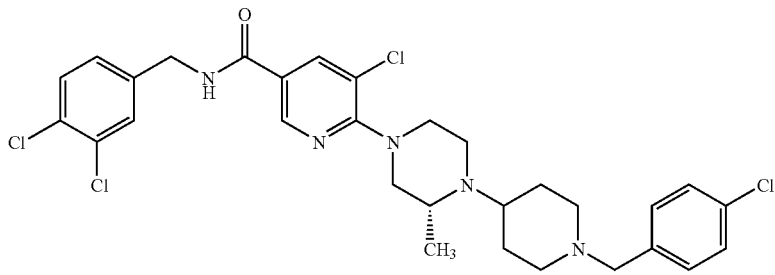 |
| 265 | 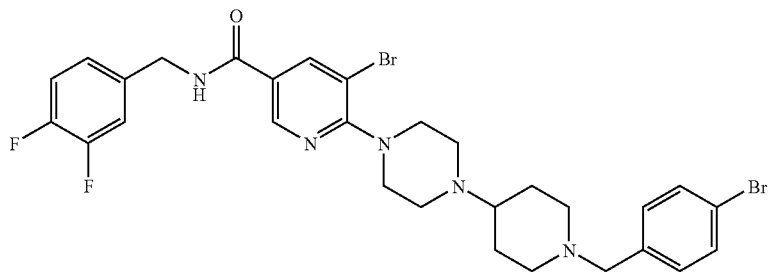 |

-continued
| Compound No. | Compound Structure |
|---|---|
| 266 | 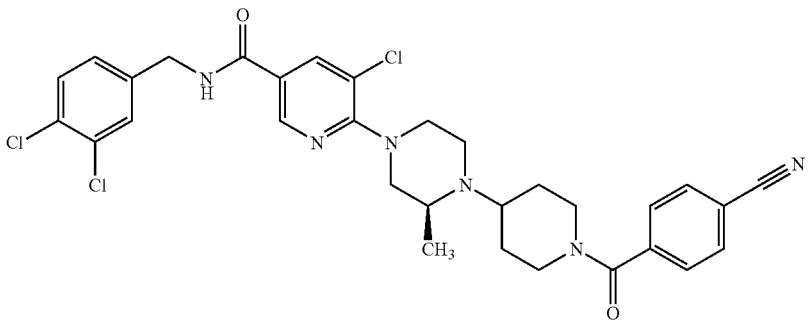 |
| 267 | 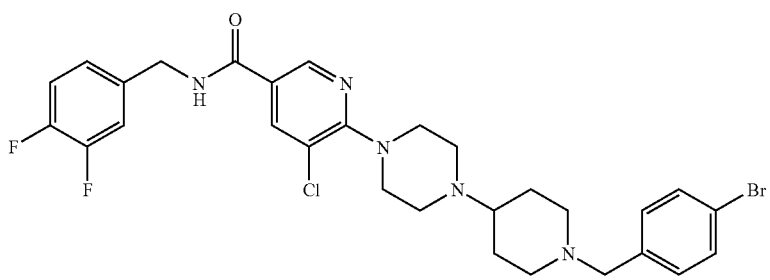 |
| 268 | 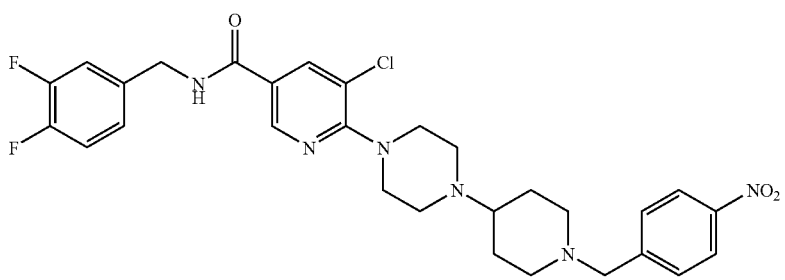 |
| 269 | 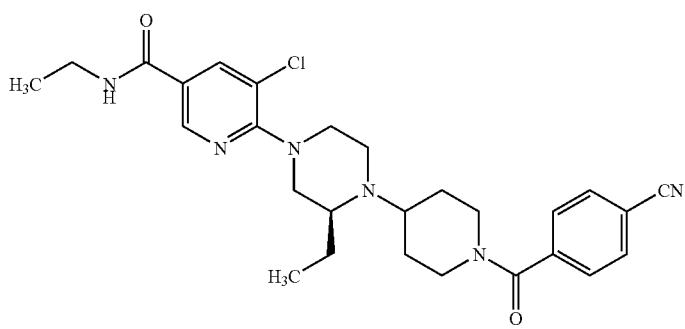 |
| 270 | 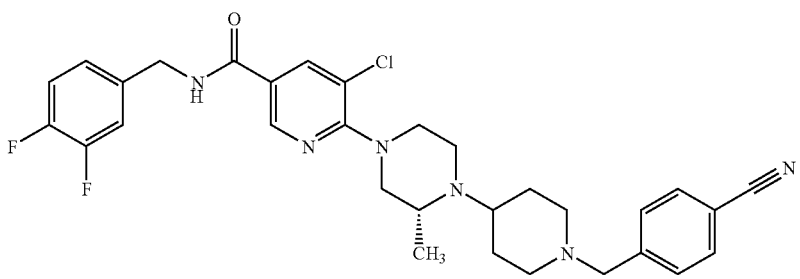 |

-continued
| Compound No. | Compound Structure |
|---|---|
| 271 | 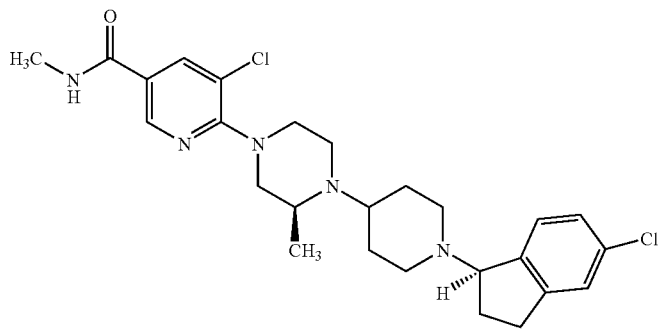 |
| 272 | 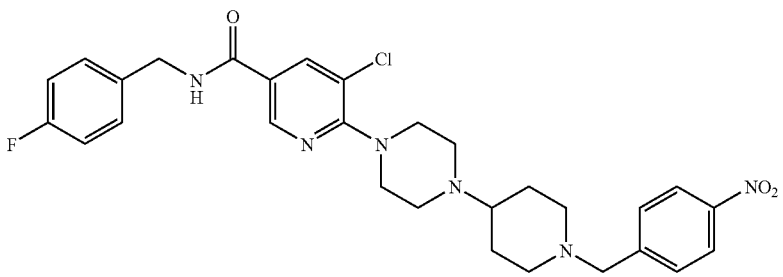 |
| 273 | 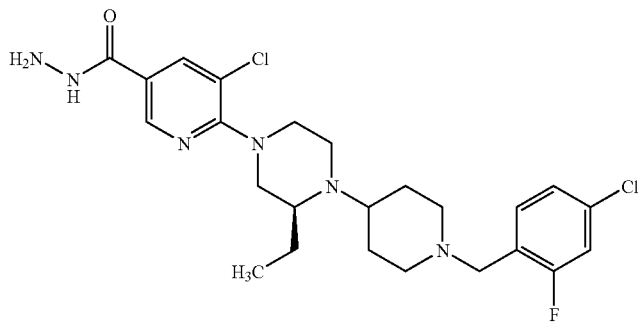 |
| 274 | 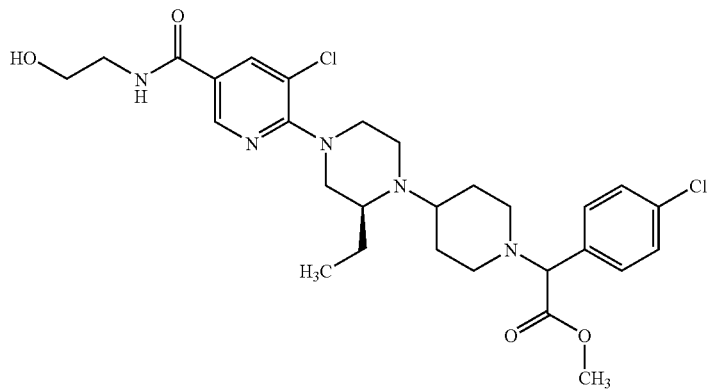 |

-continued
| Compound No. | Compound Structure |
|---|---|
| 275 | 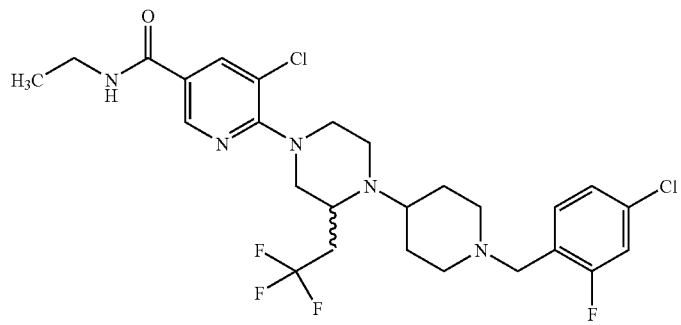 |
| 276 | 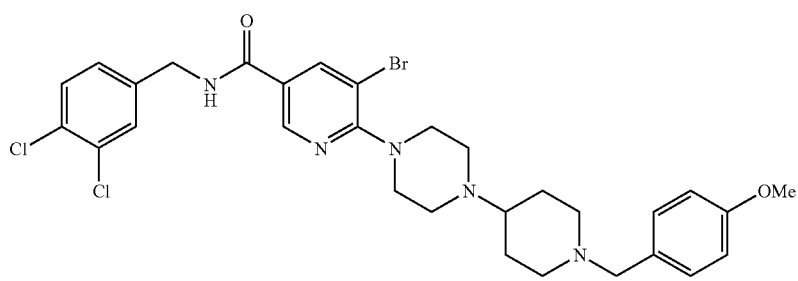 |
| 277 | 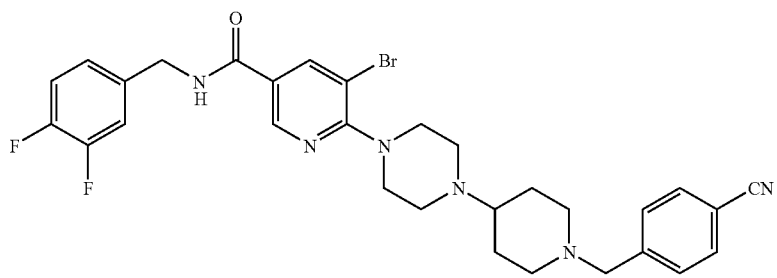 |
| 278 | 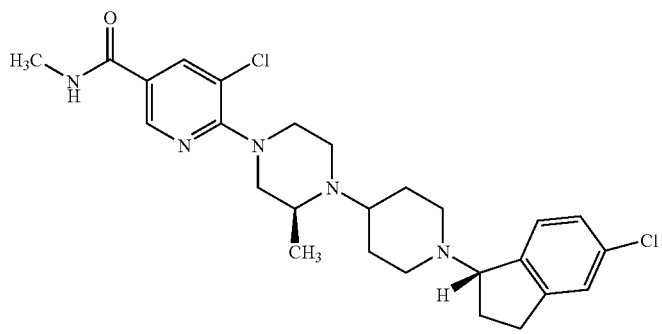 |
| 279 | 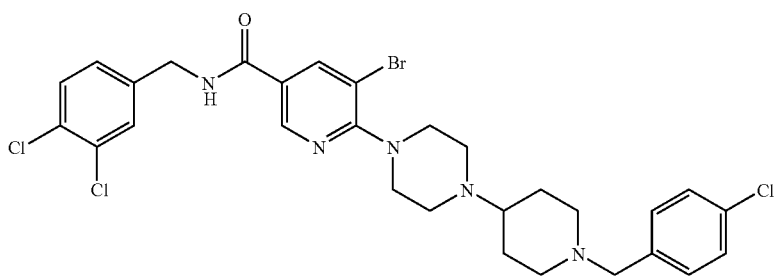 |

-continued
| Compound No. | Compound Structure |
|---|---|
| 280 | 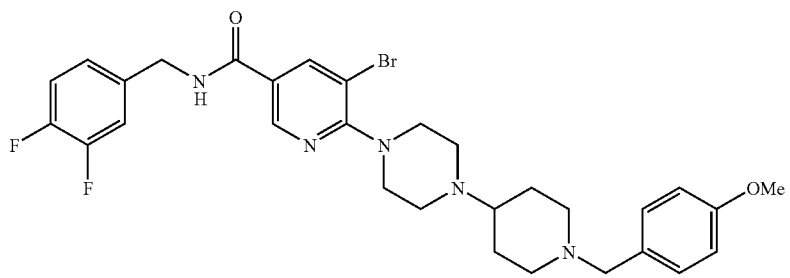 |
| 281 | 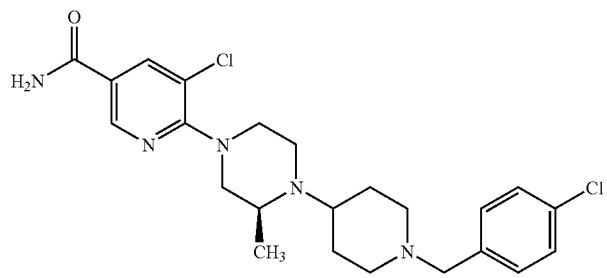 |
| 282 | 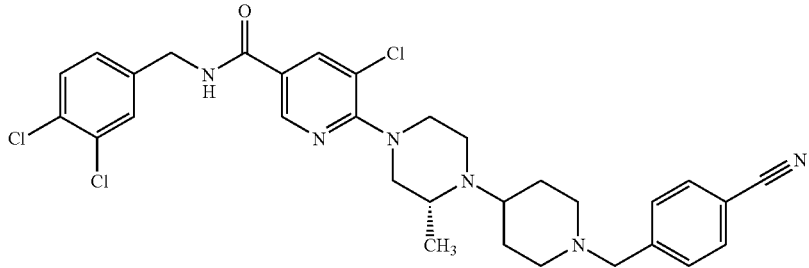 |
| 283 | 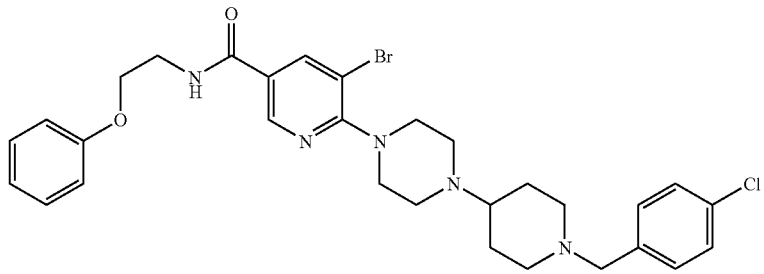 |
| 284 | 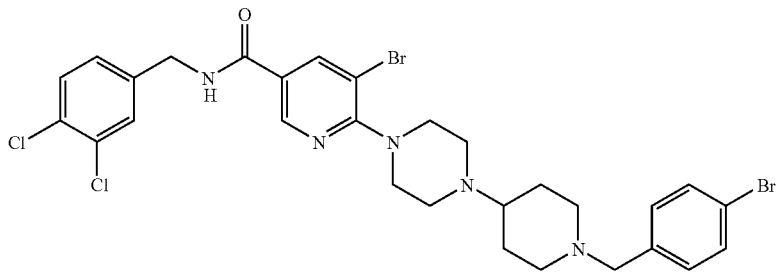 |

-continued
| Compound No. | Compound Structure |
|---|---|
| 285 | 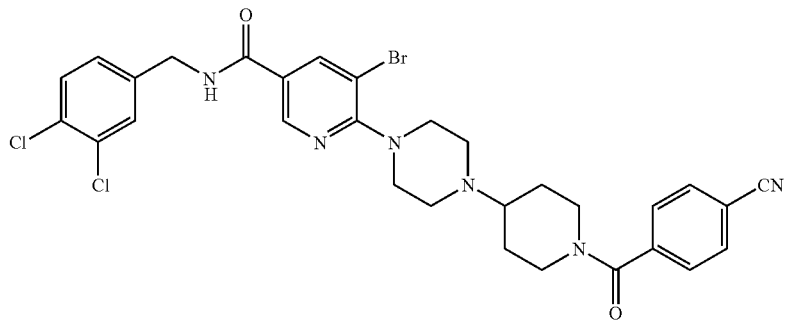 |
| 286 | 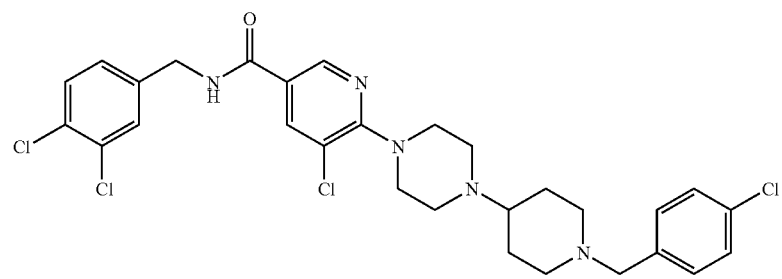 |
| 287 | 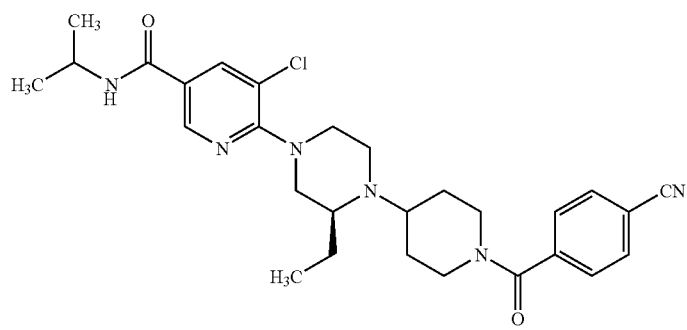 |
| 288 | 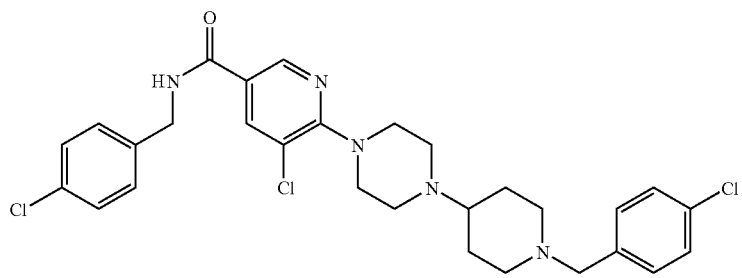 |
| 289 | 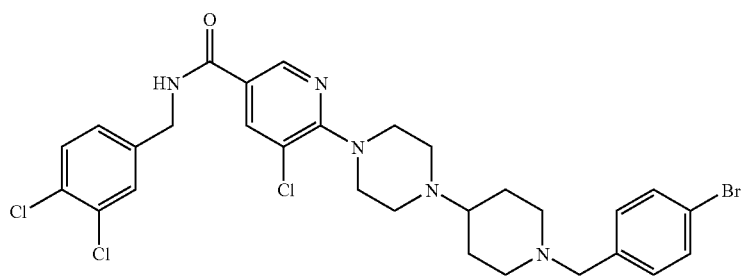 |

-continued
| Compound No. | Compound Structure |
|---|---|
| 290 | 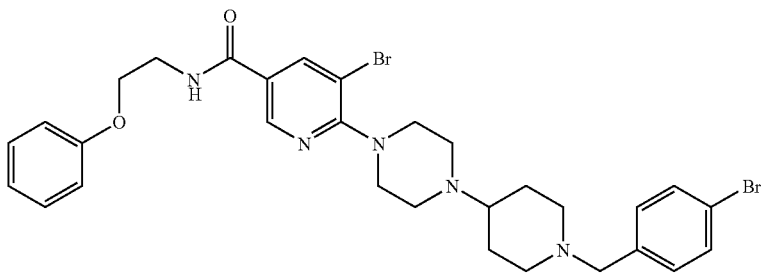 |
| 291 | 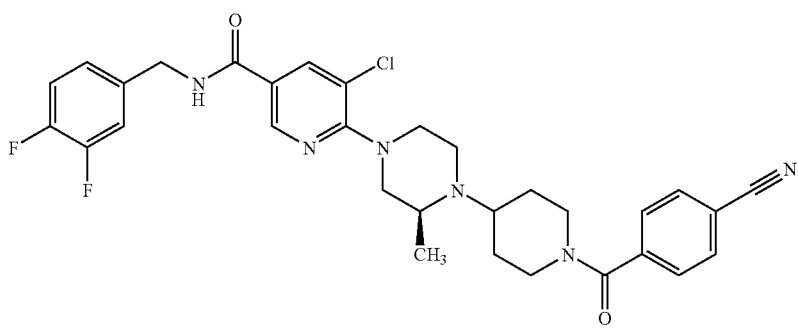 |
| 292 | 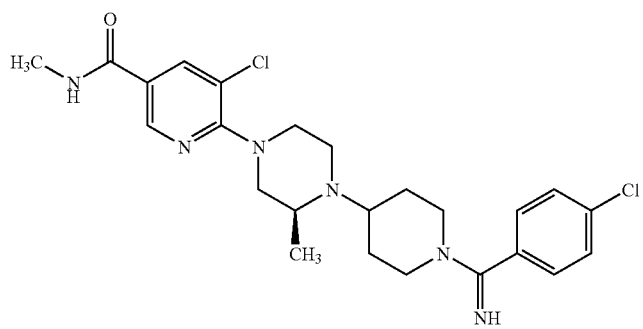 |
| 293 | 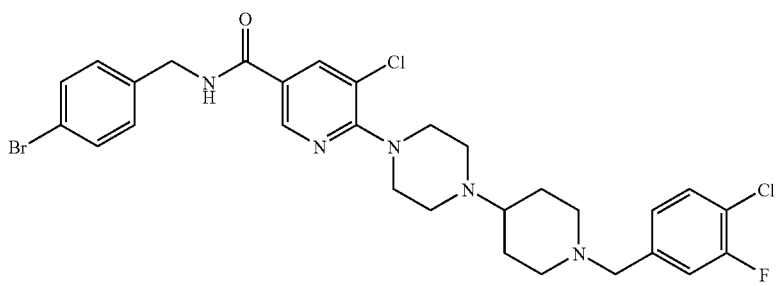 |
| 294 | 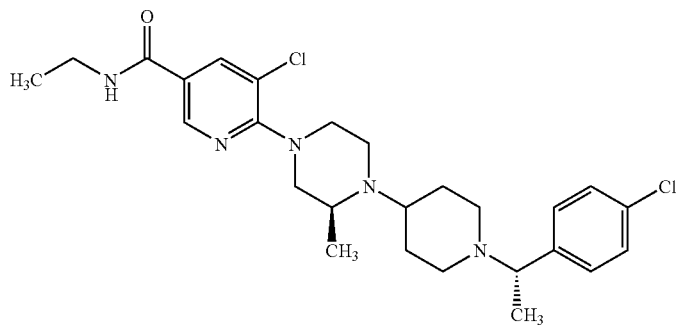 |

-continued
| Compound No. | Compound Structure |
|---|---|
| 295 | 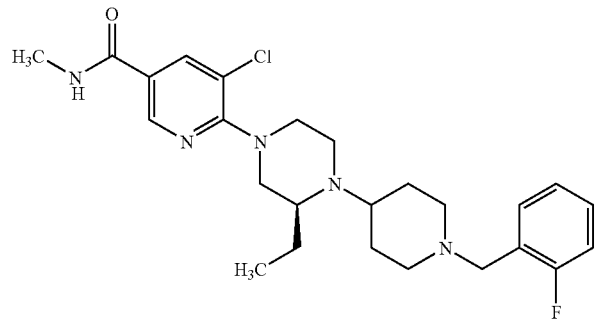 |
| 296 | 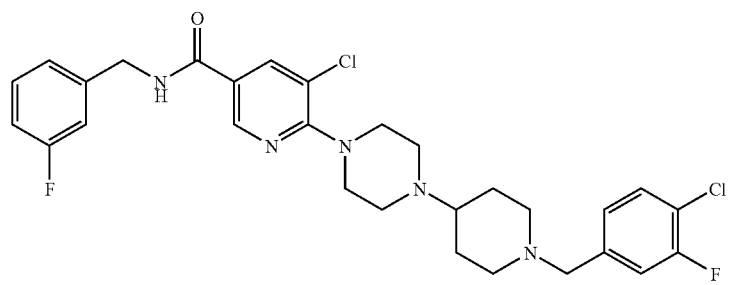 |
| 297 | 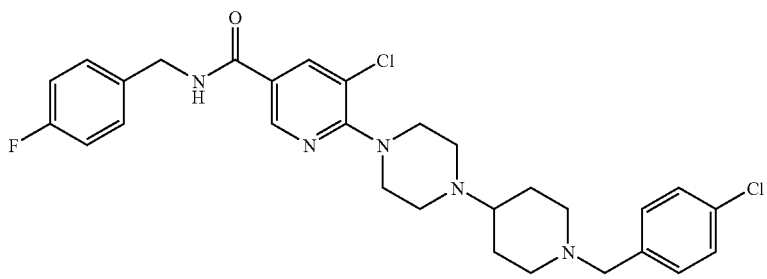 |
| 298 | 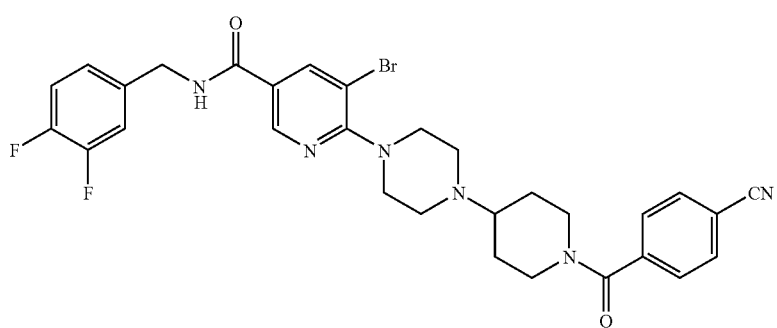 |
| 299 | 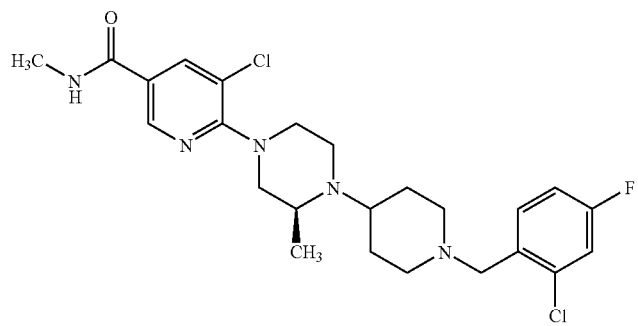 |

| Compound No. | Compound Structure |
|---|---|
| 300 | 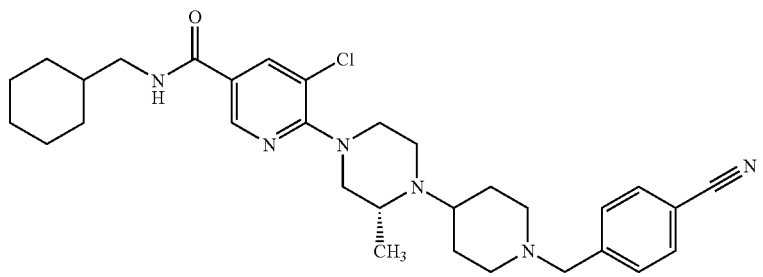 |
| 301 | 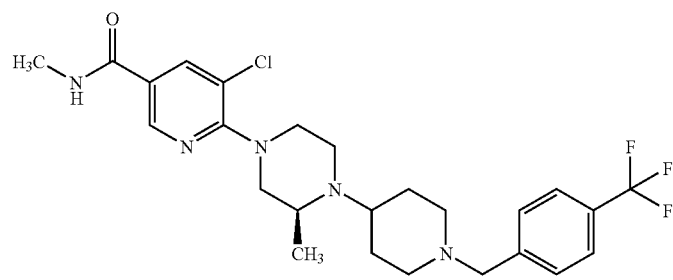 |
| 302 | 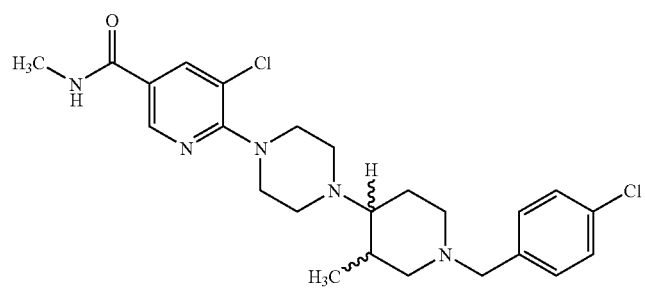 |
| 303 | 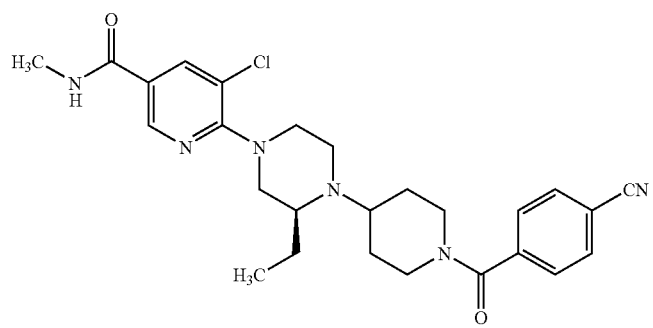 |
| 304 | 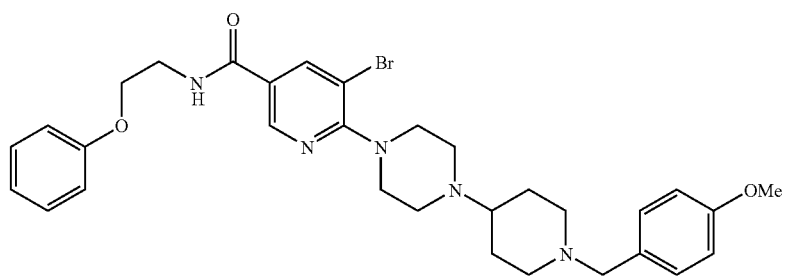 |

-continued
| Compound No. | Compound Structure |
|---|---|
| 305 | 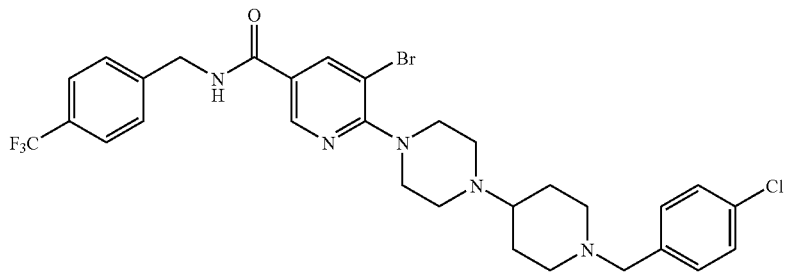 |
| 306 | 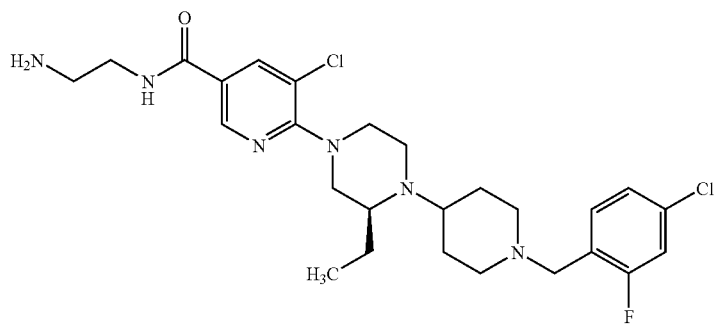 |
| 307 | 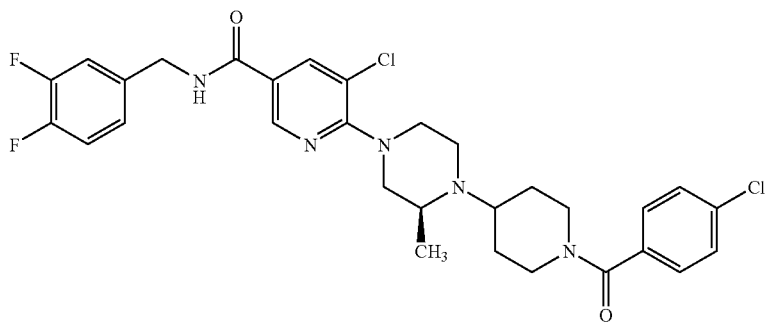 |
| 308 | 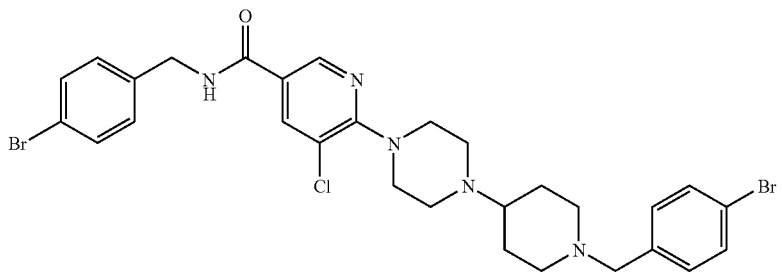 |
| 309 | 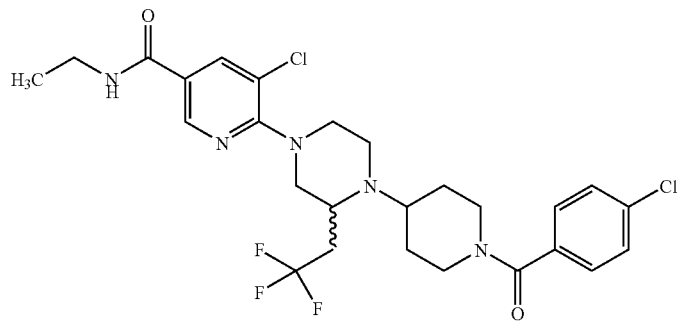 |

| Compound No. | Compound Structure |
|---|---|
| 310 | 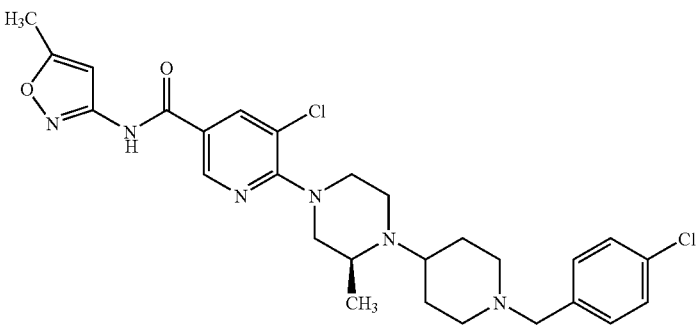 |
| 311 | 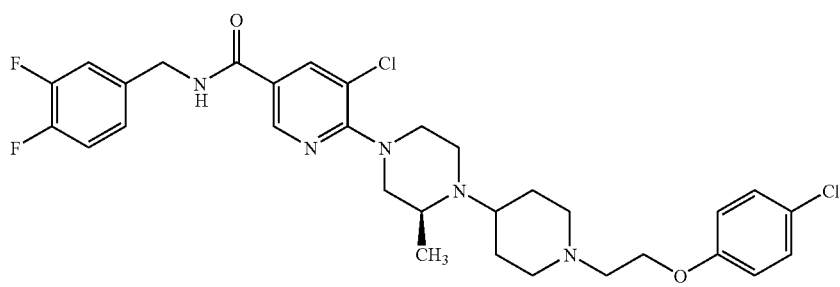 |
| 312 | 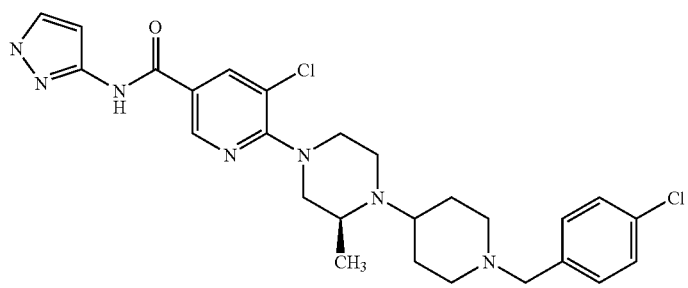 |
| 313 | 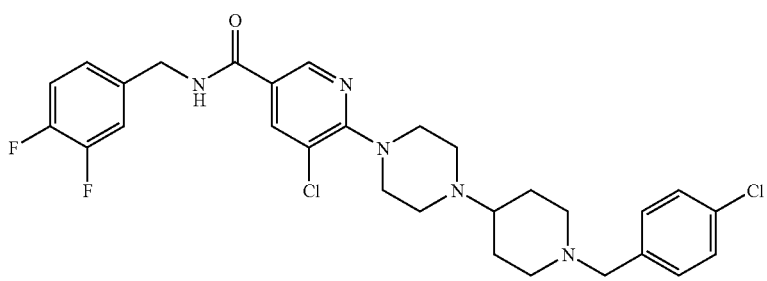 |
| 314 | 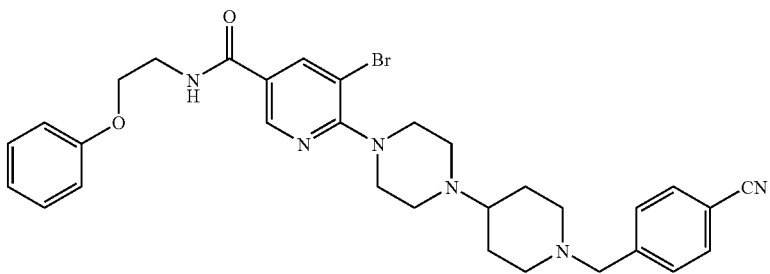 |

-continued

| Compound No. | Compound Structure |
|---|---|
| 315 | 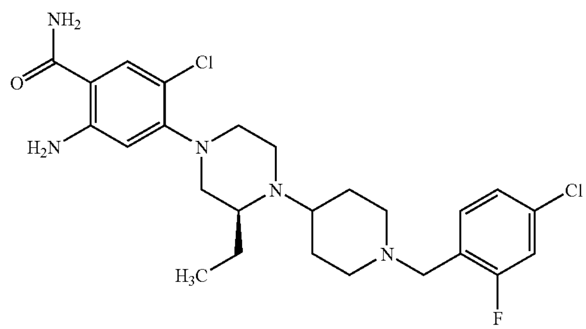 |
| 316 | 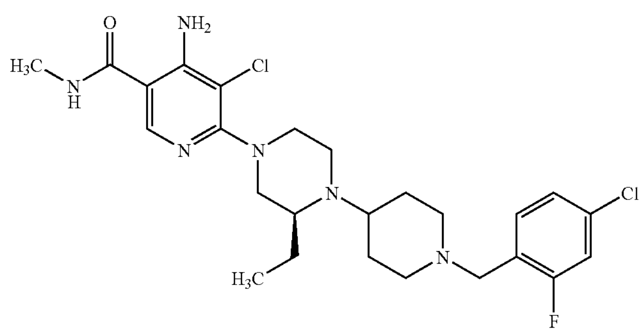 |
| 317 | 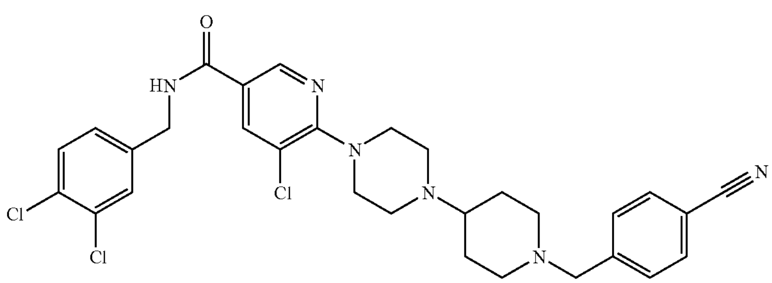 |
| 318 | 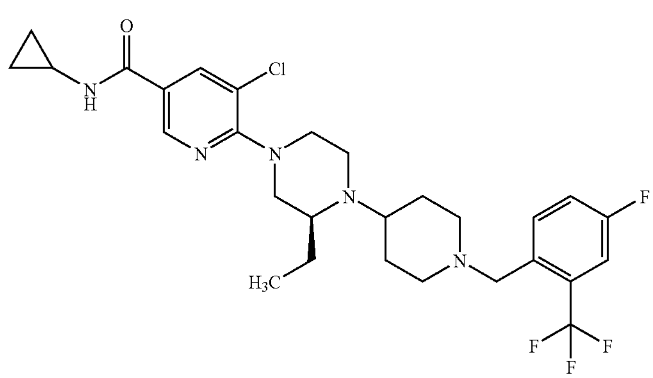 |

| Compound No. | Compound Structure |
|---|---|
| 319 | 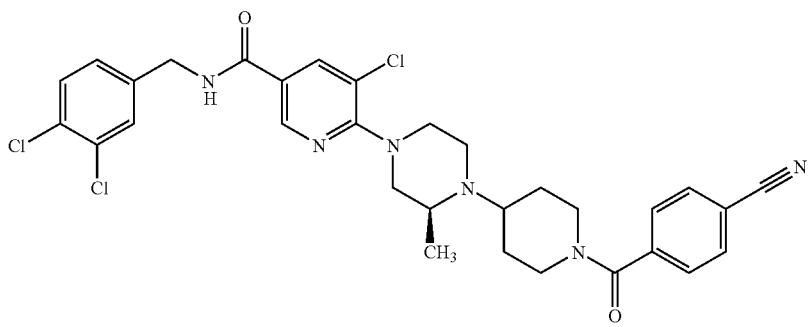 |
| 320 | 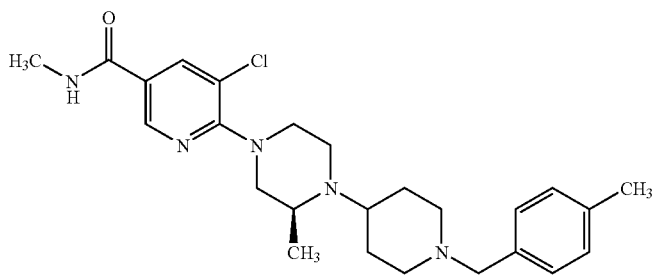 |
| 321 | 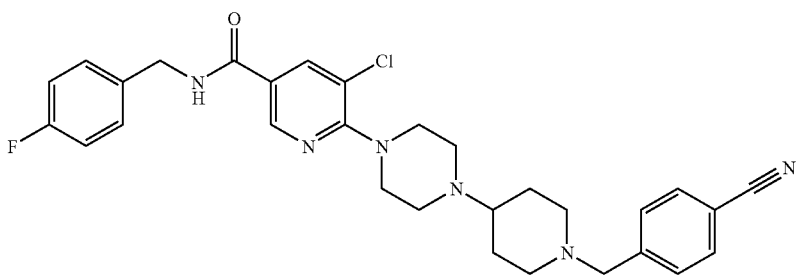 |
| 322 | 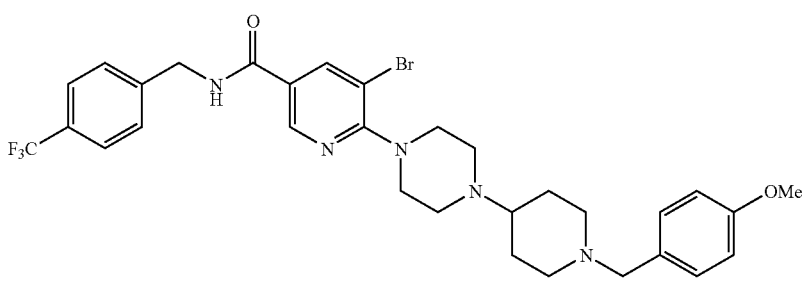 |
| 323 | 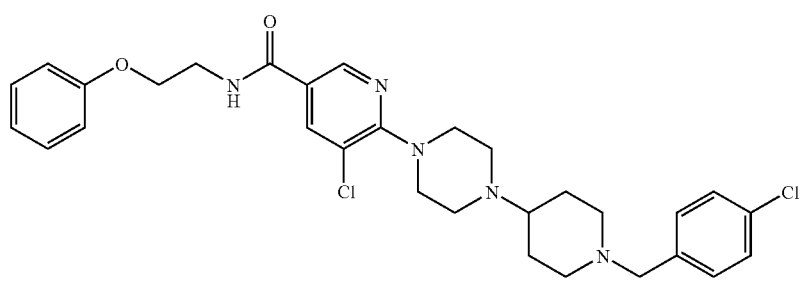 |

-continued
| Compound No. | Compound Structure |
|---|---|
| 324 | 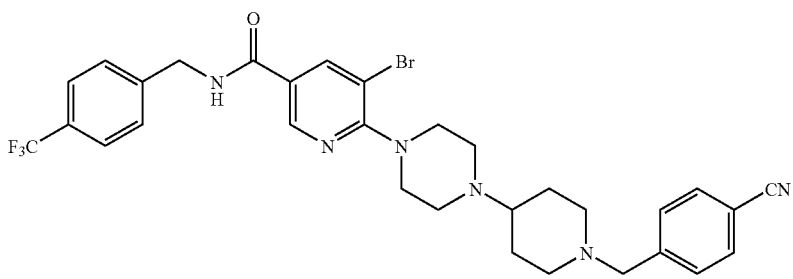 |
| 325 | 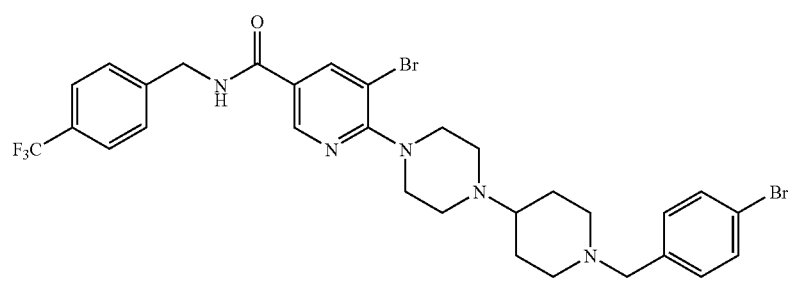 |
| 326 | 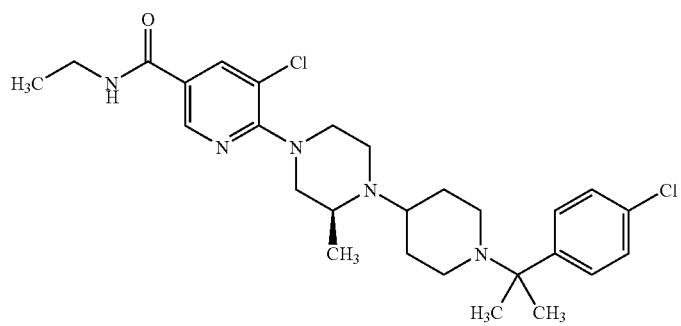 |
| 327 | 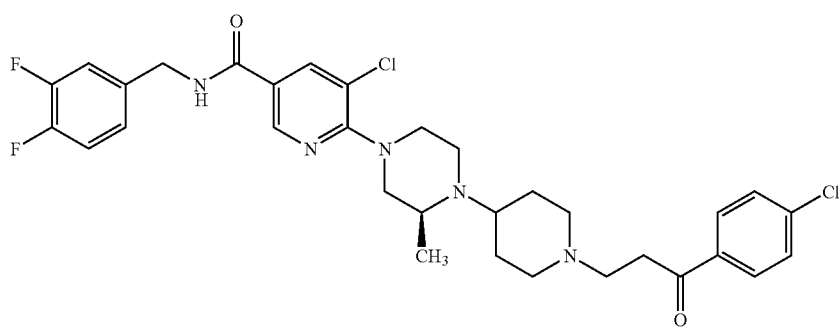 |
| 328 | 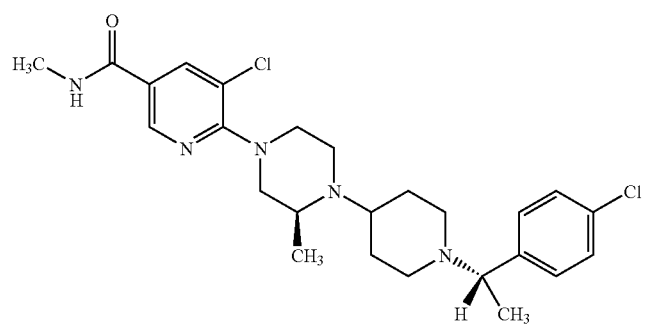 |

| Compound No. | Compound Structure |
|---|---|
| 329 | 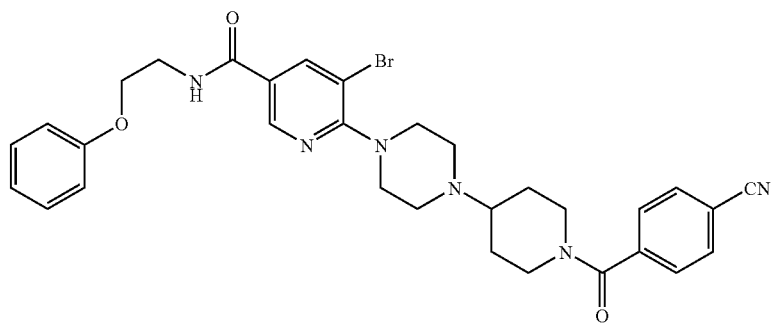 |
| 330 | 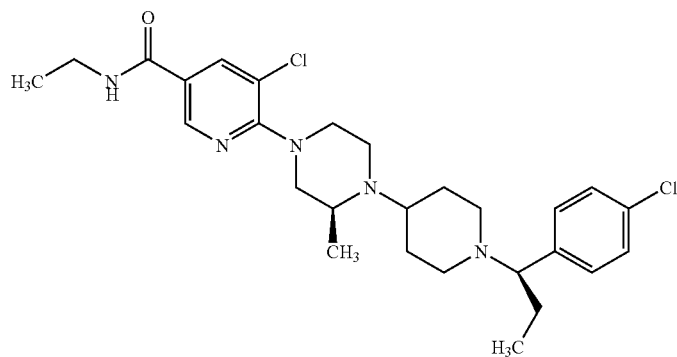 |
| 331 | 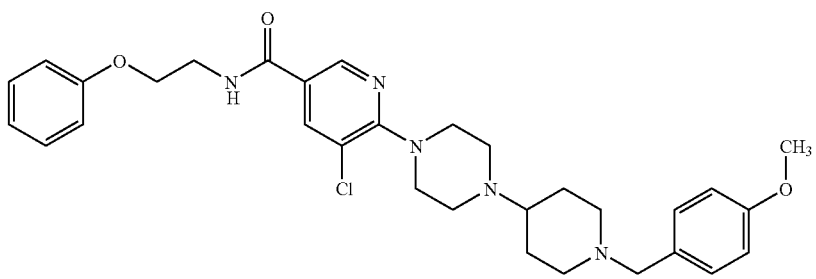 |
| 332 | 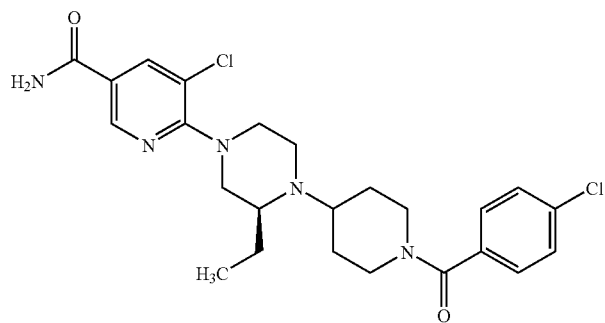 |

| Compound No. | Compound Structure |
|---|---|
| 333 | 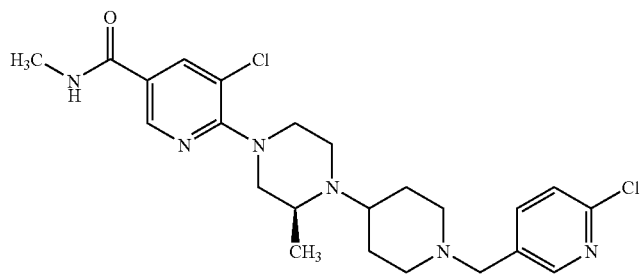 |
| 334 | 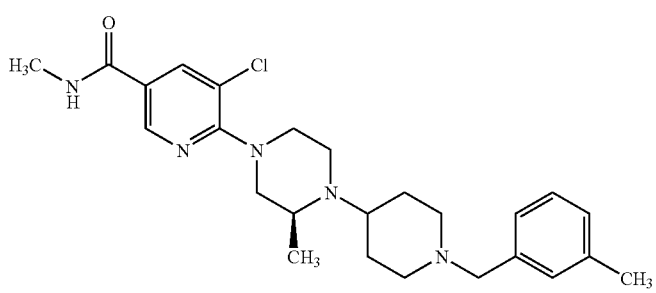 |
| 335 | 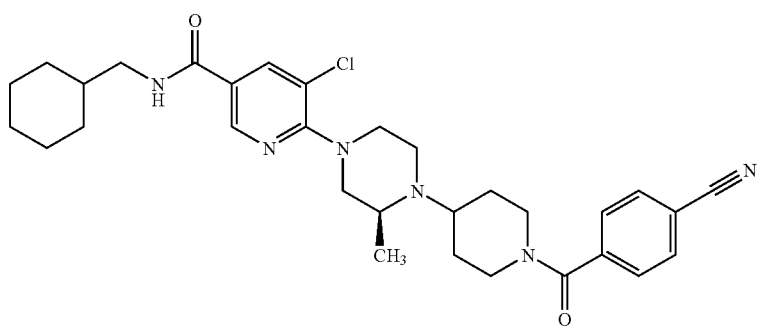 |
| 336 | 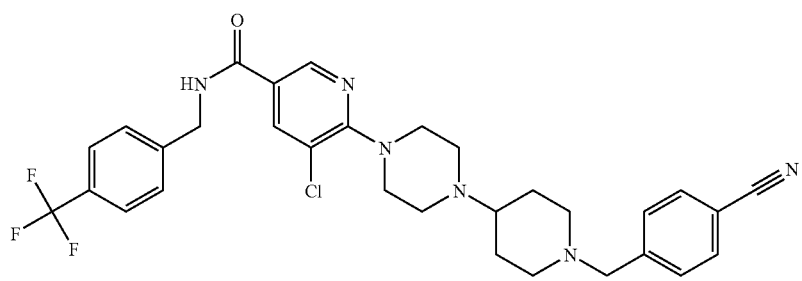 |
| 337 | 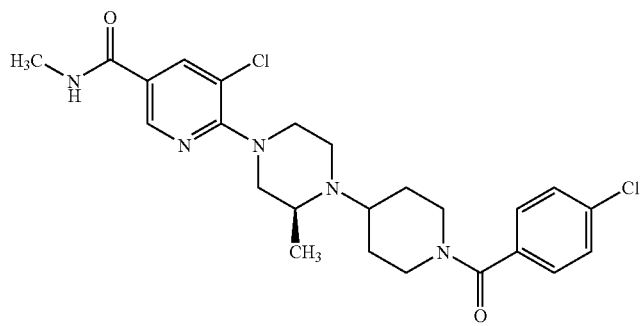 |

| Compound No. | Compound Structure |
|---|---|
| 338 | 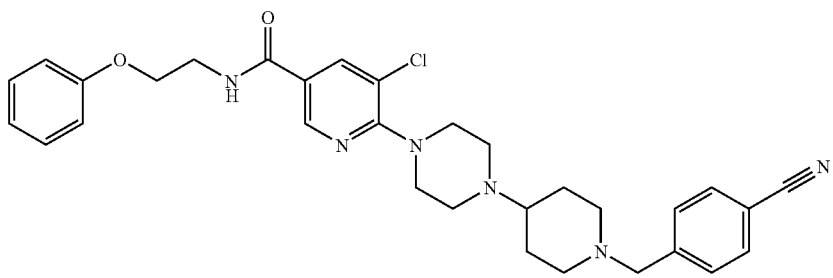 |
| 339 | 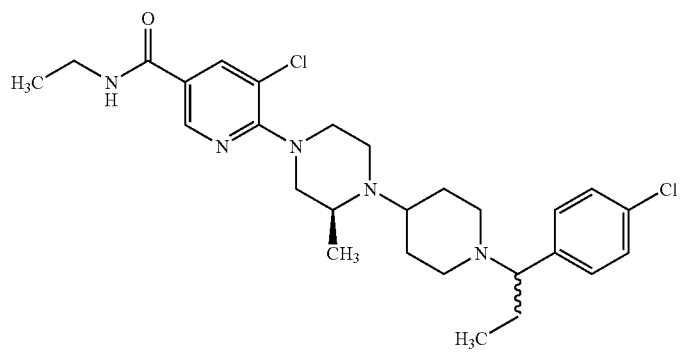 |
| 340 | 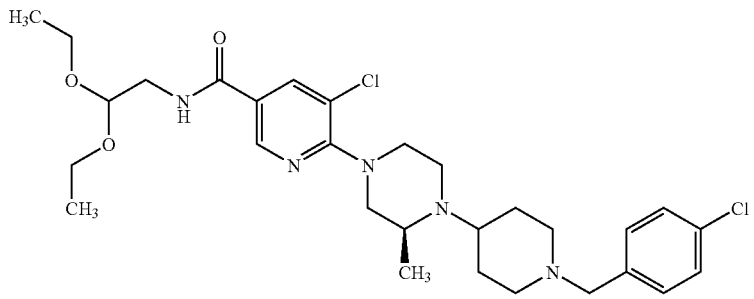 |
| 341 | 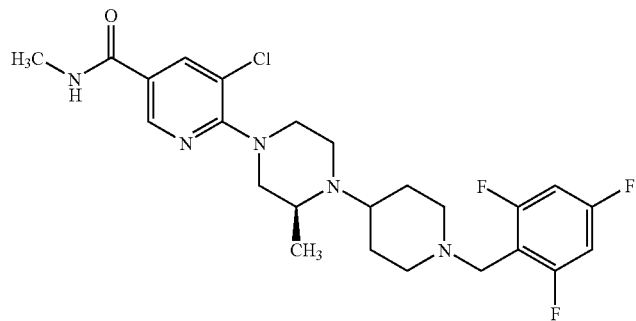 |

-continued

| Compound No. | Compound Structure |
|---|---|
| 342 | 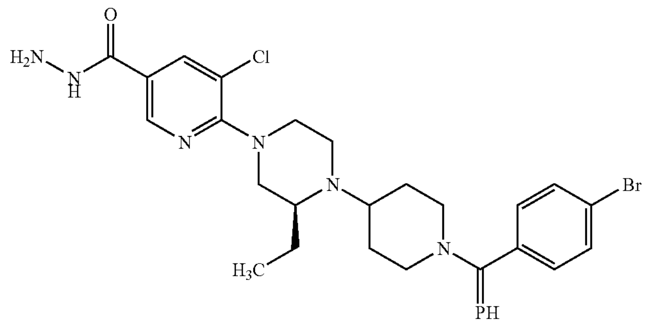 |
| 343 | 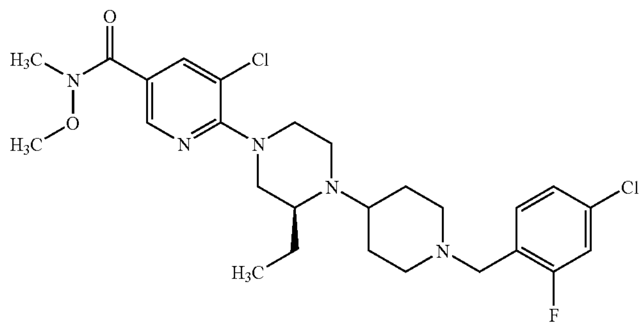 |
| 344 | 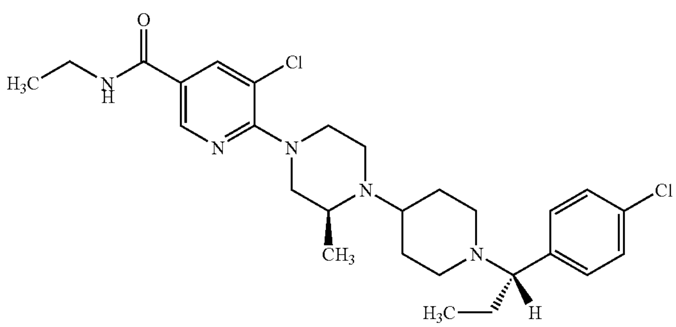 |
| 345 | 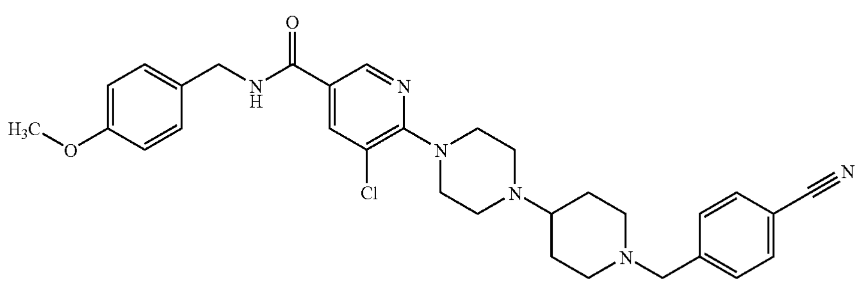 |
| 346 | 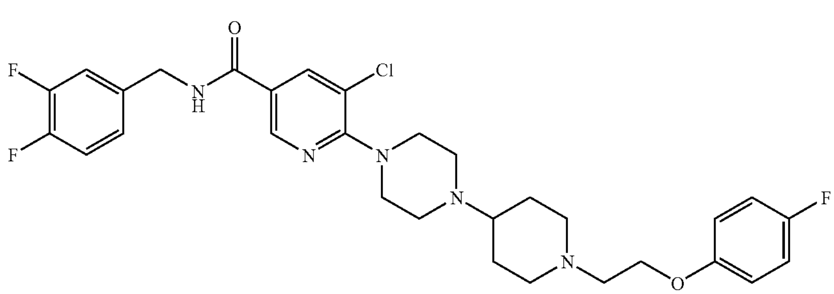 |

-continued
| Compound No. | Compound Structure |
|---|---|
| 347 | 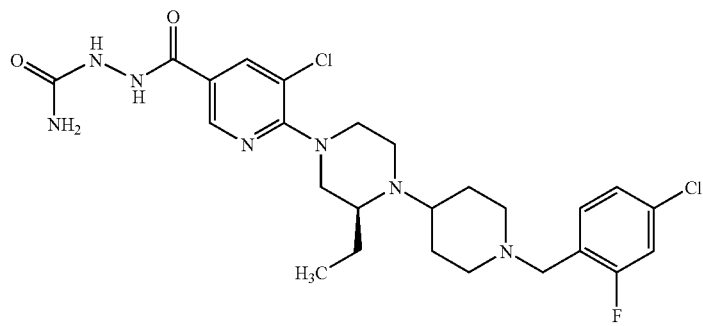 |
| 348 | 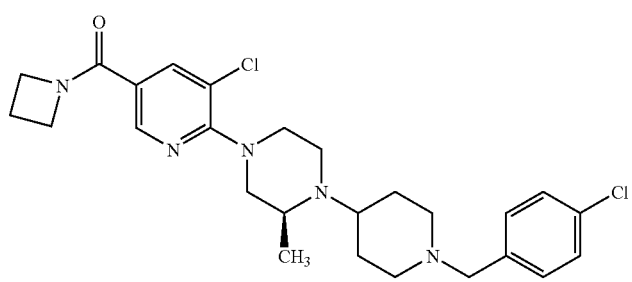 |
| 349 | 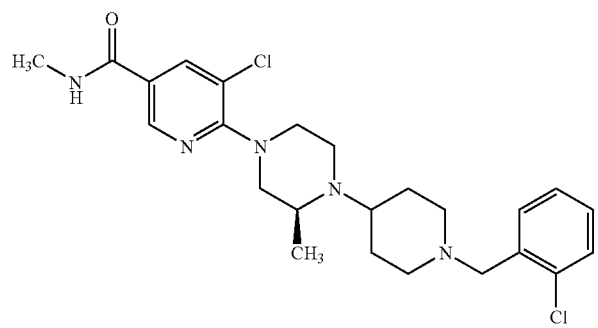 |
| 350 | 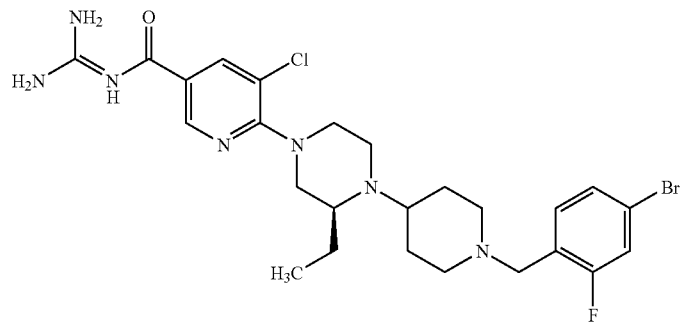 |

-continued
| Compound No. | Compound Structure |
|---|---|
| 351 | 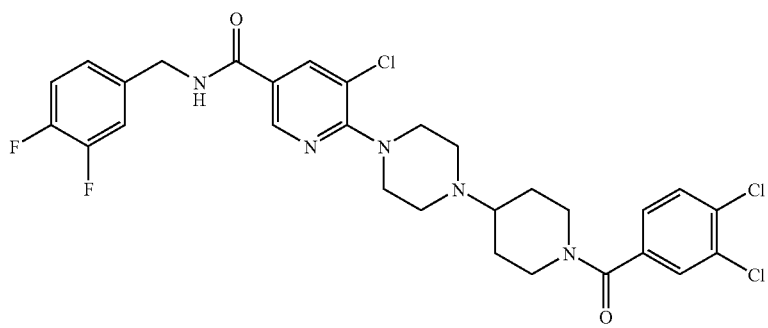 |
| 352 | 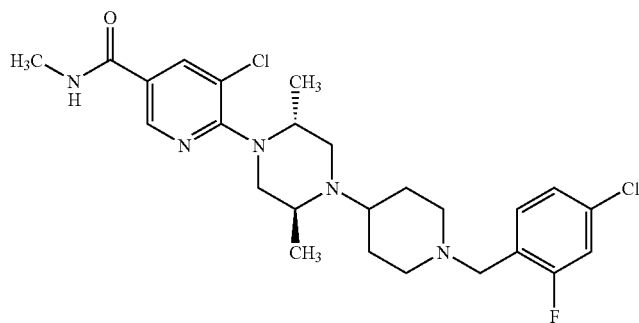 |
| 353 | 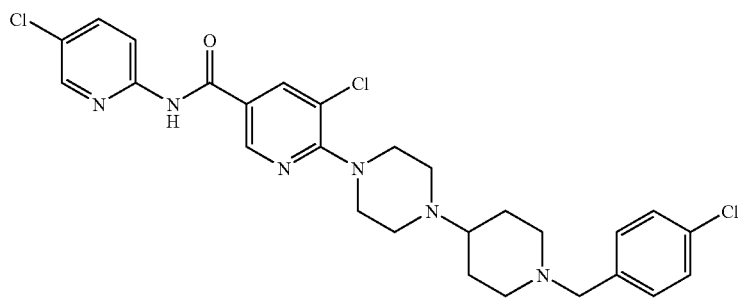 |
| 354 | 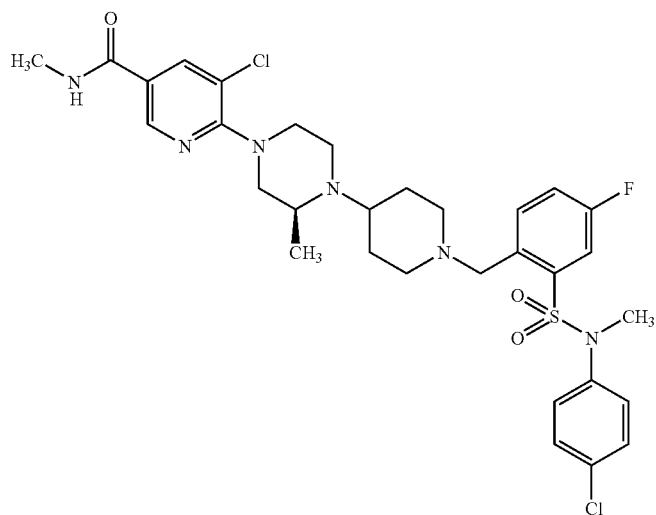 |

| Compound No. | Compound Structure |
|---|---|
| 355 | 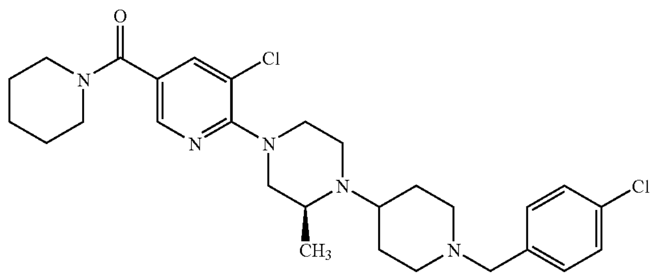 |
| 356 | 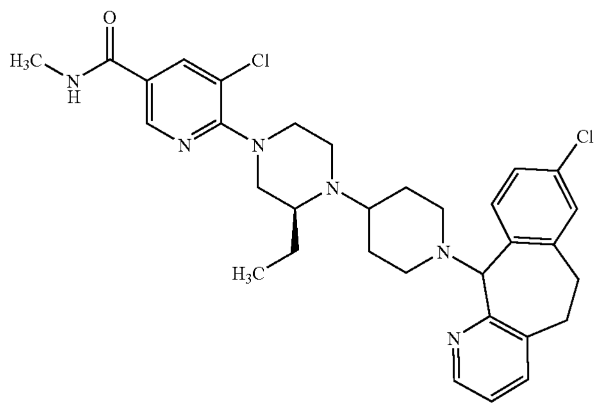 |
| 357 | 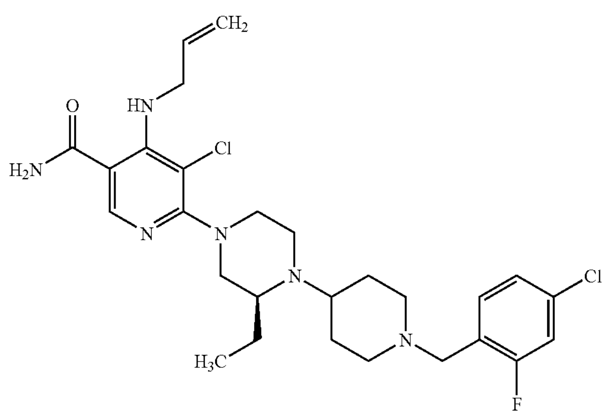 |
| 358 | 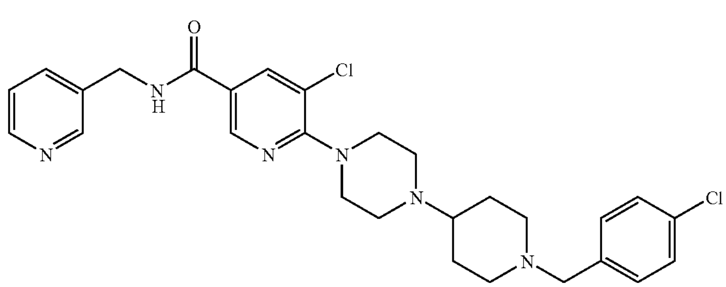 |

-continued
| Compound No. | Compound Structure |
|---|---|
| 359 | 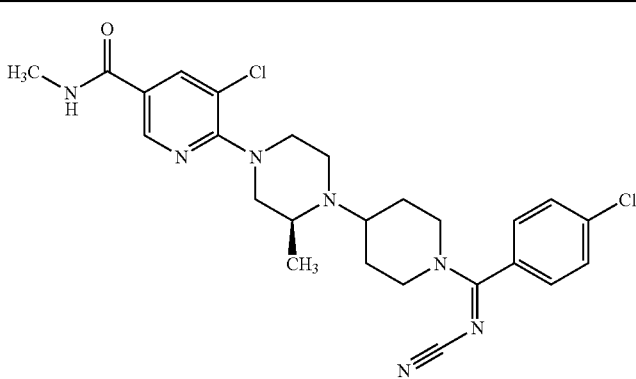 |
| 360 | 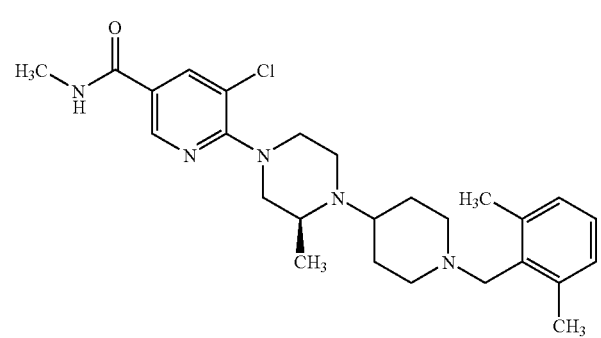 |
| 361 | 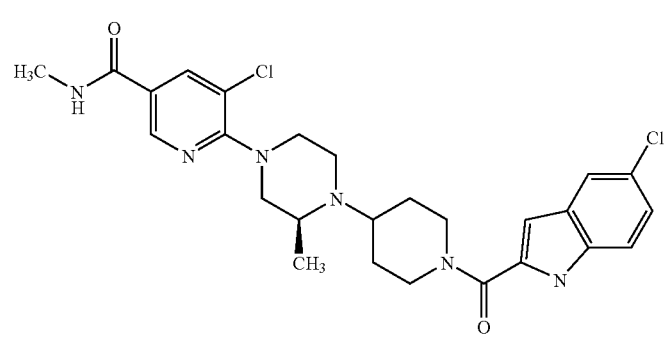 |
| 362 | 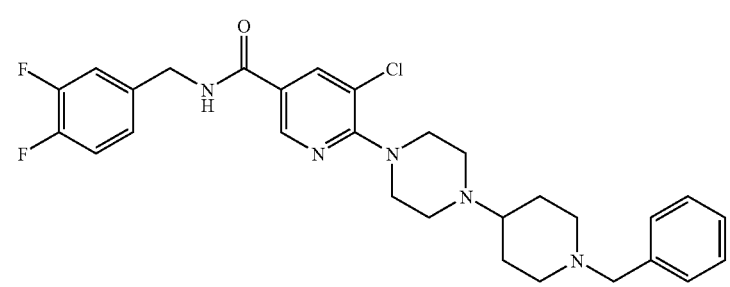 |

-continued
| Compound No. | Compound Structure |
|---|---|
| 363 | 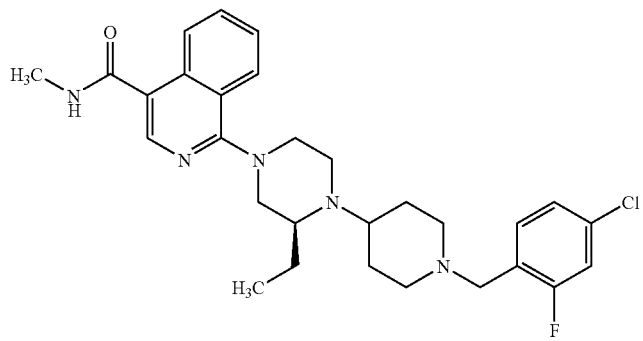 |
| 364 | 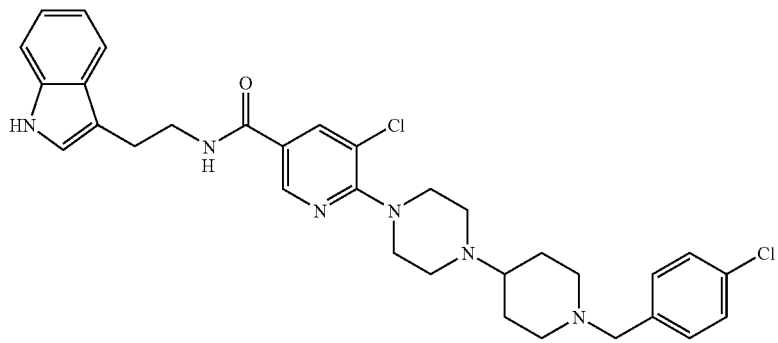 |
| 365 | 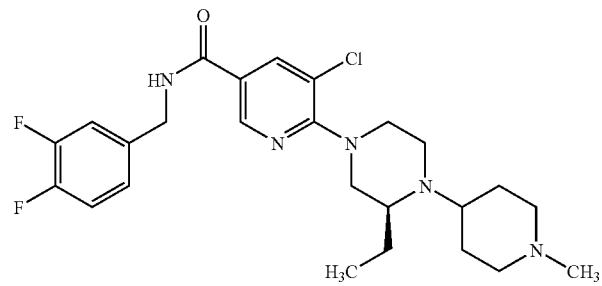 |
| 366 | 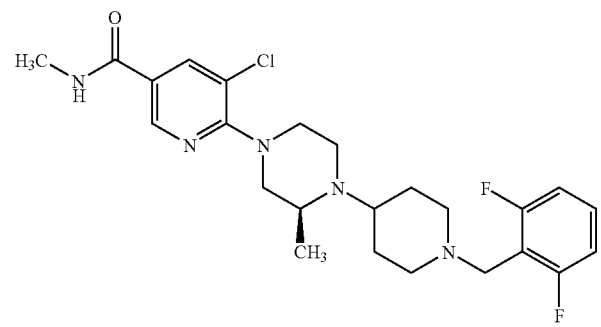 |

-continued
| Compound No. | Compound Structure |
|---|---|
| 367 | 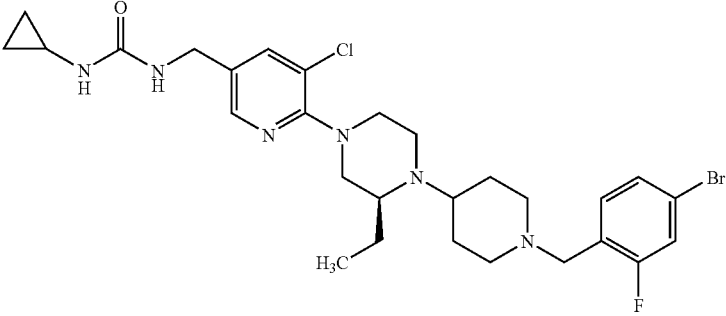 |
| 368 | 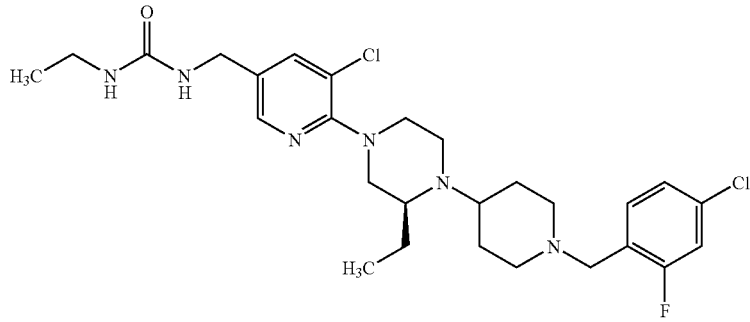 |
| 369 | 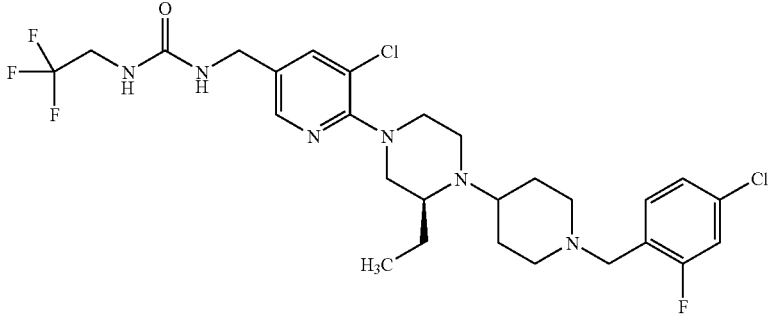 |
| 370 | 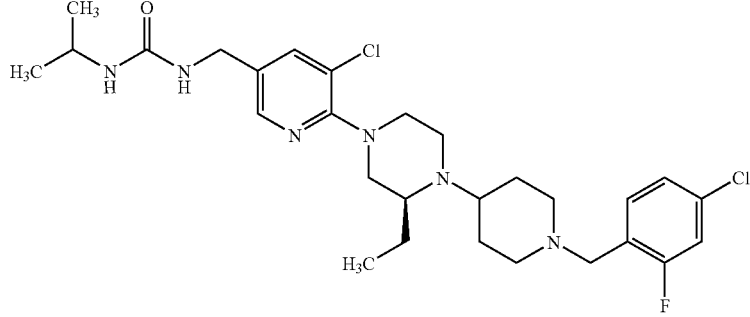 |

| Compound No. | Compound Structure |
|---|---|
| 371 | 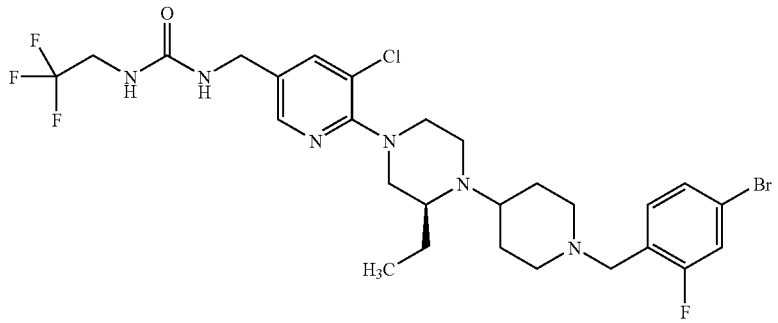 |
| 372 | 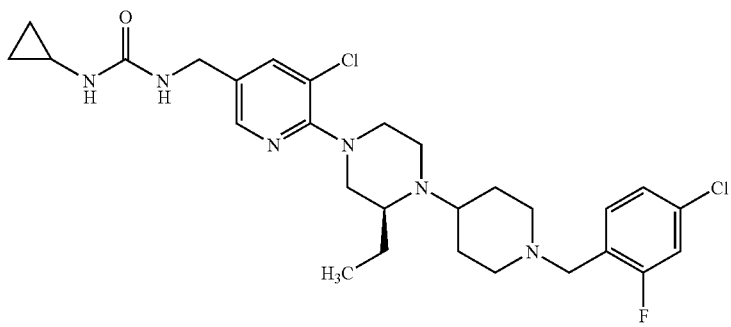 |
| 373 | 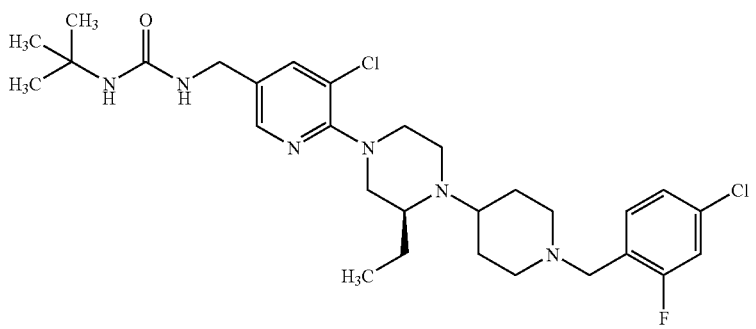 |
| 374 | 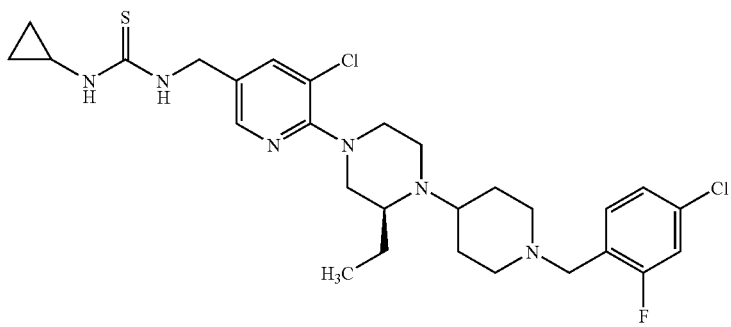 |
| 375 | 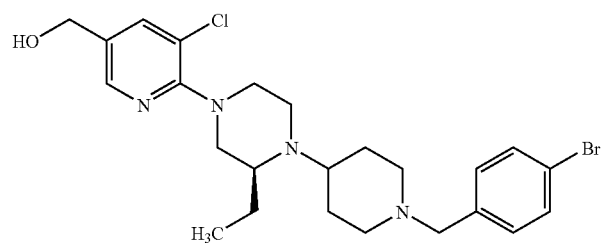 |

| Compound No. | Compound Structure |
|---|---|
| 376 | 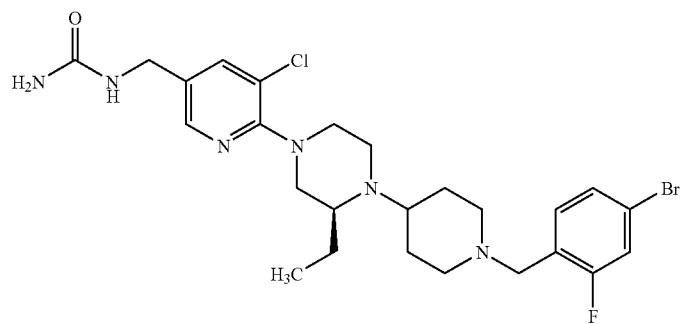 |
| 377 | 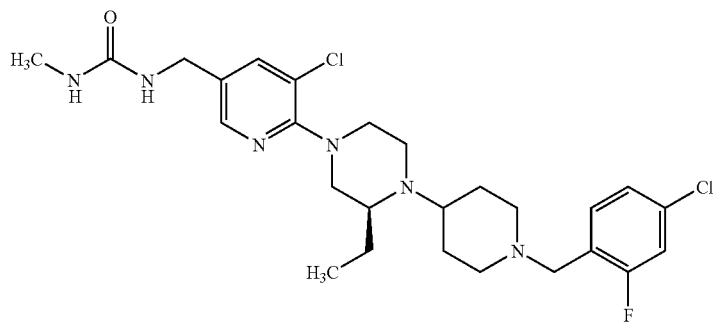 |
| 378 | 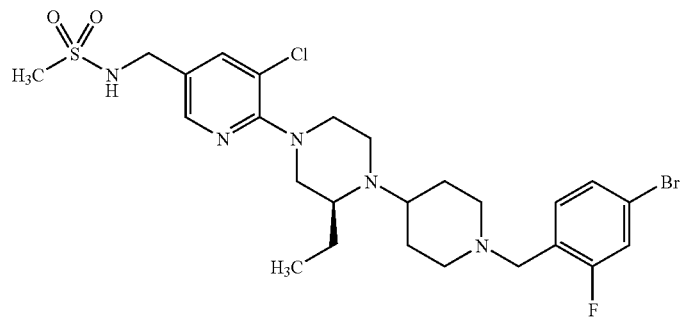 |
| 379 | 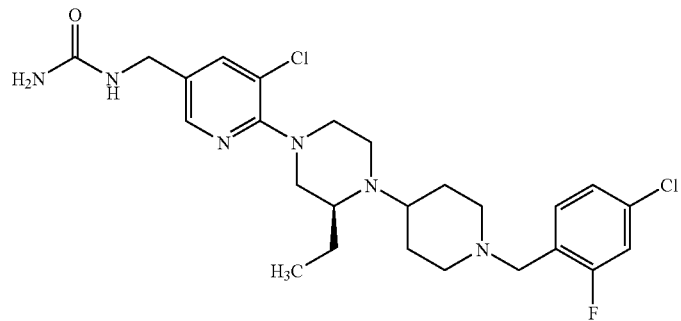 |

-continued
| Compound No. | Compound Structure |
|---|---|
| 380 | 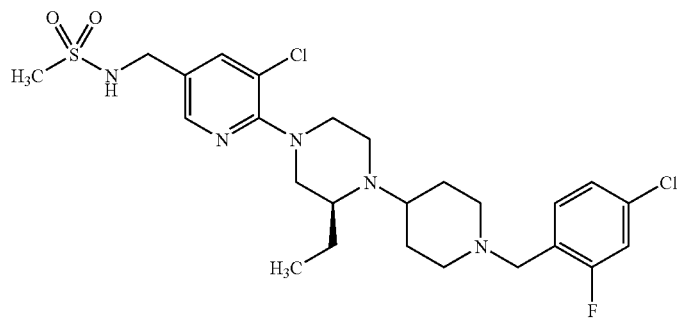 |
| 381 | 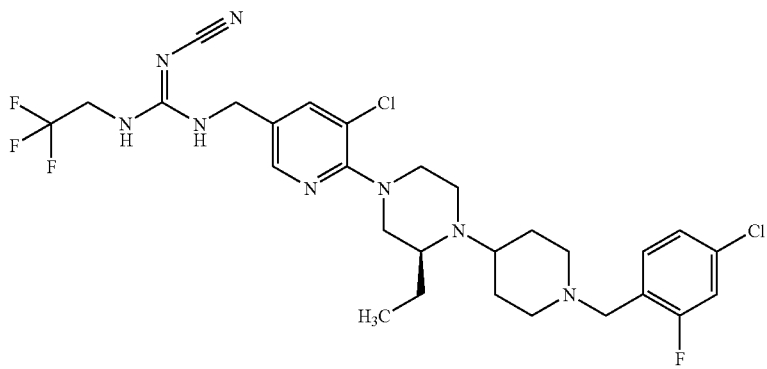 |
| 382 | 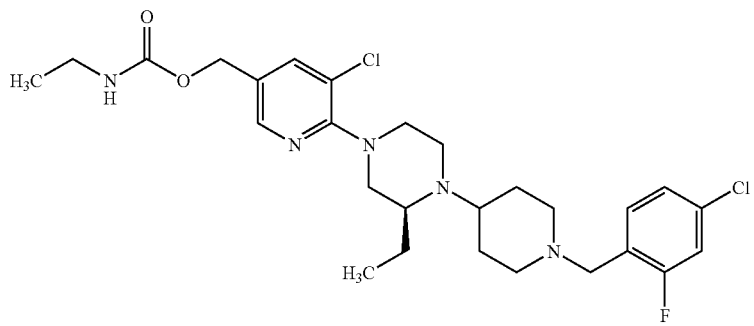 |
| 383 | 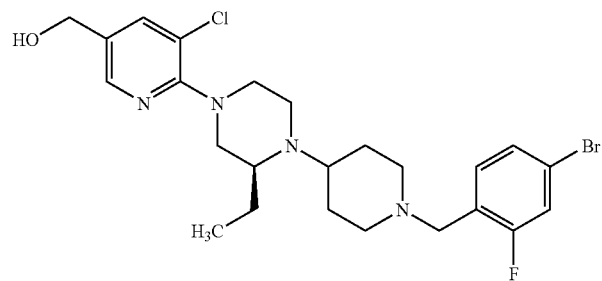 |

-continued
| Compound No. | Compound Structure |
|---|---|
| 384 | 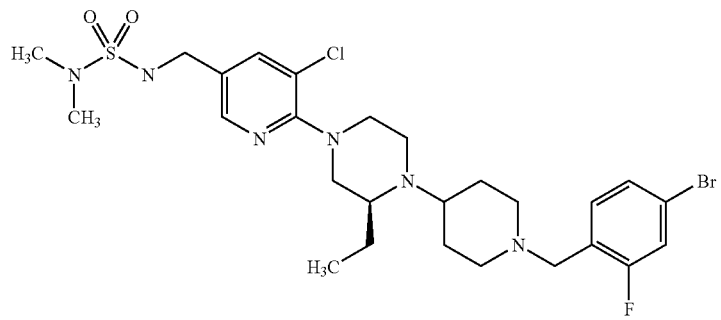 |
| 385 | 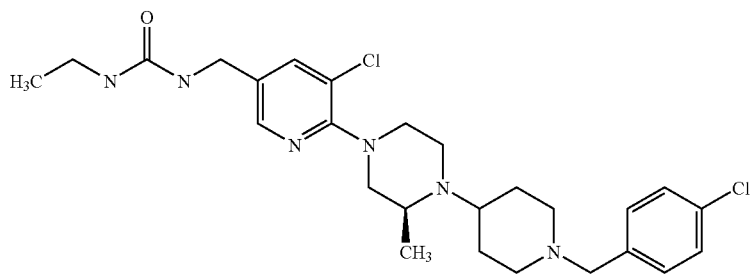 |
| 386 | 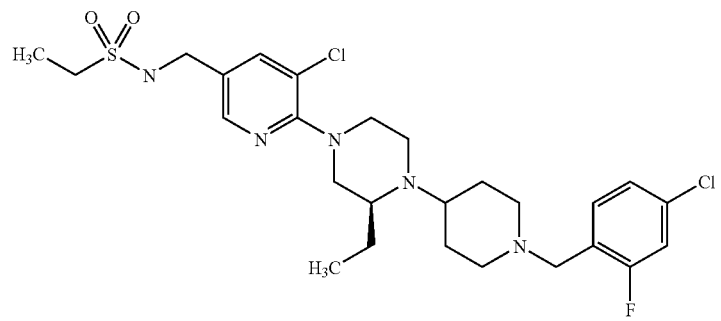 |
| 387 | 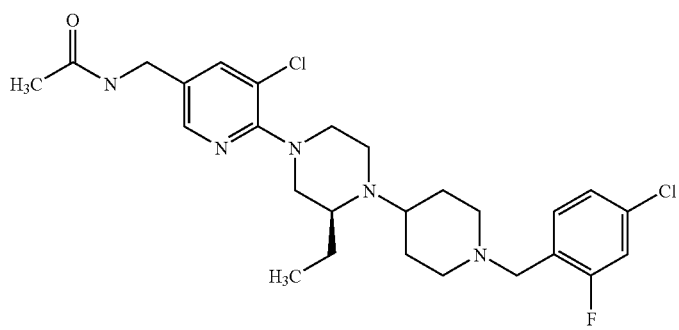 |
| 388 | 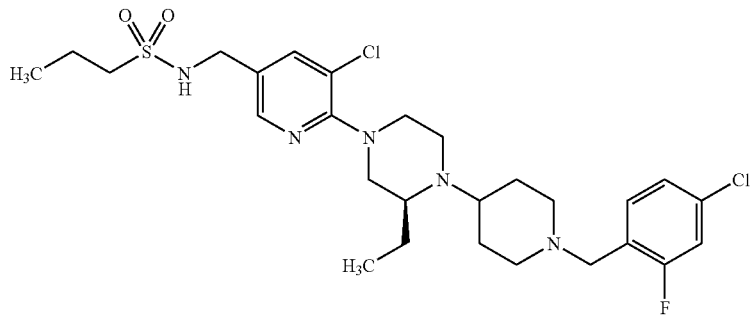 |

-continued
| Compound No. | Compound Structure |
|---|---|
| 389 | 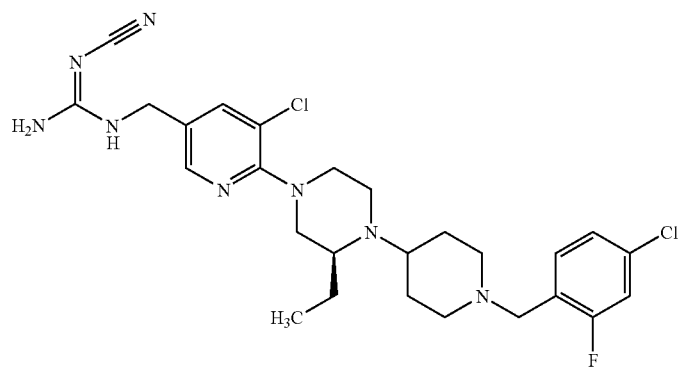 |
| 390 | 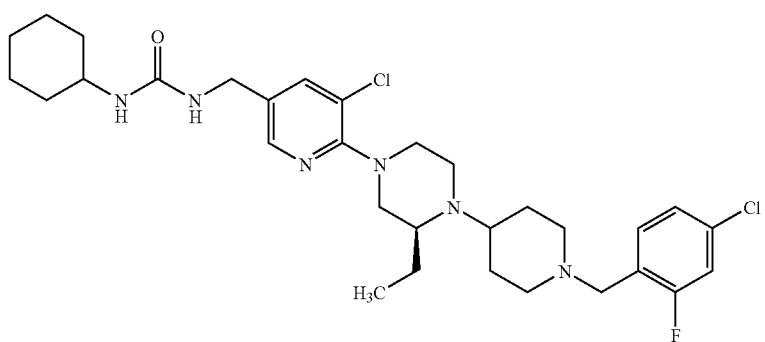 |
| 391 | 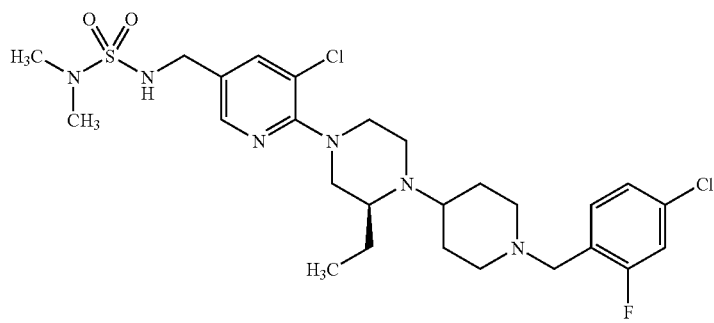 |
| 392 | 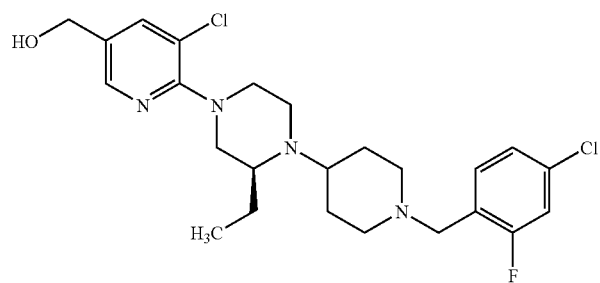 |

-continued

| Compound No. | Compound Structure |
|---|---|
| 393 | 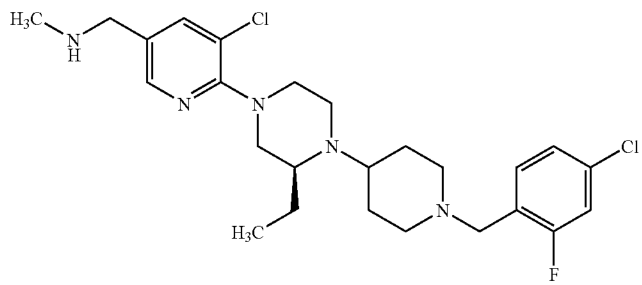 |
| 394 | 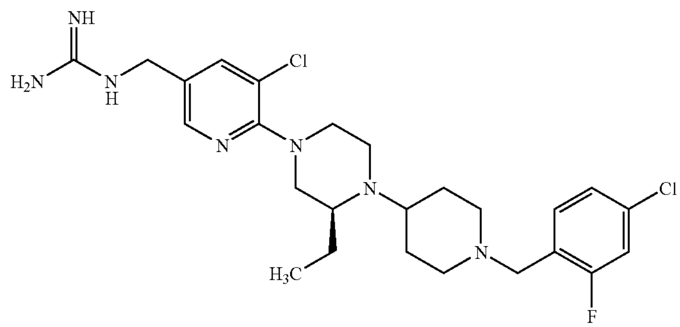 |
| 395 | 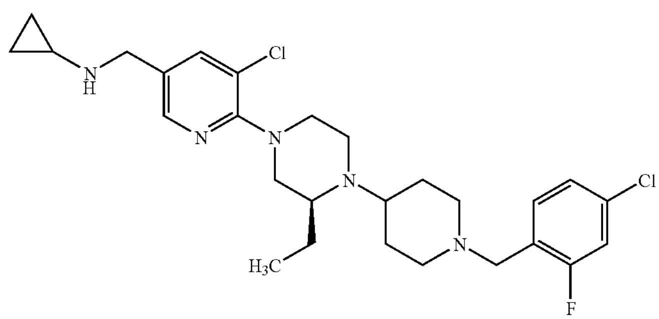 |
| 396 | 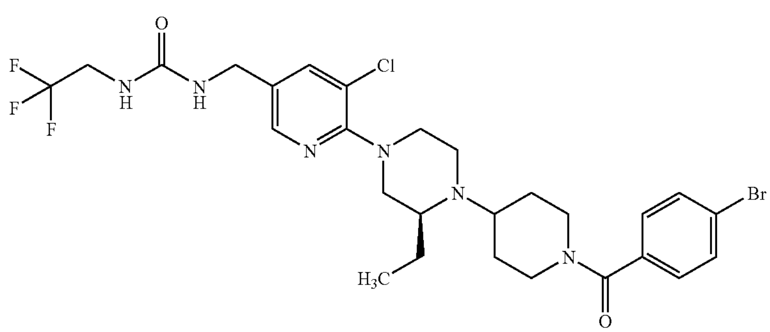 |
| 397 | 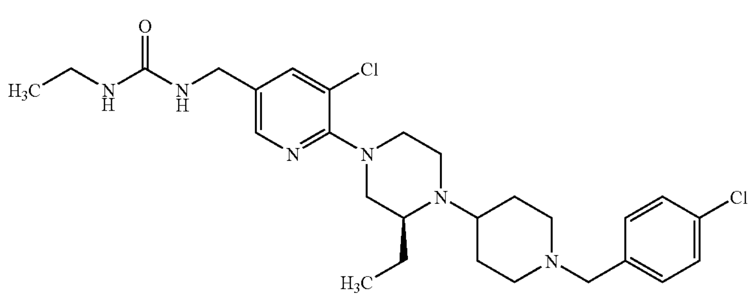 |

-continued
| Compound No. | Compound Structure |
|---|---|
| 399 | 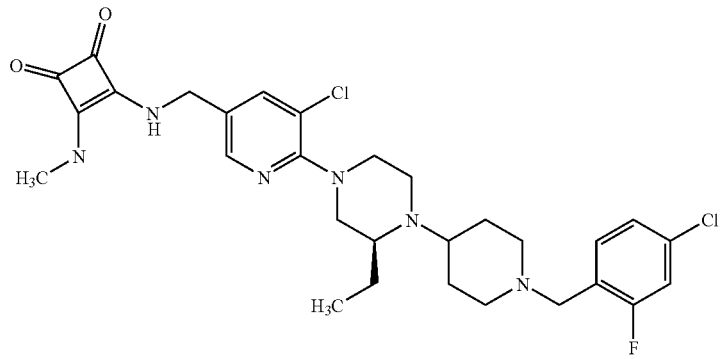 |
| 399 | 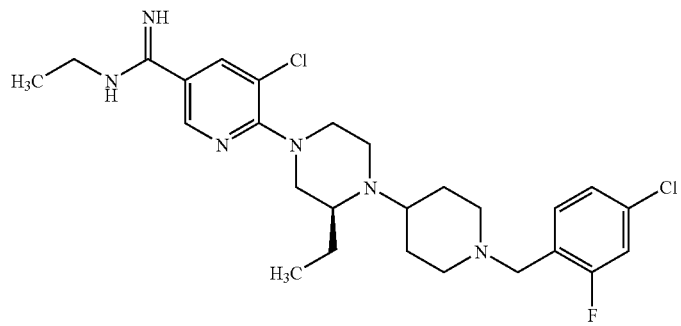 |
| 400 | 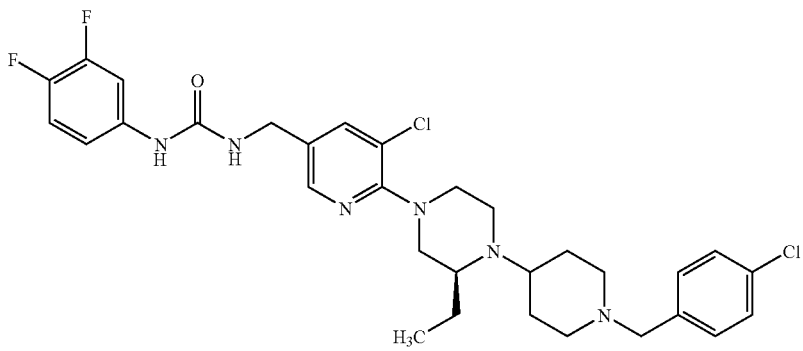 |
| 401 | 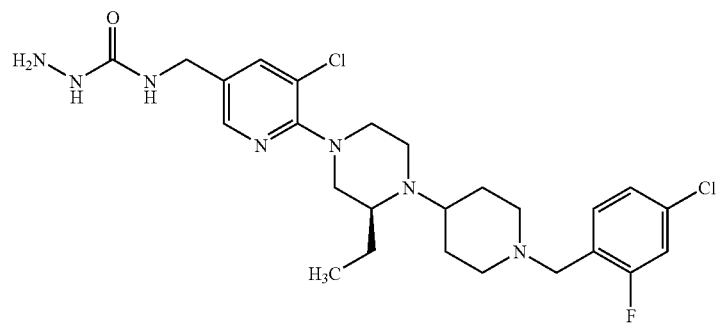 |

| Compound No. | Compound Structure |
|---|---|
| 402 | 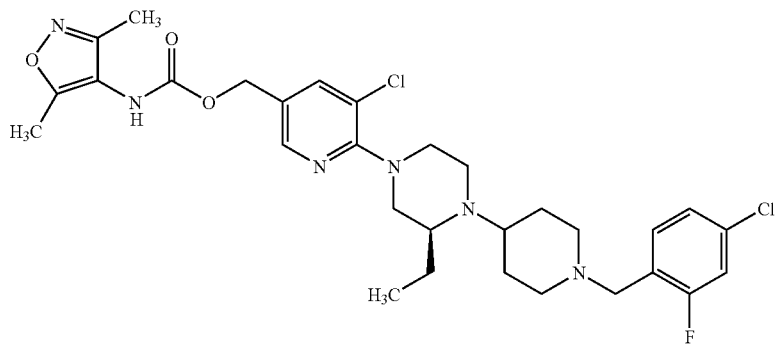 |
| 403 | 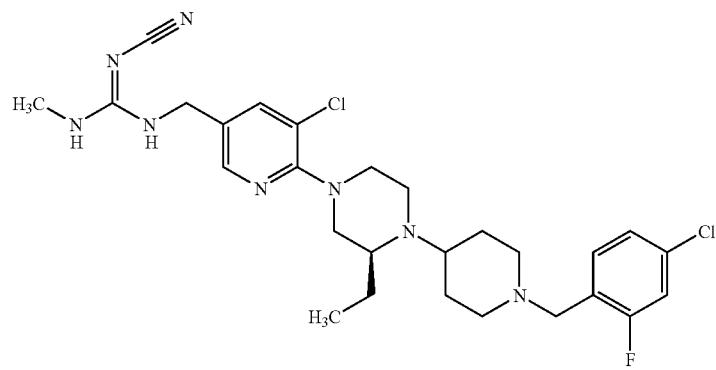 |
| 404 | 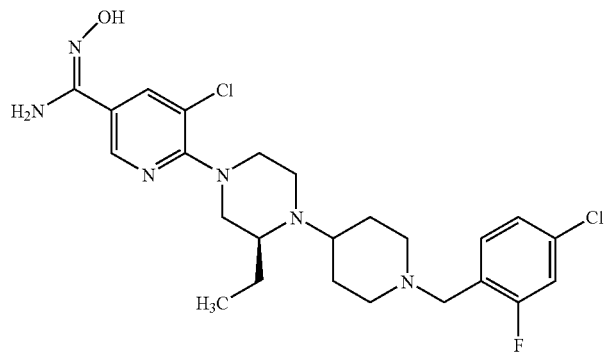 |
| 405 | 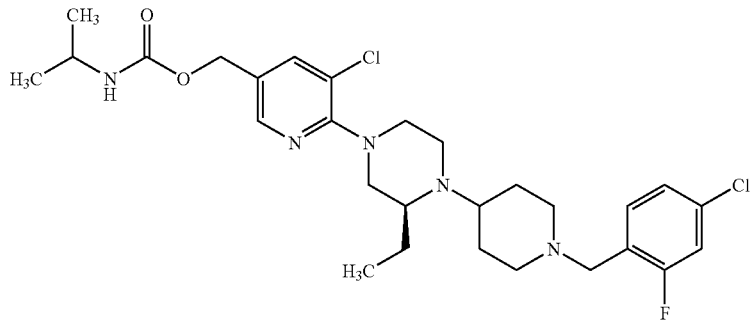 |

-continued
| Compound No. | Compound Structure |
|---|---|
| 406 | 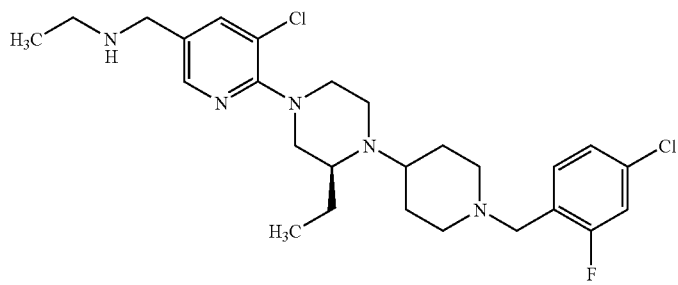 |
| 407 | 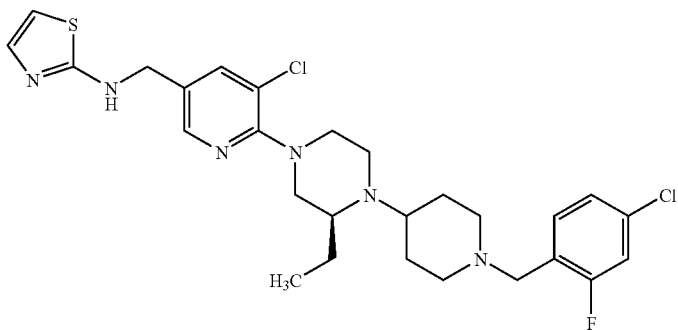 |
| 408 | 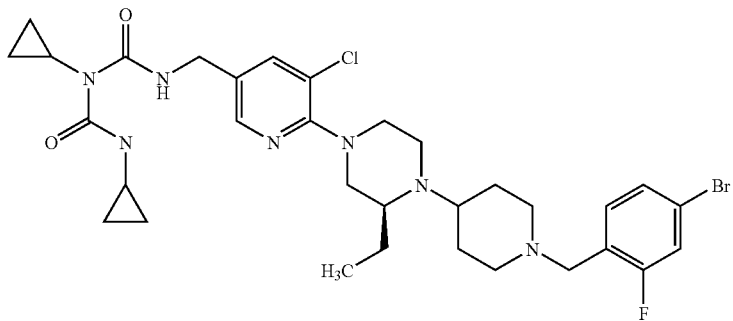 |
| 409 | 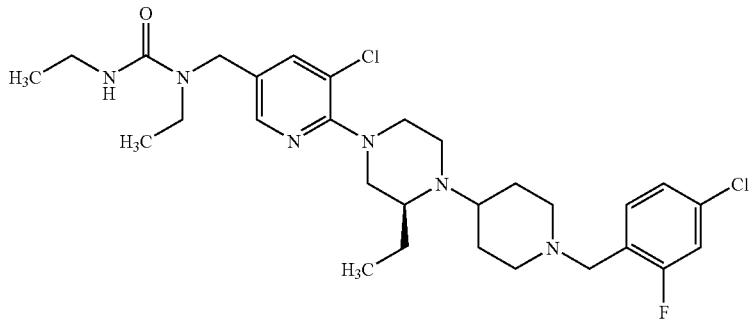 |

-continued
| Compound No. | Compound Structure |
|---|---|
| 410 | 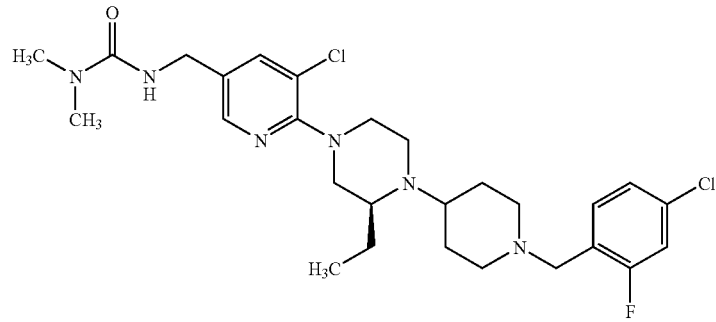 |
| 411 | 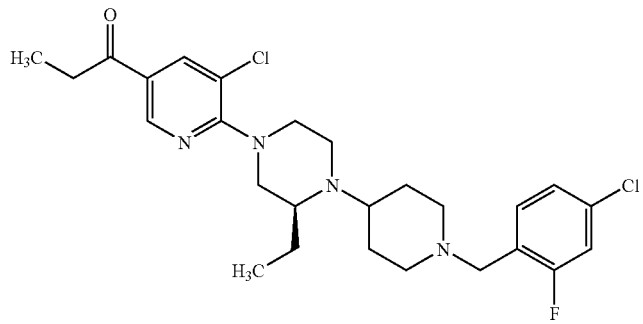 |
| 412 | 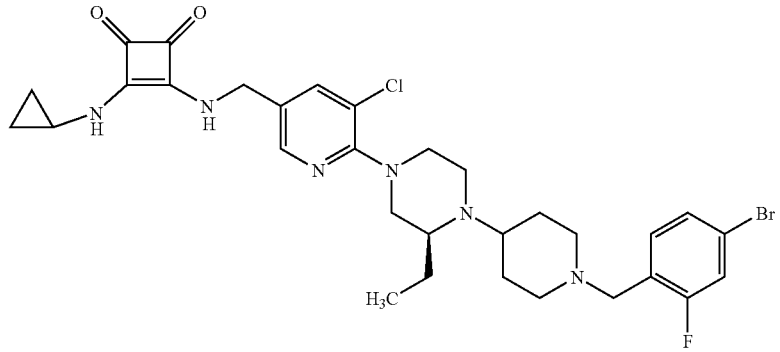 |
| 413 | 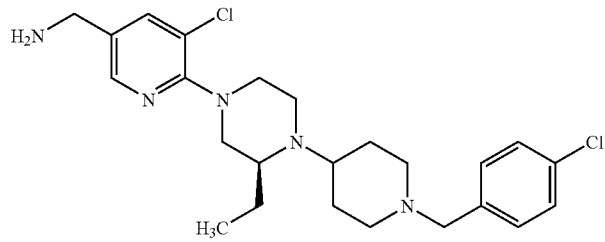 |

-continued
| Compound No. | Compound Structure |
|---|---|
| 414 | 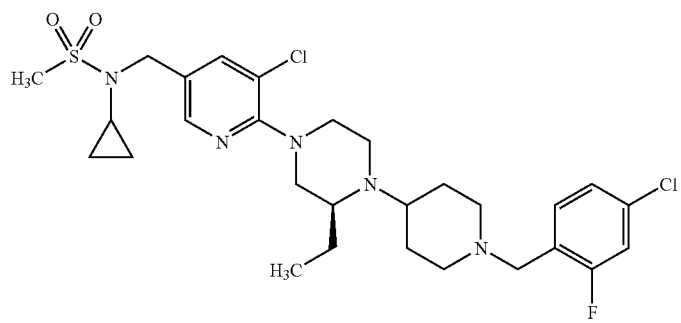 |
| 415 | 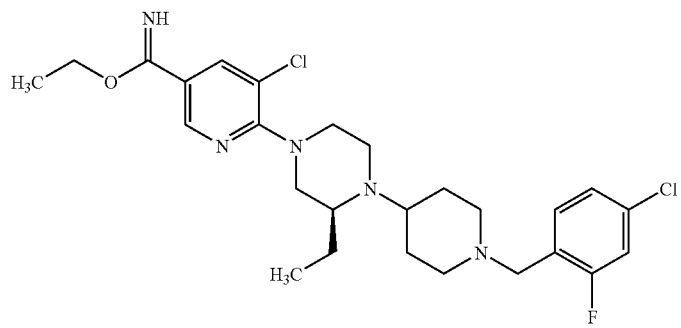 |
| 416 | 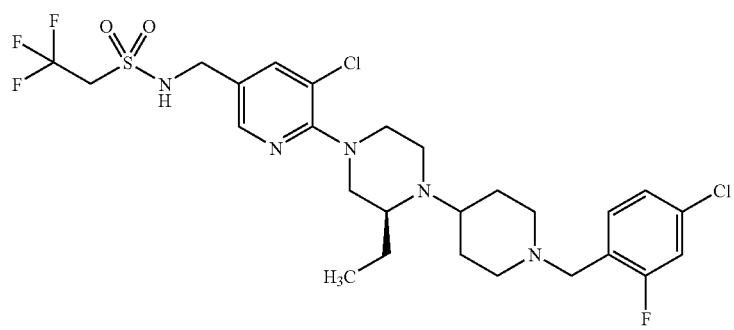 |
| 417 | 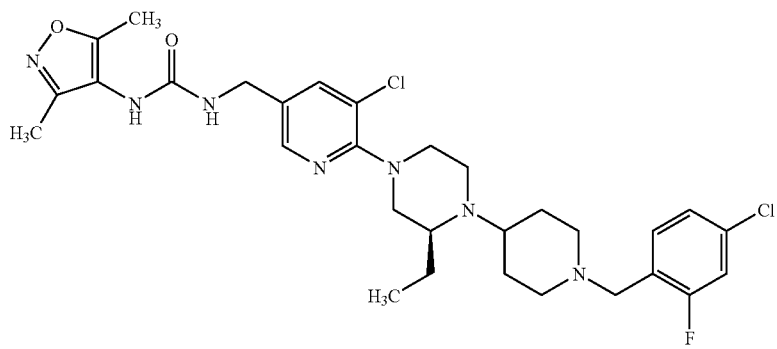 |

-continued
| Compound No. | Compound Structure |
|---|---|
| 418 | 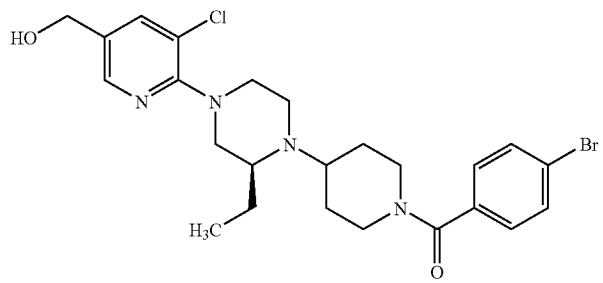 |
| 419 | 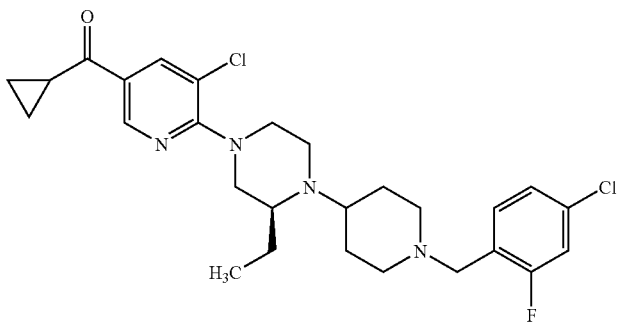 |
| 420 | 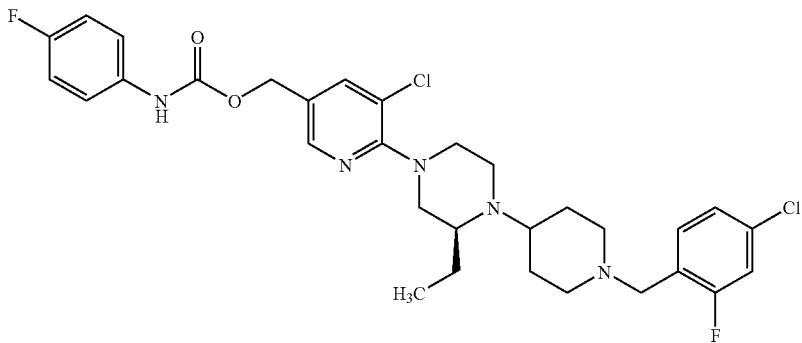 |
| 421 | 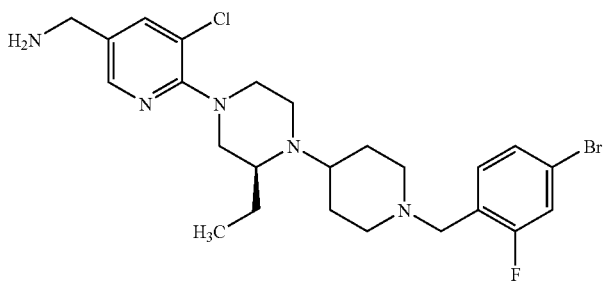 |

-continued

| Compound No. | Compound Structure |
|---|---|
| 422 | 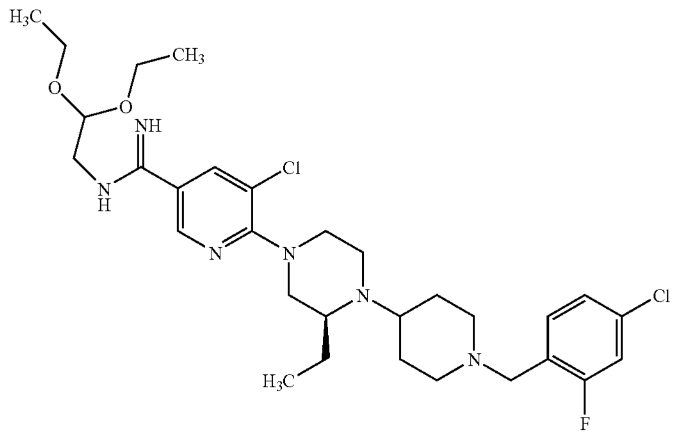 |
| 423 | 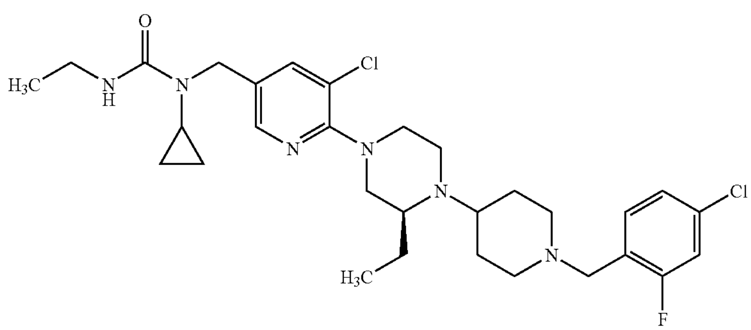 |
| 424 | 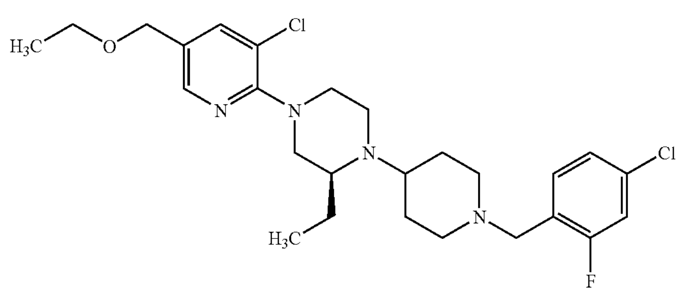 |
| 425 | 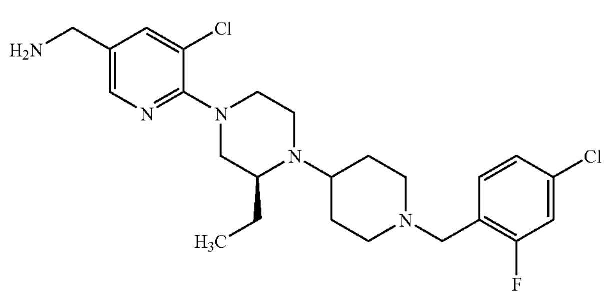 |

-continued

| Compound No. | Compound Structure |
|---|---|
| 426 | 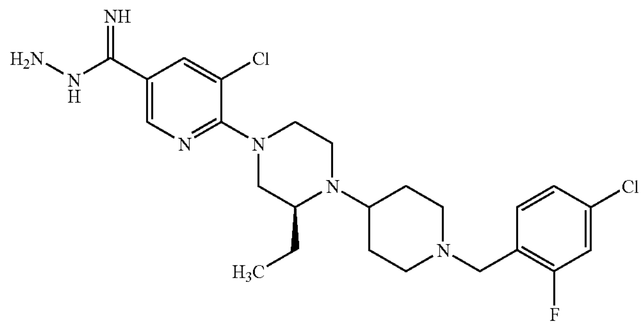 |
| 427 | 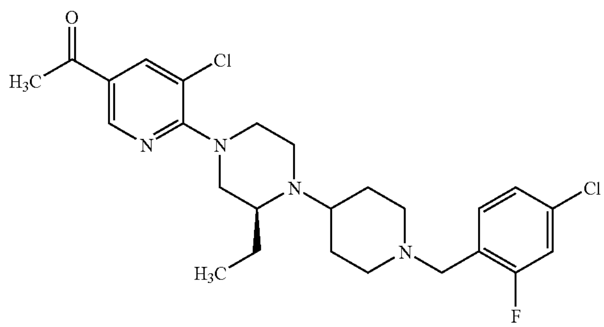 |
| 428 | 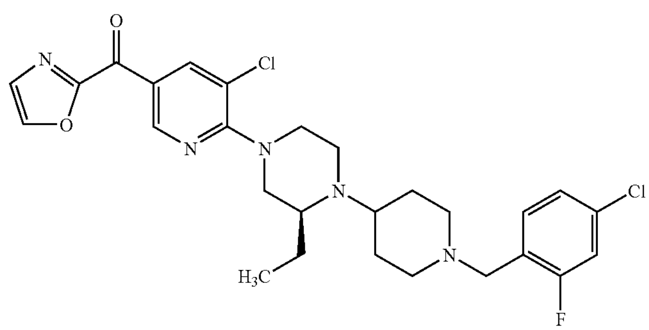 |
| 429 | 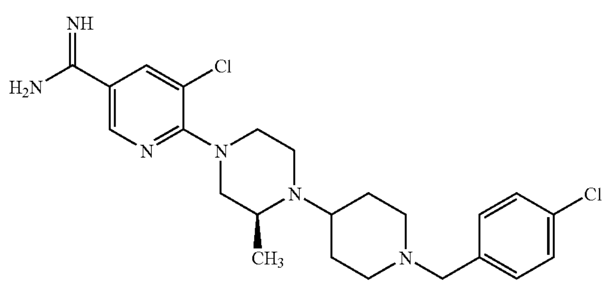 |
| 430 | 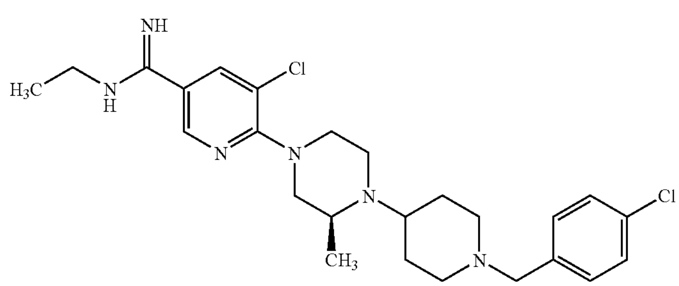 |

|Compound No.|Compound Structure|
|---|---|
|431|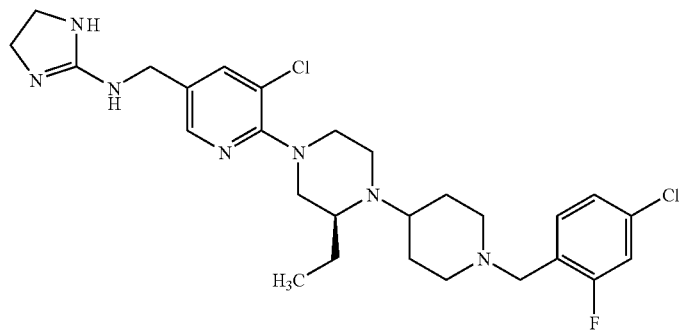|
|432|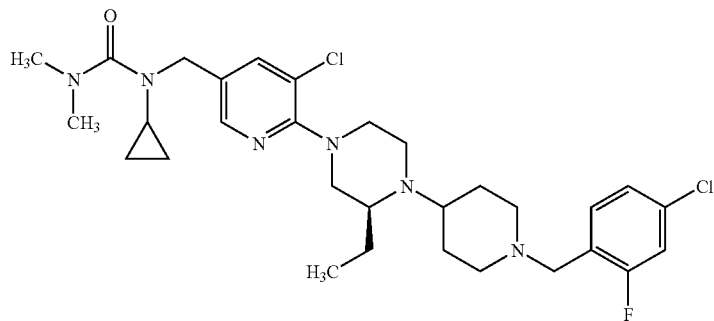|
|433|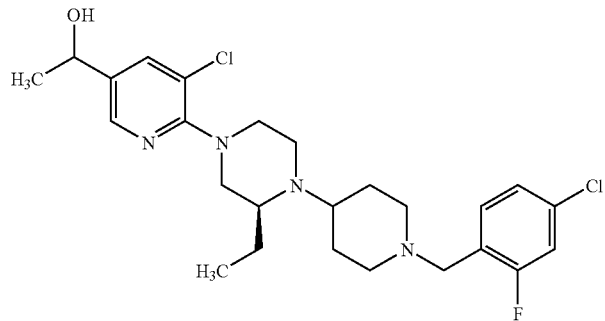|
|434|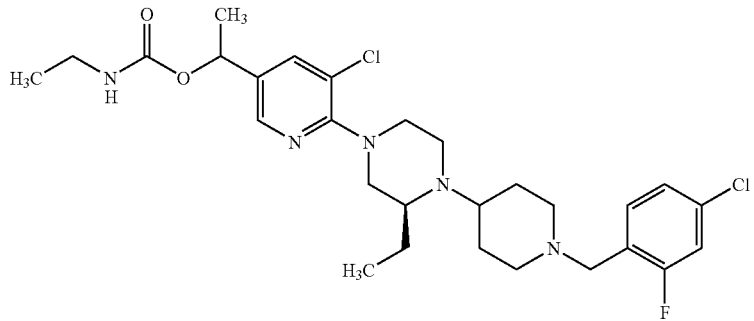|

| Compound No. | Compound Structure |
|---|---|
| 435 | 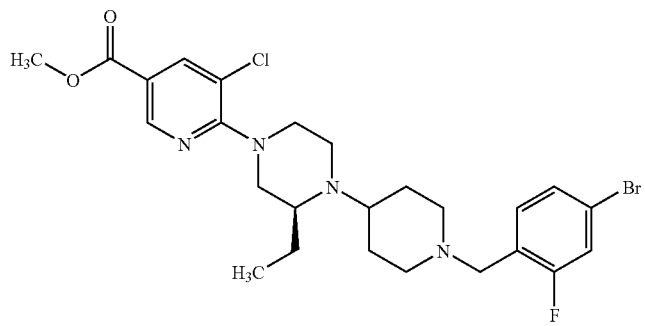 |
| 436 | 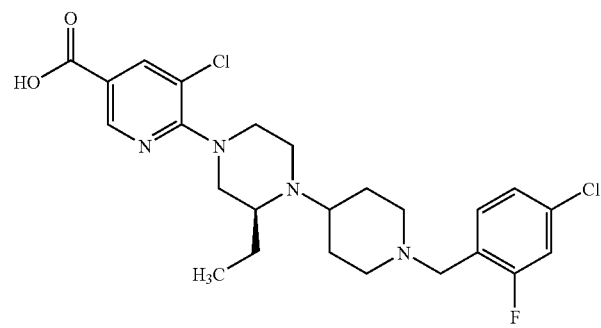 |
| 437 | 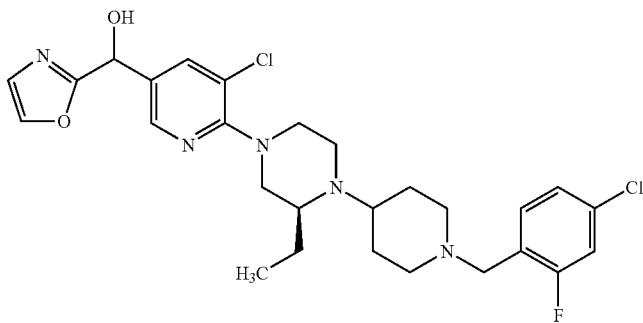 |
| 438 | 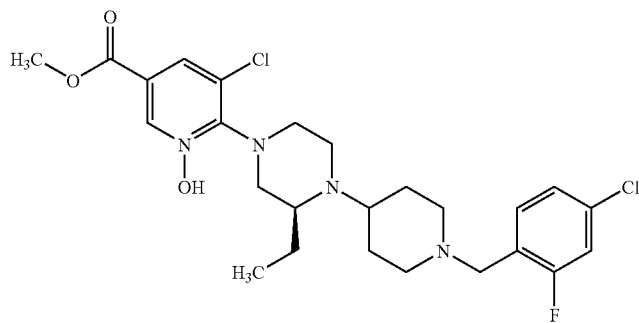 |

-continued

| Compound No. | Compound Structure |
|---|---|
| 439 | 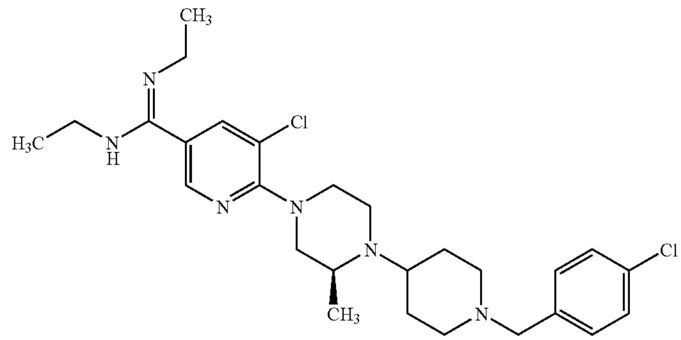 |
| 440 | 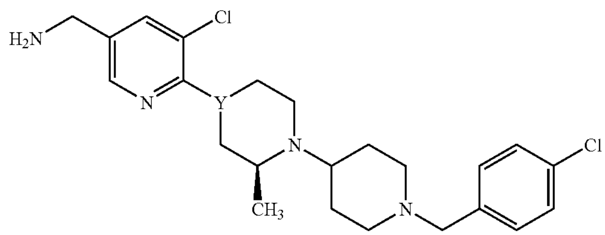 |
| 441 | 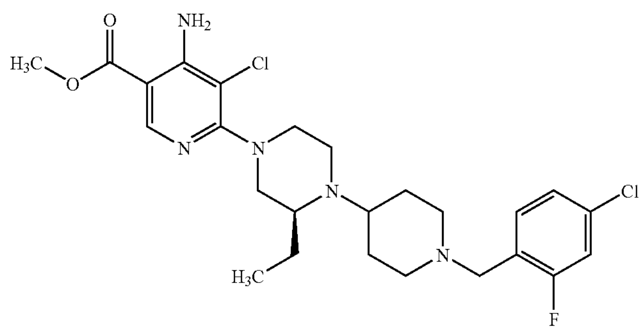 |
| 442 | 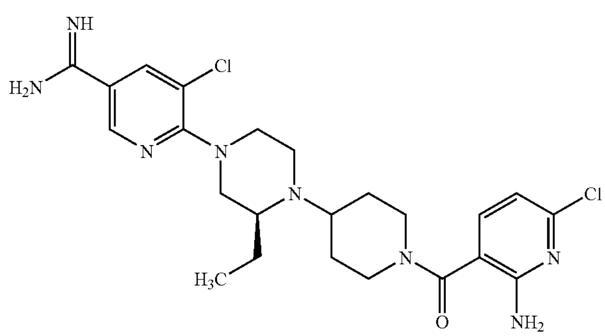 |
| 443 | 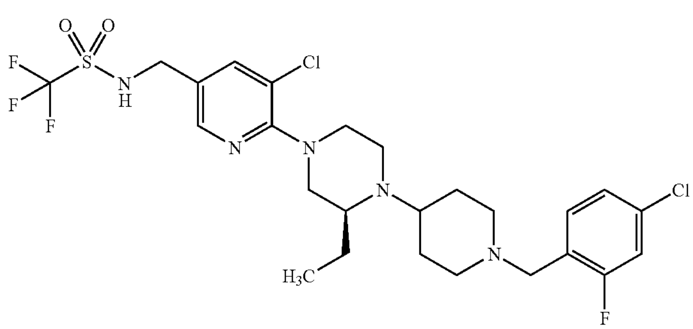 |

-continued

| Compound No. | Compound Structure |
|---|---|
| 444 | 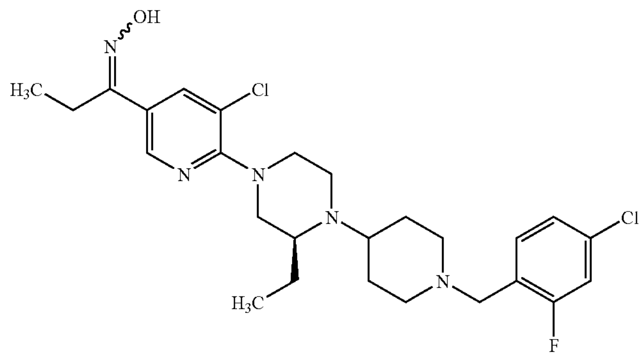 |
| 445 | 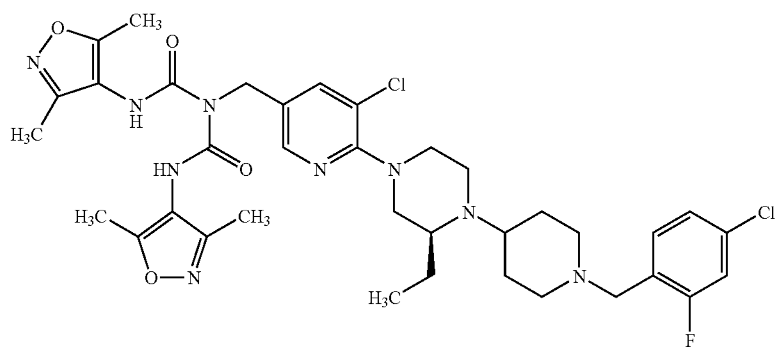 |
| 446 | 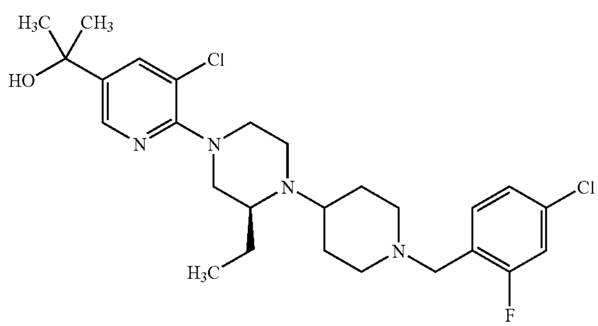 |
| 447 | 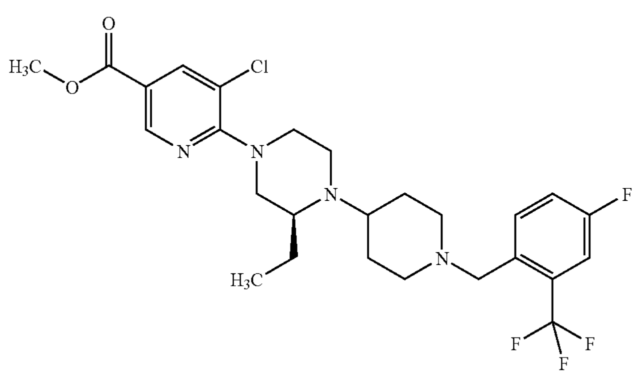 |

-continued

| Compound No. | Compound Structure |
|---|---|
| 448 | 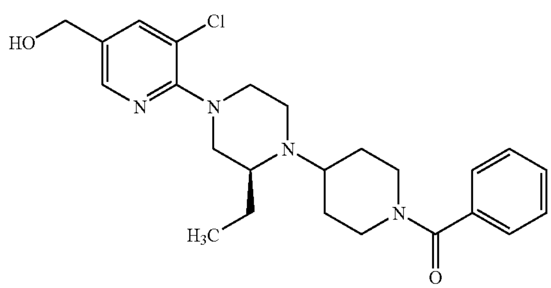 |
| 449 | 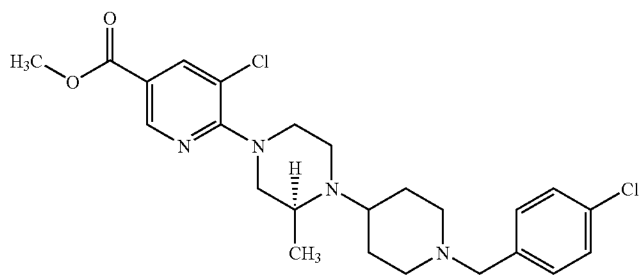 |
| 450 | 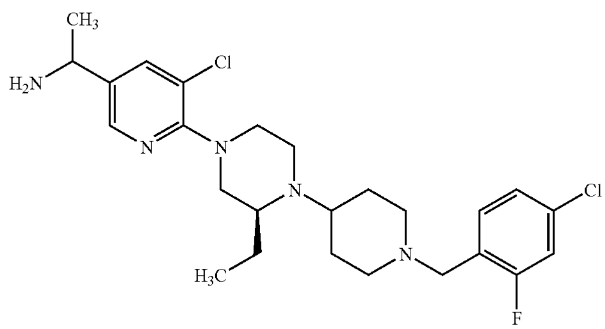 |
| 451 | 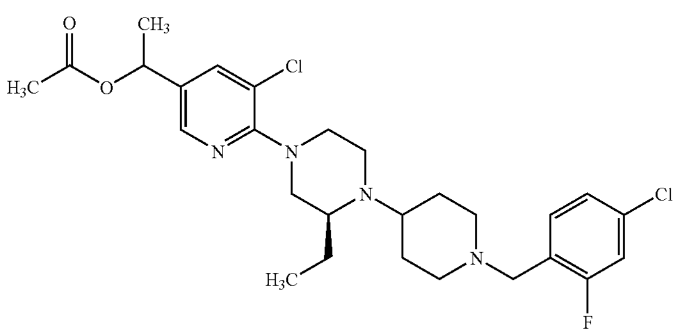 |
| 452 | 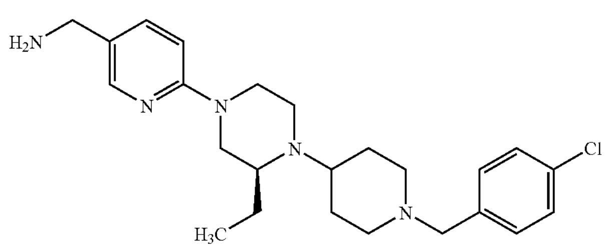 |

-continued
| Compound No. | Compound Structure |
|---|---|
| 453 | 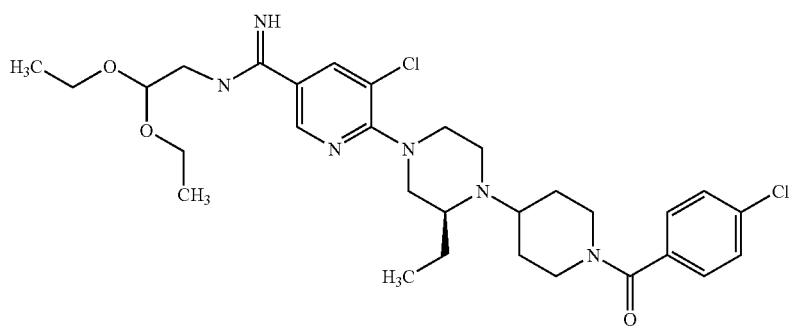 |
| 454 | 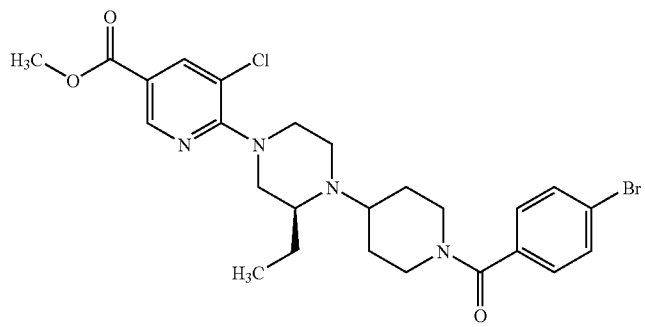 |
| 455 | 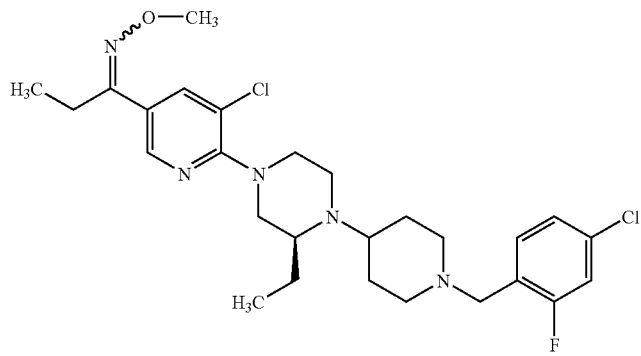 |
| 456 | 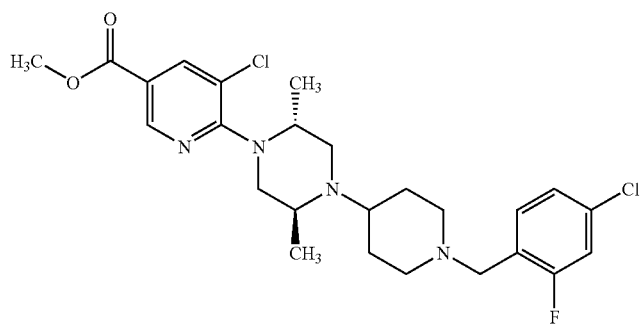 |

-continued
| Compound No. | Compound Structure |
|---|---|
| 457 | 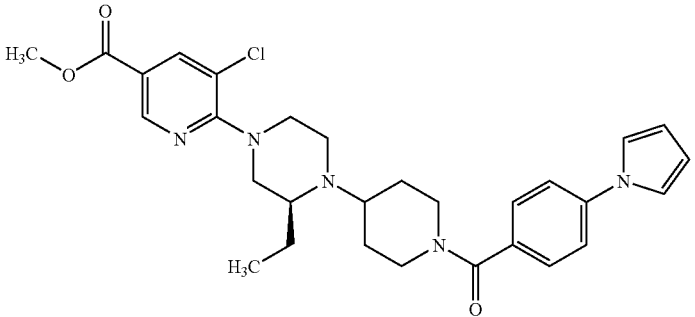 |
| 458 | 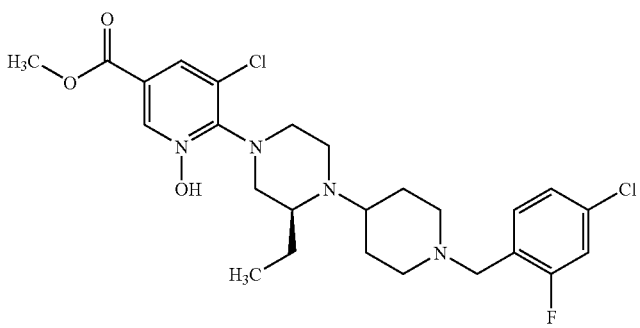 |
| 459 | 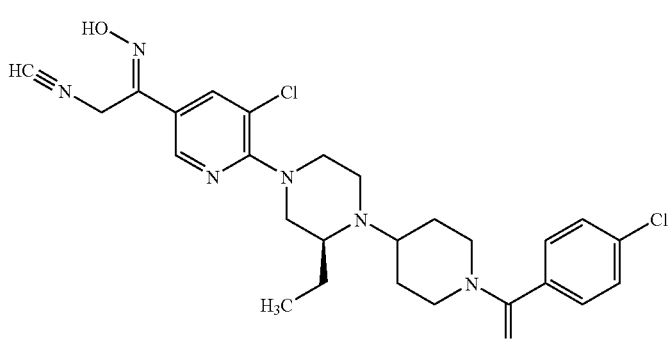 |
| 460 | 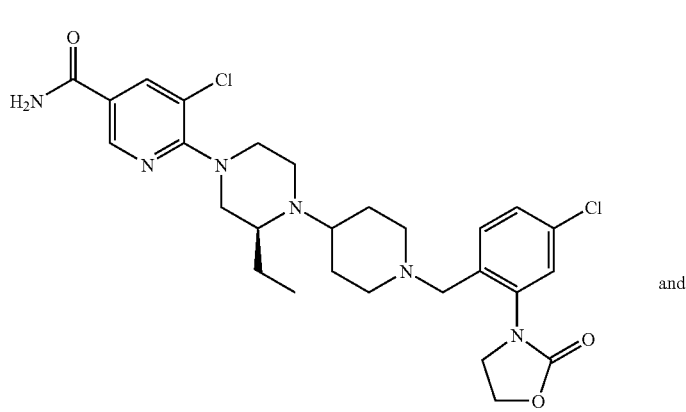 and |

-continued
| Compound No. | Compound Structure |
|---|---|
| 461 | 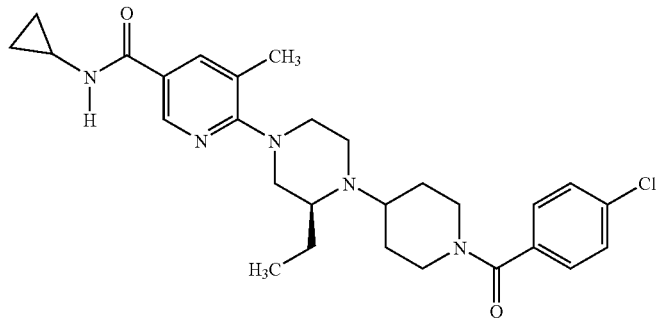 |
or a pharmaceutically acceptable salts, solvates or esters thereof.
42. A compound selected from the group consisting of:
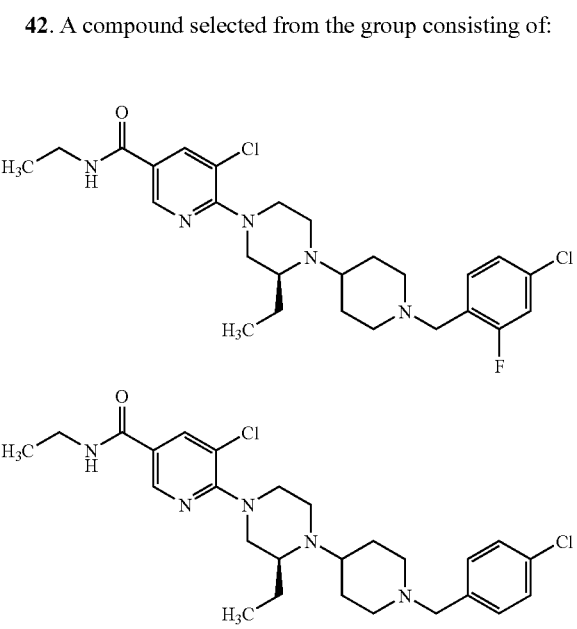
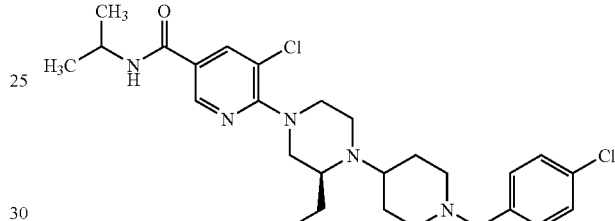
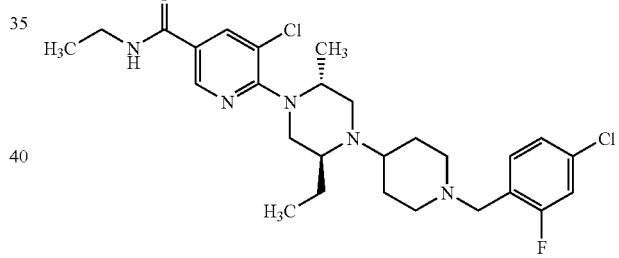
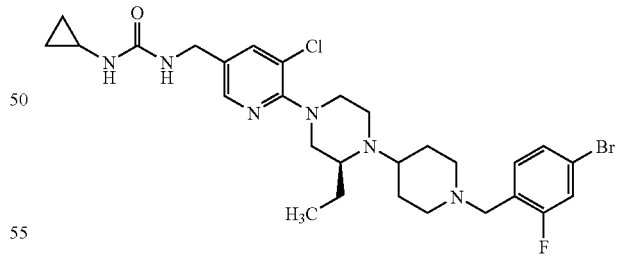
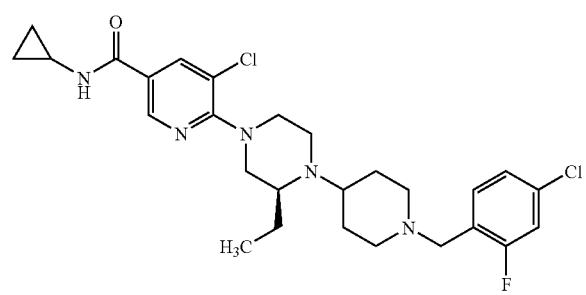
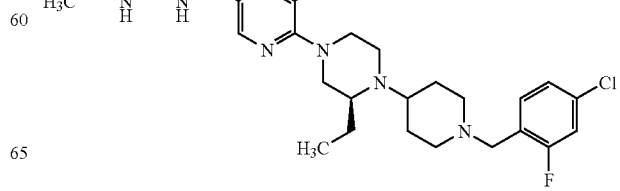

-continued

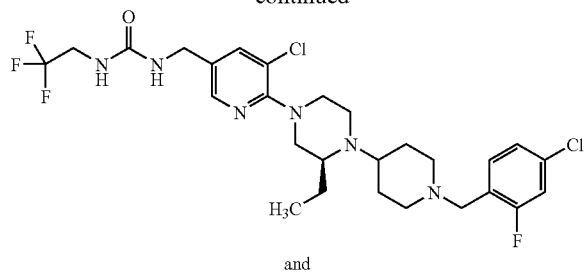

and

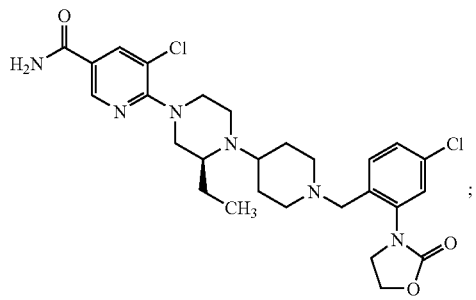

or pharmaceutically acceptable salt or ester thereof.

43. A compound selected from the group of compounds consisting of

Formula 6

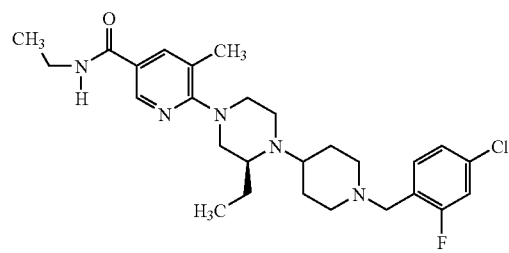

and

Formula 7

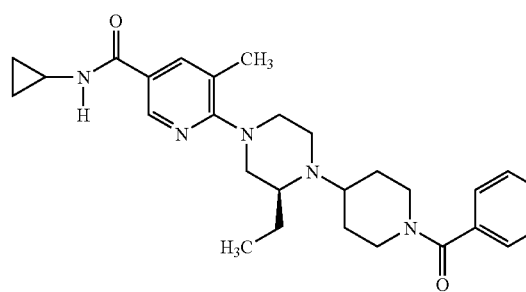

or pharmaceutically acceptable salt, or ester thereof.

44. A compound according to claim 1 in purified form.

45. A pharmaceutical composition comprising at least one compound of claim 1, or a pharmaceutically acceptable salt, or ester thereof, in combination with at least one pharmaceutically acceptable carrier.

46. The pharmaceutical composition of claim 45, further comprising at least one additional agent, drug, medicament, antibody and/or inhibitor for treating a CXCR3 chemokine receptor mediated disease.

47. A compound having the general structure shown in Formula 1:

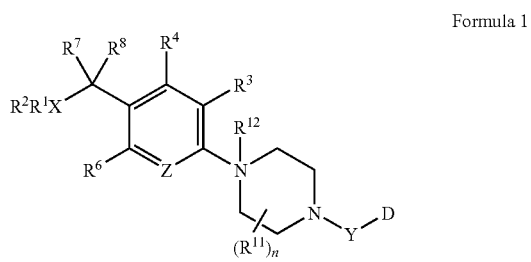

Formula 1 or pharmaceutically acceptable salt thereof, wherein:
Z is N, C($R^{29}$), or NO;
X is N, O, alkyl, cycloalkyl, heteroaryl, heterocyclyl or heterocyclenyl;
$R^1$ and $R^2$ are independently absent or present, and if present each is independently selected from the group consisting of H, alkyl, alkoxy, alkenyl, carbonyl, cycloalkyl, cycloalkenyl, alkylaryl, arylalkyl, aryl, amino, alkylamino, amidinyl, carboxamido, cyano, hydroxyl, urea, —N≡CH, ≡NCN, —$(CH_2)_q$OH, —$(CH_2)_q$O$R^{31}$, —$(CH_2)_q$NH$_2$, —$(CH_2)_q$NHR$^{31}$, —$(CH_2)_q$N($R^{31}$)$_2$, —$(CH_2)_q$C(═O)NHR$^{31}$, —$(CH_2)_q$SO$_2$R$^{31}$, —$(CH_2)_q$NHSO$_2$R$^{31}$, —$(CH_2)_q$SO$_2$NHR$^{31}$, —C(═S)N(H)alkyl, —N(H)—S(O)$_2$-alkyl, —N(H)C(═O)N(H)-alkyl, —S(O)$_2$alkyl, —S(O)$_2$N(H)alkyl, —S(O)$_2$N(alkyl)$_2$, —S(O)$_2$aryl, —C(═S)N(H)cycloalkyl, —C(═O)N(H)NH$_2$, —C(═O)alkyl, -heteroaryl, heterocyclyl, and heterocyclenyl; or alternatively when X is N, the N taken together with the $R^1$ and $R^2$ forms a heterocyclyl, heteroaryl or —N═C(NH$_2$)$_2$;
$R^3$, $R^4$, $R^6$ and $R^{29}$ moieties can be the same or different, each being independently selected from the group consisting of H, alkyl, alkylaryl, aralkyl, —CN, CF$_3$, haloalkyl, cycloalkyl, halogen, hydroxyalkyl, —N═CH—($R^{31}$), —C(═O)N($R^{30}$)$_2$, —N($R^{30}$)$_2$, —OR$^{30}$, —SO$_2$($R^{31}$), —N($R^{30}$)C(═O)N($R^{30}$)$_2$ and —N($R^{30}$)C(═O)R$^{31}$;
$R^7$ and $R^8$ are the same or different, each being independently selected from the group consisting of H, alkyl, alkylaryl, heteroaryl, hydroxyl, —CN, alkoxy, alkylamino, —N(H)S(O)$_2$alkyl and —N(H)C(═O)N(H)alkyl; or alternatively $R^7$ and $R^8$ taken together with the carbon atom to which they are shown attached is —C═O—, —C═S—, —C═N(H)—, —C═N(alkyl)—, —C═N(Oalkyl)—, —C═N(OH)— or cycloalkyl;
the $R^{10}$ moieties can be the same or different, each being independently selected from the group consisting of H, alkyl, cycloalkyl, aryl, heteroaryl, heterocyclenyl, heterocyclyl, alkylaryl, arylalkyl, —CO$_2$H, hydroxyalkyl, —C(═O)N($R^{30}$)$_2$, —$(CH_2)_q$OH, —$(CH_2)_q$OR$^{31}$—$(CH_2)_q$NHR$^{31}$, —$(CH_2)_q$N($R^{31}$)$_2$, —OR$^{30}$, halogen, ═O, and —C(═O)R$^{31}$;
the $R^{11}$ moieties can be the same or different, each being independently selected from the group consisting of H, alkyl, cycloalkyl, aryl, heteroaryl, heterocyclyl, heterocyclenyl, alkylaryl, arylalkyl, hydroxyalkyl, carboxamide, CO$_2$H, —$(CH_2)_q$OH, —$(CH_2)_q$OR$^{31}$, —$(CH_2)_q$NHR$^{31}$, —$(CH_2)_q$N($R^{31}$)$_2$, —OR$^{30}$, halogen, ═O, and —C(═O)R$^{31}$;
the $R^{12}$ moieties can be the same or different, each being independently selected from the group consisting of H, alkyl, —CN, —C(=O)N($R^{30}$)$_2$, —(CH$_2$)$_q$OH, —(CH$_2$)$_q$O$R^{31}$, —(CH$_2$)$_q$NH$R^{31}$, —(CH$_2$)$_q$N($R^{31}$)$_2$, and —S(O$_2$)$R^{31}$;

D is a five to nine membered cycloalkyl, cycloalkenyl, aryl, heteroaryl, heterocyclenyl or heterocyclyl ring having 0-4 heteroatoms independently selected from O, S or N, wherein ring D is unsubstituted or optionally substituted with 1-5 independently selected $R^{20}$ moieties;

the $R^{20}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$O$R^{31}$, —(CH$_2$)$_q$NH$_2$, —(CH$_2$)$_q$NH$R^{31}$, —(CH$_2$)$_q$N($R^{31}$)$_2$, —(CH$_2$)$_q$C(=O)NH$R^{31}$, —(CH$_2$)$_q$SO$_2$$R^{31}$, —(CH$_2$)$_q$NHSO$_2$$R^{31}$, —(CH$_2$)$_q$SO$_2$NH$R^{31}$, -alkynylC($R^{31}$)$_2$O$R^{31}$, —C(=O)$R^{30}$, —C(=O)N($R^{30}$)$_2$, —C(=NR$^{30}$)NHR$^{30}$, —C(=NOH)N($R^{30}$)$_2$, —C(=NOR$^3$)N($R^{30}$)$_2$, —C(=O)O$R^{30}$, —N($R^{30}$)$_2$, —N($R^{30}$)C(=O)$R^{31}$, —NHC(=O)N($R^{30}$)$_2$, —N($R^{30}$)C(=O)O$R^{31}$, —N($R^{30}$)C(=NCN)N($R^{30}$)$_2$, —N($R^{30}$)C(=O)N($R^{30}$)SO$_2$($R^{31}$), —N($R^{30}$)C(=O)N($R^{30}$)$_2$, —N($R^{30}$)SO$_2$($R^{31}$), —N($R^{30}$)S(O)$_2$N($R^{30}$)$_2$, —O$R^{30}$, —OC(=O)N($R^{30}$)$_2$, —S$R^{30}$, —SO$_2$N($R^{30}$)$_2$, —SO$_2$($R^{31}$), —OSO$_2$($R^{31}$), and —OSi($R^{30}$)$_3$; or alternatively two $R^{20}$ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 $R^{21}$ moieties;

the $R^{21}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, carboxamido, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$O$R^{31}$, —(CH$_2$)$_q$NH$_2$, —(CH$_2$)$_q$NH$R^{31}$, —(CH$_2$)$_q$N($R^{31}$)$_2$, —(CH$_2$)$_q$C(=O)NH$R^{31}$, —(CH$_2$)$_q$SO$_2$$R^{31}$, —(CH$_2$)$_q$NSO$_2$$R^{31}$— (CH$_2$)$_q$SO$_2$NH$R^{31}$, -alkynylC($R^{31}$)$_2$O$R^{31}$, —C(=O)$R^{30}$, —C(=O)N($R^{30}$)$_2$, —C(=NR$^{30}$)NHR$^{30}$—C(=NOH)N($R^{30}$)$_2$—C(=NO$R^{31}$)N($R^{30}$)$_2$, —C(=O)O$R^{30}$, —N($R^{30}$)$_2$, —N($R^{30}$)C(=O)$R^{31}$, —NHC(=O)N($R^{30}$)$_2$, —N($R^{30}$)C(=O)O$R^{31}$, —N($R^{30}$)C(=NCN)N($R^{30}$)$_2$, —N($R^{30}$)C(=O)N($R^{30}$)SO$_2$($R^{31}$), —N($R^{30}$)C(=O)N($R^{30}$)$_2$, —N($R^{30}$)SO$_2$($R^{31}$), —N($R^{30}$)S(O)$_2$N($R^{30}$)$_2$, —O$R^{30}$, —OC(=O)N($R^{30}$)$_2$, —S$R^{30}$, —SO$_2$N($R^{30}$)$_2$, —SO$_2$($R^{31}$), —OSO$_2$($R^{31}$), and —OSi($R^{30}$)$_3$;

Y is selected from the group consisting of —CH$_2$—, —CH(CH$_3$)—, —CH(CH$_2$OH)—, and —C(=O)—;

the $R^{30}$ moieties can be the same or different, each being independently selected from the group consisting of H, alkyl, alkylaryl, aryl, aralkyl, cycloalkyl, CN, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$NSO$_2$alkyl, —(CH$_2$)$_q$NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and heteroaryl;

the $R^{31}$ moieties can be the same or different, each being independently selected from the group consisting of alkyl, alkylaryl, aryl, aralkyl, cycloalkyl, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$NSO$_2$alkyl, —(CH$_2$)$_q$NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and heteroaryl;

m is 0 to 4;

n is 0 to 4;

each q can be the same or different, each being independently selected from 1 to 5;

with the proviso that there are no two adjacent double bonds in any ring, and that when a nitrogen is substituted by two alkyl groups, said two alkyl groups may be optionally joined to each other to form a ring.

\* \* \* \* \*